(12) United States Patent
Baldwin et al.

(10) Patent No.: US 8,487,108 B2
(45) Date of Patent: Jul. 16, 2013

(54) PIPERIDINYL CARBAMATE INTERMEDIATES FOR THE SYNTHESIS OF ASPARTIC PROTEASE INHIBITORS

(75) Inventors: John J. Baldwin, Gwynedd Valley, PA (US); David A. Claremon, Maple Glen, PA (US); Colin Tice, Ambler, PA (US); Salvacion Cacatian, Blue Bell, PA (US); Lawrence W. Dillard, Yardley, PA (US); Alexey V. Ishchenko, Somerville, PA (US); Jing Yuan, Lansdale, PA (US); Zhenrong Xu, Horsham, PA (US); Gerard McGeehan, Garnet Valley, PA (US); Robert D. Simpson, Wilmington, DE (US); Suresh B. Singh, Kendall Park, NJ (US); Wei Zhao, Eagleville, PA (US); Patrick T. Flaherty, Pittsburgh, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 842 days.

(21) Appl. No.: 12/084,928

(22) PCT Filed: Nov. 13, 2006

(86) PCT No.: PCT/US2006/043920
§ 371 (c)(1),
(2), (4) Date: Nov. 5, 2009

(87) PCT Pub. No.: WO2007/070201
PCT Pub. Date: Jun. 21, 2007

(65) Prior Publication Data
US 2010/0048636 A1    Feb. 25, 2010

Related U.S. Application Data

(60) Provisional application No. 60/736,564, filed on Nov. 14, 2005, provisional application No. 60/845,291, filed on Sep. 18, 2006, provisional application No. 60/845,331, filed on Sep. 18, 2006.

(51) Int. Cl.
*C07D 211/22* (2006.01)
*C07D 211/60* (2006.01)

(52) U.S. Cl.
USPC .......................................... 546/227; 546/232

(58) Field of Classification Search
None
See application file for complete search history.

(56) References Cited

U.S. PATENT DOCUMENTS

| | | |
|---|---|---|
| 3,071,618 A | 1/1963 | Pinson et al. |
| 4,136,163 A | 1/1979 | Watson et al. |
| 4,908,372 A | 3/1990 | Carr et al. |
| 4,923,865 A | 5/1990 | Cossement et al. |
| 5,218,002 A | 6/1993 | Stroech et al. |
| 5,371,093 A | 12/1994 | Carr et al. |
| 5,380,731 A | 1/1995 | Carr et al. |
| 5,635,523 A | 6/1997 | Kempf et al. |
| 5,767,144 A | 6/1998 | Winn et al. |
| 6,162,927 A | 12/2000 | Winn et al. |
| 6,323,368 B1 | 11/2001 | Evans |
| 6,900,329 B2 | 5/2005 | Clader et al. |
| 6,946,481 B1 | 9/2005 | Winn et al. |
| 7,176,242 B2 | 2/2007 | John et al. |
| 7,754,737 B2 | 7/2010 | Baldwin et al. |
| 7,858,624 B2 | 12/2010 | Baldwin et al. |
| 7,872,028 B2 | 1/2011 | Baldwin et al. |
| 2004/0044201 A1 | 3/2004 | Cummings et al. |
| 2007/0093492 A1 | 4/2007 | Jiaang et al. |
| 2007/0265331 A1 | 11/2007 | Decicco et al. |
| 2009/0018103 A1 | 1/2009 | Baldwin et al. |
| 2009/0186884 A1 | 7/2009 | Baldwin et al. |
| 2009/0312369 A1 | 12/2009 | Baldwin et al. |
| 2009/0318501 A1 | 12/2009 | Baldwin et al. |
| 2010/0160424 A1 | 6/2010 | Baldwin et al. |
| 2010/0317697 A1 | 12/2010 | Baldwin et al. |

FOREIGN PATENT DOCUMENTS

| | | |
|---|---|---|
| EP | 0178947 A2 | 4/1986 |
| EP | 1 882 684 A1 | 1/2008 |
| GB | 1351761 A | 5/1974 |
| JP | 51015098 A | 5/1976 |
| JP | 61100563 A | 5/1986 |
| JP | 01313467 | 12/1989 |

(Continued)

OTHER PUBLICATIONS

Notification Concerning Transmittal of International Preliminary Report on Patentability, and International Preliminary Report on Patentability, International Application No. PCT/US2007/020164, mail date Apr. 2, 2009.

(Continued)

*Primary Examiner* — David K O Dell
(74) *Attorney, Agent, or Firm* — Hamilton, Brook, Smith & Reynolds, P.C.

(57) ABSTRACT

The present invention is directed to aspartic protease inhibitors. Certain aspartic protease inhibitors of the invention can be represented by the following structural formula or a pharmaceutically acceptable salt thereof. The present invention is also directed to pharmaceutical compositions comprising the disclosed aspartic protease inhibitors. The present invention is further directed to methods of antagonizing one or more aspartic proteases in a subject in need thereof, and methods for treating an aspartic protease mediated disorder in a subject using the disclosed aspartic protease inhibitors.

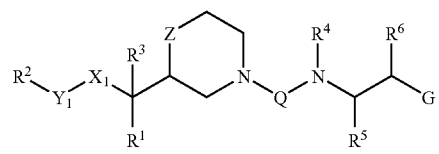

4 Claims, 4 Drawing Sheets

FOREIGN PATENT DOCUMENTS

| | | |
|---|---|---|
| WO | WO 9604232 A1 | 2/1996 |
| WO | WO 98/54179 A1 | 12/1998 |
| WO | WO 99/54321 | 10/1999 |
| WO | WO 00/18744 A1 | 4/2000 |
| WO | WO 00/40558 | 7/2000 |
| WO | WO 00/63172 | 10/2000 |
| WO | WO 03/006423 A1 | 1/2003 |
| WO | WO 03/090690 | 11/2003 |
| WO | WO 2004/002483 | 1/2004 |
| WO | WO 2004/013098 | 2/2004 |
| WO | WO 2004/024675 | 3/2004 |
| WO | WO 2005/049027 | 6/2005 |
| WO | WO 2006/023844 | 3/2006 |
| WO | WO 2006/042150 A1 | 4/2006 |
| WO | WO 2007/117557 | 10/2007 |
| WO | WO 2008/036216 A1 | 3/2008 |
| WO | WO 2008/036247 A1 | 3/2008 |
| WO | WO 2008/156817 | 12/2008 |
| WO | WO 2009/096996 | 8/2009 |
| WO | WO 2009/154766 | 12/2009 |
| WO | WO 2009/158377 | 12/2009 |
| WO | WO 2011/017533 | 2/2011 |

OTHER PUBLICATIONS

Notification Concerning Transmittal of International Preliminary Report on Patentability, and International Preliminary Report on Patentability, International Application No. PCT/US2007/020086, mail date Apr. 2, 2009.
Written Opinion of the International Searching Authority, International Application No. PCT/US08/67650 (Jun. 22, 2009).
International Search Report, International Application No. PCT/US08/67650 (Jun. 22, 2009).
Notification Concerning Transmittal of International Preliminary Report on Patentability, and International Preliminary Report on Patentability, International Application No. PCT/US2005/036230, mail date Apr. 19, 2007.
Notification Concerning Transmittal of International Preliminary Report on Patentability, and International Preliminary Report on Patentability, International Application No. PCT/US2006/043920, mail date May 22, 2008.
Office Action from European Patent Office, European Application No. 06 837 406.5, Dated Oct. 10, 2009.
Examination Report from Gulf Cooperation Council Patent Office, GCC Application No. GCC/P/2006/7201, Dated Jul. 21, 2009.
Database Casreact, AN 90:168416.
Dorwald, F. Zaragoza, "Side Reactions in Organic Synthesis: A Guide to Successful Synthesis Design," Weinheim: Wiley-VCH Verlag GmbH & Co. KGaA, Preface p. ix, (2005).
English Translation of Notification of the First Office Action, Chinese Patent Application No. 200580042064.7, Date of Notification May 8, 2009.
Jordan, V.Craig, "Tamoxifen: a Most Unlikely Pioneering Medicine," Nature Reviews: Durg Discovery, 2:205-213 (Mar., 2003).
Notice of Allowance from US Patent Office, U.S. Appl. No. 11/664,558, dated Mar. 1, 2010.
Notice of Allowance from US Patent Office, U.S. Appl. No. 12/225,985, dated Oct. 12, 2010.
Office Action from European Patent Office, European Application No. 07 838 310.6, Dated Sep. 2, 2009.
Office Action from European Patent Office, European Application No. 07 838 381.7, dated Oct. 16, 2009.
Office Action from US Patent Office, U.S. Appl. No. 12/665,213, Dated Sep. 29, 2010.
Office Action from US Patent Office, U.S. Appl. No. 12/665,213, Dated Oct. 29, 2010.
Office Action from US Patent Office, U.S. Appl. No. 12/665,213, Dated Dec. 17, 2010.
Rahuel, J. et al., "Structure-Based Drug Design: The Discovery of Novel Nonpeptide Orally Active Inhibitors of Human Renin," Chemistry & Biology, 7:493-504 (2000).
Shabat, D., et al., "Katalytische Antikorper als Sonden Fur die Evolution von Enzymen: Modellierung einer fruhen Glycosidase," Angew. Chem., 108(22):2800-2802 (1996).
Stachel, S.J. et al., "Conformationally biased P3 amide replacements of beta-secretase inhibitors," Bioorganic & Med. Chem. Letters, 16(3):641-644 (2006).
Wood, J.N., et al., "Voltage-Gated Sodium Channels and Pain Pathways," J. Neurobiol., 61:55-71 (2004).
Written Opinion of the International Searching Authority, International Application No. PCT/US2007/008518 (Oct. 10, 2007).
International Search Report, International Application No. PCT/US2007/008518 (Oct. 10, 2007).
Notification Concerning Transmittal of International Preliminary Report on Patentability, and International Preliminary Report on Patentability, International Application No. PCT/US2007/008518, mail date Oct. 16, 2008.
International Search Report, International Application No. PCT/US2008/007662 (Apr. 21, 2009).
Written Opinion of the International Searching Authority, International Application No. PCT/US2008/007662 (Apr. 21, 2009).
Notification Concerning Transmittal of International Preliminary Report on Patentability, and International Preliminary Report on Patentability, International Application No. PCT/US2008/007662, mail date Jan. 7, 2010.
Notification Concerning Transmittal of International Preliminary Report on Patentability, and International Preliminary Report on Patentability, International Application No. PCT/US2008/067650, mail date Jan. 7, 2010.
International Search Report, International Application No. PCT/US2009/48389 (Sep. 11, 2009).
Written Opinion of the International Searching Authority, International Application No. PCT/US2009/48389 (Sep. 11, 2009).
Notification Concerning Transmittal of International Preliminary Report on Patentability, and International Preliminary Report on Patentability, International Application No. PCT/US2009/48389, mail date Jan. 13, 2011.
International Search Report, International Application No. PCT/US2009/003650 (Oct. 9, 2009).
Written Opinion of the International Searching Authority, International Application No. PCT/US2009/003650 (Oct. 9, 2009).
Notification Concerning Transmittal of International Preliminary Report on Patentability, and International Preliminary Report on Patentability, International Application No. PCT/US2009/003650, mail date Jan. 6, 2011.
International Search Report and Written Opinion of the International Searching Authority, International Application No. PCT/US2010/044568 (Nov. 8, 2010).
Maibaum, J., et al., "Renin Inhibitors as Novel Treatments for Cardiovascular Disease," Expert Opinion on Therapeutic Patents, vol. 13, No. 5, pp. 589-603 (2003).
Moffett, R.B., "New Compounds with Possible Pharmacological Activity," Journal of Chemical and Engineering Data, vol. 25, No. 2, pp. 176-183 (1980).
Whitehead, C.W., "The Synthesis of 5-Carbethoxyuracils," Journal of the American Chemical Society, vol. 74, pp. 4267-4271 (1952).
Garrigues, B., et al., "Synthèse de 2-tert-butylthiophènes substitùes en position 5," Bulletin De La Societe Chimique De France, vol. 130, No. 1, pp. 58-63 (1993).
Schultz O.E., et al., "Pyridine and quinoline analogues of procaine and procainamide," Arzneimittel-Forschung, vol. 22, No. 7, pp. 1117-1120 (1972).
Praly-Deprez, I., et al., "Synthesis of 11-amino-substituted-5,6-dimethyl-5H-pyrido[3',4':4,5]pyrrolo-[2,3-g]isoquinolines as New Ellipticine Analogues," Journal of the Chemical Society, Perkin Transactions 1., No. 12, pp. 3173-3175 (1991).
Database Beilstein XP002366304, Database Accession No. 7588231, 4-(2,2-dimethoxypropyl)-N-(2-hydroxyethyl) benzamide & Angewandte Chemie, Wiley-VCH, Weinheim, vol. 108, No. 22, pp. 2800-2802 (1996).
International Search Report, International Application No. PCT/US2006/043920 (for WO/2007/070201) (Mar. 20, 2007).
Written Opinion of the International Searching Authority, International Application No. PCT/US2006/043920 (for WO/2007/070201) (Mar. 20, 2007).
International Search Report, International Application No. PCT/US2005/036230 (for WO/2006/042150) (Feb. 20, 2006).

Written Opinion of the International Searching Authority, International Application No. PCT/US2005/036230 (for WO/2006/042150) (Feb. 20, 2006).

International Search Report, International Application No. PCT/US2007/020164 (for WO/2008/036247) (Dec. 28, 2007).

Written Opinion of the International Searching Authority, International Application No. PCT/US2007/020164 (for WO/2008/036247) (Dec. 28, 2007).

International Search Report, International Application No. PCT/US2007/020086 (for WO/2008/036216) (Feb. 5, 2008).

Written Opinion of the International Searching Authority, International Application No. PCT/US2007/020086 (for WO/2008/036216) (Feb. 5, 2008).

Bhanuprakash K., et al., "Computational Design of New Cyclic Urea Inhibitors for Improved Binding of HIV-1 Aspartic Protease," *Biochemical and Biophysical Research Communications*, 268(2): 384-389 (2000).

Restriction Requirement from U.S. Patent Office, U.S. Appl. No. 12/311,020, Dated: Jun. 3, 2011.

Restriction Requirement from U.S. Patent Office, U.S. Appl. No. 12/311,012, Dated: Jun. 24, 2011.

Restriction Requirement Office Action from U.S. Patent Office, U.S. Appl. No. 12/665,213, Dated: Jun. 24, 2011.

Office Action from U.S. Patent Office, U.S. Appl. No. 12/311,012, Dated: Aug. 22, 2011.

Office Action from U.S. Patent Office, U.S. Appl. No. 12/311,020, Dated: Aug. 23, 2011.

Notice of Allowance and Fees Due, U.S. Appl. No. 12/665,213, filed Feb. 19, 2010, Date of Notice: Feb. 10, 2012.

Notification Concerning Transmittal of International Preliminary Report on Patentability, International Application No. PCT/US2010/044568, International Filing Date: Aug. 5, 2010, Date of Mailing: Feb. 16, 2012.

Hammond, et al., "Preparation of phenyloxymethylbenzamide derivatives for use as aspartic protease inhibitors," AN 2009:1589830; DN 152:74734, CAPLUS [online],[Retrieved on Mar. 16, 2012]. Retrieved from the Internet URL: https://stnweb.cas.org/cgi-bin/sdegi?SID=753964-0147118521-200&APP=stnweb&.

Notice of Allowance and Fees Due, U.S. Appl. No. 12/311,012, filed Jul. 14, 2009, Date of Notice: Feb. 14, 2012.

Office Communication, U.S. Appl. No. 12/802,142, filed May 28, 2010, Date of Communication: Mar. 19, 2012.

PIPERIDINYL CARBAMATE INTERMEDIATES FOR THE SYNTHESIS OF ASPARTIC PROTEASE INHIBITORS

RELATED APPLICATIONS

This application is the U.S. National Stage of International Application No. PCT/US2006/043920, filed Nov. 13, 2006, published in English, and claims the benefit of U.S. Provisional Application No. 60/736,564, filed on Nov. 14, 2005, U.S. Provisional Application No. 60/845,291, filed on Sep. 18, 2006 and U.S. Provisional Application No. 60/845,331, filed on Sep. 18, 2006. The entire teachings of the above applications are incorporated herein by reference.

BACKGROUND OF THE INVENTION

Aspartic proteases, including renin, β-secretase (BACE), HIV protease, HTLV protease and plasmepsins I and II, are implicated in a number of disease states. In hypertension elevated levels of angiotensin I, the product of renin catalyzed cleavage of angioteninogen are present. Elevated levels of β amyloid, the product of BACE activity on amyloid precursor protein, are widely believed to be responsible for the amyloid plaques present In the brains of Alzheimer's disease patients. The viruses HIV and HTLV depend on their respective aspartic proteases for viral maturation. *Plasmodium falciparum* uses plasmepsins I and II to degrade hemoglobin.

In the renin-angiotensin-aldosterone system (RAAS) the biologically active peptide angiotensin II (Ang II) is generated by a two-step mechanism. The highly specific aspartic protease renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAAS represents a major advance in the treatment of cardiovascular diseases (Zaman, M. A. et al *Nature Reviews Drug Discovery* 2002, 1, 621-636). ACE inhibitors and $AT_1$ blockers have been accepted as treatments of hypertension (Waeber B. et al., "The renin-angiotensin system: role in experimental and human hypertension", in Berkenhager W. H., Reid J. L. (eds): *Hypertension*, Amsterdam, Elsevier Science Publishing Co, 1996, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al, *N Engl. J. Med.*, 1992, 327, 669).

Interest in the development of renin inhibitors stems from the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be bypassed by chymase, a serine protease (Husain A., *J. Hypertens.*, 1993, 11, 1155). In patients, inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the AT1 receptor (e.g., by losartan) on the other hand overexposes other AT-receptor subtypes to Ang II, whose concentration is dramatically increased by the blockade of AT1 receptors. In summary, renin inhibitors are not only expected to be superior to ACE inhibitors and $AT_1$ blockers with regard to safety, but more importantly also with regard to their efficacy in blocking the RAAS.

Only limited clinical experience (Azizi M. et al., *J. Hypertens.*, 1994, 12, 419; Neutel J. M. et al., *Am. Heart*, 1991, 122, 1094) has been generated with renin inhibitors because their peptidomimetic character imparts insufficient oral activity (Kleinert H. D., *Cardiovasc. Drugs*, 1995, 9, 645). The clinical development of several compounds has been stopped because of this problem together with the high cost of goods. It appears as though only one compound has entered clinical trials (Rahuel J. et al., *Chem. Biol.*, 2000, 7, 493; Mealy N. E., *Drugs of the Future*, 2001, 26, 1139). Thus, metabolically stable, orally bioavailable and sufficiently soluble renin inhibitors that can be prepared on a large scale are not available. Recently, the first non-peptide renin inhibitors were described which show high in vitro activity (Oefner C. et al, *Chem. Biol.*, 1999, 6, 127; Patent Application WO 97/09311; Maerki H. P. et al., *Il Farmaco*, 2001, 56, 21). The present invention relates to the unexpected identification of renin inhibitors of a non-peptidic nature and of low molecular weight. Orally active renin inhibitors which are active in indications beyond blood pressure regulation where the tissular renin-chymase system may be activated leading to pathophysiologically altered local functions such as renal, cardiac and vascular remodeling, atherosclerosis, and restenosis, are described.

All documents cited herein are incorporated by reference.

SUMMARY OF THE INVENTION

One embodiment of the invention is an aspartic protease inhibitor represented by Structural Formula (I):

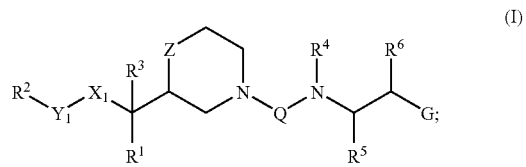

or a pharmaceutically acceptable salt thereof. The variables in Structural Formula (I) are described in the following paragraphs.

Z is —O— or —CH$_2$—.

$X_1$ is a covalent bond, —O—, —S—, —S(O)—, —S(O)$_2$—.

$Y_1$ is a covalent bond or $C_1$-$C_{10}$ alkylene, $C_2$-$C_{10}$ alkenylene or $C_2$-$C_{10}$ alkynylene, each optionally substituted at one or more substitutable carbon atom with halogen, cyano, hydroxyl, ($C_1$-$C_3$)alkyl, ($C_1$-$C_3$)alkoxy or halo($C_1$-$C_3$) alkoxy, provided that $Y_1$ is a covalent bond only when $X_1$ is a covalent bond.

$R^1$ is a) ($C_3$-$C_7$) cycloalkyl; or b) phenyl, heteroaryl, or bicyclic heteroaryl optionally substituted with 1 to 3 groups independently selected from:
  1) fluorine, chlorine, bromine, cyano, nitro, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_7$)cycloalkylalkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, halo($C_2$-$C_6$)alkenyl, halo($C_3$-$C_6$)alkynyl, halo($C_5$-$C_7$)-cycloalkylalkynyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy and ($C_1$-

$C_6$)alkanesulfonyl; or 2) phenyl, heteroaryl, phenoxy, heteroaryloxy, heteroarylthio, phenylthio, heteroarylthio, benzyl, heteroarylmethyl, benzyloxy and heteroarylmethoxy, each optionally substituted with 1 to 3 groups independently selected from: fluorine, chlorine, cyano, ($C_1$-$C_3$)alkyl, halo($C_1$-$C_3$)alkyl, ($C_1$-$C_3$)-alkoxy, halo($C_1$-$C_3$)alkoxy, and aminocarbonyl.

$R^2$ is —OC(O)(NH$_2$), —OC(S)(NH$_2$), —SC(S)(NH$_2$), —SC(O)(NH$_2$), —OC(O)(NHR$^9$), —OC(S)(NHR$^9$), —SC(S)(NHR$^9$), —SC(O)(NHR$^9$), —NHC(O)SR$^9$, —NHC(S)SR$^9$, —NHC(S)OR$^9$, —NHC(O)SR$^9$, —C(O)R$^9$, —C(S)R$^9$, —C(O)(NH$_2$), —C(S)(NH$_2$), —C(O)(NHR$^9$), —C(S)(NHR$^9$) or —NHC(O)H, wherein R$^9$ is a straight or branched $C_1$-$C_5$ alkyl, straight or branched $C_1$-$C_5$ haloalkyl, ($C_3$-$C_4$) cycloalkyl or straight or branched $C_1$-$C_5$ alkoxyalkyl.

$R^3$ is —H, —F, $C_1$-$C_5$ alkyl, —NHC(O)R$^{10}$, —OH or —OR$^{10}$, wherein R$^{10}$ is $C_1$-$C_3$ alkyl, provided that when R$^3$ is —F or —OH, then X$_1$ is not —O—, —S—, —S(O)—, —S(O)$_2$—and R$^2$—Y$_1$—X$_1$ is not —OC(O)(NH$_2$), —OC(S)(NH$_2$), —SC(S)(NH$_2$), —SC(O)(NH$_2$), —OC(O)(NHR$^9$), —OC(S)(NHR$^9$), —SC(S)(NHR$^9$), —SC(O)(NHR$^9$), —NHC(O)OR$^9$, —NHC(S)OR$^9$, —NHC(S)SR$^9$, —NHC(O)SR$^9$ or —NHC(O)H.

Q is Q1, Q2, Q3, Q4, Q5, or Q6:

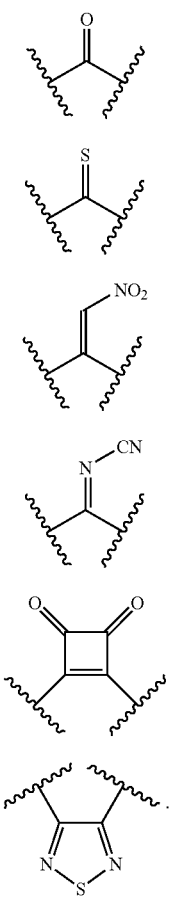

wherein N and N are attached to the truncated bonds $R^4$ is —H or ($C_1$-$C_3$)alkyl.

$R^5$ is a) H, ($C_1$-$C_{10}$)alkyl, ($C_4$-$C_{10}$)cycloalkylalkyl, halo ($C_1$-$C_{10}$)alkyl, hydroxy($C_1$-$C_{10}$)alkyl, halo($C_4$-$C_{10}$)cycloalkylalkyl, hydroxylated ($C_4$-$C_{10}$)cycloalkylalkyl, ($C_1$-$C_2$)alkyl($C_4$-$C_{10}$)cycloalkylalkyl, halogenated ($C_1$-$C_2$)alkyl ($C_4$-$C_{10}$)cycloalkylalkyl, di($C_1$-$C_2$)alkyl($C_4$-$C_{10}$) cycloalkylalkyl, hydroxylated ($C_1$-$C_2$)alkyl($C_4$-$C_{10}$) cycloalkylalkyl, hydroxylated di($C_1$-$C_2$)alkyl($C_4$-$C_{10}$) cycloalkylalkyl, ($C_4$-$C_{10}$)bicycloalkyl($C_1$-$C_3$)alkyl, ($C_8$-$C_{12}$) tricycloalkyl($C_1$-$C_3$)alkyl, ($C_1$-$C_5$)alkoxy($C_1$-$C_5$)alkyl, halo ($C_1$-$C_5$)alkoxy($C_1$-$C_5$)alkyl, ($C_1$-$C_5$)alkylthio($C_1$-$C_5$)alkyl, halo($C_1$-$C_5$)alkylthio($C_1$-$C_5$)alkyl, or saturated heterocyclyl ($C_1$-$C_3$)alkyl; or b) phenyl($C_1$-$C_2$)alkyl, phenoxymethyl, or heteroaryl($C_1$-$C_2$)alkyl each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo($C_1$-$C_3$)alkoxy; and $R^6$ is a) —H, ($C_1$-$C_{10}$)alkyl, ($C_4$-$C_{10}$)cycloalkylalkyl, halo ($C_1$-$C_{10}$)alkyl, hydroxy($C_1$-$C_{10}$)alkyl, halo($C_4$-$C_{10}$)cycloalkylalkyl, hydroxylated ($C_4$-$C_{10}$)cycloalkylalkyl, ($C_1$-$C_2$)alkyl($C_4$-$C_{10}$)cycloalkylalkyl, halogenated ($C_1$-$C_2$)alkyl ($C_4$-$C_{10}$)cycloalkylalkyl, di($C_1$-$C_2$)alkyl($C_4$-$C_{10}$) cycloalkylalkyl, hydroxylated ($C_1$-$C_2$)alkyl($C_4$-$C_{10}$) cycloalkylalkyl, hydroxylated di($C_1$-$C_2$)alkyl($C_4$-$C_{10}$) cycloalkylalkyl, ($C_4$-$C_{10}$)bicycloalkyl($C_1$-$C_3$)alkyl, ($C_8$-$C_{12}$) tricycloalkyl($C_1$-$C_3$)alkyl, ($C_1$-$C_5$)alkoxy($C_1$-$C_5$)alkyl, halo ($C_1$-$C_5$)alkoxy($C_1$-$C_5$)alkyl, ($C_1$-$C_5$)alkylthio($C_1$-$C_8$)alkyl, halo($C_1$-$C_5$)alkylthio($C_1$-$C_5$)alkyl, or saturated heterocyclyl ($C_1$-$C_3$)alkyl; or b) phenyl($C_1$-$C_2$)alkyl, phenoxymethyl or heteroaryl($C_1$-$C_2$)alkyl each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo($C_1$-$C_3$)alkoxy, provided that R$^5$ and R$^6$ are not both —H.

G is OH, NH$_2$ or NHR$^7$.

$R^7$ is a) ($C_1$-$C_6$)alkyl, halo($C_1$-$C_6$)alkyl, ($C_4$-$C_{10}$)cycloalkylalkyl, ($C_1$-$C_5$)alkoxy($C_1$-$C_5$)alkyl, or aminocarbonyl ($C_1$-$C_6$)alkyl or b) phenyl($C_1$-$C_2$)alkyl optionally substituted with 1 to 3 groups independently selected from: fluorine, chlorine, cyano, ($C_1$-$C_3$)alkyl, halo($C_1$-$C_3$)alkyl, ($C_1$-$C_3$) alkoxy, and halo($C_1$-$C_3$)alkoxy; or c) R$^5$ and R$^7$ together are —CH$_2$—, —(CH$_2$)$_2$—, —(CH$_2$)$_3$—, or —(CH$_2$)$_4$—, optionally substituted with 1 or 2 groups independently selected from fluorine, ($C_1$-$C_8$)alkyl, halo($C_1$-$C_8$)alkyl, ($C_3$-$C_6$)cycloalkyl, halo($C_3$-$C_6$)cycloalkyl, hydroxy($C_3$-$C_6$)cycloalkyl, ($C_3$-$C_6$)cycloalkyl($C_1$-$C_2$)alkyl, halo($C_3$-$C_6$)cycloalkyl($C_1$-$C_2$)alkyl, hydroxylated($C_3$-$C_6$)cycloalkyl($C_1$-$C_2$)alkyl, ($C_1$-$C_8$)alkoxy, halo($C_1$-$C_8$)alkoxy, ($C_3$-$C_6$)cycloalkoxy, halo ($C_3$-$C_6$)cycloalkoxy, and heterocyclyl.

Another embodiment of the invention is an aspartic protease inhibitor represented by Structural Formula (I*):

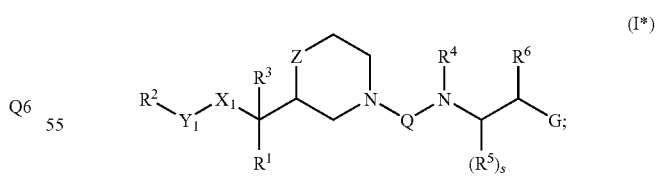

or a pharmaceutically acceptable salt thereof. The variables in Structural Formula (I*) are described in the following paragraphs.

Z is —O— or —(CH$_2$)$_{q7}$, wherein q is 0-3.

X$_1$ is a covalent bond, —O—, —S—, —S(O)—, —S(O)$_2$—.

Y$_1$ is a covalent bond or $C_1$-$C_{10}$ alkylene, $C_2$-$C_{10}$ alkenylene or $C_2$-$C_{10}$ alkynylene, each optionally substituted at one or more substitutable carbon atom with halogen, cyano, nitro, hydroxyl, $(C_1-C_3)$alkyl, $(C_1-C_3)$alkoxy or halo$(C_1-C_3)$ alkoxy, provided that $Y_1$ is a covalent bond only when $X_1$ is a covalent bond.

$R^1$ is $(C_3-C_7)$cycloalkyl, phenyl, heteroaryl, or bicyclic heteroaryl each optionally substituted with 1 to 3 groups independently selected from:

fluorine, chlorine, bromine, cyano, nitro, hydroxyl, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$-cycloalkylalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy and $(C_1-C_6)$alkanesulfonyl; and phenyl, heteroaryl, phenoxy, heteroaryloxy, phenylthio, heteroarylthio, benzyl, heteroarylmethyl, benzyloxy and heteroarylmethoxy, each optionally substituted with 1 to 3 groups independently selected from: fluorine, chlorine, bromine, cyano, nitro, hydroxyl, $(C_1-C_3)$alkyl, halo$(C_1-C_3)$alkyl, $(C_1-C_3)$-alkoxy, halo$(C_1-C_3)$alkoxy, and aminocarbonyl.

$R^2$ is —NHC(=NR$^{12}$)(NH$_2$), —NHC(=NR$^{12}$)(NHR$^9$),

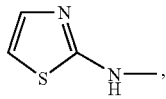

—OC(O)(NH$_2$), —OC(S)(NH$_2$), —SC(S)(NH$_2$), —SC(O)(NH$_2$), —OC(O)(NHR$^9$), —OC(S)(NHR$^9$), —SC(S)(NHR$^9$), —SC(O)(NHR$^9$), —NHC(O)OR$^9$, —NHC(S)SR$^9$, —NHC(S)OR$^9$, —NHC(O)SR$^9$, —C(O)R$^9$, —C(S)R$^9$, —C(O)(NH$_2$), —C(S)(NH$_2$), —C(O)(NHR$^9$), —C(S)(NHR$^9$) or —NHC(O)H, wherein R$^9$ is a straight or branched $C_1$-$C_5$ alkyl, straight or branched $C_1$-$C_5$ haloalkyl, $(C_3$-$C_4)$ cycloalkyl or straight or branched $C_1$-$C_5$ alkoxyalkyl and R$^{12}$ is H, $(C_1$-$C_6)$alkyl, phenyl, heteroaryl, cyano, nitro, —S(O)R$^9$, —S(O$_2$)R$^9$, —S(O$_2$)NHR$^9$, —S(O$_2$)NR$^9$R$^9$, —C(O)R$^9$, —C(S)R$^9$, —C(O)OR$^9$, —C(S)OR$^9$, —C(O)(NH$_2$), —C(O)(NHR$^9$).

$R^3$ is —H, —F, $C_1$-$C_5$ alkyl, —NHC(O)R$^{10}$, —OH or —OR$^{10}$, wherein R$^{10}$ is $C_1$-$C_3$ alkyl, provided that when R$^3$ is —F or —OH, then $X_1$ is not —O—, —S—, —S(O)—, —S(O)$_2$— and R$^2$—Y$_1$—X$_1$ is not —OC(O)(NH$_2$), —OC(S)(NH$_2$), —SC(S)(NH$_2$), —SC(O)(NH$_2$), —OC(O)(NHR$^9$), —OC(S)(NHR$^9$), —SC(S)(NHR$^9$), —SC(O)(NHR$^9$), —NHC(O)OR$^9$, —NHC(S)OR$^9$, —NHC(S)SR$^9$, —NHC(O)SR$^9$ or —NHC(O)H.

Q is Q1, Q2, Q3, Q4, Q5, or Q6:

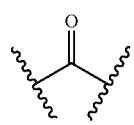

Q1

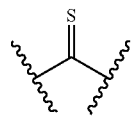

Q2

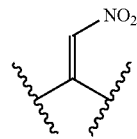

Q3

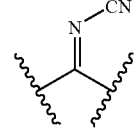

Q4

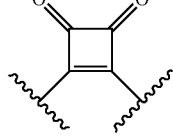

Q5

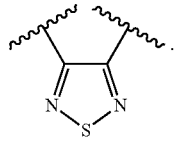

Q6 wherein N and N are attached to the truncated bonds $R^4$ is —H or $(C_1-C_3)$alkyl.

$R^5$ is a) H, $(C_1-C_{10})$alkyl, $(C_4-C_{10})$cycloalkylalkyl, halo$(C_1-C_{10})$alkyl, hydroxy$(C_1-C_{10})$alkyl, halo$(C_4-C_{10})$cycloalkylalkyl, hydroxylated $(C_4-C_{10})$cycloalkylalkyl, $(C_1-C_2)$alkyl$(C_4-C_{10})$cycloalkylalkyl, halogenated $(C_1-C_2)$alkyl $(C_4-C_{10})$cycloalkylalkyl, di$(C_1-C_2)$alkyl$(C_4-C_{10})$cycloalkylalkyl, hydroxylated $(C_1-C_2)$alkyl$(C_4-C_{10})$cycloalkylalkyl, hydroxylated di$(C_1-C_2)$alkyl$(C_4-C_{10})$cycloalkylalkyl, $(C_4-C_{10})$bicycloalkyl$(C_1-C_3)$alkyl, $(C_8-C_{12})$tricycloalkyl$(C_1-C_3)$alkyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$alkylthio$(C_1-C_5)$alkyl, or saturated heterocyclyl $(C_1-C_3)$alkyl optionally substituted with 1 to 3 groups independently selected from fluorine, chlorine, bromine, cyano, nitro, hydroxyl, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$-cycloalkylalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkanesulfonyl and aminocarbonyl; or b) phenyl$(C_1-C_2)$alkyl, phenoxymethyl, or heteroaryl$(C_1-C_2)$alkyl each optionally substituted with 1 to 3 groups independently selected from fluorine, chlorine, bromine, cyano, nitro, hydroxyl, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$-cycloalkylalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkanesulfonyl and aminocarbonyl wherein s is 1 or 2.

$R^6$ is a) —H, $(C_1-C_{10})$alkyl, $(C_4-C_{10})$cycloalkylalkyl, halo$(C_1-C_{10})$alkyl, hydroxy$(C_1-C_{10})$alkyl, halo$(C_4-C_{10})$cycloalkylalkyl, hydroxylated $(C_4-C_{10})$cycloalkylalkyl, $(C_1-C_2)$alkyl$(C_4-C_{10})$cycloalkylalkyl, halogenated $(C_1-C_2)$alkyl $(C_4-C_{10})$cycloalkylalkyl, di$(C_1-C_2)$alkyl$(C_4-C_{10})$cycloalkylalkyl, hydroxylated $(C_1-C_2)$alkyl$(C_4-C_{10})$cycloalkylalkyl, hydroxylated di$(C_1-C_2)$alkyl$(C_4-C_{10})$cycloalkylalkyl, $(C_4-C_{10})$bicycloalkyl$(C_1-C_3)$alkyl, $(C_8-C_{12})$tricycloalkyl$(C_1-C_3)$alkyl, $(C_1-C_5)$alkoxy$(C_1-C_5)$alkyl, halo$(C_1-C_5)$alkoxy$(C_1-C_5)$alkyl, $(C_1-C_5)$alkylthio$(C_1-C_5)$alkyl, halo$(C_1-C_5)$alkylthio$(C_1-C_5)$alkyl, or saturated heterocyclyl $(C_1-C_3)$alkyl optionally substituted with 1 to 3 groups independently selected from fluorine, chlorine, bromine, cyano, nitro, hydroxyl, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$cycloalkylalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkanesulfonyl and aminocarbonyl; or b) phenyl$(C_1-C_2)$alkyl, phenoxymethyl or heteroaryl$(C_1-C_2)$alkyl each optionally substituted with 1 to 3 groups independently selected from fluorine, chlorine, bromine, cyano, nitro, hydroxyl, $(C_1-C_6)$alkyl, $(C_3-C_6)$cycloalkyl, $(C_4-C_7)$cycloalkylalkyl, $(C_2-C_6)$alkenyl, $(C_5-C_7)$cycloalkylalkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, halo$(C_2-C_6)$alkenyl, halo$(C_3-C_6)$alkynyl, halo$(C_5-C_7)$cycloalkylalkynyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkanesulfonyl and aminocarbonyl provided that $R^5$ and $R^6$ are not both —H.

G is OH, $NH_2$ or $NHR^7$.

$R^7$ is a) $(C_1-C_6)$alkyl, halo$(C_1-C_6)$alkyl, $(C_4-C_{10})$cycloalkylalkyl, $(C_1-C_5)$alkoxy$(C_1-C_5)$alkyl, or aminocarbonyl $(C_1-C_6)$alkyl or b) phenyl$(C_1-C_2)$alkyl optionally substituted with 1 to 3 groups independently selected from: fluorine, chlorine, cyano, $(C_1-C_3)$alkyl, halo$(C_1-C_3)$alkyl, $(C_1-C_3)$alkoxy, and halo$(C_1-C_3)$alkoxy; or c) $R^5$ and $R^7$ together are —$CH_2$—, —$(CH_2)_2$—, —$(CH_2)_3$—, or —$(CH_2)_4$—, optionally substituted with 1 or 2 groups independently selected from fluorine, $(C_1-C_8)$alkyl, halo$(C_1-C_8)$alkyl, $(C_3-C_6)$cycloalkyl, halo$(C_3-C_6)$cycloalkyl, hydroxy$(C_3-C_6)$cycloalkyl, $(C_3-C_6)$cycloalkyl$(C_1-C_2)$alkyl, halo$(C_3-C_6)$cycloalkyl$(C_1-C_2)$alkyl, hydroxylated$(C_3-C_6)$cycloalkyl$(C_1-C_2)$alkyl, $(C_1-C_8)$alkoxy, halo$(C_1-C_8)$alkoxy, $(C_3-C_6)$cycloalkoxy, halo $(C_3-C_6)$cycloalkoxy, and heterocyclyl.

Another embodiment of the invention is a pharmaceutical composition comprising a pharmaceutically acceptable carrier or diluent and an aspartic protease inhibitor disclosed herein (e.g., a compound represented by Structural Formula (I), Structural Formula (I*) or a pharmaceutically acceptable salt thereof). The pharmaceutical composition is used in therapy, e.g., for inhibiting an aspartic protease mediated disorder in a subject.

Another embodiment of the invention is a method of antagonizing one or more aspartic proteases in a subject in need of such treatment. The method comprises administering to the subject an effective amount of an aspartic protease inhibitor disclosed herein (e.g., a compound represented by Structural Formula (I), Structural Formula (I*) or a pharmaceutically acceptable salt thereof).

Another embodiment of the invention is a method of treating an aspartic protease mediated disorder in a subject. The method comprises administering to the subject an effective amount of an aspartic protease inhibitor disclosed herein (e.g., a compound represented by Structural Formula (I), Structural Formula (I*) or a pharmaceutically acceptable salt thereof).

Another embodiment of the invention is the use of an aspartic protease inhibitor disclosed herein (e.g., a compound represented by Structural Formula (I), Structural Formula (I*) or a pharmaceutically acceptable salt thereof)) for the manufacture of a medicament for antagonizing one or more aspartic proteases in a subject in need of such treatment.

Another embodiment of the invention is the use of an aspartic protease inhibitor disclosed herein (e.g., a compound represented by Structural Formula (I), Structural Formula (I*) or a pharmaceutically acceptable salt thereof)) for the manufacture of a medicament for treating an aspartic protease mediated disorder in a subject.

BRIEF DESCRIPTION OF THE DRAWINGS

FIG. 2 is a plot showing mean plasma concentrations of compound L-6a in transgenic rats over time following oral administration of 10 mg/kg of compound L-6a.

FIG. 3 is a plot showing changes in mean arterial blood pressures of transgenic rats treated with 10 mg/kg of compound L-6a.

FIG. 4 is an x-ray powder diffraction pattern obtained from a sample of the tartrate salt of compound L-6a

DETAILED DESCRIPTION OF THE INVENTION

Figure 1:
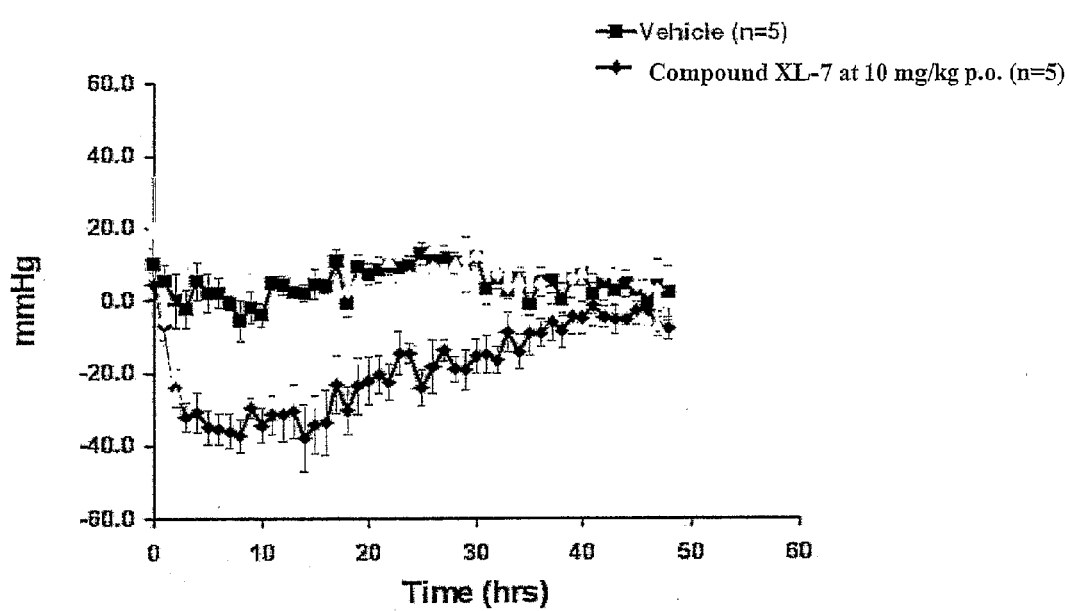
FIG. 1 is a plot showing changes in mean arterial blood pressures of transgenic rats treated with 10 mg/kg of compound XL-7.

The invention is directed to an aspartic protease inhibitor represented by Structural Formula (I), Structural Formula (I*) or a pharmaceutically acceptable salt thereof. Values and particular values for the variables in Structural Formula (I) and Structural Formula (I*) are provided in the following paragraphs. For Structural Formula I:

Z is —O— or —$CH_2$—. In a particular embodiment, Z is —$CH_2$—.

$X_1$ is a covalent bond, —O—, —S—, —S(O)—, —S(O)$_2$—. In a particular embodiment, $X_1$ is a covalent bond or —O—.

$Y_1$ is a covalent bond or $C_1-C_{10}$ alkylene, $C_2-C_{10}$ alkenylene or $C_2-C_{10}$ alkynylene, each optionally substituted at one or more substitutable carbon atoms with halogen, cyano, hydroxyl, $(C_1-C_3)$alkyl, $(C_1-C_3)$alkoxy or halo$(C_1-C_3)$alkoxy, provided that $Y_1$ is a covalent bond only when $X_1$ is a covalent bond. In a particular embodiment, $Y_1$ is $C_1-C_5$ alkylene optionally substituted at a substitutable carbon atom with halogen, cyano, hydroxyl, methyl, methoxy, halo$(C_1-C_3)$ methoxy. More particularly, $Y_1$ is $(C_1-C_2)$alkylene when $X_1$ is O or $Y_1$ is $(C_2-C_3)$alkylene when $X_1$ is a covalent bond.

$R^1$ is a) $(C_3-C_7)$cycloalkyl; or b) phenyl, heteroaryl, or bicyclic heteroaryl optionally substituted with 1 to 3 independently selected groups represented by $R^{11}$. In a particular embodiment, $R^1$ is phenyl optionally substituted with 1 to 3 independently selected groups represented by $R^{11}$.

$R^2$ is —OC(O)($NH_2$), —OC(S)($NH_2$), —SC(S)($NH_2$), —SC(O)($NH_2$), —OC(O)($NHR^9$), —OC(S)($NHR^9$), —SC(S)($NHR^9$), —SC(O)($NHR^9$), —NHC(O)$OR^9$, —NHC(S)$SR^9$, —NHC(S)$OR^9$, —NHC(O)$SR^9$, —C(O)$R^9$, —C(S)$R^9$, —C(O)($NH_2$), —C(S)($NH_2$), —C(O)($NHR^9$), —C(S)($NHR^9$) or —NHC(O)H. In a particular embodiment, $R^2$ is —OC(O)($NHR^9$), —NHC(O)$OR^9$, —C(O)$R^9$, —C(O)($NHR^9$) or —NHC(O)H.

$R^3$ is —H, —F, $C_1$-$C_5$ alkyl, —NHC(O)$R^{10}$, —OH or —O$R^{10}$, wherein $R^{10}$ is $C_1$-$C_3$ alkyl, provided that when $R^3$ is —F or —OH, then $X_1$ is not —O—, —S—, —S(O)—, —S(O)$_2$— and $R^2$—$Y_1$—$X_1$ is not —OC(O)(NH$_2$), —OC(S)(NH$_2$), —SC(S)(NH$_2$), —SC(O)(NH$_2$), —OC(O)(NHR$^9$), —OC(S)(NHR$^9$), —SC(S)(NHR$^9$), —SC(O)(NHR$^9$), —NHC(O)OR$^9$, —NHC(S)OR$^9$, —NHC(S)SR$^9$, —NHC(O)SR$^9$ or —NHC(O)H. In a particular embodiment, $R^3$ is —H, —NHC(O)$R^{10}$ or —OH.

Q is Q1, Q2, Q3, Q4, Q5, or Q6:

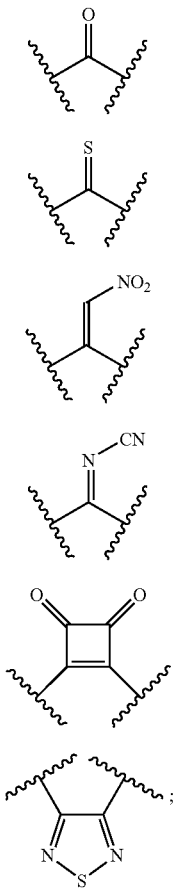

wherein N and N are attached to the truncated bonds

In a particular embodiment, Q is Q1 or Q2. More particularly, Q is Q1.

$R^5$ and $R^6$ are independently: a) H, ($C_1$-$C_{10}$)alkyl, ($C_4$-$C_{10}$)cycloalkylalkyl, halo($C_1$-$C_{10}$)alkyl, hydroxy($C_1$-$C_{10}$)alkyl, halo($C_4$-$C_{10}$)cycloalkylalkyl, hydroxylated ($C_4$-$C_{10}$)cycloalkylalkyl, ($C_1$-$C_2$)alkyl($C_4$-$C_{10}$)cycloalkylalkyl, halogenated ($C_1$-$C_2$)alkyl($C_4$-$C_{10}$)cycloalkylalkyl, di($C_1$-$C_2$)alkyl ($C_4$-$C_{10}$)cycloalkylalkyl, halogenated ($C_1$-$C_2$)alkyl($C_4$-$C_{10}$)cycloalkylalkyl, di($C_1$-$C_2$)alkyl($C_4$-$C_{10}$)cycloalkylalkyl, hydroxylated ($C_1$-$C_2$)alkyl($C_4$-$C_{10}$)cycloalkylalkyl, hydroxylated di($C_1$-$C_2$)alkyl($C_4$-$C_{10}$)cycloalkylalkyl, ($C_4$-$C_{10}$)bicycloalkyl($C_1$-$C_3$)alkyl, ($C_8$-$C_{12}$)tricycloalkyl($C_1$-$C_3$) alkyl, ($C_1$-$C_5$)alkoxy($C_1$-$C_5$)alkyl, halo($C_1$-$C_5$)alkoxy($C_1$-$C_5$)alkyl, ($C_1$-$C_5$)alkylthio($C_1$-$C_5$)alkyl, halo($C_1$-$C_5$)alkylthio($C_1$-$C_5$)alkyl, or saturated heterocyclyl($C_1$-$C_3$)alkyl; or b) phenyl($C_1$-$C_2$)alkyl, phenoxymethyl or heteroaryl ($C_1$-$C_2$)alkyl each optionally substituted with 1 to 3 groups independently selected from fluorine, chlorine, cyano, ($C_1$-$C_3$)alkyl, halo($C_1$-$C_3$)alkyl, ($C_1$-$C_3$)alkoxy, and halo($C_1$-$C_3$)alkoxy, provided that $R^5$ and $R^6$ are not both —H. In a particular embodiment, one of $R^5$ and $R^6$ is —H or methyl and the other is as just described. More particularly, $R^5$ is as just described and $R^6$ is —H or methyl. Alternatively, $R^5$ and $R^6$ are independently ($C_1$-$C_7$)alkyl, halo($C_1$-$C_7$)alkyl, hydroxy($C_1$-$C_7$)alkyl, cyclohexylmethyl, 2-(cyclohexyl)ethyl, halocyclohexylmethyl, hydroxylated cyclohexylmethyl, ($C_1$-$C_2$) alkyl cyclohexylmethyl, di($C_1$-$C_2$)alkyl cyclohexylmethyl, hydroxylated ($C_1$-$C_2$)alkyl cyclohexylmethyl, hydroxylated di($C_1$-$C_2$)alkylcyclohexylmethyl, (3-noradamantyl)methyl or (tetrahydropyranyl)methyl. In a particular embodiment, one of $R^5$ and $R^6$ is —H or methyl and the other is as just described. More particularly, $R^5$ is as just described and $R^6$ is —H or methyl. Alternatively, $R^5$ and $R^6$ are independently ($C_1$-$C_4$)alkyl, halo($C_1$-$C_4$)alkyl, hydroxy($C_1$-$C_4$)alkyl, cyclohexylmethyl, halocyclohexylmethyl or hydroxylated cyclohexylmethyl. In a particular embodiment, one of $R^5$ and $R^6$ is —H or methyl and the other is as just described. More particularly, $R^5$ is as just described and $R^6$ is —H or methyl.

G is —OH, —NH$_2$ or —NHR$^7$. In a particular embodiment, G is NH$_2$ or NHR$^7$.

$R^7$ is a) ($C_1$-$C_6$)alkyl, halo($C_1$-$C_6$)alkyl, ($C_4$-$C_{10}$)cycloalkylalkyl, ($C_1$-$C_5$)alkoxy($C_1$-$C_5$)alkyl, or aminocarbonyl ($C_1$-$C_6$)alkyl or b) phenyl($C_1$-$C_2$)alkyl optionally substituted with 1 to 3 groups independently selected from: fluorine, chlorine, cyano, ($C_1$-$C_3$)alkyl, halo($C_1$-$C_3$)alkyl, ($C_1$-$C_3$) alkoxy, and halo($C_1$-$C_3$)alkoxy; or c) $R^5$ and $R^7$ together are —CH$_2$—, —(CH$_2$)$_2$—, —(CH$_2$)$_3$—, or —(CH$_2$)$_4$—, optionally substituted with 1 or 2 groups independently selected from fluorine, ($C_1$-$C_8$)alkyl, halo($C_1$-$C_8$)alkyl, ($C_3$-$C_6$)cycloalkyl, halo($C_3$-$C_6$)cycloalkyl, hydroxy($C_3$-$C_6$)cycloalkyl, ($C_3$-$C_6$)cycloalkyl($C_1$-$C_2$)alkyl, halo($C_3$-$C_6$)cycloalkyl($C_1$-$C_2$)alkyl, hydroxylated($C_3$-$C_6$)cycloalkyl($C_1$-$C_2$)alkyl, ($C_1$-$C_8$)alkoxy, halo($C_1$-$C_8$)alkoxy, ($C_3$-$C_6$)cycloalkoxy, halo ($C_3$-$C_6$)cycloalkoxy, and heterocyclyl. In a particular embodiment, $R^7$ is methyl or $R^5$ and $R^7$ together are —(CH$_2$)$_3$— optionally substituted with $C_1$-$C_4$ alkyl or cyclohexyl.

$R^9$ is a straight or branched $C_1$-$C_5$ alkyl, straight or branched $C_1$-$C_5$ haloalkyl, ($C_3$-$C_4$)cycloalkyl or straight or branched $C_1$-$C_5$ alkoxyalkyl. In a particular embodiment, $R^9$ is a straight $C_1$-$C_5$ alkyl, straight or branched $C_1$-$C_5$ haloalkyl. In another particular embodiment, $R^9$ is methyl or ethyl.

$R^{11}$ is 1) fluorine, chlorine, bromine, cyano, nitro, ($C_1$-$C_6$) alkyl, ($C_3$-$C_6$)cycloalkyl, ($C_4$-$C_7$)cycloalkylalkyl, ($C_2$-$C_6$)alkenyl, ($C_5$-$C_7$)cycloalkylalkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, halo($C_2$-$C_6$)alkenyl, halo($C_3$-$C_6$)alkynyl, halo($C_5$-$C_7$)-cycloalkylalkynyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy and ($C_1$-$C_6$)alkanesulfonyl; or 2) phenyl, heteroaryl, phenoxy, heteroaryloxy, phenylthio, heteroarylthio, benzyl, heteroarylmethyl, benzyloxy and heteroarylmethoxy, each optionally substituted with 1 to 3 groups independently selected from: fluorine, chlorine, cyano, ($C_1$-$C_3$)alkyl, halo($C_1$-$C_3$)alkyl, ($C_1$-$C_3$)-alkoxy, halo($C_1$-$C_3$)alkoxy, and aminocarbonyl. In a particular embodiment, $R^{11}$ is chloro, fluoro or methyl.

In a particular embodiment, when $R^5$ and $R^7$ together with their intervening atoms form a ring or when G is hydroxy, $R^2$ is —OC(O)(NH$_2$), —OC(S)(NH$_2$), —SC(S)(NH$_2$), —SC(O)(NH$_2$), —OC(O)(NHR$^9$), —OC(S)(NHR$^9$), —SC(S)(NHR$^9$), —SC(O)(NHR$^9$), —NHC(O)OR$^9$, —NHC(S)SR$^9$, —NHC(S)OR⁹, —NHC(O)SR⁹, or —C(S)(NH₂), wherein R⁹ is a straight or branched $C_1$-$C_5$ alkyl, straight or branched $C_1$-$C_5$ haloalkyl, ($C_3$-$C_4$)cycloalkyl or straight or branched $C_1$-$C_5$ alkoxyalkyl.

For Structural Formula (I*):

Z is —O— or —(CH₂)$_q$—, wherein q is 0-3.

$X_1$ is a covalent bond, —O—, —S—, —S(O)—, —S(O)₂—.

$Y_1$ is a covalent bond or $C_1$-$C_{10}$ alkylene, alkenylene or $C_2$-$C_{10}$ alkynylene, each optionally substituted at one or more substitutable carbon atom with halogen, cyano, nitro, hydroxyl, ($C_1$-$C_3$)alkyl, ($C_1$-$C_3$)alkoxy or halo($C_1$-$C_3$) alkoxy, provided that $Y_1$ is a covalent bond only when $X_1$ is a covalent bond.

R¹ is ($C_3$-$C_7$)cycloalkyl, phenyl, heteroaryl, or bicyclic heteroaryl each optionally substituted with 1 to 3 groups independently selected from:

fluorine, chlorine, bromine, cyano, nitro, hydroxyl, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_7$)cycloalkylalkenyl, ($C_2$-$C_6$) alkynyl, ($C_3$-$C_6$)cycloalkyl($C_2$-$C_4$)alkynyl, halo($C_1$-$C_6$) alkyl, halo($C_3$-$C_6$)cycloalkyl, halo($C_4$-$C_7$)cycloalkylalkyl, halo($C_2$-$C_6$)alkenyl, halo($C_3$-$C_6$)alkynyl, halo($C_5$-$C_7$)-cycloalkylalkynyl, ($C_1$-$C_6$)alkoxy, ($C_3$-$C_6$) cycloalkoxy, ($C_4$-$C_7$)cycloalkylalkoxy, halo($C_1$-$C_6$) alkoxy, halo($C_3$-$C_6$)cycloalkoxy, halo($C_4$-$C_7$) cycloalkylalkoxy and ($C_1$-$C_6$)alkanesulfonyl; and phenyl, heteroaryl, phenoxy, heteroaryloxy, phenylthio, heteroarylthio, benzyl, heteroarylmethyl, benzyloxy and heteroarylmethoxy, each optionally substituted with 1 to 3 groups independently selected from: fluorine, chlorine, bromine, cyano, nitro, hydroxyl, ($C_1$-$C_3$)alkyl, halo($C_1$-$C_3$)alkyl, ($C_1$-$C_3$)-alkoxy, and halo($C_1$-$C_3$) alkoxy, and aminocarbonyl.

R² is —NHC(=NR¹²)(NH₂), —NHC(=NR¹²)(NHR⁹),

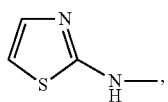

—OC(O)(NH₂), —OC(S)(NH₂), —SC(S)(NH₂), —SC(O)(NH₂), —OC(O)(NHR⁹), —OC(S)(NHR⁹), —SC(S)(NHR⁹), —SC(O)(NHR⁹), —NHC(O)OR⁹, —NHC(S)SR⁹, —NHC(S)OR⁹, —NHC(O)SR⁹, —C(O)R⁹, —C(S)R⁹, —C(O)(NH₂), —C(S)(NH₂), —C(O)(NHR⁹), —C(S)(NHR⁹) or —NHC(O)H, wherein R⁹ is a straight or branched $C_1$-$C_5$ alkyl, straight or branched $C_1$-$C_5$ haloalkyl, ($C_3$-$C_4$) cycloalkyl or straight or branched $C_1$-$C_5$ alkoxyalkyl and R¹² is H, ($C_1$-$C_6$)alkyl, phenyl, heteroaryl, cyano, nitro, —S(O)R⁹'—S(O₂)R⁹, —S(O₂)NHR⁹, —S(O₂)NR⁹R⁹, —C(O)R⁹, —C(S)R⁹, —C(O)OR⁹, —C(S)OR⁹, —C(O)(NH₂), —C(O)(NHR⁹).

R³ is —H, —F, $C_1$-$C_5$ alkyl, —NHC(O)R¹⁰, —OH or —OR¹⁰, wherein R¹⁰ is $C_1$-$C_3$ alkyl, provided that when R³ is —F or —OH, then $X_1$ is not —O—, —S—, —S(O)—, —S(O)₂— and R²—$Y_1$—$X_1$ is not —OC(O)(NH₂), —OC(S)(NH₂), —SC(S)(NH₂), —SC(O)(NH₂), —OC(O)(NHR⁹), —OC(S)(NHR⁹), —SC(S)(NHR⁹), —SC(O)(NHR⁹), —NHC(O)OR⁹, —NHC(S)OR⁹, —NHC(S)SR⁹, —NHC(O)SR⁹ or —NHC(O)H.

Q is Q1, Q2, Q3, Q4, Q5, or Q6:

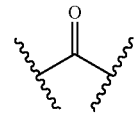
Q1

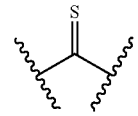
Q2

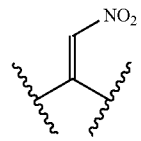
Q3

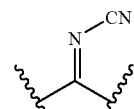
Q4

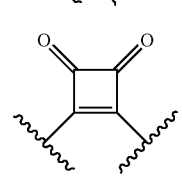
Q5

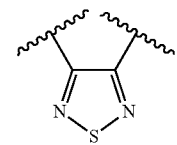
Q6 wherein N and N are attached to the truncated bonds

R⁴ is —H or ($C_1$-$C_3$)alkyl.

R⁵ is a) H, ($C_1$-$C_{10}$)alkyl, ($C_4$-$C_{10}$)cycloalkylalkyl, halo($C_1$-$C_{10}$)alkyl, hydroxy($C_1$-$C_{10}$)alkyl, halo($C_4$-$C_{10}$)cycloalkylalkyl, hydroxylated ($C_4$-$C_{10}$)cycloalkylalkyl, ($C_1$-$C_2$)alkyl($C_4$-$C_{10}$)cycloalkylalkyl, halogenated ($C_1$-$C_2$)alkyl ($C_4$-$C_{10}$)cycloalkylalkyl, di($C_1$-$C_2$)alkyl($C_4$-$C_{10}$)cycloalkylalkyl, hydroxylated ($C_1$-$C_2$)alkyl($C_4$-$C_{10}$)cycloalkylalkyl, hydroxylated di($C_1$-$C_2$)alkyl($C_4$-$C_{10}$)cycloalkylalkyl, ($C_4$-$C_{10}$)bicycloalkyl($C_1$-$C_3$)alkyl, ($C_8$-$C_{12}$) tricycloalkyl($C_1$-$C_3$)alkyl, ($C_1$-$C_5$)alkoxy($C_1$-$C_5$)alkyl, halo($C_1$-$C_5$)alkoxy($C_1$-$C_5$)alkyl, ($C_1$-$C_5$)alkylthio($C_1$-$C_5$)alkyl, halo($C_1$-$C_5$)alkylthio($C_1$-$C_5$)alkyl, or saturated heterocyclyl ($C_1$-$C_3$)alkyl optionally substituted with 1 to 3 groups independently selected from fluorine, chlorine, bromine, cyano, nitro, hydroxyl, ($C_1$-$C_6$)alkyl, ($C_3$-$C_6$)cycloalkyl, ($C_4$-$C_7$)cycloalkylalkyl, ($C_2$-$C_6$)alkenyl, ($C_5$-$C_7$)cycloalkylalkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, halo($C_2$-$C_6$)alkenyl, halo($C_3$-$C_6$)alkynyl, halo($C_5$-$C_7$)-cycloalkylalkynyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$) cycloalkoxy, halo($C_4$-$C_7$)cycloalkylalkoxy, ($C_1$-$C_6$) alkanesulfonyl and aminocarbonyl; or b) phenyl($C_1$-$C_2$) alkyl, phenoxymethyl, or heteroaryl($C_1$-$C_2$)alkyl each optionally substituted with 1 to 3 groups independently selected from fluorine, chlorine, bromine, cyano, nitro, hydroxyl, ($C_1$-$C_6$)alkyl, ($C_3$-$C_6$)cycloalkyl, ($C_4$-$C_7$)cycloalkylalkyl, (C$_2$-C$_6$)alkenyl, (C$_5$-C$_7$)cycloalkylalkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, halo(C$_2$-C$_6$)alkenyl, halo(C$_3$-C$_6$)alkynyl, halo(C$_5$-C$_7$)cycloalkylalkynyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkanesulfonyl and aminocarbonyl wherein s is 1 or 2.

R$^6$ is a) —H, (C$_1$-C$_{10}$)alkyl, (C$_4$-C$_{10}$)cycloalkylalkyl, halo (C$_1$-C$_{10}$)alkyl, hydroxy(C$_1$-C$_{10}$)alkyl, halo(C$_4$-C$_{10}$)cycloalkylalkyl, hydroxylated (C$_4$-C$_{10}$)cycloalkylalkyl, (C$_1$-C$_2$)alkyl(C$_4$-C$_{10}$)cycloalkylalkyl, halogenated (C$_1$-C$_2$)alkyl (C$_4$-C$_{10}$)cycloalkylalkyl, di(C$_1$-C$_2$)alkyl(C$_4$-C$_{10}$)cycloalkylalkyl, hydroxylated (C$_1$-C$_2$)alkyl(C$_4$-C$_{10}$)cycloalkylalkyl, hydroxylated di(C$_1$-C$_2$)alkyl(C$_4$-C$_{10}$)cycloalkylalkyl, (C$_4$-C$_{10}$)bicycloalkyl(C$_1$-C$_3$)alkyl, (C$_8$-C$_{12}$)tricycloalkyl(C$_1$-C$_3$)alkyl, (C$_1$-C$_5$)alkoxy(C$_1$-C$_5$)alkyl, halo (C$_1$-C$_5$)alkoxy(C$_1$-C$_5$)alkyl, (C$_1$-C$_5$)alkylthio(C$_1$-C$_5$)alkyl, halo(C$_1$-C$_5$)alkylthio(C$_1$-C$_8$)alkyl, or saturated heterocyclyl (C$_1$-C$_3$)alkyl optionally substituted with 1 to 3 groups independently selected from fluorine, chlorine, bromine, cyano, nitro, hydroxyl, (C$_1$-C$_6$)alkyl, (C$_3$-C$_6$)cycloalkyl, (C$_4$-C$_7$)cycloalkylalkyl, (C$_2$-C$_6$)alkenyl, (C$_5$-C$_7$)cycloalkylalkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, halo(C$_2$-C$_6$)alkenyl, halo(C$_3$-C$_6$)alkynyl, halo(C$_5$-C$_7$)cycloalkylalkynyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkanesulfonyl and aminocarbonyl; or b) phenyl(C$_1$-C$_2$)alkyl, phenoxymethyl or heteroaryl(C$_1$-C$_2$)alkyl each optionally substituted with 1 to 3 groups independently selected from fluorine, chlorine, bromine, cyano, nitro, hydroxyl, (C$_1$-C$_6$)alkyl, (C$_3$-C$_6$)cycloalkyl, (C$_4$-C$_7$)cycloalkylalkyl, (C$_2$-C$_6$)alkenyl, (C$_5$-C$_7$)cycloalkylalkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, halo(C$_2$-C$_6$)alkenyl, halo(C$_3$-C$_6$)alkynyl, halo(C$_5$-C$_7$)cycloalkylalkynyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkanesulfonyl and aminocarbonyl provided that R$^5$ and R$^6$ are not both —H.

G is OH, NH$_2$ or NHR$^7$.

R$^7$ is a) (C$_1$-C$_6$)alkyl, halo(C$_1$-C$_6$)alkyl, (C$_4$-C$_{10}$)cycloalkylalkyl, (C$_1$-C$_5$)alkoxy(C$_1$-C$_5$)alkyl, or aminocarbonyl (C$_1$-C$_6$)alkyl or b) phenyl(C$_1$-C$_2$)alkyl optionally substituted with 1 to 3 groups independently selected from: fluorine, chlorine, cyano, (C$_1$-C$_3$)alkyl, halo(C$_1$-C$_3$)alkyl, (C$_1$-C$_3$)alkoxy, and halo(C$_1$-C$_3$)alkoxy; or c) R$^5$ and R$^7$ together are —CH$_2$—, —(CH$_2$)$_2$—, —(CH$_2$)$_3$—, or —(CH$_2$)$_4$—, optionally substituted with 1 or 2 groups independently selected from fluorine, (C$_1$-C$_8$)alkyl, halo(C$_1$-C$_8$)alkyl, (C$_3$-C$_6$)cycloalkyl, halo(C$_3$-C$_6$)cycloalkyl, hydroxy(C$_3$-C$_6$)cycloalkyl, (C$_3$-C$_6$)cycloalkyl(C$_1$-C$_2$)alkyl, halo(C$_3$-C$_6$)cycloalkyl(C$_1$-C$_2$)alkyl, hydroxylated(C$_3$-C$_6$)cycloalkyl(C$_1$-C$_2$)alkyl, (C$_1$-C$_8$)alkoxy, halo(C$_1$-C$_8$)alkoxy, (C$_3$-C$_6$)cycloalkoxy, halo (C$_3$-C$_6$)cycloalkoxy, and heterocyclyl.

In a particular embodiment, when R$^5$ and R$^7$ together with their intervening atoms form a ring or when G is hydroxy, R$^2$ is —NHC(=NR$^{12}$)(NH$_2$), —NHC(=NR$^{12}$)(NHR$^9$),

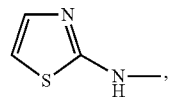

—OC(O)(NH$_2$), —OC(S)(NH$_2$), —SC(S)(NH$_2$), —SC(O)(NH$_2$), —OC(O)(NHR$^9$), —OC(S)(NHR$^9$), —SC(S)(NHR$^9$), —SC(O)(NHR$^9$), —NHC(O)OR$^9$, —NHC(S)SR$^9$, —NHC(S)OR$^9$, —NHC(O)SR$^9$, or —C(S)(NH$_2$), wherein R$^9$ is a straight or branched C$_1$-C$_5$ alkyl, straight or branched C$_1$-C$_5$ haloalkyl, (C$_3$-C$_4$)cycloalkyl or straight or branched C$_1$-C$_5$ alkoxyalkyl and R$^{12}$ is H, (C$_1$-C$_6$)alkyl, phenyl, heteroaryl, cyano, nitro, —S(O)R$^9$-S(O$_2$)R$^9$, —S(O$_2$)NHR$^9$, —S(O$_2$)NR$^9$R$^9$, —C(O)R$^9$, —C(S)R$^9$, —C(O)OR$^9$, —C(S)OR$^9$, —C(O)(NH$_2$), —C(O)(NHR$^9$).

In a specific embodiment, the aspartic protease inhibitor of the invention is represented by Structural Formula (II) or Structural Formula (IIa), or a pharmaceutically acceptable salt of the aspartic protease inhibitor represented by Structural Formula (II) or (IIa):

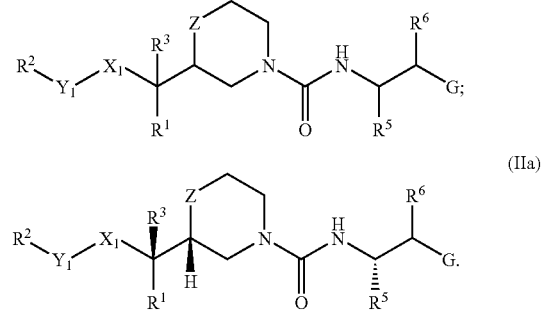

Values and particular values for the variables in Structural Formula (II) and Structural Formula (IIa) are as provided for Structural Formula (I) and Structural Formula (I*) above. In a particular embodiment, one of R$^5$ and R$^6$ is —H or methyl and the other is as described for Structural Formula (I) and Structural Formula (I*); and the remainder of the values and particular values for Structural Formula (II) and (Ia) are as described for Structural Formula (I) and Structural Formula (I*). More particularly, R$^6$ is —H or methyl and the remainder of the values and particular values for Structural Formulas (II) and (IIa) are as described for Structural Formula (I) and Structural Formula (I*).

In another specific embodiment, the aspartic protease inhibitor of the invention is represented by a structural formula selected from Structural Formulas (III)-(VII), or a pharmaceutically acceptable salt thereof:

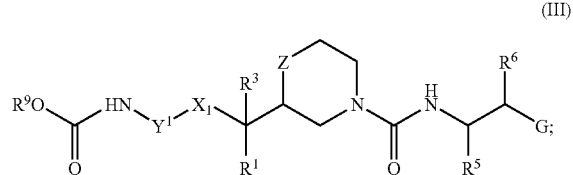

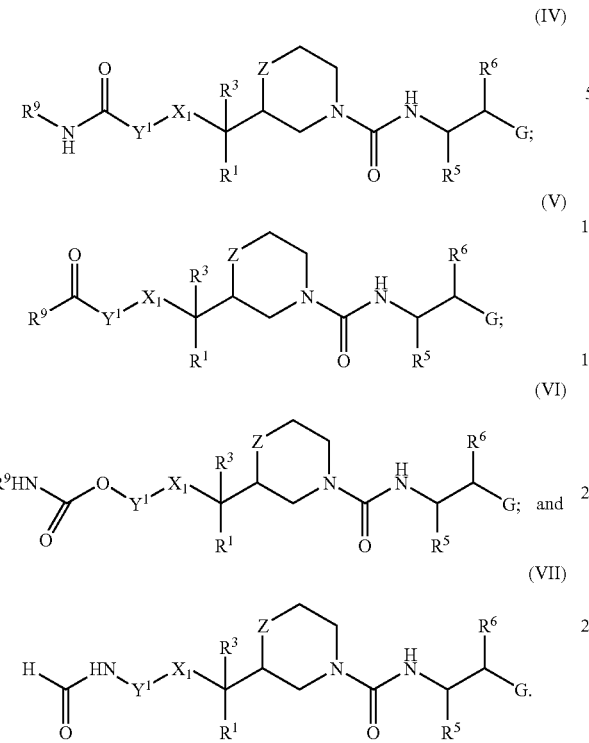

(IV)

(V)

(VI)

(VII)

Values and particular values for the variables in Structural Formulas (III)-(VII) are as provided for Structural Formula (I) and Structural Formula (I*) above. In a particular embodiment, one of $R^5$ and $R^6$ is —H or methyl and the other is as described for Structural Formula (I) and Structural Formula (I*); and the remainder of the values and particular values for Structural Formulas (III)-(VII) are as described for Structural Formula (I) and Structural Formula (I*). More particularly, $R^6$ is —H or methyl and the remainder of the values and particular values for Structural Formulas (III)-(VII) are as described for Structural Formula (I) and Structural Formula (I*).

In another specific embodiment, the aspartic protease inhibitor of the invention is represented by a structural formula selected from Structural Formulas (IIIa)-(VIIa), or a pharmaceutically acceptable salt thereof:

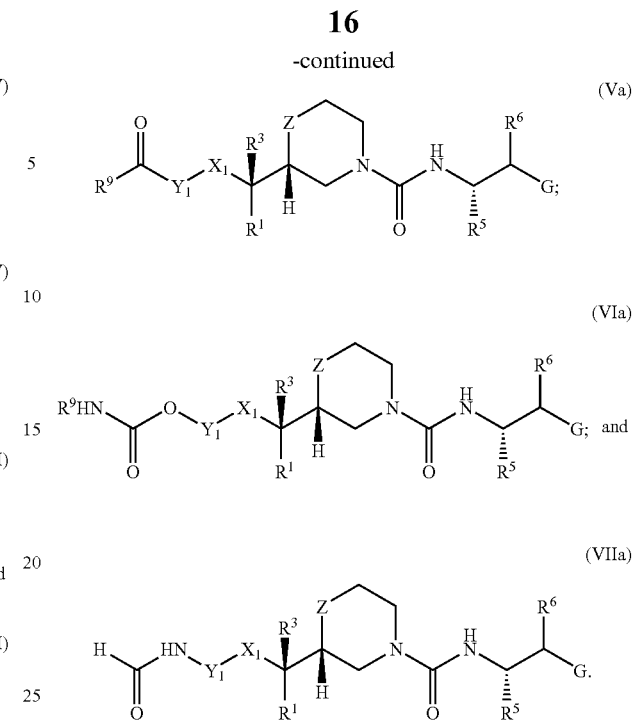

(IIIa)

(IVa)

(Va)

(VIa)

(VIIa)

Values and particular values for the variables in Structural Formulas (IIIa)-(VIIa) are as provided for Structural Formula (I) and Structural Formula (I*) above. In a particular embodiment, one of $R^5$ and $R^6$ is —H or methyl and the other is as described for Structural Formula (I) and Structural Formula (I*); and the remainder of the values and particular values for Structural Formulas (IIIa)-(VIIa) are as described for Structural Formula (I) and Structural Formula (I*). More particularly, $R^6$ is —H or methyl and the remainder of the values and particular values for Structural Formulas (IIIa)-(VIIa) are as described for Structural Formula (I) and Structural Formula (I*).

In another specific embodiment, the aspartic protease inhibitor of the invention is represented by a structural formula selected from Structural Formulas (VIII)-(XII), or a pharmaceutically acceptable salt thereof:

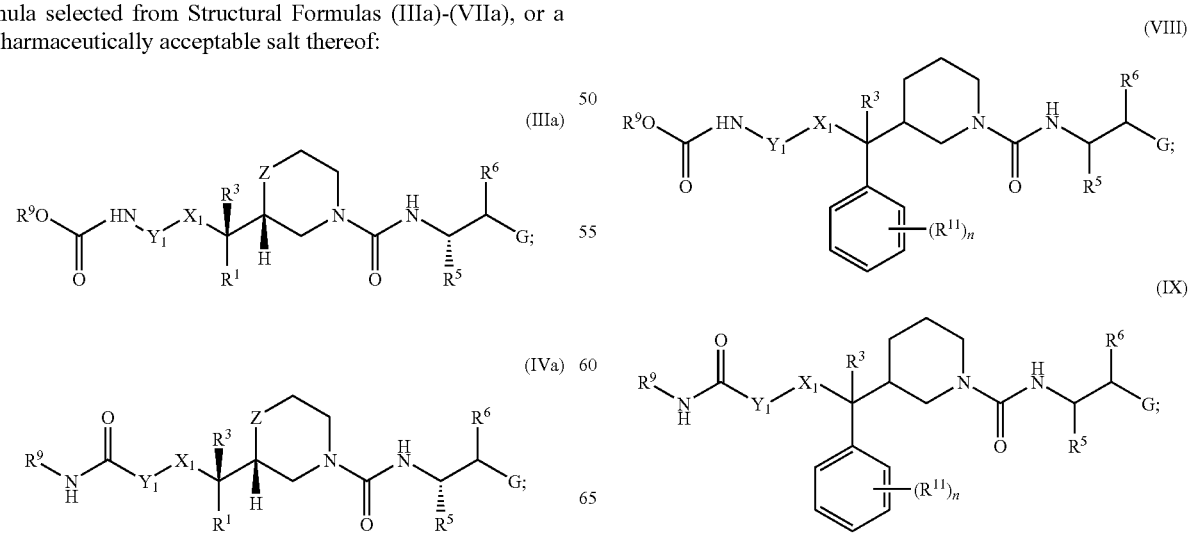

(VIII)

(IX)

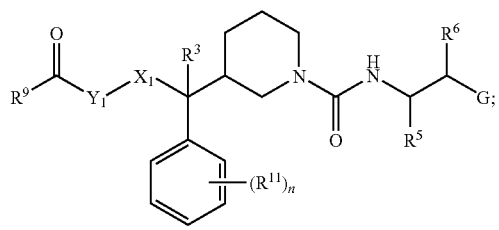
(X)

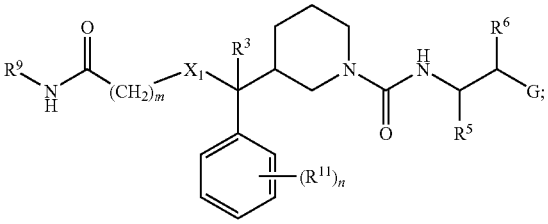
(XIV)

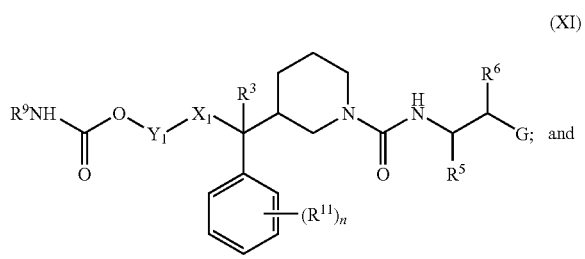
(XI)

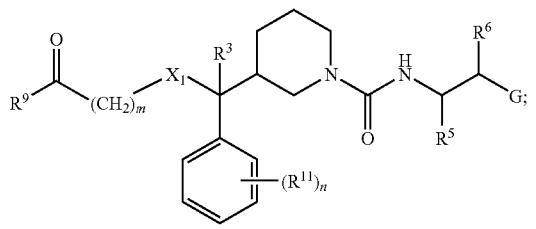
(XV)

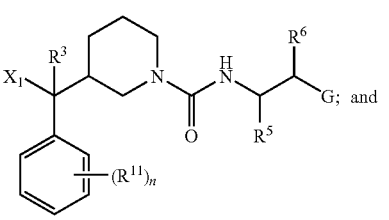
(XVI)

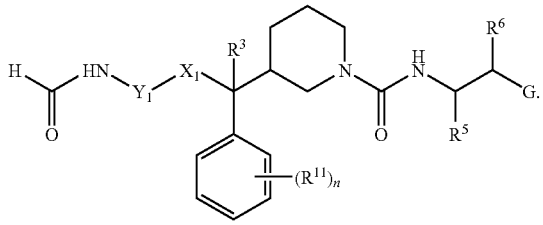
(XII)

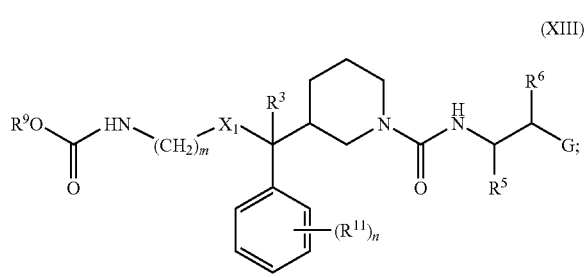
(XVII)

n is 0, 1, 2, or 3; and the values and particular values for the remainder of the variables in Structural Formulas (VIII)-(XII) are as provided for Structural Formula (I) and Structural Formula (I*) above. In a particular embodiment, one of $R^5$ and $R^6$ is —H or methyl and the other is as described for Structural Formula (I) and Structural Formula (I*); and the remainder of the values and particular values for Structural Formulas (VIII)-(XII) are as described for Structural Formula (I) and Structural Formula (I*). More particularly, $R^6$ is —H or methyl and the remainder of the values and particular values for Structural Formulas (VIII)-(XII) are as described for Structural Formula (I) and Structural Formula (I*).

In another specific embodiment, the aspartic protease inhibitor of the invention is represented by a structural formula selected from Structural Formulas (XII)-(XVII), or a pharmaceutically acceptable salt thereof:

(XIII)

A first set of values for the aspartic protease inhibitor represented by Structural Formulas (XIII)-(XVII) is provided in the following paragraphs:

$R^6$ is H or methyl;

$R^{11}$ is fluorine, chlorine, bromine, cyano, nitro, $(C_1-C_6)$ alkyl, $(C_3-C_6)$cycloalkyl, $(C_4-C_7)$cycloalkylalkyl, $(C_2-C_6)$ alkenyl, $(C_5-C_7)$cycloalkylalkenyl, $(C_2-C_6)$alkynyl, $(C_3-C_6)$ cycloalkyl$(C_2-C_4)$alkynyl, halo$(C_1-C_6)$alkyl, halo$(C_3-C_6)$ cycloalkyl, halo$(C_4-C_7)$cycloalkylalkyl, halo$(C_2-C_6)$alkenyl, halo$(C_3-C_6)$alkynyl, halo$(C_5-C_7)$-cycloalkylalkynyl, $(C_1-C_6)$ alkoxy, $(C_3-C_6)$cycloalkoxy, $(C_4-C_7)$cycloalkylalkoxy, halo $(C_1-C_6)$alkoxy, halo$(C_3-C_6)$cycloalkoxy, halo$(C_4-C_7)$cycloalkylalkoxy and $(C_1-C_6)$alkanesulfonyl; or 2) phenyl, heteroaryl, phenoxy, heteroaryloxy, phenylthio, heteroarylthio, benzyl, heteroarylmethyl, benzyloxy and heteroarylmethoxy, each optionally substituted with 1 to 3 groups independently selected from: fluorine, chlorine, cyano, $(C_1-C_3)$alkyl, halo$(C_1-C_3)$alkyl, $(C_1-C_3)$-alkoxy, halo $(C_1-C_3)$alkoxy, and aminocarbonyl;

n is 0, 1, 2 or 3;

m is 2 or 3; and values and particular values for the remainder of the variables in Structural Formulas (XIII)-(XVII) are as described for Structural Formula (I) and Structural Formula (I*).

A second set of values for the aspartic protease inhibitor represented by Structural Formulas (XIII)-(XVII) is provided in the following paragraphs:

One of R[5] and R[6] is —H, $(C_1-C_7)$alkyl, halo$(C_1-C_7)$alkyl, hydroxy$(C_1-C_7)$alkyl, cyclohexylmethyl, halocyclohexylmethyl, hydroxylated cyclohexylmethyl, $(C_1-C_2)$alkyl cyclohexylmethyl, di$(C_1-C_2)$alkyl cyclohexylmethyl, hydroxylated $(C_1-C_2)$alkyl cyclohexylmethyl, hydroxylated di$(C_1-C_2)$alkylcyclohexylmethyl, (3-noradamantyl)methyl or (tetrahydropyranyl)methyl; and the other is R[6] is —H or methyl; and values and particular values for the remainder of the variables are as described for the first set of values for Structural Formulas (XIII)-(XVII).

A third set of values for the aspartic protease inhibitor represented by Structural Formulas (XIII)-(XVII) is provided in the following paragraphs:

R[5] is $(C_1-C_7)$alkyl, halo$(C_1-C_7)$alkyl, hydroxy$(C_1-C_7)$alkyl, cyclohexylmethyl, halocyclohexylmethyl, hydroxylated cyclohexylmethyl, $(C_1-C_2)$alkyl cyclohexylmethyl, di$(C_1-C_2)$alkyl cyclohexylmethyl, hydroxylated $(C_1-C_2)$alkyl cyclohexylmethyl, hydroxylated di$(C_1-C_2)$alkylcyclohexylmethyl, (3-noradamantyl)methyl or (tetrahydropyranyl)methyl;

R[6] is —H or methyl;

G is $NH_2$ or $NHR^7$;

R[7] is methyl or R[5] and R[7] together are —$(CH_2)_3$— optionally substituted with $C_1-C_4$ alkyl or cyclohexyl; and values and particular values for the remainder of the variables are as described for the first set of values for Structural Formulas (XIII)-(XVII).

A fourth set of values for the aspartic protease inhibitor represented by Structural Formulas (XIII)-(XVII) is provided in the following paragraphs:

R[5] is —H or methyl;

R[6] is $(C_1-C_7)$alkyl, halo$(C_1-C_7)$alkyl, hydroxy$(C_1-C_7)$alkyl, cyclohexylmethyl, halocyclohexylmethyl, hydroxylated cyclohexylmethyl, $(C_1-C_2)$alkyl cyclohexylmethyl, di$(C_1-C_2)$alkyl cyclohexylmethyl, hydroxylated $(C_1-C_2)$alkyl cyclohexylmethyl, hydroxylated di$(C_1-C_2)$alkylcyclohexylmethyl, (3-noradamantyl)methyl or (tetrahydropyranyl)methyl;

G is $NH_2$ or $NHR^7$;

R[7] is methyl or R[5] and R[7] together are —$(CH_2)_3$— optionally substituted with $C_1-C_4$ alkyl or cyclohexyl; and values and particular values for the remainder of the variables are as described for the first set of values for Structural Formulas (XIII)-(XVII).

A fifth set of values for the aspartic protease inhibitor represented by Structural Formula (XIII)-(XVII) is provided in the following paragraphs:

R[9] is methyl or ethyl;

R[11] is chloro, fluoro or methyl; and values and particular values for the remainder of the variables are as described for the third set of values for Structural Formulas (XIII)-(XVII).

A sixth set of values for the aspartic protease inhibitor represented by Structural Formula (XIII)-(XVII) is provided in the following paragraphs:

R[9] is methyl or ethyl;

R[11] is chloro, fluoro or methyl; and values and particular values for the remainder of the variables are as described for the fourth set of values for Structural Formulas (XIII)-(XVII).

In another specific embodiment, the aspartic protease inhibitor of the invention is represented by a structural formula selected from Structural Formulas (XVIII)-(XXII), or a pharmaceutically acceptable salt thereof:

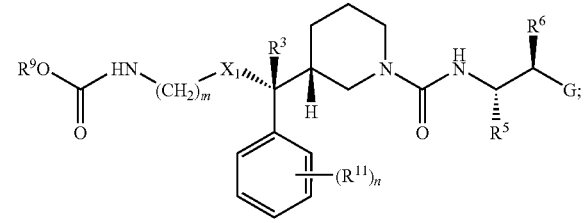

(XVIII)

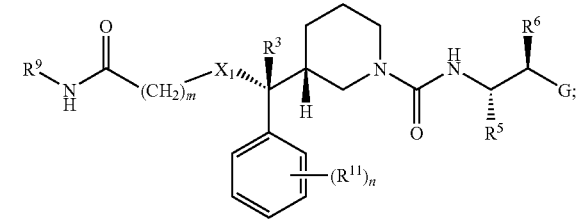

(XIX)

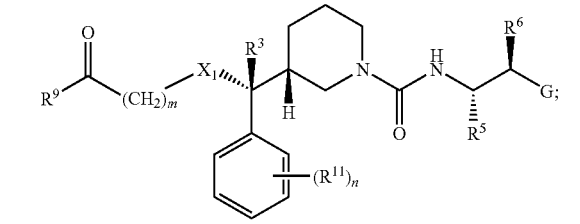

(XX)

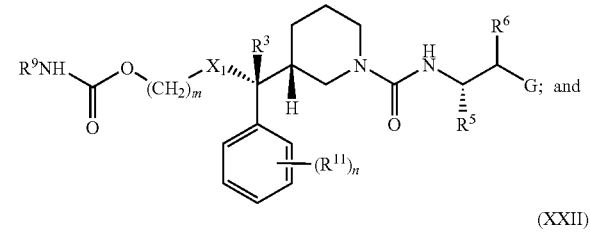

(XXI)

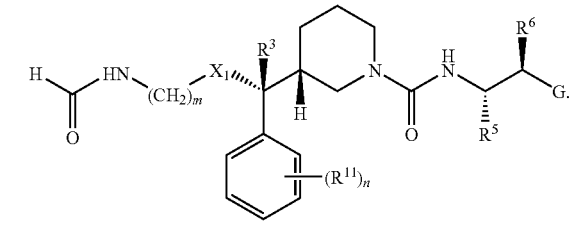

(XXII)

Values and particular values for the variables in Structural Formulas (XVIII)-(XXII) are as described for the first set of values for Structural Formulas (XIII)-(XVII). Alternatively, values and particular values for the variables in Structural Formulas (XVIII)-(XXII) are as described for the second set of values for Structural Formulas (XIII)-(XVII). In another alternative, values and particular values for the variables in Structural Formulas (XVIII)-(XXII) are as described for the third set of values for Structural Formulas (XIII)-(XVII). In yet another alternative, values and particular values for the variables in Structural Formulas (XVIII)-(XXII) are as described for the fourth set of values for Structural Formulas (XIII)-(XVII).

In another specific embodiment, the aspartic protease inhibitor of the invention is represented by a structural formula selected from Structural Formulas (XXIII)-(XXV), or a pharmaceutically acceptable salt thereof:

(XXIII)
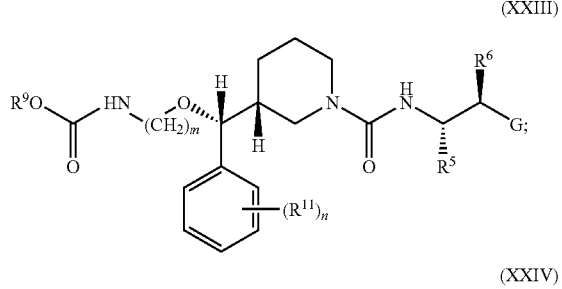

(XXIV)
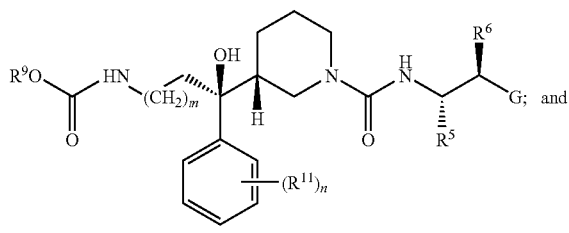

(XXV)
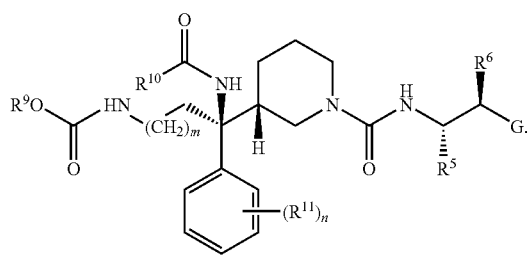

Values and particular values for the variables in Structural Formulas (XXIII)-(XXV) are as described for Structural Formulas (XIII)-(XVII).

In another specific embodiment, the aspartic protease inhibitor of the invention is represented by a structural formula selected from Structural Formulas (XXVI)-(XXVIII), or a pharmaceutically acceptable salt thereof:

(XXVI)
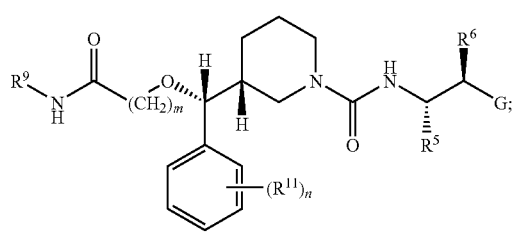

(XXVII)
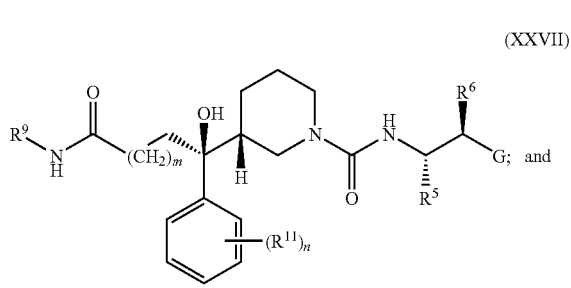

(XXVIII)
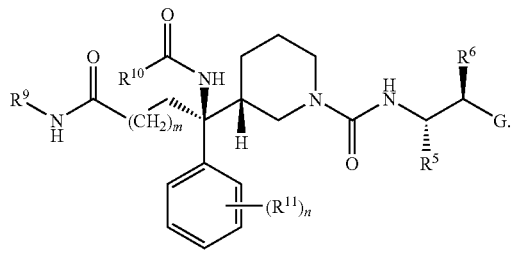

Values and particular values for the variables in Structural Formulas (XXVI)-(XXVIII) are as described for Structural Formulas (XIII)-(XVII).

In another specific embodiment, the aspartic protease inhibitor of the invention is represented by a structural formula selected from Structural Formulas (XXIX)-(XXXI), or a pharmaceutically acceptable salt thereof:

(XIX)
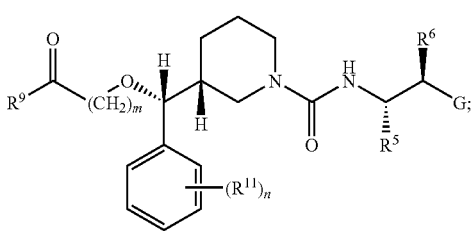

(XXX)
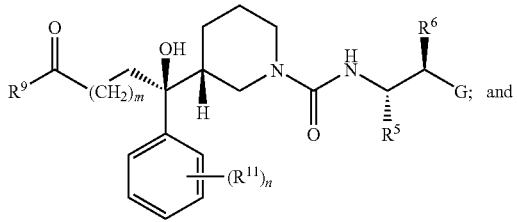

(XXXI)
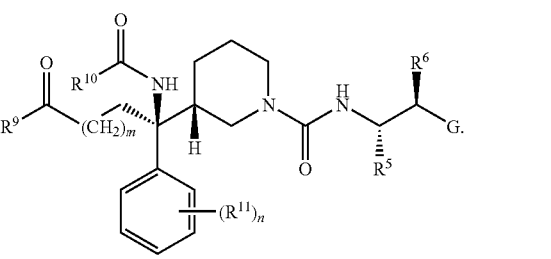

Values and particular values for the variables in Structural Formulas (XXIX)-(XXXI) are as described for Structural Formulas (XIII)-(XVII).

In another specific embodiment, the aspartic protease inhibitor of the invention is represented by a structural formula selected from Structural Formulas (XXXII)-(XXXIV), or a pharmaceutically acceptable salt thereof:

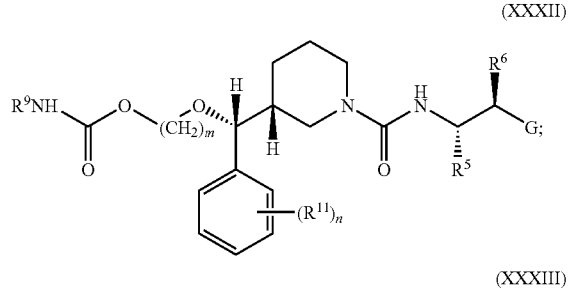

(XXXII)

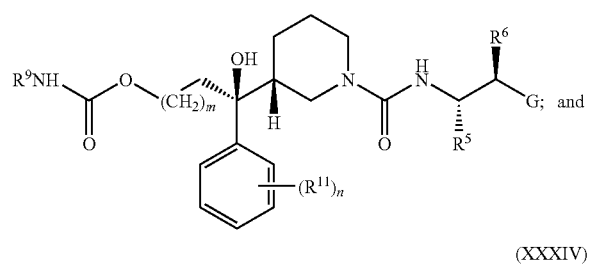

(XXXIII)

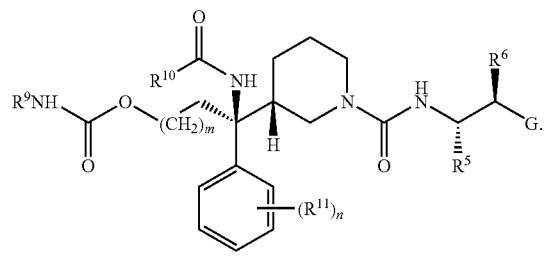

(XXXIV)

Values and particular values for the variables in Structural Formulas (XXXII)-(XXXIV) are as described for Structural Formulas (XIII)-(XVII).

In another specific embodiment, the aspartic protease inhibitor of the invention is represented by a structural formula selected from Structural Formulas (XXXV)-(XXXVII), or a pharmaceutically acceptable salt thereof:

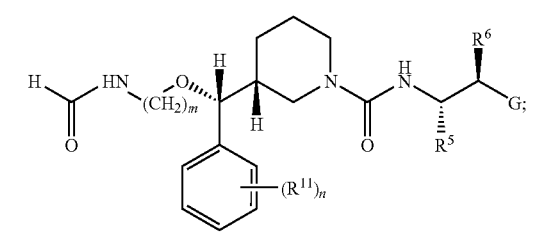

(XXXV)

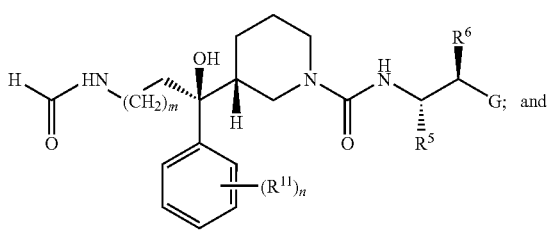

(XXXVI)

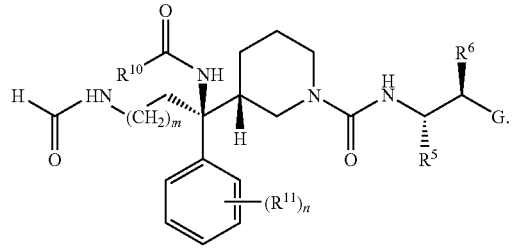

(XXXVII)

Values and particular values for the variables in Structural Formulas (XXXV)-(XXXVII) are as described for Structural Formulas (XIII)-(XVII).

Another embodiment of the invention is an aspartic protease inhibitor represented by Structural Formula (XXXVIIa-e):

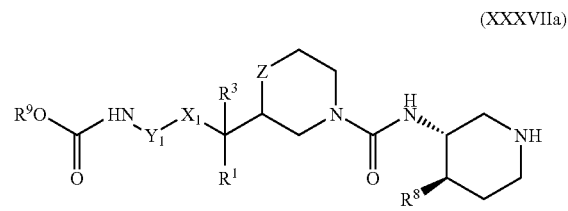

(XXXVIIa)

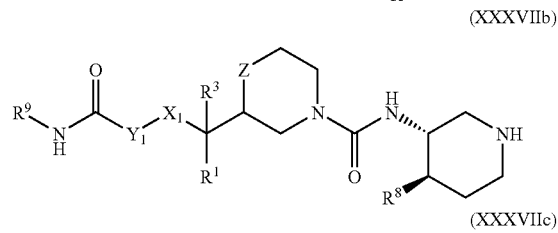

(XXXVIIb)

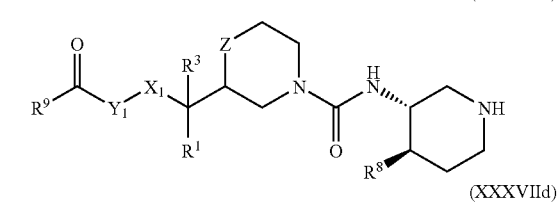

(XXXVIIc)

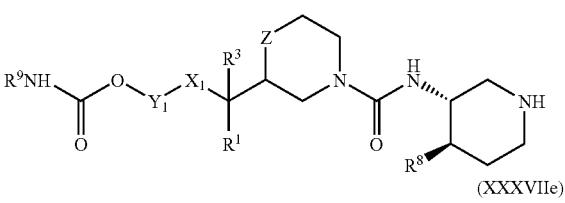

(XXXVIId)

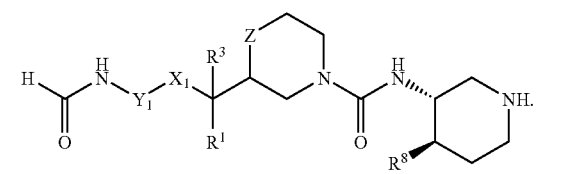

(XXXVIIe)

$R^8$ isobutyl, cyclohexyl, cyclopentyl, cyclobutylmethyl or isopropoxy and the values and particular values for the remainder of the variables are as described for Structural Formulas (III)-(VII).

Another embodiment of the invention is each of the following compounds or their enantiomers, diastereomers, or pharmaceutically acceptable salts:

| Compound Number | Name |
|---|---|
| I-1 | methyl 4-(1-(1-cyclohexyl-3-(methylamino)propan-2-ylcarbamoyl)piperidin-3-yl)-4-(2-fluorophenyl)-4-hydroxybutylcarbamate |
| I-2 | methyl 4-(3-chloro-2-fluorophenyl)-4-(1-(4,4-dimethyl-1-(methylamino)pentan-2-ylcarbamoyl)piperidin-3-yl)-4-hydroxybutylcarbamate |
| I-3 | methyl 4-(1-(1-cyclohexyl-3-(methylamino)propan-2-ylcarbamoyl)piperidin-3-yl)-4-(3,5-dimethylphenyl)-4-hydroxybutylcarbamate |
| I-4 | methyl 4-(1-(1-cyclohexyl-3-(methylamino)propan-2-ylcarbamoyl)piperidin-3-yl)-4-(3-fluoro-5-methylphenyl)-4-hydroxybutylcarbamate |
| I-5 | methyl 4-(1-(1-cyclohexyl-3-(methylamino)propan-2-ylcarbamoyl)piperidin-3-yl)-4-(2-fluoro-5-methylphenyl)-4-hydroxybutylcarbamate |
| I-6 | methyl 4-(3-chlorophenyl)-4-(1-(1-cyclohexyl-3-(methylamino)propan-2-ylcarbamoyl)piperidin-3-yl)-4-hydroxybutylcarbamate |
| I-7 | methyl 4-(1-(1-cyclohexyl-3-(methylamino)propan-2-ylcarbamoyl)piperidin-3-yl)-4-(2,3-difluorophenyl)-4-hydroxybutylcarbamate |
| I-7 | methyl 4-(1-(1-cyclohexyl-3-(methylamino)propan-2-ylcarbamoyl)piperidin-3-yl)-4-(2,3-difluorophenyl)-4-hydroxybutylcarbamate |
| I-8 | methyl 4-(1-(1-cyclohexyl-3-(methylamino)propan-2-ylcarbamoyl)piperidin-3-yl)-4-(3,5-difluorophenyl)-4-hydroxybutylcarbamate |
| I-9 | methyl 4-(1-(2-amino-3-cyclohexylpropylcarbamoyl)piperidin-3-yl)-4-(3-chloro-2-fluorophenyl)-4-hydroxybutylcarbamate |
| I-10 | methyl 4-(1-(2-amino-3-(tetrahydro-2H-pyran-2-yl)propylcarbamoyl)piperidin-3-yl)-4-(3-chloro-2-fluorophenyl)-4-hydroxybutylcarbamate |
| I-11 | ethyl 4-(3-chlorophenyl)-4-(1-(1-cyclohexyl-3-(methylamino)propan-2-ylcarbamoyl)piperidin-3-yl)-4-hydroxybutylcarbamate |
| I-12 | methyl 4-(1-(1-cyclohexyl-1-hydroxy-3-(methylamino)propan-2-ylcarbamoyl)piperidin-3-yl)-4-(2,3-difluorophenyl)-4-hydroxybutylcarbamate |
| I-13 | methyl 4-(3-chloro-2-fluorophenyl)-4-(1-(1-cyclohexyl-3-(methylamino)propan-2-ylcarbamoyl)piperidin-3-yl)-4-hydroxybutylcarbamate |
| I-14 | methyl 4-(2-chloro-3-fluorophenyl)-4-(1-(1-cyclohexyl-3-(methylamino)propan-2-ylcarbamoyl)piperidin-3-yl)-4-hydroxybutylcarbamate |
| I-15 | methyl 4-(3-chloro-5-fluorophenyl)-4-(1-(1-cyclohexyl-3-(methylamino)propan-2-ylcarbamoyl)piperidin-3-yl)-4-hydroxybutylcarbamate |
| I-16 | methyl 4-(1-(3-amino-1-cyclohexylbutan-2-ylcarbamoyl)piperidin-3-yl)-4-(3-chloro-2-fluorophenyl)-4-hydroxybutylcarbamate |
| I-17 | methyl 4-(2,3-difluorophenyl)-4-(1-(1-(4-fluorocyclohexyl)-3-(methylamino)propan-2-ylcarbamoyl)piperidin-3-yl)-4-hydroxybutylcarbamate |
| I-18 | methyl 4-(3-chloro-2-fluorophenyl)-4-hydroxy-4-(1-(1-(methylamino)-3-(tetrahydro-2H-pyran-4-yl)propan-2-ylcarbamoyl)piperidin-3-yl)butylcarbamate |
| I-19 | methyl 4-(1-(2-amino-3-cyclohexylpropylcarbamoyl)piperidin-3-yl)-4-(3-chloro-2,4-difluorophenyl)-4-hydroxybutylcarbamate |
| I-20 | methyl 4-(3-chloro-2-fluorophenyl)-4-(1-(1-cyclohexyl-1-hydroxy-3-(methylamino)propan-2-ylcarbamoyl)piperidin-3-yl)-4-hydroxybutylcarbamate |
| I-21 | methyl 4-(2-chloro-3-fluorophenyl)-4-(1-(1-cyclohexyl-1-hydroxy-3-(methylamino)propan-2-ylcarbamoyl)piperidin-3-yl)-4-hydroxybutylcarbamate |
| I-22 | methyl 4-(3-chloro-2-fluorophenyl)-4-(1-(1-(4-fluorocyclohexyl)-3-(methylamino)propan-2-ylcarbamoyl)piperidin-3-yl)-4-hydroxybutylcarbamate |
| I-23 | methyl 4-(3-chloro-2,4-difluorophenyl)-4-(1-(1-cyclohexyl-3-(methylamino)propan-2-ylcarbamoyl)piperidin-3-yl)-4-hydroxybutylcarbamate |
| I-24 | methyl 4-acetamido-4-(3-chlorophenyl)-4-(1-(1-cyclohexyl-3-(methylamino)propan-2-ylcarbamoyl)piperidin-3-yl)butylcarbamate |
| I-25 | methyl 4-(3-chlorophenyl)-4-(1-(1-cyclohexyl-3-(methylamino)propan-2-ylcarbamoyl)piperidin-3-yl)-4-propionamidobutylcarbamate |
| I-25 | methyl 4-(3-chlorophenyl)-4-(1-(1-cyclohexyl-3-(methylamino)propan-2-ylcarbamoyl)piperidin-3-yl)-4-propionamidobutylcarbamate |
| I-26 | (3-chlorophenyl)(1-(1-cyclohexyl-3-(methylamino)propan-2-ylcarbamoyl)piperidin-3-yl)methyl carbamate |
| I-27 | (3-chlorophenyl)(1-(1-cyclohexyl-3-(methylamino)propan-2-ylcarbamoyl)piperidin-3-yl)methyl methylcarbamate |

-continued

| Compound Number | Name |
|---|---|
| I-28 | (3-chlorophenyl)(1-(1-cyclohexyl-3-(methylamino)propan-2-ylcarbamoyl)piperidin-3-yl)methyl ethylcarbamate |
| I-28 | (3-chlorophenyl)(1-(1-cyclohexyl-3-(methylamino)propan-2-ylcarbamoyl)piperidin-3-yl)methyl ethylcarbamate |
| I-29 | (3-chlorophenyl)(1-(1-cyclohexyl-3-(methylamino)propan-2-ylcarbamoyl)piperidin-3-yl)methyl butylcarbamate |
| I-29 | (3-chlorophenyl)(1-(1-cyclohexyl-3-(methylamino)propan-2-ylcarbamoyl)piperidin-3-yl)methyl butylcarbamate |
| I-30 | methyl 2-((3-chlorophenyl)(1-(4,4-dimethyl-1-(methylamino)pentan-2-ylcarbamoyl)piperidin-3-yl)methoxy)ethylcarbamate |
| I-31 | methyl 2-((1-(1-cyclohexyl-3-(methylamino)propan-2-ylcarbamoyl)piperidin-3-yl)(3-fluorophenyl)methoxy)ethylcarbamate |
| I-32 | methyl 2-((1-(1-amino-3-cyclohexylpropan-2-ylcarbamoyl)piperidin-3-yl)(3-chlorophenyl)methoxy)ethylcarbamate |
| I-34 | methyl 2-((1-(1-amino-3-(tetrahydro-2H-pyran-2-yl)propan-2-ylcarbamoyl)piperidin-3-yl)(3-chlorophenyl)methoxy)ethylcarbamate |
| I-35 | methyl 2-((3-chlorophenyl)(1-(1-cyclohexyl-3-(methylamino)propan-2-ylcarbamoyl)piperidin-3-yl)methoxy)ethylcarbamate |
| I-36 | methyl 2-((1-(3-amino-1-cyclohexylbutan-2-ylcarbamoyl)piperidin-3-yl)(3-chlorophenyl)methoxy)ethylcarbamate |
| I-37 | methyl 2-((1-(1-cyclohexyl-3-(methylamino)propan-2-ylcarbamoyl)piperidin-3-yl)(2,3-difluorophenyl)methoxy)ethylcarbamate |
| I-38 | methyl 2-((3-chlorophenyl)(1-(1-(methylamino)-3-(tetrahydro-2H-pyran-4-yl)propan-2-ylcarbamoyl)piperidin-3-yl)methoxy)ethylcarbamate |
| I-38 | methyl 2-((3-chlorophenyl)(1-(1-(methylamino)-3-(tetrahydro-2H-pyran-4-yl)propan-2-ylcarbamoyl)piperidin-3-yl)methoxy)ethylcarbamate |
| I-39 | methyl 2-((1-(2-amino-3-cyclohexylpropylcarbamoyl)piperidin-3-yl)(3-chloro-2-fluorophenyl)methoxy)ethylcarbamate |
| I-41 | ethyl 2-((3-chlorophenyl)(1-(1-cyclohexyl-3-(methylamino)propan-2-ylcarbamoyl)piperidin-3-yl)methoxy)ethylcarbamate |
| I-42 | methyl 2-(1-(3-chlorophenyl)-1-(1-(1-cyclohexyl-3-(methylamino)propan-2-ylcarbamoyl)piperidin-3-yl)ethoxy)ethylcarbamate |
| I-43 | methyl 2-((3-chloro-2-fluorophenyl)(1-(1-cyclohexyl-3-(methylamino)propan-2-ylcarbamoyl)piperidin-3-yl)methoxy)ethylcarbamate |
| I-43 | methyl 2-((3-chloro-2-fluorophenyl)(1-(1-cyclohexyl-3-(methylamino)propan-2-ylcarbamoyl)piperidin-3-yl)methoxy)ethylcarbamate |
| I-43 | methyl 2-((3-chloro-2-fluorophenyl)(1-(1-cyclohexyl-3-(methylamino)propan-2-ylcarbamoyl)piperidin-3-yl)methoxy)ethylcarbamate |
| I-44 | methyl 2-((3-chloro-5-fluorophenyl)(1-(1-cyclohexyl-3-(methylamino)propan-2-ylcarbamoyl)piperidin-3-yl)methoxy)ethylcarbamate |
| I-45 | methyl 2-((3-chlorophenyl)(1-(1-(4-fluorocyclohexyl)-3-(methylamino)propan-2-ylcarbamoyl)piperidin-3-yl)methoxy)ethylcarbamate |
| I-46 | methyl 2-((3-chlorophenyl)(1-(1-(1-fluorocyclohexyl)-3-(methylamino)propan-2-ylcarbamoyl)piperidin-3-yl)methoxy)ethylcarbamate |
| I-46 | methyl 2-((3-chlorophenyl)(1-(1-(1-fluorocyclohexyl)-3-(methylamino)propan-2-ylcarbamoyl)piperidin-3-yl)methoxy)ethylcarbamate |
| I-47 | methyl 2-((3-chloro-2-fluorophenyl)(1-(1-(methylamino)-3-(tetrahydro-2H-pyran-4-yl)propan-2-ylcarbamoyl)piperidin-3-yl)methoxy)ethylcarbamate |
| I-47 | methyl 2-((3-chloro-2-fluorophenyl)(1-(1-(methylamino)-3-(tetrahydro-2H-pyran-4-yl)propan-2-ylcarbamoyl)piperidin-3-yl)methoxy)ethylcarbamate |
| I-48 | methyl 2-((3-chloro-2-fluorophenyl)(4-(1-cyclohexyl-3-(methylamino)propan-2-ylcarbamoyl)morpholin-2-yl)methoxy)ethylcarbamate |
| I-49 | ethyl 2-((3-chloro-2-fluorophenyl)(1-(1-cyclohexyl-3-(methylamino)propan-2-ylcarbamoyl)piperidin-3-yl)methoxy)ethylcarbamate |
| I-50 | methyl 2-((3-chloro-2-fluorophenyl)(1-(1-(1-fluorocyclohexyl)-3-(methylamino)propan-2-ylcarbamoyl)piperidin-3-yl)methoxy)ethylcarbamate |
| I-51 | methyl 2-((3-chloro-2-fluorophenyl)(1-(1-(4-fluorocyclohexyl)-3-(methylamino)propan-2-ylcarbamoyl)piperidin-3-yl)methoxy)ethylcarbamate |

-continued

| Compound Number | Name |
|---|---|
| I-52 | methyl 2-((3-chlorophenyl)(1-(1-(3-noradamantyl)-3-(methylamino)propan-2-ylcarbamoyl)piperidin-3-yl)methoxy)ethylcarbamate |
| I-53 | 2-((3-chlorophenyl)(1-(1-cyclohexyl-3-(methylamino)propan-2-ylcarbamoyl)piperidin-3-yl)methoxy)ethyl carbamate |
| I-54 | 2-((3-chlorophenyl)(1-(1-cyclohexyl-3-(methylamino)propan-2-ylcarbamoyl)piperidin-3-yl)methoxy)ethyl methylcarbamate |
| I-55 | 2-((3-chlorophenyl)(1-(1-cyclohexyl-3-(methylamino)propan-2-ylcarbamoyl)piperidin-3-yl)methoxy)ethyl ethylcarbamate |
| I-56 | 3-((3-chlorophenyl)(2-(methylamino)-2-oxoethoxy)methyl)-N-(1-cyclohexyl-3-(methylamino)propan-2-yl)piperidine-1-carboxamide |
| I-56 | 3-((3-chlorophenyl)(2-(methylamino)-2-oxoethoxy)methyl)-N-(1-cyclohexyl-3-(methylamino)propan-2-yl)piperidine-1-carboxamide |
| I-57 | 3-((2-amino-2-oxoethoxy)(3-chloro-2-fluorophenyl)methyl)-N-(1-cyclohexyl-3-(methylamino)propan-2-yl)piperidine-1-carboxamide |
| I-58 | 3-((3-chlorophenyl)(2-(ethylamino)-2-oxoethoxy)methyl)-N-(1-cyclohexyl-3-(methylamino)propan-2-yl)piperidine-1-carboxamide |
| I-58 | 3-((3-chlorophenyl)(2-(ethylamino)-2-oxoethoxy)methyl)-N-(1-cyclohexyl-3-(methylamino)propan-2-yl)piperidine-1-carboxamide |
| I-59 | N-(1-cyclohexyl-3-(methylamino)propan-2-yl)-3-((2,3-difluorophenyl)(2-(ethylamino)-2-oxoethoxy)methyl)piperidine-1-carboxamide |
| I-60 | 3-((3-chlorophenyl)(2-oxo-2-(propylamino)ethoxy)methyl)-N-(1-cyclohexyl-3-(methylamino)propan-2-yl)piperidine-1-carboxamide |
| I-61 | 3-((3-chlorophenyl)(2-(isopropylamino)-2-oxoethoxy)methyl)-N-(1-cyclohexyl-3-(methylamino)propan-2-yl)piperidine-1-carboxamide |
| I-62 | N-(1-cyclohexyl-3-(methylamino)propan-2-yl)-3-((2,3-difluorophenyl)(2-oxo-2-(propylamino)ethoxy)methyl)piperidine-1-carboxamide |
| I-63 | N-(1-cyclohexyl-3-(methylamino)propan-2-yl)-3-((2,3-difluorophenyl)(2-(isopropylamino)-2-oxoethoxy)methyl)piperidine-1-carboxamide |
| I-64 | 3-((3-chloro-2-fluorophenyl)(2-(ethylamino)-2-oxoethoxy)methyl)-N-(1-cyclohexyl-3-(methylamino)propan-2-yl)piperidine-1-carboxamide |
| I-64 | 3-((3-chloro-2-fluorophenyl)(2-(ethylamino)-2-oxoethoxy)methyl)-N-(1-cyclohexyl-3-(methylamino)propan-2-yl)piperidine-1-carboxamide |
| I-65 | 3-((3-chlorophenyl)(2-(2-methoxyethylamino)-2-oxoethoxy)methyl)-N-(1-cyclohexyl-3-(methylamino)propan-2-yl)piperidine-1-carboxamide |
| I-66 | 3-((3-chlorophenyl)(3-(methylamino)-3-oxopropoxy)methyl)-N-(1-cyclohexyl-3-(methylamino)propan-2-yl)piperidine-1-carboxamide |
| I-67 | 3-((3-chlorophenyl)(3-(ethylamino)-3-oxopropoxy)methyl)-N-(1-cyclohexyl-3-(methylamino)propan-2-yl)piperidine-1-carboxamide |
| I-67 | 3-((3-chlorophenyl)(3-(ethylamino)-3-oxopropoxy)methyl)-N-(1-cyclohexyl-3-(methylamino)propan-2-yl)piperidine-1-carboxamide |
| I-68 | 3-((3-chlorophenyl)(3-oxo-3-(propylamino)propoxy)methyl)-N-(1-cyclohexyl-3-(methylamino)propan-2-yl)piperidine-1-carboxamide |
| I-69 | 3-((3-chlorophenyl)(3-(isopropylamino)-3-oxopropoxy)methyl)-N-(1-cyclohexyl-3-(methylamino)propan-2-yl)piperidine-1-carboxamide |
| I-70 | 3-((3-chloro-2-fluorophenyl)(3-(ethylamino)-3-oxopropoxy)methyl)-N-(1-cyclohexyl-3-(methylamino)propan-2-yl)piperidine-1-carboxamide |
| I-71 | 3-(5-amino-1-(3-chlorophenyl)-1-hydroxy-5-oxopentyl)-N-(1-cyclohexyl-3-(methylamino)propan-2-yl)piperidine-1-carboxamide |
| I-72 | 3-(1-(3-chlorophenyl)-1-hydroxy-5-(methylamino)-5-oxopentyl)-N-(1-cyclohexyl-3-(methylamino)propan-2-yl)piperidine-1-carboxamide |
| I-73 | 3-(1-(3-chlorophenyl)-5-(ethylamino)-1-hydroxy-5-oxopentyl)-N-(1-cyclohexyl-3-(methylamino)propan-2-yl)piperidine-1-carboxamide |
| I-74 | 3-(1-(3-chlorophenyl)-4-formamido-1-hydroxybutyl)-N-(1-cyclohexyl-3-(methylamino)propan-2-yl)piperidine-1-carboxamide |
| I-75 | 3-((3-chlorophenyl)(4-oxohexyloxy)methyl)-N-(1-cyclohexyl-3-(methylamino)propan-2-yl)piperidine-1-carboxamide |
| I-76 | 3-(1-(3-chlorophenyl)-1-hydroxy-6-oxoheptyl)-N-(1-cyclohexyl-3-(methylamino)propan-2-yl)piperidine-1-carboxamide |
| I-77 | methyl 2-((3-chlorophenyl)(1-(4-isobutylpiperidin-3-ylcarbamoyl)piperidin-3-yl)methoxy)ethylcarbamate |
| I-78 | methyl 2-((3-chloro-2-fluorophenyl)(1-(4-isobutylpiperidin-3-ylcarbamoyl)piperidin-3-yl)methoxy)ethylcarbamate |
| I-79 | methyl 2-((3-chloro-2-fluorophenyl)(1-(4-cyclohexylpiperidin-3-ylcarbamoyl)piperidin-3-yl)methoxy)ethylcarbamate |
| I-80 | methyl 2-((3-chlorophenyl)(1-(4-isopropoxypiperidin-3-ylcarbamoyl)piperidin-3-yl)methoxy)ethylcarbamate |
| I-81 | methyl 2-((3-chlorophenyl)(1-(4-cyclopentylpiperidin-3-ylcarbamoyl)piperidin-3-yl)methoxy)ethylcarbamate |
| I-82 | methyl 2-((3-chlorophenyl)(1-(4-(cyclobutylmethyl)piperidin-3-ylcarbamoyl)piperidin-3-yl)methoxy)ethylcarbamate |
| I-83 | methyl 2-((3-chlorophenyl)(1-(4-cyclohexylpiperidin-3-ylcarbamoyl)piperidin-3-yl)methoxy)ethylcarbamate |

Another embodiment of the invention is each of the compounds listed below or their salts, especially their pharmaceutically acceptable salts:

I-1a 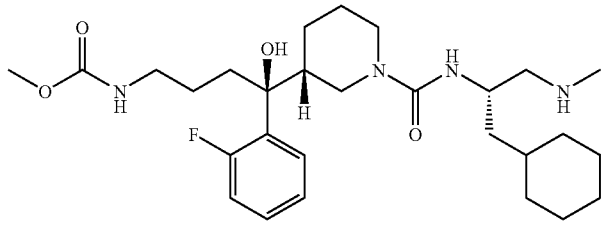 methyl (S)-4-((R)-1-((S)-1-cyclohexyl-3-(methylamino)propan-2-ylcarbamoyl)piperidin-3-yl)-4-(2-fluorophenyl)-4-hydroxybutylcarbamate I-2a 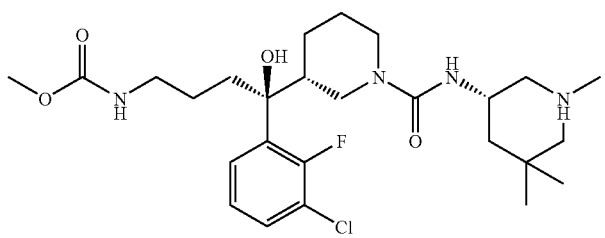 methyl (S)-4-(3-chloro-2-fluorophenyl)-4-((R)-1-((S)-4,4-dimethyl-1-(methylamino)pentan-2-ylcarbamoyl)piperidin-3-yl)-4-hydroxybutylcarbamate I-3a 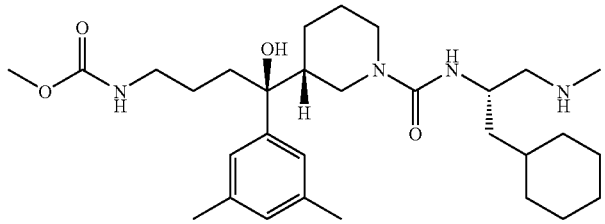 [SMILES: CNC[C@H](CC1CCCCC1)NC(=O)N1CCC[C@@H]([C@@](O)(CCCNC(=O)OC)c2cc(C)cc(C)c2)C1] methyl (S)-4-((R)-1-((S)-1-cyclohexyl-3-(methylamino)propan-2-ylcarbamoyl)piperidin-3-yl)-4-(3,5-dimethylphenyl)-4-hydroxybutylcarbamate I-4a 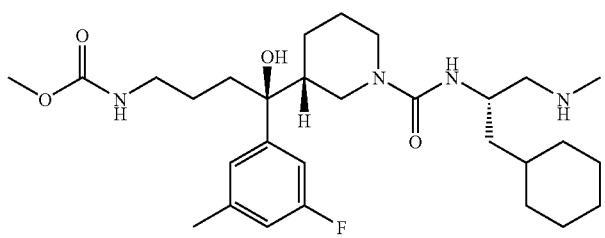 [SMILES: CNC[C@H](CC1CCCCC1)NC(=O)N1CCC[C@@H]([C@@](O)(CCCNC(=O)OC)c2cc(C)cc(F)c2)C1] methyl (S)-4-((R)-1-((S)-1-cyclohexyl-3-(methylamino)propan-2-ylcarbamoyl)piperidin-3-yl)-4-(3-fluoro-5-methylphenyl)-4-hydroxybutylcarbamate I-5a 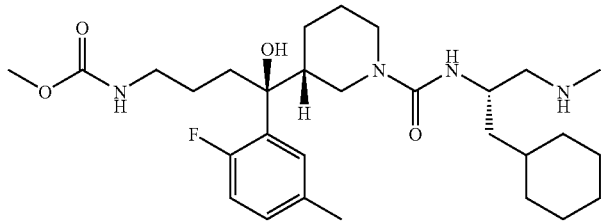 [SMILES: CNC[C@H](CC1CCCCC1)NC(=O)N1CCC[C@@H]([C@@](O)(CCCNC(=O)OC)c2cc(C)ccc2F)C1] methyl (S)-4-((R)-1-((S)-1-cyclohexyl-3-(methylamino)propan-2-ylcarbamoyl)piperidin-3-yl)-4-(2-fluoro-5-methylphenyl)-4-hydroxybutylcarbamate I-6a 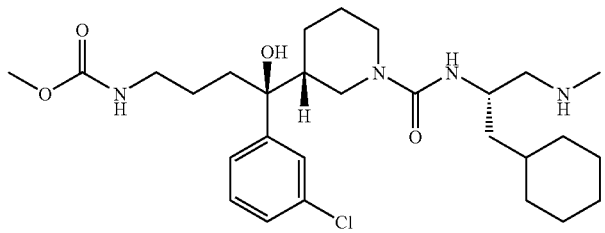 methyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate

| | | |
|---|---|---|
| I-7a | 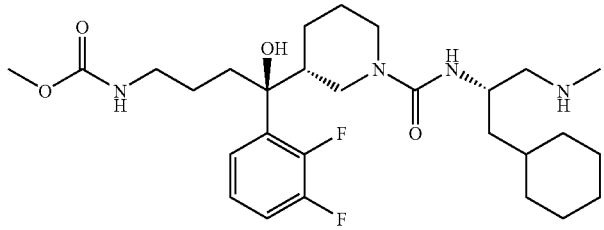 | methyl (S)-4-((R)-1-((S)-1-cyclohexyl-3-(methylamino)propan-2-ylcarbamoyl)piperidin-3-yl)-4-(2,3-difluorophenyl)-4-hydroxybutylcarbamate |
| I-7b | 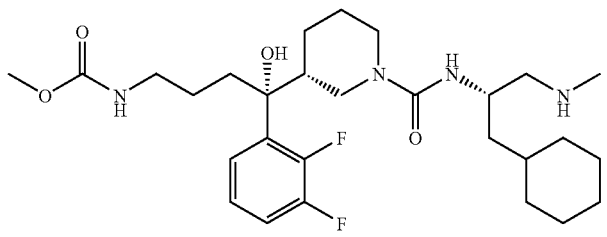 [SMILES: CNC[C@H](CC1CCCCC1)NC(=O)N1CCC[C@@H]([C@](O)(CCCNC(=O)OC)c2cccc(F)c2F)C1] | methyl (R)-4-((R)-1-((S)-1-cyclohexyl-3-(methylamino)propan-2-ylcarbamoyl)piperidin-3-yl)-4-(2,3-difluorophenyl)-4-hydroxybutylcarbamate |
| I-8a | 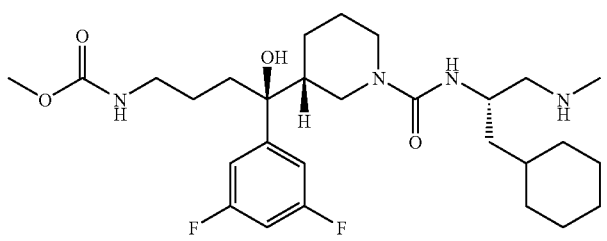 [SMILES: CNC[C@H](CC1CCCCC1)NC(=O)N1CCC[C@@H]([C@@](O)(CCCNC(=O)OC)c2cc(F)cc(F)c2)C1] | methyl (S)-4-((R)-1-((S)-1-cyclohexyl-3-(methylamino)propan-2-ylcarbamoyl)piperidin-3-yl)-4-(3,5-difluorophenyl)-4-hydroxybutylcarbamate |
| I-9a | 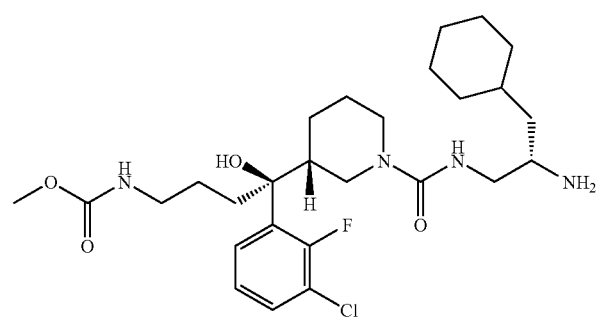 [SMILES: COC(=O)NCCC[C@@](O)(c1cccc(Cl)c1F)[C@@H]1CCCN(C(=O)NC[C@@H](N)CC2CCCCC2)C1] | methyl (S)-4-((R)-1-((S)-2-amino-3-cyclohexylpropylcarbamoyl)piperidin-3-yl)-4-(3-chloro-2-fluorophenyl)-4-hydroxybutylcarbamate |
| I-10a | 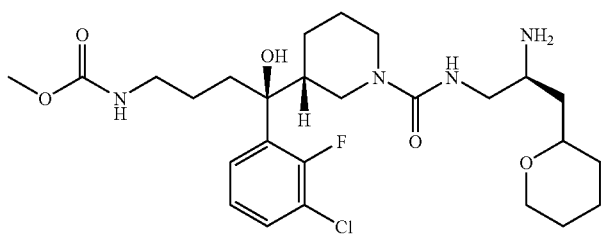 [SMILES: COC(=O)NCCC[C@@](O)(c1cccc(Cl)c1F)[C@@H]1CCCN(C(=O)NC[C@@H](N)CC2CCCCO2)C1] | methyl (4S)-4-((3R)-1-((2S)-2-amino-3-(tetrahydro-2H-pyran-2-yl)propylcarbamoyl)piperidin-3-yl)-4-(3-chloro-2-fluorophenyl)-4-hydroxybutylcarbamate |
| I-11a | 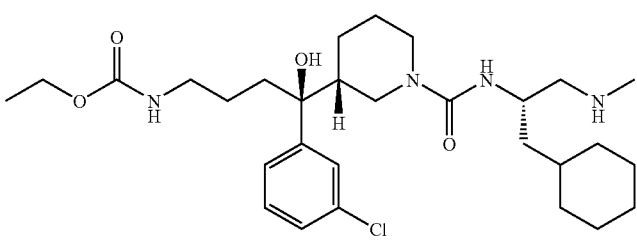 [SMILES: CCOC(=O)NCCC[C@@](O)(c1cccc(Cl)c1)[C@@H]1CCCN(C(=O)N[C@H](CNC)CC2CCCCC2)C1] | ethyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate |

| | | |
|---|---|---|
| I-12a | 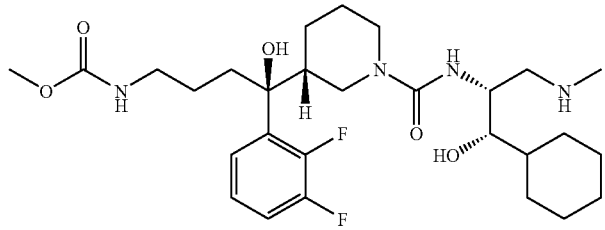 [SMILES: CNC[C@@H](NC(=O)N1CCC[C@@H]([C@@](O)(CCCNC(=O)OC)c2cccc(F)c2F)C1)[C@@H](O)C1CCCCC1] | methyl (S)-4-((R)-1-((1S,2R)-1-cyclohexyl-1-hydroxy-3-(methylamino)propan-2-ylcarbamoyl)piperidin-3-yl)-4-(2,3-difluorophenyl)-4-hydroxybutylcarbamate |
| I-13a | 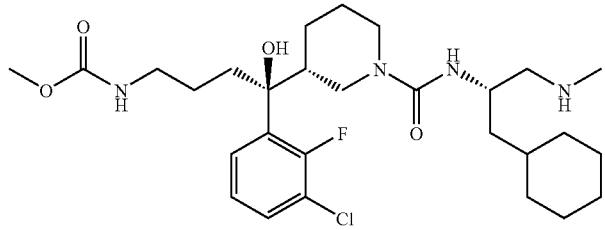 [SMILES: CNC[C@H](CC1CCCCC1)NC(=O)N1CCC[C@@H]([C@@](O)(CCCNC(=O)OC)c2cccc(Cl)c2F)C1] | methyl (S)-4-(3-chloro-2-fluorophenyl)-4-((R)-1-((S)-1-cyclohexyl-3-(methylamino)propan-2-ylcarbamoyl)piperidin-3-yl)-4-hydroxybutylcarbamate |
| I-14a | 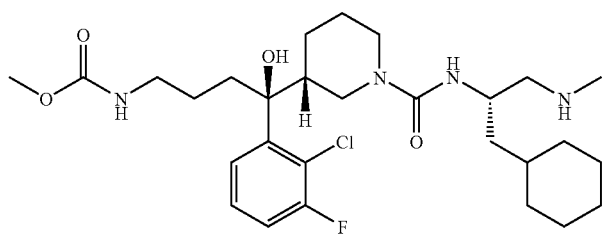 | methyl (S)-4-(2-chloro-3-fluorophenyl)-4-((R)-1-((S)-1-cyclohexyl-3-(methylamino)propan-2-ylcarbamoyl)piperidin-3-yl)-4-hydroxybutylcarbamate |
| I-15a | 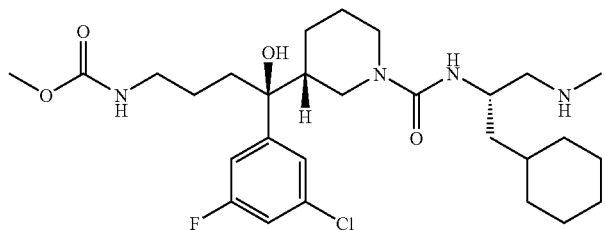 | methyl (S)-4-(3-chloro-5-fluorophenyl)-4-((R)-1-((S)-1-cyclohexyl-3-(methylamino)propan-2-ylcarbamoyl)piperidin-3-yl)-4-hydroxybutylcarbamate |
| I-16a | 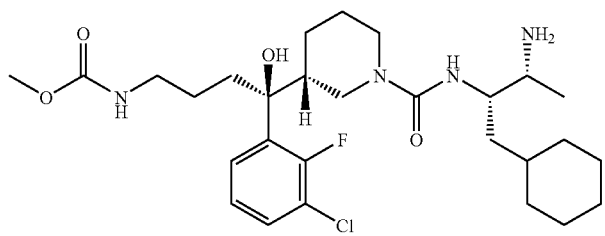 [SMILES: COC(=O)NCCC[C@@](O)(c1cccc(Cl)c1F)[C@@H]1CCCN(C(=O)N[C@@H](CC2CCCCC2)[C@@H](C)N)C1] | methyl (S)-4-((R)-1-((2S,3R)-3-amino-1-cyclohexylbutan-2-ylcarbamoyl)piperidin-3-yl)-4-(3-chloro-2-fluorophenyl)-4-hydroxybutylcarbamate |
| I-17a | 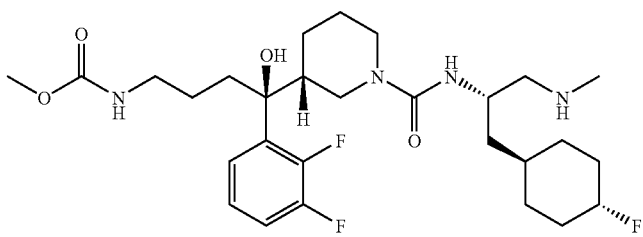 [SMILES: CNC[C@H](C[C@H]1CC[C@H](F)CC1)NC(=O)N1CCC[C@@H]([C@@](O)(CCCNC(=O)OC)c2cccc(F)c2F)C1] | methyl (S)-4-(2,3-difluorophenyl)-4-((R)-1-((S)-1-(trans-4-fluorocyclohexyl)-3-(methylamino)propan-2-ylcarbamoyl)piperidin-3-yl)-4-hydroxybutylcarbamate |

| | | |
|---|---|---|
| I-18a | 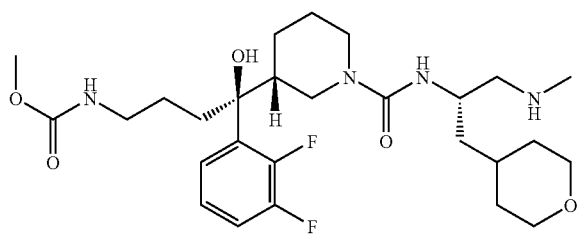 [SMILES: CNC[C@H](CC1CCOCC1)NC(=O)N1CCC[C@@H]([C@@](O)(CCCNC(=O)OC)c2cccc(F)c2F)C1] | methyl (S)-4-(3-chloro-2-fluorophenyl)-4-hydroxy-4-((R)-1-((S)-1-(methylamino)-3-(tetrahydro-2H-pyran-4-yl)propan-2-ylcarbamoyl)piperidin-3-yl)butylcarbamate |
| I-19a | 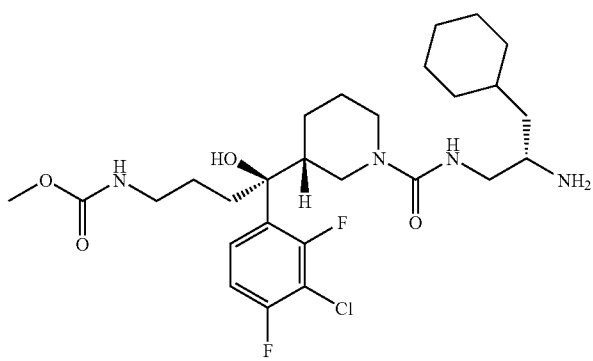 [SMILES: COC(=O)NCCC[C@@](O)(c1ccc(F)c(Cl)c1F)[C@@H]1CCCN(C(=O)NC[C@@H](N)CC2CCCCC2)C1] | methyl (S)-4-((R)-1-((S)-2-amino-3-cyclohexylpropylcarbamoyl)piperidin-3-yl)-4-(3-chloro-2,4-difluorophenyl)-4-hydroxybutylcarbamate |
| I-20a | 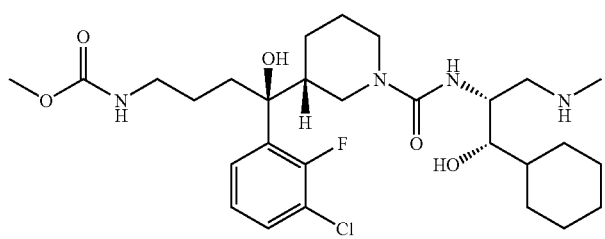 [SMILES: CNC[C@@H](NC(=O)N1CCC[C@@H]([C@@](O)(CCCNC(=O)OC)c2cccc(Cl)c2F)C1)[C@@H](O)C1CCCCC1] | methyl (S)-4-(3-chloro-2-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate |
| I-21a | 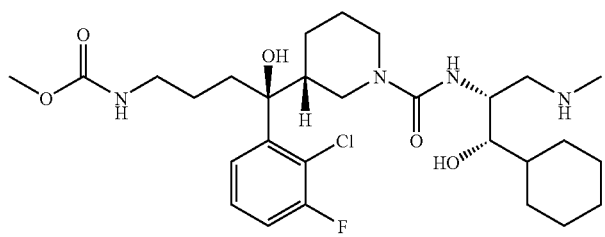 [SMILES: CNC[C@@H](NC(=O)N1CCC[C@@H]([C@@](O)(CCCNC(=O)OC)c2cccc(F)c2Cl)C1)[C@@H](O)C1CCCCC1] | methyl (S)-4-(2-chloro-3-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate |
| I-22a | 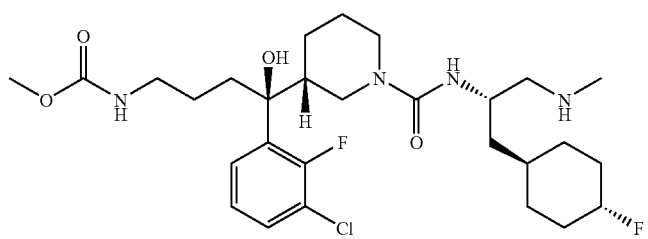 [SMILES: CNC[C@H](C[C@H]1CC[C@H](F)CC1)NC(=O)N1CCC[C@@H]([C@@](O)(CCCNC(=O)OC)c2cccc(Cl)c2F)C1] | methyl (S)-4-(3-chloro-2-fluorophenyl)-4-((R)-1-((S)-1-(trans-4-fluorocyclohexyl)-3-(methylamino)propan-2-ylcarbamoyl)piperidin-3-yl)-4-hydroxybutylcarbamate |
| I-23a | 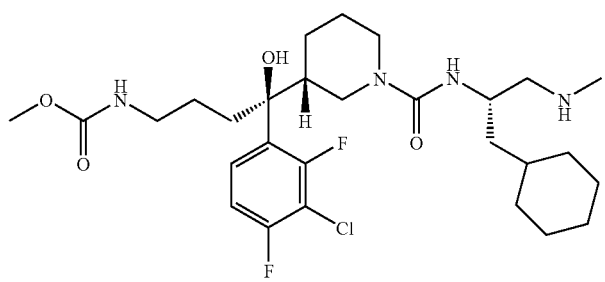 | methyl (S)-4-(3-chloro-2,4-difluorophenyl)-4-((R)-1-((S)-1-cyclohexyl-3-(methylamino)propan-2-ylcarbamoyl)piperidin-3-yl)-4-hydroxybutylcarbamate |

-continued

| | | |
|---|---|---|
| I-24a | 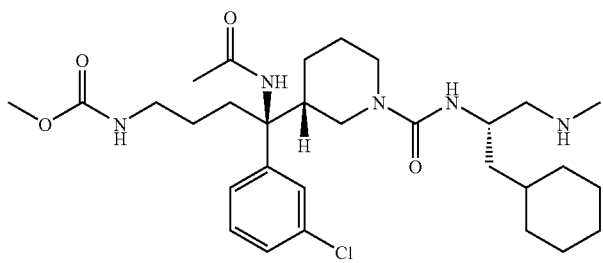 [SMILES: CNC[C@H](CC1CCCCC1)NC(=O)N1CCC[C@@H]([C@](CCCNC(=O)OC)(NC(C)=O)c2cccc(Cl)c2)C1] | methyl (S)-4-acetamido-4-(3-chlorophenyl)-4-((R)-1-((S)-1-cyclohexyl-3-(methylamino)propan-2-ylcarbamoyl)piperidin-3-yl)butylcarbamate |
| I-25a | 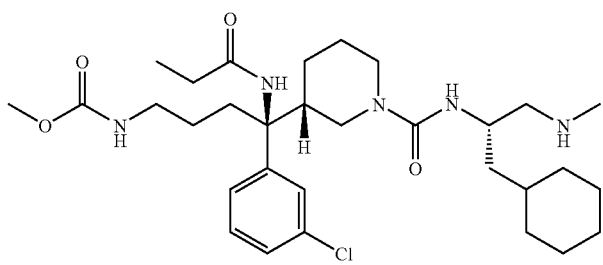 [SMILES: CCC(=O)N[C@](CCCNC(=O)OC)(c1cccc(Cl)c1)[C@@H]1CCCN(C(=O)N[C@H](CNC)CC2CCCCC2)C1] | methyl (S)-4-(3-chlorophenyl)-4-((R)-1-((S)-1-cyclohexyl-3-(methylamino)propan-2-ylcarbamoyl)piperidin-3-yl)-4-propionamidobutylcarbamate |
| I-25b | 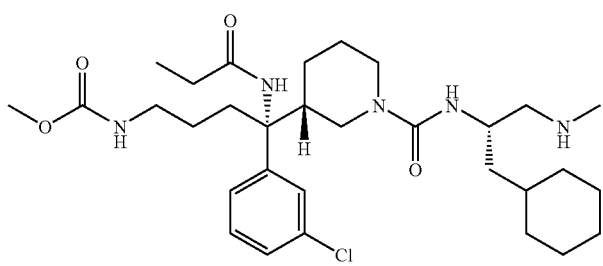 [SMILES: CCC(=O)N[C@@](CCCNC(=O)OC)(c1cccc(Cl)c1)[C@@H]1CCCN(C(=O)N[C@H](CNC)CC2CCCCC2)C1] | methyl (R)-4-(3-chlorophenyl)-4-((R)-1-((S)-1-cyclohexyl-3-(methylamino)propan-2-ylcarbamoyl)piperidin-3-yl)-4-propionamidobutylcarbamate |
| I-26a | 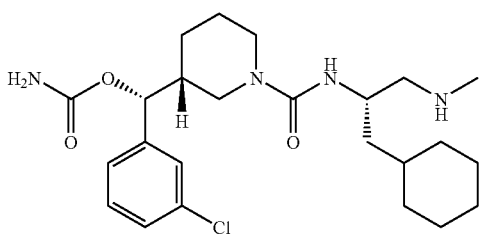 [SMILES: CNC[C@H](CC1CCCCC1)NC(=O)N1CCC[C@@H]([C@@H](OC(N)=O)c2cccc(Cl)c2)C1] | (R)-(3-chlorophenyl)((R)-1-((S)-1-cyclohexyl-3-(methylamino)propan-2-ylcarbamoyl)piperidin-3-yl)methyl carbamate |
| I-27a | 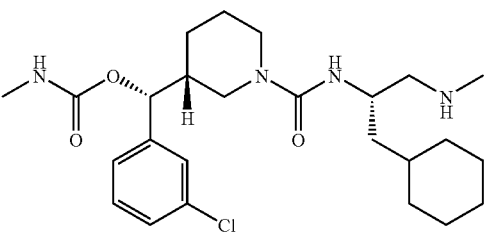 [SMILES: CNC[C@H](CC1CCCCC1)NC(=O)N1CCC[C@@H]([C@@H](OC(=O)NC)c2cccc(Cl)c2)C1] | (R)-(3-chlorophenyl)((R)-1-((S)-1-cyclohexyl-3-(methylamino)propan-2-ylcarbamoyl)piperidin-3-yl)methyl methylcarbamate |
| I-28a | 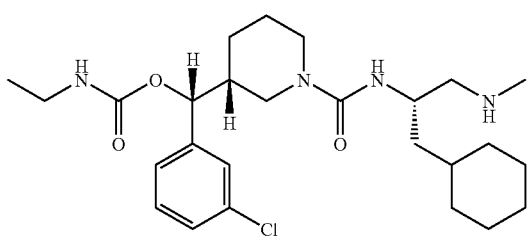 [SMILES: CCNC(=O)O[C@@H](c1cccc(Cl)c1)[C@@H]1CCCN(C(=O)N[C@H](CNC)CC2CCCCC2)C1] | (R)-(3-chlorophenyl)((R)-1-((S)-1-cyclohexyl-3-(methylamino)propan-2-ylcarbamoyl)piperidin-3-yl)methyl ethylcarbamate |

I-28b 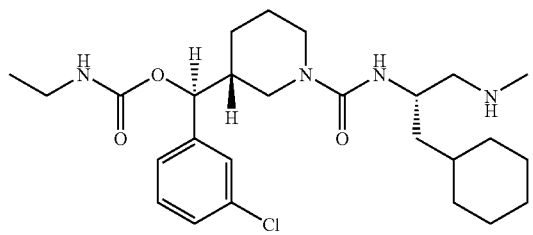 [SMILES: CCNC(=O)O[C@H](c1cccc(Cl)c1)[C@@H]1CCCN(C(=O)N[C@H](CNC)CC2CCCCC2)C1] (S)-(3-chlorophenyl)((R)-1-((S)-1-cyclohexyl-3-(methylamino)propan-2-ylcarbamoyl)piperidin-3-yl)methyl ethylcarbamate I-29a 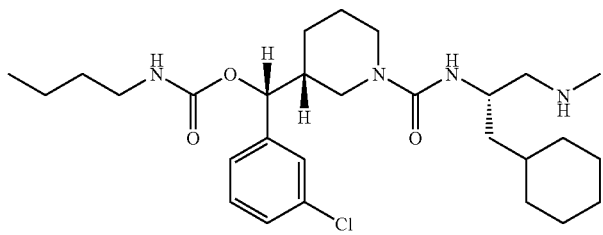 [SMILES: CCCCNC(=O)O[C@@H](c1cccc(Cl)c1)[C@@H]1CCCN(C(=O)N[C@H](CNC)CC2CCCCC2)C1] (R)-(3-chlorophenyl)((R)-1-((S)-1-cyclohexyl-3-(methylamino)propan-2-ylcarbamoyl)piperidin-3-yl)methyl butylcarbamate I-29b 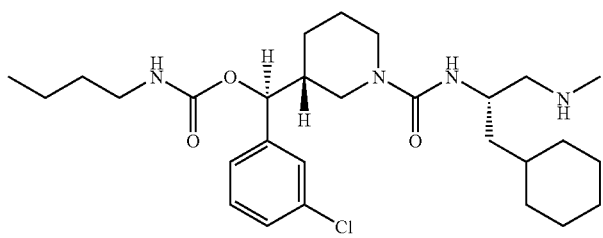 [SMILES: CCCCNC(=O)O[C@H](c1cccc(Cl)c1)[C@@H]1CCCN(C(=O)N[C@H](CNC)CC2CCCCC2)C1] (S)-(3-chlorophenyl)((R)-1-((S)-1-cyclohexyl-3-(methylamino)propan-2-ylcarbamoyl)piperidin-3-yl)methyl butylcarbamate I-30a 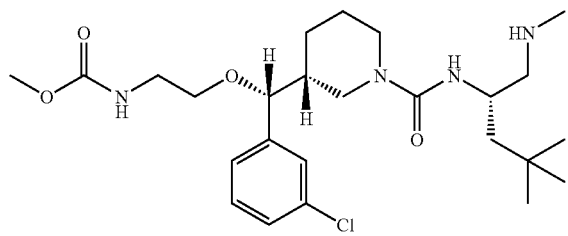 methyl 2-((R)-(3-chlorophenyl)((R)-1-((S)-4,4-dimethyl-1-(methylamino)pentan-2-ylcarbamoyl)piperidin-3-yl)methoxy)ethylcarbamate I-31a 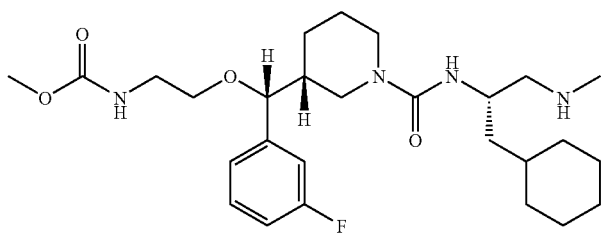 [SMILES: CNC[C@H](CC1CCCCC1)NC(=O)N1CCC[C@@H]([C@@H](OCCNC(=O)OC)c2cccc(F)c2)C1] methyl 2-((R)-((R)-1-((S)-1-cyclohexyl-3-(methylamino)propan-2-ylcarbamoyl)piperidin-3-yl)(3-fluorophenyl)methoxy)ethylcarbamate I-32a 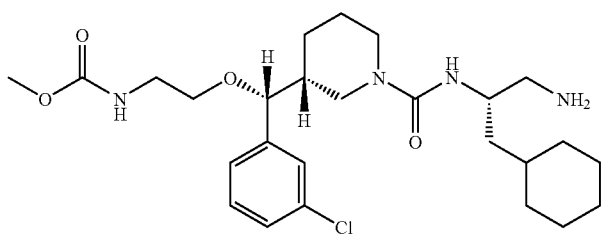 [SMILES: COC(=O)NCCO[C@@H](c1cccc(Cl)c1)[C@@H]1CCCN(C(=O)N[C@H](CN)CC2CCCCC2)C1] methyl 2-((R)-((R)-1-((S)-1-amino-3-cyclohexylpropan-2-ylcarbamoyl)piperidin-3-yl)(3-chlorophenyl)methoxy)ethylcarbamate

| | | |
|---|---|---|
| I-34a | 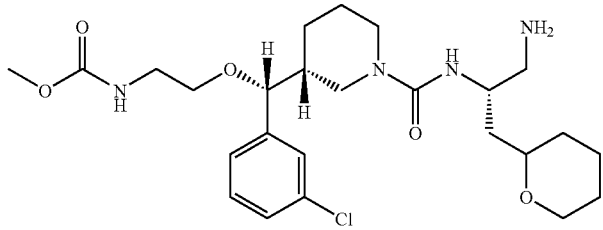 [SMILES: COC(=O)NCCO[C@@H](c1cccc(Cl)c1)[C@@H]1CCCN(C(=O)N[C@H](CN)CC2CCCCO2)C1] | methyl 2-((1R)-((3R)-1-((2S)-1-amino-3-(tetrahydro-2H-pyran-2-yl)propan-2-ylcarbamoyl)piperidin-3-yl)(3-chlorophenyl)methoxy)ethylcarbamate |
| I-35a | 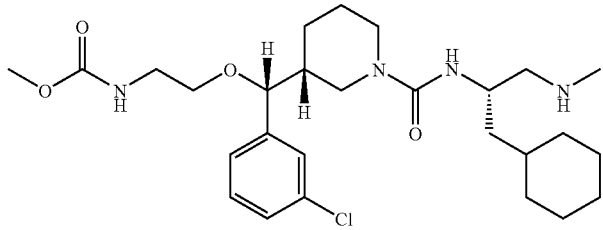 | methyl 2-((R)-(3-chlorophenyl)((R)-1-((S)-1-cyclohexyl-3-(methylamino)propan-2-ylcarbamoyl)piperidin-3-yl)methoxy)ethylcarbamate |
| I-36a | 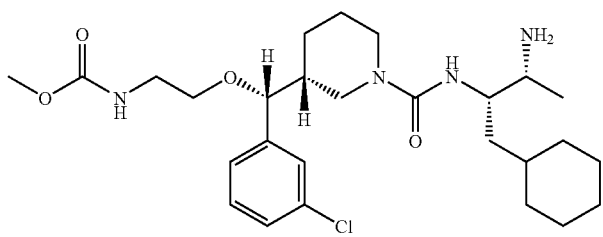 [SMILES: COC(=O)NCCO[C@@H](c1cccc(Cl)c1)[C@@H]1CCCN(C(=O)N[C@@H](CC2CCCCC2)[C@@H](C)N)C1] | methyl 2-((R)-((R)-1-((2S,3R)-3-amino-1-cyclohexylbutan-2-ylcarbamoyl)piperidin-3-yl)(3-chlorophenyl)methoxy)ethylcarbamate |
| I-37a | 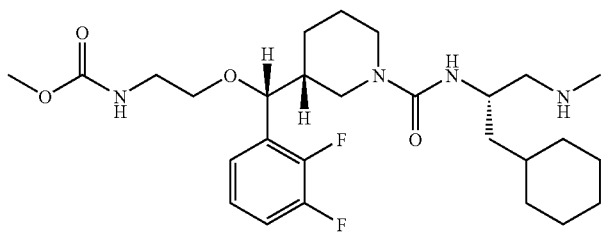 [SMILES: CNC[C@H](CC1CCCCC1)NC(=O)N1CCC[C@@H]([C@@H](OCCNC(=O)OC)c2cccc(F)c2F)C1] | methyl 2-((R)-((3R)-1-((2S)-1-cyclohexyl-3-(methylamino)propan-2-ylcarbamoyl)piperidin-3-yl)(2,3-difluorophenyl)methoxy)ethylcarbamate |
| I-38a | 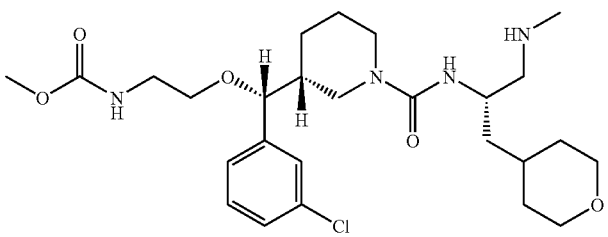 [SMILES: CNC[C@H](CC1CCOCC1)NC(=O)N1CCC[C@@H]([C@@H](OCCNC(=O)OC)c2cccc(Cl)c2)C1] | methyl 2-((R)-(3-chlorophenyl)((R)-1-((S)-1-methylamino)-3-(tetrahydro-2H-pyran-4-yl)propan-2-ylcarbamoyl)piperidin-3-yl)methoxy)ethylcarbamate |
| I-38b | 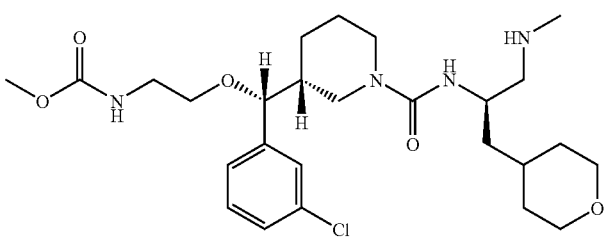 [SMILES: CNC[C@@H](CC1CCOCC1)NC(=O)N1CCC[C@@H]([C@@H](OCCNC(=O)OC)c2cccc(Cl)c2)C1] | methyl 2-((R)-(3-chlorophenyl)((R)-1-((R)-1-(methylamino)-3-(tetrahydro-2H-pyran-4-yl)propan-2-ylcarbamoyl)piperidin-3-yl)methoxy)ethylcarbamate |

| | | |
|---|---|---|
| I-39a | 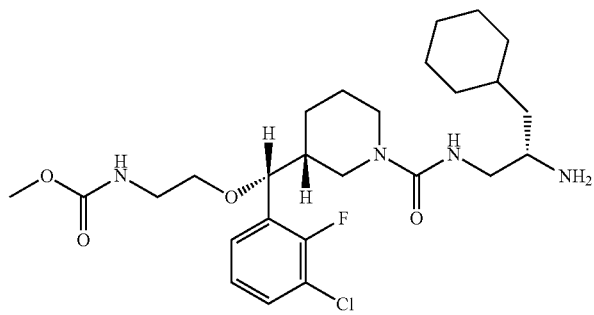 [SMILES: COC(=O)NCCO[C@@H](c1cccc(Cl)c1F)[C@@H]1CCCN(C(=O)NC[C@@H](N)CC2CCCCC2)C1] | methyl 2-((R)-((R)-1-((S)-2-amino-3-cyclohexylpropylcarbamoyl)piperidin-3-yl)(3-chloro-2-fluorophenyl)methoxy)ethylcarbamate |
| I-41a | 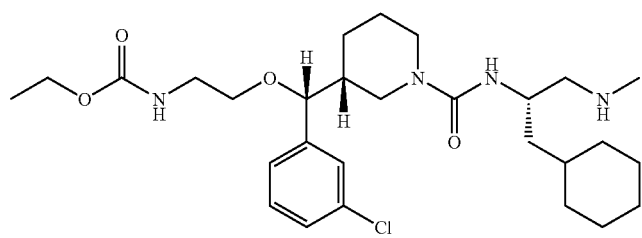 | ethyl 2-((R)-(3-chlorophenyl)((R)-1-((S)-1-cyclohexyl-3-(methylamino)propan-2-ylcarbamoyl)piperidin-3-yl)methoxy)ethylcarbamate |
| I-42a | 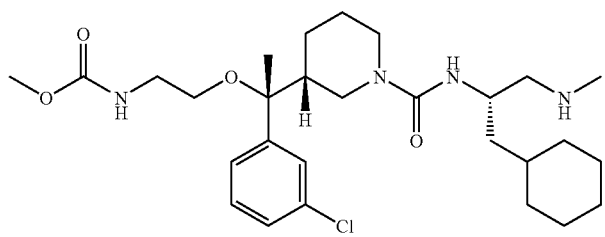 | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate |
| I-43a | 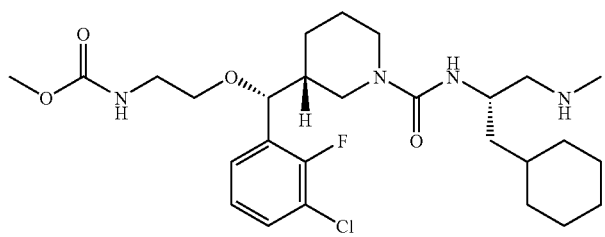 | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-44a | 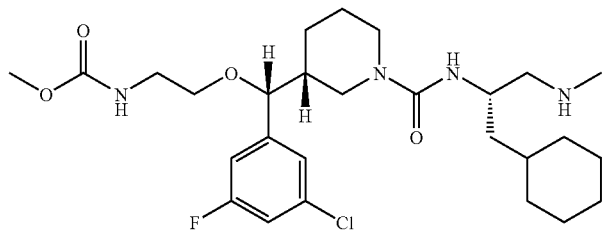 | methyl 2-((R)-(3-chloro-5-fluorophenyl)((R)-1-((S)-1-cyclohexyl-3-(methylamino)propan-2-ylcarbamoyl)piperidin-3-yl)methoxy)ethylcarbamate |
| I-45a | 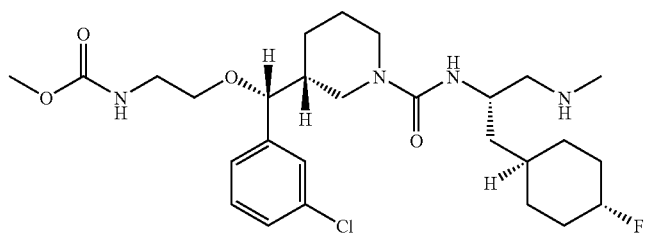 [SMILES: CNC[C@H](C[C@H]1CC[C@H](F)CC1)NC(=O)N1CCC[C@@H]([C@@H](OCCNC(=O)OC)c2cccc(Cl)c2)C1] | methyl 2-((R)-(3-chlorophenyl)((R)-1-((S)-1-(trans-4-fluorocyclohexyl)-3-(methylamino)propan-2-ylcarbamoyl)piperidin-3-yl)methoxy)ethylcarbamate |

| | | |
|---|---|---|
| I-46a | 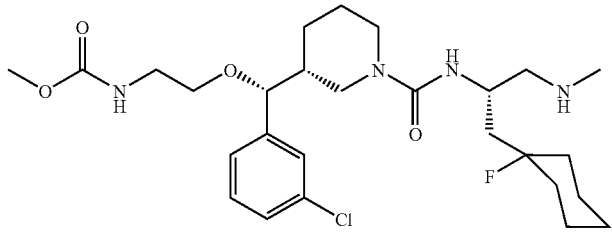 [SMILES: CNC[C@H](CC1(F)CCCCC1)NC(=O)N1CCC[C@@H]([C@@H](OCCNC(=O)OC)c2cccc(Cl)c2)C1] | methyl 2-((R)-(3-chlorophenyl)((R)-1-((S)-1-(1-fluorocyclohexyl)-3-(methylamino)propan-2-ylcarbamoyl)piperidin-3-yl)methoxy)ethylcarbamate |
| I-47a | 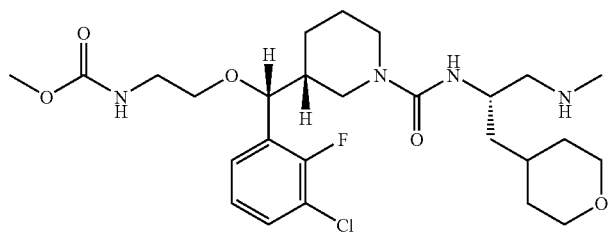 | methyl 2-((R)-(3-chloro-2-fluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I-47b | 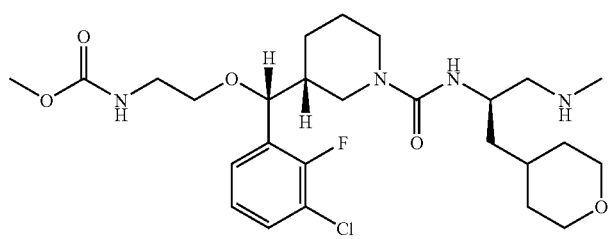 | methyl 2-((R)-(3-chloro-2-fluorophenyl)((R)-1-((R)-1-(methylamino)-3-(tetrahydro-2H-pyran-4-yl)propan-2-ylcarbamoyl)piperidin-3-yl)methoxy)ethylcarbamate |
| I-48a | 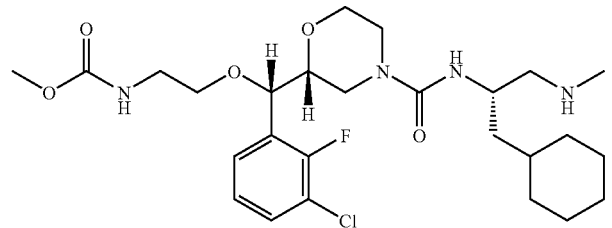 | methyl 2-((S)-(3-chloro-2-fluorophenyl)((R)-4-((S)-1-cyclohexyl-3-(methylamino)propan-2-ylcarbamoyl)morpholin-2-yl)methoxy)ethylcarbamate |
| I-49a | 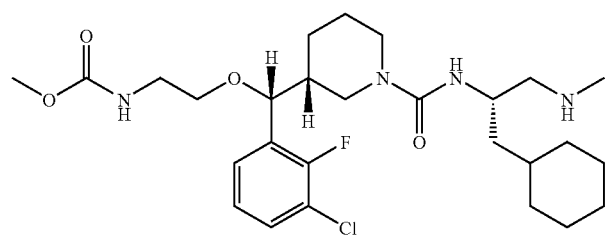 | ethyl 2-((R)-(3-chloro-2-fluorophenyl)((3R)-1-((2S)-1-cyclohexyl-3-(methylamino)propan-2-ylcarbamoyl)piperidin-3-yl)methoxy)ethylcarbamate |
| I-50a | 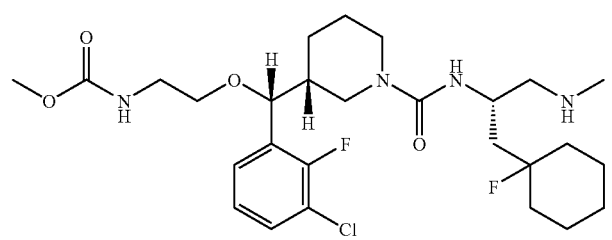 | methyl 2-((1R)-(3-chloro-2-fluorophenyl)((3R)-1-(1-(1-fluorocyclohexyl)-3-(methylamino)propan-2-ylcarbamoyl)piperidin-3-yl)methoxy)ethylcarbamate |

| | | |
|---|---|---|
| I-51a | 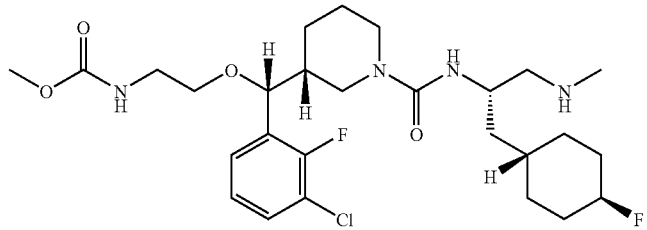 [SMILES: CNC[C@H](C[C@H]1CC[C@H](F)CC1)NC(=O)N1CCC[C@@H]([C@@H](OCCNC(=O)OC)c2cccc(Cl)c2F)C1] | methyl 2-((R)-(3-chloro-2-fluorophenyl)((R)-1-((S)-1-(trans-4-fluorocyclohexyl)-3-(methylamino)propan-2-ylcarbamoyl)piperidin-3-yl)methoxy)ethylcarbamate |
| I-52a | 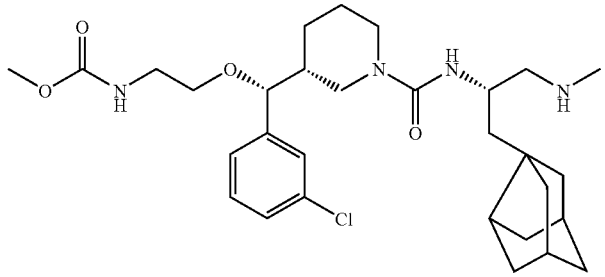 | methyl 2-((R)-(3-chlorophenyl)((R)-1-((S)-1-(3-noradamantyl)-3-(methylamino)propan-2-ylcarbamoyl)piperidin-3-yl)methoxy)ethylcarbamate |
| I-53a | 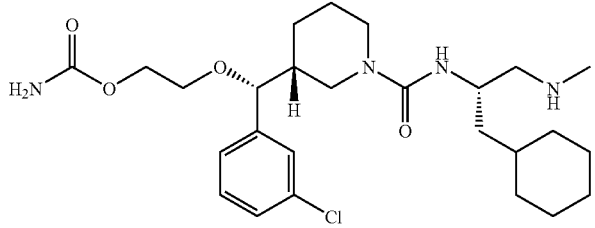 [SMILES: CNC[C@H](CC1CCCCC1)NC(=O)N1CCC[C@@H]([C@@H](OCCOC(N)=O)c2cccc(Cl)c2)C1] | 2-((R)-(3-chlorophenyl)((R)-1-((S)-1-cyclohexyl-3-(methylamino)propan-2-ylcarbamoyl)piperidin-3-yl)methoxy)ethyl carbamate |
| I-54a | 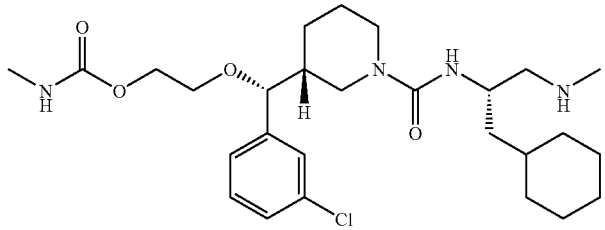 | 2-((R)-(3-chlorophenyl)((R)-1-((S)-1-cyclohexyl-3-(methylamino)propan-2-ylcarbamoyl)piperidin-3-yl)methoxy)ethyl methylcarbamate |
| I-55a | 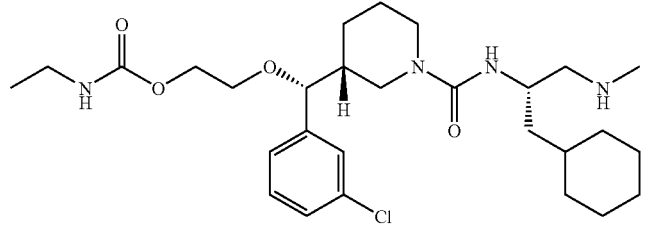 [SMILES: CCNC(=O)OCCO[C@@H](c1cccc(Cl)c1)[C@@H]1CCCN(C(=O)N[C@H](CNC)CC2CCCCC2)C1] | 2-((R)-(3-chlorophenyl)((R)-1-((S)-1-cyclohexyl-3-(methylamino)propan-2-ylcarbamoyl)piperidin-3-yl)methoxy)ethyl ethylcarbamate |
| I-56a | 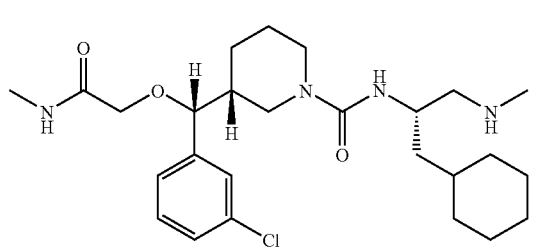 | (3R)-3-((R)-(3-chlorophenyl)(2-(methylamino)-2-oxoethoxy)methyl)-N-((S)-1-cyclohexyl-3-(methylamino)propan-2-yl)piperidine-1-carboxamide |

I-56b 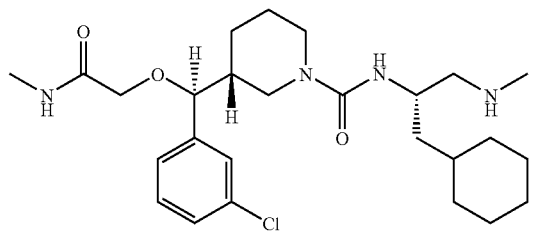 (3R)-3-((S)-(3-chlorophenyl)(2-(methylamino)-2-oxoethoxy)methyl)-N-((S)-1-cyclohexyl-3-(methylamino)propan-2-yl)piperidine-1-carboxamide I-57a 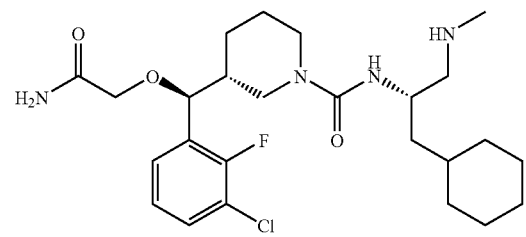 [SMILES: CNC[C@H](CC1CCCCC1)NC(=O)N1CCC[C@@H]([C@H](OCC(N)=O)c2cccc(Cl)c2F)C1] (3R)-3-((S)-(2-amino-2-oxoethoxy)(3-chloro-2-fluorophenyl)methyl)-N-((S)-1-cyclohexyl-3-(rnethylamino)propan-2-yl)piperidine-1-carboxamide I-58a 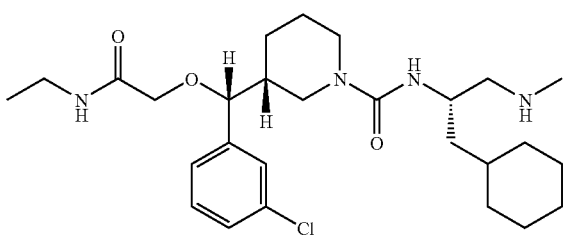 [SMILES: CCNC(=O)CO[C@@H](c1cccc(Cl)c1)[C@@H]1CCCN(C(=O)N[C@H](CNC)CC2CCCCC2)C1] (3R)-3-((R)-(3-chlorophenyl)(2-(ethylamino)-2-oxoethoxy)methyl)-N-((S)1-cyclohexyl-3-(methylamino)propan-2-yl)piperidine-1-carboxamide I-58b 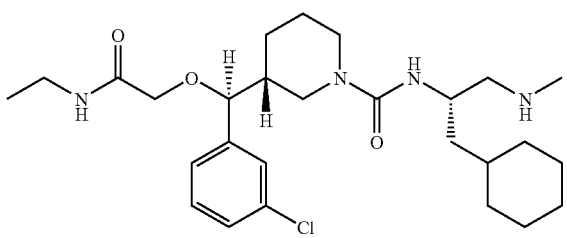 [SMILES: CCNC(=O)CO[C@H](c1cccc(Cl)c1)[C@@H]1CCCN(C(=O)N[C@H](CNC)CC2CCCCC2)C1] (3R)-3-((S)-(3-chlorophenyl)(2-(ethylamino)-2-oxoethoxy)methyl)-N-((S)-1-cyclohexyl-3-(methylamino)propan-2-yl)piperidine-1-carboxamide I-59a 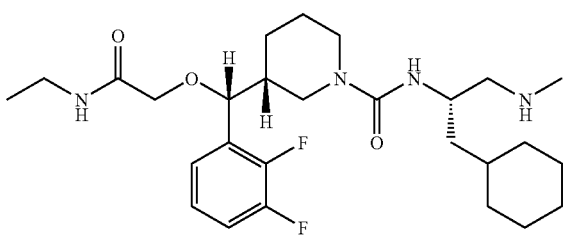 (3R)-N-((2S)-1-cyclohexyl-3-(methylamino)propan-2-yl)-3-((R)-(2,3-difluorophenyl)(2-(ethylamino)-2-oxoethoxy)methyl)piperidine-1-carboxamide I-60a 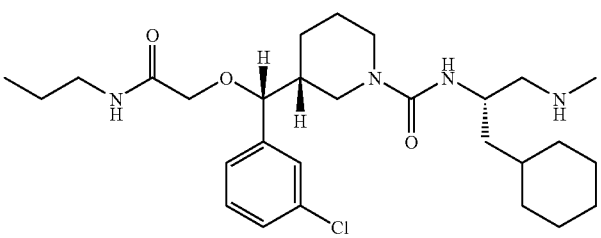 [SMILES: CCCNC(=O)CO[C@@H](c1cccc(Cl)c1)[C@@H]1CCCN(C(=O)N[C@H](CNC)CC2CCCCC2)C1] (3R)-3-((R)-(3-chlorophenyl)(2-oxo-2-(propylamino)ethoxy)methyl)-N-((S)-1-cyclohexyl-3-(methylamino)propan-2-yl)piperidine-1-carboxamide

| | | |
|---|---|---|
| I-61a | 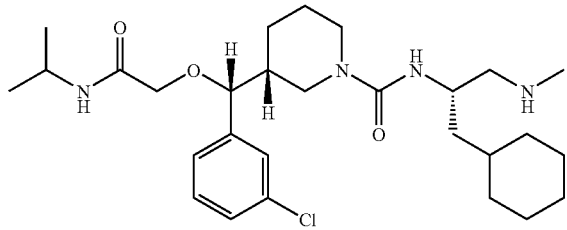 [SMILES: CNC[C@H](CC1CCCCC1)NC(=O)N1CCC[C@@H]([C@@H](OCC(=O)NC(C)C)c2cccc(Cl)c2)C1] | (3R)-3-((R)-(3-chlorophenyl)(2-(isopropylamino)-2-oxoethoxy)methyl)-N-((S)-1-cyclohexyl-3-(methylamino)propan-2-yl)piperidine-1-carboxamide |
| I-62a | 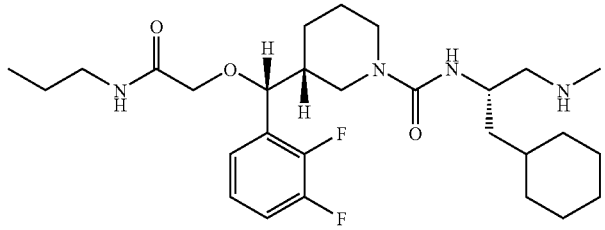 [SMILES: CCCNC(=O)CO[C@@H](c1cccc(F)c1F)[C@@H]1CCCN(C(=O)N[C@H](CNC)CC2CCCCC2)C1] | (3R)-N-((2S)-1-cyclohexyl-3-(methylamino)propan-2-yl)-3-((R)-(2,3-difluorophenyl)(2-oxo-2-(propylamino)ethoxy)methyl)piperidine-1-carboxamide |
| I-63a | 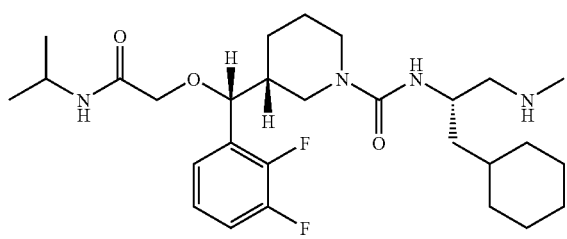 [SMILES: CNC[C@H](CC1CCCCC1)NC(=O)N1CCC[C@@H]([C@@H](OCC(=O)NC(C)C)c2cccc(F)c2F)C1] | (3R)-N-((S)-1-cyclohexyl-3-(methylamino)propan-2-yl)-3-((R)-(2,3-difluorophenyl)(2-(isopropylamino)-2-oxoethoxy)methyl)piperidine-1-carboxamide |
| I-64a | 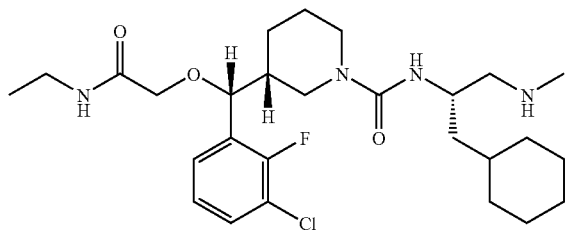 [SMILES: CCNC(=O)CO[C@@H](c1cccc(Cl)c1F)[C@@H]1CCCN(C(=O)N[C@H](CNC)CC2CCCCC2)C1] | (3R)-3-((R)-(3-chloro-2-fluorophenyl)(2-(ethylamino)-2-oxoethoxy)methyl)-N-((2S)-1-cyclohexyl-3-(methylamino)propan-2-yl)piperidine-1-carboxamide |
| I-65a | 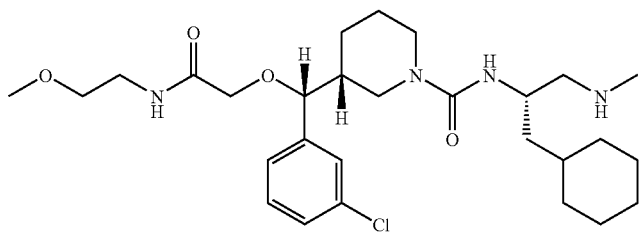 | (3R)-3-((R)-(3-chlorophenyl)(2-(2-methoxyethylamino)-2-oxoethoxy)methyl)-N-((S)-1-cyclohexyl-3-(methylamino)propan-2-yl)piperidine-1-carboxamide |
| I-66a | 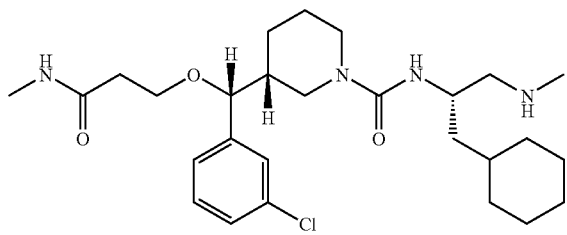 | (3R)-3-((R)-(3-chlorophenyl)(3-(methylamino)-3-oxopropoxy)methyl)-N-((S)-1-cyclohexyl-3-(methylamino)propan-2-yl)piperidine-1-carboxamide |

| | | |
|---|---|---|
| I-67a | 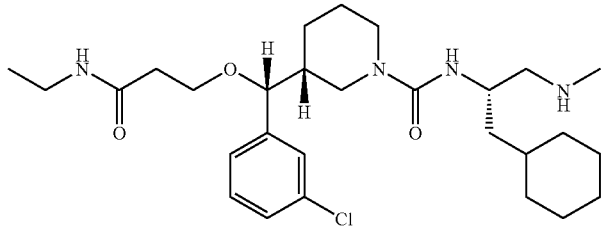 | (3R)-3-((R)-(3-chlorophenyl)(3-(ethylamino)-3-oxopropoxy)methyl)-N-((S)-1-cyclohexyl-3-(methylamino)propan-2-yl)piperidine-1-carboxamide |
| I-67b | 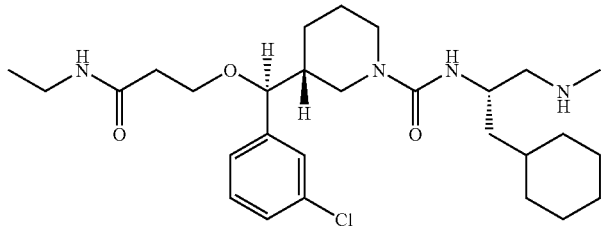 [SMILES: CCNC(=O)CCO[C@H](c1cccc(Cl)c1)[C@@H]1CCCN(C(=O)N[C@H](CNC)CC2CCCCC2)C1] | (3R)-3-((S)-(3-chlorophenyl)(3-(ethylamino)-3-oxopropoxy)methyl)-N-((S)-1-cyclohexyl-3-(methylamino)propan-2-yl)piperidine-1-carboxamide |
| I-68a | 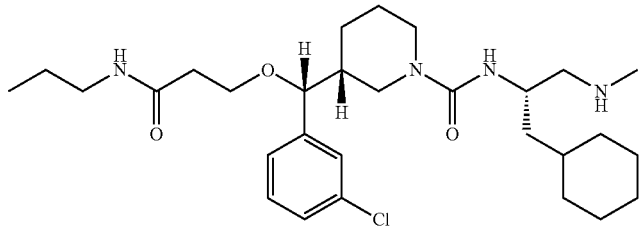 [SMILES: CCCNC(=O)CCO[C@@H](c1cccc(Cl)c1)[C@@H]1CCCN(C(=O)N[C@H](CNC)CC2CCCCC2)C1] | (3R)-3-((R)-(3-chlorophenyl)(3-oxo-3-propylamino)propoxy)methyl)-N-((2S)-1-cyclohexyl-3-(methylamino)propan-2-yl)piperidine-1-carboxamide |
| I-69a | 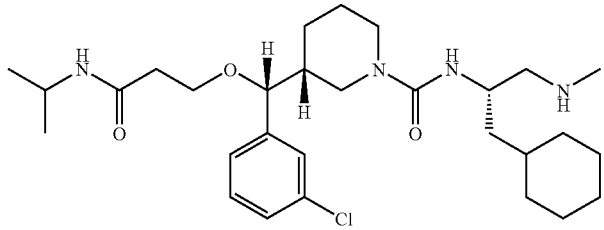 [SMILES: CNC[C@H](CC1CCCCC1)NC(=O)N1CCC[C@@H]([C@@H](OCCC(=O)NC(C)C)c2cccc(Cl)c2)C1] | (3R)-3-((R)-(3-chlorophenyl)(3-(isopropylamino)-3-oxopropoxy)methyl)-N-((S)-1-cyclohexyl-3-(methylamino)propan-2-yl)piperidine-1-carboxamide |
| I-70a | 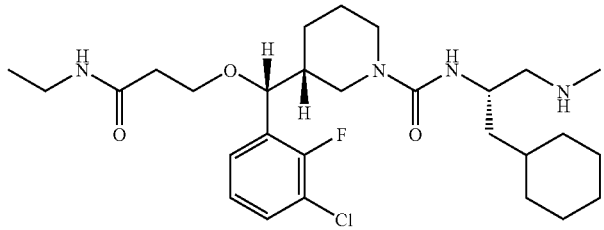 [SMILES: CCNC(=O)CCO[C@@H](c1cccc(Cl)c1F)[C@@H]1CCCN(C(=O)N[C@H](CNC)CC2CCCCC2)C1] | (3R)-3-((R)-(3-chloro-2-fluorophenyl)(3-(ethylamino)-3-oxopropoxy)methyl)-N-((S)-1-cyclohexyl-3-(methylamino)propan-2-yl)piperidine-1-carboxamide |
| I-71a | 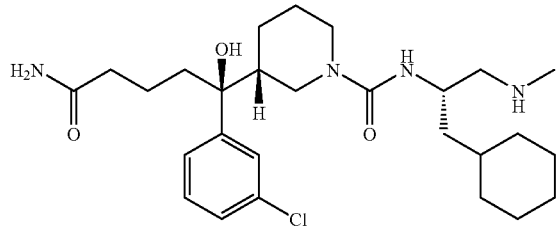 [SMILES: CNC[C@H](CC1CCCCC1)NC(=O)N1CCC[C@@H]([C@@](O)(CCCC(N)=O)c2cccc(Cl)c2)C1] | (3R)-3-((S)-5-amino-1-(3-chlorophenyl)-1-hydroxy-5-oxopentyl)-N-((S)-1-cyclohexyl-3-(methylamino)propan-2-yl)piperidine-1-carboxamide |

| | | |
|---|---|---|
| I-72a | 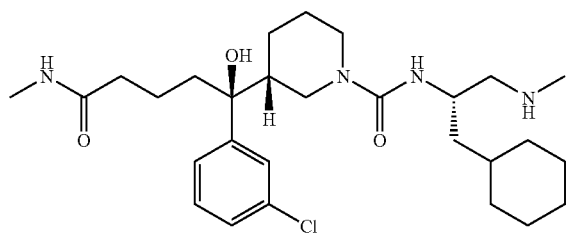 | (3R)-3-((S)-1-(3-chlorophenyl)-1-hydroxy-5-(methylamino)-5-oxopentyl)-N-((S)-1-cyclohexyl-3-(methylamino)propan-2-yl)piperidine-1-carboxamide |
| I-73a | 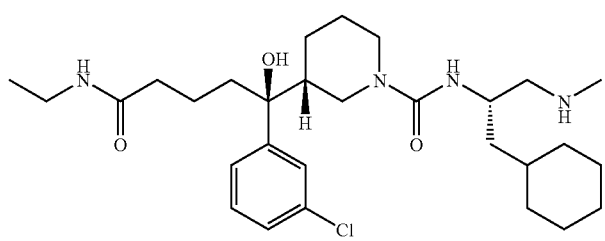 [SMILES: CCNC(=O)CCC[C@@](O)(c1cccc(Cl)c1)[C@@H]1CCCN(C(=O)N[C@H](CNC)CC2CCCCC2)C1] | (3R)-3-((S)-1-(3-chlorophenyl)-5-(ethylamino)-1-hydroxy-5-oxopentyl)-N-((S)-1-cyclohexyl-3-(methylamino)propan-2-yl)piperidine-1-carboxamide |
| I-74a | 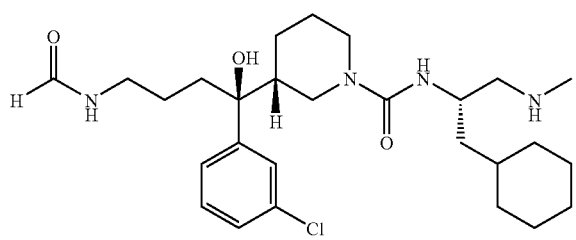 [SMILES: CNC[C@H](CC1CCCCC1)NC(=O)N1CCC[C@@H]([C@@](O)(CCCNC=O)c2cccc(Cl)c2)C1] | (3R)-3-((S)-1-(3-chlorophenyl)-4-formamido-1-hydroxybutyl)-N-((S)-1-cyclohexyl-3-(methylamino)propan-2-yl)piperidine-1-carboxamide |
| I-75a | 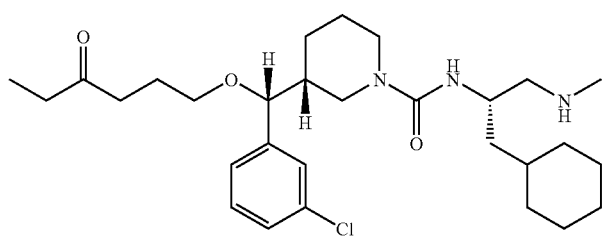 [SMILES: CCC(=O)CCCO[C@@H](c1cccc(Cl)c1)[C@@H]1CCCN(C(=O)N[C@H](CNC)CC2CCCCC2)C1] | (3R)-3-((R)-(3-chlorophenyl)(4-oxohexyloxy)methyl)-N-((S)-1-cyclohexyl-3-(methylamino)propan-2-yl)piperidine-1-carboxamide |
| I-76a | 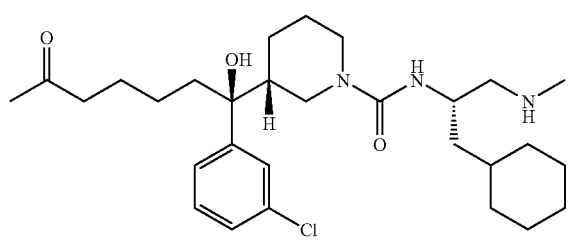 [SMILES: CNC[C@H](CC1CCCCC1)NC(=O)N1CCC[C@@H]([C@@](O)(CCCCC(C)=O)c2cccc(Cl)c2)C1] | (3R)-3-((S)-1-(3-chlorophenyl)-1-hydroxy-6-oxoheptyl)-N-((S)-1-cyclohexyl-3-(methylamino)propan-2-yl)piperidine-1-carboxamide |
| I-77a | 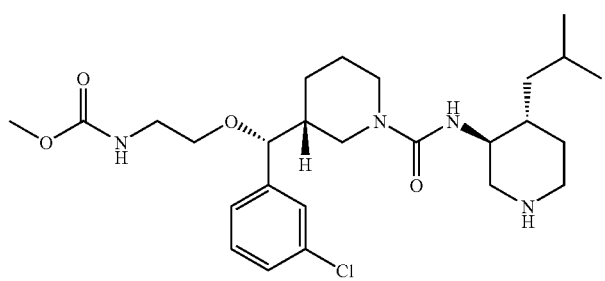 [SMILES: COC(=O)NCCO[C@@H](c1cccc(Cl)c1)[C@@H]1CCCN(C(=O)N[C@@H]2CNCC[C@H]2CC(C)C)C1] | methyl 2-((R)-(3-chlorophenyl)((R)-1-((3S,4R)-4-isobutylpiperidin-3-ylcarbamoyl)piperidin-3-yl)methoxy)ethylcarbamate |

| | | |
|---|---|---|
| I-78a | 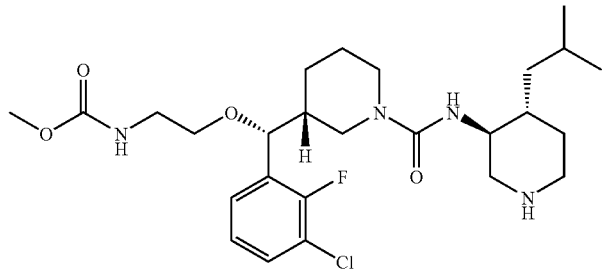 [SMILES: COC(=O)NCCO[C@@H](c1cccc(Cl)c1F)[C@@H]1CCCN(C(=O)N[C@@H]2CNCC[C@H]2CC(C)C)C1] | methyl 2-((R)-(3-chloro-2-fluorophenyl)((R)-1-((3S,4R)-4-isobutylpiperidin-3-ylcarbamoyl)piperidin-3-yl)methoxy)ethylcarbamate |
| I-79a | 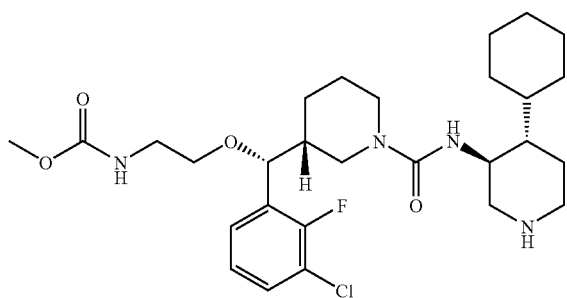 [SMILES: COC(=O)NCCO[C@@H](c1cccc(Cl)c1F)[C@@H]1CCCN(C(=O)N[C@@H]2CNCC[C@H]2C2CCCCC2)C1] | methyl 2-((R)-(3-chloro-2-fluorophenyl)((R)-1-((3S,4S)-4-cyclohexylpiperidin-3-ylcarbamoyl)piperidin-3-yl)methoxy)ethylcarbamate |
| I-80a | 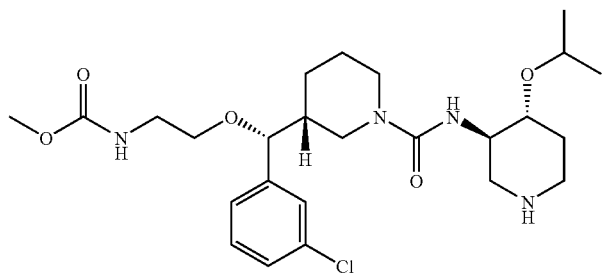 | methyl 2-((R)-(3-chlorophenyl)((R)-1-((3S,4S)-4-cyclopentylpiperidin-3-ylcarbamoyl)piperidin-3-yl)methoxy)ethylcarbamate |
| I-81a | 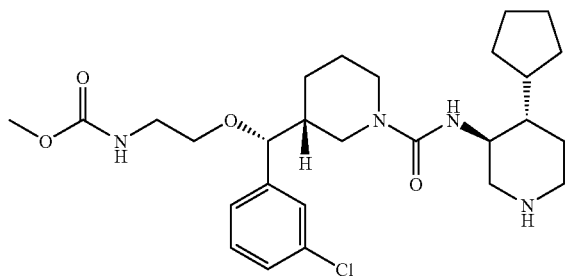 [SMILES: COC(=O)NCCO[C@@H](c1cccc(Cl)c1)[C@@H]1CCCN(C(=O)N[C@@H]2CNCC[C@H]2C2CCCC2)C1] | methyl 2-((R)-(3-chlorophenyl)((R)-1-((3R,4R)-4-cyclopentylpiperidin-3-ylcarbamoyl)piperidin-3-yl)methoxy)ethylcarbamate |
| I-82a | 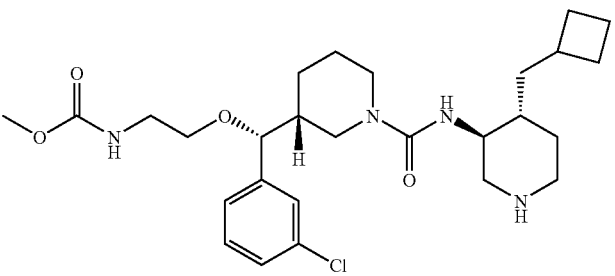 [SMILES: COC(=O)NCCO[C@@H](c1cccc(Cl)c1)[C@@H]1CCCN(C(=O)N[C@@H]2CNCC[C@H]2CC2CCC2)C1] | methyl 2-((R)-(3-chlorophenyl)((R)-1-((3S,4R)-4-(cyclobutylmethyl)piperidin-3-ylcarbamoyl)piperidin-3-yl)methoxy)ethylcarbamate |

| | |
|---|---|
| I-83a | 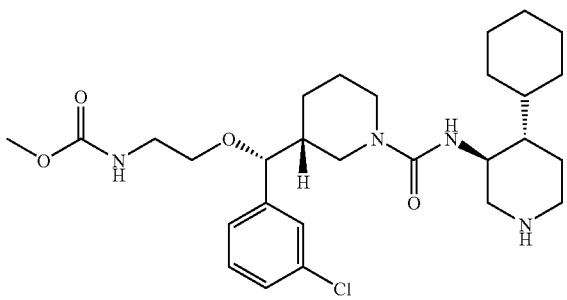 [SMILES: COC(=O)NCCO[C@@H](c1cccc(Cl)c1)[C@@H]1CCCN(C(=O)N[C@@H]2CNCC[C@H]2C2CCCCC2)C1] methyl 2-((R)-(3-chlorophenyl)((R)-1-((3S,4S)-4-cyclohexylpiperidin-3-ylcarbamoyl)piperidin-3-yl)methoxy)ethylcarbamate |

Another embodiment of the invention is each of the compounds listed below or their salts, especially their pharmaceutically acceptable salts:

| | |
|---|---|
| I-1a | methyl (S)-4-((R)-1-((S)-1-cyclohexyl-3-(methylamino)propan-2-ylcarbamoyl)piperidin-3-yl)-4-(2-fluorophenyl)-4-hydroxybutylcarbamate |
| I-2a | methyl (S)-4-(3-chloro-2-fluorophenyl)-4-((R)-1-((S)-4,4-dimethyl-1-(methylamino)pentan-2-ylcarbamoyl)piperidin-3-yl)-4-hydroxybutylcarbamate |
| I-3a | methyl (S)-4-((R)-1-((S)-1-cyclohexyl-3-(methylamino)propan-2-ylcarbamoyl)piperidin-3-yl)-4-(3,5-dimethylphenyl)-4-hydroxybutylcarbamate |
| I-4a | methyl (S)-4-((R)-1-((S)-1-cyclohexyl-3-(methylamino)propan-2-ylcarbamoyl)piperidin-3-yl)-4-(3-fluoro-5-methylphenyl)-4-hydroxybutylcarbamate |
| I-5a | methyl (S)-4-((R)-1-((S)-1-cyclohexyl-3-(methylamino)propan-2-ylcarbamoyl)piperidin-3-yl)-4-(2-fluoro-5-methylphenyl)-4-hydroxybutylcarbamate |
| I-6a | methyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate |
| I-7a | methyl (S)-4-((R)-1-((S)-1-cyclohexyl-3-(methylamino)propan-2-ylcarbamoyl)piperidin-3-yl)-4-(2,3-difluorophenyl)-4-hydroxybutylcarbamate |
| I-8a | methyl (S)-4-((R)-1-((S)-1-cyclohexyl-3-(methylamino)propan-2-ylcarbamoyl)piperidin-3-yl)-4-(3,5-difluorophenyl)-4-hydroxybutylcarbamate |
| I-9a | methyl (S)-4-((R)-1-((S)-2-amino-3-cyclohexylpropylcarbamoyl)piperidin-3-yl)-4-(3-chloro-2-fluorophenyl)-4-hydroxybutylcarbamate |
| I-10a | methyl (4S)-4-((3R)-1-((2S)-2-amino-3-(tetrahydro-2H-pyran-2-yl)propylcarbamoyl)piperidin-3-yl)-4-(3-chloro-2-fluorophenyl)-4-hydroxybutylcarbamate |
| I-11a | ethyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate |
| I-12a | methyl (S)-4-((R)-1-((1S,2R)-1-cyclohexyl-1-hydroxy-3-(methylamino)propan-2-ylcarbamoyl)piperidin-3-yl)-4-(2,3-difluorophenyl)-4-hydroxybutylcarbamate |
| I-13a | methyl (S)-4-(3-chloro-2-fluorophenyl)-4-((R)-1-((S)-1-cyclohexyl-3-(methylamino)propan-2-ylcarbamoyl)piperidin-3-yl)-4-hydroxybutylcarbamate |
| I-14a | methyl (S)-4-(2-chloro-3-fluorophenyl)-4-((R)-1-((S)-1-cyclohexyl-3-(methylamino)propan-2-ylcarbamoyl)piperidin-3-yl)-4-hydroxybutylcarbamate |
| I-15a | methyl (S)-4-(3-chloro-5-fluorophenyl)-4-((R)-1-((S)-1-cyclohexyl-3-(methylamino)propan-2-ylcarbamoyl)piperidin-3-yl)-4-hydroxybutylcarbamate |
| I-16a | methyl (S)-4-((R)-1-((2S,3R)-3-amino-1-cyclohexylbutan-2-ylcarbamoyl)piperidin-3-yl)-4-(3-chloro-2-fluorophenyl)-4-hydroxybutylcarbamate |
| I-17a | methyl (S)-4-(2,3-difluorophenyl)-4-((R)-1-((S)-1-(trans-4-fluorocyclohexyl)-3-(methylamino)propan-2-ylcarbamoyl)piperidin-3-yl)-4-hydroxybutylcarbamate |
| I-18a | methyl (S)-4-(3-chloro-2-fluorophenyl)-4-hydroxy-4-((R)-1-((S)-1-(methylamino)-3-(tetrahydro-2H-pyran-4-yl)propan-2-ylcarbamoyl)piperidin-3-yl)butylcarbamate |
| I-19a | methyl (S)-4-((R)-1-((S)-2-amino-3-cyclohexylpropylcarbamoyl)piperidin-3-yl)-4-(3-chloro-2,4-difluorophenyl)-4-hydroxybutylcarbamate |
| I-20a | methyl (S)-4-(3-chloro-2-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate |
| I-21a | methyl (S)-4-(2-chloro-3-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate |

| | -continued |
|---|---|
| I-22a | methyl (S)-4-(3-chloro-2-fluorophenyl)-4-((R)-1-((S)-1-(trans-4-fluorocyclohexyl)-3-(methylamino)propan-2-ylcarbamoyl)piperidin-3-yl)-4-hydroxybutylcarbamate |
| I-23a | methyl (S)-4-(3-chloro-2,4-difluorophenyl)-4-((R)-1-((S)-1-cyclohexyl-3-(methylamino)propan-2-ylcarbamoyl)piperidin-3-yl)-4-hydroxybutylcarbamate |
| I-24a | methyl (S)-4-acetamido-4-(3-chlorophenyl)-4-((R)-1-((S)-1-cyclohexyl-3-(methylamino)propan-2-ylcarbamoyl)piperidin-3-yl)butylcarbamate |
| I-25a | methyl (S)-4-(3-chlorophenyl)-4-((R)-1-((S)-1-cyclohexyl-3-(methylamino)propan-2-ylcarbamoyl)piperidin-3-yl)-4-propionamidobutylcarbamate |
| I-25b | methyl (R)-4-(3-chlorophenyl)-4-((R)-1-((S)-1-cyclohexyl-3-(methylamino)propan-2-ylcarbamoyl)piperidin-3-yl)-4-propionamidobutylcarbamate |
| I-30a | methyl 2-((R)-(3-chlorophenyl)((R)-1-((S)-4,4-dimethyl-1-(methylamino)pentan-2-ylcarbamoyl)piperidin-3-yl)methoxy)ethylcarbamate |
| I-31a | methyl 2-((R)-((R)-1-((S)-1-cyclohexyl-3-(methylamino)propan-2-ylcarbamoyl)piperidin-3-yl)(3-fluorophenyl)methoxy)ethylcarbamate |
| I-32a | methyl 2-((R)-((R)-1-((S)-1-amino-3-cyclohexylpropan-2-ylcarbamoyl)piperidin-3-yl)(3-chlorophenyl)methoxy)ethylcarbamate |
| I-34a | methyl 2-((1R)-((3R)-1-((2S)-1-amino-3-(tetrahydro-2H-pyran-2-yl)propan-2-ylcarbamoyl)piperidin-3-yl)(3-chlorophenyl)methoxy)ethylcarbamate |
| I-35a | methyl 2-((R)-(3-chlorophenyl)((R)-1-((S)-1-cyclohexyl-3-(methylamino)propan-2-ylcarbamoyl)piperidin-3-yl)methoxy)ethylcarbamate |
| I-36a | methyl 2-((R)-((R)-1-((2S,3R)-3-amino-1-cyclohexylbutan-2-ylcarbamoyl)piperidin-3-yl)(3-chlorophenyl)methoxy)ethylcarbamate |
| 1-37a | methyl 2-((R)-((3R)-1-((2S)-1-cyclohexyl-3-(methylamino)propan-2-ylcarbamoyl)piperidin-3-yl)(2,3-difluorophenyl)methoxy)ethylcarbamate |
| I-38a | methyl 2-((R)-(3-chlorophenyl)((R)-1-((S)-1-(methylamino)-3-(tetrahydro-2H-pyran-4-yl)propan-2-ylcarbamoyl)piperidin-3-yl)methoxy)ethylcarbamate |
| I-39a | methyl 2-((R)-((R)-1-((S)-2-amino-3-cyclohexylpropylcarbamoyl)piperidin-3-yl)(3-chloro-2-fluorophenyl)methoxy)ethylcarbamate |
| I-41a | ethyl 2-((R)-(3-chlorophenyl)((R)-1-((S)-1-cyclohexyl-3-(methylamino)propan-2-ylcarbamoyl)piperidin-3-yl)methoxy)ethylcarbamate |
| I-42a | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate |
| I-43a | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-43a | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-43b | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-44a | methyl 2-((R)-(3-chloro-5-fluorophenyl)((R)-1-((S)-1-cyclohexyl-3-(methylamino)propan-2-ylcarbamoyl)piperidin-3-yl)methoxy)ethylcarbamate |
| I-45a | methyl 2-((R)-(3-chlorophenyl)((R)-1-((S)-1-(trans-4-fluorocyclohexyl)-3-(methylamino)propan-2-ylcarbamoyl)piperidin-3-yl)methoxy)ethylcarbamate |
| I-46a | methyl 2-((R)-(3-chlorophenyl)((R)-1-((S)-1-(1-fluorocyclohexyl)-3-(methylamino)propan-2-ylcarbamoyl)piperidin-3-yl)methoxy)ethylcarbamate |
| I-47a | methyl 2-((R)-(3-chloro-2-fluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I-48a | methyl 2-((S)-(3-chloro-2-fluorophenyl)((R)-4-((S)-1-cyclohexyl-3-(methylamino)propan-2-ylcarbamoyl)morpholin-2-yl)methoxy)ethylcarbamate |
| I-49a | ethyl 2-((R)-(3-chloro-2-fluorophenyl)((3R)-1-((2S)-1-cyclohexyl-3-(methylamino)propan-2-ylcarbamoyl)piperidin-3-yl)methoxy)ethylcarbamate |
| I-51a | methyl 2-((R)-(3-chloro-2-fluorophenyl)((R)-1-((S)-1-(trans-4-fluorocyclohexyl)-3-(methylamino)propan-2-ylcarbamoyl)piperidin-3-yl)methoxy)ethylcarbamate |
| I-52a | methyl 2-((R)-(3-chlorophenyl)((R)-1-((S)-1-(3-noradamantyl)-3-(methylamino)propan-2-ylcarbamoyl)piperidin-3-yl)methoxy)ethylcarbamate |
| I-56a | (3R)-3-((R)-(3-chlorophenyl)(2-(methylamino)-2-oxoethoxy)methyl)-N-((S)-1-cyclohexyl-3-(methylamino)propan-2-yl)piperidine-1-carboxamide |
| I-58a | (3R)-3-((R)-(3-chlorophenyl)(2-(ethylamino)-2-oxoethoxy)methyl)-N-((S)-1-cyclohexyl-3-(methylamino)propan-2-yl)piperidine-1-carboxamide |
| I-59a | (3R)-N-((2S)-1-cyclohexyl-3-(methylamino)propan-2-yl)-3-((R)-(2,3-difluorophenyl)(2-(ethylamino)-2-oxoethoxy)methyl)piperidine-1-carboxamide |

| | -continued |
|---|---|
| I-64a | (3R)-3-((R)-(3-chloro-2-fluorophenyl)(2-(ethylamino)-2-oxoethoxy)methyl)-N-((2S)-1-cyclohexyl-3-(methylamino)propan-2-yl)piperidine-1-carboxamide |
| I-64b | (3R)-3-((R)-(3-chloro-2-fluorophenyl)(2-(ethylamino)-2-oxoethoxy)methyl)-N-((2S)-1-cyclohexyl-3-(methylamino)propan-2-yl)piperidine-1-carboxamide |
| I-65a | (3R)-3-((R)-(3-chlorophenyl)(2-(2-methoxyethylamino)-2-oxoethoxy)methyl)-N-((S)-1-cyclohexyl-3-(methylamino)propan-2-yl)piperidine-1-carboxamide |
| I-67a | (3R)-3-((R)-(3-chlorophenyl)(3-(ethylamino)-3-oxopropoxy)methyl)-N-((S)-1-cyclohexyl-3-(methylamino)propan-2-yl)piperidine-1-carboxamide |
| 1-68a | (3R)-3-((R)-(3-chlorophenyl)(3-oxo-3-(propylamino)propoxy)methyl)-N-((2S)-1-cyclohexyl-3-(methylamino)propan-2-yl)piperidine-1-carboxamide |
| I-74a | (3R)-3-((S)-1-(3-chlorophenyl)-4-formamido-1-hydroxybutyl)-N-((S)-1-cyclohexyl-3-(methylamino)propan-2-yl)piperidine-1-carboxamide |
| I-76a | (3R)-3-((S)-1-(3-chlorophenyl)-1-hydroxy-6-oxoheptyl)-N-((S)-1-cyclohexyl-3-(methylamino)propan-2-yl)piperidine-1-carboxamide |
| I-77a | methyl 2-((R)-(3-chlorophenyl)((R)-1-((3S,4R)-4-isobutylpiperidin-3-ylcarbamoyl)piperidin-3-yl)methoxy)ethylcarbamate |
| I-78a | methyl 2-((R)-(3-chloro-2-fluorophenyl)((R)-1-((3S,4R)-4-isobutylpiperidin-3-ylcarbamoyl)piperidin-3-yl)methoxy)ethylcarbamate |
| I-79a | methyl 2-((R)-(3-chloro-2-fluorophenyl)((R)-1-((3S,4S)-4-cyclohexylpiperidin-3-ylcarbamoyl)piperidin-3-yl)methoxy)ethylcarbamate |
| I-80a | methyl 2-((R)-(3-chlorophenyl)((R)-1-((3S,4S)-4-cyclopentylpiperidin-3-ylcarbamoyl)piperidin-3-yl)methoxy)ethylcarbamate |
| I-81a | methyl 2-((R)-(3-chlorophenyl)((R)-1-((3R,4R)-4-cyclopentylpiperidin-3-ylcarbamoyl)piperidin-3-yl)methoxy)ethylcarbamate |
| I-82a | methyl 2-((R)-(3-chlorophenyl)((R)-1-((3S,4R)-4-(cyclobutylmethyl)piperidin-3-ylcarbamoyl)piperidin-3-yl)methoxy)ethylcarbamate |
| I-83a | methyl 2-((R)-(3-chlorophenyl)((R)-1-((3S,4S)-4-cyclohexylpiperidin-3-ylcarbamoyl)piperidin-3-yl)methoxy)ethylcarbamate |

Another embodiment of the invention is each of the following compounds or their enantiomers, diastereomers, or pharmaceutically acceptable salts:

| | |
|---|---|
| I-1a | methyl (S)-4-((R)-1-((S)-1-cyclohexyl-3-(methylamino)propan-2-ylcarbamoyl)piperidin-3-yl)-4-(2-fluorophenyl)-4-hydroxybutylcarbamate |
| I-3a | methyl (S)-4-((R)-1-((S)-1-cyclohexyl-3-(methylamino)propan-2-ylcarbamoyl)piperidin-3-yl)-4-(3,5-dimethylphenyl)-4-hydroxybutylcarbamate |
| I-4a | methyl (S)-4-((R)-1-((S)-1-cyclohexyl-3-(methylamino)propan-2-ylcarbamoyl)piperidin-3-yl)-4-(3-fluoro-5-methylphenyl)-4-hydroxybutylcarbamate |
| I-5a | methyl (S)-4-((R)-1-((S)-1-cyclohexyl-3-(methylamino)propan-2-ylcarbamoyl)piperidin-3-yl)-4-(2-fluoro-5-methylphenyl)-4-hydroxybutylcarbamate |
| I-6a | methyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate |
| I-7a | methyl (S)-4-((R)-1-((S)-1-cyclohexyl-3-(methylamino)propan-2-ylcarbamoyl)piperidin-3-yl)-4-(2,3-difluorophenyl)-4-hydroxybutylcarbamate |
| I-9a | methyl (S)-4-((R)-1-((S)-2-amino-3-cyclohexylpropylcarbamoyl)piperidin-3-yl)-4-(3-chloro-2-fluorophenyl)-4-hydroxybutylcarbamate |
| I-13a | methyl (S)-4-(3-chloro-2-fluorophenyl)-4-((R)-1-((S)-4-cyclohexyl-3-(methylamino)propan-2-ylcarbamoyl)piperidin-3-yl)-4-hydroxybutylcarbamate |
| I-14a | methyl (S)-4-(2-chloro-3-fluorophenyl)-4-((R)-1-((S)-1-cyclohexyl-3-(methylamino)propan-2-ylcarbamoyl)piperidin-3-yl)-4-hydroxybutylcarbamate |
| I-15a | methyl (S)-4-(3-chloro-5-fluorophenyl)-4-((R)-1-((S)-1-cyclohexyl-3-(methylamino)propan-2-ylcarbamoyl)piperidin-3-yl)-4-hydroxybutylcarbamate |
| I-16a | methyl (S)-4-((R)-1-((2S,3R)-3-amino-1-cyclohexylbutan-2-ylcarbamoyl)piperidin-3-yl)-4-(3-chloro-2-fluorophenyl)-4-hydroxybutylcarbamate |
| I-20a | methyl (S)-4-(3-chloro-2-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate |
| I-22a | methyl (S)-4-(3-chloro-2-fluorophenyl)-4-((R)-1-((S)-1-(trans-4-fluorocyclohexyl)-3-(methylamino)propan-2-ylcarbamoyl)piperidin-3-yl)-4-hydroxybutylcarbamate |

-continued

| | |
|---|---|
| I-23a | methyl (S)-4-(3-chloro-2,4-difluorophenyl)-4-((R)-1-((S)-1-cyclohexyl-3-(methylamino)propan-2-ylcarbamoyl)piperidin-3-yl)-4-hydroxybutylcarbamate |
| I-24a | methyl (S)-4-acetamido-4-(3-chlorophenyl)-4-((R)-1-((S)-1-cyclohexyl-3-(methylamino)propan-2-ylcarbamoyl)piperidin-3-yl)butylcarbamate |
| I-25a | methyl (S)-4-(3-chlorophenyl)-4-((R)-1-((S)-1-cyclohexyl-3-(methylamino)propan-2-ylcarbamoyl)piperidin-3-yl)-4-propionamidobutylcarbamate |
| I-31a | methyl 2-((R)-((R)-1-((S)-1-cyclohexyl-3-methylamino)propan-2-ylcarbamoyl)piperidin-3-yl)(3-fluorophenyl)methoxy)ethylcarbamate |
| I-32a | methyl 2-((R)-((R)-1-((S)-1-amino-3-cyclohexylpropan-2-ylcarbamoyl)piperidin-3-yl)(3-chlorophenyl)methoxy)ethylcarbamate |
| I-35a | methyl 2-((R)-(3-chlorophenyl)((R)-1-((S)-1-cyclohexyl-3-(methylamino)propan-2-ylcarbamoyl)piperidin-3-yl)methoxy)ethylcarbamate |
| I-36a | methyl 2-((R)-1-((2S,3R)-3-amino-1-cyclohexylbutan-2-ylcarbamoyl)piperidin-3-yl)(3-chlorophenyl)methoxy)ethylcarbamate |
| I-37a | methyl 2-((R)-((3R)-1-((2S)-1-cyclohexyl-3-(methylamino)propan-2-ylcarbamoyl)piperidin-3-yl)(2,3-difluorophenyl)methoxy)ethylcarbamate |
| I-39a | methyl 2-((R)-((R)-1-((S)-2-amino-3-cyclohexylpropylcarbamoyl)piperidin-3-yl)(3-chloro-2-fluorophenyl)methoxy)ethylcarbamate |
| I-42a | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate |
| I-43a | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-43a | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-44a | methyl 2-((R)-(3-chloro-5-fluorophenyl)((R)-1-((S)-1-cyclohexyl-3-(methylamino)propan-2-ylcarbamoyl)piperidin-3-yl)methoxy)ethylcarbamate |
| I-45a | methyl 2-((R)-(3-chlorophenyl)((R)-1-((S)-1-(trans-4-fluorocyclohexyl)-3-(methylamino)propan-2-ylcarbamoyl)piperidin-3-yl)methoxy)ethylcarbamate |
| I-46a | methyl 2-((R)-(3-chlorophenyl)((R)-1-((S)-1-(1-fluorocyclohexyl)-3-(methylamino)propan-2-ylcarbamoyl)piperidin-3-yl)methoxy)ethylcarbamate |
| I-48a | methyl 2-((S)-(3-chloro-2-fluorophenyl)((R)-4-((S)-1-cyclohexyl-3-(methylamino)propan-2-ylcarbamoyl)morpholin-2-yl)methoxy)ethylcarbamate |
| I-51a | methyl 2-((R)-(3-chloro-2-fluorophenyl)((R)-1-((S)-1-(trans-4-fluorocyclohexyl)-3-(methylamino)propan-2-ylcarbamoyl)piperidin-3-yl)methoxy)ethylcarbamate |
| I-52a | methyl 2-((R)-(3-chlorophenyl)((R)-1-((S)-1-(3-noradamantyl)-3-(methylamino)propan-2-ylcarbamoyl)piperidin-3-yl)methoxy)ethylcarbamate |
| I-58a | (3R)-3-((R)-(3-chlorophenyl)(2-(ethylamino)-2-oxoethoxy)methyl)-N-((S)-1-cyclohexyl-3-(methylamino)propan-2-yl)piperidine-1-carboxamide |
| I-76a | (3R)-3-((S)-1-(3-chlorophenyl)-1-hydroxy-6-oxoheptyl)-N-((S)-1-cyclohexyl-3-(methylamino)propan-2-yl)piperidine-1-carboxamide |
| I-83a | methyl 2-((R)-(3-chlorophenyl)((R)-1-((3S,4S)-4-cyclohexylpiperidin-3-ylcarbamoyl)piperidin-3-yl)methoxy)ethylcarbamate |

A particular embodiment of the invention is each of the following compounds or their enantiomers, diastereomers, or pharmaceutically acceptable salts:

| Cpd. No. | Cpd. Name |
|---|---|
| I-6a | methyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate |
| I-13a | methyl (S)-4-(3-chloro-2-fluorophenyl)-4-((R)-1-((S)-1-cyclohexyl-3-(methylamino)propan-2-ylcarbamoyl)piperidin-3-yl)-4-hydroxybutylcarbamate |
| I-15a | methyl (S)-4-(3-chloro-5-fluorophenyl-4-((R)-1-((S)-1-cyclohexyl-3-(methylamino)propan-2-ylcarbamoyl)piperidin-3-yl)-4-hydroxybutylcarbamate |
| I-22a | methyl (S)-4-(3-chloro-2-fluorophenyl)-4-((R)-1-((S)-1-(trans-4-fluorocyclohexyl)-3-(methylamino)propan-2-ylcarbamoyl)piperidin-3-yl)-4-hydroxybutylcarbamate |
| I-24a | methyl (S)-4-acetamido-4-(3-chlorophenyl)-4-((R)-1-((S)-1-cyclohexyl-3-(methylamino)propan-2-ylcarbamoyl)piperidin-3-yl)butylcarbamate |

| Cpd. No. | Cpd. Name |
| --- | --- |
| I-25a | methyl (S)-4-(3-chlorophenyl)-4-((R)-1-((S)-1-cyclohexyl-3-(methylamino)propan-2-ylcarbamoyl)piperidin-3-yl)-4-propionamidobutylcarbamate |
| I-31a | methyl 2-((R)-((R)-1-((S)-1-cyclohexyl-3-(methylamino)propan-2-ylcarbamoyl)piperidin-3-yl)(3-fluorophenyl)methoxy)ethylcarbamate |
| I-32a | methyl 2-((R)-((R)-1-((S)-1-amino-3-cyclohexylpropan-2-ylcarbamoyl)piperidin-3-yl)(3-chlorophenyl)methoxy)ethylcarbamate |
| I-35a | methyl 2-((R)-(3-chlorophenyl)((R)-1-((S)-1-cyclohexyl-3-(methylamino)propan-2-ylcarbamoyl)piperidin-3-yl)methoxy)ethylcarbamate |
| I-36a | methyl 2-((R)-((R)-1-((2S,3R)-3-amino-1-cyclohexylbutan-2-ylcarbamoyl)piperidin-3-yl)(3-chlorophenyl)methoxy)ethylcarbamate |
| I-37a | methyl 2-((R)-((3R)-1-((2S)-1-cyclohexyl-3-(methylamino)propan-2-ylcarbamoyl)piperidin-3-yl)(2,3-difluorophenyl)methoxy)ethylcarbamate |
| I-42a | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate |
| I-43a | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-43a | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-44a | methyl 2-((R)-(3-chloro-5-fluorophenyl)((R)-1-((S)-1-cyclohexyl-3-(methylamino)propan-2-ylcarbamoyl)piperidin-3-yl)methoxy)ethylcarbamate |
| I-45a | methyl 2-((R)-(3-chlorophenyl)((R)-1-((S)-1-(trans-4-fluorocyclohexyl)-3-(methylamino)propan-2-ylcarbamoyl)piperidin-3-yl)methoxy)ethylcarbamate |
| I-51a | methyl 2-((R)-(3-chloro-2-fluorophenyl)((R)-1-((S)-1-(trans-4-fluorocyclohexyl)-3-(methylamino)propan-2-ylcarbamoyl)piperidin-3-yl)methoxy)ethylcarbamate |
| I-52a | methyl 2-((R)-(3-chlorophenyl)((R)-1-((S)-1-(3-noradamantyl)-3-(methylamino)propan-2-ylcarbamoyl)piperidin-3-yl)methoxy)ethylcarbamate |

Another embodiment of the invention is each of the compounds listed below or their enantiomers, diastereomers, or pharmaceutically acceptable salts:

| Compound Number | Name |
| --- | --- |
| I*-1 | methyl 2-((3-fluorophenyl)(1-(5-methoxy-1-(methylamino)pentan-2-ylcarbamoyl)piperidin-3-yl)methoxy)ethylcarbamate |
| I*-2 | methyl 2-((1-(1-cyclohexyl-3-(methylamino)propan-2-ylcarbamoyl)piperidin-3-yl)(phenyl)methoxy)ethylcarbamate |
| I*-3 | methyl 2-((1-(1-(methylamino)-3-(tetrahydro-2H-pyran-4-yl)propan-2-ylcarbamoyl)piperidin-3-yl)(phenyl)methoxy)ethylcarbamate |
| I*-4 | methyl 2-((1-(1-amino-3-cyclohexylpropan-2-ylcarbamoyl)piperidin-3-yl)(3-fluorophenyl)methoxy)ethylcarbamate |
| I*-5 | methyl 2-((1-(1-cyclopentyl-3-(methylamino)propan-2-ylcarbamoyl)piperidin-3-yl)(3-fluorophenyl)methoxy)ethylcarbamate |
| I*-6 | methyl 2-((3-fluorophenyl)(1-(1-(methylamino)-3-(tetrahydrofuran-3-yl)propan-2-ylcarbamoyl)piperidin-3-yl)methoxy)ethylcarbamate |
| I*-7 | methyl 2-((1-(4,4-dimethyl-1-(methylamino)hexan-2-ylcarbamoyl)piperidin-3-yl)(3-fluorophenyl)methoxy)ethylcarbamate |
| I*-8 | methyl 2-((1-(5,5-dimethyl-1-(methylamino)hexan-2-ylcarbamoyl)piperidin-3-yl)(3-fluorophenyl)methoxy)ethylcarbamate |
| I*-9 | methyl 2-((1-(1-cyclohexyl-3-(methylamino)propan-2-ylcarbamoyl)piperidin-3-yl)(thiophen-2-yl)methoxy)ethylcarbamate |
| I*-10 | methyl 2-(cyclohexyl(1-(1-cyclohexyl-3-(methylamino)propan-2-ylcarbamoyl)piperidin-3-yl)methoxy)ethylcarbamate |
| I*-11 | methyl 2-((3-chlorophenyl)(1-(4-isobutylpyrrolidin-3-ylcarbamoyl)piperidin-3-yl)methoxy)ethylcarbamate |
| I*-12 | methyl 2-((1-(1-cyclohexyl-3-(methylamino)propan-2-ylcarbamoyl)piperidin-3-yl)(thiazol-2-yl)methoxy)ethylcarbamate |
| I*-13 | methyl 2-((1-(1-cyclohexyl-3-(methylamino)propan-2-ylcarbamoyl)piperidin-3-yl)(thiazol-2-yl)methoxy)ethylcarbamate |
| I*-14 | methyl 2-((1-(2-amino-5-methoxy-4,4-dimethylpentylcarbamoyl)piperidin-3-yl)(3-fluorophenyl)methoxy)ethylcarbamate |
| I*-15 | methyl 2-((1-(1-(methylamino)-3-(tetrahydro-2H-pyran-4-yl)propan-2-ylcarbamoyl)piperidin-3-yl)(thiophen-2-yl)methoxy)ethylcarbamate |
| I*-16 | methyl 2-((1-(1-(methylamino)-3-(tetrahydro-2H-pyran-4-yl)propan-2-ylcarbamoyl)piperidin-3-yl)(thiophen-2-yl)methoxy)ethylcarbamate |
| I*-17 | methyl 2-((3-chlorophenyl)(1-(5-methoxy-1-(methylamino)pentan-2-ylcarbamoyl)piperidin-3-yl)methoxy)ethylcarbamate |
| I*-18 | methyl 2-((1-(1-cyclohexyl-3-(methylamino)propan-2-ylcarbamoyl)piperidin-3-yl)(m-tolyl)methoxy)ethylcarbamate |
| I*-19 | methyl 2-((1-(1-cyclohexyl-1-hydroxy-3-(methylamino)propan-2-ylcarbamoyl)piperidin-3-yl)(phenyl)methoxy)ethylcarbamate |
| I*-20 | methyl 2-((1-(1-(methylamino)-3-(tetrahydro-2H-pyran-4-yl)propan-2-ylcarbamoyl)piperidin-3-yl)(m-tolyl)methoxy)ethylcarbamate |
| I*-21 | methyl 2-((1-(1-(methylamino)-3-(oxepan-3-yl)propan-2-ylcarbamoyl)piperidin-3-yl)(phenyl)methoxy)ethylcarbamate |
| I*-22 | methyl 4-(1-(1-cyclohexyl-3-(methylamino)propan-2-ylcarbamoyl)piperidin-3-yl)-4-(3-fluorophenyl)butylcarbamate |
| I*-23 | methyl 4-(1-(1-cyclohexyl-3-(methylamino)propan-2-ylcarbamoyl)piperidin-3-yl)-4-(3-fluorophenyl)butylcarbamate |
| I*-24 | methyl 2-((1-(1-cyclopentyl-3-(methylamino)propan-2-ylcarbamoyl)piperidin-3-yl)(5-fluoro-2-methylphenyl)methoxy)ethylcarbamate |

-continued

| Compound Number | Name |
|---|---|
| I*-25 | 3-(1-(3-chlorophenyl)-1-(2-(methylamino)-2-oxoethoxy)ethyl)-N-(1-cyclohexyl-3-(methylamino)propan-2-yl)piperidine-1-carboxamide |
| I*-26 | methyl 2-((3-fluorophenyl)(1-(1-(methylamino)-3-(tetrahydro-2H-pyran-4-yl)propan-2-ylcarbamoyl)piperidin-3-yl)methoxy)ethylcarbamate |
| I*-27 | methyl 2-((1-(1-cyclopentyl-1-hydroxy-3-(methylamino)propan-2-ylcarbamoyl)piperidin-3-yl)(3-fluorophenyl)methoxy)ethylcarbamate |
| I*-28 | methyl 2-((1-(2-amino-3-(oxepan-3-yl)propylcarbamoyl)piperidin-3-yl)(3-fluorophenyl)methoxy)ethylcarbamate |
| I*-29 | methyl 2-((3-chlorophenyl)(1-(1-cyclopentyl-3-(methylamino)propan-2-ylcarbamoyl)piperidin-3-yl)methoxy)ethylcarbamate |
| I*-30 | 3-((3-chlorophenyl)(2-(ethylamino)-2-oxoethoxy)methyl)-N-(1-(methylamino)-3-(etrahydro-2H-pyran-3-yl)propan-2-yl)piperidine-1-carboxamide |
| I*-31 | 3-((3-chlorophenyl)(2-(ethylamino)-2-oxoethoxy)methyl)-N-(1-(methylamino)-3-(tetrahydro-2H-pyran-4-yl)propan-2-yl)piperidine-1-carboxamide |
| I*-32 | methyl 2-((1-(1-cyclohexyl-3-(methylamino)propan-2-ylcarbamoyl)piperidin-3-yl)(4-methylthiazol-2-yl)methoxy)ethylcarbamate |
| I*-33 | methyl 2-((1-(1-cyclohexyl-3-(methylamino)propan-2-ylcarbamoyl)piperidin-3-yl)(4-methylthiazol-2-yl)methoxy)ethylcarbamate |
| I*-34 | methyl 2-((3-chlorophenyl)(1-(4,4-dimethyl-1-(methylamino)hexan-2-ylcarbamoyl)piperidin-3-yl)methoxy)ethylcarbamate |
| I*-35 | methyl 2-((1-(2-amino-5-methoxy-4,4-dimethylpentylcarbamoyl)piperidin-3-yl)(3-chlorophenyl)methoxy)ethylcarbamate |
| I*-36 | methyl 2-((3,5-dimethylphenyl)(1-(1-(methylamino)-3-(tetrahydro-2H-pyran-4-yl)propan-2-ylcarbamoyl)piperidin-3-yl)methoxy)ethylcarbamate |
| I*-37 | methyl 2-((2,5-dimethylphenyl)(1-(1-(methylamino)-3-(tetrahydro-2H-pyran-4-yl)propan-2-ylcarbamoyl)piperidin-3-yl)methoxy)ethylcarbamate |
| I*-38 | methyl 2-((1-(2-amino-3-phenoxypropylcarbamoyl)piperidin-3-yl)(3-chlorophenyl)methoxy)ethylcarbamate |
| I*-39 | methyl 2-((1-(1-cycloheptyl-3-(methylamino)propan-2-ylcarbamoyl)piperidin-3-yl)(3-fluorophenyl)methoxy)ethylcarbamate |
| I*-40 | methyl 2-((1-(1-cyclohexyl-3-(methylamino)propan-2-ylcarbamoyl)piperidin-3-yl)(5-fluoro-2-methylphenyl)methoxy)ethylcarbamate |
| I*-41 | methyl 2-((1-(1-cyclohexyl-3-(ethylamino)propan-2-ylcarbamoyl)piperidin-3-yl)(3-fluorophenyl)methoxy)ethylcarbamate |
| I*-42 | methyl 2-((3-fluorophenyl)(1-(1-(methylamino)-3-(1-methylcyclohexyl)propan-2-ylcarbamoyl)piperidin-3-yl)methoxy)ethylcarbamate |
| I*-43 | methyl 2-((3-chlorophenyl)(1-(1-(methylamino)-3-(1-methylcyclohexyl)propan-2-ylcarbamoyl)piperidin-3-yl)methoxy)ethylcarbamate |
| I*-44 | methyl 2-((3-chlorophenyl)(1-(4-(cyclobutylmethyl)piperidin-3-ylcarbamoyl)piperidin-3-yl)methoxy)ethylcarbamate |
| I*-45 | 3-((3-chlorophenyl)(4-(methylamino)-4-oxobutoxy)methyl)-N-(1-cyclohexyl-3-(methylamino)propan-2-yl)piperidine-1-carboxamide |
| I*-46 | methyl 2-((3-fluorophenyl)(1-(1-(methylamino)-3-(2-oxopiperidin-1-yl)propan-2-ylcarbamoyl)piperidin-3-yl)methoxy)ethylcarbamate |
| I*-47 | methyl 2-((3-fluorophenyl)(1-(1-(methylamino)-3-(oxepan-4-yl)propan-2-ylcarbamoyl)piperidin-3-yl)methoxy)ethylcarbamate |
| I*-48 | methyl 2-((1-(1-cyclohexyl-1-hydroxy-3-(methylamino)propan-2-ylcarbamoyl)piperidin-3-yl)(3-fluorophenyl)methoxy)ethylcarbamate |
| I*-49 | methyl 2-((2-fluoro-5-methylphenyl)(1-(1-(methylamino)-3-(tetrahydro-2H-pyran-4-yl)propan-2-ylcarbamoyl)piperidin-3-yl)methoxy)ethylcarbamate |
| I*-50 | methyl 2-((5-fluoro-2-methylphenyl)(1-(1-(methylamino)-3-(tetrahydro-2H-pyran-4-yl)propan-2-ylcarbamoyl)piperidin-3-yl)methoxy)ethylcarbamate |
| I*-51 | methyl 2-((3-fluorophenyl)(1-(1-(4-hydroxycyclohexyl)-3-(methylamino)propan-2-ylcarbamoyl)piperidin-3-yl)methoxy)ethylcarbamate |
| I*-52 | methyl 2-((3-fluoro-5-methylphenyl)(1-(1-(methylamino)-3-(tetrahydro-2H-pyran-4-yl)propan-2-ylcarbamoyl)piperidin-3-yl)methoxy)ethylcarbamate |
| I*-53 | methyl 2-((1-(1-cyclopentyl-1-hydroxy-3-(methylamino)propan-2-ylcarbamoyl)piperidin-3-yl)(5-fluoro-2-methylphenyl)methoxy)ethylcarbamate |
| I*-54 | methyl 4-(3-fluorophenyl)-4-hydroxy-4-(1-(1-(methylamino)-3-(tetrahydro-2H-pyran-3-yl)propan-2-ylcarbamoyl)piperidin-3-yl)butylcarbamate |
| I*-55 | methyl 2-((3-fluorophenyl)(1-(1-(methylamino)-3-(oxepan-3-yl)propan-2-ylcarbamoyl)piperidin-3-yl)methoxy)ethylcarbamate |
| I*-56 | methyl 2-((3-fluorophenyl)(1-(1-(methylamino)-3-(tetrahydro-2H-pyran-3-yl)propan-2-ylcarbamoyl)azepan-3-yl)methoxy)ethylcarbamate |
| I*-57 | methyl 2-((2-fluorophenyl)(1-(1-(methylamino)-3-(oxepan-3-yl)propan-2-ylcarbamoyl)piperidin-58yl)methoxy)ethylcarbamate |
| I*-58 | methyl 2-((1-(2-amino-3-(oxepan-3-yl)propylcarbamoyl)piperidin-3-yl)(5-fluoro-2-methylphenyl)methoxy)ethylcarbamate |
| I*-59 | methyl 2-((1-(1-amino-3-cyclohexyl-2-methylpropan-2-ylcarbamoyl)piperidin-3-yl)(3-chlorophenyl)methoxy)ethylcarbamate |
| I*-60 | methyl 2-((5-chloro-2-methylphenyl)(1-(1-cyclopentyl-3-(methylamino)propan-2-ylcarbamoyl)piperidin-3-yl)methoxy)ethylcarbamate |
| I*-61 | 3-((3-chlorophenyl)(2-(ethylamino)-2-oxoethoxy)methyl)-N-(1-(methylamino)-3-(oxepan-3-yl)propan-2-yl)piperidine-1-carboxamide |
| I*-62 | methyl 2-((3-chlorophenyl)(1-(1-(methylamino)-3-(2-oxopyrrolidin-1-yl)propan-2-ylcarbamoyl)piperidin-3-yl)methoxy)ethylcarbamate |
| I*-63 | methyl 2-((1-(1-cyclohexyl-3-(methylamino)propan-2-ylcarbamoyl)piperidin-3-yl)(2,5-difluorophenyl)methoxy)ethylcarbamate |
| I*-64 | methyl 2-((1-(1-cyclohexyl-3-(methylamino)propan-2-ylcarbamoyl)piperidin-3-yl)(3,5-difluorophenyl)methoxy)ethylcarbamate |
| I*-65 | methyl 2-((1-(1-cyclohexyl-3-(methylamino)propan-2-ylcarbamoyl)piperidin-3-yl)(3,4-difluorophenyl)methoxy)ethylcarbamate |
| I*-66 | methyl 2-((3-chlorophenyl)(4-(cyclohexyl-3-(methylamino)propan-2-ylcarbamoyl)morpholin-2-yl)methoxy)ethylcarbamate |
| I*-67 | methyl 2-((3-chlorophenyl)(1-(1-cyclopentyl-1-hydroxy-3-(methylamino)propan-2-ylcarbamoyl)piperidin-3-yl)methoxy)ethylcarbamate |
| I*-68 | methyl 2-((1-(2-amino-3-(oxepan-3-yl)propylcarbamoyl)piperidin-3-yl)(3-chlorophenyl)methoxy)ethylcarbamate |
| I*-69 | methyl 2-((2,5-difluorophenyl)(1-(1-(methylamino)-3-(tetrahydro-2H-pyran-4-yl)propan-2-ylcarbamoyl)piperidin-3-yl)methoxy)ethylcarbamate |
| I*-70 | methyl 2-((3,5-difluorophenyl)(1-(1-(methylamino)-3-(tetrahydro-2H-pyran-4-yl)propan-2-ylcarbamoyl)piperidin-3-yl)methoxy)ethylcarbamate |
| I*-71 | methyl 2-((2,3-difluorophenyl)(1-(1-(methylamino)-3-(tetrahydro-2H-pyran-4-yl)propan-2-ylcarbamoyl)piperidin-3-yl)methoxy)ethylcarbamate |
| I*-72 | methyl 2-((1-(1-cyclopentyl-1-hydroxy-3-(methylamino)propan-2-ylcarbamoyl)piperidin-3-yl)(2,3-difluorophenyl)methoxy)ethylcarbamate |
| I*-73 | methyl 2-((1-(2-amino-3-(oxepan-3-yl)propylcarbamoyl)piperidin-3-yl)(3,5-difluorophenyl)methoxy)ethylcarbamate |
| I*-74 | methyl 2-((1-(1-(3-noradamantyl)-3-(methylamino)propan-2-ylcarbamoyl)piperidin-3-yl)(phenyl)methoxy)ethylcarbamate |
| I*-75 | methyl 2-((3-chlorophenyl)(4-(1-(methylamino)-3-(tetrahydro-2H-pyran-4-yl)propan-2-ylcarbamoyl)morpholin-2-yl)methoxy)ethylcarbamate |

| Compound Number | Name |
|---|---|
| I*-76 | methyl 2-((3-fluorophenyl)(1-(1-(1-methyl-6-oxopiperidin-3-yl)-3-(methylamino)propan-2-ylcarbamoyl)piperidin-3-yl)methoxy)ethylcarbamate |
| I*-77 | methyl 2-((-1-(1-(2,6-dimethyl-tetrahydro-2H-pyran-4-yl)-3-(methylamino)propan-2-ylcarbamoyl)piperidin-3-yl)(3-fluorophenyl)methoxy)ethylcarbamate |
| I*-78 | methyl 2-((3-fluorophenyl)(1-(4-(1-methoxycyclopentyl)-1-(methylamino)butan-2-ylcarbamoyl)piperidin-3-yl)methoxy)ethylcarbamate |
| I*-79 | methyl 2-((5-fluoro-2-methylphenyl)(1-(1-(methylamino)-3-(oxepan-3-yl)propan-2-ylcarbamoyl)piperidin-3-yl)methoxy-ethylcarbamate |
| I*-80 | methyl 2-((3-chlorophenyl)(1-(1-(methylamino)-3-4-oxocyclohexyl)propan-2-ylcarbamoyl)piperidin-3-yl)methoxy)ethylcarbamate |
| I*-81 | methyl 2-(1-(3-chlorophenyl)-1-(1-(1-cyclohexyl-3-(methylamino)propan-2-ylcarbamoyl)piperidin-3-yl)ethoxy)ethylcarbamate |
| I*-82 | methyl 2-((3-chlorophenyl)(1-(1-cyclohexyl-3-(methylamino)butan-2-ylcarbamoyl)piperidin-3-yl)methoxy)ethylcarbamate |
| I*-83 | methyl 2-((1-(3-amino-1-cyclohexylpentan-2-ylcarbamoyl)piperidin-3-yl)(3-chlorophenyl)methoxy)ethylcarbamate |
| I*-84 | methyl 2-((3-chloropheny)(1-(1-cycloheptyl-3-(methylamino)propan-2-ylcarbamoyl)piperidin-3-yl)methoxy)ethylcarbamate |
| I*-85 | methyl 2-((5-chloro-2-methylphenyl)(1-(1-cyclohexyl-3-(methylamino)propan-2-ylcarbamoyl)piperidin-3-yl)methoxy)ethylcarbamate |
| I*-86 | methyl 2-((3-chlorophenyl)(1-(1-(methylamino)-3-(4-methylcyclohexyl)propan-2-ylcarbamoyl)piperidin-3-yl)methoxy)ethylcarbamate |
| I*-87 | methyl 1-((3-chlorophenyl)(1-(1-cyclohexyl-3-(methylamino)propan-2-ylcarbamoyl)piperidin-3-yl)methoxy)propan-2-ylcarbamate |
| I*-88 | methyl 2-((3-chlorophenyl)(1-(1-cyclohexyl-3-(ethylamino)propan-2-ylcarbamoyl)piperidin-3-yl)methoxy)ethylcarbamate |
| I*-89 | methyl 2-((3-chlorophenyl)(1-(1-(methylamino)-3-(1-methylcyclohexyl)propan-2-ylcarbamoyl)piperidin-3-yl)methoxy)ethylcarbamate |
| I*-90 | methyl 2-((3-chlorophenyl)(1-(1-(methylamino)-3-(1-methylcyclohexyl)propan-2-ylcarbamoyl)piperidin-3-yl)methoxy)ethylcarbamate |
| I*-91 | methyl 2-((3-chlorophenyl)(1-(1-cyclohexyl-3-(methylamino)propan-2-ylcarbamoyl)azepan-3-yl)methoxy)ethylcarbamate |
| I*-92 | methyl 2-((3-chlorophenyl)(1-(1-cyclohexyl-3-(methylamino)propan-2-ylcarbamoyl)azepan-3-yl)methoxy)ethylcarbamate |
| I*-93 | methyl 2-((3-chlorophenyl)(1-(1-(methylamino)-3-(2-oxopiperidin-1-yl)propan-2-ylcarbamoyl)piperidin-3-yl)methoxy)ethylcarbamate |
| I*-94 | methyl 2-((3,5-difluorophenyl)(1-(1-(methylamino)-3-(1-methylcyclohexyl)propan-2-ylcarbamoyl)piperidin-3-yl)methoxy)ethylcarbamate |
| I*-95 | methyl 2-((3,5-difluorophenyl)(1-(1-(methylamino)-3-(1-methylcyclohexyl)propan-2-ylcarbamoyl)piperidin-3-yl)methoxy)ethylcarbamate |
| I*-96 | methyl 2-((1-(1-cyclohexyl-3-(methylamino)propan-2-ylcarbamoyl)piperidin-3-yl)(2,3-difluoro-6-methylphenyl)methoxy)ethylcarbamate |
| I*-97 | methyl 2-((1-(1-cyclohexyl-3-(methylamino)propan-2-ylcarbamoyl)piperidin-3-yl)(2,3-difluoro-6-methylphenyl)methoxy)ethylcarbamate |
| I*-98 | methyl 2-((3-chlorophenyl)(1-(1-(methylamino)-3-(oxepan-4-yl)propan-2-ylcarbamoyl)piperidin-3-yl)methoxy)ethylcarbamate |
| I*-99 | methyl 2-((R)-(3-chlorophenyl)((R)-1-((S)-1-(methylamino)-3-((S)-oxepan-4-yl)propan-2-ylcarbamoyl)piperidin-3-yl)methoxy)ethylcarbamate |
| I*-100 | methyl 2-((3-chlorophenyl)(1-(1-cyclohexyl-1-hydroxy-3-(methylamino)propan-2-ylcarbamoyl)piperidin-3-yl)methoxy)ethylcarbamate |
| I*-101 | methyl 2-((5-chloro-2-methylphenyl)(1-(1-(methylamino)-3-(tetrahydro-2H-pyran-4-yl)propan-2-ylcarbamoyl)piperidin-3-yl)methoxy)ethylcarbamate |
| I*-102 | methyl 2-((3-chlorophenyl)(1-(1-(4-hydroxycyclohexyl)-3-(methylamino)propan-2-ylcarbamoyl)piperidin-3-yl)methoxy)ethylcarbamate |
| I*-103 | methyl 2-(1-(3-chlorophenyl)-1-(1-(1-(methylamino)-3-(tetrahydro-2H-pyran-4-yl)propan-2-ylcarbamoyl)piperidin-3-yl)ethoxy)ethylcarbamate |
| I*-104 | methyl 2-((3-chlorophenyl)(1-(1-(2-hydroxycyclohexyl)-3-(methylamino)propan-2-ylcarbamoyl)piperidin-3-yl)methoxy)ethylcarbamate |
| I*-105 | methyl 2-((3-chlorophenyl)(1-(1-(2-hydroxycyclohexyl)-3-(methylamino)propan-2-ylcarbamoyl)piperidin-3-yl)methoxy)ethylcarbamate |
| I*-106 | methyl 2-((3-chlorophenyl)(1-(1-(methylamino)-3-(oxepan-3-yl)propan-2-ylcarbamoyl)piperidin-3-yl)methoxy)ethylcarbamate |
| I*-107 | methyl 2-((5-chloro-2-methylphenyl)(1-(1-cyclopentyl-1-hydroxy-3-(methylamino)propan-2-ylcarbamoyl)piperidin-3-yl)methoxy)ethylcarbamate |
| I*-108 | methyl 2-((3-chlorophenyl)(1-(1-(methylamino)-3-(tetrahydro-2H-pyran-4-yl)propan-2-ylcarbamoyl)azepan-3-yl)methoxy)ethylcarbamate |
| I*-109 | methyl 2-((1-(2-amino-3-(oxepan-3-yl)propylcarbamoyl)piperidin-3-yl)(5-chloro-2-methylphenyl)methoxy)ethylcarbamate |
| I*-110 | methyl 2-((3-chlorophenyl)(1-(2-(methylamino)-3-(oxepan-3-yl)propylcarbamoyl)piperidin-3-yl)methoxy-ethylcarbamate |
| I*-111 | methyl 2-((3-chlorophenyl)(1-(1-cyclohexyl-3-(methylamino)propan-2-ylcarbamothioyl)piperidin-3-yl)methoxy)ethylcarbamate |
| I*-112 | methyl 2-((1-(1-cyclohexyl-1-hydroxy-3-(methylamino)propan-2-ylcarbamoyl)piperidin-3-yl)(3,5-difluorophenyl)methoxy)ethylcarbamate |
| I*-113 | methyl 2-((3,5-difluorophenyl)(1-(1-(methylamino)-3-(oxepan-3-yl)propan-2-ylcarbamoyl)piperidin-3-yl)methoxy)ethylcarbamate |
| I*-114 | methyl 2-((1-(1-cyclohexyl-3-(methylamino)propan-2-ylcarbamoyl)piperidin-3-yl)(3,5-difluoro-2-hydroxyphenyl)methoxy)ethylcarbamate |
| I*-115 | methyl 2-((2,3-difluoro-6-methylphenyl)(1-(1-(methylamino)-3-(tetrahydro-2H-pyran-4-yl)propan-2-ylcarbamoyl)piperidin-3-yl)methoxy)ethylcarbamate |
| I*-116 | methyl 2-((5-chloro-2-fluorophenyl)(1-(1-cyclohexyl-3-(methylamino)propan-2-ylcarbamoyl)piperidin-3-yl)methoxy)ethylcarbamate |
| I*-117 | methyl 2-((5-chloro-2-fluorophenyl)(1-(1-cyclohexyl-3-(methylamino)propan-2-ylcarbamoyl)piperidin-3-yl)methoxy)ethylcarbamate |
| I*-118 | methyl 2-((3-chloro-4-fluorophenyl)(1-(1-cyclohexyl-3-(methylamino)propan-2-ylcarbamoyl)piperidin-3-yl)methoxy)ethylcarbamate |
| I*-119 | methyl 2-((1-(1-cyclohexyl-3-(methylamino)propan-2-ylcarbamoyl)piperidin-3-yl)(3,4,5-trifluorophenyl)methoxy)ethylcarbamate |
| I*-120 | methyl 2-((1-(1-(4,4-difluorocyclohexyl)-3-(methylamino)propan-2-ylcarbamoyl)piperidin-3-yl)(3-fluorophenyl)methoxy)ethylcarbamate |
| I*-121 | methyl 2-((3-chloro-5-fluorophenyl)(1-(1-(methylamino)-3-(tetrahydro-2H-pyran-4-yl)propan-2-ylcarbamoyl)piperidin-3-yl)methoxy)ethylcarbamate |
| I*-122 | methyl 2-((1-(2-amino-3-(oxepan-3-yl)propylcarbamoyl)piperidin-3-yl)(3-chloro-5-fluorophenyl)methoxy)ethylcarbamate |
| I*-123 | methyl 2-((1-(1-(3-noradamantyl)-3-(methylamino)propan-2-ylcarbamoyl)piperidin-3-yl)(3-fluorophenyl)methoxy)ethylcarbamate |
| I*-124 | methyl 2-((3-chlorophenyl)(1-(1-(3,4-difluorocyclopentyl)-3-(methylamino)propan-2-ylcarbamoyl)piperidin-3-yl)methoxy)ethylcarbamate |
| I*-125 | methyl 2-((3-chlorophenyl)(1-(1-(3,4-difluorocyclopentyl)-3-(methylamino)propan-2-ylcarbamoyl)piperidin-3-yl)methoxy)ethylcarbamate |

| Compound Number | Name |
|---|---|
| I*-126 | 3-((3-chlorophenyl)(2-(2-cyano-3-methylguanidino)ethoxy)methyl)-N-(1-cyclohexyl-3-(methylamino)propan-2-yl)piperidine-1-carboxamide |
| I*-127 | methyl 2-((3-chlorophenyl)(1-(N'-cyano-N-(1-cyclohexyl-3-(methylamino)propan-2-yl)carbamimidoyl)piperidin-3-yl)methoxy-ethylcarbamate |
| I*128 | 3-((3-chlorophenyl)(2-(thiazol-2-ylamino)ethoxy)methyl)-N-(1-cyclohexyl-3-(methylamino)propan-2-yl)piperidine-1-carboxamide |
| I*-129 | methyl 2-((1-(1-(bicyclo[2.2.2]octan-1-yl)-3-(methylamino)propan-2-ylcarbamoyl)piperidin-3-yl)(3-chlorophenyl)methoxy)ethylcarbamate |
| I*-130 | methyl 2-((3-chlorophenyl)(1-(1-cyclohexyl-3-(methylamino)pentan-2-ylcarbamoyl)piperidin-3-yl)methoxy)ethylcarbamate |
| I*-131 | methyl 2-((3-chlorophenyl)(1-(1-(1-methyl-6-oxopiperidin-3-yl)-3-(methylamino)propan-2-ylcarbamoyl)piperidin-3-yl)methoxy)ethylcarbamate |
| I*-132 | methyl 2-((3-chlorophenyl)(1-(1-(2,6-dimethyl-tetrahydro-2H-pyran-4-yl)-3-(methylamino)propan-2-ylcarbamoyl)piperidin-3-yl)methoxy)ethylcarbamate |
| I*-133 | methyl 2-((5-chloro-2-methylphenyl)(1-(2-(methylamino)-3-(oxepan-3-yl)propylcarbamoyl)piperidin-3-yl)methoxy)ethylcarbamate |
| I*-134 | methyl 2-((3,5-difluorophenyl)(1-(4-(1-methoxycyclopentyl)-1-(methylamino)butan-2-ylcarbamoyl)piperidin-3-yl)methoxy)ethylcarbamate |
| I*-135 | methyl 2-((3-chloto-2-fluorophenyl)(1-(1-cycloheptyl-3-(methylamino)propan-2-ylcarbamoyl)piperidin-3-yl)methoxy)ethylcarbamate |
| I*-136 | methyl 2-((1-(1-cyclohexyl-3-(methylamino)propan-2-ylcarbamoyl)piperidin-3-yl)(3-(trifluoromethyl)phenyl)methoxy)ethylcarbamate |
| I*-137 | methyl 2-((3-chloro-2-fluorophenyl)(1-(1-(methylamino)-3-(oxepan-4-yl)propan-2-ylcarbamoyl)piperidin-3-yl)methoxy)ethylcarbamate |
| I*-138 | methyl 2-((3-chloro-2-fluorophenyl)(1-(1-cyclohexyl-1-hydroxy-3-(methylamino)propan-2-ylcarbamoyl)piperidin-3-yl)methoxy)ethylcarbamate |
| I*-139 | methyl 4-(3-chloro-2-fluorophenyl)-4-hydroxy-4-(1-(1-(methylamino)-3-(tetrahydro-2H-pyran-3-yl)propan-2-ylcarbamoyl)piperidin-3-yl)butylcarbamate |
| I*-140 | methyl 2-((3-chloro-2-fluorophenyl)(1-(1-(methylamino)-3-(oxepan-3-yl)propan-2-ylcarbamoyl)piperidin-3-yl)methoxy)ethylcarbamate |
| I*-141 | methyl 2-((3-chloro-5-fluorophenyl)(1-(1-(methylamino)-3-(oxepan-3-yl)propan-2-ylcarbamoyl)piperidin-3-yl)methoxy)ethylcarbamate |
| I*-142 | methyl 4-(3-chloro-2-fluorophenyl)-4-hydroxy-4-(1-(1-(methylamino)-3-(tetrahydro-2H-pyran-3-yl)propan-2-ylcarbamoyl)piperidin-3-yl)butylcarbamate |
| I*-143 | methyl 2-((3-chloro-5-fluorophenyl)(1-(2-(methylamino)-3-(oxepan-3-yl)propylcarbamoyl)piperidin-3-yl)methoxy)ethylcarbamate |
| I*-144 | methyl 2-((1-(1-(methylamino)-3-(tetrahydro-2H-pyran-4-yl)propan-2-ylcarbamoyl)piperidin-3-yl)(3-(trifluoromethyl)phenyl)methoxy)ethylcarbamate |
| I*-145 | methyl 2-((1-(1-(1-adamantyl)-3-(methylamino)propan-2-ylcarbamoyl)piperidin-3-yl)(3-fluorophenyl)methoxy)ethylcarbamate |
| I*-146 | methyl 2-((3-chlorophenyl)(1-(1-(4,4-difluorocyclohexyl)-3-(methylamino)propan-2-ylcarbamoyl)piperidin-3-yl)methoxy)ethylcarbamate |
| I*-147 | methyl 2-((1-(1-(4,4-difluorocyclohexyl)-3-(methylamino)propan-2-ylcarbamoyl)piperidin-3-yl)(3,5-difluorophenyl)methoxy)ethylcarbamate |
| I*-148 | methyl 2-((3-chloro-2,4-difluorophenyl)(1-(1-(methylamino)-3-(tetrahydro-2H-pyran-4-yl)propan-2-ylcarbamoyl)piperidin-3-yl)methoxy)ethylcarbamate |
| I*-149 | methyl 2-((1-(1-(3-noradamantyl)-3-(methylamino)propan-2-ylcarbamoyl)piperidin-3-yl)(2,5-difluorophenyl)methoxy)ethylcarbamate |
| I*-150 | methyl 2-(1-(3-chlorophenyl)-1-(1-(1-cyclohexyl-3-(methylamino)propan-2-ylcarbamoyl)piperidin-3-yl)butoxy)ethylcarbamate |
| I*-151 | methyl 2-(1-(3-chlorophenyl)-1-(1-(1-(3-noradamantyl)-3-(methylamino)propan-2-ylcarbamoyl)piperidin-3-yl)ethoxy)ethylcarbamate |
| I*-152 | methyl 2-((1-(1-(1-adamantyl)-3-(methylamino)propan-2-ylcarbamoyl)piperidin-3-yl)(2,5-difluorophenyl)methoxy)ethylcarbamate |
| I*-153 | methyl 2-((3-chloro-5-fluorophenyl)(1-(4,4-difluorocyclohexyl)-3-(methylamino)propan-2-ylcarbamoyl)piperidin-3-yl)methoxy)ethylcarbamate |

Another embodiment of the invention is each of the compounds listed below or their salts, especially their pharmaceutically acceptable salts:

| Compound Number | | |
|---|---|---|
| I*-1a | | methyl 2-((R)-(3-chlorophenyl)((R)-1-((S)-5-methoxy-1-(methylamino)pentan-2-ylcarbamoyl)piperidin-3-yl)methoxy)ethylcarbamate |
| I*-2a | | methyl 2-((R)-((R)-1-((S)-1-cyclohexyl-3-(methylamino)propan-2-ylcarbamoyl)piperidin-3-yl)(phenyl)methoxy)-ethylcarbamate |

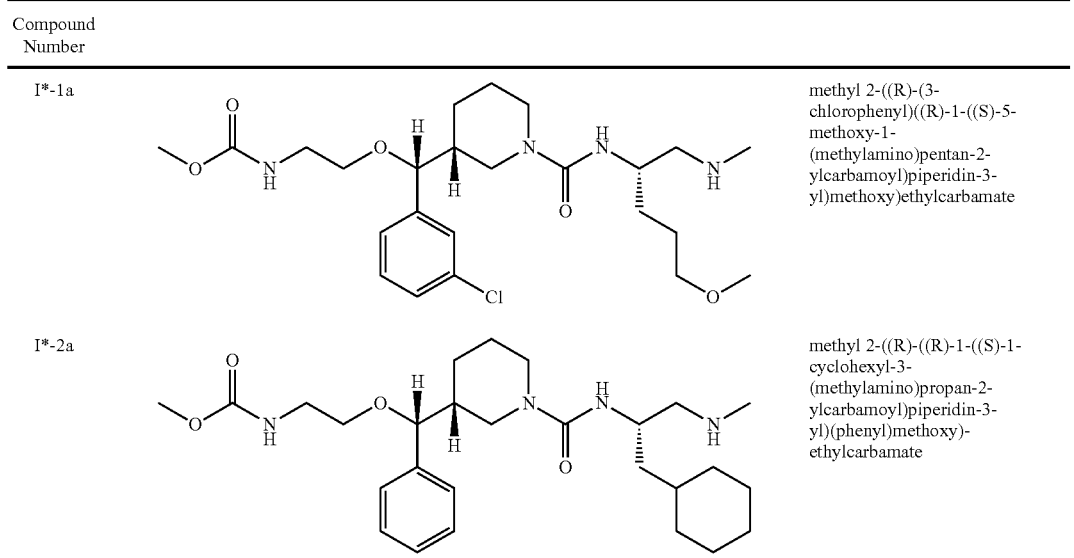

| Compound Number | | |
|---|---|---|
| I*-3a | 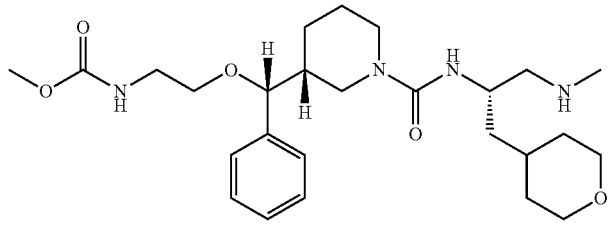 [SMILES: CNC[C@H](CC1CCOCC1)NC(=O)N1CCC[C@@H]([C@@H](OCCNC(=O)OC)c2ccccc2)C1] | methyl 2-((R)-((R)-1-((S)-1-(methylamino)-3-(tetrahydro-2H-pyran-4-yl)propan-2-ylcarbamoyl)piperidin-3-yl)(phenylmethoxy)-ethylcarbamate |
| I*-4a | 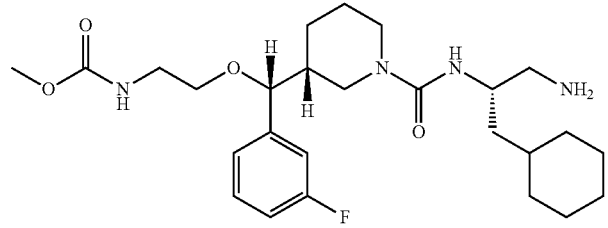 [SMILES: COC(=O)NCCO[C@@H](c1cccc(F)c1)[C@@H]1CCCN(C(=O)N[C@H](CN)CC2CCCCC2)C1] | methyl 2-((R)-((R)-1-((S)-1-amino-3-cyclohexylpropan-2-ylcarbamoyl)piperidin-3-yl)(3-fluorophenyl)methoxy)-ethylcarbamate |
| I*-5a | 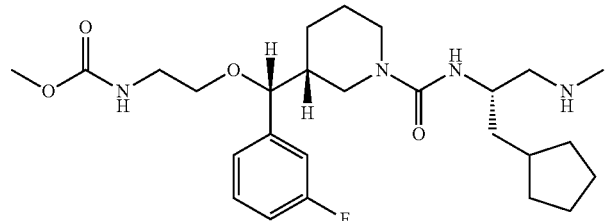 | methyl 2-((R)-((R)-1-((S)-1-cyclopentyl-3-(methylamino)propan-2-ylcarbamoyl)piperidin-3-yl)-(3-fluorophenyl)methoxy)-ethylcarbamate |
| I*-6a | 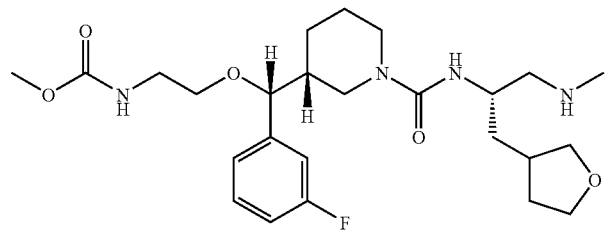 | methyl 2-((R)-(3-fluorophenyl)((3R)-1-((S)-1-(methylamino)-3-(tetrahydrofuran-3-yl)propan-2-ylcarbamoyl)piperidin-3-yl)methoxy)ethylcarbamate |
| I*-7a | 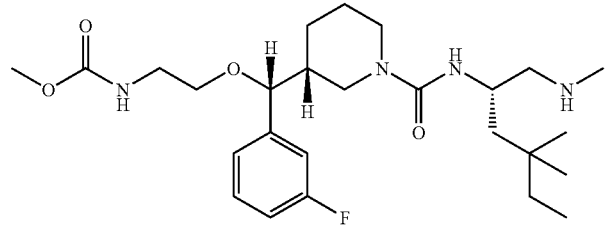 | methyl 2-((R)-((R)-1-((S)-4,4-dimethyl-1-(methylamino)hexan-2-ylcarbamoyl)piperidin-3-yl)(3-fluorophenyl)-methoxy)ethylcarbamate |
| I*-8a | 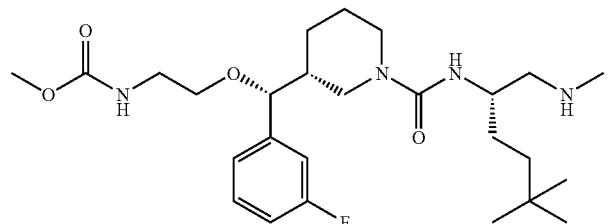 | methyl 2-((R)-((R)-1-((S)-5,5-dimethyl-1-(methylamino)hexyl-2-ylcarbamoyl)piperidin-3-yl)-(3-fluorophenyl)methoxy)-ethylcarbamate |

| Compound Number | | |
|---|---|---|
| I*-9a | 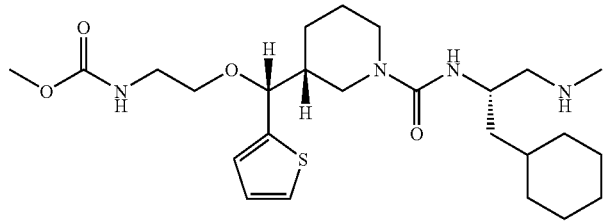 [SMILES: CNC[C@H](CC1CCCCC1)NC(=O)N1CCC[C@@H]([C@@H](OCCNC(=O)OC)c2cccs2)C1] | methyl 2-((R)-((R)-1-((S)-yl-cyclohexyl-3-(methylamino)propan-2-ylcarbamoyl)piperidin-3-yl)(thiophen-2-yl)-methoxy)ethylcarbamate |
| I*-10a | 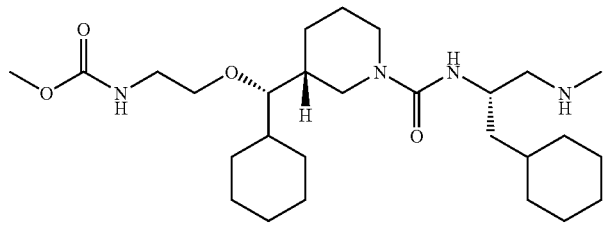 [SMILES: CNC[C@H](CC1CCCCC1)NC(=O)N1CCC[C@@H]([C@@H](OCCNC(=O)OC)C2CCCCC2)C1] | methyl 2-((S)-cyclohexyl((R)-1-((S)-1-cyclohexyl-3-(methylamino)propan-2-ylcarbamoyl)piperidin-3-yl)methoxy)-ethylcarbamate |
| I*-11a | 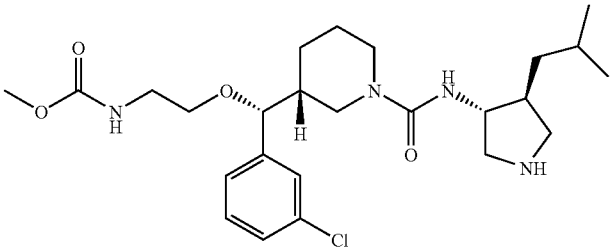 [SMILES: COC(=O)NCCO[C@@H](c1cccc(Cl)c1)[C@@H]1CCCN(C(=O)N[C@H]2CNC[C@@H]2CC(C)C)C1] | methyl 2-((R)-(3-chlorophenyl)((R)-1-((3R*,4S*)-4-isobutylpyrrolidin-3-ylcarbamoyl)piperidin-3-yl)methoxy)ethylcarbamate |
| I*-12a | 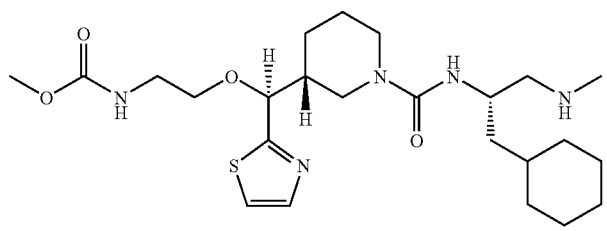 [SMILES: CNC[C@H](CC1CCCCC1)NC(=O)N1CCC[C@@H]([C@H](OCCNC(=O)OC)c2nccs2)C1] | methyl 2-((S)-((R)-1-((S)-1-cyclohexyl-3-(methylamino)propan-2-ylcarbamoyl)piperidin-3-yl)(thiazol-2-yl)-methoxy)ethylcarbamate |
| I*-13a | 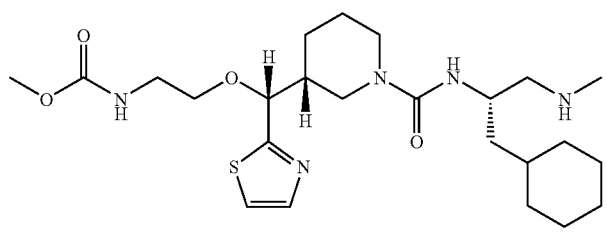 [SMILES: CNC[C@H](CC1CCCCC1)NC(=O)N1CCC[C@@H]([C@@H](OCCNC(=O)OC)c2nccs2)C1] | methyl 2-((R)-((R)-1-((S)-1-cyclohexyl-3-(methylamino)propan-2-ylcarbamoyl)piperidin-3-yl)(thiazo)-2-yl)-methoxy)ethylcarbamate |
| I*-14a | 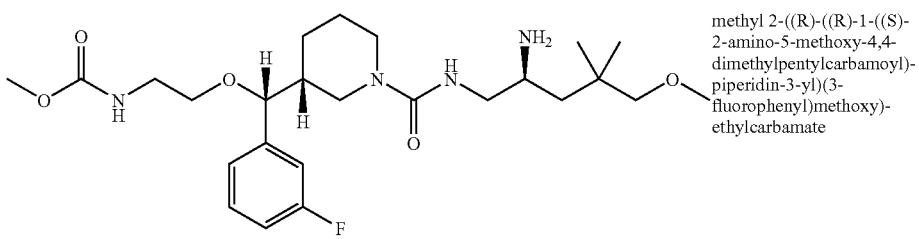 | methyl 2-((R)-((R)-1-((S)-2-amino-5-methoxy-4,4-dimethylpentylcarbamoyl)-piperidin-3-yl)(3-fluorophenyl)methoxy)-ethylcarbamate |

| Compound Number | | |
|---|---|---|
| I*-15a | 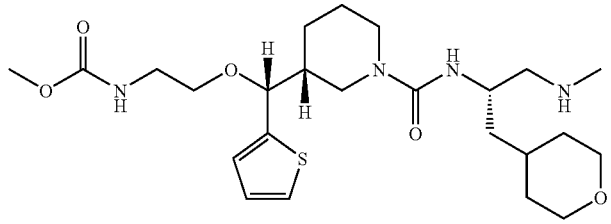 [SMILES: CNC[C@H](CC1CCOCC1)NC(=O)N1CCC[C@@H]([C@@H](OCCNC(=O)OC)c2cccs2)C1] | methyl 2-((R)-((R)-1-((S)-1-(methylamino)-3-(tetrahydro-2H-pyran-4-yl)propan-2-ylcarbamoyl)piperidin-3-yl)(thiophen-2-yl)methoxy)ethylcarbamate |
| I*-16a | 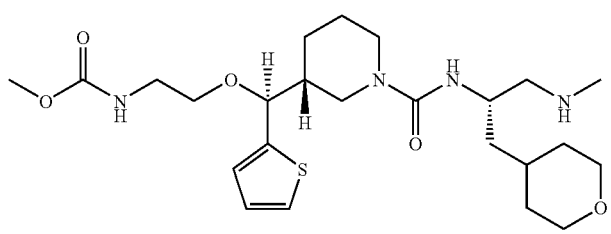 [SMILES: CNC[C@H](CC1CCOCC1)NC(=O)N1CCC[C@@H]([C@H](OCCNC(=O)OC)c2cccs2)C1] | methyl 2-((S)-((R)-1-((S)-1-(methylamino)-3-(tetrahydro-2H-pyran-4-yl)propan-2-ylcarbamoyl)piperidin-3-yl)(thiophen-2-yl)methoxy)ethylcarbamate |
| I*-17a | 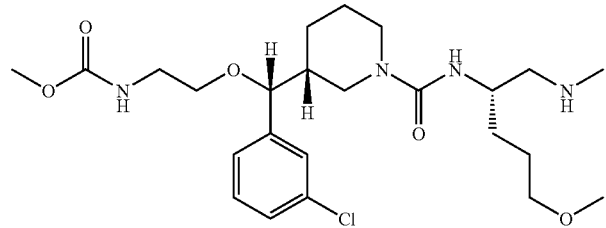 | methyl 2-((R)-(3-methoxy-1-(methylamino)pentan-2-ylcarbamoyl)piperidin-3-yl)methoxy)ethylcarbamate |
| I*-18a | 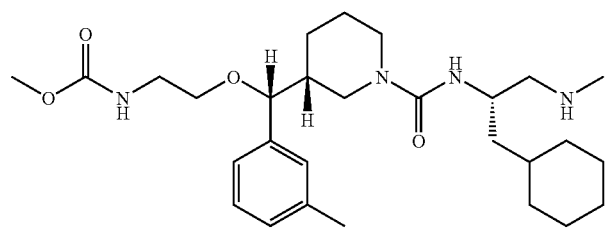 [SMILES: CNC[C@H](CC1CCCCC1)NC(=O)N1CCC[C@@H]([C@@H](OCCNC(=O)OC)c2cccc(C)c2)C1] | methyl 2-((R)-((R)-1-((S)-1-cyclohexyl-3-(methylamino)propan-2-ylcarbamoyl)piperidin-3-yl)(m-tolyl)methoxy)ethylcarbamate |
| I*-19a | 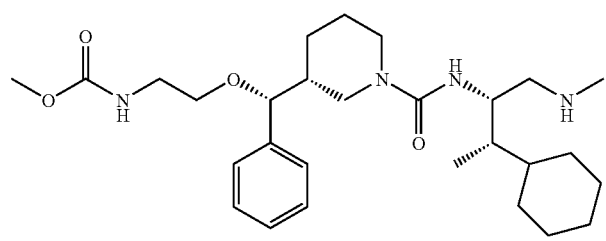 | methyl 2-((R)-((R)-1-((1S,2R)-1-cyclohexyl-1-hydroxy-3-(methylamino)propan-2-ylcarbamoyl)piperidin-3-yl)(phenyl)methoxy)-ethylcarbamate |
| I*-20a | 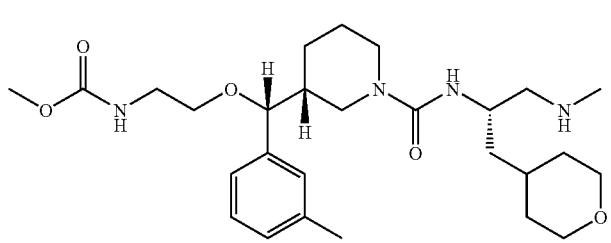 [SMILES: CNC[C@H](CC1CCOCC1)NC(=O)N1CCC[C@@H]([C@@H](OCCNC(=O)OC)c2cccc(C)c2)C1] | methyl 2-((R)-((R)-1-((S)-1-(methylamino)-3-(tetrahydro-2H-pyran-4-yl)-propan-2-ylcarbamoyl)-piperidin-3-yl)(m-tolyl)methoxy)ethylcarbamate |

| Compound Number | | |
|---|---|---|
| I*-21a | 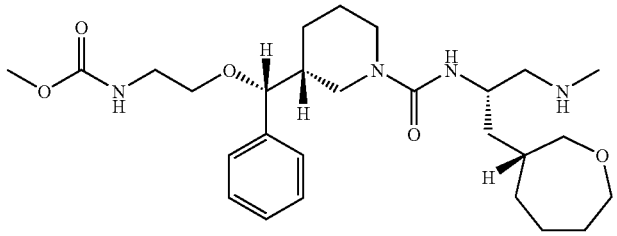 [SMILES: CNC[C@H](C[C@H]1CCCCOC1)NC(=O)N1CCC[C@@H]([C@@H](OCCNC(=O)OC)c2ccccc2)C1] | methyl 2-((R)-((R)-1-((S)-1-(methylamino)-3-((R)-oxepan-3-yl)propan-2-ylcarbamoyl)piperidin-3-yl)(phenyl)methoxy)-ethylcarbamate |
| I*-22a | 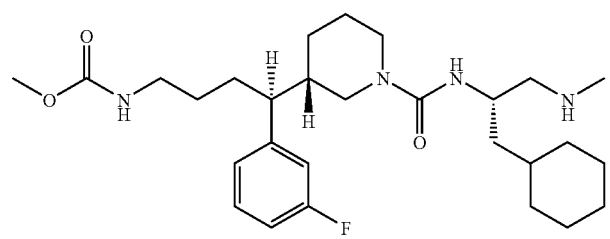 [SMILES: CNC[C@H](CC1CCCCC1)NC(=O)N1CCC[C@@H]([C@H](CCCNC(=O)OC)c2cccc(F)c2)C1] | methyl (S)-4-((S)-1-((S)-1-cyclohexyl-3-(methylamino)propan-2-ylcarbamoyl)piperidin-3-yl)-4-(3-fluorophenyl)-butylcarbamate |
| I*-23a | 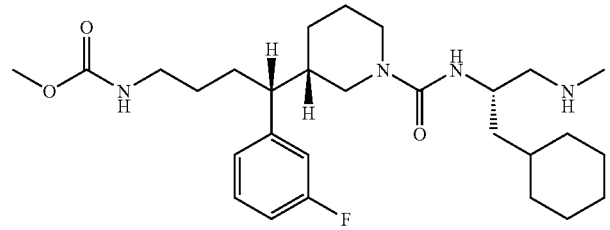 [SMILES: CNC[C@H](CC1CCCCC1)NC(=O)N1CCC[C@@H]([C@@H](CCCNC(=O)OC)c2cccc(F)c2)C1] | methyl (R-4-((S)-1-((S)-1-cyclohexyl-3-(methylamino)propan-2-ylcarbamoyl)piperidin-3-yl)-4-(3-fluorophenyl)-butylcarbamate |
| I*-24a | 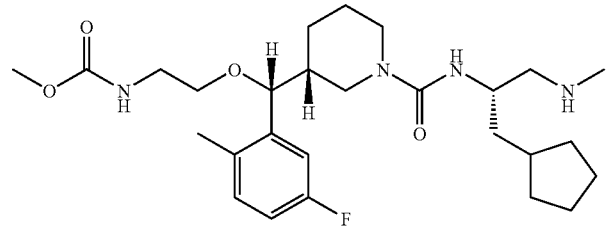 | methyl 2-((R)-((R)-1-((S)-1-cyclopentyl-3-(methylamino)propan-2-ylcarbamoyl)piperidin-3-yl)(5-fluoro-2-methylphenyl)methoxy)-ethylcarbamate |
| I*-25a | 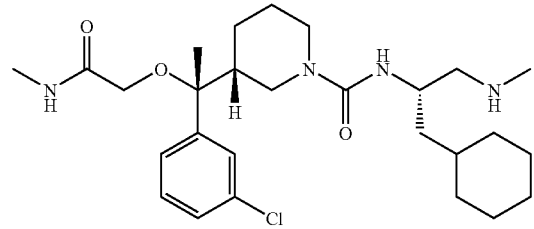 [SMILES: CNC[C@H](CC1CCCCC1)NC(=O)N1CCC[C@@H]([C@@](C)(OCC(=O)NC)c2cccc(Cl)c2)C1] | R)-3-((R)-1-(3-chlorophenyl)-1-(2-(methylamino)-2-oxoethoxy)ethyl)-N-((S)-1-cyclohexyl-3-(methylamino)propan-2-yl)piperidine-1-carboxamide |
| I*-26a | 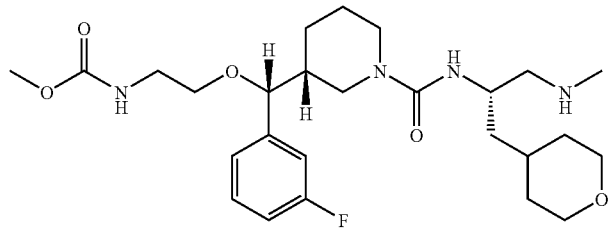 [SMILES: CNC[C@H](CC1CCOCC1)NC(=O)N1CCC[C@@H]([C@@H](OCCNC(=O)OC)c2cccc(F)c2)C1] | methyl 2-((R)-(3-fluorophenyl)((R)-1-((S)-1-(methylamino)-3-(tetrahydro-2H-pyran-4-yl)propan-2-ylcarbamoyl)piperidin-3-yl)methoxy)ethylcarbamate |

| Compound Number | | |
|---|---|---|
| I*-27a | 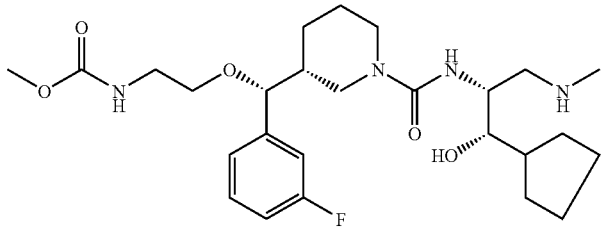 [SMILES: CNC[C@@H](NC(=O)N1CCC[C@@H]([C@@H](OCCNC(=O)OC)c2cccc(F)c2)C1)[C@@H](O)C1CCCC1] | methyl 2-((R)-((R)-1-((1S,2R)-1-cyclopentyl-1-hydroxy-3-(methylamino)propan-2-ylcarbamoyl)piperidin-3-yl)-(3-fluorophenyl)methoxy)-ethylcarbamate |
| I*-28a | 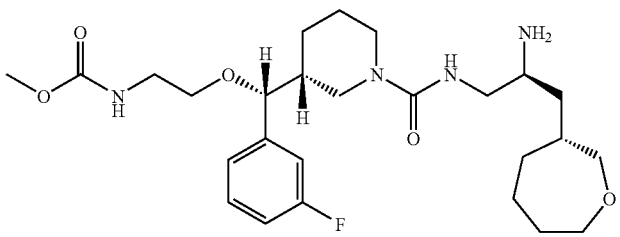 [SMILES: COC(=O)NCCO[C@@H](c1cccc(F)c1)[C@@H]1CCCN(C(=O)NC[C@@H](N)C[C@H]2CCCCOC2)C1] | methyl 2-((R)-((R)-1-((S)-2-amino-3-((R)-oxepan-3-yl)-propylcarbamoyl)piperidin-3-yl)-(3-fluorophenyl)methoxy)-ethylcarbamate |
| I*-29a | 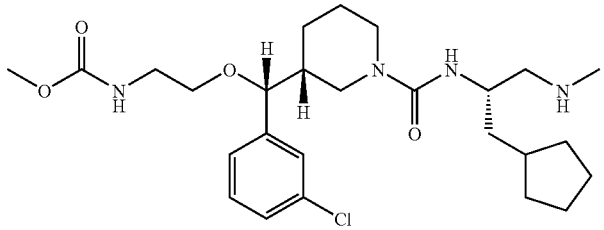 | methyl 2-((R)-(3-chlorophenyl)((R)-1-((S)-1-cyclopentyl-3-(methylamino)propan-2-ylcarbamoyl)piperidin-3-yl)methoxy)ethylcarbamate |
| I*-30a | 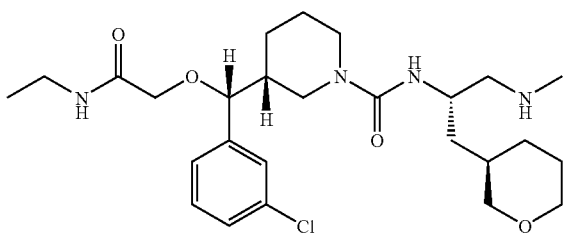 [SMILES: CCNC(=O)CO[C@@H](c1cccc(Cl)c1)[C@@H]1CCCN(C(=O)N[C@H](CNC)C[C@H]2CCCOC2)C1] | (R)-3-((R)-(3-chlorophenyl)(2-(ethylamino)-2-oxoethoxy)-methyl)-N-((S)-1-(methylamino)-3-((R)-tetrahydro-2H-pyran-3-yl)propan-2-yl)piperidine-1-carboxamide |
| I*-31a | 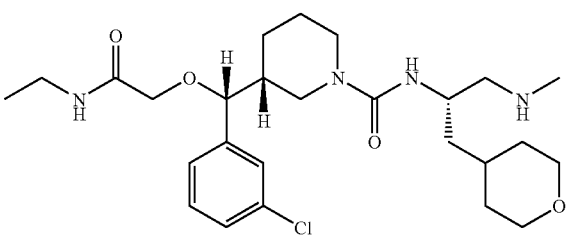 [SMILES: CCNC(=O)CO[C@@H](c1cccc(Cl)c1)[C@@H]1CCCN(C(=O)N[C@H](CNC)CC2CCOCC2)C1] | (R)-3-((R)-(3-chlorophenyl)(2-(ethylamino)-2-oxoethoxy)-methyl)-N-((S)-1-(methylamino)-3-(tetrahydro-2H-pyran-4-yl)propan-2-yl)piperidine-1-carboxamide |
| I*-32a | 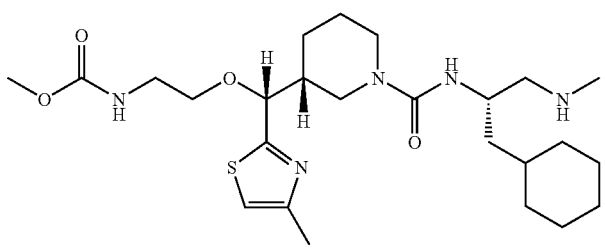 | methyl 2-((R)-((R)-1-((S)1-cyclohexyl-3-(methylamino)-propan-2-ylcarbamoyl)-piperidin-3-yl)-(4-methylthiazol-2-yl)-methoxy-ethylcarbamate |

| Compound Number | | |
|---|---|---|
| I*-33a | 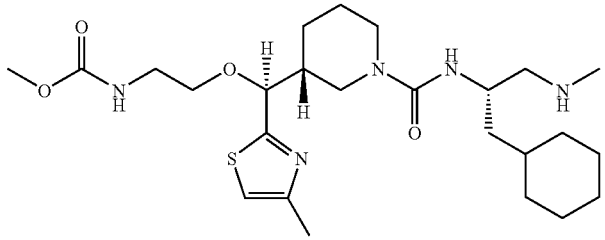 [SMILES: CNC[C@H](CC1CCCCC1)NC(=O)N1CCC[C@@H]([C@H](OCCNC(=O)OC)c2nc(C)cs2)C1] | methyl 2-((S)-((R)-1-((S)-1-cyclohexyl-3-(methylamino)propan-2-ylcarbamoyl)piperidin-3-yl)(4-methylthiazol-2-yl)methoxy)ethylcarbamate |
| I*-34a | 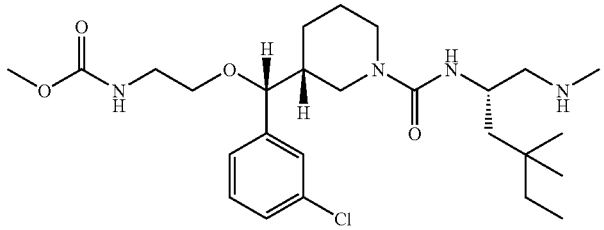 | methyl 2-((R)-(3-chlorophenyl)((R)-1-((S)-4,4-dimethyl-1-(methylamino)hexan-2-ylcarbamoyl)piperidin-3-yl)methoxy)ethylcarbamate |
| I*-35a | 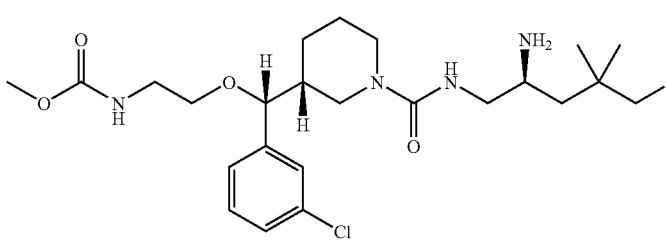 | methyl 2-((R)-((R)-1-((S)-2-amino-5-methoxy-4,4-dimethylpentylcarbamoyl)-piperidin-3-yl(3-chlorophenyl)methoxy)-ethylcarbamate |
| I*-36a | 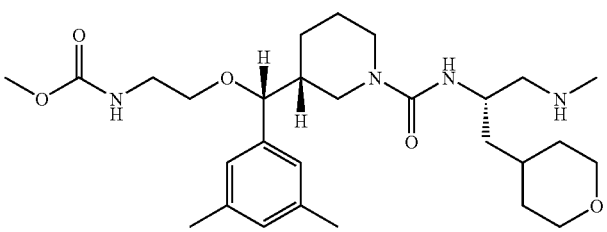 [SMILES: CNC[C@H](CC1CCOCC1)NC(=O)N1CCC[C@@H]([C@@H](OCCNC(=O)OC)c2cc(C)cc(C)c2)C1] | methyl 2-((R)-(3,5-dimethylphenyl)((R)-1-((S)-1-(methylamino)-3-(tetrahydro-2N-pyran-4-yl)propan-2-ylcarbamoyl)piperidin-3-yl)methoxy)ethylcarbamate |
| I*-37a | 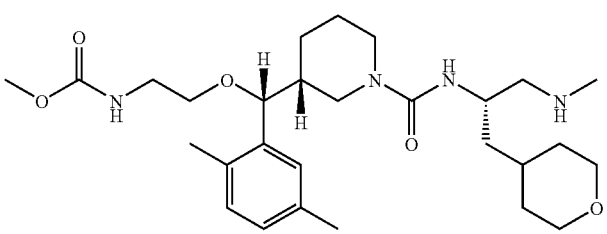 [SMILES: CNC[C@H](CC1CCOCC1)NC(=O)N1CCC[C@@H]([C@@H](OCCNC(=O)OC)c2cc(C)ccc2C)C1] | methyl 2-((R)-(2,5-dimethylphenyl)((R)-1-((S)-1-(methylamino)-3-(tetrahydro-2H-pyran-4-yl)propan-2-ylcarbamoyl)piperidin-3-yl)methoxy)ethyldcarbamate |
| I*-38a | 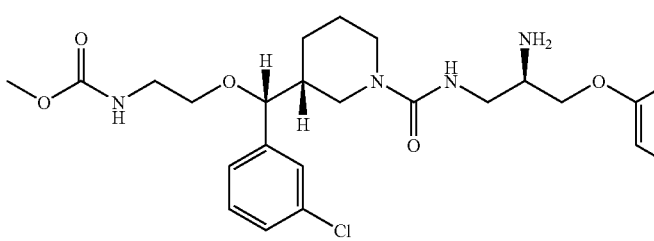 | methyl 2-((R)-((R)-1-((R)-2-amino-3-phenoxypropylcarbamoyl)-piperidin-3-yl)(3-chlorophenyl)methoxy)-ethylcarbamate |

| Compound Number | | |
|---|---|---|
| I*-39a | 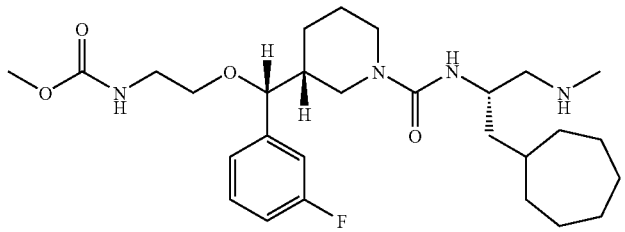 [SMILES: CNC[C@H](CC1CCCCCC1)NC(=O)N1CCC[C@@H]([C@@H](OCCNC(=O)OC)c2cccc(F)c2)C1] | methyl 2-((R)-((R)-1-((S)-1-cycloheptyl-3-(methylamino)propan-2-ylcarbamoyl)piperidin-3-yl)(3-fluorophenyl)methoxy)ethylcarbamate |
| I*-40a | 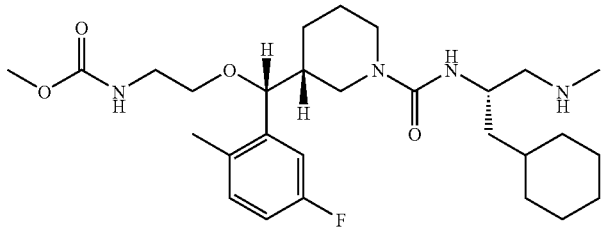 [SMILES: CNC[C@H](CC1CCCCC1)NC(=O)N1CCC[C@@H]([C@@H](OCCNC(=O)OC)c2cc(F)ccc2C)C1] | methyl 2-((R)-((R)-1-((S)-1-cyclohexyl-3-(methylamino)propan-2-ylcarbamoyl)piperidin-3-yl)(5-fluoro-2-methylphenyl)methoxy)-ethylcarbamate |
| I*-41a | 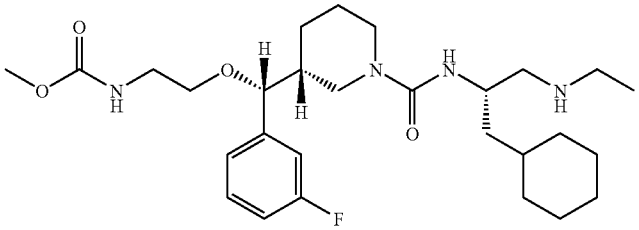 | methyl 2-((R)-((R)-1-((S)-(ethylamino)propan-2-ylcarbamoyl)piperidin-3-yl)(3-fluorophenyl)methoxy)ethylcarbamate |
| I*-42a | 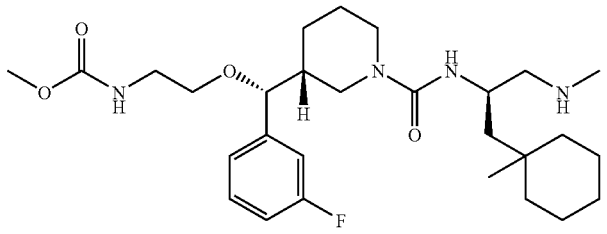 | methyl 2-((R)-(3-fluorophenyl)((R)-1-((R)-1-(methylamino)-3-(1-methylcyclohexyl)propan-2-ylcarbamoyl)piperidin-3-yl)methoxy)ethylcarbamate |
| I*-43a | 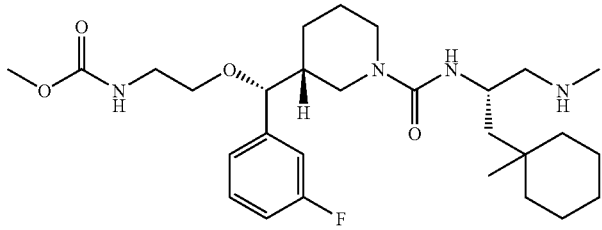 [SMILES: CNC[C@H](CC1(C)CCCCC1)NC(=O)N1CCC[C@@H]([C@@H](OCCNC(=O)OC)c2cccc(F)c2)C1] | methyl 2-((R)-(3-fluorophenyl)((R)-1-((S)-1-(methylamino)-3-(1-methylcyclohexyl)propa-2-ylcarbamoyl)piperidin-3-yl)methoxy)ethylcarbamate |
| I*-44a | 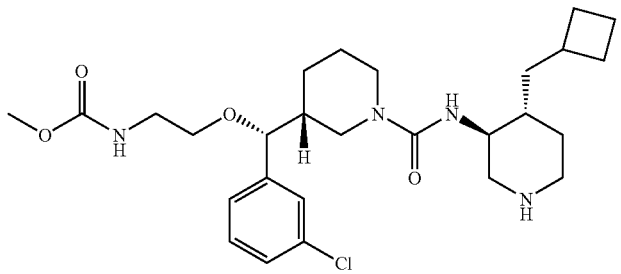 [SMILES: COC(=O)NCCO[C@@H](c1cccc(Cl)c1)[C@@H]1CCCN(C(=O)N[C@@H]2CNCC[C@H]2CC2CCC2)C1] | methyl 2-((R)-(3-chlorophenyl)((R)-1-((3S*,4R*)-4-(cyclobutylmethyl)piperidin-3-ylcarbamoyl)piperidin-3-yl)methoxy)-ethylcarbamate |

| Compound Number | | |
|---|---|---|
| I*-45a | 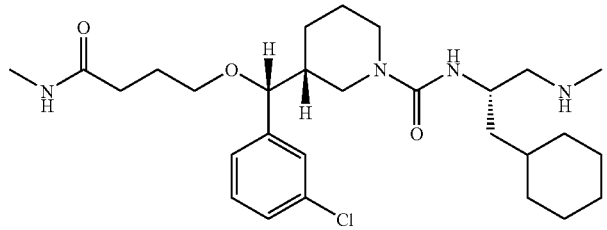 [SMILES: CNC[C@H](CC1CCCCC1)NC(=O)N1CCC[C@@H]([C@@H](OCCCC(=O)NC)c2cccc(Cl)c2)C1] | R)-3-((3R)-(3-chlorophenyl)(4-(methylamino)-4-oxobutoxy)methyl)-N-((S)-1-cyclohexyl-3-(methylamino)propan-2-yl)piperidine-1-carboxamide |
| I*-46a | 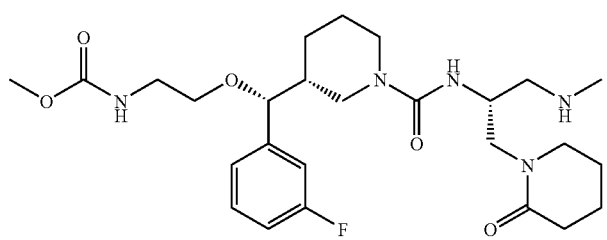 [SMILES: CNC[C@H](CN1CCCCC1=O)NC(=O)N1CCC[C@@H]([C@@H](OCCNC(=O)OC)c2cccc(F)c2)C1] | methyl 2-((R)-(3-fluorophenyl)((R)-1-((R)-1-(methylamino)-3-(2-oxopiperidin-1-yl)propan-2-ylcarbamoyl)piperidin-3-yl)methoxy)ethylcarbamate |
| I*-47a | 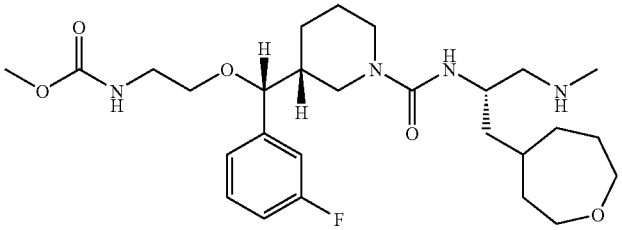 | methyl 2-((R)-(3-fluorophenyl)((3R)-1-((S)-1-(methylamino)-3-(oxepan-4-yl)propan-2-ylcarbamoyl)piperidin-3-yl)methoxy-ethylcarbamate |
| I*-48a | 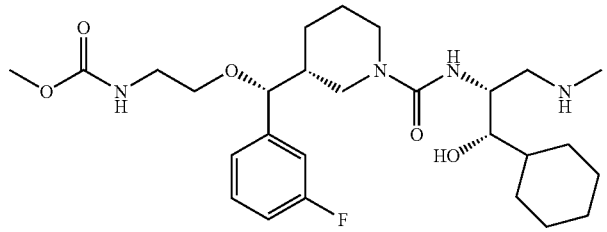 | methyl 2-((R)-((R)-1-((1S,2R)-1-cyclohexyl-1-hydroxy-3-(methylamino)propan-2-ylcarbamoyl)piperidin-3-yl)(3-fluorophenyl)methoxy)ethylcarbamate |
| I*-49a | 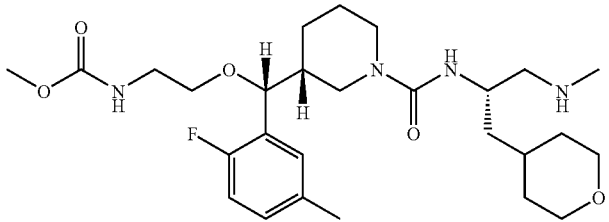 [SMILES: CNC[C@H](CC1CCOCC1)NC(=O)N1CCC[C@@H]([C@@H](OCCNC(=O)OC)c2cc(C)ccc2F)C1] | methyl 2-((R)-(2-fluoro-5-methylphenyl)((R)-1-((S)-1-(methylamino)-3-(tetrahydro-2H-pyran-4-yl)propan-2-ylcarbamoyl)piperidin-3-yl)methoxy)ethylcarbamate |
| 1*-50a | 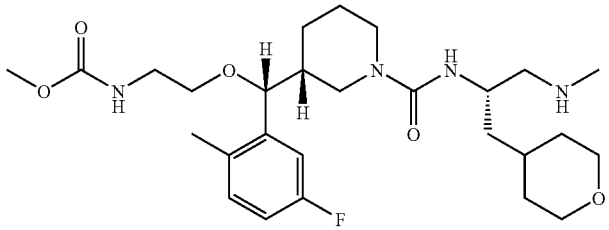 [SMILES: CNC[C@H](CC1CCOCC1)NC(=O)N1CCC[C@@H]([C@@H](OCCNC(=O)OC)c2cc(F)ccc2C)C1] | methyl 2-((R)-(5-fluoro-2-methylphenyl)((R)-1-((S)-1-(methylamino)-3-(tetrahydro-2H-pyran-4-yl)propan-2-ylcarbamoyl)piperidin-3-yl)methoxy)ethylcarbamate |

| Compound Number | | |
|---|---|---|
| I*-51a | 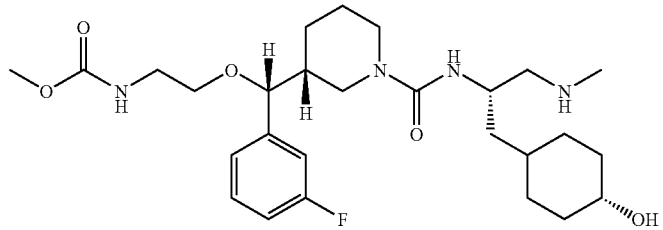 | methyl 2-((R)-(3-fluorophenyl)((R)-1-((S)-1-(4-hydroxycyclohexyl)-3-(methylamino)propan-2-ylcarbamoyl)piperidin-3-yl)methoxy)ethylcarbamate |
| I*-52a | 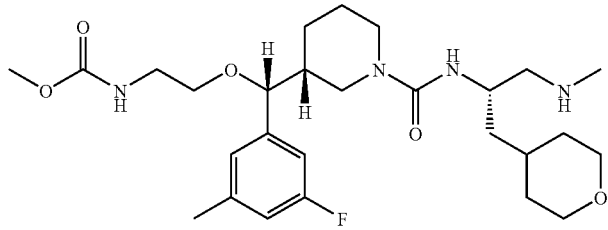 [SMILES: CNC[C@H](CC1CCOCC1)NC(=O)N1CCC[C@@H]([C@@H](OCCNC(=O)OC)c2cc(C)cc(F)c2)C1] | methyl 2-((R)-(3-fluoro-5-methylphenyl)((R)-1-((S)-1-(methylamino)-3-(tetrahydro-2H-pyran-4-yl)propan-2-ylcarbamoyl)piperidin-3-yl)methoxy)ethylcarbamate |
| I*-53a | 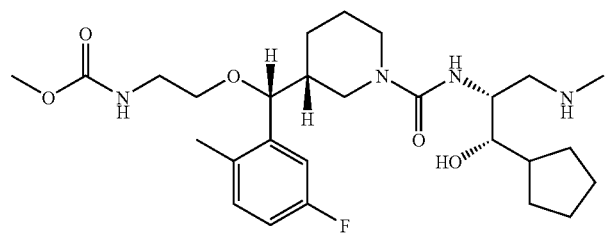 | methyl 2-((R)-((R)-1-((1S,2R)-1-cyclopentyl-1-hydroxy-3-(methylamino)propan-2-ylcarbamoyl)piperidin-3-yl)(5-fluoro-2-methylphenyl)methoxy)ethylcarbamate |
| I*-54a | 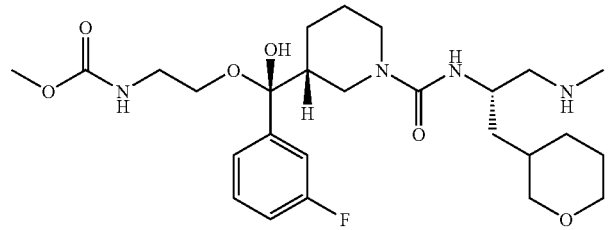 [SMILES: CNC[C@H](CC1CCCOC1)NC(=O)N1CCC[C@@H]([C@@](O)(OCCNC(=O)OC)c2cccc(F)c2)C1] | methyl (S)-4-(3-fluorophenyl)-4-hydroxy-4-((3R)-1-((S)-1-(methylamino)-3-(tetrahydro-2H-pyran-3-yl)propan-2-ylcarbamoyl)piperidin-3-yl)butylcarbamate |
| I*-55a | 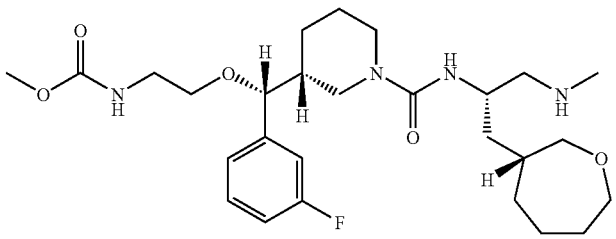 [SMILES: CNC[C@H](C[C@H]1CCCCOC1)NC(=O)N1CCC[C@@H]([C@@H](OCCNC(=O)OC)c2cccc(F)c2)C1] | methyl 2-((R)-(3-fluorophenyl)((R)-1-((S)-1-(methylamino)-3-((R)-oxepan-3-yl)propan-2-ylcarbamoyl)piperidin-3-yl)methoxy)ethylcarbamate |
| I*-56a | 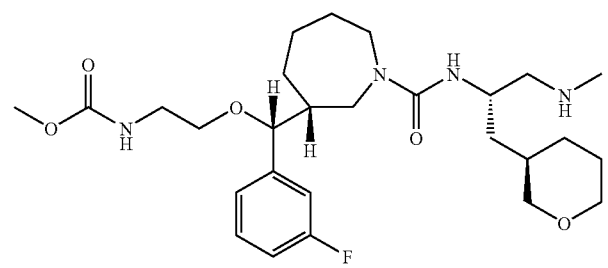 [SMILES: CNC[C@H](C[C@H]1CCCOC1)NC(=O)N1CCCC[C@@H]([C@@H](OCCNC(=O)OC)c2cccc(F)c2)C1] | methyl 2-((R)-(3-fluorophenyl)((R)-1-((S)-1-(methylamino)-3-((R)-tetrahydro-2H-pyran-3-yl)propan-2-ylcarbamoyl)azepan-3-yl)methoxy)ethylcarbamate |

| Compound Number | | |
|---|---|---|
| I*-57a | 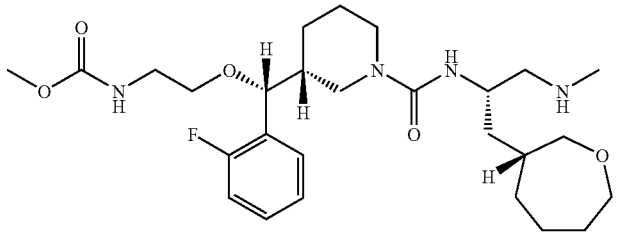 [SMILES: CNC[C@H](C[C@H]1CCCCOC1)NC(=O)N1CCC[C@@H]([C@@H](OCCNC(=O)OC)c2ccccc2F)C1] | methyl 2-((R)-(2-fluorophenyl)((R)-1-((S)-1-(methylamino)-3-((R)-oxepan-3-yl)propan-2-ylcarbamoyl)piperidin-3-yl)methoxy)ethylcarbamate |
| I*-58a | 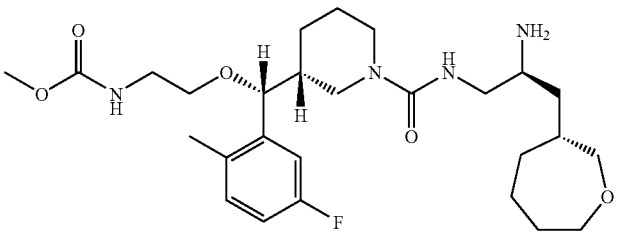 [SMILES: COC(=O)NCCO[C@@H](c1cc(F)ccc1C)[C@@H]1CCCN(C(=O)NC[C@@H](N)C[C@H]2CCCCOC2)C1] | methyl 2-((R)-((R)-1((S)-2-amino-3-((R)-oxepan-3-yl)propylcarbamoyl)piperidin-3-yl)(5-fluoro-2-methylphenyl)methoxy)ethylcarbamate |
| I*-59a | 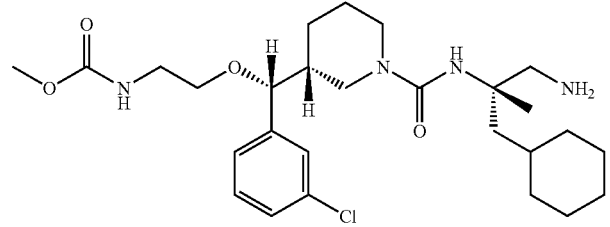 [SMILES: COC(=O)NCCO[C@@H](c1cccc(Cl)c1)[C@@H]1CCCN(C(=O)N[C@](C)(CN)CC2CCCCC2)C1] | methyl 2-((R)-((R)-1-((S)-1-amino-3-cyclohexyl-2-methylpropan-2-ylcarbamoyl)piperidin-3-yl)(3-chlorophenyl)methoxy)ethylcarbamate |
| I*-60a | 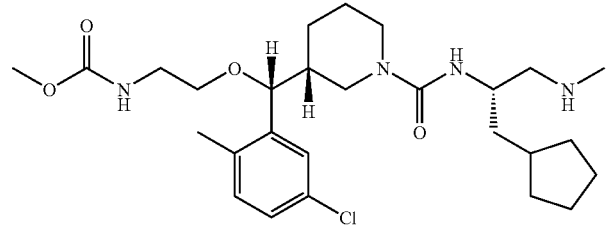 | methyl 2-((R)-(5-chloro-2-methylphenyl)((R)-1-((S)-1-cyolopentyl-3-(methylamino)propan-2-ylcarbamoyl)piperidin-3-yl)methoxy)ethylcarbamate |
| I*-61a | 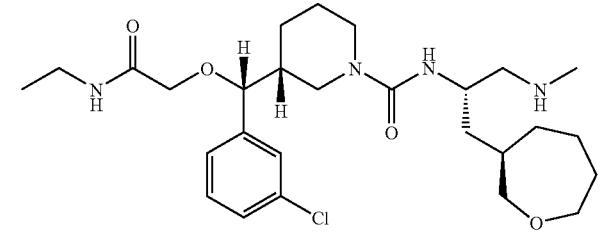 [SMILES: CCNC(=O)CO[C@@H](c1cccc(Cl)c1)[C@@H]1CCCN(C(=O)N[C@H](CNC)C[C@H]2CCCCOC2)C1] | R)-3-((R)-(3-chlorophenyl)(2-(ethylamino)-2-oxoethoxy)methyl)-N-((2S)-1-(methylamino)-3-((R)-oxepan-3-yl)propan-2-yl)piperidine-1-carboxamide |
| I*-62a | 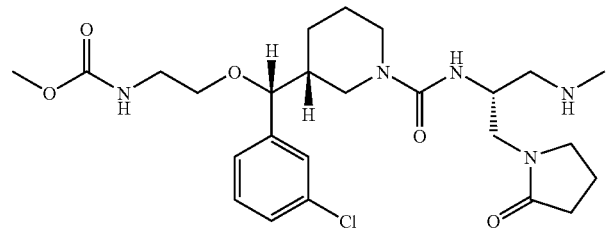 | methyl 2-((R)-(3-chlorophenyl)((R)-1-((R)-1-(methylamino)-3-(2-oxopyrrolidin-1-yl)propan-2-ylcarbamoyl)piperidin-3-yl)methoxy)ethylcarbamate |

| Compound Number | | |
|---|---|---|
| I*-63a | 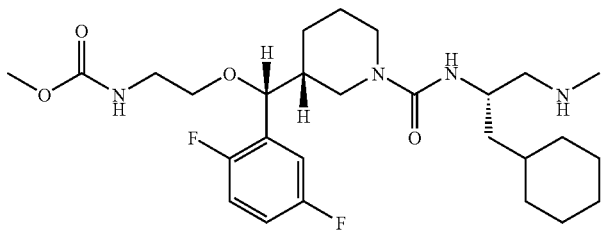 | methyl 2-((R)-((R)-1-((S)-1-cyclohexyl-3-(methylamino)propan-2-ylcarbamoyl)piperidin-3-yl)(2,5-difluorophenyl)methoxy)ethylcarbamate |
| I*-64a | 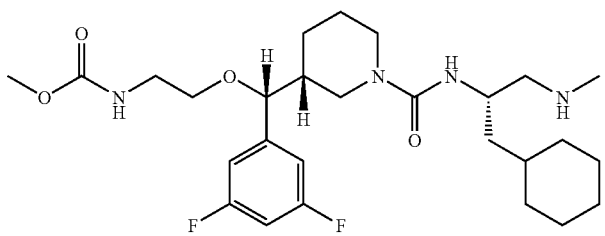 | methyl 2-((R)-((R)-1-((S)-1-cyclohexyl-3-(methylamino)propan-2-ylcarbamoyl)piperidin-3-yl)(3,5-difluorophenyl)methoxy)ethylcarbamate |
| I*-65a | 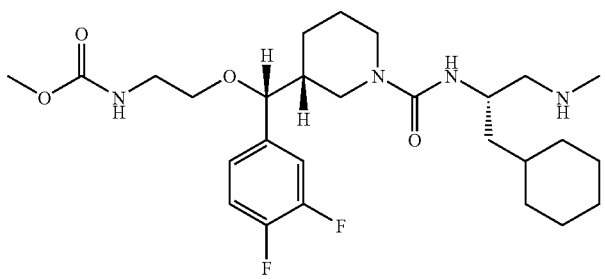 [SMILES: CNC[C@H](CC1CCCCC1)NC(=O)N1CCC[C@@H]([C@@H](OCCNC(=O)OC)c2ccc(F)c(F)c2)C1] | methyl 2-((R)-((R)-1-((S)-1-cyclohexyl-3-(methylamino)propan-2-ylcarbamoyl)piperidin-3-yl)(3,4-difluorophenyl)methoxy)ethylcarbamate |
| I*-66a | 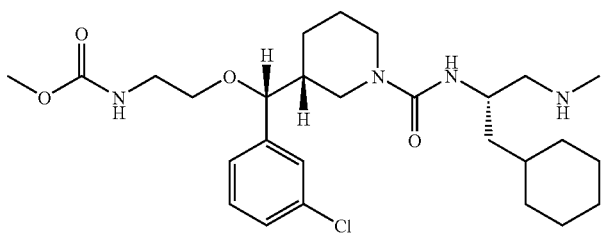 | methyl 2-((S)-(3-chlorophenyl)((R)-4-((S)-1-cyclohexyl-3-(methylamino)propan-2-ylcarbamoyl)morpholin-2-yl)methoxy)ethylcarbamate |
| I*-67a | 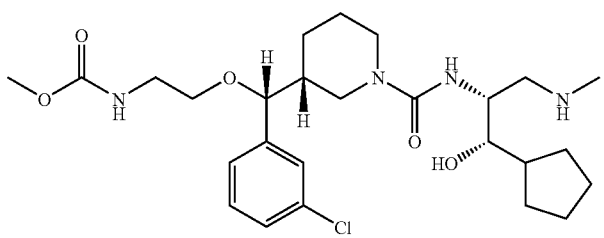 | methyl 2-((R)-(3-chlorophenyl)((R)-1-((1S,2R)-1-cyclopentyl-1-hydroxy-3-(methylamino)propan-2-ylcarbamoyl)piperidin-3-yl)methoxy)ethylcarbamate |
| I*-68a | 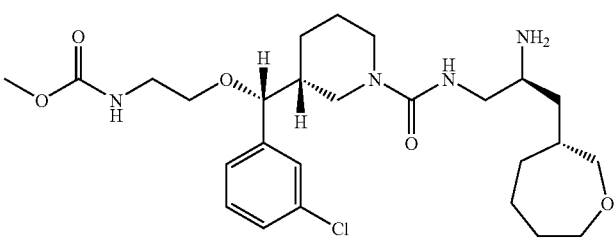 | methyl 2-((R)-((R)-1-((S)-2-amino-3-((R)-oxepan-3-yl)propylcarbamoyl)piperidin-3-yl)(3-chlorophenyl)methoxy)ethylcarbamate |

| Compound Number | | |
|---|---|---|
| I*-69a | 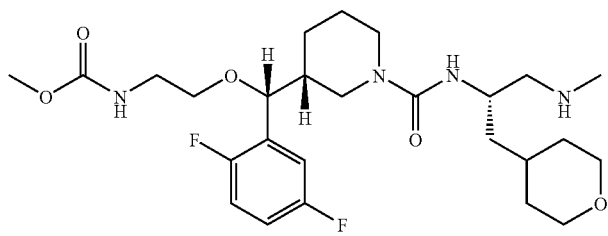 [SMILES: CNC[C@H](CC1CCOCC1)NC(=O)N1CCC[C@@H]([C@@H](OCCNC(=O)OC)c2cc(F)ccc2F)C1] | methyl 2-((R)-(2,5-difluorophenyl)((R)-1-((S)-1-(methylamino)-3-tetrahydro-2H-pyran-4-yl)propan-2-ylcarbamoyl)piperidin-3-yl)methoxy)ethylcarbamate |
| I*-70a | 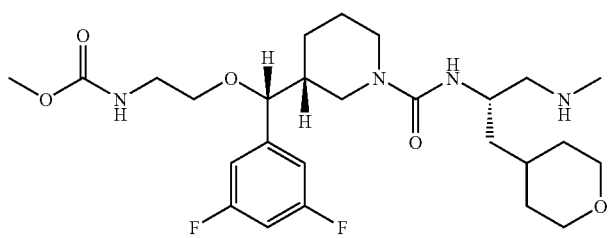 | methyl 2-((R)-(3,5-difluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-71a | 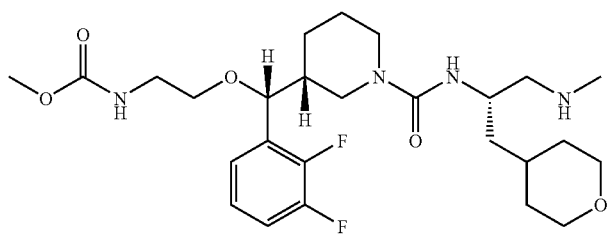 | methyl 2-((R)-(2,3-difluorophenyl)((R)-1-((S)--1-(methylamino)-3-(tetrahydro-2H-pyran-4-yl)propan-2-ylcarbamoyl)piperidin-3-yl)methoxy)ethylcarbamate |
| I*-72a | 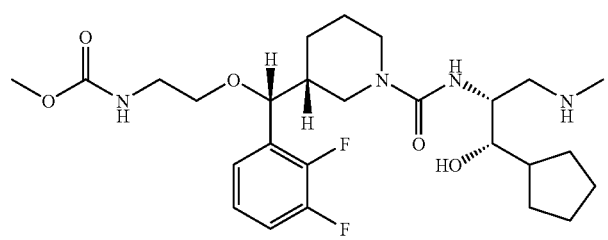 | methyl 2-((R)-((R)-1-((1S,2R)-1-cyclopentyl-1-hydroxy-3-(methylamino)propan-2-ylcarbamoyl)piperidin-3-yl)(2,3-difluorophenyl)methoxy)ethylcarbamate |
| I*-73a | 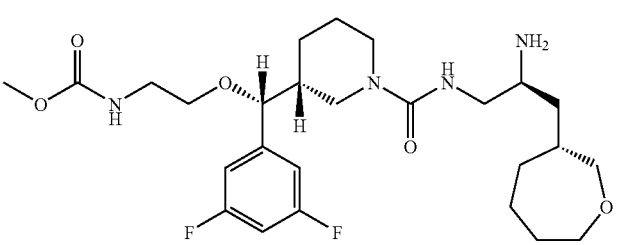 | methyl 2-((R)-((R)-1-((S)-2-amino-3-((R)-oxepan-3-yl)propylcarbamoyl)piperidin-3-yl)(3,5-difluorophenyl)methoxy)ethylcarbamate |
| I*-74a | 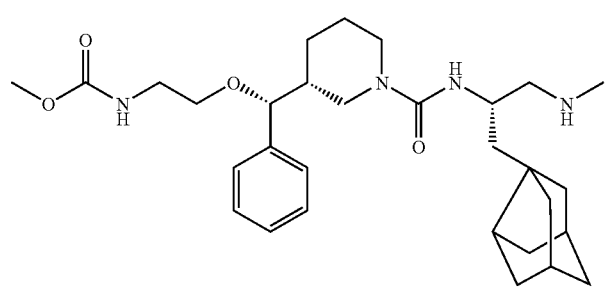 | methyl 2-((R)-((3R)-1-((S)-1-(3-noradamantyl)-3-(methylamino)propan-2-ylcarbamoyl)piperidin-3-yl)(phenyl)methoxy)ethylcarbamate |

| Compound Number | | |
|---|---|---|
| I*-75a | 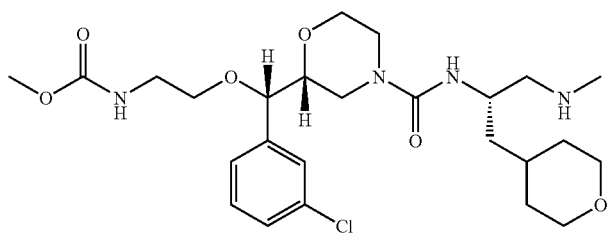 | methyl 2-((S)-(3-chlorophenyl)((R)-4-((S)-1-(methylamino)-3-(tetrahydro-2H-pyran-4-yl)propan-2-ylcarbamoyl)morpholin-2-yl)methoxy)ethylcarbamate |
| I*-76a | 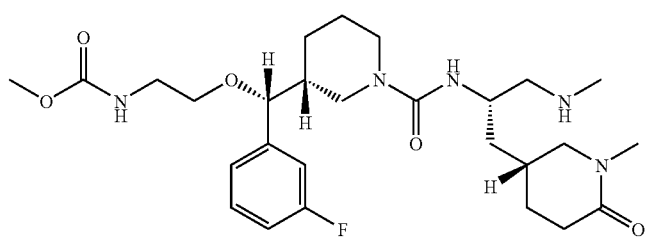 | methyl 2-((R)-(3-fluorophenyl)((R)-1-((S)-1-((R)-1-methyl-6-oxopiperidin-3-yl)-3-(methylamino)propan-2-ylcarbamoyl)piperidin-3-yl)methoxy)ethylcarbamate |
| I*-77a | 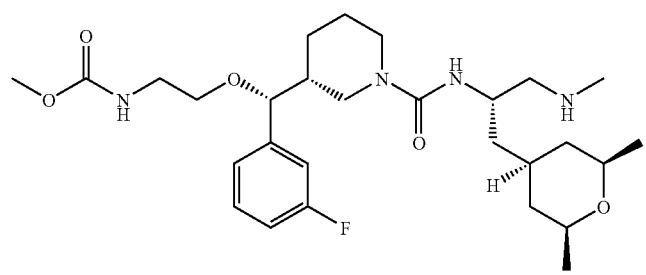 | methyl 2-((R)-((R)-1-((S)-1-((2S,4r,6R)-2,6-dimethyl-tetrahydro-2H-pyran-4-yl)-3-(methylamino)propan-2-ylcarbamoyl)piperidin-3-yl)(3-fluorophenyl)methoxy)ethylcarbamate |
| I*-78a | 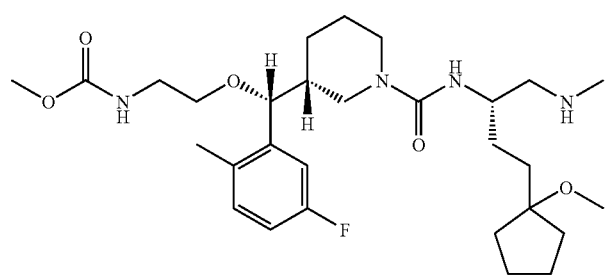 | methyl 2-((R)-(3-fluorophenyl)((R)-1-((S)-4-(1-methoxycyclopentyl)-1-(methylamino)butan-2-ylcarbamoyl)piperidin-3-yl)methoxy)ethylcarbamate |
| I*-79a | 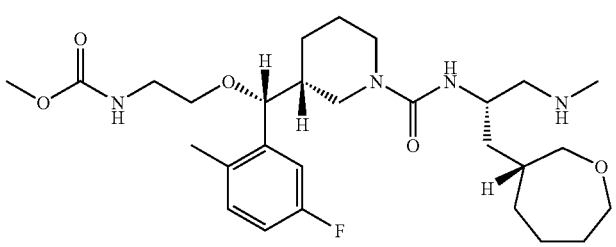 [SMILES: CNC[C@H](C[C@H]1CCCCOC1)NC(=O)N1CCC[C@@H]([C@@H](OCCNC(=O)OC)c2cc(F)ccc2C)C1] | methyl 2-((R)-(5-fluoro-2-methylphenyl)((R)-1-((S)-1-methylamino)-3-((R)-oxepan-3-yl)propan-2-ylcarbamoyl)piperidin-3-yl)methoxy)ethylcarbamate |
| I*-80a | 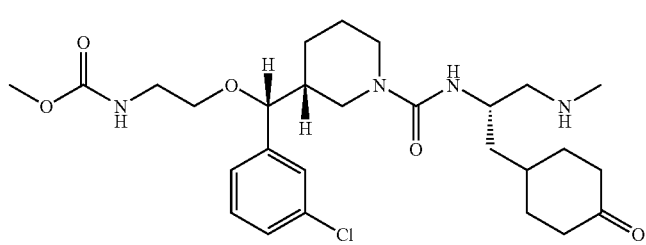 [SMILES: CNC[C@H](CC1CCC(=O)CC1)NC(=O)N1CCC[C@@H]([C@@H](OCCNC(=O)OC)c2cccc(Cl)c2)C1] | methyl 2-((R)-(3-chlorophenyl)((R)-1-((S)-1-(methylamino)-3-(4-oxocyclohexyl)propan-2-ylcarbamoyl)piperidin-3-yl)methoxy)ethylcarbamate |

| Compound Number | | |
|---|---|---|
| I*-81a | 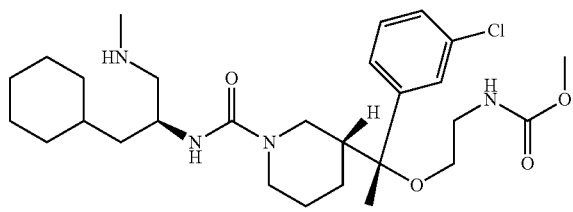 [SMILES: CNC[C@H](CC1CCCCC1)NC(=O)N1CCC[C@@H]([C@@](C)(OCCNC(=O)OC)c2cccc(Cl)c2)C1] | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate |
| I*-82a | 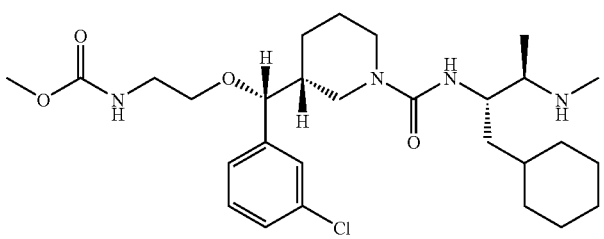 [SMILES: CN[C@H](C)[C@H](CC1CCCCC1)NC(=O)N1CCC[C@@H]([C@@H](OCCNC(=O)OC)c2cccc(Cl)c2)C1] | methyl 2-((R)-(3-chlorophenyl)((R)-1-((2S,3R)-1-cyclohexyl-3-(methylamino)butan-2-ylcarbamoyl)piperidin-3-yl)methoxy)ethylcarbamate |
| I*-83a | 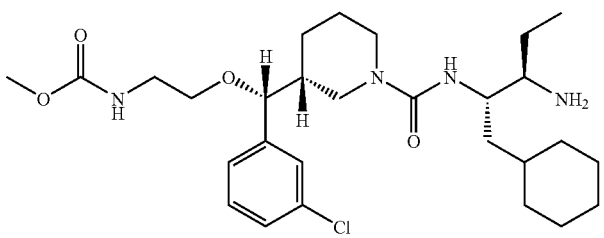 [SMILES: CC[C@@H](N)[C@H](CC1CCCCC1)NC(=O)N1CCC[C@@H]([C@@H](OCCNC(=O)OC)c2cccc(Cl)c2)C1] | methyl 2-((R)-((R)-1-((2S,3R)-3-amino-1-cyclohexylpentan-2-ylcarbamoyl)piperidin-3-yl)(3-chlorophenyl)methoxy)ethylcarbamate |
| I*-84a | 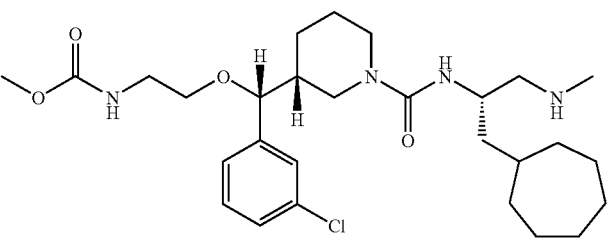 [SMILES: CNC[C@H](CC1CCCCCC1)NC(=O)N1CCC[C@@H]([C@@H](OCCNC(=O)OC)c2cccc(Cl)c2)C1] | methyl 2-((R)-(3-chlorophenyl)((R)-1-((S)-1-cycloheptyl-3-(methylamino)propan-2-ylcarbamoyl)piperidin-3-yl)methoxy)ethylcarbamate |
| I*-85a | 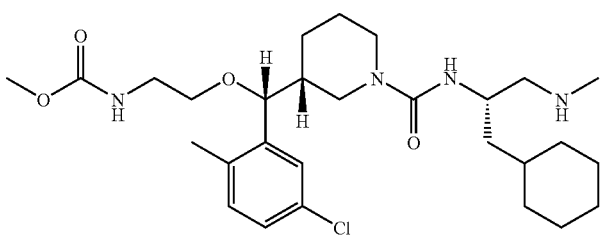 [SMILES: CNC[C@H](CC1CCCCC1)NC(=O)N1CCC[C@@H]([C@@H](OCCNC(=O)OC)c2cc(Cl)ccc2C)C1] | methyl 2-((R)-(5-chloro-2-methylphenyl)((R)-1-((S)-1-cyclohexyl-3-(methylamino)propan-2-ylcarbamoyl)piperidin-3-yl)methoxy)ethylcarbamate |
| I*-86a | 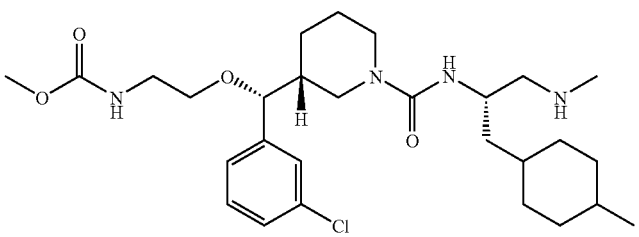 | methyl 2-((R)-(3-chlorophenyl)((R)-1-((S)-1-(methylamino)-3-(4-methylcyclohexyl)propan-2-ylcarbamoyl)piperidin-3-yl)methoxy)ethylcarbamate |

| Compound Number | | |
|---|---|---|
| I*-87a | 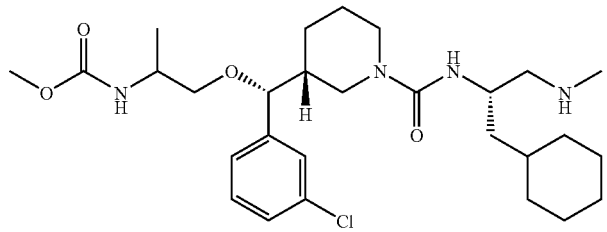 [SMILES: CNC[C@H](CC1CCCCC1)NC(=O)N1CCC[C@@H]([C@@H](OCC(C)NC(=O)OC)c2cccc(Cl)c2)C1] | methyl 1-((R)-(3-chlorophenyl)((R)-1-((S)-1-cyclohexyl-3-(methylamino)propan-2-ylcarbamoyl)piperidin-3-yl)methoxy)propan-2-ylcarbamate |
| I*-88a | 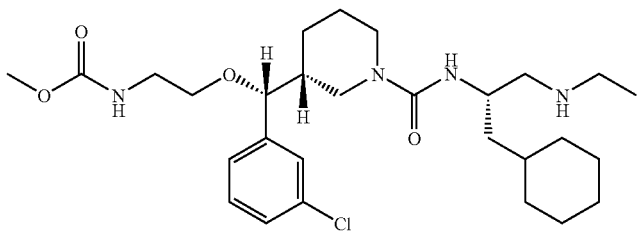 [SMILES: CCNC[C@H](CC1CCCCC1)NC(=O)N1CCC[C@@H]([C@@H](OCCNC(=O)OC)c2cccc(Cl)c2)C1] | methyl 2-((R)-(3-chlorophenyl)((R)-1-((S)-1-cyclohexyl-3-(ethylamino)propan-2-ylcarbamoyl)piperidin-3-yl)methoxy)ethylcarbamate |
| I*-89a | 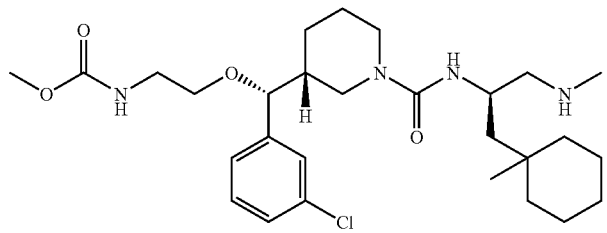 [SMILES: CNC[C@@H](CC1(C)CCCCC1)NC(=O)N1CCC[C@@H]([C@@H](OCCNC(=O)OC)c2cccc(Cl)c2)C1] | methyl 2-((R)-(3-chlorophenyl)((R)-1-((R)-1-(methylamino)-3-(1-methylcyclohexyl)propan-2-ylcarbamoyl)piperidin-3-yl)methoxy)ethylcarbamate |
| I*-90a | 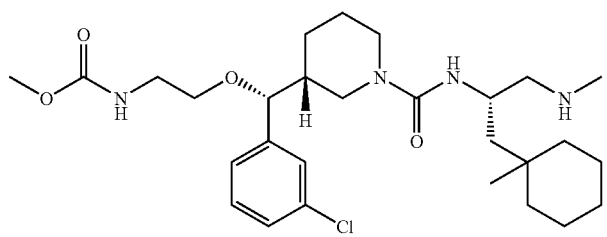 | methyl 2-((R)-(3-chlorophenyl)((R)-1-((S)-1-(methylamino)-3-(1-methylcyclohexyl)propan-2-ylcarbamoyl)piperidin-3-yl)methoxy)ethylcarbamate |
| I*-91a | 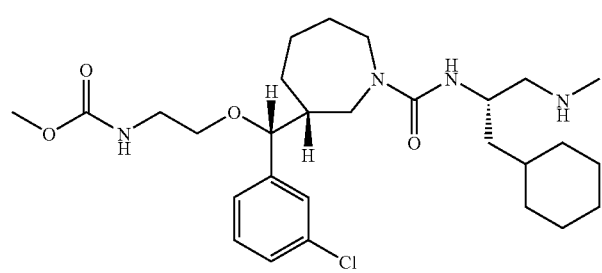 [SMILES: CNC[C@H](CC1CCCCC1)NC(=O)N1CCCC[C@@H]([C@@H](OCCNC(=O)OC)c2cccc(Cl)c2)C1] | methyl 2-((R)-(3-chlorophenyl)((R)-1-((S)-1-cyclohexyl-3-(methylamino)propan-2-ylcarbamoyl)azepan-3-yl)methoxy)ethylcarbamate |
| I*-92a | 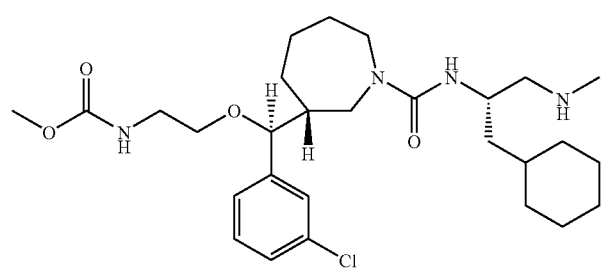 [SMILES: CNC[C@H](CC1CCCCC1)NC(=O)N1CCCC[C@@H]([C@H](OCCNC(=O)OC)c2cccc(Cl)c2)C1] | methyl 2-((S)-(3-chlorophenyl)((R)-1-((S)-1-cyclohexyl-3-(methylamino)propan-2-ylcarbamoyl)azepan-3-yl)methoxy)ethylcarbamate |

| Compound Number | | |
|---|---|---|
| I*-93a | 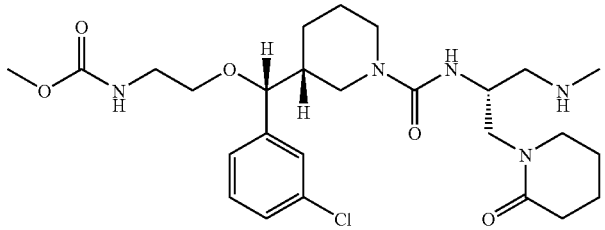 [SMILES: CNC[C@H](CN1CCCCC1=O)NC(=O)N1CCC[C@@H]([C@@H](OCCNC(=O)OC)c2cccc(Cl)c2)C1] | methyl 2-((R)-(3-chlorophenyl)((R)-1-((R)-1-(methylamino)-3-(2-oxopiperidin-1-yl)propan-2-ylcarbamoyl)piperidin-3-yl)methoxy)ethylcarbamate |
| I*-94a | 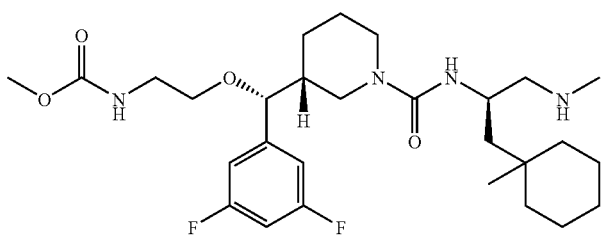 [SMILES: CNC[C@@H](CC1(C)CCCCC1)NC(=O)N1CCC[C@@H]([C@@H](OCCNC(=O)OC)c2cc(F)cc(F)c2)C1] | methyl 2-((R)-(3,5-difluorophenyl)((R)-1-((R)-1-(methylamino)-3-(1-methylcyclohexyl)propan-2-ylcarbamoyl)piperidin-3-yl)methoxy)ethylcarbamate |
| I*-95a | 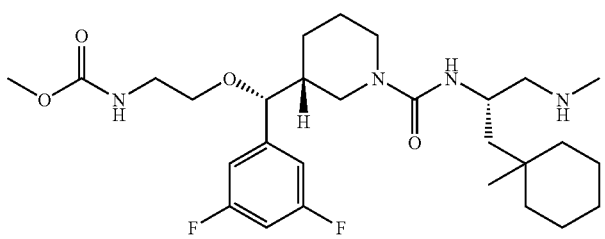 [SMILES: CNC[C@H](CC1(C)CCCCC1)NC(=O)N1CCC[C@@H]([C@@H](OCCNC(=O)OC)c2cc(F)cc(F)c2)C1] | methyl 2-((R)-(3,5-difluorophenyl)((R)-1-((S)-1-(methylamino)-3-(1-methylcyclohexyl)propan-2-ylcarbamoyl)piperidin-3-yl)methoxy)ethylcarbamate |
| I*-96a | 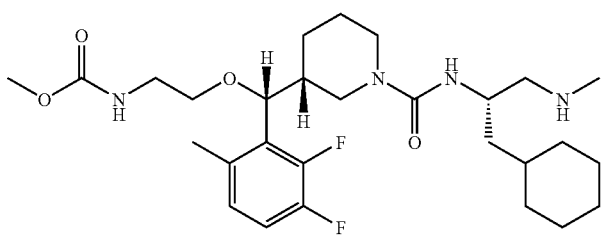 | methyl 2-((R)-((R)-1-((S)-1-cyclohexyl-3-(methylamino)propan-2-ylcarbamoyl)piperidin-3-yl)(2,3-difluoro-6-methylphenyl)methoxy)-ethylcarbamate |
| I*-97a | 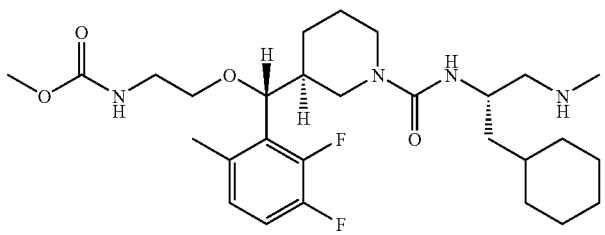 [SMILES: CNC[C@H](CC1CCCCC1)NC(=O)N1CCC[C@H]([C@@H](OCCNC(=O)OC)c2c(C)ccc(F)c2F)C1] | methyl 2-((R)-((S)-1-((S)-1-cyclohexyl-3-(methylamino)propan-2-ylcarbamoyl)piperidin-3-yl)(2,3-difluoro-6-methylphenyl)methoxy)-ethylcarbamate |
| I*-98a | 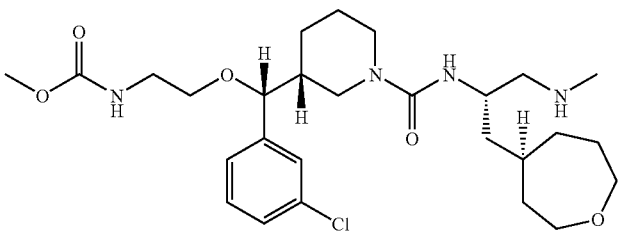 [SMILES: CNC[C@H](C[C@H]1CCCOCC1)NC(=O)N1CCC[C@@H]([C@@H](OCCNC(=O)OC)c2cccc(Cl)c2)C1] | methyl 2-((R)-(3-chlorophenyl)((R)-1-((S)-1-(methylamino)-3-((R)-oxepan-4-yl)propan-2-ylcarbamoyl)piperidin-3-yl)methoxy)ethylcarbamate |

| Compound Number | | |
|---|---|---|
| I*-99a | 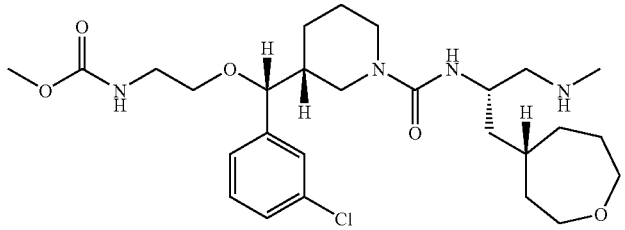 [SMILES: CNC[C@H](C[C@@H]1CCCOCC1)NC(=O)N1CCC[C@@H]([C@@H](OCCNC(=O)OC)c2cccc(Cl)c2)C1] | methyl 2-((R)-(3-chlorophenyl)((R)-1-((S)-1-(methylamino)-3-((S)-oxepan-4-yl)propan-2-ylcarbamoyl)piperidin-3-yl)methoxy)ethylcarbamate |
| I*-100a | 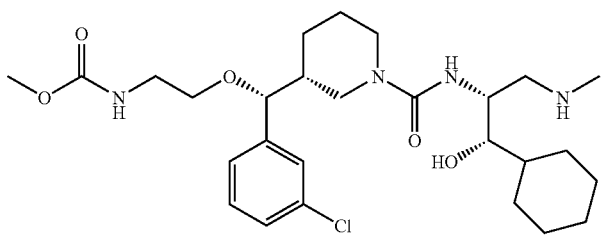 | methyl 2-((R)-(3-chlorophenyl)((R)-1-((1S,2R)-1-cyclohexyl-1-hydroxy-3-(methylamino)propan-2-ylcarbamoyl)piperidin-3-yl)methoxy)ethylcarbamate |
| I*-101a | 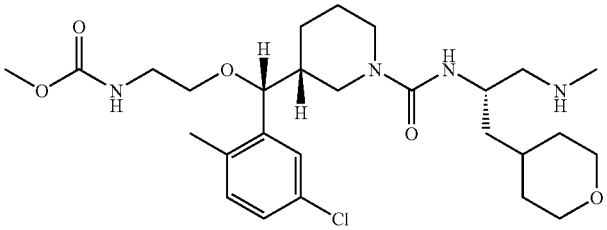 [SMILES: CNC[C@H](CC1CCOCC1)NC(=O)N1CCC[C@@H]([C@@H](OCCNC(=O)OC)c2cc(Cl)ccc2C)C1] | methyl 2-((R)-(5-chloro-2-methylphenyl)((R)-1-((S)-1-(methylamino)-3-(tetrahydro-2H-pyran-4-yl)propan-2-ylcarbamoyl)piperidin-3-yl)methoxy)ethylcarbamate |
| I*-102a | 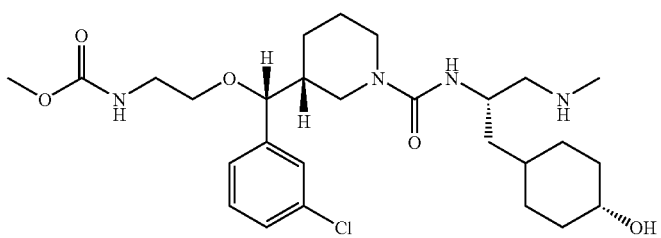 | methyl 2-((R)-(3-chlorophenyl)((R)-1-((S)-1-(4-hydroxycyclohexyl)-3-(methylamino)propan-2-ylcarbamoyl)piperidin-3-yl)methoxy)ethylcarbamate |
| I*-103a | 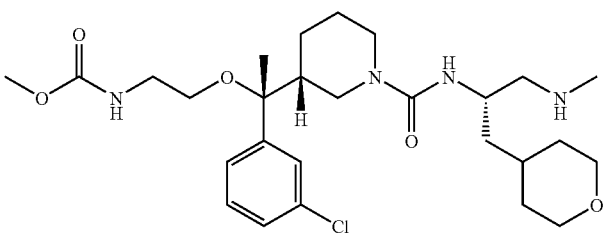 [SMILES: CNC[C@H](CC1CCOCC1)NC(=O)N1CCC[C@@H]([C@@](C)(OCCNC(=O)OC)c2cccc(Cl)c2)C1] | methyl 2-((R)-1-(3-chlorophenyl)-1-((R)-1-((S)-1-(methylamino)-3-(tetrahydro-2H-pyran-4-yl)propan-2-ylcarbamoyl)piperidin-3-yl)ethoxy)ethylcarbamate |
| I*-104a | 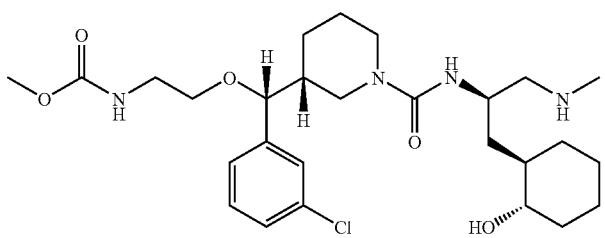 [SMILES: CNC[C@@H](C[C@H]1CCCC[C@@H]1O)NC(=O)N1CCC[C@@H]([C@@H](OCCNC(=O)OC)c2cccc(Cl)c2)C1] | methyl 2-((R)-(3-chlorophenyl)((R)-1-((R)-1-((1R*,2S*)-2-hydroxycyclohexyl)-3-(methylamino)propan-2-ylcarbamoyl)piperidin-3-yl)methoxy)ethylcarbamate |

-continued

| Compound Number | | |
|---|---|---|
| I*-105a | 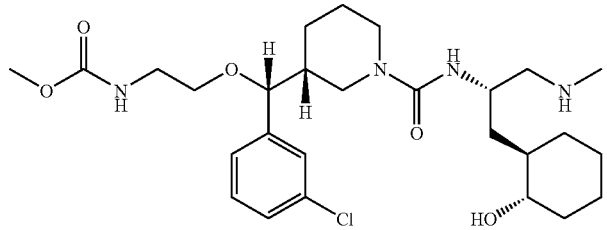 [SMILES: CNC[C@H](C[C@H]1CCCC[C@@H]1O)NC(=O)N1CCC[C@@H]([C@@H](OCCNC(=O)OC)c2cccc(Cl)c2)C1] | methyl 2-((R)-(3-chlorophenyl)((R)-1-((S)-1-((1R*,2S*)-2-hydroxycyclohexyl)-3-(methylamino)propan-2-ylcarbamoyl)piperidin-3-yl)methoxy)ethylcarbamate |
| I*-106a | 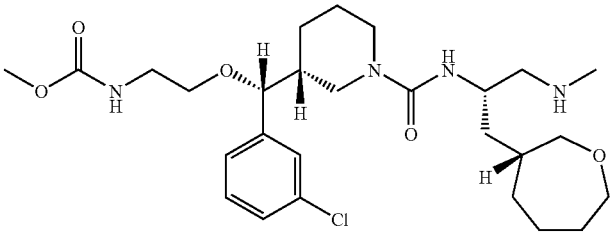 [SMILES: CNC[C@H](C[C@H]1CCCCOC1)NC(=O)N1CCC[C@@H]([C@@H](OCCNC(=O)OC)c2cccc(Cl)c2)C1] | methyl 2-((R)-(3-chlorophenyl)((R)-1-((S)-1-(methylamino)-3-((R)-oxepan-3-yl)propan-2-ylcarbamoyl)piperidin-3-yl)methoxy)ethylcarbamate |
| I*-107a | 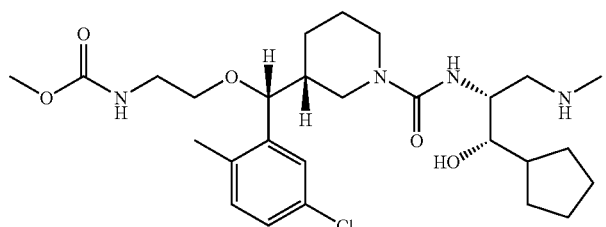 | methyl 2-((R)-(5-chloro-2-methylphenyl)((R)-1-((1S,2R)-1-cyclopentyl-1-hydroxy-3-(methylamino)propan-2-ylcarbamoyl)piperidin-3-yl)methoxy)ethylcarbamate |
| I*-108a | 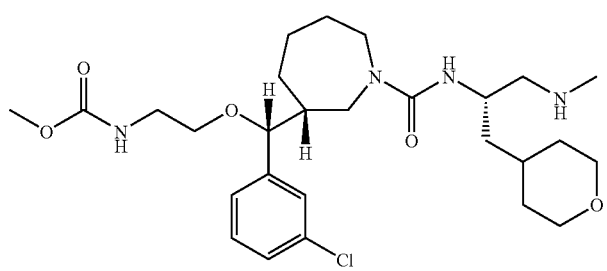 [SMILES: CNC[C@H](CC1CCOCC1)NC(=O)N1CCCC[C@@H]([C@@H](OCCNC(=O)OC)c2cccc(Cl)c2)C1] | methyl 2-((R)-(3-chlorophenyl)((R)-1-((S)-1-(methylamino)-3-(tetrahydro-2H-pyran-4-yl)prop-2-ylcarbamoyl)azepan-3-yl)methoxy)ethylcarbamate |
| I*-109a | 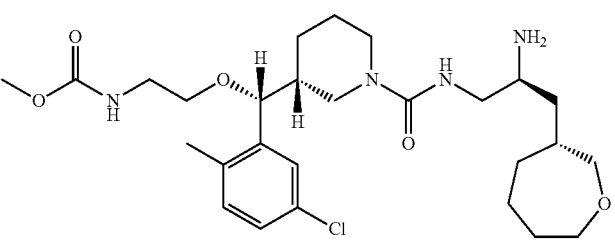 [SMILES: COC(=O)NCCO[C@@H](c1cc(Cl)ccc1C)[C@@H]1CCCN(C(=O)NC[C@@H](N)C[C@H]2CCCCOC2)C1] | methyl 2-((R)-((R)-1-((S)-2-amino-3-((R)-oxepan-3-yl)propylcarbamoyl)piperidin-3-yl)(5-chloro-2-methylphenyl)methoxy)-ethylcarbamate |
| I*-110a | 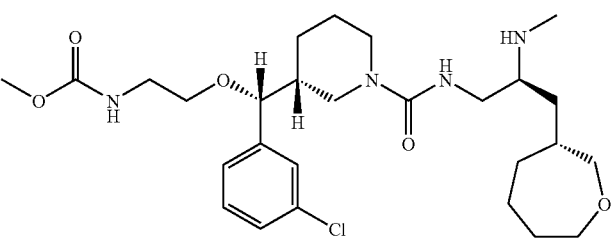 [SMILES: CN[C@H](CNC(=O)N1CCC[C@@H]([C@@H](OCCNC(=O)OC)c2cccc(Cl)c2)C1)C[C@H]1CCCCOC1] | methyl 2-((R)-(3-chlorophenyl)((R)-1-((S)-2-(methylamino)-3-((R)-oxepan-3-yl)propylcarbamoyl)piperidin-3-yl)methoxy)-ethylcarbamate |

| Compound Number | | |
|---|---|---|
| I*-111a | 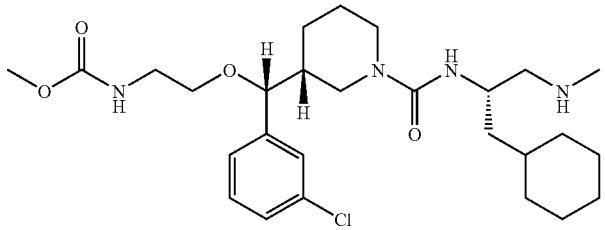 | methyl 2-((R)-(3-chlorophenyl)((R)-1-((S)-1-cyclohexyl-3-(methylamino)propan-2-ylcarbamothioyl)piperidin-3-yl)methoxy)ethylcarbamate |
| I*-112a | 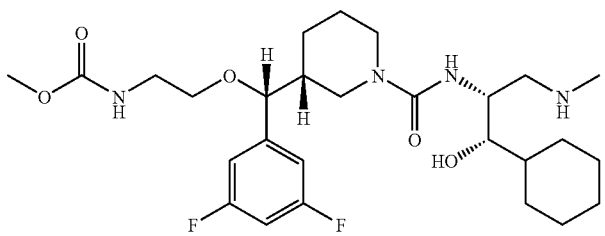 [SMILES: CNC[C@@H](NC(=O)N1CCC[C@@H]([C@@H](OCCNC(=O)OC)c2cc(F)cc(F)c2)C1)[C@@H](O)C1CCCCC1] | methyl 2-((R)-((R)-1-(1S,2R)-1-cyclohexyl-1-hydroxy-3-(methylamino)propan-2-ylcarbamoyl)piperidin-3-yl)(3,5-difluorophenyl)methoxy)-ethylcarbamate |
| I*-113a | 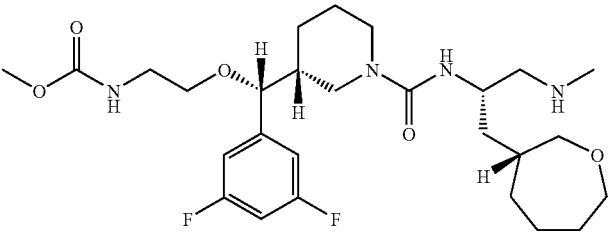 [SMILES: CNC[C@H](C[C@H]1CCCCOC1)NC(=O)N1CCC[C@@H]([C@@H](OCCNC(=O)OC)c2cc(F)cc(F)c2)C1] | methyl 2-((R)-(3,5-difluorophenyl)((R)-1-((S)-1-(methylamino)-3-((R)-oxepan-3-yl)propan-2-ylcarbamoyl)piperidin-3-yl)methoxy)ethylcarbamate |
| I*-114a | 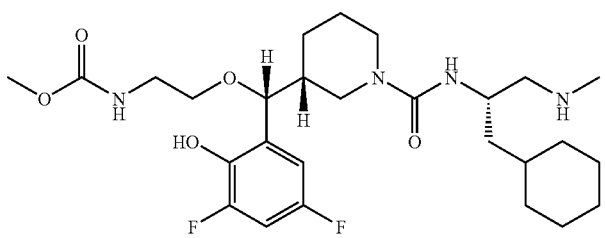 [SMILES: CNC[C@H](CC1CCCCC1)NC(=O)N1CCC[C@@H]([C@@H](OCCNC(=O)OC)c2cc(F)cc(F)c2O)C1] | methyl 2-((R)-((R)-1-((S)-1-cyclohexyl-3-(methylamino)propan-2-ylcarbamoyl)piperidin-3-yl)(3,5-difluoro-2-hydroxyphenyl)methoxy)-ethylcarbamate |
| I*-115a | 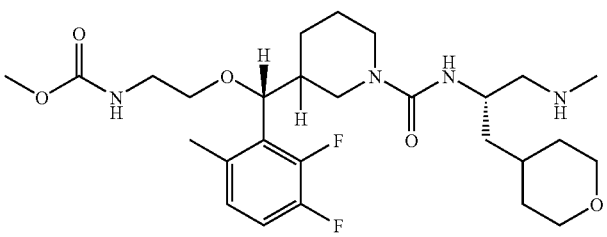 [SMILES: CNC[C@H](CC1CCOCC1)NC(=O)N1CCCC([C@@H](OCCNC(=O)OC)c2c(C)ccc(F)c2F)C1] | methyl 2-((R)-2,3-difluoro-6-methylphenyl)(1-((S)-1-(methylamino)-3-(tetrahydro-2H-pyran-4-yl)propan-2-y)carbamoyl-piperidin-3-yl)methoxy)ethylcarbamate |
| I*-116a | 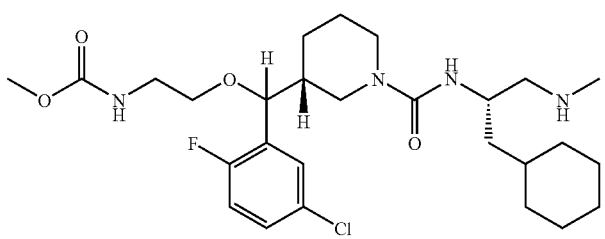 [SMILES: CNC[C@H](CC1CCCCC1)NC(=O)N1CCC[C@@H](C(OCCNC(=O)OC)c2cc(Cl)ccc2F)C1] | methyl 2-((5-chloro-2-fluorophenyl)((R)-1-((S)-1-cyclohexyl-3-(methylamino)propan-2-ylcarbamoyl)piperidin-3-yl)methoxy)ethylcarbamate |

| Compound Number | | |
|---|---|---|
| I*-117a | 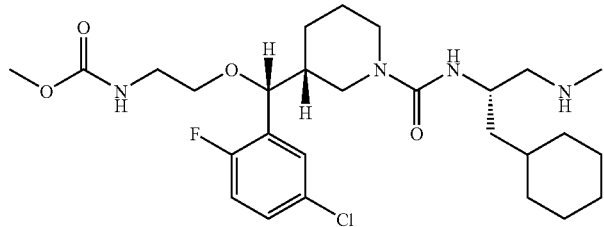 [SMILES: CNC[C@H](CC1CCCCC1)NC(=O)N1CCC[C@@H]([C@@H](OCCNC(=O)OC)c2cc(Cl)ccc2F)C1] | methyl 2-((R)-(5-chloro-2-fluorophenyl)((R)-1-((S)-1-cyclohexyl-3-(methylamino)propan-2-ylcarbamoyl)piperidin-3-yl)methoxy)ethylcarbamate |
| I*-118a | 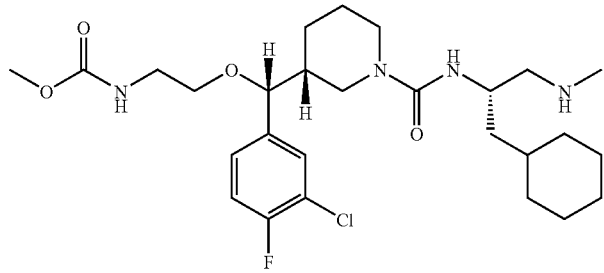 [SMILES: CNC[C@H](CC1CCCCC1)NC(=O)N1CCC[C@@H]([C@@H](OCCNC(=O)OC)c2ccc(F)c(Cl)c2)C1] | methyl 2-((R)-(3-chloro-4-fluorophenyl)((R)-1-((S)-1-cyclohexyl-3-(methylamino)propan-2-ylcarbamoyl)piperidin-3-yl)methoxy)ethylcarbamate |
| I*-119a | 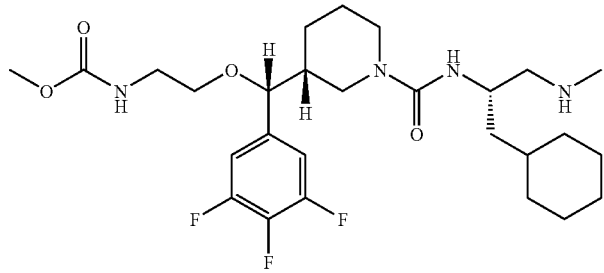 [SMILES: CNC[C@H](CC1CCCCC1)NC(=O)N1CCC[C@@H]([C@@H](OCCNC(=O)OC)c2cc(F)c(F)c(F)c2)C1] | methyl 2-((R)-((R)-1-((S)-1-cyclohexyl-3-(methylamino)propan-2-ylcarbamoyl)piperidin-3-yl)(3,4,5-trifluorophenyl)methoxy)-ethylcarbamate |
| I*-120a | 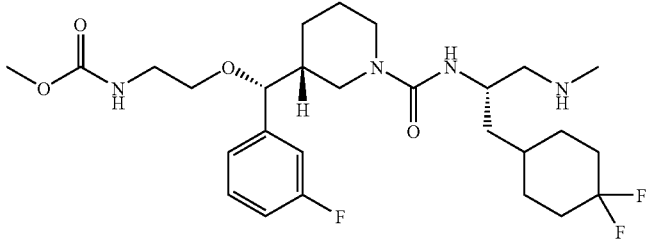 [SMILES: CNC[C@H](CC1CCC(F)(F)CC1)NC(=O)N1CCC[C@@H]([C@@H](OCCNC(=O)OC)c2cccc(F)c2)C1] | methyl 2-((R)-((R)-1-((S)-1-(4,4-difluorocyclohexyl)-3-(methylamino)propan-2-ylcarbamoyl)piperidin-3-yl)(3-fluorophenyl)methoxy)-ethylcarbamate |
| I*-121a | 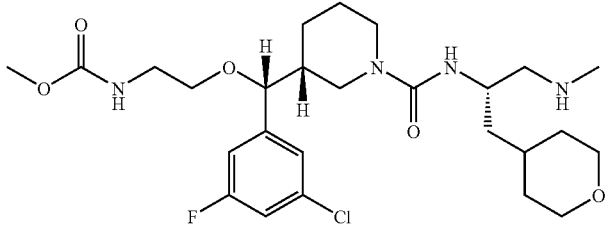 [SMILES: CNC[C@H](CC1CCOCC1)NC(=O)N1CCC[C@@H]([C@@H](OCCNC(=O)OC)c2cc(F)cc(Cl)c2)C1] | methyl 2-((R)-(3-chloro-5-fluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-122a | 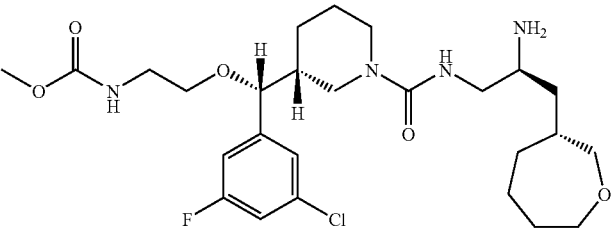 [SMILES: COC(=O)NCCO[C@@H](c1cc(F)cc(Cl)c1)[C@@H]1CCCN(C(=O)NC[C@@H](N)C[C@H]2CCCCOC2)C1] | methyl 2-((R)-((R)-1-((S)-2-amino-3-((R)-oxepan-3-yl)propylcarbamoyl)piperidin-3-yl)(3-chloro-5-fluorophenyl)methoxy)-ethylcarbamate |

| Compound Number | | |
|---|---|---|
| I*-123a | 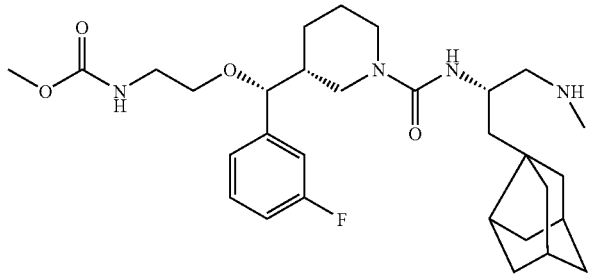 [SMILES: CNC[C@H](CC12CC3CC(CC1C3)C2)NC(=O)N1CCC[C@@H]([C@@H](OCCNC(=O)OC)c2cccc(F)c2)C1] | methyl 2-((R)-((3R)-1-((S)-1-(3-noradamantyl)-3-(methylamino)propan-2-ylcarbamoyl)piperidin-3-yl)(3-fluorophenyl)methoxy)-ethylcarbamate |
| I*-124a | 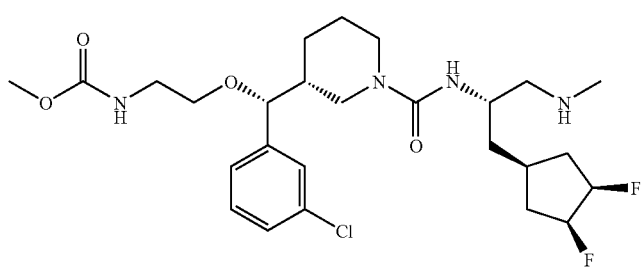 [SMILES: CNC[C@H](C[C@H]1C[C@@H](F)[C@@H](F)C1)NC(=O)N1CCC[C@@H]([C@@H](OCCNC(=O)OC)c2cccc(Cl)c2)C1] | methyl 2-((R)-(3-chlorophenyl)((R)-1-((S)-1-((1r,3S,4R)-3,4-difluorocyclopentyl)-3-(methylamino)propan-2-ylcarbamoyl)piperidin-3-yl)methoxy)ethylcarbamate |
| I*-125a | 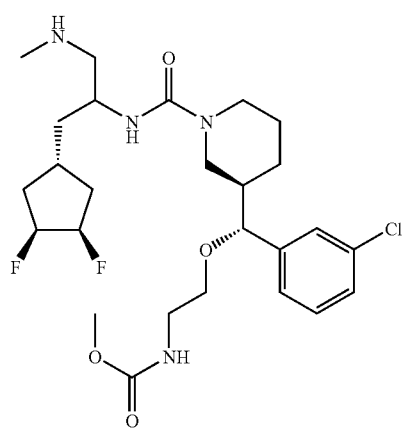 [SMILES: CNCC(C[C@@H]1C[C@@H](F)[C@@H](F)C1)NC(=O)N1CCC[C@@H]([C@@H](OCCNC(=O)OC)c2cccc(Cl)c2)C1] | methyl 2-((R)-(3-chlorophenyl)((R)-1-((S)-1-((1s,3R,4S)-3,4-difluorocyclopentyl)-3-(methylamino)propan-2-ylcarbamoyl)piperidin-3-yl)methoxy)ethylcarbamate |
| I*-126a | 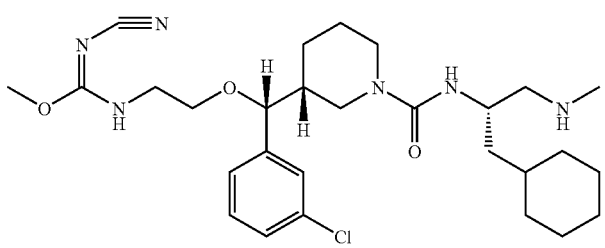 [SMILES: CNC[C@H](CC1CCCCC1)NC(=O)N1CCC[C@@H]([C@@H](OCCN/C(=N\C#N)OC)c2cccc(Cl)c2)C1] | (R)-3-((R)-(3-chlorophenyl)(2-(2-cyano-3-methylguanidino)ethoxy)-methyl)-N-((S)-1-cyclohexyl-3-(methylamino)propan-2-yl)piperidine-1-carboxamide |
| I*-127a | 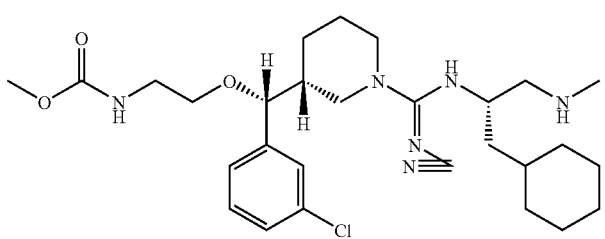 [SMILES: CNC[C@H](CC1CCCCC1)N/C(=N\C#N)N1CCC[C@@H]([C@@H](OCCNC(=O)OC)c2cccc(Cl)c2)C1] | methyl 2-((R)-(3-chlorophenyl)((R)-1-(N'-cyano-N-((S)-1-cyclohexyl-3-(methylamino)propan-2-yl)carbamimidoyl)piperidin-3-yl)-methoxy)ethylcarbamate |

| Compound Number | | |
|---|---|---|
| I*-128a | 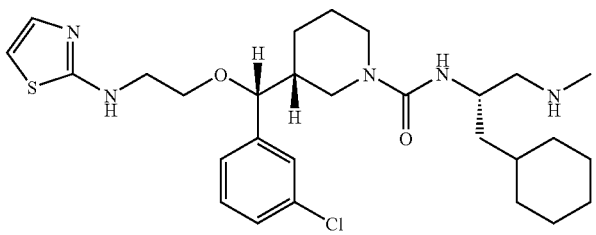 [SMILES: CNC[C@H](CC1CCCCC1)NC(=O)N1CCC[C@@H]([C@@H](OCCNc2nccs2)c2cccc(Cl)c2)C1] | (R)-3-((R)-(3-chlorophenyl)(2-(thiazol-2-ylamino)ethoxy)methyl)-N-((S)-1-cyclohexyl-3-(methylamino)propan-2-yl)piperidine-1-carboxamide |
| I*-129a | 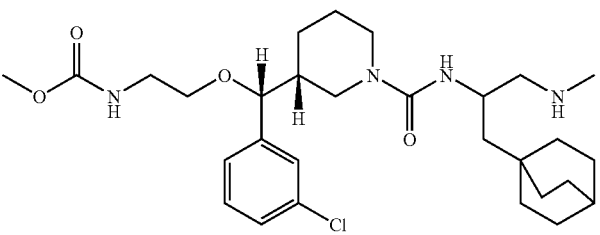 [SMILES: CNCC(CC12CCC(CC1)CC2)NC(=O)N1CCC[C@@H]([C@@H](OCCNC(=O)OC)c2cccc(Cl)c2)C1] | methyl 2-((R)-((3R)-1-(1-(bicyclo[2.2.2]octan-1-yl)-3-(methylamino)propan-2-ylcarbamoyl)piperidin-3-yl)(3-chlorophenyl)methoxy)-ethylcarbamate |
| I*-130a | 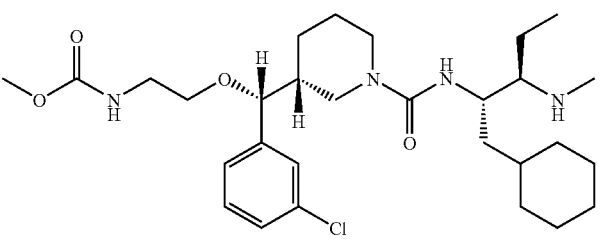 [SMILES: CC[C@@H](NC)[C@H](CC1CCCCC1)NC(=O)N1CCC[C@@H]([C@@H](OCCNC(=O)OC)c2cccc(Cl)c2)C1] | methyl 2-((R)-(3-chlorophenyl)((R)-1-((2S,3R)-1-cyclohexyl-3-(methylamino)pentan-2-ylcarbamoyl)piperidin-3-yl)methoxy)ethylcarbamate |
| I*-131a | 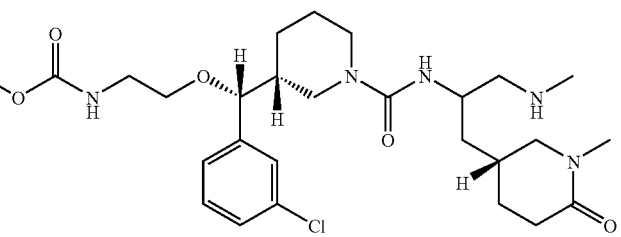 | methyl 2-((R)-(3-chlorophenyl)((R)-1-((S)-1-((R)-1-methyl-6-oxopiperidin-3-yl)-3-(methylamino)propan-2-ylcarbamoyl)piperidin-3-yl)methoxy)ethylcarbamate |
| I*-132a | 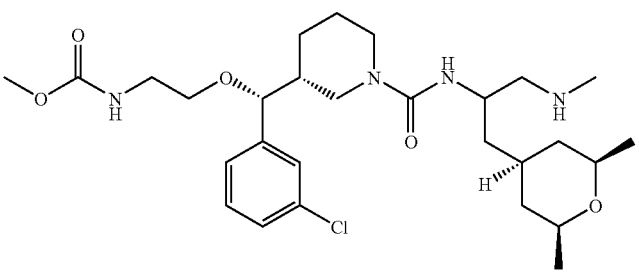 | methyl 2-((R)-(3-chlorophenyl)((R)-1-((S)-1-((2S,4r,6R)-2,6-dimethyl-tetrahydro-2H-pyran-4-yl)-3-(methylamino)propan-2-ylcarbamoyl)piperidin-3-yl)methoxy)ethylcarbamate |
| I*-133a | 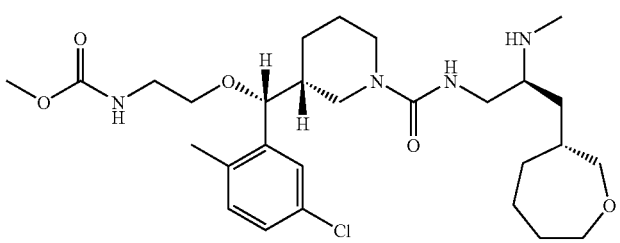 [SMILES: CN[C@H](CNC(=O)N1CCC[C@@H]([C@@H](OCCNC(=O)OC)c2cc(Cl)ccc2C)C1)C[C@H]1CCCCOC1] | methyl 2-((R)-(5-chloro-2-methylphenyl)((R)-1-((S)-2-(methylamino)-3-((R)-oxepan-3-yl)propylcarbamoyl)piperidin-3-yl)methoxy)ethylcarbamate |

| Compound Number | | |
|---|---|---|
| I*-134a | 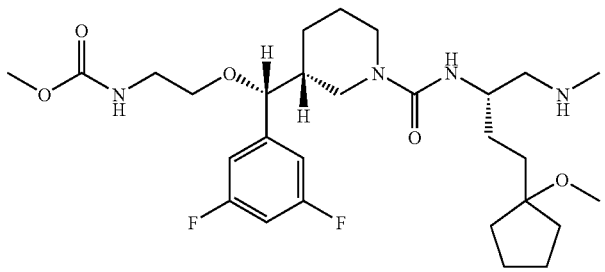 | methyl 2-((R)-(3,5-difluorophenyl)((R)-1-((S)-4-(1-methoxycyclopentyl)-1-(methylamino)butan-2-ylcarbamoyl)piperidin-3-yl)methoxy)ethylcarbamate |
| I*-135a | 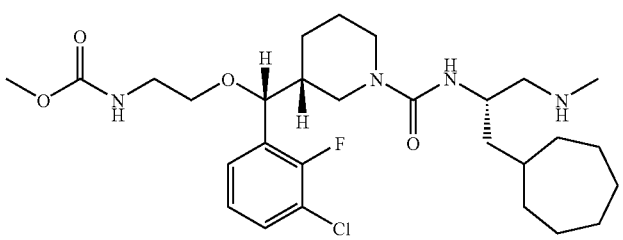 | methyl 2-((R)-(3-chloro-2-fluorophenyl)((R)-1-((S)-1-cycloheptyl-3-(methylamino)propan-2-ylcarbamoyl)piperidin-3-yl)methoxy)ethylcarbamate |
| I*-136a | 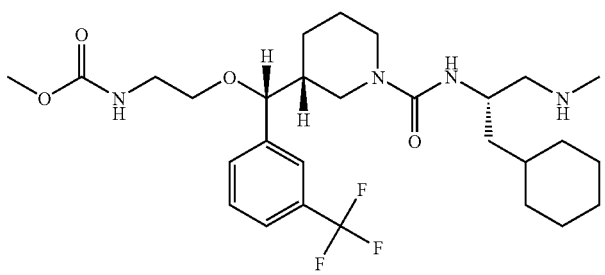 [SMILES: CNC[C@H](CC1CCCCC1)NC(=O)N1CCC[C@@H]([C@@H](OCCNC(=O)OC)c2cccc(C(F)(F)F)c2)C1] | methyl 2-((R)-((R)-1-((S)-1-cyclohexyl-3-(methylamino)propan-2-ylcarbamoyl)piperidin-3-yl)(3-(trifluoromethyl)phenyl)-methoxy)ethylcarbamate |
| I*-137a | 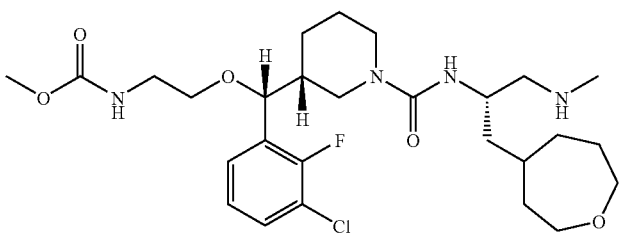 [SMILES: CNC[C@H](CC1CCCOCC1)NC(=O)N1CCC[C@@H]([C@@H](OCCNC(=O)OC)c2cccc(Cl)c2F)C1] | methyl 2-((R)-(3-chloro-2-fluorophenyl)((3R)-1-((S)-1-(methylamino)-3-(oxepan4-yl)propan-2-ylcarbamoyl)piperidin-3-yl)methoxy)ethylcarbamate |
| I*-138a | 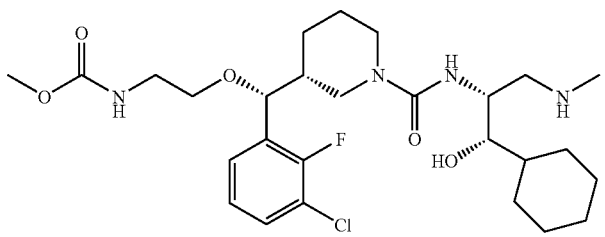 | methyl 2-((R)-(3-chloro-2-fluorophenyl)((R)-1-((1S,2R)-1-cyclohexyl-1-hydroxy-3-(methylamino)propan-2-ylcarbamoyl)piperidin-3-yl)methoxy)ethylcarbamate |
| I*-139a | 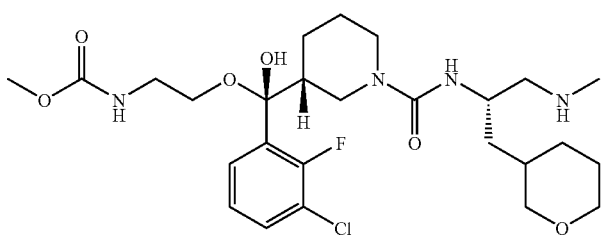 | methyl (S)-4-(3-chloro-2-fluorophenyl)-4-hydroxy-4-((3R)-1-((S)-1-(methylamino)-3-(tetrahydro-2H-pyran-3-yl)propan-2-ylcarbamoyl)piperidin-3-yl)butylcarbamate |

| Compound Number | | |
|---|---|---|
| I*-140a | 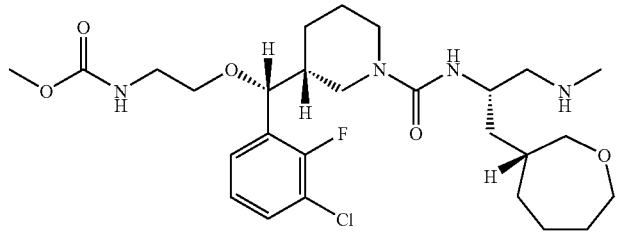 [SMILES: CNC[C@H](C[C@H]1CCCCOC1)NC(=O)N1CCC[C@@H]([C@@H](OCCNC(=O)OC)c2cccc(Cl)c2F)C1] | methyl 2-((R)-(3-chloro-2-fluorophenyl)((R)-1-((S)-1-(methylamino)-3-((R)-oxepan-3-yl)propan-2-ylcarbamoyl)piperidin-3-yl)methoxy)ethylcarbamate |
| I*-141a | 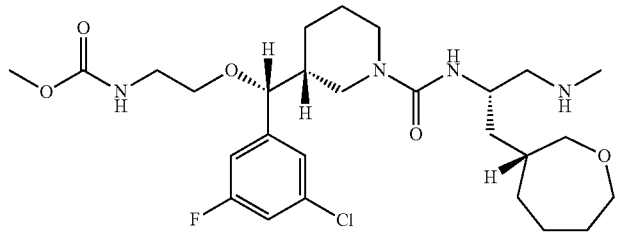 [SMILES: CNC[C@H](C[C@H]1CCCCOC1)NC(=O)N1CCC[C@@H]([C@@H](OCCNC(=O)OC)c2cc(F)cc(Cl)c2)C1] | methyl 2-((R)-(3-chloro-5-fluorophenyl)((R)-1-((S)-1-(methylamino)-3-((R)-oxepan-3-yl)propan-2-ylcarbamoyl)piperidin-3-yl)methoxy)ethylcarbamate |
| I*-142a | 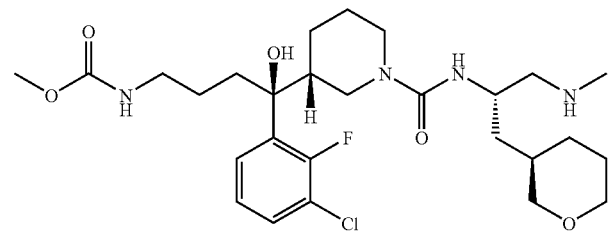 [SMILES: CNC[C@H](C[C@H]1CCCOC1)NC(=O)N1CCC[C@@H]([C@@](O)(CCCNC(=O)OC)c2cccc(Cl)c2F)C1] | methyl (S)-4-(3-chloro-2-fluorophenyl)-4-hydroxy-4-((R)-1-((S)-1-(methylamino)-3-((R)-tetrahydro-2H-pyran-3-yl)propan-2-ylcarbamoyl)piperidin-3-yl)butylcarbamate |
| I*-143a | 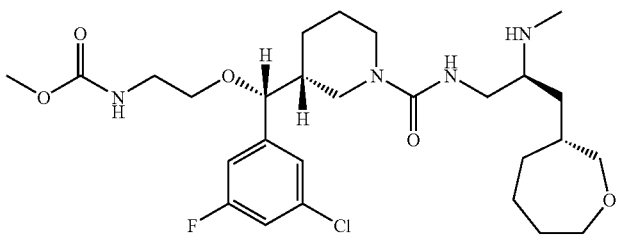 [SMILES: CN[C@H](CNC(=O)N1CCC[C@@H]([C@@H](OCCNC(=O)OC)c2cc(F)cc(Cl)c2)C1)C[C@H]1CCCCOC1] | methyl 2-((R)-(3-chloro-5-fluorophenyl)((R)-1-((S)-2-(methylamino)-3-((R)-oxepan-3-yl)propylcarbamoyl)piperidin-3-yl)methoxy)ethylcarbamate |
| I*-144a | 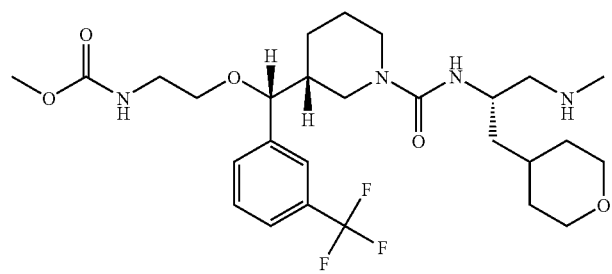 [SMILES: CNC[C@H](CC1CCOCC1)NC(=O)N1CCC[C@@H]([C@@H](OCCNC(=O)OC)c2cccc(C(F)(F)F)c2)C1] | methyl 2-((R)-((R)-1-((S)-1-(methylamino)-3-(tetrahydro-2H-pyran-4-yl)propan-2-ylcarbamoyl)piperidin-3-yl)(3-(trifluoromethyl)phenyl)methoxy)ethylcarbamate |
| I*-145a | 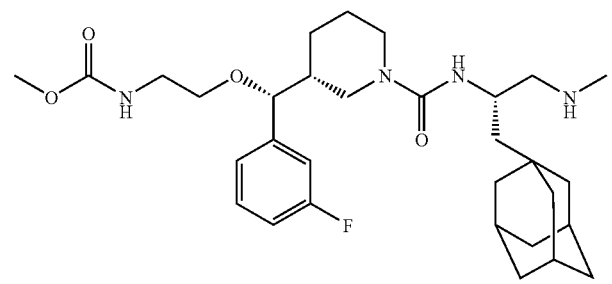 | methyl 2-((R)-((R)-1-((S)-1-(1-adamantyl)-3-(methylamino)propan-2-ylcarbamoyl)piperidin-3-yl)(3-fluorophenyl)methoxy)-ethylcarbamate |

| Compound Number | | |
|---|---|---|
| I*-146a | 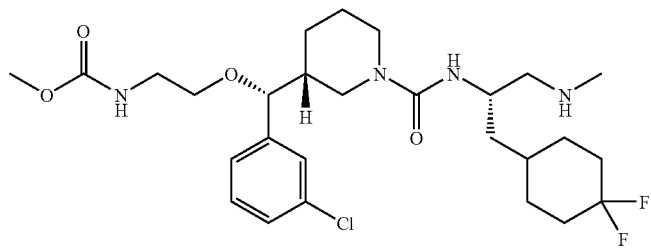 | methyl 2-((R)-(3-chlorophenyl)((R)-1-((S)-1-(4,4-difluorocyclohexyl)-3-(methylamino)propan-2-ylcarbamoyl)piperidin-3-yl)methoxy)ethylcarbamate |
| I*-147a | 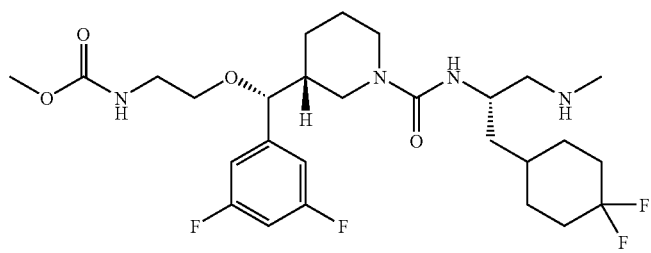 [SMILES: CNC[C@H](CC1CCC(F)(F)CC1)NC(=O)N1CCC[C@@H]([C@@H](OCCNC(=O)OC)c2cc(F)cc(F)c2)C1] | methyl 2-((R)-((R)-1-((S)-1-(4,4-difluorocyclohexyl)-3-(methylamino)propan-2-ylcarbamoyl)piperidin-3-yl)(3,5-difluorophenyl)methoxy)-ethylcarbamate |
| I*-148a | 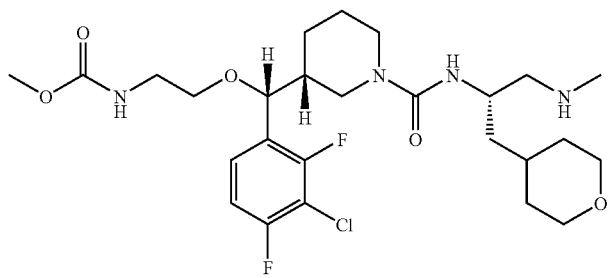 [SMILES: CNC[C@H](CC1CCOCC1)NC(=O)N1CCC[C@@H]([C@@H](OCCNC(=O)OC)c2ccc(F)c(Cl)c2F)C1] | methyl 2-((R)-(3-chloro-2,4-difluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-149a | 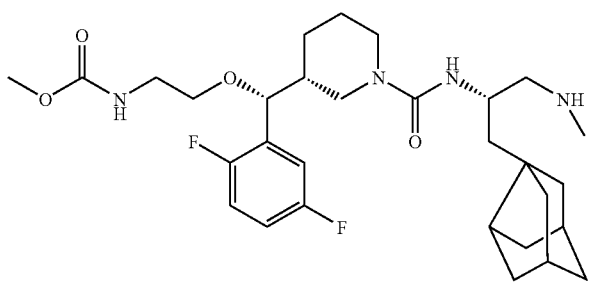 [SMILES: CNC[C@H](CC12CC3CC(CC1C3)C2)NC(=O)N1CCC[C@@H]([C@@H](OCCNC(=O)OC)c2cc(F)ccc2F)C1] | methyl 2-((R)-((R)-1-((S)-1-(3-noradamantyl)-3-(methylamino)propan-2-ylcarbamoyl)piperidin-3-yl)(2,5-difluorophenyl)methoxy)-ethylcarbamate |
| I*-150a | 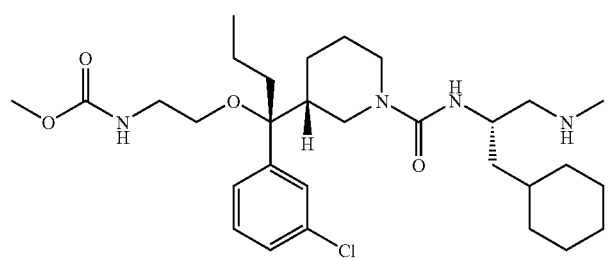 [SMILES: CCC[C@](OCCNC(=O)OC)(c1cccc(Cl)c1)[C@@H]1CCCN(C(=O)N[C@H](CNC)CC2CCCCC2)C1] | methyl 2-((R)-1-(3-chlorophenyl)-1-((R)-1-((S)-1-cyclohexyl-3-(methylamino)propan-2-ylcarbamoyl)piperidin-3-yl)butoxy)ethylcarbamate |

-continued

| Compound Number | | |
|---|---|---|
| I*-151a | 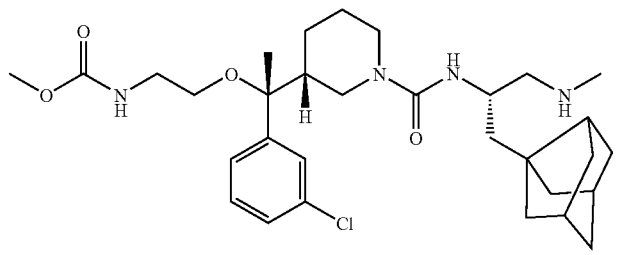 [SMILES: CNC[C@H](CC12CC3CC(CC1C3)C2)NC(=O)N1CCC[C@@H]([C@@](C)(OCCNC(=O)OC)c2cccc(Cl)c2)C1] | methyl 2-((R)-1-(3-chlorophenyl)-1-((3R)-1-((S)-1-(3-noradamantyl)-3-(methylamino)propan-2-ylcarbamoyl)piperidin-3-yl)ethoxy)ethylcarbamate |
| I*-152a | 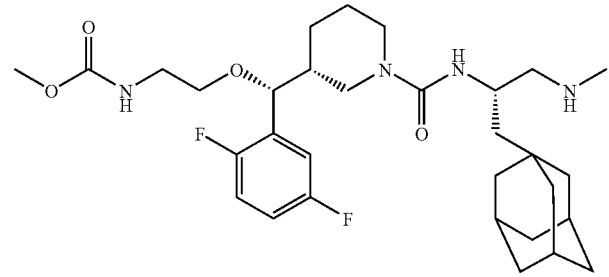 | methyl 2-((R)-((R)-1-((S)-1-(1-adamantyl)-3-(methylamino)propan-2-ylcarbamoyl)piperidin-3-yl)(2,5-difluorophenyl)methoxy)-ethylcarbamate |
| I*-153a | 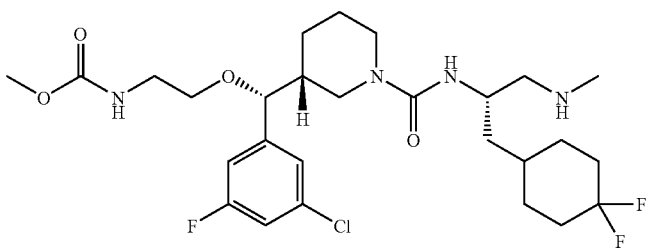 | methyl 2-((R)-(3-chloro-5-fluorophenyl)((R)-1-((S)-1-(4,4-difluorocyclohexyl)-3-(methylamino)propan-2-ylcarbamoyl)piperidin-3-yl)methoxy)ethylcarbamate |
| I*-154a | 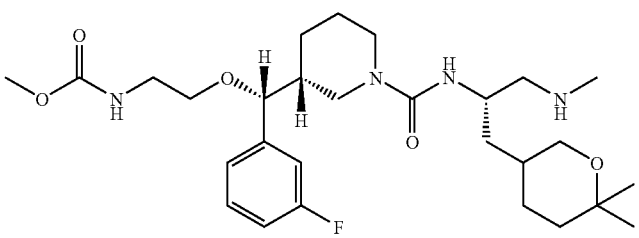 | methyl 2-((R)-(3-fluorophenyl)((R)-1-((S)-1-((R)-6,6-dimethyl-tetrahydro-2H-pyran-3-yl)-3-(methylamino)propan-2-ylcarbamoyl)piperidin-3-yl)methoxy)ethylcarbamate |
| I*-155a | 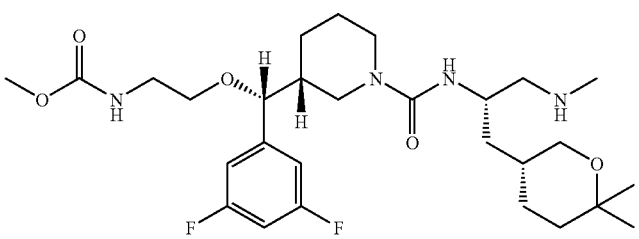 | methyl 2-((R)-(3,5-difluorophenyl)((R)-1-((S)-1-((R)-6,6-dimethyl-tetrahydro-2H-pyran-3-yl)-3-(methylamino)propan-2-ylcarbamoyl)piperidin-3-yl)methoxy)ethylcarbamate |
| I*-156a | 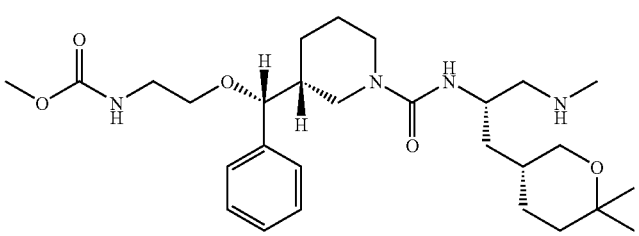 | methyl 2-((R)-((R)-1-((S)-1-((R)-6,6-dimethyl-tetrahydro-2H-pyran-3-yl)-3-(methylamino)propan-2-ylcarbamoyl)piperidin-3-yl)(phenyl)methoxy)-ethylcarbamate |

| Compound Number | | |
|---|---|---|
| I*-157a | 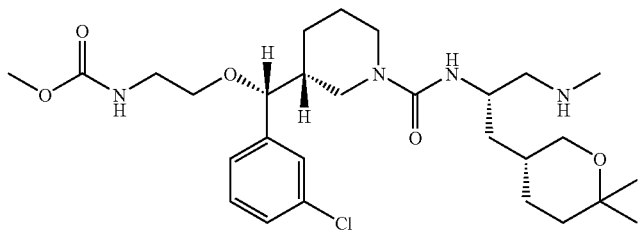 | methyl 2-((R)-(3-chlorophenyl)((R)-1-((S)-1-((R)-6,6-dimethyl-tetrahydro-2H-pyran-3-yl)-3-(methylamino)propan-2-ylcarbamoyl)piperidin-3-yl)methoxy)ethylcarbamate |
| I*-158a |  | methyl 2-((R)-(3-chlorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate |
| I*-159a | 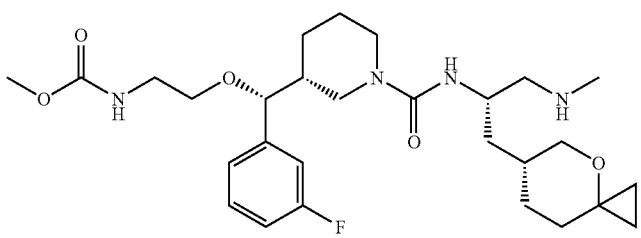 [SMILES: CNC[C@H](C[C@H]1CCC2(CC2)OC1)NC(=O)N1CCC[C@@H]([C@@H](OCCNC(=O)OC)c2cccc(Cl)c2)C1] | methyl 2-((R)-(3-fluorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate |
| I*-160a | 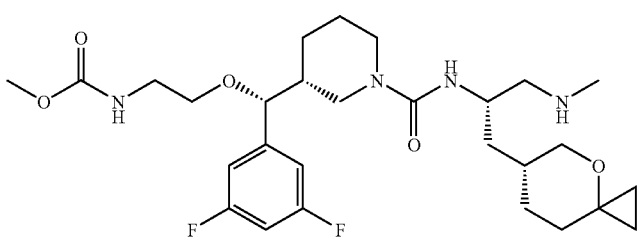 [SMILES: CNC[C@H](C[C@H]1CCC2(CC2)OC1)NC(=O)N1CCC[C@@H]([C@@H](OCCNC(=O)OC)c2cc(F)cc(F)c2)C1] | methyl 2-((R)-(3,5-difluorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate |

Another embodiment of the invention is an aspartic protease inhibitor represented by Structural Formula (XL):

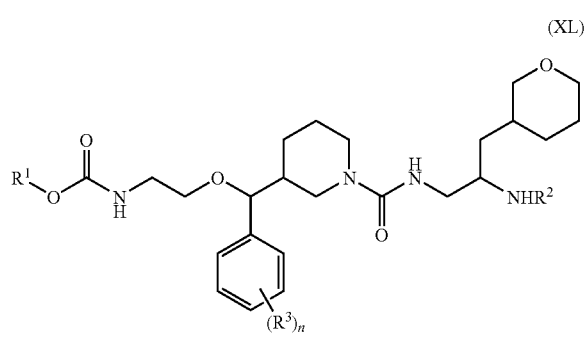

(XL)

or a pharmaceutically acceptable salt thereof, wherein:

$R^1$ is alkyl, cycloalkyl or cycloalkylalkyl;

$R^2$ is H or alkyl;

$R^3$ is F, Cl, Br, cyano, nitro, alkyl, haloalkyl, alkoxy, haloalkoxy, or alkanesulfonyl; and n is 0, 1, 2, or 3.

In another specific embodiment, the aspartic protease inhibitor of the present invention is one of the following compounds or their enantiomers or diastereomers. Also included are pharmaceutically acceptable salts, solvates, or hydrates of all of the following and their enantiomers and diastereomers:

| Cpd No. | Structural | Name |
|---|---|---|
| XL-1 | | methyl 2-((R)-((R)-1-((S)-2-amino-3-((R)-tetrahydro-2H-pyran-3-yl)propylcarbamoyl)piperidin-3-yl)(3-chlorophenyl)methoxy)ethylcarbamate |
| XL-2 | | methyl 2-((R)-((R)-1-((S)-2-amino-3-((R)-tetrahydro-2H-pyran-3-yl)propylcarbamoyl)piperidin-3-yl)(3-fluorophenyl)methoxy)ethylcarbamate |
| XL-3 | | methyl 2-((R)-((R)-1-((S)-2-amino-3-((R)-tetrahydro-2H-pyran-3-yl)(3-chloro-5-fluorophenyl)methoxy)-ethylcarbamate |
| XL-4 | | methyl 2-((R)-((R)-1-((S)-2-amino-3-((R)-tetrahydro-2H-pyran-3-yl)propylcarbamoyl)piperidin-3-yl)(3,5-difluorophenyl)methoxy)ethylcarbamate |
| XL-5 | | methyl 2-((R)-((R)-1-((S)-2-amino-3-((R)-tetrahydro-2H-pyran-3-yl)propylcarbamoyl)piperidin-3-yl)(5-chloro-2-methylphenyl)methoxy)-ethylcarbamate |
| XL-6 | | methyl 2-((R)-((R)-1-((S)-2-amino-3-((R)-tetrahydro-2H-pyran-3-yl)propylcarbamoyl)piperidin-3-yl)(5-fluoro-2-methylphenyl)methoxy)-ethylcarbamate |

| Cpd No. | Structural | Name |
|---|---|---|
| XL-7 | | methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate |
| XL-8 | | methyl 2-((R)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate |

Another embodiment of the invention is an aspartic protease inhibitor represented by Structural Formula (L):

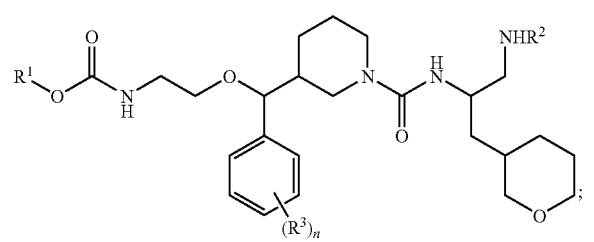

(L)

or a pharmaceutically acceptable salt thereof, wherein:

$R^1$ is alkyl, cycloalkyl or cycloalkylalkyl;

$R^2$ is H or alkyl;

$R^3$ is F, Cl, Br, cyano, nitro, alkyl, haloalkyl, alkoxy, haloalkoxy or alkanesulfonyl; and n is 0, 1, 2, or 3.

In a specific embodiment, the aspartic protease inhibitor of the present invention is one of the following compounds or their enantiomers or diastereomers. Also included are pharmaceutically acceptable salts, solvates or hydrates of all of the following and their enantiomers and diastereomers:

| Compound Number | Structure | Name |
|---|---|---|
| L-1 | 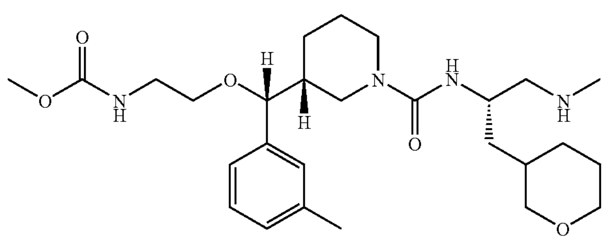 | methyl 2-((R)-((R)-1-((S)-1-(methylamino)-3-(tetrahydro-2H-pyran-3-yl)propan-2-ylcarbamoyl)piperidin-3-yl)(m-tolyl)-methoxy)ethylcarbamate |
| L-2a | 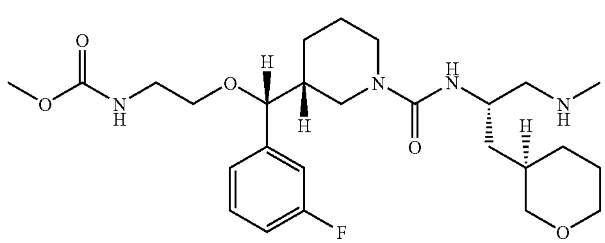 | methyl 2-((R)-(3-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate |

| Compound Number | Structure | Name |
| --- | --- | --- |
| L-2b | 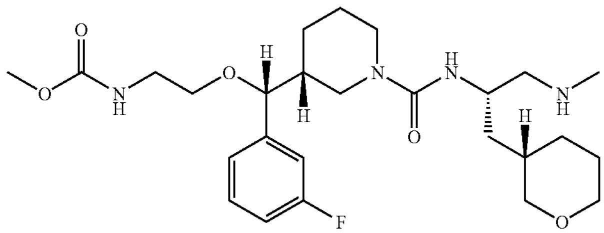 | methyl 2-((R)-(3-fluorophenyl)((R)-1-((S)-1-(methylamino)-3-((S)-tetrahydro-2H-pyran-3-yl)propan-2-ylcarbamoyl)piperidin-3-yl)methoxy)ethylcarbamate |
| L-3a | 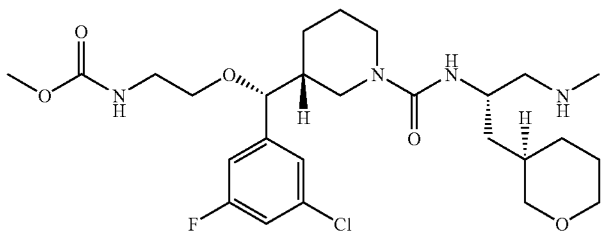 | methyl 2-((R)-(3-chloro-5-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate |
| L-3b | 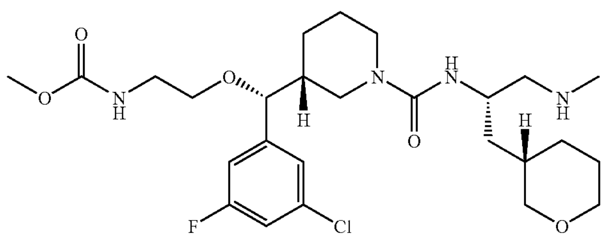 | methyl 2-((R)-(3-chloro-5-fluorophenyl)((R)-1-((S)-1-(methylamino)-3-((S)-tetrahydro-2H-pyran-3-yl)propan-2-ylcarbamoyl)piperidin-3-yl)methoxy)ethylcarbamate |
| L-3c,3d | 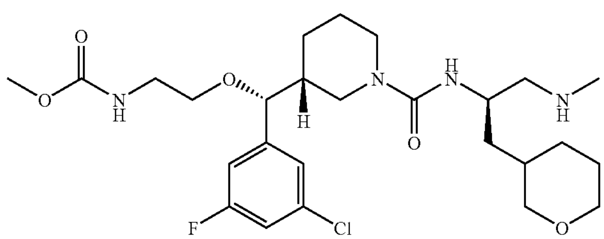 | methyl 2-((R)-(3-chloro-5-fluorophenyl)((3R)-1-((R)-1-(methylamino)-3-(tetrahydro-2H-pyran-3-yl)propan-2-ylcarbamoyl)piperidin-3-yl)methoxy)ethylcarbamate |
| L-4a | 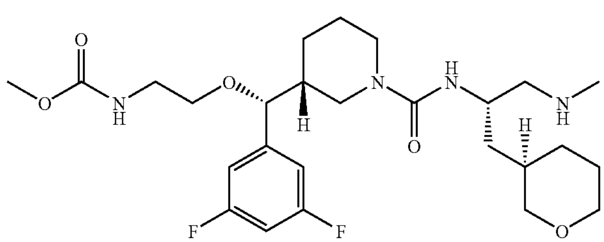 | methyl 2-((R)-(3,5-difluorophenyl)((R)-1-((S)-1-(methylamino)-3-((R)-tetrahydro-2H-pyran-3-yl)propan-2-ylcarbamoyl)piperidin-3-yl)methoxy)ethylcarbamate |
| L-4b | 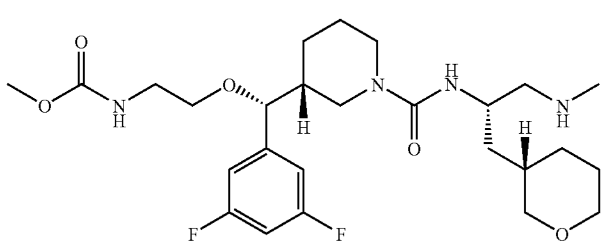 | methyl 2-((R)-(3,5-difluorophenyl)((R)-1-((S)-1-(methylamino)-3-((S)-tetrahydro-2H-pyran-3-yl)propan-2-ylcarbamoyl)piperidin-3-yl)methoxy)ethylcarbamate |

| Compound Number | Structure | Name |
|---|---|---|
| L-5a | 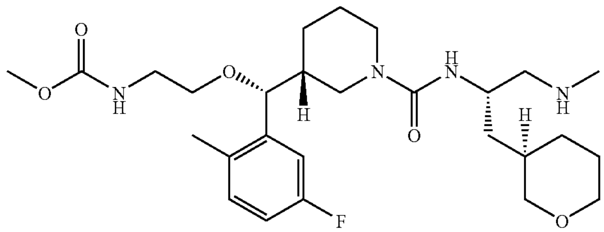 | methyl 2-((R)-(5-fluoro-2-methylphenyl)((R)-1-((S)-1-(methylamino)-3-((R)-tetrahydro-2H-pyran-3-yl)propan-2-ylcarbamoyl)piperidin-3-yl)methoxy)ethylcarbamate |
| L-5b | 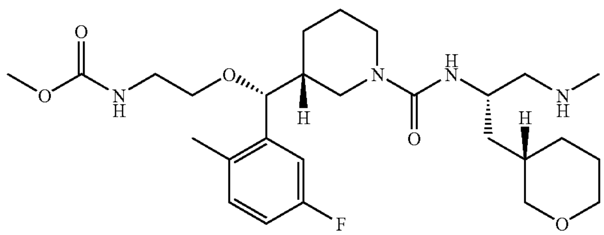 | methyl 2-((R)-(5-fluoro-2-methylphenyl)((R)-1-((S)-1-(methylamino)-3-((S)-tetrahydro-2H-pyran-3-yl)propan-2-ylcarbamoyl)piperidin-3-yl)methoxy)ethylcarbamate |
| L-6a | 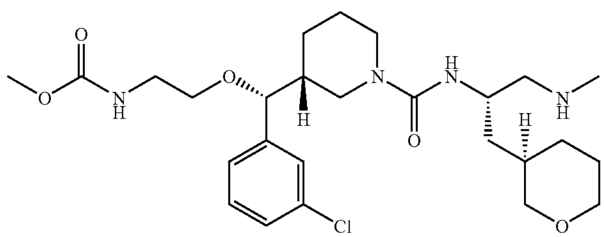 | methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate |
| L-6b | 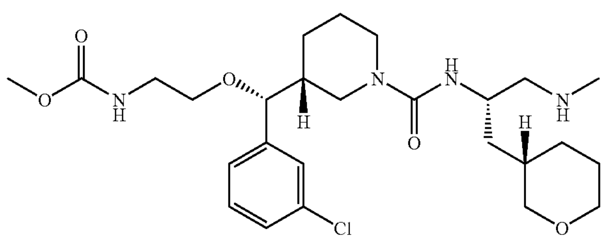 | methyl 2-((R)-(3-chlorophenyl)((R)-1-((S)-1-(methylamino)-3-((S)-tetrahydro-2H-pyran-3-yl)propan-2-ylcarbamoyl)piperidin-3-yl)methoxy)ethylcarbamate |
| L-7 | 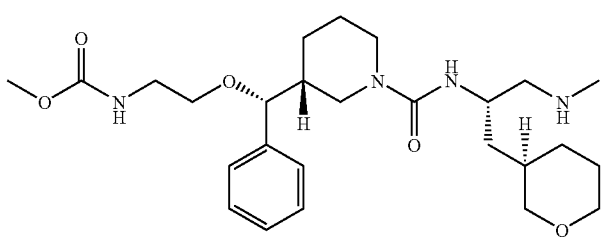 | methyl 2-((R)-((R)-1-((S)-1-(methylamino)-3-((R)-tetrahydro-2H-pyran-3-yl)propan-2-ylcarbamoyl)piperidin-3-yl)(phenyl)methoxy)ethylcarbamate |
| L-8 | 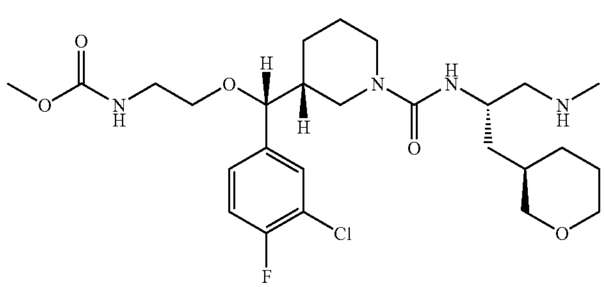 | methyl 2-((R)-(3-chloro-4-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate |

| Compound Number | Structure | Name |
|---|---|---|
| L-9 | 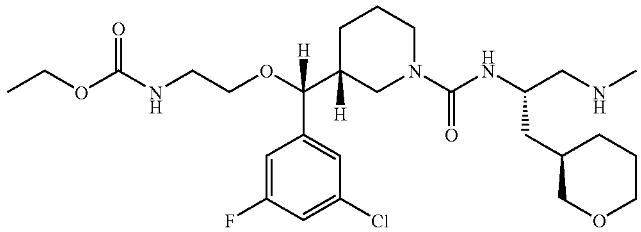 [SMILES: CCOC(=O)NCCO[C@@H](c1cc(F)cc(Cl)c1)[C@@H]1CCCN(C(=O)N[C@H](CNC)C[C@H]2CCCOC2)C1] | ethyl 2-((R)-(3-chloro-5-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate |
| L-10 | 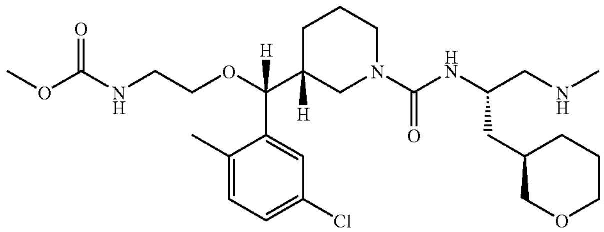 | methyl 2-((R)-(5-chloro-2-methylphenyl)((R)-1-((S)-1-(methylamnino)-3-((R)-tetrahydro-2H-pyran-3-yl)propan-2-ylcarbamoyl)piperidin-3-yl)methoxy)ethylcarbamate |

Another embodiment of the invention is an intermediate represented by Structural Formula (XXXVIII) and salts thereof (preferably pharmaceutically acceptable salts):

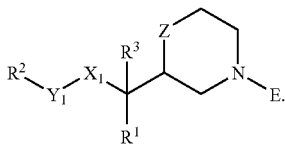

(XXXVIII)

E═H or a nitrogen protecting group. Amine protecting groups include carbamate, amide, and sulfonamide protecting groups known in the at (T. W. Greene and P. G. M. Wuts "Protective Groups in Organic Synthesis" John Wiley & Sons, Inc., New York 1999). Specific amine protecting groups include tert-butoxycarbon or benzyloxycarbonyl.

The remainder of the variables in Structural Formula (XXXVIII) are as described for Structural Formula (I) and Structural Formula (I*).

Another embodiment of the invention is an intermediate represented by Structural Formula (XXXIX) and salts thereof:

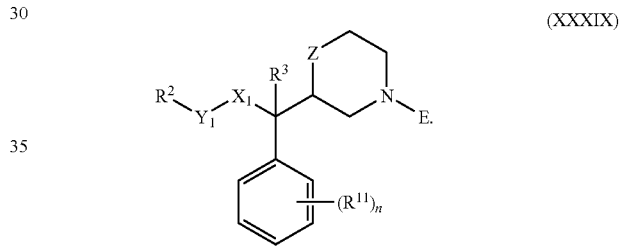

(XXXIX)

E═H or a nitrogen protecting group; n is 0, 1, 2 or 3; and the remainder of the variables in Structural Formula (XXXIX) are as described for Structural Formula (I) and Structural Formula (I*).

Another embodiment of the invention is each of the following compounds or their enantiomers, diastereomers, or pharmaceutically acceptable salts:

| Cpd. No. | Cpd. Name |
|---|---|
| XXXVIII-1 | (3-chlorophenyl)(piperidin-3-yl)methyl carbamate |
| XXXVIII-2 | (3-chlorophenyl)(piperidin-3-yl)methyl methylcarbamate |
| XXXVIII-3 | (3-chlorophenyl)(piperidin-3-yl)methyl ethylcarbamate |
| XXXVIII-4 | 2-((3-chlorophenyl)(piperidin-3-yl)methoxy)-N-methylacetamide |
| XXXVIII-5 | 2-((2,3-difluorophenyl)(piperidin-3-yl)methoxy)-N-propylacetamide |
| XXXVIII-6 | 2-((3-chloro-2-fluorophenyl)(piperidin-3-yl)methoxy)acetamide |
| XXXVIII-7 | methyl 2-((3-fluorophenyl)(piperidin-3-yl)methoxy)ethylcarbamate |
| XXXVIII-7 | methyl 2-((3-fluorophenyl)(piperidin-3-yl)methoxy)ethylcarbamate |
| XXXVIII-8 | N-(4-(3-chlorophenyl)-4-hydroxy-4-(piperidin-3-yl)butyl)formamide |
| XXXVIII-9 | 3-((3-chlorophenyl)(piperidin-3-yl)methoxy)-N-methylpropanamide |
| XXXVIII-10 | 2-((3-chlorophenyl)(piperidin-3-yl)methoxy)-N-ethylacetamide |
| XXXVIII-11 | 5-(3-chlorophenyl)-5-hydroxy-5-(piperidin-3-yl)pentanamide |
| XXXVIII-12 | 2-((2,3-difluorophenyl)(piperidin-3-yl)methoxy)-N-ethylacetamide |
| XXXVIII-13 | 2-((3-chlorophenyl)(piperidin-3-yl)methoxy)ethyl carbamate |
| XXXVIII-14 | 7-(3-chlorophenyl)-7-hydroxy-7-(piperidin-3-yl)heptan-2-one |
| XXXVIII-15 | 6-((3-chlorophenyl)(piperidin-3-yl)methoxy)hexan-3-one |
| XXXVIII-16 | methyl 4-(2-fluorophenyl)-4-hydroxy-4-(piperidin-3-yl)butylcarbamate |
| XXXVIII-17 | (3-chlorophenyl)(piperidin-3-yl)methyl butylcarbamate |
| XXXVIII-18 | 3-((3-chlorophenyl)(piperidin-3-yl)methoxy)-N-ethylpropanamide |

| Cpd. No. | Cpd. Name |
| --- | --- |
| XXXVIII-19 | 5-(3-chlorophenyl)-5-hydroxy-N-methyl-5-(piperidin-3-yl)pentanamide |
| XXXVIII-20 | 2-((3-chlorophenyl)(piperidin-3-yl)methoxy)-N-propylacetamide |
| XXXVIII-21 | 2-((2,3-difluorophenyl)(piperidin-3-yl)methoxy)-N-isopropylacetamide |
| XXXVIII-22 | methyl 2-((3-chlorophenyl)(piperidin-3-yl)methoxy)ethylcarbamate |
| XXXVIII-23 | 2-methoxyethyl (3-chlorophenyl)(piperidin-3-yl)methylcarbamate |
| XXXVIII-24 | 2-((3-chloro-2-fluorophenyl)(piperidin-3-yl)methoxy)-N-ethylacetamide |
| XXXVIII-25 | methyl 4-(3,5-dimethylphenyl)-4-hydroxy-4-(piperidin-3-yl)butylcarbamate |
| XXXVIII-26 | methyl 4-(3-fluoro-5-methylphenyl)-4-hydroxy-4-(piperidin-3-yl)butylcarbamate |
| XXXVIII-27 | methyl 4-(2-fluoro-5-methylphenyl)-4-hydroxy-4-(piperidin-3-yl)butylcarbamate |
| XXXVIII-28 | 5-(3-chlorophenyl)-N-ethyl-5-hydroxy-5-(piperidin-3-yl)pentanamide |
| XXXVIII-29 | 3-((3-chlorophenyl)(piperidin-3-yl)methoxy)-N-propylpropanamide |
| XXXVIII-30 | 3-((3-chlorophenyl)(piperidin-3-yl)methoxy)-N-isopropylpropanamide |
| XXXVIII-31 | methyl 4-(3-chlorophenyl)-4-hydroxy-4-(piperidin-3-yl)butylcarbamate |
| XXXVIII-32 | ethyl 2-((3-chlorophenyl)(piperidin-3-yl)methoxy)ethylcarbamate |
| XXXVIII-33 | 2-((3-chlorophenyl)(piperidin-3-yl)methoxy)-N-(2-methoxyethyl)acetamide |
| XXXVIII-34 | 2-((3-chlorophenyl)(piperidin-3-yl)methoxy)ethyl ethylcarbamate |
| XXXVIII-35 | methyl 4-(2,3-difluorophenyl)-4-hydroxy-4-(piperidin-3-yl)butylcarbamate |
| XXXVIII-36 | methyl 4-(3,5-difluorophenyl)-4-hydroxy-4-(piperidin-3-yl)butylcarbamate |
| XXXVIII-37 | methyl 2-((3-chloro-2-fluorophenyl)(piperidin-3-yl)methoxy)ethylcarbamate |
| XXXVIII-38 | methyl 2-((3-chloro-5-fluorophenyl)(piperidin-3-yl)methoxy)ethylcarbamate |
| XXXVIII-40 | ethyl 4-(3-chlorophenyl)-4-hydroxy-4-(piperidin-3-yl)butylcarbamate |
| XXXVIII-41 | methyl 4-(3-chlorophenyl)-4-hydroxy-4-(piperidin-3-yl)butyl(methyl)carbamate |
| XXXVIII-42 | methyl 4-(3-chloro-2-fluorophenyl)-4-hydroxy-4-(piperidin-3-yl)butylcarbamate |
| XXXVIII-43 | methyl 4-(2-chloro-3-fluorophenyl)-4-hydroxy-4-(piperidin-3-yl)butylcarbamate |
| XXXVIII-44 | methyl 4-(3-chloro-5-fluorophenyl)-4-hydroxy-4-(piperidin-3-yl)butylcarbamate |
| XXXVIII-45 | ethyl 2-((3-chloro-2-fluorophenyl)(piperidin-3-yl)methoxy)ethylcarbamate |
| XXXVIII-46 | methyl 4-(3-chloro-2,4-difluorophenyl)-4-hydroxy-4-(piperidin-3-yl)butylcarbamate |
| XXXVIII-47 | methyl 4-acetamido-4-(3-chlorophenyl)-4-(piperidin-3-yl)butylcarbamate |
| XXXVIII-48 | methyl 4-(3-chlorophenyl)-4-(piperidin-3-yl)-4-propionamidobutylcarbamate |
| XXXVIII-49 | methyl 2-((2,3-difluorophenyl)(piperidin-3-yl)methoxy)ethylcarbamate |
| XXXVIII-50 | 2-((3-chlorophenyl)(piperidin-3-yl)methoxy)-N-isopropylacetamide |
| XXXVIII-51 | methyl 2-((3-chloro-2-fluorophenyl)(morpholin-2-yl)methoxy)ethylcarbamate |
| XXXVIII-52 | 2-((3-chlorophenyl)(piperidin-3-yl)methoxy)ethanol |

A further embodiment of the invention is each of the following compounds or their enantiomers, diastereomers, or pharmaceutically acceptable salts:

| Cpd. No. | Cpd. Name |
| --- | --- |
| XXXVIII-1a | (R)-(3-chlorophenyl)((R)-piperidin-3-yl)methyl carbamate |
| XXXVIII-2a | (R)-(3-chlorophenyl)((R)-piperidin-3-yl)methyl methylcarbamate |
| XXXVIII-3a | (R)-(3-chlorophenyl)((R)-piperidin-3-yl)methyl ethylcarbamate |
| XXXVIII-3a | (R)-(3-chlorophenyl)((R)-piperidin-3-yl)methyl ethylcarbamate |
| XXXVIII-4a | 2-((R)-(3-chlorophenyl)((R)-piperidin-3-yl)methoxy)-N-methylacetamide |
| XXXVIII-5a | 2-((R)-(2,3-difluorophenyl)((R)-piperidin-3-yl)methoxy)-N-propylacetamide |
| XXXVIII-6a | 2-((S)-(3-chloro-2-fluorophenyl)((R)-piperidin-3-yl)methoxy)acetamide |
| XXXVIII-7a | methyl 2-((R)-(3-fluorophenyl)((R)-piperidin-3-yl)methoxy)ethylcarbamate |
| XXXVIII-8a | N-((S)-4-(3-chlorophenyl)-4-hydroxy-4-((R)-piperidin-3-yl)butyl)formamide |
| XXXVIII-9a | 3-((R)-(3-chlorophenyl)((R)-piperidin-3-yl)methoxy)-N-methylpropanamide |
| XXXVIII-10a | 2-((R)-(3-chlorophenyl)((R)-piperidin-3-yl)methoxy)-N-ethylacetamide |

| Cpd. No. | Cpd. Name |
|---|---|
| XXXVIII-11a | (S)-5-(3-chlorophenyl)-5-hydroxy-5-((R)-piperidin-3-yl)pentanamide |
| XXXVIII-12a | 2-((R)-(2,3-difluorophenyl)((R)-piperidin-3-yl)methoxy)-N-ethylacetamide |
| XXXVIII-13a | 2-((R)-(3-chlorophenyl)((R)-piperidin-3-yl)methoxy)ethyl carbamate |
| XXXVIII-14a | (S)-7-(3-chlorophenyl)-7-hydroxy-7-((R)-piperidin-3-yl)heptan-2-one |
| XXXVIII-15a | 6-((R)-(3-chlorophenyl)((R)-piperidin-3-yl)methoxy)hexan-3-one |
| XXXVIII-16a | methyl (S)-4-(2-fluorophenyl)-4-hydroxy-4-((R)-piperidin-3-yl)butylcarbamate |
| XXXVIII-17a | (R)-(3-chlorophenyl)((R)-piperidin-3-yl)methyl butylcarbamate |
| XXXVIII-18a | 3-((R)-(3-chlorophenyl)((R)-piperidin-3-yl)methoxy)-N-ethylpropanamide |
| XXXVIII-19a | (S)-5-(3-chlorophenyl)-5-hydroxy-N-methyl-5-((R)-piperidin-3-yl)pentanamide |
| XXXVIII-20a | 2-((R)-(3-chlorophenyl)((R)-piperidin-3-yl)methoxy)-N-propylacetamide |
| XXXVIII-21a | 2-((R)-(2,3-difluorophenyl)((R)-piperidin-3-yl)methoxy)-N-isopropylacetamide |
| XXXVIII-22a | methyl 2-((R)-(3-chlorophenyl)((R)-piperidin-3-yl)methoxy)ethylcarbamate |
| XXXVIII-23a | 2-methoxyethyl (R)-(3-chlorophenyl)((R)-piperidin-3-yl)methylcarbamate |
| XXXVIII-24a | 2-((3-chloro-2-fluorophenyl)((R)-piperidin-3-yl)methoxy)-N-ethylacetamide |
| XXXVIII-25a | methyl (S)-4-(3,5-dimethylphenyl)-4-hydroxy-4-((R)-piperidin-3-yl)butylcarbamate |
| XXXVIII-26a | methyl (S)-4-(3-fluoro-5-methylphenyl)-4-hydroxy-4-((R)-piperidin-3-yl)butylcarbamate |
| XXXVIII-27a | methyl (S)-4-(2-fluoro-5-methylphenyl)-4-hydroxy-4-((R)-piperidin-3-yl)butylcarbamate |
| XXXVIII-28a | (S)-5-(3-chlorophenyl)-N-ethyl-5-hydroxy-5-((R)-piperidin-3-yl)pentanamide |
| XXXVIII-29a | 3-((R)-(3-chlorophenyl)((R)-piperidin-3-yl)methoxy)-N-propylpropanamide |
| XXXVIII-30a | 3-((R)-(3-chlorophenyl)((R)-piperidin-3-yl)methoxy)-N-isopropylpropanamide |
| XXXVIII-31a | methyl (S)-4-(3-chlorophenyl)-4-hydroxy-4-((R)-piperidin-3-yl)butylcarbamate |
| XXXVIII-32a | ethyl 2-((R)-(3-chlorophenyl)((R)-piperidin-3-yl)methoxy)ethylcarbamate |
| XXXVIII-33a | 2-((R)-(3-chlorophenyl)((R)-piperidin-3-yl)methoxy)-N-(2-methoxyethyl)acetamide |
| XXXVIII-34a | 2-((R)-(3-chlorophenyl)((R)-piperidin-3-yl)methoxy)ethyl ethylcarbamate |
| XXXVIII-35a | methyl (S)-4-(2,3-difluorophenyl)-4-hydroxy-4-((R)-piperidin-3-yl)butylcarbamate |
| XXXVIII-36a | methyl (S)-4-(3,5-difluorophenyl)-4-hydroxy-4-((R)-piperidin-3-yl)butylcarbamate |
| XXXVIII-37a | methyl 2-((R)-(3-chloro-2-fluorophenyl)((R)-piperidin-3-yl)methoxy)ethylcarbamate |
| XXXVIII-38a | methyl 2-((R)-(3-chloro-5-fluorophenyl)((R)-piperidin-3-yl)methoxy)ethylcarbamate |
| XXXVIII-40a | ethyl (S)-4-(3-chlorophenyl)-4-hydroxy-4-((R)-piperidin-3-yl)butylcarbamate |
| XXXVIII-41a | methyl (S)-4-(3-chlorophenyl)-4-hydroxy-4-((R)-piperidin-3-yl)butyl(methyl)carbamate |
| XXXVIII-42a | methyl (S)-4-(3-chloro-2-fluorophenyl)-4-hydroxy-4-((R)-piperidin-3-yl)butylcarbamate |
| XXXVIII-43a | methyl (S)-4-(2-chloro-3-fluorophenyl)-4-hydroxy-4-((R)-piperidin-3-yl)butylcarbamate |
| XXXVIII-43a | methyl (S)-4-(2-chloro-3-fluorophenyl)-4-hydroxy-4-((R)-piperidin-3-yl)butylcarbamate |
| XXXVIII-44a | methyl (S)-4-(3-chloro-5-fluorophenyl)-4-hydroxy-4-((R)-piperidin-3-yl)butylcarbamate |
| XXXVIII-45a | ethyl 2-((R)-(3-chloro-2-fluorophenyl)((R)-piperidin-3-yl)methoxy)ethylcarbamate |
| XXXVIII-46a | methyl (S)-4-(3-chloro-2,4-difluorophenyl)-4-hydroxy-4-((R)-piperidin-3-yl)butylcarbamate |
| XXXVIII-47a | methyl (S)-4-acetamido-4-(3-chlorophenyl)-4-((R)-piperidin-3-yl)butylcarbamate |
| XXXVIII-48a | methyl (R)-4-(3-chlorophenyl)-4-((R)-piperidin-3-yl)-4-propionamidobutylcarbamate |
| XXXVIII-49a | methyl 2-((R)-(2,3-difluorophenyl)((R)-piperidin-3-yl)methoxy)ethylcarbamate |
| XXXVIII-50a | 2-((3-chlorophenyl)((R)-piperidin-3-yl)methoxy)-N-isopropylacetamide |

| Cpd. No. | Cpd. Name |
| --- | --- |
| XXXVIII-51a | methyl 2-((S)-(3-chloro-2-fluorophenyl)((R)-morpholin-2-yl)methoxy)ethylcarbamate |
| XXXVIII-52a | 2-((R)-(3-chlorophenyl)((R)-piperidin-3-yl)methoxy)ethanol |

Additional compounds of the invention are listed below. Also included are the enantiomers or diastereomers or pharmaceutically acceptable salts thereof.

| Cpd. No. | Cpd. Name |
| --- | --- |
| XXXVIII-53a | (R)-tert-butyl 3-((R)-(3-fluorophenyl)(2-(methoxycarbonylamino)ethoxy)methyl)piperidine-1-carboxylate |
| XXXVIII-54a | (R)-tert-butyl 3-((R)-(2,5-difluorophenyl)(2-(methoxycarbonylamino)ethoxy)methyl)piperidine-1-carboxylate |
| XXXVIII-55a | (R)-tert-butyl 3-((R)-(3,4-difluorophenyl)(2-(methoxycarbonylamino)ethoxy)methyl)piperidine-1-carboxylate |
| XXXVIII-56a | (R)-tert-butyl 3-((R)-(3-chloro-2-fluorophenyl)(2-(methoxycarbonylamino)ethoxy)methyl)piperidine-1-carboxylate |
| XXXVIII-57a | (R)-tert-butyl 3-((R)-(5-chloro-2-fluorophenyl)(2-(methoxycarbonylamino)ethoxy)methyl)piperidine-1-carboxylate |
| XXXVIII-58a | (R)-tert-butyl 3-((R)-(2-fluoro-5-methylphenyl)(2-(methoxycarbonylamino)ethoxy)methyl)piperidine-1-carboxylate |
| XXXVIII-59a | R)-tert-butyl 3-((R)-(2-(methoxycarbonylamino)ethoxy)(3,4,5-trifluorophenyl)methyl)piperidine-1-carboxylate |
| XXXVIII-60a | (R)-tert-butyl 3-((R)-(2-(methoxycarbonylamino)ethoxy)(thiophen-2-yl)methyl)piperidine-1-carboxylate |
| XXXVIII-61a | (R)-tert-butyl 3-((R)-(2-(methoxycarbonylamino)ethoxy)(thiazol-2-yl)methyl)piperidine-1-carboxylate |
| XXXVIII-62a | (3R)-tert-butyl 3-((2-(methoxycarbonylamino)ethoxy)(4-methylthiazol-2-yl)methyl)piperidine-1-carboxylate |
| XXXVIII-63a | (R)-tert-butyl 3-((R)-(2,3-difluorophenyl)(2-(methoxycarbonylamino)ethoxy)methyl)piperidine-1-carboxylate |
| XXXVIII-64a | (R)-tert-butyl 3-((R)-(3-chlorophenyl)(2-(methoxycarbonylamino)ethoxy)methyl)piperidine-1-carboxylate |
| XXXVIII-65a | (R)-tert-butyl 3-((R)-(3,5-difluorophenyl)(2-(methoxycarbonylamino)ethoxy)methyl)piperidine-1-carboxylate |
| XXXVIII-66a | (R)-tert-butyl 3-((R)-(5-chloro-2-methylphenyl)(2-(methoxycarbonylamino)ethoxy)methyl)piperidine-1-carboxylate |
| XXXVIII-67a | (R)-tert-butyl 3-((R)-(2-(methoxycarbonylamino)ethoxy)(m-tolyl)methyl)piperidine-1-carboxylate |
| XXXVIII-68a | (R)-tert-butyl 3-((R)-(2-(methoxycarbonylamino)ethoxy)(3-(trifluoromethyl)phenyl)methyl)piperidine-1-carboxylate |
| XXXVIII-69a | (R)-tert-butyl 3-((R)-(2,5-dimethylphenyl)(2-(methoxycarbonylamino)ethoxy)methyl)piperidine-1-carboxylate |
| XXXVIII-70a | (R)-tert-butyl 3-((R)-(3,5-dimethylphenyl)(2-(methoxycarbonylamino)ethoxy)methyl)piperidine-1-carboxylate |
| XXXVIII-71a | (R)-tert-butyl 3-((R)-(5-fluoro-2-methylphenyl)(2-(methoxycarbonylamino)ethoxy)methyl)piperidine-1-carboxylate |
| XXXVIII-72a | (R)-tert-butyl 3-((R)-(3-chloro-4-fluorophenyl)(2-(methoxycarbonylamino)ethoxy)methyl)piperidine-1-carboxylate |
| XXXVIII-73a | (R)-tert-butyl 3-((R)-(3-chloro-5-fluorophenyl)(2-(methoxycarbonylamino)ethoxy)methyl)piperidine-1-carboxylate |
| XXXVIII-74a | (R)-tert-butyl 3-((R)-(3-chloro-2,4-difluorophenyl)(2-(methoxycarbonylamino)ethoxy)methyl)piperidine-1-carboxylate |
| XXXVIII-75a | (R)-tert-butyl 3-((R)-(2-(benzyloxy)-3,5-difluorophenyl)(2-(methoxycarbonylamino)ethoxy)methyl)piperidine-1-carboxylate |
| XXXVIII-76a | (R)-tert-butyl 3-((R)-(2-(benzyloxy)-3,5-difluorophenyl)(2-(methoxycarbonylamino)ethoxy)methyl)piperidine-1-carboxylate |
| XXXVIII-77a | (R)-tert-butyl 3-((R)-(3-fluoro-5-methylphenyl)(2-(methoxycarbonylamino)ethoxy)methyl)piperidine-1-carboxylate |
| XXXVIII-78a | (R)-tert-butyl 3-((R)-(3-fluoro-5-methylphenyl)(2-(methoxycarbonylamino)ethoxy)methyl)piperidine-1-carboxylate |
| XXXVIII-79a | (R)-tert-butyl 3-((2,3-difluoro-6-methylphenyl)(2-(methoxycarbonylamino)ethoxy)methyl)piperidine-1-carboxylate |
| XXXVIII-80a | (R)-tert-butyl 3-((2,3-difluoro-6-methylphenyl)(2-(methoxycarbonylamino)ethoxy)methyl)piperidine-1-carboxylate |
| XXXVIII-81a | (R)-tert-butyl 2-((S)-(3-chlorophenyl)(2-(methoxycarbonylamino)ethoxy)methyl)morpholine-4-carboxylate |
| XXXVIII-82a | (R)-tert-butyl 3-((R)-(3-chlorophenyl)(2-(methoxycarbonylamino)ethoxy)methyl)piperidine-1-carboxylate |
| XXXVIII-83a | (R)-tert-butyl 3-((R)-(3-chlorophenyl)(2-(2-cyano-3-methylguanidino)ethoxy)methyl)piperidine-1-carboxylate |

| Cpd. No. | Cpd. Name |
|---|---|
| XXXVIII-84a | (R)-tert-butyl 3-((R)-(3-chlorophenyl)(2-(thiazol-2-ylamino)ethoxy)methyl)piperidine-1-carboxylate |
| XXXVIII-85a | (R)-tert-butyl 3-((R)-(3-chlorophenyl)(2-(methoxycarbonylamino)ethoxy)methyl)azepane-1-carboxylate |
| XXXVIII-86a | (R)-tert-butyl 3-((R)-(3-fluorophenyl)(2-(methoxycarbonylamino)ethoxy)methyl)azepane-1-carboxylate |
| XXXVIII-87a | (3S)-tert-butyl 3-(1-(3-fluorophenyl)-4-(methoxycarbonylamino)butyl)piperidine-1-carboxylate |
| XXXVIII-88a | (R)-tert-butyl 3-((R)-1-(3-chlorophenyl)-1-(2-(methoxycarbonylamino)ethoxy)ethyl)piperidine-1-carboxylate |
| XXXVIII-89a | (R)-tert-butyl 3-((R)-1-(3-chlorophenyl)-1-(2-(methoxycarbonylamino)ethoxy)butyl)piperidine-1-carboxylate |
| XXXVIII-90a | (R)-tert-butyl 3-((S)-1-(3-fluorophenyl)-1-hydroxy-4-(methoxycarbonylamino)butyl)piperidine-1-carboxylate |
| XXXVIII-91a | (R)-tert-butyl 3-((S)-1-(3-chloro-2-fluorophenyl)-1-hydroxy-4-(methoxycarbonylamino)butyl)piperidine-1-carboxylate |

When any variable (e.g., aryl, heterocyclyl, $R_1$, $R_2$, etc.) occurs more than once in a compound, its definition on each occurrence is independent of any other occurrence.

"Alkyl" means a saturated aliphatic branched or straight-chain mono- or di-valent hydrocarbon radical having the specified number of carbon atoms. Thus, "$(C_1-C_8)$alkyl" means a radical having from 1-8 carbon atoms in a linear or branched arrangement. "$(C_1-C_6)$alkyl" includes methyl, ethyl, propyl, butyl, pentyl, and hexyl.

"Alkylene" means $—[CH_2]_x—$, wherein x is a positive integer. x is typically a positive integer from 1-10, more typically from 1-5, even more typically 2-4 and more typically yet from 2-3. Alkylene groups are optionally substituted at any one or more substitutable carbon atom, i.e., a carbon atom that is bonded to a hydrogen, wherein the hydrogen is replaced with a substituent.

"Alkenylene" is an alkylene group in which at least one single bond connecting adjacent methylene groups has been replaced with a double bond. Alkenylene groups are optionally substituted at any one or more substitutable carbon atom, i.e., a carbon atom that is bonded to a hydrogen, wherein the hydrogen is replaced with a substituent.

"Alkynylene" is an alkylene group in which at least one single bond connecting adjacent methylene groups has been replaced with a double bond. Alkynylene groups are optionally substituted at any one or more substitutable carbon atom, i.e., a carbon atom that is bonded to a hydrogen, wherein the hydrogen is replaced with a substituent.

"Cycloalkyl" means a saturated aliphatic cyclic hydrocarbon radical having the specified number of carbon atoms. Thus, $(C_3-C_7)$cycloalkyl means a radical having from 3-7 carbon atoms arranged in a ring. $(C_3-C_7)$cycloalkyl includes cyclopropyl, cyclobutyl, cyclopentyl, cyclohexyl, and cycloheptyl.

Haloalkyl and halocycloalkyl include mono, poly, and per-haloalkyl groups where the halogens are independently selected from fluorine, chlorine, and bromine.

Saturated heterocyclic rings are 4-, 5-, 6-, and 7-membered heterocyclic rings containing 1 to 4 heteroatoms independently selected from N, O, and S, and include pyrrolidine, piperidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, morpholine, thiomorpholine, thiomorpholine 1,1-dioxide, tetrahydro-2H-1,2-thiazine 1,1-dioxide, and isothiazolidine 1,1-dioxide. Oxo substituted saturated heterocyclic rings include tetrahydrothiophene 1-oxide, tetrahydrothiophene 1,1-dioxide, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one.

"Heteroaryl" means a monovalent heteroaromatic monocyclic and polycyclic ring radical containing 1 to 4 heteroatoms independently selected from N, O, and S. Heteroaryl rings include furyl, thienyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridinyl-N-oxide, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, 1,2,3-triazolyl, 1,2,4-triazolyl, 1,3,4-oxadiazolyl, 1,2,5-thiadiazolyl, 1,2,5-thiadiazolyl-1-oxide, 1,2,5-thiadiazolyl-1,1-dioxide, 1,3,4-thiadiazolyl, 1,2,4-triazinyl, 1,3,5-triazinyl, tetrazolyl, and pteridinyl.

Bicyclic heteroaryl rings are bicyclo[4.4.0] and bicyclo[4,3.0] fused ring systems of which at least one ring is aromatic containing 1 to 4 heteroatoms independently selected from N, O, and S, and include indole, quinoline, isoquinoline, quinazoline, benzothiophene, benzofuran, 2,3-dihydrobenzofuran, benzodioxole, benzimidazole, indazole, benzisoxazole, benzoxazole, and benzothiazole.

Bicycloalkyl rings are fused, bridged and Spiro ring systems and include bicyclo[1.1.0]butane, bicyclo[1.2.0]pentane, bicyclo[2.2.0]hexane, bicyclo[3.2.0]heptane, bicyclo[3.3.0]octane, bicyclo[4.2.0]octane, bicyclo[2.2.1]heptane, bicyclo[2.2.2]octane, bicyclo[3.2.1]octane, bicyclo[3.2.2]nonane, bicyclo[3.3.1]nonane, bicyclo[3.3.2]decane and bicyclo[3.3.3]undecane, spiro[2.2]pentane, spiro[2.3]hexane, spiro[3.3]heptane, spiro[2.4]heptane, spiro[3.4]octane and spiro[2.5]octane.

"Alkoxy" means an alkyl radical attached through an oxygen linking atom. "$(C_1-C_4)$-alkoxy" includes the methoxy, ethoxy, propoxy, and butoxy.

"Aromatic" means an unsaturated cycloalkyl ring system.

"Aryl" means an aromatic monocyclic or polycyclic ring system. Aryl systems include phenyl, naphthalenyl, fluorenyl, indenyl, azulenyl, and anthracenyl.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Oxo" refers to $=O$. When an oxo group is a substituent on a carbon atom, they form a carbonyl group ($—C(O)—$). When one oxo group is a substituent on a sulfur atom, they form a sulfinyl (sulfoxide —S(O)—) group. When two oxo groups are a substituent on a sulfur atom, they form a sulfonyl (sulfone —S(O)$_2$—) group.

Enantiomers, Diastereomers, and Salts

Certain of the disclosed aspartic protease inhibitors may exist in various tautomeric forms. The invention encompasses all such forms, including forms those not depicted structurally.

Certain of the disclosed aspartic protease inhibitors may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. When a chiral center is not defined as R or S and the configuration at the chiral center is not defined by other means, either configuration can be present or a mixture of both configurations is present.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

Atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. A mixture of "cis" and "trans" species is designated "cis/trans".

"R," "S," "S*," "R*,", "E," "Z," "cis," and "trans," indicate configurations relative to the core molecule.

The point at which a group or moiety is attached to the remainder of the compound or another group or moiety can be indicated by "〰" which represents "⋯⋯", "━▬" or "___".

The disclosed aspartic protease inhibitors may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed aspartic protease inhibitor is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed aspartic protease inhibitor is named or depicted by structure without indicating the stereochemistry, and the inhibitor has at least one chiral center, it is to be understood that the name or structure encompasses one enantiomer of inhibitor free from the corresponding optical isomer, a racemic mixture of the inhibitor and mixtures enriched in one enantiomer relative to its corresponding optical isomer.

When a disclosed aspartic protease inhibitor is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

Pharmaceutically acceptable salts of the compounds of the aspartic protease inhibitors are included in the present invention. For example, an acid salt of an aspartic protease inhibitor containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of aspartic protease inhibitors containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

When a disclosed aspartic protease inhibitor or its pharmaceutically acceptable salt is named or depicted by structure, it is to be understood that solvates or hydrates of the aspartic protease inhibitor or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include stoichiometric hydrates as well as compositions containing variable amounts of water.

When a disclosed aspartic protease inhibitor or its pharmaceutically acceptable salt is named or depicted by structure, it is to be understood that the compound, including solvates thereof, may exist in crystalline forms, non-crystalline forms or a mixture thereof. The aspartic protease inhibitor or its pharmaceutically acceptable salts or solvates may also exhibit polymorphism (i.e. the capacity to occur in different crystalline forms). These different crystalline forms are typically known as "polymorphs." It is to be understood that when named or depicted by structure, the disclosed aspartic protease inhibitors and their pharmaceutically acceptable salts, solvates or hydrates also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

It may be necessary and/or desirable during synthesis to protect sensitive or reactive groups on any of the molecules concerned. Representative conventional protecting groups are described in T. W. Greene and P. G. M. Wuts "Protective Groups in Organic Synthesis" John Wiley & Sons, Inc., New York 1999. Protecting groups may be added and removed using methods well known in the art.

The disclosed aspartic protease inhibitors are useful for ameliorating or treating disorders or diseases in which decreasing the levels of aspartic protease products is effective in treating the disease state or in treating infections in which the infectious agent depends upon the activity of an aspartic protease. In hypertension elevated levels of angiotensin I, the product of renin catalyzed cleavage of angioteninogen are present. Elevated levels of β amyloid, the product of BACE activity on amyloid precursor protein, are believed to be responsible for the amyloid plaques present in the brains of Alzheimer's disease patients. The viruses HIV and HTLV depend on their respective aspartic proteases for viral maturation. *Plasmodium falciparum* uses plasmepsins I and II to degrade hemoglobin.

The disclosed aspartic protease inhibitors are useful for ameliorating or treating disorders or diseases in which decreasing the levels of renin products is effective in treating a disease state. In hypertension elevated levels of angiotensin I, the product of renin catalyzed cleavage of angioteninogen are present. Thus, the disclosed aspartic protease inhibitors can be used in the treatment of hypertension; heart failure such as (acute and chronic) congestive heart failure; left ventricular dysfunction; cardiac hypertrophy; cardiac fibrosis; cardiomyopathy (e.g., diabetic cardiac myopathy and post-infarction cardiac myopathy); supraventricular and ventricular arrhythmias; arial fibrillation; atrial flutter; detrimental vascular remodeling; myocardial infarction and its sequelae; atherosclerosis; angina (whether unstable or stable); renal failure conditions, such as diabetic nephropathy; glomerulonephritis; renal fibrosis; scleroderma; glomerular sclerosis; microvascular complications, for example, diabetic retinopathy; renal vascular hypertension; vasculopathy; neuropathy; diseases of the coronary vessels; proteinuria; albumenuria; post-surgical hypertension; metabolic syndrome; obesity, restenosis following angioplasty; ocular vascular complications, for example, raised intra-ocular pressure, glaucoma, and retinopathy; abnormal vascular growth; angiogenesis-related disorders, such as neovascular age related macular degeneration; hyperaldosteronism; anxiety states; and cognitive disorders (Fisher N. D.; Hollenberg N. K. *Expert Opin. Investig. Drugs*. 2001, 10, 417-26).

A pharmaceutical composition of the invention may, alternatively or in addition to a disclosed aspartic protease inhibitor, comprise a pharmaceutically acceptable salt of a disclosed aspartic protease inhibitor or a prodrug or pharmaceutically active metabolite of such a compound or salt and one or more pharmaceutically acceptable carriers therefor.

The invention includes a therapeutic method for treating or ameliorating an aspartic protease mediated disorder in a subject in need thereof comprising administering to a subject in need thereof an effective amount of a compound of the aspartic protease inhibitors disclosed herein, or a pharmaceutically acceptable salt thereof.

Administration methods include administering an effective amount (i.e., a therapeutically effective amount) of a compound or composition of the invention at different times during the course of therapy or concurrently in a combination form. The methods of the invention include all known therapeutic treatment regimens.

"Effective amount" means that amount of active compound agent that elicits the desired biological response in a subject. Such response includes alleviation of the symptoms of the disease or disorder being treated. The effective amount of a disclosed aspartic protease inhibitor in such a therapeutic method is from about 0.01 mg/kg/day to about 10 mg/kg/day, preferably from about 0.5 mg/kg/day to 5 mg/kg/day.

The invention includes the use of a disclosed aspartic protease inhibitor for the preparation of a composition for treating or ameliorating an aspartic protease mediated chronic disorder or disease or infection in a subject in need thereof, wherein the composition comprises a mixture one or more of the disclosed aspartic protease inhibitors and an optional pharmaceutically acceptable carrier.

"Pharmaceutically acceptable carrier" means compounds and compositions that are of sufficient purity and quality for use in the formulation of a composition of the invention and that, when appropriately administered to an animal or human, do not produce an adverse reaction.

"Aspartic protease mediated disorder or disease" includes disorders or diseases associated with the elevated expression or overexpression of aspartic proteases and conditions that accompany such diseases.

An embodiment of the invention includes administering an aspartic protease inhibitor disclosed herein in a combination therapy (see U.S. Pat. No. 5,821,232, U.S. Pat. No. 6,716,875, U.S. Pat. No. 5,663,188, or Fossa, A. A.; DePasquale, M. J.; Ringer, L. J.; Winslow, R. L. "Synergistic effect on reduction in blood pressure with coadministration of a renin inhibitor or an angiotensin-converting enzyme inhibitor with an angiotensin II receptor antagonist" *Drug Development Research* 1994, 33(4), 422-8) with one or more additional agents for the treatment of hypertension including α-blockers, β-blockers, calcium channel blockers, diuretics, natriuretics, saluretics, centrally acting antihypertensives-antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

α-Blockers include doxazosin, prazosin, tamsulosin, and terazosin.

β-Blockers for combination therapy are selected from atenolol, bisoprol, metoprolol, acetutolol, esmolol, celiprolol, taliprolol, acebutolol, oxprenolol, pindolol, propanolol, bupranolol, penbutolol, mepindolol, caiteolol, nadolol, carvedilol, and their pharmaceutically acceptable salts.

Calcium channel blockers include dihydropyridines (DHPs) and non-DHPs. Cetain DHPs are amlodipine, felodipine, ryosidine, isradipine, lacidipine, nicardipine, nifedipine, nigulpidine, niludipine, nimodiphine, nisoldipine, nitrendipine, and nivaldipine, and their pharmaceutically acceptable salts. Non-DHPs are flunarizine, prenylamine, diltiazem, fendiline, gallopamil, mibefradil, anipamil, tiapamil, and verampimil, and their pharmaceutically acceptable salts.

A diuretic is, for example, a thiazide derivative selected from amiloride, chlorothiazide, hydrochlorothiazide, methylchlorothiazide, and chlorothalidon.

Centrally acting antihypertensives include clonidine, guanabenz, guanfacine and methyldopa.

ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Specific ACE inhibitors are benazepril, enalpril, lisinopril, and ramipril.

Dual ACE/NEP inhibitors are, for example, omapatrilat, fasidotril, and fasidotrilat.

Specific ARBs include candesartan, eprosartan, irbesartan, losartan, olmesartan, tasosaitan, telmisartan, and valsartan.

Specific aldosterone synthase inhibitors are anastrozole, fadrozole, and exemestane.

Specific aldosterone-receptor antagonists are spironolactone and eplerenone.

A specific endothelin antagonist is, for example, bosentan, enrasentan, atrasentan, darusentan, sitaxsentan, and tezosentan, and their pharmaceutically acceptable salts.

An embodiment of the invention includes administering an aspartic protease inhibitor disclosed herein or composition thereof in a combination therapy with one or more additional agents for the treatment of AIDS including reverse transcriptase inhibitors, non-nucleoside reverse transcriptase inhibitors, other HIV protease inhibitors, HIV integrase inhibitors, attachment and fusion inhibitors, antisense drugs, and immune stimulators.

Specific reverse transcriptase inhibitors are zidovudine, didanosine, zalcitabine, stavudine, lamivudine, abacavir, tenofovir, and emtricitabine.

Specific non-nucleoside reverse transcriptase inhibitors are nevirapine, delaviridine, and efavirenz.

Specific HIV protease inhibitors are saquinavir, ritonavir, indinavir, nelfinavir, amprenavir, lopinavir, atazanavir, and fosamprenavir.

Specific HIV integrase inhibitors are L-870, 810 and S-1360.

A specific attachment and fusion inhibitor is enfuvirtide.

An embodiment of the invention includes administering an aspartic protease inhibitor disclosed herein or composition thereof in a combination therapy with one or more additional agents for the treatment of Alzheimer's disease including tacrine, donepezil, rivastigmine, galantamine, and memantine.

An embodiment of the invention includes administering an aspartic protease inhibitor disclosed herein or composition thereof in a combination therapy with one or more additional agents for the treatment of malaria including artemisinin, chloroquine, halofantrine, hydroxychloroquine, mefloquine, primaquine, pyrimethamine, quinine, and sulfadoxine Combination therapy includes co-administration of an aspartic protease inhibitor disclosed herein and said other agent, sequential administration of the disclosed aspartic protease inhibitor and the other agent, administration of a composition containing the aspartic protease inhibitor and the other agent, or simultaneous administration of separate compositions containing the aspartic protease inhibitor and the other agent.

The invention further includes the process for making the composition comprising mixing one or more of the disclosed aspartic protease inhibitors and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic and/or prophylactic effect. The composition may contain from about 5,000 mg to about 0.5 mg (preferably, from about 1,000 mg to about 0.5 mg) of a disclosed aspartic protease inhibitor or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a disclosed aspartic protease inhibitor. Preferably, the compositions are prepared by mixing a disclosed aspartic protease inhibitor (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

The disclosed aspartic protease inhibitors may also be administered via a slow release composition; wherein the composition includes a disclosed aspartic protease inhibitor and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, preferably about 50-200 nm in diameter, and most preferably about 100 nm in diameter). In a process for preparing a slow release composition, a slow release carrier and a disclosed aspartic protease inhibitor are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the disclosed aspartic protease inhibitor.

The disclosed aspartic protease inhibitors may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The disclosed aspartic protease inhibitors may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

The disclosed aspartic protease inhibitors may be administered intranasally using a suitable intranasal vehicle.

The disclosed aspartic protease inhibitors may also be administered topically using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the disclosed aspartic protease inhibitor, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration in the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

The invention is further defined by reference to the examples, which are intended to be illustrative and not limiting.

Representative compounds of the invention can be synthesized in accordance with the general synthetic schemes described above and are illustrated in the examples that follow. The methods for preparing the various starting materials used in the schemes and examples are well within the knowledge of persons skilled in the art.

The following abbreviations have the indicated meanings:

| Abbreviation | Meaning |
| --- | --- |
| Aq | aqueous |
| Boc | tert-butoxy carbonyl or t-butoxy carbonyl |
| (Boc)$_2$O | di-tert-butyl dicarbonate |
| Brine | saturated aqueous NaCl |
| Cbz | Benzyloxycarbonyl |
| CbzCl | Benzyl chloroformate |
| CDI | carbonyl diimidazole |
| CH$_2$Cl$_2$ | methylene chloride |
| CH$_3$CN or MeCN | acetonitrile |

-continued

| Abbreviation | Meaning |
|---|---|
| Cpd | compound |
| d | day |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| EDC.HCl | 1-[3-(dimethylamino)propyl]-3-ethylcarbodiimide hydrochloride |
| Equiv | equivalents |
| Et | ethyl |
| $Et_2O$ | ethyl ether |
| EtOAc | ethyl acetate |
| EtOH | ethanol |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazole-1-yl)-1,1,3,3-tetramethyluronium hexafluorophosphate |
| IPA | isopropyl alcohol |
| KHMDS | potassium hexamethyldisilazane |
| LAH or $LiAlH_4$ | lithium aluminum hydride |
| LC-MS | liquid chromatography-mass spectroscopy |
| LHMDS | lithium hexamethyldisilazane |
| Me | methyl |
| MeCN | acetonitrile |
| MeOH | methanol |
| MsCl | methanesulfonyl chloride |
| min | minute |
| MS | mass spectrum |
| NaH | sodium hydride |
| $NaHCO_3$ | sodium bicarbonate |
| $NaN_3$ | sodium azide |
| NaOH | sodium hydroxide |
| $Na_2SO_4$ | sodium sulfate |
| $NH_4Cl$ | ammonium chloride |
| NMM | N-methylmorpholine |
| NMP | N-methylpyrrolidinone |
| $Pd_2(dba)_3$ | tris(dibenzylideneacetone)dipalladium(0) |
| PE | petroleum ether |
| Ph | phenyl |
| Quant | quantitative yield |
| Rt | room temperature |
| Satd | saturated |
| $SOCl_2$ | thionyl chloride |
| SPE | solid phase extraction |
| TBS | t-butyldimethylsilyl |
| TBSCl | t-butyldimethylsilyl chloride |
| TEA | triethylamine or $Et_3N$ |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| THF | tetrahydrofuran |
| tlc | thin layer chromatography |
| TMS | trimethylsilyl |
| TMSCl | chlorotrimethylsilane or trimethylsilyl chloride |
| $t_R$ | retention time |
| TsOH/tosic acid | p-toluenesulfonic acid |

Purification Methods

Prep HPLC refers to preparative reverse phase HPLC on a C-18 column eluted with a water/acetonitrile gradient containing 0.01% TFA run on a Gilson 215 system.

Analytical Methods

LC-MS (3 min)

Column: Chromolith SpeedRod, RP-18e, 50×4.6 mm; Mobil phase: A: 0.01% TFA/water, B: 0.01% TFA/$CH_3CN$; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

PREPARATIONS OF INTERMEDIATES

Preparation 1

Methyl (S)-4-(3-chlorophenyl)-4-hydroxy-4-((R)-piperidin-3-yl)butylcarbamate (31)

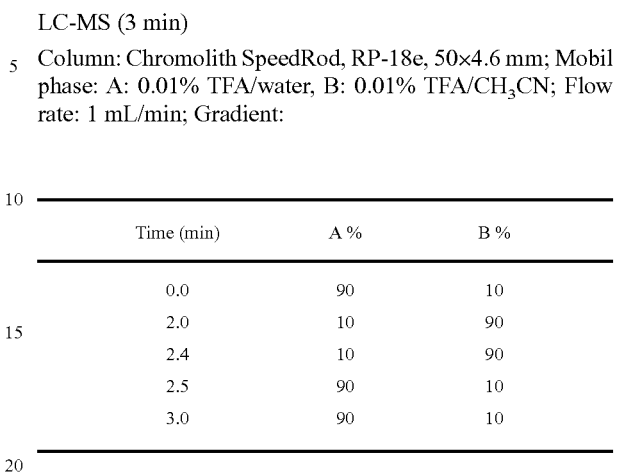

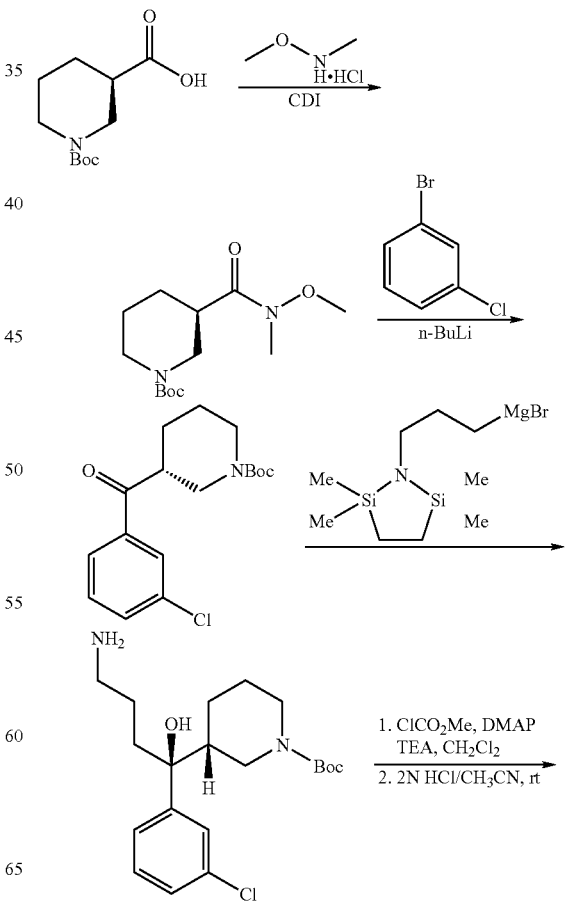

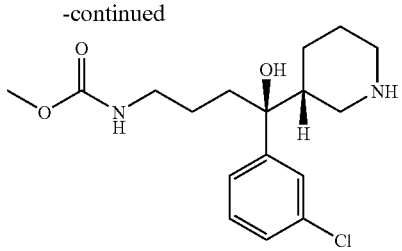

Step 1. (R)-tert-butyl 3-(methoxy(methyl)carbamoyl) piperidine-1'-carboxylate To a stirred solution of (R)-1-(tert-butoxycarbonyl)piperidine-3-carboxylic acid (233 g, 1.2 mol) in THF (1.2 L) was added carbonyldiimidazole (230 g, 1.42 mol). The mixture was stirred for 1 h in an ice-water bath. A suspension of triethylamine (207 mL, 1.41 mol) and N,O-dimethylhydroxylamine hydrochloride (138 g, 1.42 mol) in THF (900 mL) was added. The reaction mixture was allowed to warm to rt and stirred overnight. After tlc showed the reaction was complete, the solvent was evaporated. The residue was dissolved in $CH_2Cl_2$ (1.2 L) and washed successively with 0.5 N aq HCl, satd aq $Na_2CO_3$ and brine, dried over anhydrous sodium sulfate and evaporated to give (R)-tert-butyl 3-(methoxy(methyl)-carbamoyl)piperidine-1-carboxylate (250 g, 91%), which was used in the next step directly without purification. $^1$H NMR (400 MHz, $CDCl_3$): 1.44 (s, 9H), 1.60-1.78 (m, 2H), 1.90 (m, 1H), 2.65 (m, 1H), 2.75-2.85 (m, 2H), 3.16 (s, 3H), 3.71 (s, 3H), 4.05-4.19 (m, 2H). MS (E/Z): 273 (M+H$^+$).

Step 2. (R)-tert-butyl 3-(3-chlorobenzoyl)piperidine-1-carboxylate

To a solution of 1-bromo-3-chlorobenzene (15 g, 78.3 mmol) in anhydrous THF (150 mL) cooled to −78° C. was added dropwise a solution of 2.5 M n-BuLi in hexanes (31.3 mL, 78.34 mmol). The reaction mixture was stirred at −78° C. for 1 h and a solution of (R)-tert-butyl 3-(methoxy(methyl)carbamoyl)piperidine-1-carboxylate (17.8 g, 65.3 mmol) in anhydrous THF (50 mL) was added dropwise. After addition, the mixture was allowed to warm to rt and stirred for 2 h. The mixture was quenched with satd aq $NH_4Cl$ (250 mL) and extracted with EtOAc (3×150 mL). The combined organic layers were washed with brine, dried over $Na_2SO_4$ and concentrated in vacuo. The residue was purified by flash column chromatography (petroleum ether/EtOAc 5:95) to give (R)-tert-butyl 3-(3-chlorobenzoyl)piperidine-1-carboxylate (12.9 g, 51%). $^1$H NMR (400 MHz, $CDCl_3$): 1.45 (s, 9H), 1.54-1.73 (m, 2H), 1.75 (m, 1H), 2.00 (m, 1H), 2.71-2.78 (m, 1H), 2.93 (m, 2H), 3.30-3.35 (m, 1H), 4.22 (m, 1H), 7.39-7.42 (t, 1H), 7.52 (d, 1H), 7.89 (d, 1H), 7.90 (m, 1H). MS m/z 324 (M+H$^+$).

Step 3. (R)-tert-butyl 3-((S)-4-amino-1-(3-chlorophenyl)-1-hydroxybutyl)piperidine-1-carboxylate A 250 mL, round bottom flask was charged with magnesium turnings (0.528 g, 21.7 mmol, 1.16 equiv) and THF (10 mL). The flask was flushed with $N_2$ and heated to 100° C. A small crystal of iodine was added. A solution of 1-(3-bromopropyl)-2,2,5,5-tetramethyl-1-aza-2,5-disilacyclopentane (5.239 g, 18.7 mmol, 1.0 equiv) in THF (15 mL) was added dropwise to the boiling THF mixture over 10 min. The reaction mixture was stirred and heated under reflux until most of the Mg was consumed (2.5 h) to afford a solution of [3-(2,2,5,5-tetramethyl-1-aza-2,5-disilacyclopent-1-yl)propyl]magnesium bromide.

To a 250-mL, round bottom flask were added (3-chlorophenyl)((R)—N-Boc-piperidin-3-yl)methanone (0.800 g, 2.47 mmol) and THF (10 mL). The flask was evacuated and refilled with $N_2$. The mixture was cooled with a dry ice-acetone bath and the [3-(2,2,5,5-tetramethyl-1-aza-2,5-disilacyclopent-1-yl)propyl]magnesium bromide solution was added via a cannula. The reaction mixture was allowed to slowly warm to −8° C. while stirring overnight. The mixture was quenched with 10% aq $Na_2CO_3$ (10 mL), stirred at rt for 3 h and extracted with $CH_2Cl_2$ (3×). The combined organic extracts were dried over $Na_2SO_4$ and concentrated. The crude product was purified by reversed-phase HPLC (Phenomenex® Luna 5µ C18(2) 100 A, 250×21.20 mm, 5 micron, 10%→90% $CH_3CN/H_2O$, 0.1% $CF_3COOH$ over 13 min and then 90% $CH_3CN/H_2O$, 0.1% $CF_3COOH$ over 3.5 min, flow rate 25 mL/min) to give (R)-tert-butyl 3-((s)-4-amino-1-(3-chlorophenyl)-1-hydroxybutyl)piperidine-1-carboxylate as its TFA salt (0.883 g, 72%). LC-MS (3 min) $t_R$=1.30 min, m/z 383, 385 (MH$^+$), 327, 329; $^1$H NMR (400 MHz, $CD_3OD$) δ 7.36 (m, 1H), 7.27-7.13 (m, 3H), 4.26 (br s, 1H), 3.89 (d, J=12.9 Hz, 1H), 2.82-2.68 (m, 2H), 2.44 (br s, 1H), 2.36 (t, J=12.2 Hz, 1H), 1.97-1.79 (m, 2H), 1.64-1.08 (m, 16H), 1.34 (s); $^{13}$C NMR (100 MHz, $CD_3OD$) δ 156.69, 148.15, 135.39, 130.69, 127.74, 127.36, 125.41, 81.04, 78.10, 40.95, 28.69, 26.64, 26.51, 23.30.

Step 4. (R)-tert-butyl 3-((S)-4-(methoxycarbonylamino)-1-(3-chlorophenyl)-1-hydroxybutyl)-piperidine-1-carboxylate To a 100-mL round bottom flask were added the TFA salt of (R)-tert-butyl 3-((S-4-amino-1-(3-chlorophenyl)-1-hydroxybutyl)piperidine-1-carboxylate (0.8164 g, 1.64 mmol, 1.0 equiv), DMAP (0.542 g), $CH_2Cl_2$ (40 mL) and triethylamine (6 mL). The mixture was cooled in an ice bath and a solution of methyl chloroformate (0.550 g, 5.82 mmol, 3.5 equiv) in $CH_2Cl_2$ (10 mL) was added. The reaction mixture was allowed to slowly warm to rt and stirred overnight. After the solvents were removed in vacuo, the residue was purified by reversed-phase HPLC (Phenomenex® Luna 5µ C18(2) 100 A, 250×21.20 mm, 5 micron, 70%→90% $CH_3CN/H_2O$, 0.1% $CF_3COOH$ over 8 min and then 90% $CH_3CN/H_2O$, 0.1% $CF_3COOH$ over 1.5 min, flow rate 25 mL/min) to give (R)-tert-butyl 3-((S)-4-(methoxycarbonylamino)-1-(3-chlorophenyl)-1-hydroxybutyl)piperidine-1-carboxylate (0.5020 g, 69%). LC-MS (3 min) $t_R$=1.91 min, m/z 463 (MNa$^+$), 441 (MH$^+$), 343 341; $^1$H NMR (400 MHz, $CDCl_3$) δ 7.37-7.36 (m, H), 7.28-7.17 (m, 3H), 4.90 (br s, 2H), 4.37 (d, J=12.0 Hz, 1H), 3.97 (d, J=12.3 Hz, 1H), 3.64 (s, 3H), 3.16-3.04 (m, 2H), 2.58-2.49 (m, 2H), 1.98-1.86 (m, 2H), 1.76-1.70 (m, 1H), 1.61-1.56 (m, 1H), 1.45 (s, 9H), 1.48-1.13 (m, 5H); $^{13}$C NMR (100 MHz, $CDCl_3$) δ 157.60, 155.31, 146.51, 134.31, 129.36, 126.72, 125.96, 123.76, 80.08, 77.65, 52.21, 46.45, 44.91, 44.56, 40.91, 35.97, 28.42, 25.33, 25.25, 24.34.

Step 5. Methyl (S)-4-(3-chlorophenyl)-4-hydroxy-4-((R)-piperidin-3-yl)butylcarbamate A mixture of (R)-tert-butyl 3-((S)-4-(methoxycarbonylamino)-1-(3-chlorophenyl)-1-hydroxybutyl)piperidine-1-carboxylate (0.0322 g, 0.073 mmol), $CH_3CN$ (30 mL) and 2 N aq HCl (25 mL) was vigorously stirred at rt for 24 h. The solvents were removed in vacuo to give the HCl salt of methyl (S)-4-(3-chlorophenyl)-4-hydroxy-4-((R)-piperidin-3-yl) butylcarbamate, which was used without further purification. LC-MS (3 min) $t_R$=0.98 min, m/z 343, 341 (M+H$^+$), 323.

The following compounds were prepared following procedures analogous to those described above:

| | |
|---|---|
| XXXVIII-16a | methyl (S)-4-(2-fluorophenyl)-4-hydroxy-4-((R)-piperidin-3-yl)butylcarbamate using 2-fluorophenyllithium in Step 2 |
| XXXVIII-25a | methyl (S)-4-(3,5-dimethylphenyl)-4-hydroxy-4-((R)-piperidin-3-yl)butylcarbamate using 3,5-dimethylphenyllithium in Step 2 |
| XXXVIII-26a | methyl (S)-4-(3-fluoro-5-methylphenyl)-4-hydroxy-4-((R)-piperidin-3-yl)butylcarbamate using 3-fluoro-5-methylphenyllithium in Step 2. |
| XXXVIII-27a | methyl (S)-4-(2-fluoro-5-methylphenyl)-4-hydroxy-4-((R)-piperidin-3-yl)butylcarbamate using 2-fluoro-5-methylphenyllithium in Step 2. |
| XXXVIII-35a | methyl (S)-4-(2,3-difluorophenyl)-4-hydroxy-4-((R)-piperidin-3-yl)butylcarbamate using 2,3-difluorophenyllithium in Step 2. |
| XXXVIII-36a | methyl (S)-4-(3,5-difluorophenyl)-4-hydroxy-4-((R)-piperidin-3-yl)butylcarbamate using 3,5-difluorophenyllithium in Step 2. |
| XXXVIII-40a | ethyl (S)-4-(3-chlorophenyl)-4-hydroxy-4-((R)-piperidin-3-yl)butylcarbamate using ethyl chloroformate in Step 4. |
| XXXVIII-42a | methyl (S)-4-(3-chloro-2-fluorophenyl)-4-hydroxy-4-((R)-piperidin-3-yl)butylcarbamate. |
| XXXVIII-43a | methyl (S)-4-(2-chloro-3-fluorophenyl)-4-hydroxy-4-((R)-piperidin-3-yl)butylcarbamate |
| XXXVIII-44a | methyl (S)-4-(3-chloro-5-fluorophenyl)-4-hydroxy-4-((R)-piperidin-3-yl)butylcarbamate using 3-chloro-5-fluorophenyllithium in Step 2/ |
| XXXVIII-46a | methyl (S)-4-(3-chloro-2,4-difluorophenyl)-4-hydroxy-4-((R)-piperidin-3-yl)butylcarbamate using 3-chloro-2,4-difluorophenyllithium in Step 2. |

Preparation 2

(R)-2-((3-chloro-2-fluorophenyl)(piperidin-3-yl)methoxy)acetamide

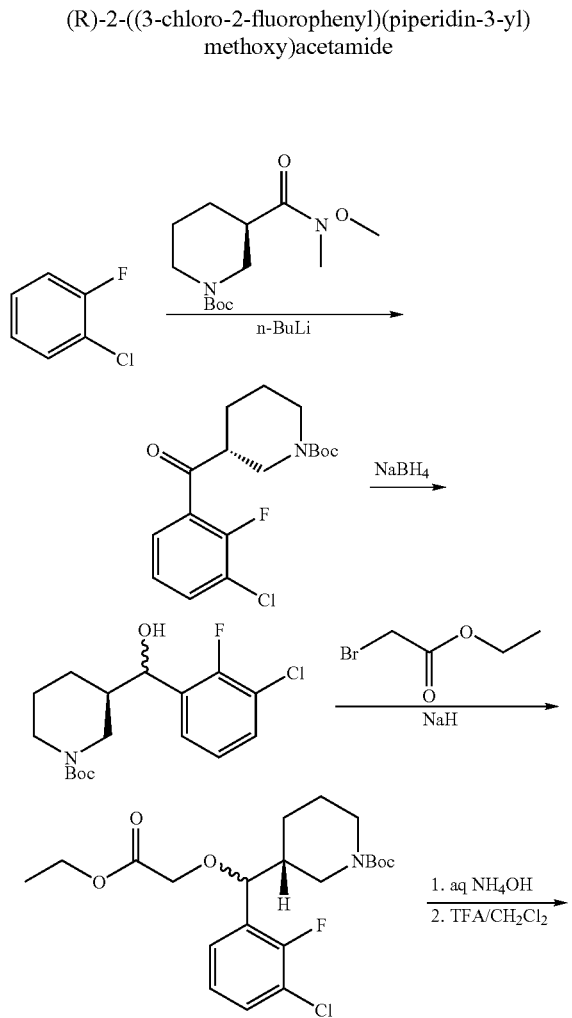

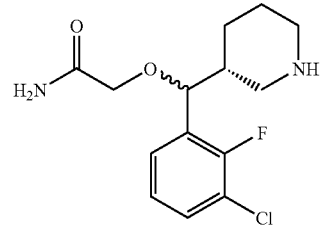

Step 1. (R)-tert-butyl 3-(3-chloro-2-fluorobenzoyl)piperidine-1-carboxylate

To a stirred solution of 1-chloro-2-fluoro-benzene (13.0 g, 0.1 mol) in THF (250 mL) at −75° C. was added dropwise 2.5 M BuLi in hexane (40 mL, 0.1 mol) during 45 min. After additional stirring for 30 min at −75° C., a solution of (R)-tert-butyl 3-(methoxy(methyl)-carbamoyl)piperidine-1-carboxylate (21.76 g, 0.08 mol) in THF (100 mL) was added dropwise over 30 min. The mixture was allowed to warm from −70° C. to 0° C. The mixture was quenched with sat'd aq NH$_4$Cl, extracted with EtOAc (3×) and the combined organic layers were dried over Na$_2$SO$_4$. Solvent removal and flash column chromatography, eluting with 5% EtOAc in petroleum ether, afforded (R)-tert-butyl 3-(3-chloro-2-fluorobenzoyl)piperidine-1-carboxylate (19.2 g, 70%). $^1$H NMR (400 MHz, CDCl$_3$): 1.45 (s, 9H), 1.63 (m, 2H), 1.76 (m, 1H), 2.06 (m, 1H), 2.87 (m, 1H), 3.15 (m, 1H), 3.25 (m, 1H), 3.9 (m, 1H), 4.2 (m, 1H), 7.18 (m, 1H), 7.60 (m, 2H). MS (E/Z): 342 (M+H$^+$).

Step 2. (R)-tert-butyl 3-((3-chloro-2-fluorophenyl)(hydroxy)methyl)piperidine-1-carboxylate To a solution of (R)-tert-butyl 3-(3-chloro-2-fluorobenzoyl)piperidine-1-carboxylate (7.75 g, 22.7 mmol) in MeOH (160 mL) was added NaBH$_4$ (6.9 g, 182 mmol) in portions such that the temperature remained below 40° C. After addition, the mixture was stirred at rt for 3 h. Tlc showed the starting material had disappeared. The solvent was removed in vacuo and the residue was partitioned between water and EtOAc. The organic layer was washed with H$_2$O and brine, dried over Na₂SO₄ and evaporated to give (R)-tert-butyl 3-((3-chloro-2-fluorophenyl)(hydroxy)methyl)piperidine-1-carboxylate (4.35 g, 56%) which was used in the next step without purification. MS (E/Z): 344 (M+H⁺).

Step 3. (R)-tert-butyl 3-((3-chloro-2-fluorophenyl)(2-ethoxy-2-oxoethoxy)methyl)piperidine-1-carboxylate To a stirred suspension of NaH (0.608 g, 15.2 mmol) in THF (100 mL) at 0-5° C. was added dropwise a solution of (R)-tert-butyl 3-((3-chloro-2-fluorophenyl)(hydroxy)methyl)-piperidine-1-carboxylate (4.35 g, 12.68 mmol) in THF (30 mL). The reaction mixture was stirred for an additional 1 h at rt. A solution of ethyl bromoacetate (2.52 g, 15.2 mmol) in THF (30 mL) was added dropwise and the mixture was refluxed for 5 h. Tlc showed the starting material had disappeared. The reaction mixture was poured into satd aq NH₄Cl, extracted with EtOAc (3×100 mL), dried over Na₂SO₄, filtered and concentrated in vacuo. The residue was purified by chromatography on silica gel to afford (R)-tert-butyl 3-((3-chloro-2-fluorophenyl)(2-ethoxy-2-oxoethoxy)methyl)piperidine-1-carboxylate (4.368 g, 80%). ¹H NMR (400 MHz, CDCl₃): 0.861 (m, 2H), 1.25 (m, 6H), 1.38&1.43 (s, 9H), 1.59-2.10 (m, 3H), 2.75 (m, 1H), 3.80 (s, 1H), 3.96 (m, 2H), 4.18 (m, 2H), 4.62 (m, 1H), 7.12 (m, 1H), 7.33 (m, 2H); MS (E/Z): 430 (M+1)

Step 4. (R)-tert-butyl 3-((2-amino-2-oxoethoxy)(3-chloro-2-fluorophenyl)methyl)piperidine-1-carboxylate To a solution of (R)-tert-butyl 3-((R)-(3-chloro-2-fluorophenyl)(2-ethoxy-2-oxoethoxy)-methyl)piperidine-1-carboxylate (500 mg, 1.16 mmol) in MeOH (10 mL) was added NH₃ (aq) (28%, 15 mL) at rt. The resulting clear solution was stirred at rt overnight. Solvent and excess ammonia was removed in vacuo to afford (R)-tert-butyl 3-((2-amino-2-oxoethoxy)(3-chloro-2-fluorophenyl)methyl)piperidine-1-carboxylate (350 mg, 0.87 mmol, 75%). ¹H NMR (400 MHz, CD₃OD): 1.45 (s, 9H), 1.56 (m, 1H), 1.90 (m, 1H), 2.95 (m, 2H), 3.55-3.85 (m, 3H), 4.15 (m, 1H), 4.56 (m, 1H), 7.22 (m, 1H), 7.42 (m, 2H); MS (E/Z): 401 (M+H⁺). The diastereomers can be separated by preparative HPLC if desired.

Step 5. (R)-2-((3-chloro-2-fluorophenyl)(piperidin-3-yl)methoxy)acetamide

A solution of (R)-tert-butyl 3-((2-amino-2-oxoethoxy)(3-chloro-2-fluorophenyl)methyl)piperidine-1-carboxylate (100 mg, 0.25 mmol) in 20% TFA/CH₂Cl₂ (5 mL) was stirred at 0° C. for 30 min. The solvent was neutralized by adding saturated NaHCO₃, extracted three times with CH₂Cl₂ and dried over Na₂SO₄. Evaporation of the solvent gave (R)-2-((3-chloro-2-fluorophenyl)(piperidin-3-yl)methoxy)acetamide (72 mg, 0.24 mmol, 98%). MS (E/Z): 301 (M+H⁺)

Preparation 3

2-((3-chlorophenyl)((R)-piperidin-3-yl)methoxy)-N-ethylacetamide

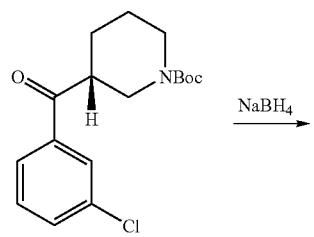

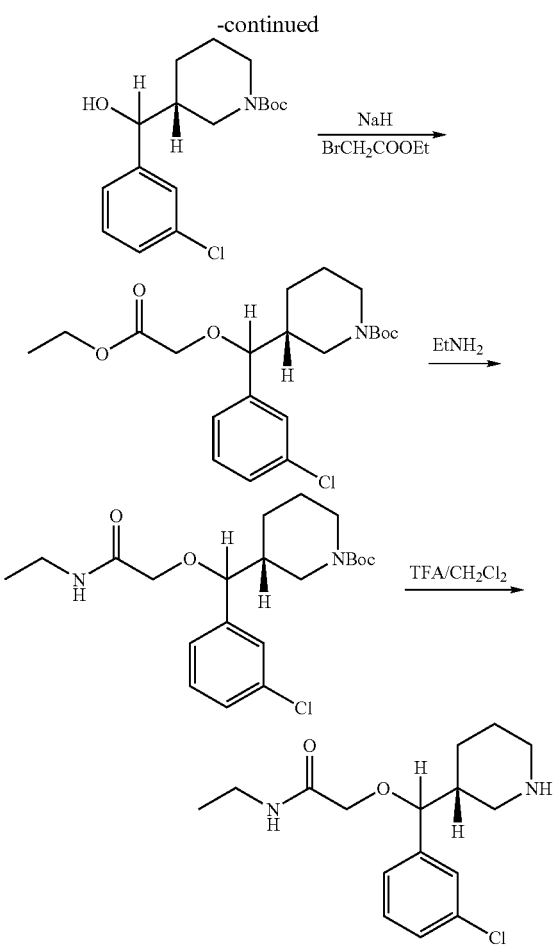

Step 1. (3R)-tert-butyl 3-((3-chlorophenyl)(hydroxy)methyl)piperidine-1-carboxylate To a solution of (R)-tert-butyl 3-(3-chlorobenzoyl)piperidine-1-carboxylate (10 g, 0.031 mol) in ethanol was added NaBH₄ (4.71 g, 0.124 mol) portionwise. When the reaction was complete, the ethanol was distilled off, and water (100 mL) and EtOAc (100 mL) were added to the mixture. The organic phase was separated and the aqueous layer was extracted with EtOAc (3×50 mL). The combined organic phases ware washed with water, dried over Na₂SO₄ and concentrated to give (3R)-tert-butyl 3-((3-chlorophenyl)(hydroxy)methyl)piperidine-1-carboxylate (9.1 g, 90%), which used without purification. ¹H NMR (400 MHz, CDCl₃): 1.24-1.45 (m, 4H), 1.46 (m, 9H), 1.61-1.68 (m, 1H), 1.73-1.84 (m, 1H), 3.05-3.26 (m, 2H), 3.55-3.66 (m, 1H), 3.82-3.96 (m, 1H), 4.42 (m, 1H), 7.20 (m, 1H), 7.27-7.30 (m, 2H), 7.32 (s, 1H). MS (E/Z): 326 (M+H⁺)

Step 2. (3R)-tert-butyl 3-((3-chlorophenyl)(2-ethoxy-2-oxoethoxy)methyl)piperidine-1-carboxylate To a suspension of NaH (0.608 g, 15.2 mmol) in DMF (60 mL) at 0-5° C. was added dropwise with a solution of (3R)-tert-butyl 3-((3-chlorophenyl)(hydroxy)methyl)piperidine-1-carboxylate (4.35 g, 12.68 mmol) in DMF (30 mL). The mixture was stirred for 1 h at rt. A solution of ethyl bromoacetate (2.52 g, 15.2 mmol) in DMF (30 mL) was added dropwise and the mixture was heated to reflux for 3 h. When the reaction was complete, the mixture was poured into satd aq NH₄Cl, and extracted with EtOAc (3×100 mL). The combined organic layers were dried over Na₂SO₄ and concentrated in vacuo to give (3R)-tert-butyl 3-((3-chlorophenyl)(2-ethoxy-2-oxoethoxy)methyl)piperidine-1-carboxylate (2.09 g, 40%). ¹H NMR (400 MHz, CDCl₃): 1.23-1.27 (m, 3H), 1.43-1.45 (m, 9H), 3.95-3.99 (m, 3H), 4.12-4.17 (m, 4H), 4.32-4.38 (d, 1H), 7.14-7.17 (m, 1H), 7.26-7.28 (m, 3H). MS (E/Z): 412 (M+H⁺).

Step 3. (3R)-tert-butyl 3-((3-chlorophenyl)(2-(ethylamino)-2-oxoethoxy)methyl)piperidine-1-carboxylate To a solution of EtNH₂ in alcohol (30% by weight, 10 mL) was added (3R)-tert-butyl 3-((3-chlorophenyl)(2-ethoxy-2-oxoethoxy)methyl)piperidine-1-carboxylate (100 mg, 0.243 mmol). The mixture was stirred at rt overnight. The mixture was concentrated under vacuum to give crude product, which was purified by preparative tlc (elution solvent: 5:1 petroleum ether/EtOAc) to give (3R)-tert-butyl 3-((3-chlorophenyl)(2-(ethylamino)-2-oxoethoxy)methyl)piperidine-1-carboxylate (57.9 mg, 58%) as a colorless oil. MS (E/Z): 411 (M+H⁺).

Step 4. 2-((3-chlorophenyl)((R)-piperidin-3-yl)methoxy)-N-ethylacetamide

To a stirred solution of TFA in CH₂Cl₂ (20% v/v, 5 mL) was added (3R)-tert-butyl 3-((3-chlorophenyl)(2-(ethylamino)-2-oxoethoxy)methyl)piperidine-1-carboxylate (57.9 mg, 0.0141 mmol). The reaction was monitored by tlc (elution solvent: 5:1 petroleum ether/EtOAc). When the reaction was complete, the mixture was washed with satd aq NaHCO₃ and water, dried over Na₂SO₄ and concentrated to give 2-((3-chlorophenyl)((R)-piperidin-3-yl)methoxy)-N-ethylacetamide (40 mg, 91%). MS (E/Z): 311 (M+H⁺).

The following compounds were prepared using procedures analogous to those described above:

| | |
|---|---|
| XXXVIII-4a | 2-((3-chlorophenyl)((R)-piperidin-3-yl)methoxy)-N-methylacetamide |
| XXXVIII-5a | 2-((2,3-difluorophenyl)((R)-piperidin-3-yl)methoxy)-N-propylacetamide |
| XXXVIII-12a | 2-((2,3-difluorophenyl)((R)-piperidin-3-yl)methoxy)-N-ethylacetamide |
| XXXVIII-20a | 2-((3-chlorophenyl)((R)-piperidin-3-yl)methoxy)-N-propylacetamide |
| XXXVIII-21a | 2-((2,3-difluorophenyl)((R)-piperidin-3-yl)methoxy)-N-isopropylacetamide |
| XXXVIII-24a | 2-((3-chloro-2-fluorophenyl)((R)-piperidin-3-yl)methoxy)-N-ethylacetamide |
| XXXVIII-33a | 2-((3-chlorophenyl)((R)-piperidin-3-yl)methoxy)-N-(2-methoxyethyl)acetamide |
| XXXVIII-50a | 2-((3-chlorophenyl)((R)-piperidin-3-yl)methoxy)-N-isopropylacetamide |

Preparation 4

Methyl 2-((R)-(3-chlorophenyl)((R)-piperidin-3-yl)methoxy)ethylcarbamate

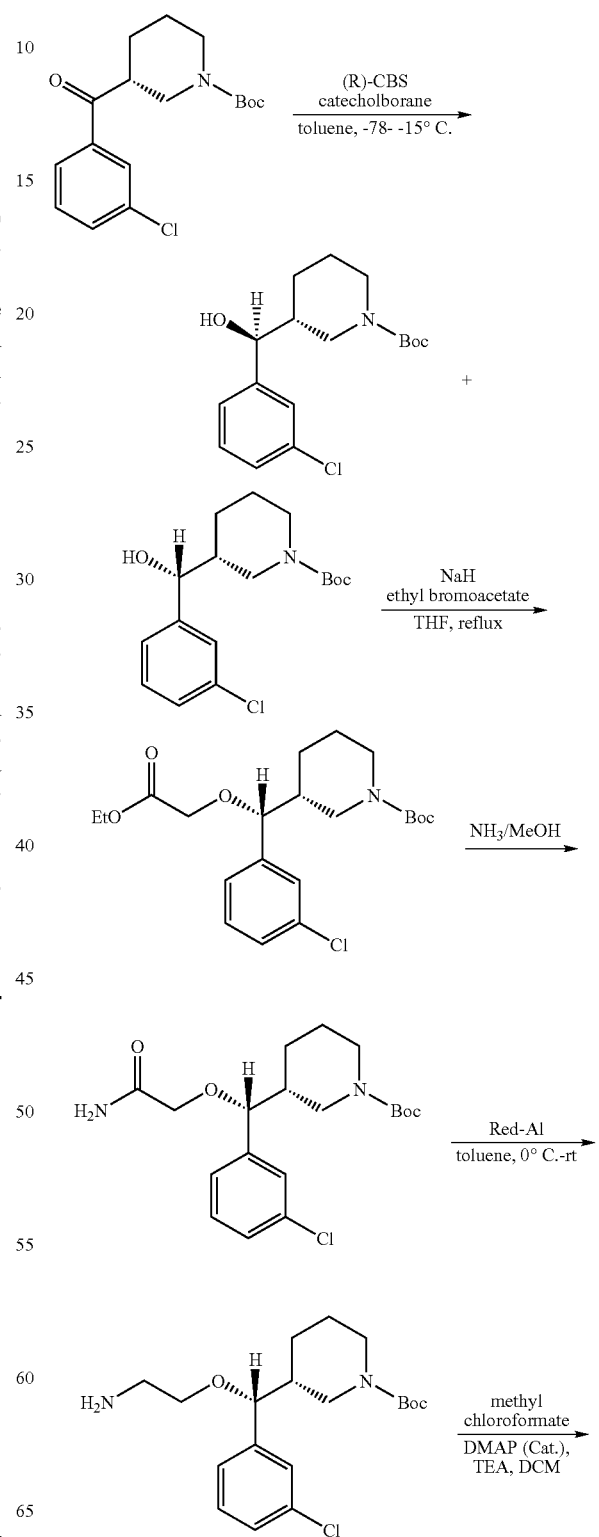

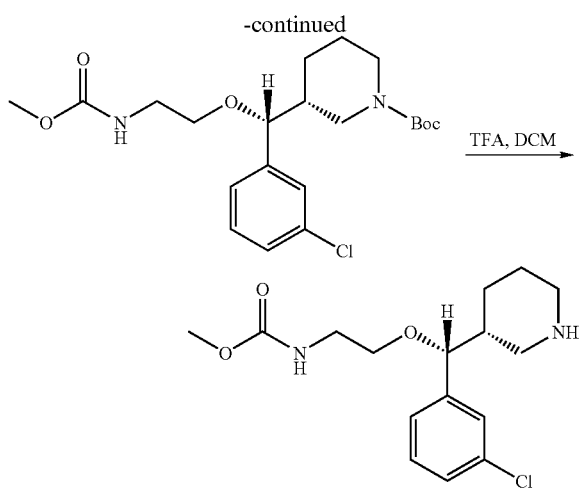

Step 1: (R)-tert-Butyl 3-((R)-(3-chlorophenyl)(hydroxy)methyl)piperidine-1-carboxylate To a solution of (R)-tert-butyl 3-(3-chlorobenzoyl)piperidine-1-carboxylate (5.60 g, 17.29 mmol) and (R)-2-methyl-CBS-oxazaborolidine (1 M in toluene, 9 mL, 9.00 mmol) cooled to −78° C. was added catecholborane (5.6 mL, 54.0 mmol) dropwise. After 20 min, the reaction temperature was allowed to warm to −15° C. and stirred overnight. The reaction was quenched at 0° C. by careful addition of water and diluted with ether. The resulting suspension was filtered through Celite and washed with ether. The filtrate was washed successively with 1 M aq NaOH (3×50 mL), 1 M aq HCl (3×50 mL), satd aq NaHCO$_3$ and brine, and dried over Na$_2$SO$_4$. The solution was filtered, the filtrate was evaporated under vacuum, and the residue was purified by preparative HPLC to afford (R)-tert-butyl 3-((R)-(3-chlorophenyl)(hydroxy)methyl)piperidine-1-carboxylate (2.44 g) and (R)-tert-butyl 3-((S)-(3-chlorophenyl)(hydroxy)methyl)piperidine-1-carboxylate (1.21 g). MS: 348 (M+Na)$^+$.

Step 2: (R)-tert-Butyl 3-((R)-(3-chlorophenyl)(2-ethoxy-2-oxoethoxy)methyl)piperidine-1-carboxylate To a suspension of 60% NaH in oil (960 mg, 24.0 mmol) in anhydrous THF at 0° C. was added a solution of (R)-tert-butyl 3-((R)-(3-chlorophenyl)(2-ethoxy-2-oxoethoxy)methyl)piperidine-1-carboxylate (1.429 g, 4.40 mmol) in anhydrous THF (10 mL). The reaction mixture was stirred at rt for 30 min and a solution of ethyl bromoacetate (2.204 g, 13.2 mmol) in anhydrous THF (10 mL) was added dropwise. The resulting suspension was heated at reflux for 3 h and cooled to 0° C. again. The same amount of NaH as before was added and stirred for 30 min at rt, followed by addition the same amount of ethyl bromoacetate, and the mixture was heated at reflux overnight. The reaction mixture was cooled to 0° C. and quenched by careful addition of aq NH$_4$Cl. The mixture was extracted with EtOAc (3×). The combined organic phases were washed with brine, dried over Na$_2$SO$_4$, and filtered. The filtrate was evaporated and the residue was purified by flash chromatography on silica gel to afford (R)-tert-butyl 3-((R)-(3-chlorophenyl)(2-ethoxy-2-oxoethoxy)methyl)piperidine-1-carboxylate (1.62 g). MS: 412 (M+H)$^+$.

Step 3: (R)-tert-Butyl 3-((R)-(2-amino-2-oxoethoxy)(3-chlorophenyl)methyl)piperidine-1-carboxylate (R)-tert-Butyl 3-((R)-(3-chlorophenyl)(2-ethoxy-2-oxoethoxy)methyl)piperidine-1-carboxylate (1.50 g, 3.65 mmol) was dissolved in 7 M NH$_3$ in MeOH, and stirred at rt for 6 h. The mixture was evaporated under reduced pressure to afford the (R)-tert-butyl 3-((R)-(2-amino-2-oxoethoxy)(3-chlorophenyl)methyl)piperidine-1-carboxylate in quantitative yield. MS: 383 (M+H)$^+$.

Step 4: (R)-tert-butyl 3-((R)-(2-aminoethoxy)(3-chlorophenyl)methyl)piperidine-1-carboxylate (R)-tert-butyl 3-((R)-(2-amino-2-oxoethoxy)(3-chlorophenyl)methyl)piperidine-1-carboxylate (1.10 g, 2.60 mmol) was dissolved in anhydrous toluene (30 mL) and cooled to 0° C. Red-Al (65% in toluene, 2.6 mL, 8.64 mmol) was added dropwise. After the addition, the reaction was stirred at rt for 12 h and quenched by adding water slowly. The resulting mixture was filtered through Celite and washing with THF. The filtrate was evaporated under reduced pressure to give crude product 1.05 g. It was used for next step without further purification.

Step 5: (R)-tert-Butyl 3-((R)-(3-chlorophenyl)(2-(methoxycarbonylamino)ethoxy)methyl)piperidine-1-carboxylate To a solution of (R)-tert-butyl 3-((R)-(2-aminoethoxy)(3-chlorophenyl)methyl)piperidine-1-carboxylate (1.05 g, ca. 2.6 mmol), Et$_3$N (3.96 mL, 2.85 mmol), and DMAP (174 mg, 1.43 mmol) in anhydrous CH$_2$Cl$_2$ (20 mL) cooled to 0° C. was added a solution of methyl chloroformate (1.35 g, 14.25 mmol) in dichloromethane (20 mL) within 30 min. The reaction was stirred overnight, and evaporated under vacuum. The residue was purified by flash chromatography on silica gel to afford (R)-tert-butyl 3-((R)-(3-chlorophenyl)(2-(methoxycarbonylamino)ethoxy)methyl)piperidine-1-carboxylate (0.65 g). MS: 427 (M+H)$^+$.

Step 6: Methyl 2-((R)-(3-chlorophenyl)((R)-piperidin-3-yl)methoxy)ethylcarbamate To a stirred solution of (R)-tert-butyl 3-((R)-(3-chlorophenyl)(2-(methoxycarbonylamino)ethoxy)methyl)piperidine-1-carboxylate (91 mg, 0.21 mmol) in CH$_2$Cl$_2$ (3 mL) at rt was added TFA (0.5 mL). The mixture was stirred until complete removal of the Boc group had occurred. The solvent was removed under vacuum to give methyl 2-((R)-(3-chlorophenyl)((R)-piperidin-3-yl)methoxy)ethylcarbamate as its TFA salt. MS: 327 (M+H)$^+$.

The following compounds were prepared using procedures analogous to those described above:

| | |
|---|---|
| XXXVIII-7a | methyl 2-((R)-(3-fluorophenyl)((R)-piperidin-3-yl)methoxy)ethylcarbamate |
| XXXVIII-32a | ethyl 2-((R)-(3-chlorophenyl)((R)-piperidin-3-yl)methoxy)ethylcarbamate |
| XXXVIII-37a | methyl 2-((R)-(3-chloro-2-fluorophenyl)((R)-piperidin-3-yl)methoxy)ethylcarbamate |
| XXXVIII-38a | methyl 2-((R)-(3-chloro-5-fluorophenyl)((R)-piperidin-3-yl)methoxy)ethylcarbamate |
| XXXVIII-45a | ethyl 2-((R)-(3-chloro-2-fluorophenyl)((R)-piperidin-3-yl)methoxy)ethylcarbamate |
| XXXVIII-49a | methyl 2-((R)-(2,3-difluorophenyl)((R)-piperidin-3-yl)methoxy)ethylcarbamate |

Preparation 5

3-((R)-(3-chlorophenyl)((R)-piperidin-3-yl)methoxy)-N-methylpropanamide

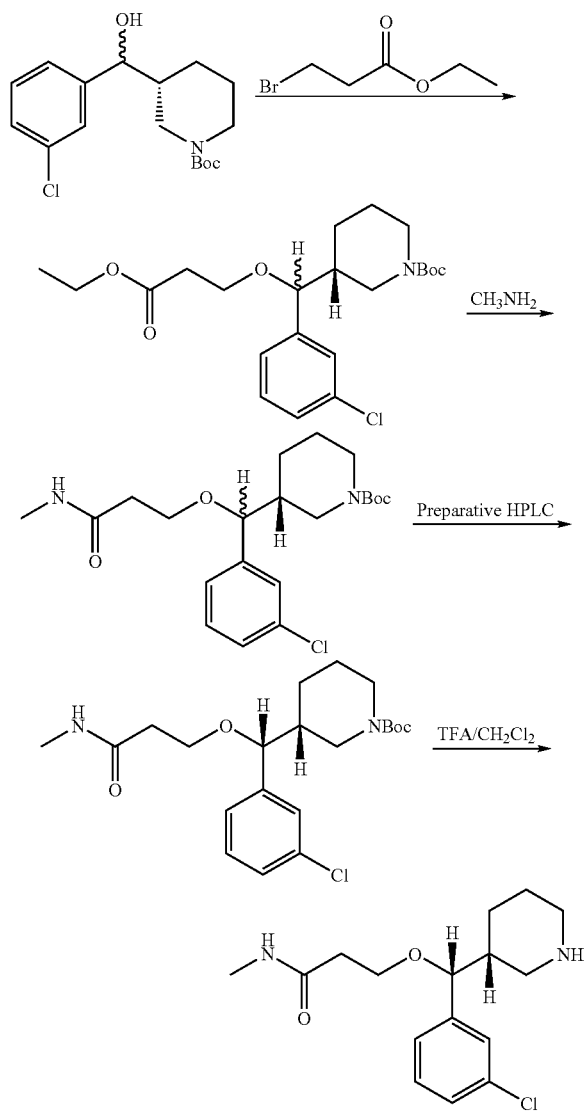

Step 1. (3R)-tert-butyl 3-((3-chlorophenyl)(3-ethoxy-3-oxopropoxy)methyl)piperidine-1-carboxylate To a slurry of NaH (0.835 g, 0.0348 mol) in DMF (50 mL) was added a solution of (R)-tert-butyl 3-((3-chlorophenyl)(hydroxy)methyl)piperidine-1-carboxylate (3.8 g, 0.0116 mol) in DMF (30 mL) dropwise at −15~−5° C. and the reaction mixture was stirred for about 1 h at rt. A solution of 3-bromopropionic acid ethyl ester (4.2 g, 0.0232 mol) in DMF (30 mL) was added to the reaction mixture dropwise while the temperature was maintained at −15~−5° C. and the mixture was warmed slowly to rt and stirred overnight. The reaction was cooled in an ice bath and quenched with satd aq NH$_4$Cl (80 mL). The product was extracted with EtOAc, washed with brine, dried over NaSO$_4$ and purified by flash chromatography to afford (3R)-tert-butyl 3-((3-chlorophenyl)(3-ethoxy-3-oxopropoxy)methyl)piperidine-1-carboxylate (2.0 g, 4.71 mmol, 41%). $^1$H NMR (400 MHz, CDCl$_3$): 1.12-1.37 (m, 4H), 1.45 (s, 9H), 1.47-1.75 (m, 3H), 1.82-1.93 (m, 1H), 2.50-2.58 (m, 4H), 3.43-3.52 (m, 2H), 3.80-4.01 (m, 2H), 4.07-4.17 (m, 3H), 7.13-7.23 (m, 1H), 7.25-7.27 (m, 3H). MS (E/Z): 426 (M+H$^+$).

Step 2. (R)-tert-butyl 3-((R)-(3-chlorophenyl)(3-(methylamino)-3-oxopropoxy)methyl)piperidine-1-carboxylate (3R)-tert-butyl 3-((3-chlorophenyl)(3-ethoxy-3-oxopropoxy)methyl)piperidine-1-carboxylate (2.0 g, 4.71 mmol) was dissolved in a solution CH$_3$NH$_2$ in CH$_3$OH ((180 mL) and stirred overnight at rt. After the reaction was complete by HPLC analysis, the solvent was removed in vacuo. The residue was purified by preparative HPLC and afforded the desired isomerically pure product (R)-tert-butyl 3-((R)-(3-chlorophenyl)(3-(methylamino)-3-oxopropoxy)methyl)piperidine-1-carboxylate (0.80 g, 1.95 mmol, 41% yield). MS (E/Z): 411 (M+H$^+$).

Step 3. Preparation of 3-[S-(3-chloro-phenyl)-(piperidin-3R-yl)-methoxy]-N-methyl-propionamide (R)-tert-butyl 3-((R)-(3-chlorophenyl)(3-(methylamino)-3-oxopropoxy)methyl)piperidine-1-carboxylate (0.80 g, 1.95 mmol) was dissolved in a 20% solution of TFA in CH$_2$Cl$_2$ (20.6 mL) and stirred for about 1 h at rt until the reaction was complete. The solvent was removed by evaporation and the crude product was purified with preparative HPLC to afford 3-((R)-(3-chlorophenyl)((R)-piperidin-3-yl)methoxy)-N-methylpropanamide (542 mg, 1.75 mmol, 90% yield). MS (E/Z): 311 (M+H$^+$).

The following compounds were prepared using procedures analogous to those described above:

| | |
|---|---|
| XXXVIII-18a | 3-((R)-(3-chlorophenyl)((R)-piperidin-3-yl)methoxy)-N-ethylpropanamide |
| XXXVIII-29a | 3-((R)-(3-chlorophenyl)((R)-piperidin-3-yl)methoxy)-N-propylpropanamide |
| XXXVIII-30a | 3-((R)-(3-chlorophenyl)((R)-piperidin-3-yl)methoxy)-N-isopropylpropanamide |

Preparation 6

(S)-5-(3-chlorophenyl)-5-hydroxy-N-methyl-5-((R)-piperidin-3-yl)pentanamide

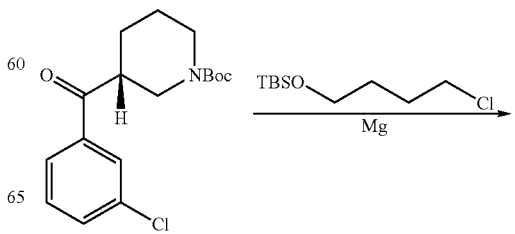

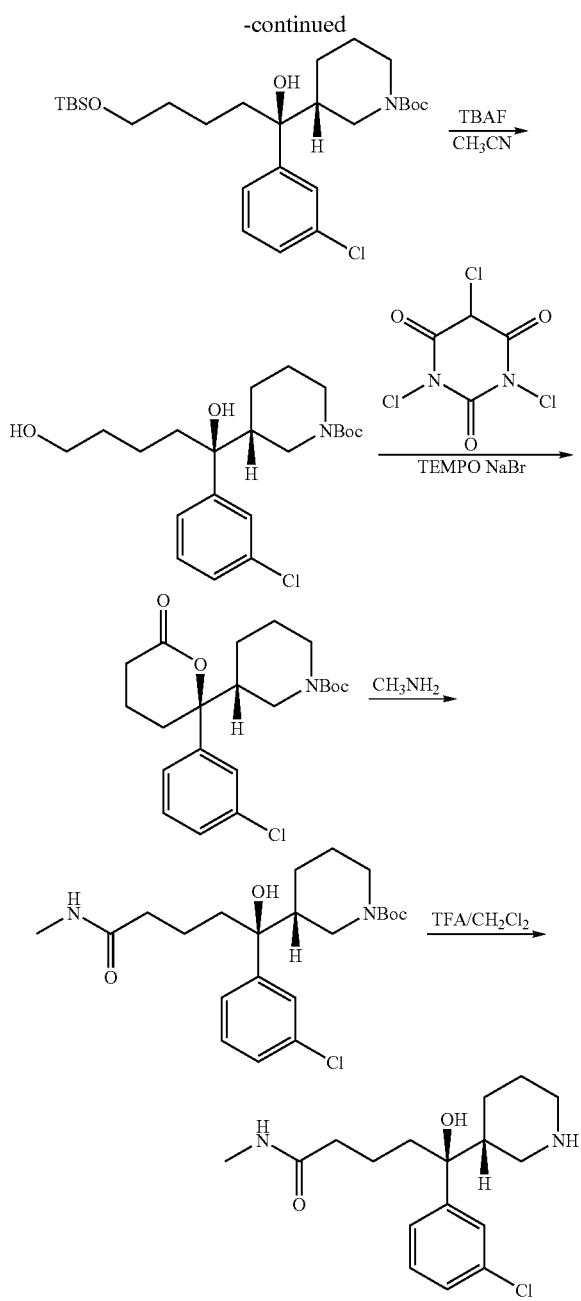

Step 1. (R)-tert-butyl 3-((S)-5-(tert-butyldimethylsilyloxy)-1-(3-chlorophenyl)-1-hydroxypentyl)piperidine-1-carboxylate A stirred mixture of magnesium turnings (1.32 g, 55 mmol) and anhydrous THF (10 mL) under N₂ was treated with a crystal of iodine and 5 percent of a solution of tert-butyl(4-chlorobutoxy)dimethylsilane (11.15 g, 50 mmol) in THF (40 mL). When the reaction started, the remainder of the chloride solution was added dropwise at a rate sufficient to maintain a gentle reflux. After addition, the reaction mixture was heated under reflux for 1 h and most of magnesium was consumed. The reaction mixture cooled to rt.

A solution of (R)-tert-butyl 3-(3-chlorobenzoyl)piperidine-1-carboxylate (1.62 g, 5 mmol) in anhydrous THF (20 mL) under N₂ was cooled in a dry ice-acetone bath. The Grignard reagent derived from tert-butyl-(4-chloro-butoxy)-dimethyl-silane (50 mL) prepared above was added dropwise. After addition, the mixture was allowed to warm to rt and stirred for 2 h (monitored by tlc). The reaction was quenched with satd aq NH₄Cl (70 mL) and extracted with EtOAc (3×40 mL). The combined organic layers were washed with brine, dried over Na₂SO₄ and concentrated in vacuo. The residue was purified by chromatography on silica gel eluting with 10:90 EtOAc/hexane to afford (R)-tert-butyl 3-((S)-5-(tert-butyldimethylsilyloxy)-1-(3-chlorophenyl)-1-hydroxypentyl)piperidine-1-carboxylate (1.65 g, 65%). $^1$H NMR (400 MHz, CDCl₃): 0.02 (s, 6H), 7.30 (d, 2H), 0.85 (s, 9H), 1.47 (s, 9H), 1.92 (m, 3H), 2.52 (m, 3H), 3.56 (m, 2H), 3.63 (m, 2H), 3.97-4.21 (m, 2H), 4.36 (m, 1H), 7.16-7.25 (m, 3H), 7.36 (m, 1H). MS (E/Z): 512 (M+H⁺)

Step 2. (R)-tert-butyl 3-((S)-1-(3-chlorophenyl)-1,5-dihydroxypentyl)piperidine-1-carboxylate To a solution of (R)-tert-butyl 3-((S)-5-(tert-butyldimethylsilyloxy)-1-(3-chlorophenyl)-1-hydroxypentyl)piperidine-1-carboxylate (511 mg, 1 mmol) in CH₃CN (10 mL) was added tetrabutylammonium fluoride (550 mg, 2 mmol) in one portion. The reaction mixture was stirred at 60° C. for 2 h. The solvent was removed under reduced pressure. The residue was purified by column chromatography on silica gel with EtOAc/hexane to give (R)-tert-butyl 3-((S)-1-(3-chlorophenyl)-1,5-dihydroxypentyl)piperidine-1-carboxylate (350 mg, 80%). $^1$H NMR (400 MHz, CDCl₃): 1.05-1.42 (m, 6H), 1.46 (s, 9H), 1.52-1.79 (m, 4H), 1.94-2.03 (m, 2H), 2.55 (m, 2H), 3.56 (m, 2H), 3.97 (m, 1H), 4.36 (m, 1H), 7.20-7.25 (m, 3H), 7.37 (s, 1H). MS (E/Z): 398 (M+H⁺)

Step 3. (R)-tert-butyl 3-((S)-2-(3-chlorophenyl)-6-oxotetrahydro-2H-pyran-2-yl)piperidine-1-carboxylate To a stirred solution of (R)-tert-butyl 3-((S)-1-(3-chlorophenyl)-1,5-dihydroxypentyl)piperidine-1-carboxylate (200 mg, 0.5 mmol) in acetone (3 mL) maintained at 0° C. was added an 15% aq NaHCO₃ (2 mL), followed by solid NaBr (10.3 mg, 0.1 mmol) and TEMPO (1.56 mg, 0.01 mmol). Trichloroisocyanuric acid (231 mg, 1 mmol) was then slowly added at 0° C. The mixture was warmed to rt, stirred for 3 h and treated with 2-propanol (0.5 mL). The mixture was filtered through celite and the filtrate was concentrated in vacuo. The residue was partitioned between water and EtOAc and the aqueous phase was extracted with EtOAc (3×20 mL). The organic layers were combined, washed with brine, dried over Na₂SO₄ and concentrated under reduced pressure to provide (R)-tert-butyl 3-((S)-2-(3-chlorophenyl)-6-oxotetrahydro-2H-pyran-2-yl)piperidine-1-carboxylate (160 mg, 81%). $^1$H NMR (400 MHz, CDCl₃): 1.12-1.45 (m, 3H), 1.46 (s, 9H), 1.58-1.81 (m, 6H), 2.22 (m, 2H), 2.42 (m, 2H), 2.56 (m, 2H), 4.05 (m, 1H), 4.36 (m, 1H), 7.16 (m, 1H), 7.27-7.32 (s, 1H). MS (E/Z): 394 (M+H⁺).

Step 4. (R)-tert-butyl 3-((S)-1-(3-chlorophenyl)-1-hydroxy-5-(methylamino)-5-oxopentyl)piperidine-1-carboxylate (R)-tert-butyl 3-((S)-2-(3-chlorophenyl)-6-oxotetrahydro-2H-pyran-2-yl)piperidine-1-carboxylate (60 mg, 0.153 mmol) was dissolved in a ca 30% solution of methylamine in methanol (3 mL). The mixture was stirred at it for 2 h then concentrated under reduced pressure to give (R)-tert-butyl 3-((S)-1-(3-chlorophenyl)-1-hydroxy-5-(methylamino)-5-oxopentyl)piperidine-1-carboxylate (60 mg, 93%), which was used directly without purification. ¹H NMR (400 MHz, CDCl₃): 1.12-1.45 (m, 3H), 1.46 (s, 9H), 1.58-1.81 (m, 6H), 2.05-2.17 (m, 2H), 2.50-2.58 (m, 2H), 2.69 (m, 3H), 4.06 (m, 1H), 4.12-4.28 (m, 2H), 7.22-7.32 (m, 3H), 7.43 (s, 1H). MS (E/Z): 425 (M+H⁺).

Step 5. (S)-5-(3-chlorophenyl)-5-hydroxy-N-methyl-5-((R)-piperidin-3-yl)pentanamide (R)-tert-butyl 3-((S)-1-(3-chlorophenyl)-1-hydroxy-5-(methylamino)-5-oxopentyl)piperidine-1-carboxylate (60 mg, 0.14 mmol) was dissolved in a solution of 20% (V/V) TFA/CH₂Cl₂ (3 mL). The reaction mixture was stirred at rt for 1 h, and a solution of saturated sodium bicarbonate was added dropwise to adjust the pH to 7-8. The resulting mixture was extracted with CH₂Cl₂ (3×10 mL), washed with brine, dried over Na₂SO₄ and concentrated in vacuo to afford 5S-(3-chloro-phenyl)-5-hydroxy-5-(piperidin-3R-yl)-pentanoic acid methylamide (42 mg, 91%), which was used directly in the next step without purification. MS (E/Z): 325 (M+H⁺)

The following compounds were made by procedures analogous to those described above:

| | |
|---|---|
| XXXVIII-11a | (S)-5-(3-chlorophenyl)-5-hydroxy-5-((R)-piperidin-3-yl)pentanamide |
| XXXVIII-28a | (S)-5-(3-chlorophenyl)-N-ethyl-5-hydroxy-5-((R)-piperidin-3-yl)pentanamide |

Preparation 7

2-((R)-(3-chlorophenyl)((R)-piperidin-3-yl)methoxy)ethanol

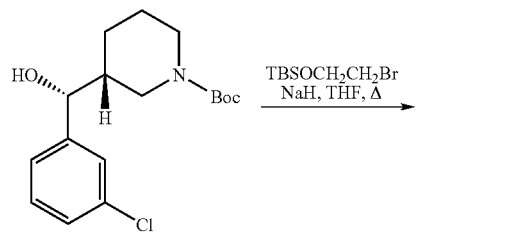
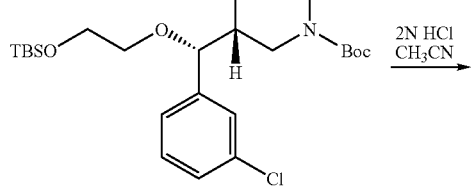
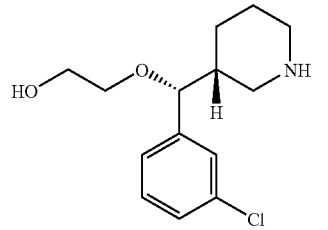

Step 1. (R)-tert-butyl 3-((R)-(2-(tert-butyldimethylsilyloxy)ethoxy)(3-chlorophenyl)methyl)piperidine-1-carboxylate To a mixture of (R)-tert-butyl 3-((R)-(3-chlorophenyl)(hydroxy)methyl)piperidine-1-carboxylate (0.1964 g, 0.60 mmol, 1.0 equiv) and 60% NaH in oil (0.753 g, 18.8 mmol, 31 equiv) in THF (15 mL) was added (2-bromoethoxy)-tert-butyldimethylsilane (2.042 g, 8.5 mmol, 14 equiv). The resulting mixture was heated at 80° C. for 19 h and then quenched with water, extracted with EtOAc and dried over Na₂SO₄. After the solvent was removed, the crude product was used in the next step without further purification.

Step 2. 2-((R)-(3-chlorophenyl)((R)-piperidin-3-yl)methoxy)ethanol

A solution of crude (R)-tert-butyl 3-((R)-(2-(tert-butyldimethylsilyloxy)ethoxy)(3-chlorophenyl)methyl)piperidine-1-carboxylate in CH₃CN (100 mL) and 2 N aq HCl (100 mL) was vigorously stirred at rt for 2 d. The solvents were removed in vacuo to give the HCl salt of 2-((R)-(3-chlorophenyl)((R)-piperidin-3-yl)methoxy)ethanol, which was used in the next step without further purification. LC-MS (3 min) t_R=1.05 min m/z 272, 270 (M+H)⁺.

Preparation 8

(R)-tert-butyl 3-((R)-(2-aminoethoxy)(3-chloro-2-fluorophenyl)methyl)piperidine-1-carboxylate

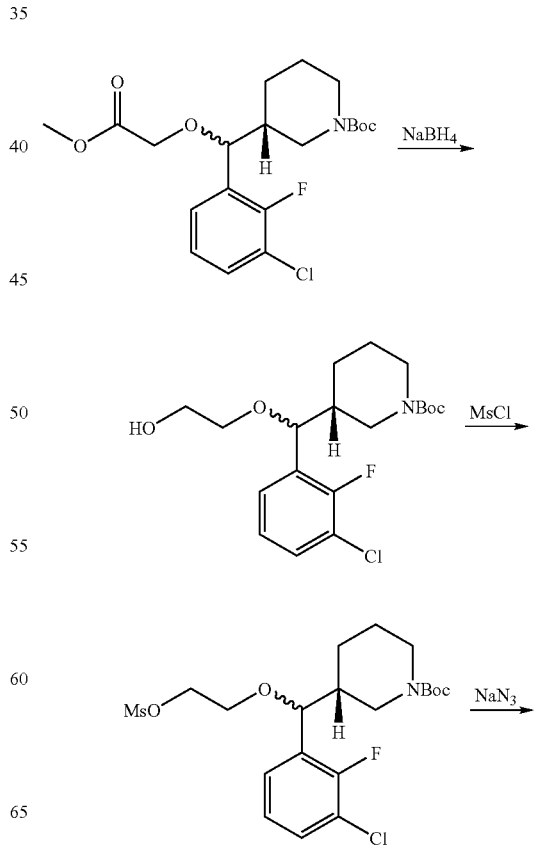

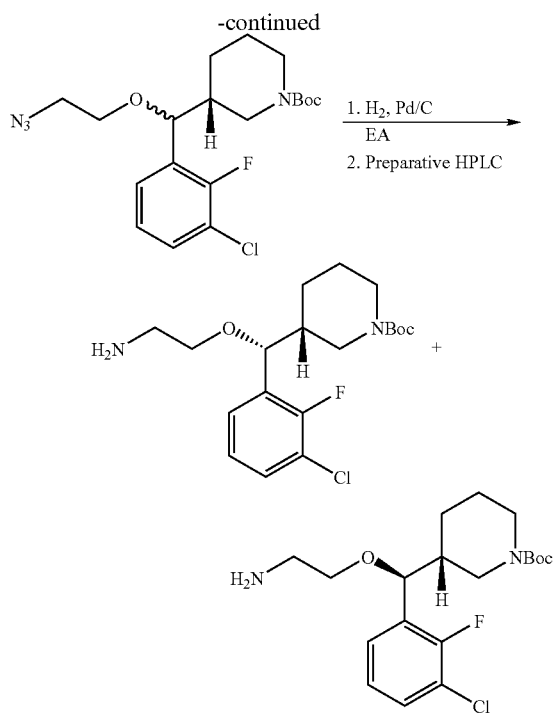

Step 1. (R)-tert-butyl 3-((3-chloro-2-fluorophenyl)(2-hydroxyethoxy)methyl)piperidine-1-carboxylate To a solution of (R)-tert-butyl 3-((3-chloro-2-fluorophenyl)(2-ethoxy-2-oxoethoxy)-methyl)piperidine-1-carboxylate (4.368 g, 10.2 mmol) in MeOH (85 mL) was added NaBH (3.18 g, 81.5 mmol) in portions such that the temperature remained below 40° C. After addition, the mixture was stirred at rt for 2-3 h. TLC showed the starting material had disappeared. The solvent was removed in vacuo and the residue was partitioned between water and EtOAc. The organic layer was washed with H$_2$O and brine, dried over Na$_2$SO$_4$ and evaporated to give (R)-tert-butyl 3-((3-chloro-2-fluorophenyl)(2-hydroxyethoxy)methyl)piperidine-1-carboxylate (3.5 g, 89%). $^1$H NMR (400 MHz, CDCl$_3$): 1.18 (m, 1H), 1.38-1.46 (s, 9H), 1.65 (m, 1H), 1.85 (m, 2H), 2.66 (m, 1H), 3.25 (m, 1H), 3.38 (m, 2H), 3.69 (m, 3H), 3.93 (m, 1H), 4.52 (m, 6H); MS (E/Z): 388 (M+1)

Step 2. (R)-tert-butyl 3-((3-chloro-2-fluorophenyl)(2-(methylsulfonyloxy)ethoxy)methyl)-piperidine-1-carboxylate To a solution of (R)-tert-butyl 3-((3-chloro-2-fluorophenyl)(2-hydroxyethoxy)methyl)-piperidine-1-carboxylate (3.5 g, 9 mmol) in dry CH$_2$Cl$_2$ (50 mL) was added Et$_3$N (3.2 g, 4.2 mL, 27 mmol, 4 eq) at 0~−5° C. Then a solution of MsCl (1.23 g, 10.8 mmol, 1.2 eq) in dry CH$_2$Cl$_2$ (20 mL) was added dropwise at the same temperature. After addition, the mixture was allowed to warm to rt gradually. TLC showed the starting material had disappeared. Water (30 mL) was added and the mixture was extracted with CH$_2$Cl$_2$ (3×20 mL). The combined organic layers were washed with 10% aq citric acid, sat'd aq NaHCO$_3$ and brine, then dried over Na$_2$SO$_4$, filtered and concentrated to give 3R-3-[(3-chloro-2-fluoro-phenyl)-(2-methanesulfonyloxy-ethoxy)-methyl]-piperidine-1-carboxylic acid tert-butyl ester (4.13 g, 99%), which was used in the next step without purification. $^1$H NMR (400 MHz, CDCl$_3$): 1.35 (m, 4H), 1.46 (s, 9H), 1.62 (m, 3H), 1.83 (m, 1H), 2.52-2.81 (m, 2H), 3.05 (m, 3H), 3.56 (m, 2H), 3.92 (m, 1H), 4.30 (m, 2H), 4.48 (m, 1H), 7.13 (m, 1H), 7.28 (m, 1H), 7.35 (m, 1H); MS (E/Z): 466 (M$^+$)

Step 3. (R)-tert-butyl 3-((2-azidoethoxy)(3-chloro-2-fluorophenyl)methyl)piperidine-1-carboxylate 3R-3[(3-chloro-2-fluoro-phenyl)-(2-methanesulfonyloxy-ethoxy)-methyl]-piperidine-1-carboxylic acid tert-butyl ester (4 g, 8.6 mmol) was dissolved in anhydrous DMF (30 mL), solid NaN$_3$ (0.84 g, 12.9 mmol) was added and the reaction mixture was heated at 80° C. overnight. The reaction mixture was cooled to rt and EtOAc (100 mL) was added. The mixture was washed with water (3×30 mL), dried over Na$_2$SO$_4$ and evaporated. The residue was separated on a silica column to give (R)-tert-butyl 3-((2-azidoethoxy)(3-chloro-2-fluorophenyl)methyl)piperidine-1-carboxylate (2.6 g, 73%). $^1$H NMR: (400 MHz, CDCl$_3$): 1.24 (m, 1H), 1.38&1.46 (s, 9H), 1.67 (m, 3H), 1.83 (m, 1H), 2.58-2.81 (m, 2H), 3.32 (m, 2H), 3.45 (m, 2H), 3.92 (m, 1H), 4.20 (m, 1H), 4.50 (m, 1H), 7.13 (t, 1H), 7.34 (m, 2H), 8.02 (s, 1H);

Step 4. (R)-tert-butyl 3-((R)-(2-aminoethoxy)(3-chloro-2-fluorophenyl)methyl)piperidine-1-carboxylate To a solution of (R)-tert-butyl 3-((2-azidoethoxy)(3-chloro-2-fluorophenyl)methyl)-piperidine-1-carboxylate (2.6 g, 6.31 mmol) in EtOAc (50 mL) was added wetted Pd/C (0.1 g) and the mixture was stirred overnight under a hydrogen atmosphere maintained by a balloon. The reaction mixture was filtered through a pad of Celite and the solvent was removed to give (R)-tert-butyl 3-((2-aminoethoxy)(3-chloro-2-fluorophenyl)methyl)piperidine-1-carboxylate which was submitted to reverse phase the preparative HPLC to give (R)-tert-butyl 3-((S)-(2-aminoethoxy)(3-chloro-2-fluorophenyl)methyl)piperidine-1-carboxylate (990 mg, 81%) and (R)-tert-butyl 3-((R)-(2-aminoethoxy)(3-chloro-2-fluorophenyl)methyl)piperidine-1-carboxylate (792 mg, 65%). MS (E/Z): 387 (M+H$^+$).

Preparation 9

(R)-tert-butyl 3-((R)-(3-fluorophenyl)(2(methoxycarbonylamino)ethoxy)-methyl)piperidine-1-carboxylate

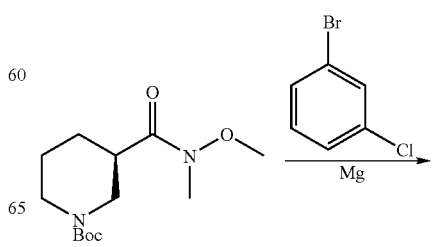

-continued

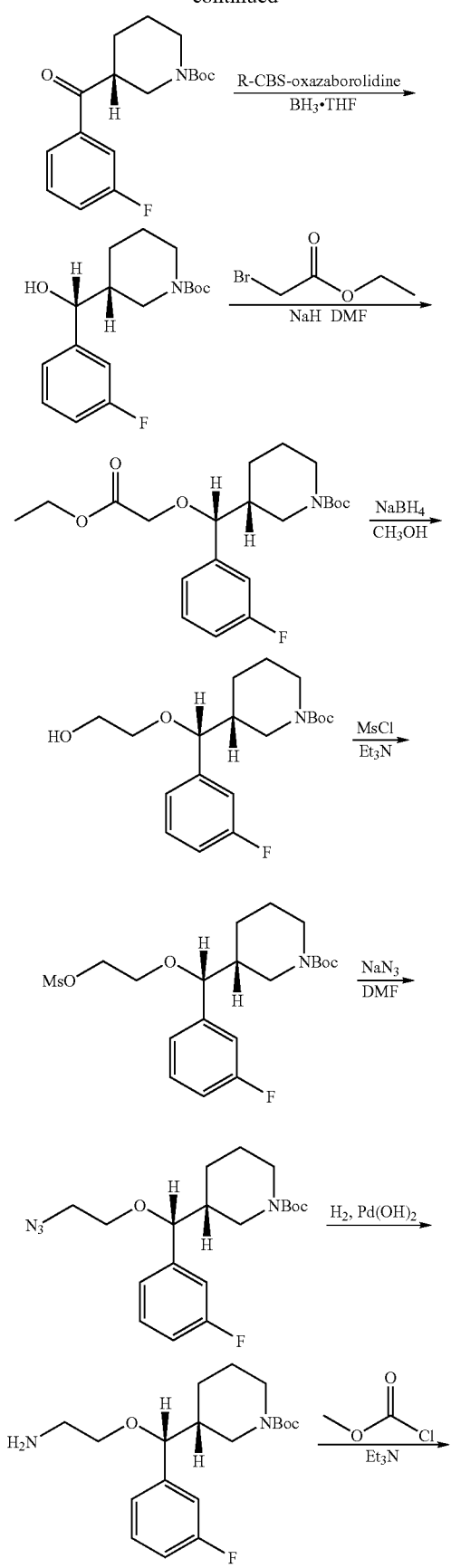

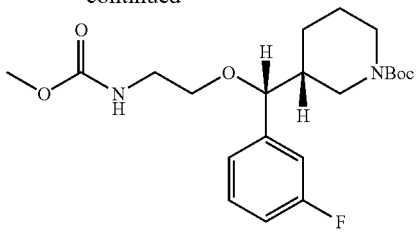

Step 1. (R)-tert-butyl 3-(3-fluorobenzoyl)piperidine-1-carboxylate

A solution of 1-bromo-3-fluoro-benzene (57.7 g, 0.33 mol) in anhydrous THF (480 mL) was added dropwise to Mg (10.6 g, 0.44 mol) at rt under nitrogen. The mixture was stirred at 50-60° C. for 1 hr. The resulting Grignard reagent was used for the next step. The Grignard reagent was added dropwise to a solution of (R)-tert-butyl 3-(methoxy(methyl)carbamoyl)piperidine-1-carboxylate (60 g, 0.22 mol) in anhydrous THF (600 mL) at −78° C. under nitrogen. After addition, the mixture was allowed to stir at rt for 1.5 hr. The mixture was quenched with saturated $NH_4Cl$ solution (300 mL) and extracted with ethyl acetate (3×200 mL). The combined organic layers were washed with brine, dried over $Na_2SO_4$ and concentrated in vacuo to give crude (R)-tert-butyl 3-(3-fluorobenzoyl)piperidine-1-carboxylate (67.5 g, 100%), which was used immediately in the next step without purification.

Step 2. (R)-tert-butyl 3-((R)-(3-fluorophenyl)(hydroxy)methyl)piperidine-1-carboxylate To a solution of 1 M R-CBS-oxazaborolidine in toluene (33 mL, 33 mmol, 0.15 eq) and 10 M $BH_3$ in THF (22 mL, 0.22 mol, 1.0 eq) at −15° C. under nitrogen was added dropwise a solution of (R)-tert-butyl 3-(3-fluorobenzoyl)piperidine-1-carboxylate (67.5 g, 0.22 mol) in anhydrous THF (300 mL). After addition, the reaction mixture was stirred for 1 hr at rt. Methanol (200 mL) was added dropwise carefully at 0° C. The solvent was removed under reduced pressure to provide the crude product. The crude product was dissolved in ethyl acetate until the alcohol was just dissolved (about 5 mL/1 g), the solvent was removed on the rotary evaporator until a few crystals appeared. To the above solution was added petroleum ether (about 300 mL) under stirring, which was allowed to stir at rt for 2 hr and then filtered, the crystals were washed with petroleum ether and re-crystallized to afford the pure R)-tert-butyl 3-((R)-(3-fluorophenyl)(hydroxy)methyl)piperidine-1-carboxylate (26 g, 39%).

Step 3. (R)-tert-butyl 3-((R)-(2-ethoxy-2-oxoethoxy)(3-fluorophenyl)methyl)piperidine-1-carboxylate To a suspension of NaH (4.8 g, 120 mmol) in THF (400 mL) at 0-5° C. was added dropwise a solution of (R)-tert-butyl 3-((R)-(2-ethoxy-2-oxoethoxy)(3-fluorophenyl)methyl)piperidine-1-carboxylate (30.9 g, 100 mmol) in anhydrous THF (100 mL), the reaction mixture was stirred for 1 hr at rt. A solution of ethyl bromoacetate (20.04 g, 13.40 mL, 120 mmol) in anhydrous THF (100 mL) was added dropwise to the above mixture, and the reaction was heated to reflux for 3-5 hr. The reaction mixture was poured into saturated aqueous $NH_4Cl$, then extracted with ethyl acetate (3×100 mL). The organic layer was washed with water (3×100 mL) and brine, dried over Na₂SO₄, filtered and concentrated in vacuo to afford crude (R)-tert-butyl 3-((R)-(2-ethoxy-2-oxoethoxy)(3-fluorophenyl)methyl)piperidine-1-carboxylate (29.88 g, 76%), which was used for next step without purification.

Step 4. (R)-tert-butyl 3-((R)-(3-fluorophenyl)(2-hydroxyethoxy)methyl)piperidine-1-carboxylate To a solution of (R)-tert-butyl 3-((R)-(2-ethoxy-2-oxoethoxy)(3-fluorophenyl)methyl)piperidine-1-carboxylate (29.88 g, 75.9 mmol) in MeOH (300 mL) was added NaBH₄ (23 g, 605.2 mmol) in portions while the temperature was lower than 40° C. After addition, the mixture was stirred at rt for 2-3 hr. The solvent was removed in vacuo to give a residue which was partitioned between water and ethyl acetate. The organic layer was washed with H₂O and brine, dried over Na₂SO₄, filtered and concentrated in vacuo. The residue was purified on silica gel chromatography to afford (R)-tert-butyl 3-((R)-(3-fluorophenyl)(2-hydroxyethoxy)methyl)piperidine-1-carboxylate (11 g, 41%).

Step 5. (R)-tert-butyl 3-((R)-(3-fluorophenyl)(2-(methylsulfonyloxy)ethoxy)methyl)piperidine-1-carboxylate To a solution of (R)-tert-butyl 3-((R)-(3-fluorophenyl)(2-hydroxyethoxy)methyl)piperidine-1-carboxylate (11 g, 31.16 mmol) in dry CH₂Cl₂ (140 mL) was added Et₃N (12.60 g, 16.68 mL, 124.65 mmol, 4 eq) at −5-0° C. Then a solution of MsCl (7.1 g, 4.72 mL, 62.32 mmol, 2 eq) in dry CH₂Cl₂ (40 mL) was added dropwise at the same temperature. After addition, it was allowed to warm to rt gradually. Water (100 mL) was added. The aqueous layer was extracted with CH₂Cl₂ (3×80 mL), the combined organic layers was washed with 10% citric acid, sat. NaHCO₃ and brine, then dried over Na₂SO₄, filtered and concentrated to give (R)-tert-butyl 3-((R)-(3-fluorophenyl)(2-(methylsulfonyloxy)ethoxy)methyl)piperidine-1-carboxylate (13.8 g), which was used in the next step without purification.

Step 6. (R)-tert-butyl 3-((R)-(2-azidoethoxy)(3-fluorophenyl)methyl)piperidine-1-carboxylate (R)-tert-Butyl 3-((R)-(3-fluorophenyl)(2-(methylsulfonyloxy)ethoxy)methyl)piperidine-1-carboxylate (13.8 g, 32 mmol) was dissolved into anhydrous DMF (150 mL), solid NaN₃ (6.1 g, 96 mmol, 3 eq) was added and the reaction mixture was heated to 80° for overnight. The reaction mixture was cooled to rt and then was added with ethyl acetate (500 mL), the organic phase was washed with water (3×100 mL) and brine (2×80 mL), dried over Na₂SO₄ and concentrated in vacuo to give crude (R)-tert-butyl 3-((R)-(2-azidoethoxy)(3-fluorophenyl)methyl)piperidine-1-carboxylate (12 g), which was used in the next step without further purification.

Step 7. (R)-tert-butyl 3-((R)-(2-aminoethoxy)(3-fluorophenyl)methyl)piperidine-1-carboxylate A suspension of (R)-tert-butyl 3-((R)-(2-azidoethoxy)(3-fluorophenyl)methyl)piperidine-1-carboxylate (12 g, 31.75 mmol) and Pd(OH)₂/C (1.2 g) in MeOH (240 ml) was stirred under H₂ for 1 hr. The mixture was filtered and evaporated under reduced pressure to give desired (R)-tert-butyl 3-((R)-(2-aminoethoxy)(3-fluorophenyl)methyl)piperidine-1-carboxylate (10 g).

Step 8. (R)-tert-butyl 3-((R)-(3-fluorophenyl)(2-(methoxycarbonylamino)ethoxy)methyl)piperidine-1-carboxylate To a solution of (R)-tert-butyl 3-((R)-(2-aminoethoxy)(3-fluorophenyl)methyl)piperidine-1-carboxylate (10 g, 28.41 mmol) and DMAP (1.8 g, 14.21 mmol, 0.5 eq) in dry CH₂Cl₂ (150 mL), Et₃N (8.62 g, 11.42 mL, 85.23 mmol) was added. The resulting mixture was cooled to 0-5° C. under ice-water bath, a solution of methyl chloroformate (10.95 mL, 142.05 mmol, 5 eq) in dry CH₂Cl₂ (60 mL) was added dropwise. After addition, the reaction mixture was stirred for 1-2 hr at 0-5° C. Water (80 mL) was added to quench the reaction. The aqueous layer was extracted with CH₂Cl₂ (3×50 mL), the combined organic layers were washed with 10% citric acid (2×80 mL) and brine, then dried over Na₂SO₄, filtered and concentrated to the crude product, which was purified by silica gel to afford (R)-tert-butyl 3-((R)-(3-fluorophenyl)(2-(methoxycarbonylamino)ethoxy)methyl)piperidine-1-carboxylate (11.3 g, 97%).

The following compounds were prepared following procedures analogous to those described above:
1) (R)-tert-butyl 3-((R)-(2,5-difluorophenyl)(2-(methoxycarbonylamino)ethoxy)methyl)piperidine-1-carboxylate using (2,5-difluorophenyl)magnesium bromide in Step 1.
2) (R)-tert-butyl 3-((R)-(3,4-difluorophenyl)(2-(methoxycarbonylamino)ethoxy)methyl)piperidine-1-carboxylate using (3,4-difluorophenyl)magnesium bromide in Step 1.
3) (R)-tert-butyl 3-((R)-(3-chloro-2-fluorophenyl)(2-(methoxycarbonylamino)ethoxy)methyl)piperidine-1-carboxylate using (3-chloro-2-fluorophenyl)lithium in Step 1.
4) (R)-tert-butyl 3-((R)-(5-chloro-2-fluorophenyl)(2-(methoxycarbonylamino)ethoxy)methyl)piperidine-1-carboxylate using (5-chloro-2-fluorophenyl)lithium in Step 1.
5) (R)-tert-butyl 3-((R)-(2-fluoro-5-methylphenyl)(2-(methoxycarbonylamino)ethoxy)methyl)piperidine-1-carboxylate using (2-fluoro-5-methylphenyl)magnesium bromide in Step 1.
6) (R)-tert-butyl 3-((R)-(2-(methoxycarbonylamino)ethoxy)(3,4,5-trifluorophenyl)methyl)piperidine-1-carboxylate using (3,4,5-trifluorophenyl)magnesium bromide in Step 1.
7) (R)-tert-butyl 3-((R)-(2-(methoxycarbonylamino)ethoxy)(thiophen-2-yl)methyl)piperidine-1-carboxylate using thiophen-2-ylmagnesium bromide in Step 1.
8) (R)-tert-butyl 3-((R)-(2-(methoxycarbonylamino)ethoxy)(thiazol-2-yl)methyl)piperidine-1-carboxylate using thiazol-2-yllithium in Step 1.
9) (3R)-tert-butyl 3-((2-(methoxycarbonylamino)ethoxy)(4-methylthiazol-2-yl)methyl)piperidine-1-carboxylate using (4-methylthiazol-2-yl)lithium in Step 1.

Preparation 10

(R)-tert-butyl 3-((R)-(2,3-difluorophenyl)(2-(methoxycarbonylamino)ethyl)methyl)piperidine-1-carboxylate

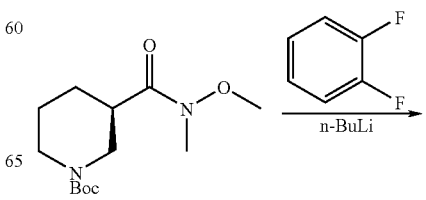

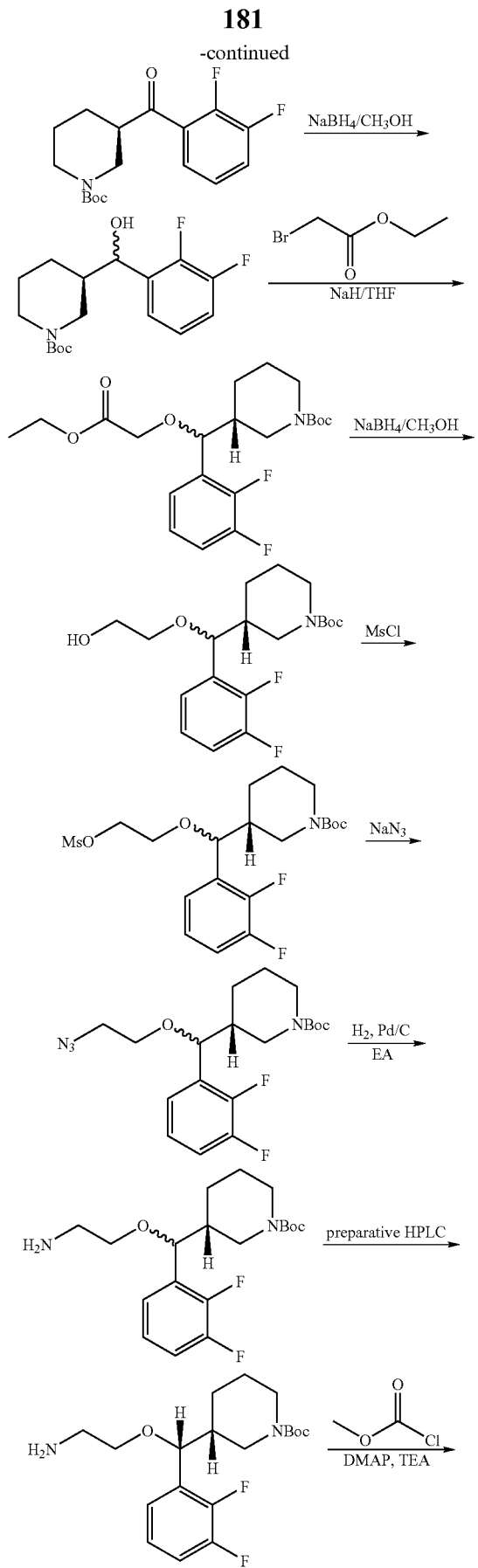

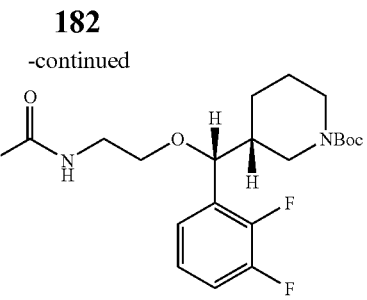

Step 1. (R)-tert-butyl 3-(2,3-difluorobenzoyl)piperidine-1-carboxylate

Under protection of $N_2$, 1,2-difluorobenzene (22 g, 0.19 mol) in anhydrous THF (300 mL) was cooled to −78° C. and 2.5 M n-BuLi solution in hexanes (76 mL, 0.19 mol) was added dropwise slowly. The reaction mixture was stirred at −78° C. for 1 hr, the solution of (R)-tert-butyl 3-(methoxy (methyl)carbamoyl)piperidine-1-carboxylate (47.7 g, 0.175 mol) in anhydrous THF (200 mL) was slowly added dropwise. The reaction mixture warmed to rt and stirred for 2 hrs. The mixture was quenched with saturated $NH_4Cl$ (300 mL), extracted three times with ethyl acetate, and dried over $Na_2SO_4$. Solvent removal and flash column chromatography afforded crude (R)-tert-butyl 3-(2,3-difluorobenzoyl)piperidine-1-carboxylate (R)-tert-butyl 3-(2,3-difluorobenzoyl)piperidine-1-carboxylate (40 g, 70%). $^1$H NMR ($CDCl_3$, 400 MHz) δ 7.51 (m, 1H), 7.34 (m, 1H), 7.19 (m, 1H), 4.19 (d, 1H), 3.96 (m, 1H), 3.23 (m, 1H), 3.04 (t, 1H), 2.85 (m, 1H), 2.06 (m, 1H), 1.75 (m, 1H), 1.62 (m, 4H), 1.44 (s, 9H).

Step 2. (3R)-tert-butyl 3-((2,3-difluorophenyl)(hydroxy)methyl)piperidine-1-carboxylate To a solution of (R)-tert-butyl 3-(2,3-difluorobenzoyl)piperidine-1-carboxylate (10 g, 30.8 mmol) in MeOH (200 mL) was added $NaBH_4$ (9.3 g, 246 mmol) in portions while the temperature was lower than 40° C. After addition, the mixture was stirred at rt for 2-3 hrs. The solvent was removed in vacuo to afford a residue which was partitioned between water and ethyl acetate. The organic layer was washed with water and brine, dried over $Na_2SO_4$ and evaporated to give the crude product (R)-tert-butyl 3-((2,3-difluorophenyl)(hydroxy)methyl)piperidine-1-carboxylate (10 g, 99%), which was used in the next step without purification. $^1$H NMR ($CDCl_3$, 400 MHz) δ 7.22 (m, 1H), 7.08 (m, 2H), 4.85 (t, 1H), 3.94 (d, 0.5H), 3.78 (d, 1H), 3.55 (m, 0.5H), 3.28 (d, 1H), 2.65 (m, 1H), 1.90 (m, 2H), 1.68 (m, 3H), 1.44 (d, 9H).

Step 3. (3R)-tert-butyl 3-((2,3-difluorophenyl)(2-ethoxy-2-oxoethoxy)methyl)piperidine-1-carboxylate To a suspension of NaH (3.5 g, 88.4 mmol) in THF (100 mL) at 0-5° C. was added dropwise a solution of (R)-tert-butyl 3-((2,3-difluorophenyl)(hydroxy)methyl)piperidine-1-carboxylate (9.6 g, 29.5 mmol) in THF (50 mL), the reaction mixture was stirred for 1 h at rt. A solution of ethyl bromoacetate (14.7 g, 88.4 mmol) in THF (50 mL) was added dropwise to the above mixture, and then refluxed for 3-5 h. The reaction mixture was poured into saturated aqueous $NH_4Cl$, then extracted with ethyl acetate, dried over $Na_2SO_4$, filtered and concentrated in vacuo. The residue was purified on silica gel chromatography to afford (3R)-tert-butyl 3-((2,3-difluorophenyl)(2-ethoxy-2-oxoethoxy)methyl)piperidine-1-carboxylate (9.5 g, 79%). $^1$H NMR ($CDCl_3$, 400 MHz) δ 7.22

(m, 1H), 7.08 (m, 2H), 4.62 (d, 2H), 4.33 (d, 2H), 4.18 (q, 3H), 3.95 (m, 4H), 3.82 (d, 2H), 2.77 (m, 4H), 1.88 (m, 3H), 1.44 (s, 9H), 1.26 (t, 3H).

Step 4. (3R)-tert-butyl 3-((2,3-difluorophenyl)(2-hydroxyethoxy)methyl)piperidine-1-carboxylate To a solution of (3R)-tert-butyl 3-((2,3-difluorophenyl)(2-ethoxy-2-oxoethoxy)methyl)piperidine-1-carboxylate (4 g, 9.7 mmol) in MeOH (80 mL) was added NaBH$_4$ (2.9 g, 77.4 mmol) in portions while the temperature was lower than 40° C. After addition, the mixture was stirred at rt for 2-3 hrs. The solvent was removed in vacuo to give a residue, which was partitioned between water and ethyl acetate. The organic layer was washed with water and brine, dried over Na$_2$SO$_4$ and evaporated to give (3R)-tert-butyl 3-((2,3-difluorophenyl)(2-hydroxyethoxy)methyl)piperidine-1-carboxylate (3.5 g, 97%). $^1$H NMR (CDCl$_3$, 400 MHz) δ 7.12 (m, 3H), 4.52 (q, 1H), 4.11 (m, 1H), 3.69 (m, 3H), 3.41 (m, 3H), 2.65 (m, 1H), 2.02 (m, 1H), 1.65 (m, 1H), 1.42 (d, 9H).

Step 5. (3R)-tert-butyl 3-((2,3-difluorophenyl)(2-(methylsulfonyloxy)ethoxy)methyl)piperidine-1-carboxylate To a solution of (3R)-tert-butyl 3-((2,3-difluorophenyl)(2-hydroxyethoxy)methyl)piperidine-1-carboxylate in dry CH$_2$Cl$_2$ (50 mL) was added Et$_3$N (5.2 mL, 37.6 mmol) at −5-0° C. Then a solution of MsCl (1.3 g, 11.3 mmol) in dry CH$_2$Cl$_2$ (20 mL) was added dropwise at the same temperature. After addition, the reaction was allowed to gradually warm to rt. Upon completion of the reaction, 50 mL of water was added, the aqueous layer was extracted with CH$_2$Cl$_2$, the combined organic layers were washed with 10% citric acid, sat. NaHCO$_3$ and brine, then dried over Na$_2$SO$_4$, filtered and concentrated to give (3R)-tert-butyl 3-((2,3-difluorophenyl)(2-(methylsulfonyloxy)ethoxy)methyl)piperidine-1-carboxylate (4.2 g, 99%), which was used in the next step without purification. $^1$H NMR (CDCl$_3$, 400 MHz) δ 7.12 (m, 3H), 4.52 (q, 1H), 4.31 (m, 3H), 4.09 (t, 1H), 3.57 (m, 2H), 3.06 (d, 3H), 2.70 (m, 2H), 1.93 (m, 2H), 1.44 (d, 9H).

Step 6. (3R)-tert-butyl 3-((2-azidoethoxy)(2,3-difluorophenyl)methyl)piperidine-1-carboxylate A solution of (3R)-tert-butyl 3-((2,3-difluorophenyl)(2-(methylsulfonyloxy)ethoxy)methyl)piperidine-1-carboxylate (4.2 g, 9.4 mmol) and solid NaN$_3$ (0.92 g, 14.1 mmol) in anhydrous DMF (30 mL) was heated to 80° C. overnight. The reaction mixture was cooled to rt and diluted with ethyl acetate (80 mL), the organic phase was washed with water (30 mL×3), dried over Na$_2$SO$_4$ and evaporated. The residue was separated on a silica column to give (3R)-tert-butyl 3-((2-azidoethoxy)(2,3-difluorophenyl)methyl)piperidine-1-carboxylate (3.4 g, 92%). $^1$H NMR (CDCl$_3$, 400 MHz) δ 7.14 (m, 3H), 4.50 (q, 1H), 4.10 (m, 1H), 3.40 (m, 4H), 2.70 (m, 2H), 1.90 (m, 2H), 1.65 (m, 1H), 1.41 (d, 9H).

Step 7. (R)-tert-butyl 3-((R)-(2-aminoethoxy)(2,3-difluorophenyl)methyl)piperidine-1-carboxylate To a solution of (3R)-tert-butyl 3-((2-azidoethoxy)(2,3-difluorophenyl)methyl)piperidine-1-carboxylate (3.4 g, 8.58 mmol) in ethyl acetate (50 mL) was added wet Pd/C (0.1 g). Under a hydrogen filled balloon the reaction was allowed to stir overnight. The reaction mixture was filtered through a pad of Celite and the solvent was removed. The residue was isolated by the preparative HPLC to give (R)-tert-butyl 3-((R)-(2-aminoethoxy)(2,3-difluorophenyl)methyl)piperidine-1-carboxylate (3 g, 94%). $^1$H NMR (CDCl$_3$, 400 MHz) δ 7.22 (m, 3H), 4.48 (d, 1H), 4.01 (d, 1H), 3.65 (m, 1H), 3.42 (m, 2H), 3.08 (m, 4H), 1.88 (m, 1H), 1.55 (m, 1H), 1.43 (s, 9H).

Step 8. (R)-tert-butyl 3-((R)-(2,3-difluorophenyl)(2-(methoxycarbonylamino)ethoxy)methyl)piperidine-1-carboxylate To a solution of (R)-tert-butyl 3-((R)-(2-aminoethoxy)(2,3-difluorophenyl)methyl)piperidine-1-carboxylate (195 mg, 0.402 mmol), DMAP (25.8 mg, 0.201 mmol) and Et$_3$N (0.18 mL) in dry CH$_2$Cl$_2$ at 0° C. was added methyl chloroformate (189 mg, 2.013 mmol), the mixture was allowed to warm to rt and stirred overnight. The mixture was concentrated in vacuo to give the crude product (R)-tert-butyl 3-((R)-(2,3-difluorophenyl)(2-(methoxycarbonylamino)ethoxy)methyl)piperidine-1-carboxylate (168 mg, 98%), which was used in the next step without further purification. $^1$H NMR (CDCl$_3$, 400 MHz) δ 7.21 (m, 3H), 4.57 (m, 1H), 4.44 (d, 1H), 4.08 (m, 1H), 3.82 (m, 1H), 3.53 (s, 3H), 3.29 (d, 2H), 2.93 (m, 2H), 1.79 (m, 1H), 1.63 (m, 1H), 1.43 (s, 9H), 1.34 (m, 3H).

Preparation 11

(R)-tert-butyl 3-((R)-(3-chlorophenyl)(2-(methoxycarbonylamino)ethoxy)methyl)-piperidine-1-carboxylate

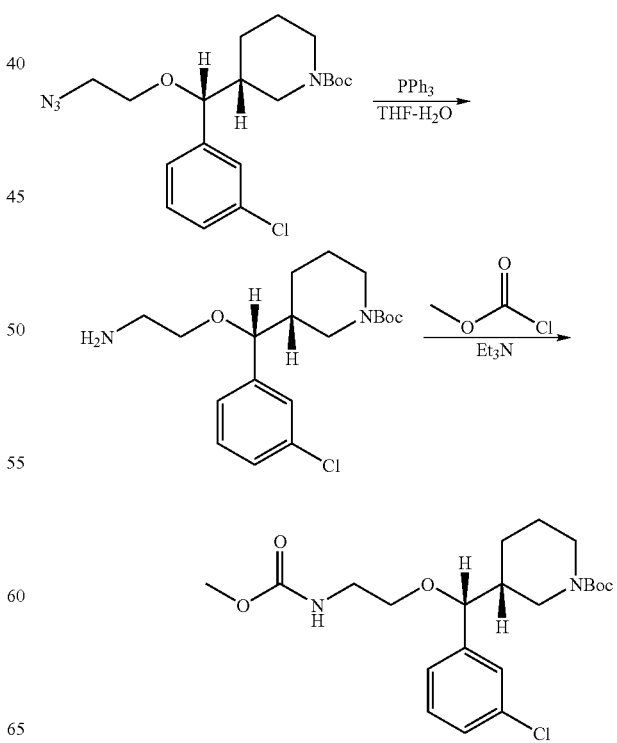

Step 1-6. (R)-tert-Butyl 3-((R)-(2-azidoethoxy)(3-chlorophenyl)methyl)piperidine-1-carboxylate (R)-tert-Butyl 3-((R)-(2-azidoethoxy)(3-chlorophenyl) methyl)piperidine-1-carboxylate was obtained following Preparation 9, Steps 1-6, using (3-chlorophenyl)lithium in Step 1.

Step 7. (R)-tert-butyl 3-((R)-(3-chlorophenyl)(2-(methoxycarbonylamino)ethoxy)methyl)piperidine-1-carboxylate To a solution of (R)-tert-Butyl 3-((R)-(2-azidoethoxy)(3-chlorophenyl)methyl)piperidine-1-carboxylate (13.3 g, 33.8 mmol) in THF/H$_2$O (20:1, 180 mL/9 mL), triphenylphosphane (36.0 g, 135 mmol) was added in portions. The reaction mixture was stirred overnight at rt. The solvent was removed under reduced pressure to afford a residue, which was purified on silica gel chromatography to provide (R)-tert-butyl 3-((R)-(2-aminoethoxy)(3-chlorophenyl)methyl)piperidine-1-carboxylate (10.4 g, purity: HPLC=75%).

Step 8. (R)-tert-butyl 3-((R)-(3-chlorophenyl)(2-(methoxycarbonylamino)ethoxy)methyl)piperidine-1-carboxylate (R)-tert-butyl 3-((R)-(2-aminoethoxy)(3-chlorophenyl) methyl)piperidine-1-carboxylate was converted to (R)-tert-butyl 3-((R)-(3-chlorophenyl)(2-(methoxycarbonylamino) ethoxy)methyl)piperidine-1-carboxylate following Preparation 9, Step 8.

The following compounds were prepared following procedures analogous to those described above:
1) (R)-tert-butyl 3-((R)-(3,5-difluorophenyl)(2-(methoxycarbonylamino)ethoxy)methyl)piperidine-1-carboxylate using (3,5-difluorophenyl)lithium in Preparation 9, Step 1.

Preparation 12

(R)-tert-butyl 3-((R)-(5-chloro-2-methylphenyl)(2-(methoxycarbonylamino)ethoxy)methyl)piperidine-1-carboxylate

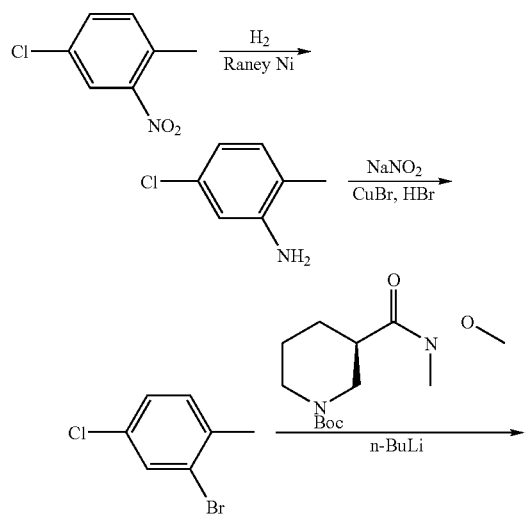

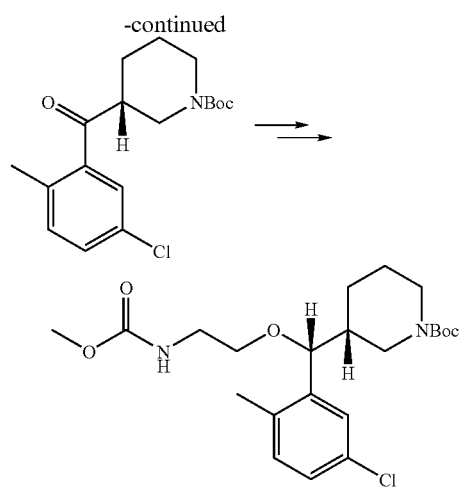

Step 1. 5-chloro-2-methylbenzenamine

A 2 L flask was charged the solution of 4-chloro-1-methyl-2-nitrobenzene (60 g, 0.35 mol) in MeOH (1 L), Raney Ni was added, the air in flask was replaced three times with H$_2$, the mixture was stirred for 3 h at rt. The solution was filtered and concentrated. The residue was dissolved in CH$_2$Cl$_2$ (500 mL), and the solution was washed with brine, dried over Na$_2$SO$_4$. Solvent removal gave 5-chloro-2-methylbenzenamine (50 g, 0.35 mol). $^1$H NMR (CDCl$_3$, 400 MHz) δ 7.02-6.93 (d, 2H), 6.70-6.60 (d, 2H), 3.67 (s, 2H), 2.14 (s, 3H).

Step 2. 2-bromo-4-chloro-1-methylbenzene

5-Chloro-2-methylbenzenamine (50 g, 0.355 mol) was dissolved in HBr solution (1.5 M, 100 mL) and cooled to 0° C., a solution of NaNO$_2$ (27.6 g, 0.4 mol) in water (200 mL) was added dropwise. After addition, the mixture was stirred for 1 hr. In another flask CuBr (30 g, 0.21 mol) was added to HBr solution (1.5 M, 30 mL) and heated to 60° C., then the mixture was added to the above solution. The mixture was heated to reflux for 1 hr then cooled to rt. The reaction was quenched with water (500 mL), the aqueous layer was extracted 3 times with CH$_2$Cl$_2$, dried over Na$_2$SO$_4$, solvent removal and purification by column chromatography afforded 2-bromo-4-chloro-1-methylbenzene (53 g, 0.26 mol). $^1$H NMR (CDCl$_3$, 400 MHz) δ 7.53 (s, 1H), 7.20-7.10 (m, 2H), 2.36 (s, 3H).

Step 3. (R)-tert-butyl 3-(5-chloro-2-methylbenzoyl) piperidine-1-carboxylate To a solution of 2-bromo-4-chloro-1-methylbenzene (53 g, 0.26 mol) in anhydrous THF (600 mL) at −78° C. under nitrogen was added dropwise a solution of 2.5 M n-BuLi in hexane (103 mL, 0.26 mol). After stirring for 1 hr at −78° C., a solution of the (R)-tert-butyl 3-(methoxy(methyl)carbamoyl)piperidine-1-carboxylate (67 g, 0.246 mol) in anhydrous THF (300 mL) was added dropwise. After addition, the reaction mixture was allowed to warm to rt and stirred for 2 hr. The mixture was quenched with saturated NH$_4$Cl solution (500 mL) and extracted with ethyl acetate (3×400 mL). The combined organic layers were washed with brine, dried over Na$_2$SO$_4$ and concentrated in vacuo to give crude (R)-tertbutyl 3-(5-chloro-2-methylbenzoyl)piperidine-1-carboxylate (86 g), which was used immediately in the next step without purification.

Step 4-10. (R)-tert-butyl 3-((R)-(5-chloro-2-methylphenyl)(2-(methoxycarbonylamino)ethoxy)methyl)piperidine-1-carboxylate (R)-tert-butyl 3-(5-chloro-2-methylbenzoyl)piperidine-1-carboxylate was carried thru Preparation 9, Steps 2-8, to afford (R)-tert-butyl 3-((R)-(5-chloro-2-methylphenyl)(2-(methoxycarbonylamino)ethoxy)methyl)piperidine-1-carboxylate.

Preparation 13

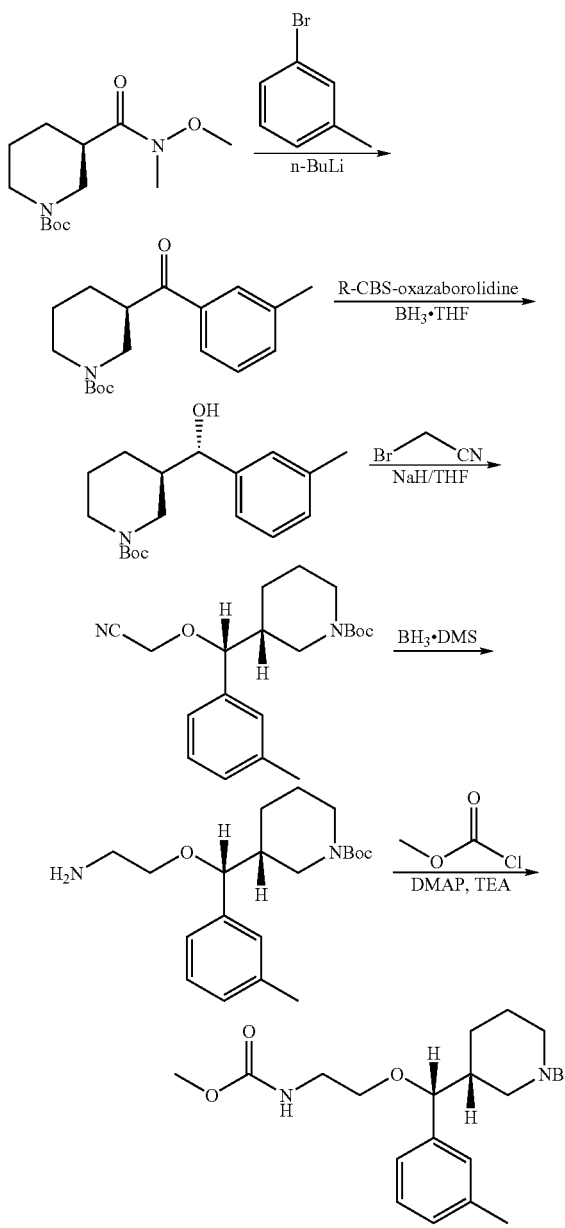

Step 1. (R)-tert-butyl 3-(3-methylbenzoyl)piperidine-1-carboxylate

To a solution of 1-bromo-3-methylbenzene (88.4 g, 0.52 mol) in anhydrous THF (550 mL) at −78° C. under nitrogen was added dropwise a solution of 2.5 M n-BuLi in hexane (210 mL, 0.52 mol). After stirring for 1 hr at −78° C., a solution of (R)-tert-butyl 3-((R)-(2-(methoxycarbonylamino)ethoxy)(m-tolyl)methyl)piperidine-1-carboxylate (120 g, 0.44 mol) in anhydrous THF (500 mL) was added dropwise. After addition, the reaction mixture was allowed to warm to rt and stirred for 2 hr. The mixture was quenched with saturated $NH_4Cl$ solution (500 mL) and extracted with ethyl acetate (3×400 mL). The combined organic layers were washed with brine, dried over $Na_2SO_4$ and concentrated in vacuo to give crude (R)-tert-butyl 3-(3-methylbenzoyl)piperidine-1-carboxylate (168 g), which was used immediately for next step without purification.

Step 2. (R)-tert-butyl 3-((S)-hydroxy(m-tolyl)methyl)piperidine-1-carboxylate To a solution of (R)-tert-butyl 3-(3-methylbenzoyl)piperidine-1-carboxylate (168 g, 0.55 mol) in anhydrous THF (600 mL) at −15° C. under nitrogen was added dropwise a solution of 1 M R-CBS-oxazaborolidine in toluene (82 mL, 82 mmol, 0.15 eq). After stirring for 1 hr at −15° C., a solution of 10 M $BH_3$ in THF (60 mL, 0.60 mol, 1.1 eq) was added dropwise. After addition, the reaction mixture was stirred for 2 hr at −15° C. TLC indicated the starting material was disappeared. Methanol (400 mL) was added dropwise carefully at −15° C. The solvent was removed under reduced pressure, the residue was purified by column chromatography on silica gel eluting with AcOEt/hexane (1:30→1:15) to provide the light yellow oil (95 g, HPLC≧70%, ratio≧3:1). The mixture was dissolved in ethyl acetate until the alcohol was just dissolved (about 5 mL/1 g), the solvent was removed on the rotary evaporator until a few crystals appeared. The solution was cooled to rt slowly and stood for 1-2 hr. To the above solution was added hexane (about 300 mL) and then filtered, the crystals were washed with cool hexane and re-crystallized two more times to afford the pure isomer (R)-tert-butyl 3-((S)-hydroxy(m-tolyl)methyl)piperidine-1-carboxylate (20 g, ee≧99%).

Step 3. (R)-tert-butyl 3-((R)-(cyanomethoxy)(m-tolyl)methyl)piperidine-1-carboxylate To a solution of (R)-tert-butyl 3-((S)-hydroxy(m-tolyl)methyl)piperidine-1-carboxylate (30.5 g, 0.1 mol) in MeCN (300 mL), NaH (12 g, 0.3 mol) was added at 0° C. The mixture was stirred for 1 hr at rt. The mixture was cooled to −40° C., then bromoacetonitrile (35.7 g, 0.3 mol) was added in portions. The mixture was stirred for 0.5 hr at −20° C. continually. The reaction was quenched with sat. $NH_4Cl$. The mixture was extracted with $CH_2Cl_2$. The organic layer was dried over $Na_2SO_4$, concentrated. Crude (R)-tert-butyl 3-((R)-(cyanomethoxy)(m-tolyl)methyl)piperidine-1-carboxylate was used for the next step without purification.

Step 4. (R)-tert-butyl 3-((R)-(2-aminoethoxy)(m-tolyl)methyl)piperidine-1-carboxylate (R)-tert-Butyl 3-((R)-(cyanomethoxy)(m-tolyl)methyl)piperidine-1-carboxylate (20 g, 0.04 mol) was dissolved in anhydrous THF (300 mL), and the solution was heated to reflux under nitrogen. A solution of $BH_3 \cdot Me_2S$ (12 mL, 0.12 mol) in THF was added dropwise, and stirring was continued under reflux overnight. The resulting solution was cooled to rt and MeOH was added dropwise to quench the excess borane. After evaporation of the solution, the crude (R)-tert-butyl 3-((R)-(2-aminoethoxy)(m-tolyl)methyl)piperidine-1-carboxylate was obtained and used without further purification.

Step 5. (R)-tert-butyl 3-((R)-(2-(methoxycarbonylamino)ethoxy)(m-tolyl)methyl)piperidine-1-carboxylate To a solution of (R)-tert-butyl 3-((R)-(2-aminoethoxy)(m-tolyl)methyl)piperidine-1-carboxylate and DMAP in anhydrous CH$_2$Cl$_2$, Et$_3$N was added. The resulting mixture was cooled to 0-5° C. under ice-water bath, a solution of methyl chloroformate in anhydrous CH$_2$Cl$_2$ was added dropwise. After addition, the reaction mixture was stirred for 1-2 hr at 0-5° C. Water was added to quench the reaction. The aqueous layer was extracted with CH$_2$Cl$_2$, the combined organic layers were washed with 10% citric acid and brine, then dried over Na$_2$SO$_4$, filtered and concentrated to the crude product, which was purified by preparative TLC to afford (R)-tert-butyl 3-((R)-(2-(methoxycarbonylamino)ethoxy)(m-tolyl)methyl)piperidine-1-carboxylate.

The following compounds were prepared following procedures analogous to those described above:
1) (R)-tert-butyl 3-((R)-(2-(methoxycarbonylamino)ethoxy)(3-(trifluoromethyl)phenyl)methyl)piperidine-1-carboxylate using (3-(trifluoromethyl)phenyl)magnesium bromide in Step 1.
2) (R)-tert-butyl 3-((R)-(2,5-dimethylphenyl)(2-(methoxycarbonylamino)ethoxy)methyl)piperidine-1-carboxylate using (2,5-dimethylphenyl)magnesium bromide in Step 1.
3) (R)-tert-butyl 3-((R)-(3,5-dimethylphenyl)(2-(methoxycarbonylamino)ethoxy)methyl)piperidine-1-carboxylate using (3,5-dimethylphenyl)magnesium bromide in Step 1.
4) (R)-tert-butyl 3-((R)-(5-fluoro-2-methylphenyl)(2-(methoxycarbonylamino)ethoxy)methyl)piperidine-1-carboxylate using (5-fluoro-2-methylphenyl)lithium in Step 1.
5) (R)-tert-butyl 3-((R)-(3-chloro-4-fluorophenyl)(2-(methoxycarbonylamino)ethoxy)methyl)piperidine-1-carboxylate using (3-chloro-4-fluorophenyl)magnesium bromide in Step 1.
6) (R)-tert-butyl 3-((R)-(3-chloro-5-fluorophenyl)(2-(methoxycarbonylamino)ethoxy)methyl)piperidine-1-carboxylate using (3-chloro-5-fluorophenyl)magnesium bromide in Step 1.
7) (R)-tert-butyl 3-((R)-(3-chloro-2,4-difluorophenyl)(2-(methoxycarbonylamino)ethoxy)methyl)piperidine-1-carboxylate using (3-chloro-2,4-difluorophenyl)lithium in Step 1.

Preparation 14

(R)-tert-butyl 3-((R)-(2-(benzyloxy)-3,5-difluorophenyl)(2-(methoxycarbonylamino)ethoxy)methyl)piperidine-1-carboxylate

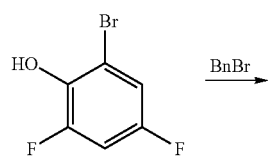

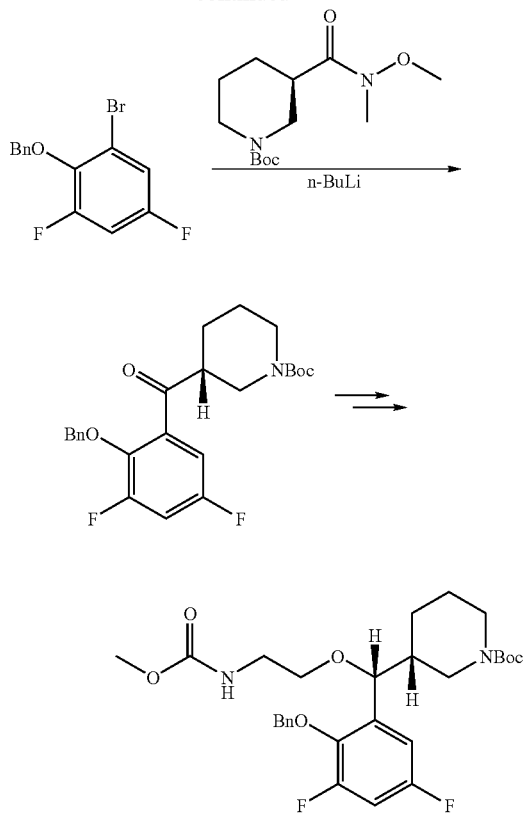

Step 1. 2-(benzyloxy)-1-bromo-3,5-difluorobenzene

2-Bromo-4,6-difluoro-phenol (10 g, 48 mmol), Bu$_4$NBr (0.24 g, 0.72 mol) and BnBr (8.22 g, 48 mmol) was mixed in THF (100 mL). 50% KOH (13.46 g, 240 mmol) was added to the mixture, heated to 64° C. and stirred for 2 h. Water was added to the mixture, the aqueous layer was extracted with EtOAc. The organic layer was washed with brine, dried over Na$_2$SO$_4$ and concentrated in vacuo to give the crude product 2-(benzyloxy)-1-bromo-3,5-difluorobenzene (13.7 g, 96%), which was used immediately without purification.

Step 2. (R)-tert-butyl 3-(2-(benzyloxy)-3,5-difluorobenzoyl)piperidine-1-carboxylate To a solution of 2-(benzyloxy)-1-bromo-3,5-difluorobenzene (13.7 g, 46 mmol) in anhydrous THF (100 mL) at −78° C. under nitrogen was added dropwise a solution of 2.5 M n-BuLi in hexane (18.4 mL, 46 mmol). After stirring for 1 hr at −78° C., a solution of (R)-tert-butyl 3-(methoxy(methyl)carbamoyl)piperidine-1-carboxylate (10.43 g, 38.3 mmol) in anhydrous THF (40 mL) was added dropwise. After addition, the reaction mixture was allowed to warm to rt and stirred for 2 h. The mixture was quenched with saturated NH$_4$Cl solution (100 mL) and extracted with ethyl acetate (3×50 mL). The combined organic layers were washed with brine, dried over Na$_2$SO$_4$ and concentrated in vacuo. The residue was purified by column chromatography on silica gel eluting with AcOEt/hexane (1:20→1:10) to provide (R)-tert-butyl 3-(2-

(benzyloxy)-3,5-difluorobenzoyl)piperidine-1-carboxylate (6.4 g, 32%) as a light yellow oil.

Step 3-6. (R)-tert-butyl 3-((R)-(2-(benzyloxy)-3,5-difluorophenyl)(2-(methoxycarbonylamino)ethoxy)methyl)piperidine-1-carboxylate (R)-tert-butyl 3-((R)-(2-(benzyloxy)-3,5-difluorophenyl)(2-(methoxycarbonylamino)ethoxy)methyl)piperidine-1-carboxylate was obtained analogously to Preparation 13, Steps 2-5.

Preparation 15

(R)-tert-butyl 3-((R)-(3-fluoro-5-methylphenyl)(2-(methoxycarbonylamino)ethoxy)methyl)piperidine-1-carboxylate

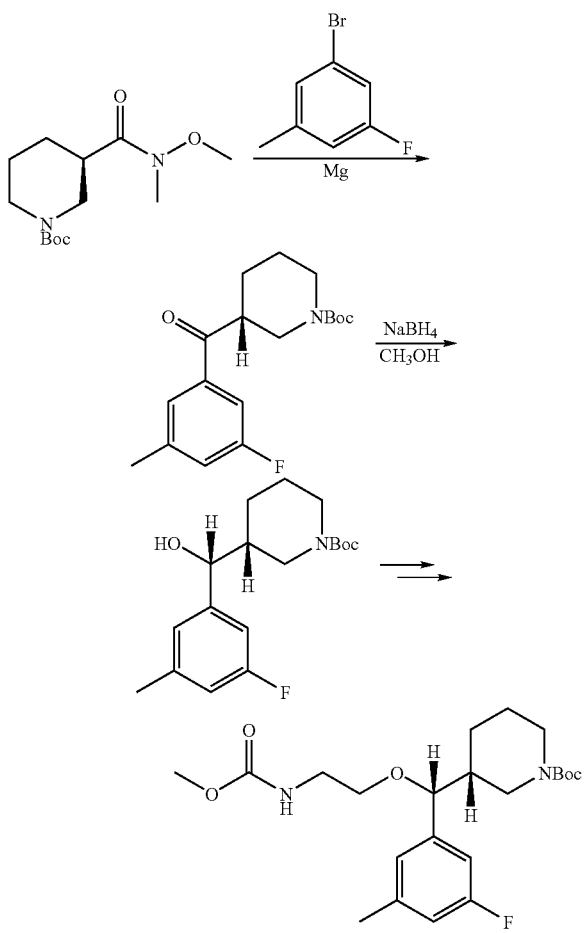

Step 1. (R)-tert-butyl 3-(3-fluoro-5-methylbenzoyl)piperidine-1-carboxylate

A 100 mL three-neck flask was charged with Mg (638 mg, 26.6 mmol), a small crystal of iodine. The flask was degassed and refilled into $N_2$. A solution of 1-bromo-3-fluoro-5-methyl-benzene (5 g, 26.6 mmol) in anhydrous THF was added. The reaction mixture was stirred and heated to reflux for 2 h. Once most of the Mg disappeared the reaction was cooled to −78° C. Then (R)-tert-butyl 3-(methoxy(methyl)carbamoyl) piperidine-1-carboxylate (1.45 g, 5.32 mmol) in anhydrous THF was added dropwise slowly, and the mixture was stirred overnight. The mixture was quenched with saturated $NH_4Cl$ solution (30 mL) and extracted with ethyl acetate (3×20 mL). The combined organic layers were washed with brine, dried over $Na_2SO_4$ and concentrated in vacuo to give the crude product (R)-tert-butyl 3-(3-fluoro-5-methylbenzoyl)piperidine-1-carboxylate (1.7 g, 99%), which was used immediately without further purification.

Step 2. (R)-tert-butyl 3-((R)-(3-fluoro-5-methylphenyl)(hydroxy)methyl)piperidine-1-carboxylate To a solution of (R)-tert-butyl 3-(3-fluoro-5-methylbenzoyl)piperidine-1-carboxylate (1.7 g, 5.3 mmol) in MeOH (30 mL), $NaBH_4$ (1.61 g, 42.3 mmol) was added in portions and stirred overnight. The reaction was quenched with the addition of water (50 mL) and evaporated in vacuo until MeOH was removed. The aqueous layer was extracted with EA, washed with brine and dried over $Na_2SO_4$. The crude product was purified by chromatography to give (R)-tert-butyl 3-((R)-(3-fluoro-5-methylphenyl)(hydroxy)methyl)piperidine-1-carboxylate (730 mg, 42.9%).

Step 3-5. (R)-tert-butyl 3-((R)-(3-fluoro-5-methylphenyl)(2-(methoxycarbonylamino)ethoxy)methyl)piperidine-1-carboxylate (R)-tert-butyl 3-((R)-(3-fluoro-5-methylphenyl)(2-(methoxycarbonylamino)ethoxy)methyl)piperidine-1-carboxylate analogously to Preparation 13, Steps 3-5.

Preparation 16

(R)-tert-butyl 3-((2,3-difluoro-6-methylphenyl)(2-(methoxycarbonylamino)ethoxy)methyl)piperidine-1-carboxylate

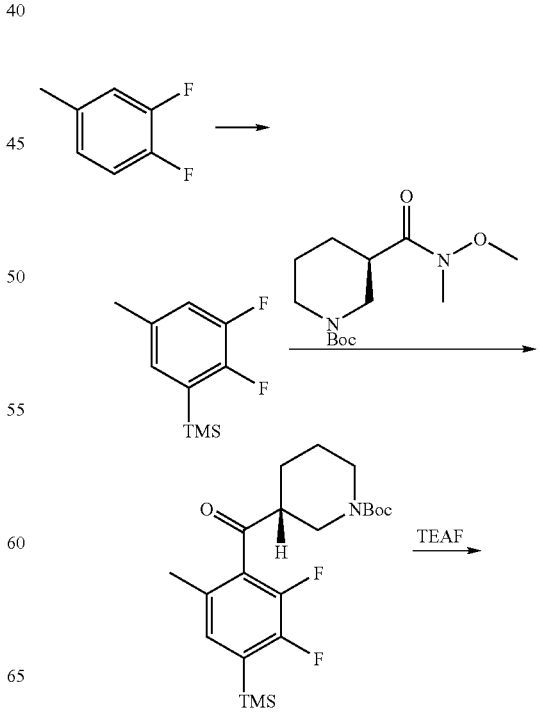

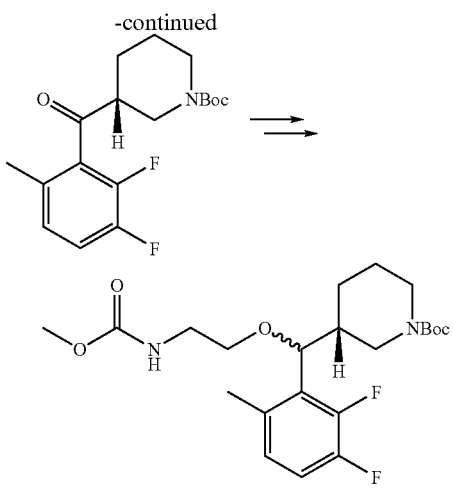

Step 1. (2,3-difluoro-5-methylphenyl)trimethylsilane

To a solution of diisopropylamine (20.2 g, 0.2 mol) in THF (500 mL) cooled with an ice-water bath was added a solution of n-BuLi in hexane (2.5 M, 80 mL) dropwise for over 30 min. The mixture was stirred in the ice bath for 30 min then cooled to −78° C. A solution of 1,2-difluoro-4-methylbenzene (12.8 g, 0.1 mol) in THF (80 mL) was added dropwise, after 20-30 min, a solution of TMSCl (21.6 g, 0.2 mol) in THF (20 mL) was added dropwise. The mixture was stirred at −78° C. for 2-3 h. Sat. NH$_4$Cl (300 mL) was added to the mixture, diluted with water (200 mL) and extracted with ether. The ether layer was washed with brine and dried over Na$_2$SO$_4$, the solvent was removed to give (2,3-difluoro-5-methylphenyl)trimethylsilane (26 g, 100%), which was used for the next step without purification. $^1$H NMR (CDCl$_3$) δ 6.90 (m, 2H), 2.40 (s, 3H), 0.33 (s, 9H).

Step 2. (R)-tert-butyl 3-(2,3-difluoro-6-methyl-4-(trimethylsilyl)benzoyl)piperidine-1-carboxylate To a solution of (2,3-difluoro-5-methylphenyl)trimethylsilane (10 g, 0.05 mol) in anhydrous THF (100 mL) at −78° C., under nitrogen, was added dropwise a solution of 2.5 M n-BuLi in hexane (20 mL). After stirring for 1 hr at −78° C., a solution of (R)-tert-butyl 3-(methoxy(methyl)carbamoyl) piperidine-1-carboxylate (13.6 g, 0.05 mol) in anhydrous THF (60 mL) was added dropwise. After addition, the reaction mixture was allowed to warm to rt and stirred for 2 h. The mixture was quenched with saturated NH$_4$Cl solution (100 mL) and extracted with ethyl acetate (3×100 mL). The combined organic layers were washed with brine, dried over Na$_2$SO$_4$ and concentrated in vacuo to give (R)-tert-butyl 3-(2,3-difluoro-6-methyl-4-(trimethylsilyl)benzoyl)piperidine-1-carboxylate, which was purified by column chromatography on silica gel elating with hexane (2 g, 10%). $^1$H NMR δ 6.90 (m, 2H), 4.00 (m, 4H), 2.20 (s, 3H), 1.47 (s, 9H), 1.30 (m, 4H), 0.35 (s, 9H).

Step 3. (R)-tert-butyl 3-(2,3-difluoro-6-methylbenzoyl)piperidine-1-carboxylate To a solution of (R)-tert-butyl 3-(2,3-difluoro-6-methyl-4-(trimethylsilyl)benzoyl)piperidine-1-carboxylate (2 g, 4.9 mmol) in THF (20 mL) was added TEAF (0.22 g, 1.5 mmol) in THF (5 mL) at 0° C. The mixture was stirred for 4 h, after which brine was added, and the mixture was extracted with Et$_2$O. The organic layer was washed with brine and dried over Na$_2$SO$_4$, concentrated. The residue was purified by column chromatography on silica gel to afford (R)-tert-butyl 3-(2,3-difluoro-6-methylbenzoyl)piperidine-1-carboxylate (1 g, 61%). $^1$H-NMR δ 7.07 (m, 1H), 6.90 (m, 1H), 4.10 (m, 2H), 3.92 (m, 2H), 2.21 (s, 3H), 1.97 (m, 2H), 1.60 (m, 4H), 1.49 (s, 9H), 1.30 (m, 3H).

Step 4-7. (R)-tert-butyl 3-((2,3-difluoro-6-methylphenyl)(2-(methoxycarbonylamino)ethoxy)methyl) piperidine-1-carboxylate (R)-tert-butyl 3-((2,3-difluoro-6-methylphenyl)-(2-(methoxycarbonylamino)ethoxy)methyl)piperidine-1-carboxylate analogously to Preparation 15, Steps 2-5.

Preparation 17

(R)-tert-butyl 2-((S)-(3-chlorophenyl)(2-(methoxycarbonylamino)ethoxy)methyl)-morpholine-4-carboxylate was prepared according to Preparation 13, Step 1-5, using (R)-tert-butyl 2-(methoxy(methyl)carbamoyl)morpholine-4-carboxylate and (3-chlorophenyl)lithium in Step 1.

Preparation 18

(R)-tert-butyl 3-((R)-(3-chlorophenyl)(2-(methoxycarbonylamino)ethoxy)methyl)-piperidine-1-carboxylate

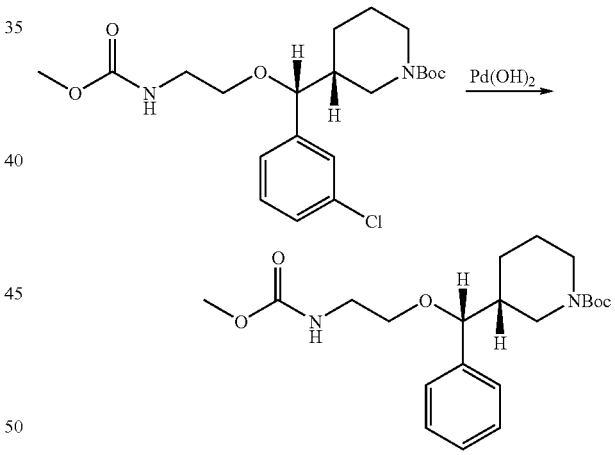

Step 1. (R)-tert-butyl 3-((R)-(phenyl)(2-(methoxycarbonylamino)ethoxy)methyl)piperidine-1-carboxylate To a solution of (R)-tert-butyl 3-((R)-(3-chlorophenyl)(2-(methoxycarbonylamino)ethoxy)methyl)piperidine-1-carboxylate (3 g, 7.04 mmol) in MeOH (60 mL) was added wet Pd(OH)$_2$/C (300 mg). The reaction mixture was stirred under 50 psi of hydrogen at 50° C. for 3 h. The suspension was filtered and the filtrate was concentrated in vacuo. The crude product was purified by preparative HPLC to afford (R)-tert-butyl 3-((R)-(phenyl)(2-(methoxycarbonylamino)ethoxy) methyl)-piperidine-1-carboxylate (1.4 g, 51%). $^1$H NMR (CD$_3$OD) δ 7.40-7.22 (m, 5H), 4.20 (m, 1H), 4.01 (m, 1H), 3.81 (m, 1H), 3.6 (s, 3H), 3.27 (m, 3H), 2.84 (m, 2H), 1.8-1.5 (m, 2H), 1.45 (s, 9H). MS ESI+ve m/z 393 (M+1).

Preparation 19

(R)-tert-butyl 3-((R)-(3-chlorophenyl)(2-(2-cyano-3-methylguanidino)ethoxy)methyl)piperidine-1-carboxylate

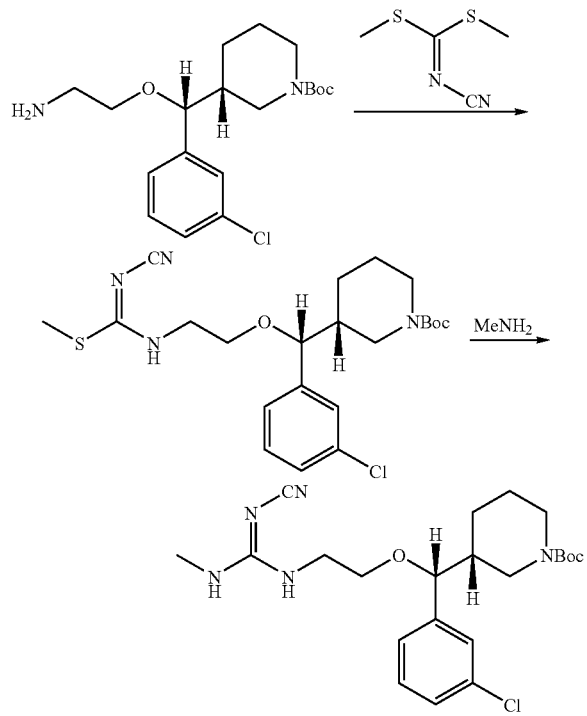

Step 1. (R)-tert-butyl 3-((R)-(3-chlorophenyl)(2-((cyanoimino)(methylthio)methylamino)ethoxy)methyl)piperidine-1-carboxylate A 25 mL flask was charged with (R)-tert-butyl 3-((R)-(2-aminoethoxy)(3-chlorophenyl)methyl)piperidine-1-carboxylate (3 g, 8.15 mmol) and dimethyl cyanocarbonimidodithioate (1.2 g, 8.15 mmol) dissolved in 50 mL of MeCN, and 1 mL Et₃N was added and the mixture was stirred for overnight. The mixture was evaporated in vacuo and the residue was purified by chromatography to give desired (R)-tert-butyl 3-((R)-(3-chlorophenyl)(2-((cyanoimino)(methylthio)methylamino)ethoxy)methyl)-piperidine-1-carboxylate (2.2 g, 58%). ¹H NMR (CDCl₃, 400 MHz) δ 7.28 (m, 2H), 7.23 (m, 1H), 7.16 (m, 1H), 4.10 (m, 2H), 3.86 (m, 1H), 3.68 (m, 2H), 3.22 (m, 2H), 2.72 (m, 2H), 1.62 (m, 2H), 1.46 (s, 9H), 1.40-1.10 (m, 4H).

Step 2. (R)-tert-butyl 3-((R)-(3-chlorophenyl)(2-(2-cyano-3-methylguanidino)ethoxy)methyl)piperidine-1-carboxylate A 100 mL flask was charged with (R)-tert-butyl 3-((R)-(3-chlorophenyl)(2-((cyanoimino)(methylthio)methylamino)ethoxy)methyl)piperidine-1-carboxylate (2.2 g, 4.72 mmol) dissolved in 50 mL MeNH₂/EtOH solution and stirred overnight. The mixture was concentrated in vacuo and used without any further purification.

Preparation 20

(R)-tert-butyl 3-((R)-(3-chlorophenyl)(2-(thiazol-2-ylamino)ethoxy)methyl)piperidine-1-carboxylate Step 1. (R)-tert-butyl 3-((R)-(3-chlorophenyl)(2-(thiazol-2-ylamino)ethoxy)methyl)piperidine-1-carboxylate A 25 mL flask was charged with (R)-tert-butyl 3-((R)-(2-aminoethoxy)(3-chlorophenyl)methyl)piperidine-1-carboxylate (100 mg, 0.27 mmol) and 2-bromo-thiazole (22 mg, 0.135 mmol) dissolved in propan-2-ol (5 mL) and stirred for 96 hr under reflux. The solvent and excess reagent was removed in vacuo to afford a residue purified by chromatography to give the pure (R)-tert-butyl 3-((R)-(3-chlorophenyl)(2-(thiazol-2-ylamino)ethoxy)methyl)piperidine-1-carboxylate (30 mg, 25%)

Preparation 21

(R)-tert-butyl 3-((R)-(3-chlorophenyl)(2-(methoxycarbonylamino)ethoxy)methyl)-azepane-1-carboxylate

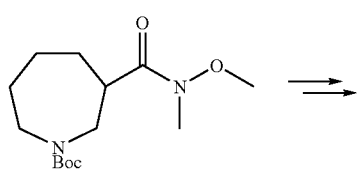

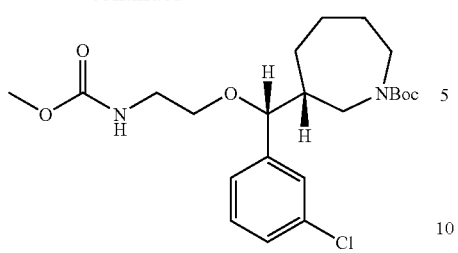

(R)-tert-butyl 3-((R)-(3-chlorophenyl)(2-(methoxycarbonylamino)ethoxy)methyl)azepane-1-carboxylate was obtained analogously to Preparation 13, using tert-butyl 3-(methoxy(methyl)carbamoyl)azepane-1-carboxylate in Step 1.

The following compounds were prepared following procedures analogous to those described above:

1) (R)-tert-butyl 3-((R)-(3-fluorophenyl)(2-(methoxycarbonylamino)ethoxy)methyl)azepane-1-carboxylate Preparation 22

(3S)-tert-butyl 3-(1-(3-fluorophenyl)-4-(methoxycarbonylamino)butyl)piperidine-1-carboxylate

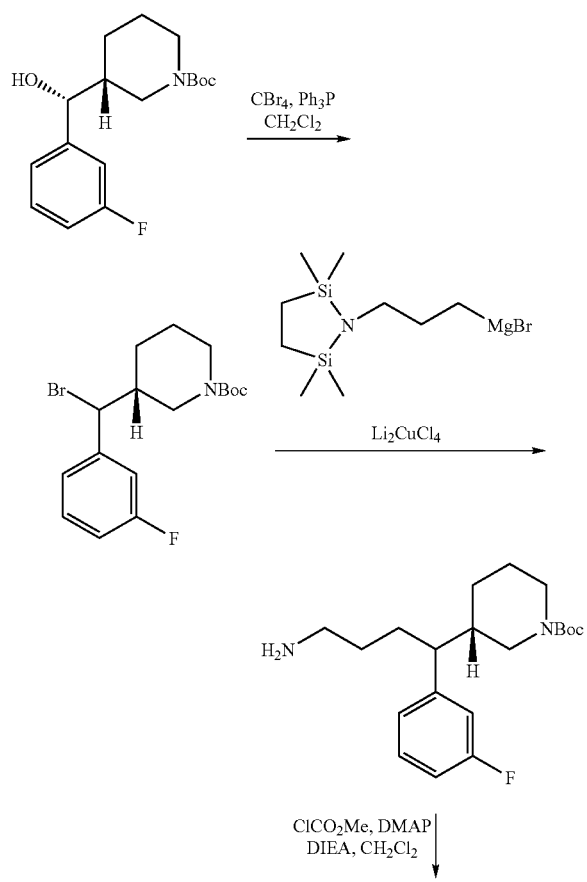

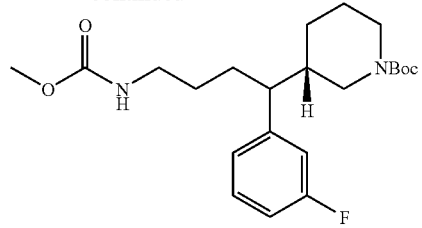

Step 1. (3R)-tert-butyl 3-(bromo(3-fluorophenyl)methyl)piperidine-1-carboxylate

A 250 mL round bottom flask was charged with 0.4845 g (1.56 mmol, 1.0 equiv) of (R)-tert-butyl 3-((R)-(3-fluorophenyl)(hydroxy)methyl)piperidine-1-carboxylate, 0.7920 g (2.39 mmol, 1.52 equiv) of carbon tetrabromide, and 15 mL of $CH_2Cl_2$. The flask was cooled with an ice bath and then 0.6258 g (2.38 mmol, 1.52 equiv) of triphenylphosphine was added in portions over 5 min. The reaction mixture was allowed to slowly warm to rt while stirring overnight. Analysis of the mixture by LC-MS showed two peaks with the same mass 236 $[M-C_4H_8-Br]^+$, consistent with a ca 62:38 mixture of two isomers: $t_R$=10.48 min and 10.93 min in 16 min chromatography, respectively. After the solvent was removed in vacuo, the residue was purified by ISCO (40 g silica gel column, 0%→30% ethyl acetate/hexanes over 40 min, flow rate 40 mL/min) to afford 0.2470 g (42%) of (3R)-tert-butyl 3-(bromo(3-fluorophenyl)methyl)piperidine-1-carboxylate. MS ESI +ve m/z 236 ($M-C_4H_8-Br$). Isomer 1 and 2, MS ESI +ve m/z 236 ($M-C_4H_8-Br$), $t_R$=2.13, 2.17 min in 3 min chromatography.

Step 2. (3S-tert-butyl 3-(4-amino-1-(3-fluorophenyl)butyl)piperidine-1-carboxylate An 100 mL round bottom flask was charged with 0.2470 g (0.66 mmol, 1.0 equiv) of (3R)-tert-butyl 3-(bromo(3-fluorophenyl)methyl)piperidine-1-carboxylate, 10 mL of THF, and 7 mL (0.70 mmol, 1.05 equiv) of 0.1 M $Li_2CuCl_4$ in THF. The mixture was cooled with an ice bath and then a (3-(2,2,5,5-tetramethyl-1,2,5-azadisilolidin-1-yl)propyl)magnesium bromide solution in THF, freshly prepared from 5.2900 g of 1-(3-bromopropyl)-2,2,5,5-tetramethyl-1,2,5-azadisilolidine and 0.5366 g of magnesium turnings in THF, was added via cannula. The resulting deep purple solution was stirred at 0° C. for 3 h. The reaction mixture was quenched with 10 mL of 10% $Na_2CO_3$, filtered through filter agent, Celite® 545, washed with $CH_2Cl_2$, and dried over $K_2CO_3$. After solvents were evaporated under reduced pressure, the crude product was purified by reversed-phase HPLC (Phenomenex® Luna 5μ C18(2) 100 A, 250×21.20 mm, 5 micron, 10%→90% $CH_3CN/H_2O$, 0.1% $CF_3COOH$ over 13 min and then 90% $CH_3CN/H_2O$, 0.1% $CF_3COOH$ over 6 min, flow rate 25 mL/min) to afford 0.092 g (30%) of TFA salt of (3S)-tert-butyl 3-(4-amino-1-(3-fluorophenyl)butyl)piperidine-1-carboxylate. Isomer 1 and 2, MS ESI +ve m/z 351 (M+H), $t_R$=1.41, 1.49 min in 3 min chromatography.

Step 3. (3S)-tert-butyl 3-(1-(3-fluorophenyl)-4-(methoxycarbonylamino)butyl)piperidine-1-carboxylate A 100 mL round bottom flask was charged with 0.092 g of TFA salt of (3S)-tert-butyl 3-(4-amino-1-(3-fluorophenyl)

butyl)piperidine-1-carboxylate, 0.152 g of DMAP, 10 mL of CH₂Cl₂, and 2 mL of DIPEA. The mixture was cooled with an ice bath and then a solution of methyl chloroformate (0.280 g) in CH₂Cl₂ (3 mL) was added. The reaction mixture was allowed to slowly warm to rt while stirring overnight. After the reaction mixture was evaporated under reduced pressure, the crude product was purified by reversed-phase HPLC (Phenomenex® Luna 5μ C18(2) 100 A, 250×21.20 mm, 5 micron, 70%→90% CH₃CN/H₂O, 0.1% CF₃COOH over 8 min and then 90% CH₃CN/H₂O, 0.1% CF₃COOH over 2 min, flow rate 25 mL/min) to afford 0.0306 g (38%) of (3S)-tert-butyl 3-(1-(3-fluorophenyl)-4-(methoxycarbonylamino) butyl)piperidine-1-carboxylate. Isomer 1 and 2, MS ESI +ve m/z 431 (MNa⁺), 409 (MH⁺), $t_R$=1.91, 1.98 min in 3 min chromatography.

Preparation 23

(R)-tert-butyl 3-((R)-1-(3-chlorophenyl)-1-(2-(methoxycarbonylamino)ethoxy)ethyl)piperidine-1-carboxylate

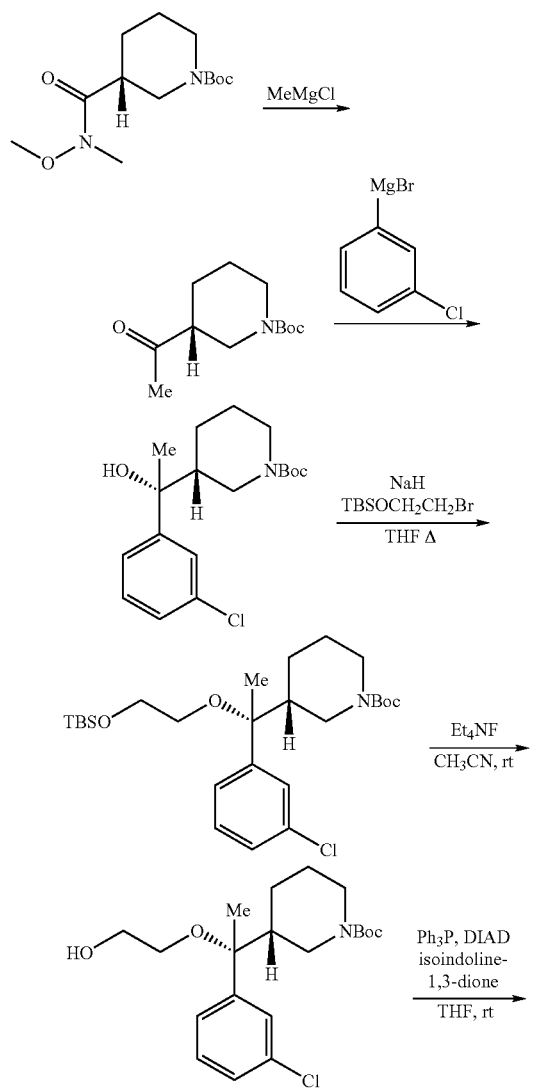

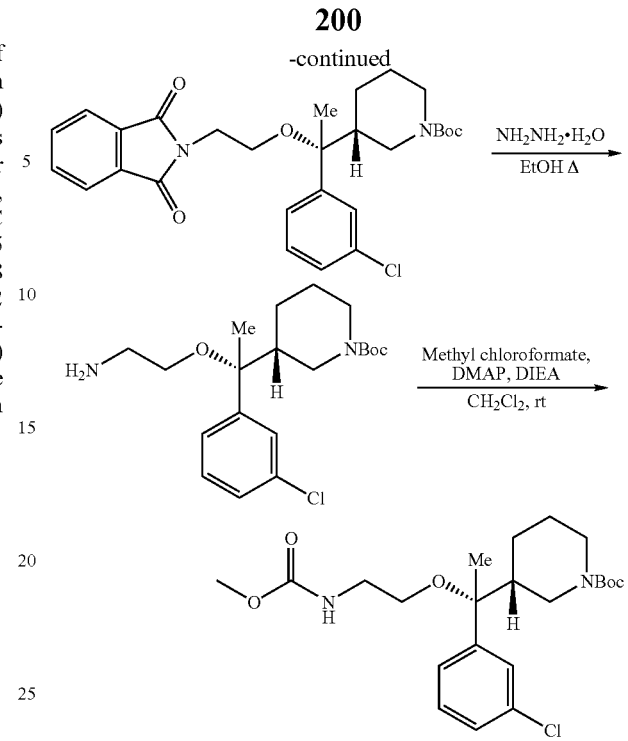

Step 1. (R)-tert-butyl 3-acetylpiperidine-1-carboxylate

To a solution of (R)-tert-butyl 3-(methoxy(methyl)carbamoyl)piperidine-1-carboxylate (3.320 g, 12.2 mmol) in THF (30 mL) was added 15 mL of 3.0 M MeMgCl in THF at −15° C. under N₂. After 0.5 h, the mixture was allowed to warm to rt for 4 h. The reaction mixture was then quenched with 40 mL of 1 NHCl and extracted with ethyl acetate (3×), dried over Na₂SO₄. After the solvent was evaporated under reduced pressure, the crude (R)-tert-butyl 3-acetylpiperidine-1-carboxylate was directly used in the next step without further purification. MS ESI +ve m/z 250 (M+Na).

Step 2. (R)-tert-butyl 3-((R)-1-(3-chlorophenyl)-1-hydroxyethyl)piperidine-1-carboxylate To a solution of (R)-tert-butyl 3-acetylpiperidine-1-carboxylate, obtained as described above, in THF (20 mL) was added 70 mL of 0.5 M (3-chlorophenyl)magnesium bromide in THF at −78° C. under N₂. The mixture was allowed to slowly warm to 12° C. for 18 h. The reaction mixture was then quenched with 10 mL of 10% Na₂CO₃ and extracted with ethyl acetate (3×), dried over Na₂SO₄. After the solvent was evaporated under reduced pressure, the crude product was purified by reversed-phase HPLC to afford 2.5463 g (62% in two steps) of (R)-tert-butyl 3-((R)-1-(3-chlorophenyl)-1-hydroxyethyl)piperidine-1-carboxylate. MS ESI +ve m/z 362 (M+Na).

Step 3. (R)-tert-butyl 3-((R)-1-(2-(tert-butyldimethylsilyloxy)ethoxy)-1-(3-chlorophenyl)ethyl)piperidine-1-carboxylate A mixture of (R)-tert-butyl 3-((R)-1-(3-chlorophenyl)-1-hydroxyethyl)piperidine-1-carboxylate (2.5463 g, 7.49 mmol), 60% NaH (2.120 g, 53 mmol), and (2-bromoethoxy)(tert-butyl)dimethylsilane (7.820 g, 32.7 mmol) in THF was heated at 80° C. for 25 h and then cooled to rt. The reaction mixture was then quenched with water and extracted with ethyl acetate (3×), dried over Na₂SO₄. After the solvent was evaporated under reduced pressure, crude (R)-tert-butyl 3-((R)-1-(2-(tert-butyldimethylsilyloxy)ethoxy)-1-(3-chlorophenyl)ethyl)piperidine-1-carboxylate was used directly in the next step without further purification.

Step 4. (R)-tert-butyl 3-((R)-1-(3-chlorophenyl)-1-(2-hydroxyethoxy)ethyl)piperidine-1-carboxylate A mixture of (R)-tert-butyl 3-((R)-1-(2-(tert-butyldimethylsilyloxy)ethoxy)-1-(3-chlorophenyl)ethyl)piperidine-1-carboxylate, tetraethylammonium fluoride (7.600 g, 50.9 mmol) in CH₃CN was heated at 45° C. for 1 h and then was allowed to stir at rt overnight. The reaction mixture was evaporated under reduced pressure, the residue was dissolved into water and extracted with Et₂O (3×), dried over Na₂SO₄. After the solvent was removed in vacuo, the crude product was purified by reversed-phase HPLC to give 1.000 g (35% in two steps) of (R)-tert-butyl 3-((R)-1-(3-chlorophenyl)-1-(2-hydroxyethoxy)ethyl)piperidine-1-carboxylate. MS ESI +ve m/z 406 (M+Na).

Step 5. (R)-tert-butyl 3-((R)-1-(3-chlorophenyl)-1-(2-(1,3-dioxoisoindolin-2-yl)ethoxy)ethyl)piperidine-1-carboxylate A mixture of (R)-tert-butyl 3-((R)-1-(3-chlorophenyl)-1-(2-hydroxyethoxy)ethyl)piperidine-1-carboxylate (1.000 g, 2.6 mmol), phthalimide (1.490 g, 10.1 mmol), triphenylphosphine (4.130 g, 15.7 mmol), and DIAD (3.430 g, 17.0 mmol) in THF was stirred at rt for 40 h. After the reaction mixture was evaporated under reduced pressure, the crude product was purified by reversed-phase HPLC to afford 0.6792 g (51%) of (R)-tert-butyl 3-((R)-1-(3-chlorophenyl)-1-(2-(1,3-dioxoisoindolin-2-yl)ethoxy)ethyl)piperidine-1-carboxylate. MS ESI +ve m/z 537 (M+Na).

Step 6. (R)-tert-butyl 3-((R)-1-(2-aminoethoxy)-1-(3-chlorophenyl)ethyl)piperidine-1-carboxylate A mixture of (R)-tert-butyl 3-((R)-1-(3-chlorophenyl)-1-(2-(1,3-dioxoisoindolin-2-yl)ethoxy)ethyl)piperidine-1-carboxylate (0.6792 g, 1.32 mmol) and hydrazine monohydrate (2.350 g) in ethanol (20 mL) was heated at 100° C. for 19 h and then cooled to rt. The precipitates were filtered off and washed with CH₂Cl₂. After the filtrate was evaporated under reduced pressure, the crude (R)-tert-butyl 3-((R)-1-(2-aminoethoxy)-1-(3-chlorophenyl)ethyl)piperidine-1-carboxylate (0.410 g, 81%) was used in the next step without further purification. MS ESI +ve m/z 385 (M+H).

Step 7. (R)-tert-butyl 3-((R)-1-(3-chlorophenyl)-1-(2-(methoxycarbonylamino)ethoxy)ethyl)piperidine-1-carboxylate A mixture of (R)-tert-butyl 3-((R)-1-(2-aminoethoxy)-1-(3-chlorophenyl)ethyl)piperidine-1-carboxylate (0.410 g, 1.07 mmol), DMAP (0.380 g), DIPEA (4 mL), and methyl chloroformate (0.960 g) in CH₂Cl₂ was stirred at rt for 20 h. After the reaction mixture was evaporated under reduced pressure, the crude product was purified by reversed-phase HPLC to afford (R)-tert-butyl 3-((R)-1-(3-chlorophenyl)-1-(2-(methoxycarbonylamino)ethoxy)ethyl)piperidine-1-carboxylate. MS ESI +ve m/z 465 (M+Na).

Preparation 24

(R)-tert-butyl 3-((R)-1-(3-chlorophenyl)-1-(2-(methoxycarbonylamino)ethoxy)butyl)piperidine-1-carboxylate

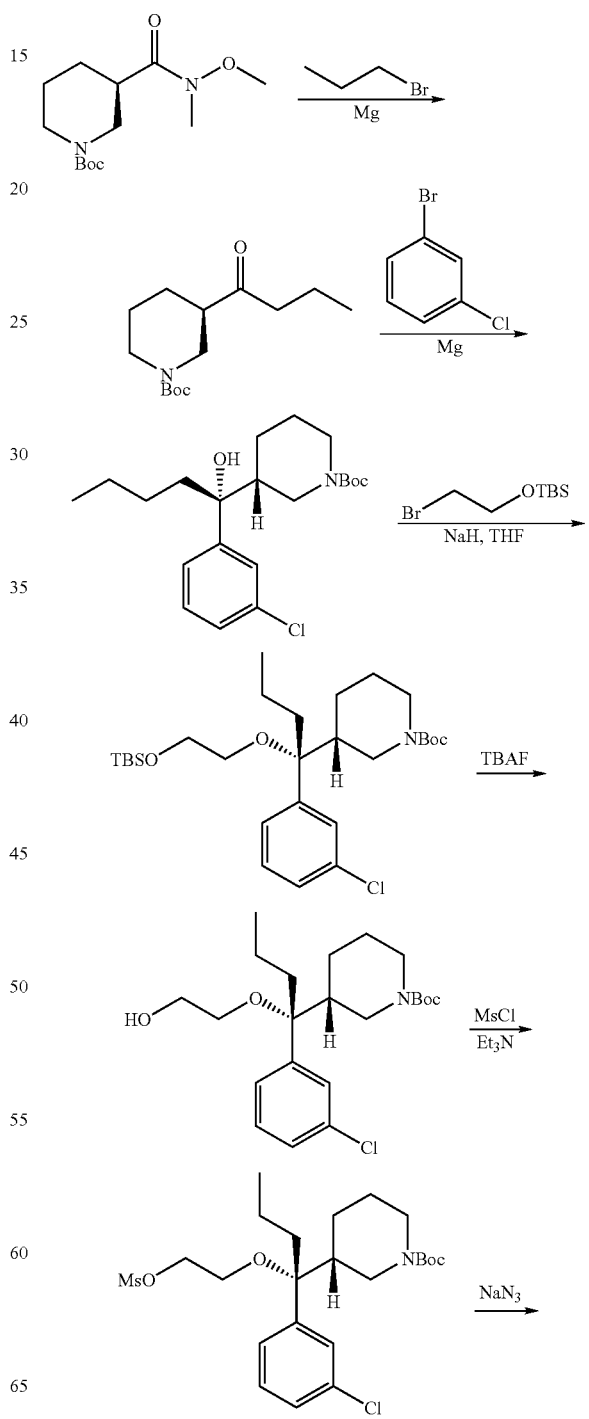

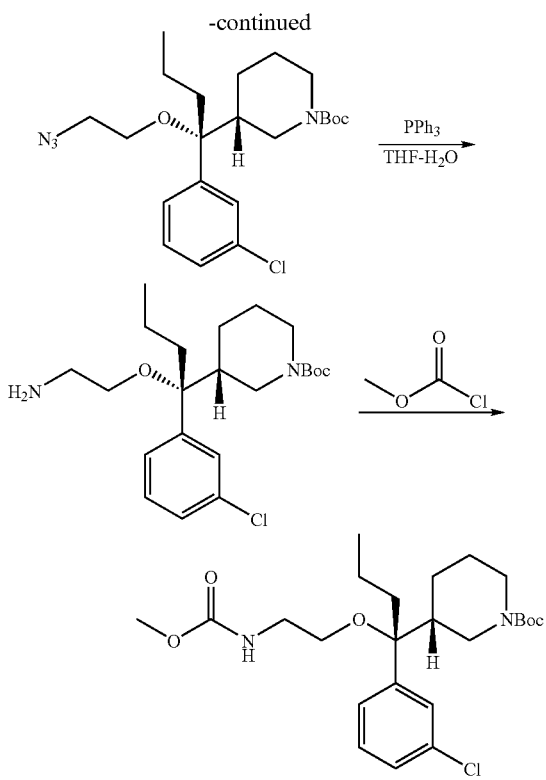

Step 1-2. (R)-tert-butyl 3-((R)-1-(3-chlorophenyl)-1-hydroxybutyl)piperidine-1-carboxylate (R)-tert-butyl 3-((R)-1-(3-chlorophenyl)-1-hydroxybutyl)piperidine-1-carboxylate was obtained using procedures analogous to Preparation 20, Steps 1-2, using propylmagnesium bromide in Step 1.

Step 3. (R)-tert-butyl 3-((R)-1-(2-(tert-butyldimethylsilyloxy)ethoxy)-1-(3-chlorophenyl)butyl)piperidine-1-carboxylate To a suspension of NaH (2.4 g, 60 mmol) in dry THF (20 mL) was added a solution of (R)-tert-butyl 3-((R)-1-(3-chlorophenyl)-1-hydroxybutyl)piperidine-1-carboxylate (7.34 g, 20 mmol) in dry THF (80 mL) at 0° C. The reaction mixture was stirred at rt for 2 h. Then a solution of (2-bromoethoxy)(tert-butyl)dimethylsilane (14.3 g, 60 mmol) in THF (100 mL) was added dropwise. After addition, the resulting mixture was stirred under reflux overnight. To the reaction mixture was added dropwise saturated NH$_4$Cl solution, extracted by EtOAc (2×100 mL), washed with brine, dried over Na$_2$SO$_4$, and concentrated in vacuo to give the crude product. The crude product was purified by column chromatography on silica gel to afford (R)-tert-butyl 3-((R)-1-(2-(tert-butyldimethylsilyloxy)ethoxy)-1-(3-chlorophenyl)butyl)piperidine-1-carboxylate (1.1 g, 10%). $^1$H NMR (CDCl$_3$, 400 MHz) δ 7.35 (s, 1H), 7.22 (m, 3H), 4.05 (m, 2H), 3.81 (m, 2H), 3.31 (m, 2H), 2.42 (t, 3H), 2.06 (m, 3H), 1.85 (m, 2H), 1.58 (m, 2H), 1.44 (s, 9H), 1.41-1.01 (m, 7H), 0.92 (s, 9H), 0.095 (s, 6H).

Step 4. (R)-tert-butyl 3-((R)-1-(3-chlorophenyl)-1-(2-hydroxyethoxy)butyl)piperidine-1-carboxylate To a solution of (R)-tert-butyl 3-((R)-1-(2-(tert-butyldimethylsilyloxy)ethoxy)-1-(3-chlorophenyl)butyl)piperidine-1-carboxylate (1.1 g, 2.1 mmol) in MeCN (5 mL), TBAF (1.1 g, 4.2 mmol) was added in portions at rt. The reaction mixture was stirred for 2-3 h at 50-60° C. The solvent was removed in vacuo to the crude product, which was purified by column chromatography to afford (R)-tert-butyl 3-((R)-1-(3-chlorophenyl)-1-(2-hydroxyethoxy)butyl)piperidine-1-carboxylate (750 mg, 87%). $^1$H NMR (CDCl$_3$, 400 MHz) δ 7.31 (s, 1H), 7.24 (m, 2H), 7.17 (m, 1H), 4.21-3.90 (m, 2H), 3.80 (m, 2H), 3.37 (m, 2H), 2.31 (m, 1H), 2.05 (m, 3H), 1.88 (m, 4H), 1.56 (m, 1H), 1.44 (s, 9H), 1.38-1.10 (m, 2H), 0.95 (t, 3H).

Step 5. (R)-tert-butyl 3-((R)-1-(3-chlorophenyl)-1-(2-(methylsulfonyloxy)ethoxy)butyl)piperidine-1-carboxylate To a solution of (R)-tert-butyl 3-((R)-1-(3-chlorophenyl)-1-(2-hydroxyethoxy)butyl)piperidine-1-carboxylate (750 mg, 1.82 mmol) in dry CH$_2$Cl$_2$ (10 mL) was added Et$_3$N (550 mg, 5.46 mmol) at −5-0° C. Then a solution of MsCl (270 mg, 2.37 mmol) in dry CH$_2$Cl$_2$ (5 mL) was added dropwise at the same temperature. After addition, it was allowed to warm to rt gradually. Upon completion of the reaction, water (20 mL) was added. The aqueous layer was extracted with CH$_2$Cl$_2$ (3×30 mL). The combined organic layers was washed with 10% citric acid, sat. NaHCO$_3$ and brine, then dried over Na$_2$SO$_4$, filtered and concentrated to give (R)-tert-butyl 3-((R)-1-(3-chlorophenyl)-1-(2-(methylsulfonyloxy)ethoxy)butyl)piperidine-1-carboxylate (900 mg, 99%), which was used in the next step without purification.

Step 6. (R)-tert-butyl 3-((R)-1-(2-azidoethoxy)-1-(3-chlorophenyl)butyl)piperidine-1-carboxylate (R)-tert-butyl 3-((R)-1-(3-chlorophenyl)-1-(2-(methylsulfonyloxy)ethoxy)butyl)piperidine-1-carboxylate (900 mg, 1.82 mmol) was dissolved into anhydrous DMF (15 mL), solid NaN$_3$ (230 mg, 3.51 mmol) was added and the reaction mixture was heated to 70° C. overnight. The reaction mixture was cooled to rt and then was diluted with ethyl acetate (110 mL), and water (30 mL), the organic phase was washed with water (3×20 mL), dried over Na$_2$SO$_4$ and evaporated to give (R)-tert-butyl 3-((R)-1-(2-azidoethoxy)-1-(3-chlorophenyl)butyl)piperidine-1-carboxylate (790 mg, 99%).

Step 7. (R)-tert-butyl 3-((R)-1-(2-aminoethoxy)-1-(3-chlorophenyl)butyl)piperidine-1-carboxylate To a solution of (R)-tert-butyl 3-((R)-1-(2-azidoethoxy)-1-(3-chlorophenyl)butyl)piperidine-1-carboxylate (790 mg, 1.81 mmol) in the mixture of THF/H$_2$O (20:1, 10.5 mL) was added PPh$_3$ (1.9 g, 7.25 mmol). The reaction mixture was stirred at rt overnight. The solvent was removed under reduced pressure to the residue, which was purified by column chromatography on silica gel to afford (R)-tert-butyl 3-((R)-1-(2-aminoethoxy)-1-(3-chlorophenyl)butyl)piperidine-1-carboxylate (410 mg, 55%). $^1$HNMR (CDCl$_3$, 400 MHz) δ 7.31 (s, 1H), 7.24 (m, 2H), 7.15 (m, 1H), 4.31-3.52 (m, 3H), 3.27 (m, 2H), 2.93 (m, 1H), 2.41-2.22 (m, 3H), 2.15-1.95 (m, 3H), 1.85 (m, 4H), 1.57 (m, 1H), 1.44 (s, 9H), 1.38-1.10 (m, 2H), 0.95 (t, 31).

Step 8. (R)-tert-butyl 3-((R)-1-(3-chlorophenyl)-1-(2-(methoxycarbonylamino)ethoxy)butyl)piperidine-1-carboxylate To a solution of (R)-tert-butyl 3-((R)-1-(2-aminoethoxy)-1-(3-chlorophenyl)butyl)piperidine-1-carboxylate (410 mg, 1 mmol) and DMAP (61 mg, 0.5 mmol) in dry CH$_2$Cl$_2$ (3 mL), Et$_3$N (303 mg, 3 mmol) was added. The resulting mixture was cooled to 0-5° C. using a ice-water bath, a solution of methyl chloroformate (472 mg, 5 mmol) in dry CH$_2$Cl$_2$ (2 mL) was added dropwise. After addition, the reaction mixture was stirred for 1-2 h at 0-5° C. Upon completion of the reaction water (5 mL) was added and the aqueous layer was extracted with CH$_2$Cl$_2$ (3×15 mL). The combined organic layers were washed with 10% citric acid (2×10 mL) and brine, then dried over Na$_2$SO$_4$, filtered and concentrated to afford (R)-tert-butyl 3-((R)-1-(3-chlorophenyl)-1-(2-(methoxycarbonylamino)ethoxy)butyl)piperidine-1-carboxylate (460 mg, 98%), which was used in the next step without further purification.

Preparation 25

1) (R)-tert-butyl 3-((S)-1-(3-fluorophenyl)-1-hydroxy-4-(methoxycarbonylamino)butyl)piperidine-1-carboxylate was obtained analogous to PREPARATION 1 above.

2) (R)-tert-butyl 3-((S)-1-(3-chloro-2-fluorophenyl)-1-hydroxy-4-(methoxycarbonylamino)butyl)piperidine-1-carboxylate was obtained analogously to PREPARATION 1 above.

Preparation 26

(R)-4-(tert-Butoxycarbonyl)morpholine-2-carboxylic acid

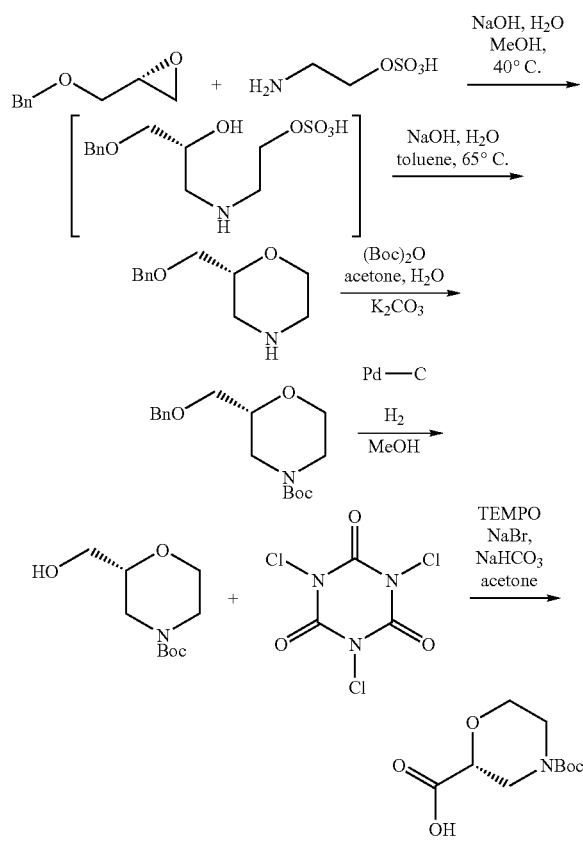

Step 1. (R)-2-(Benzyloxymethyl)morpholine

To a stirred mixture of (R)-2-(benzyloxymethyl)oxirane (10.0 g, 60.9 mmol) and NaOH (19.49 g, 487.2 mmol) in H$_2$O (46 mL) and MeOH (18 mL), there was added 2-aminoethyl hydrogen sulfate (36.8 g, 255.8 mmol) in portions. After addition the reaction mixture was stirred at 40° C. for 2 h. After cooling, the mixture was treated with NaOH (15.0 g, 375.0 mmol) then toluene (70 mL) and stirred at 65° C. overnight. The mixture was cooled, diluted with toluene (27 mL) and H$_2$O (92 mL). The toluene layer was separated and the aqueous layer was extracted with CH$_2$Cl$_2$ (2×50 mL). The combined organic layers were concentrated to give crude (R)-2-(benzyloxymethyl)morpholine (~14 g), which was used without purification. MS m/z 208 (M+H$^+$).

Step 2. (R)-tert-Butyl 2-(benzyloxymethyl)morpholine-4-carboxylate

To a solution of crude (R)-2-(benzyloxymethyl)morpholine (~14 g) in acetone (100 mL) and H$_2$O (30 mL) at 0° C., there was added K$_2$CO$_3$ (25.2 g, 182.7 mmol), followed by (Boc)$_2$O (14.6 g, 67.0 mmol). The resulting solution was warmed to rt, and stirred until no starting material remained (~30 min), acetone was removed under vacuum, and the aqueous solution was extracted with CH$_2$Cl$_2$ (4×10 mL). The combined organic layers were washed with H$_2$O (10 mL) and the solvent was removed. The residue was purified by flash column chromatography to give (R)-tert-butyl 2-(benzyloxymethyl)morpholine-4-carboxylate (8.33 g, 44% over 2 steps). $^1$H NMR (400 MHz, CDCl$_3$): 7.34 (m, 5H), 4.56 (s, 2H), 3.88 (d, 2H), 3.82 (br, 1H), 3.40 (m, 1H), 3.48 (m, 3H), 2.94 (m, 1H), 2.76 (m, 1H), 1.44 (s, 9H); MS m/z 330 (M+Na$^+$).

Step 3. (R)-tert-Butyl 2-(hydroxymethyl)morpholine-4-carboxylate

To a solution of (R)-tert-butyl 2-(benzyloxymethyl)morpholine-4-carboxylate (8.33 g, 27.1 mmol) in EtOH was added Pd—C (wet, 3.6 g), and the resulting mixture was stirred at rt under a H$_2$ balloon overnight. After filtration, the solvent was removed under vacuum, and the residue was purified by flash column chromatography to give (R)-tert-butyl 2-(hydroxymethyl)morpholine-4-carboxylate (5.84 g, 99%) as a clear oil. $^1$H NMR (400 MHz, CDCl$_3$): 3.88 (d, 2H), 3.82 (br, 1H), 3.64 (d, 1H), 3.56 (m, 3H), 2.94 (m, 1H), 2.76 (m, 1H), 1.90 (br, 1H), 1.44 (s, 9H); MS m/z 218 (M+H$^+$).

Step 4. (R)-4-(tert-Butoxycarbonyl)morpholine-2-carboxylic acid

Sat'd aq NaHCO$_3$ (15 mL) was added to a solution of (R)-tert-butyl 2-(hydroxymethyl)-morpholine-4-carboxylate (1.09 g, 5.0 mmol) in acetone (50 mL), stirred and maintained at 0° C. Solid NaBr (0.1 g, 1 mmol) and TEMPO (0.015 g, 0.1 mmol) were added. Trichloroisocyanuric acid (2.32 g, 10.0 mmol) was then added slowly within 20 min at 0° C. After addition the mixture was warmed to rt and stirred overnight. 2-Propanol (3 mL) was added, and the resulting solution was stirred at rt for 30 min, filtered through a pad of Celite, concentrated under vacuum, and treated with sat'd aq Na$_2$CO$_3$ (15 mL). The aqueous solution was washed with EtOAc (5 mL), acidified with 6 N HCl, and extracted with EtOAc (5×10 mL). The combined organic layers were dried over Na$_2$SO$_4$ and the solvent was removed to give (R)-4-(tert-butoxycarbonyl)morpholine-2-carboxylic acid (1.07 g, 92%) as a white solid. $^1$H NMR (400 MHz, CDCl$_3$): 4.20 (br, 1H), 4.12 (d, 1H), 4.02 (d, 1H), 3.84 (m, 1H), 3.62 (m, 1H), 3.04 (m, 2H), 1.44 (s, 9H); MS m/z 232 (M+H$^+$).

Preparation 27

Methyl 2-((S)-(3-chloro-2-fluorophenyl)((R)-morpholin-2-yl)methoxy)ethylcarbamate was prepared from (R)-4-(tert-butoxycarbonyl)morpholine-2-carboxylic acid using procedures analogous to those described in Preparation 1 Steps 1 and 2 and Preparation 4.

Preparation A (S)-2-(Trimethylsilyl)ethyl 2-amino-3-cyclohexylpropylcarbamate

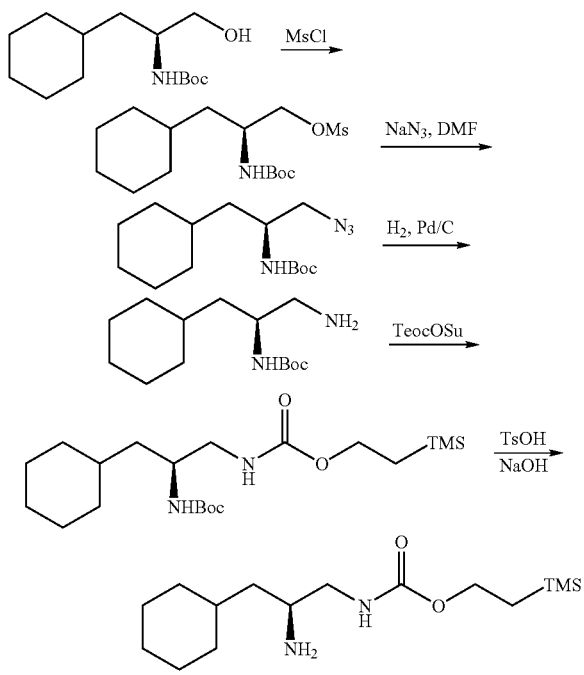

Step 1. (S)-2-(tert-Butoxycarbonylamino)-3-cyclohexylpropyl methanesulfonate

A solution of (S)—N-Boc-2-amino-3-cyclohexylpropanol (20 g, 0.078 mol) in CH$_2$Cl$_2$ (400 mL) and triethylamine (19.6 g, 0.195 mol) was cooled to −20° C. Methanesulfonyl chloride (19.5 g, 0.171 mol) was added with fast dropwise addition maintaining the internal temperature at −20° C. The reaction mixture was stirred at −20° C. for an additional 30 min then for 1 h at 0° C. and then quenched with ice-cold water (200 mL). The mixture was extracted with CH$_2$Cl$_2$ (3×100 mL), washed with water (3×50 mL), dried over Na$_2$SO$_4$, concentrated to give the crude (S)-2-(tert-butoxycarbonylamino)-3-cyclohexylpropyl methanesulfonate (23.3 g, 90%), which was used for the next reaction without further purification. $^1$H NMR (400 MHz, CDCl$_3$): 4.93 (m, 1H), 4.60 (d, J=7.6 Hz, 1H), 3.67 (m, 2H), 3.12 (s, 3H), 1.87-1.50 (m, 5H), 1.45 (s, 9H), 1.40-0.72 (m, 8H), MS (E/Z): 336 (M+H$^+$).

Step 2. (S)-tert-butyl 1-azido-3-cyclohexylpropan-2-ylcarbamate

To a solution of (S)-2-(tert-butoxycarbonylamino)-3-cyclohexylpropyl methanesulfonate (23.3 g, 0.070 mol) in anhydrous DMF (300 mL) was added solid NaN$_3$ (13.5 g, 0.21 mol). The reaction mixture was heated at 80° C. overnight. After cooling to rt, the reaction solution was diluted with EtOAc (1200 mL) and water (400 mL). The organic phase was separated and washed with brine (3×300 mL), dried over Na$_2$SO$_4$ and evaporated. The residue was purified by column chromatography on silica gel to give (S)-tert-butyl 1-azido-3-cyclohexylpropan-2-ylcarbamate as a clear oil (13.6 g, 69%). $^1$H NMR (400 MHz, CDCl$_3$): 4.45 (d, J=8.0 Hz, 1H), 3.84 (m, 1H), 3.45 (m, 1H), 3.31 (m, 1H), 1.81-1.60 (m, 5H), 1.45 (s, 9H), 1.40-0.78 (m, 8H). MS (E/Z): 383 (M+H$^+$).

Step 3. (S)-tert-butyl 1-amino-3-cyclohexylpropan-2-ylcarbamate

A mixture of (S)-tert-butyl 1-azido-3-cyclohexylpropan-2-ylcarbamate (13.6 g, 0.048 mol) and Pd/C (1.4 g) in methanol (200 mL) was hydrogenated with a balloon overnight. The mixture was filtered through a pad of Celite and the solvent was removed to give (S)-tert-butyl 1-amino-3-cyclohexylpropan-2-ylcarbamate (10.5 g, 86%), which was used in the next step without purification. $^1$H NMR (400 MHz, CDCl$_3$): 4.52 (d, J=8.4 Hz, 1H), 3.68 (m, 2H), 2.73 (dd, J=13.6&4.4 Hz, 1H), 2.58 (dd, J=13.6&6.0 Hz, 1H), 1.81 (m, 1H), 1.65 (m, 4H), 1.42 (s, 9H), 1.40-1.00 (m, 6H), 1.00-0.70 (m, 2H). MS (E/Z): 257 (M+H$^+$).

Step 4. (S)-tert-Butyl 1-(2-(trimethylsilyl)ethoxycarbonylamino)-3-cyclohexylpropan-2-ylcarbamate To a vigorously stirred biphasic solution of (S)-tert-butyl 1-amino-3-cyclohexylpropan-2-ylcarbamate (10.5 g, 0.041 mol), K$_2$CO$_3$ (10.2 g, 73.8 mol), H$_2$O (60 mL), and CH$_2$Cl$_2$ (120 mL) was added 1-[2-trimethylsilyl)ethoxycarbonyloxy]pyrrolidin-2,5-dione (TeocOSu) (11.14 g, 0.043 mol). The mixture was stirred for 2 h at rt, and then the reaction was washed with brine (3×20 mL), dried over Na$_2$SO$_4$, decanted, stripped, and separated on 50 g of SiO$_2$ to give (S)-tert-butyl 1-(2-(trimethylsilyl)ethoxycarbonylamino)-3-cyclohexylpropan-2-ylcarbamate (8.5 g, 52%) as a clear oil. $^1$H NMR (400 MHz, CDCl$_3$): 5.52 (brs, 1H), 4.42 (brs, 1H), 4.11 (m, 2H), 3.73 (brs, 1H), 3.30-3.03 (m, 2H), 1.81-1.50 (m, 5H), 1.43 (s, 9H), 1.42-1.02 (m, 6H), 1.02-0.76 (m, 4H), 0.03 (s, 9H); MS (E/Z): 401 (M+H$^+$).

Step 5. (S)-2-(Trimethylsilyl)ethyl 2-amino-3-cyclohexylpropylcarbamate (S)-tert-butyl 1-(2-(trimethylsilyl)ethoxycarbonylamino)-3-cyclohexylpropan-2-ylcarbamate (8.5 g, 0.0213 mol) was dissolved into a minimal volume of ethyl ether (120 mL) and added to a solution of tosic acid (4.46 g, 0.023 mol) in 25 mL of absolute EtOH. This solution was placed on a rotary evaporator and ethyl ether was removed at ambient temp. The flask was then lowered into the water bath (temperature: 60° C.) and the selective de-protection of the Boc group proceeded concurrently with removal of the remainder of solvent. The reaction was completed by 2 h and gave an off-white solid. This material was cooled to rt and dissolved in 100 mL of a mixture EtOH:H$_2$O (1:1, v/v). This was washed with hexanes:EtOAc (5:1, v/v, 3×12 mL), basified with 1N NaOH (pH>10), and extracted with EtOAc (3×50 mL). The combined organic extracts were washed (3×5 mL 1N NaOH, 3×5 mL brine), dried, decanted and stripped to give the free base of (S)-2-(trimethylsilyl)ethyl 2-amino-3-cyclohexylpropylcarbamate (5.24 g, 82%). ¹H NMR (400 MHz, CDCl₃): 5.09 (brs, 1H), 4.14 (t, J=8.4 Hz, 2H), 3.23 (m, 1H), 2.88 (m, 2H), 1.75-1.48 (m, 5H), 1.5-0.75 (m, 10H), 0.05 (s, 9H). MS (E/Z): 301 (M+H⁺).

Preparation B (S)-2-(trimethylsilyl)ethyl 2-amino-3-cyclohexylpropyl(methyl)carbamate

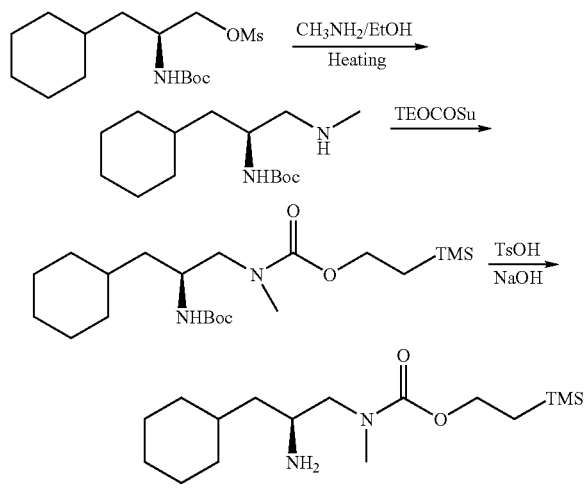

Step 1. (S)-tert-Butyl 1-cyclohexyl-3-(methylamino)propan-2-ylcarbamate (S)-2-(tert-butoxycarbonylamino)-3-cyclohexylpropyl methanesulfonate (28 g, 83.6 mmol) was dissolved into a solution of methylamine in ethanol (about 30% by weight, 300 mL). The reaction was heated at 50-60° C. overnight and concentrated in vacuo. The residue was dissolved in EtOAc, washed with brine (2×100 mL), dried over MgSO₄, and concentrated to give the crude product. This crude product was purified by flash chromatography (AcOEt:Hex.=2:1 first, then EtOAc:MeOH=1:1) to afford pure (S)-tert-butyl 1-cyclohexyl-3-(methylamino)propan-2-ylcarbamate (10.6 g, 47%). ¹H NMR (400 MHz, CDCl₃): 4.81 (brs, 1H), 3.89 (m, 1H), 2.77 (m, 2H), 2.54 (s, 3H), 2.44 (m, 2H), 1.78 (m, 1H), 1.67 (m, 4H), 1.44 (s, 9H), 1.50-1.10 (m, 6H), 1.00-0.77 (m, 2H), 0.05 (s, 9H). MS (E/Z): 271 (M+H⁺).

Step 2. (S)-tert-butyl 1-cyclohexyl-3-(N-methyl-N-(2-(trimethylsilyl)ethoxycarbonyl)amino)propan-2-ylcarbamate To a vigorously stirred 2-phase solution of (S)-tert-butyl 1-cyclohexyl-3-(methylamino)propan-2-ylcarbamate (7.25 g, 0.027 mol), K₂CO₃ (6.66 g, 0.048 mol), H₂O (40 mL) and CH₂Cl₂ (80 mL) was added 1-[2-trimethylsilyl)ethoxycarbonyloxy]pyrrolidin-2,5-dione (TeocOSu) solid (7.3 g, 0.028 mol). After stirring for 2 h at rt, the reaction was added to CH₂Cl₂ (200 mL), washed with satd aq NaHCO₃ (3×15 mL) then brine (3×15 mL), dried over Na₂SO₄ and concentrated. The residue was purified by column chromatography on 40 g of silica gel to give (S)-tert-butyl 1-cyclohexyl-3-(N-methyl-N-(2-(trimethylsilyl)ethoxycarbonyl)amino)propan-2-ylcarbamate as a clear oil (5.78 g, 50%). ¹H NMR (400 MHz, CDCl₃) δ 4.50 (d, J=7.6 Hz, 1H), 4.15 (t, J=7.6 Hz, 2H), 3.89 (m, 1H), 3.56-2.95 (m, 2H), 2.92&2.90 (s, 3H), 1.82 (m, 1H), 1.66 (m, 4H), 1.41 (s, 9H), 1.50-1.10 (m, 6H), 1.00-0.70 (m, 4H), 0.01 (s, 9H). MS (E/Z): 415 (M+H⁺).

Step 3. (S)-2-(Trimethylsilyl)ethyl 2-amino-3-cyclohexylpropyl(methyl)carbamate (S)-tert-butyl 1-cyclohexyl-3-(N-methyl-N-(2-(trimethylsilyl)ethoxycarbonyl)amino)propan-2-ylcarbamate (5.78 g, 0.014 mol) was dissolved into a minimal volume of ethyl ether (100 mL) and added to a solution of TsOH (2.92 g, 0.0154 mol) in 20.0 mL of absolute EtOH. This solution was placed on a rotary evaporator and the Et₂O was removed at ambient temp. The flask was then lowered into the water bath (temperature: 60° C.) and the selective de-protection of the BOC group proceeded concurrently with removal of the remainder of the solvent. The reaction was completed by 2 h and gave an off-white solid, which was washed with hexanes: EtOAc (5:1, v/v, 3×100 mL), basified with 1N NaOH (pH>10), and extracted with ethyl ether (3×50 mL). The combined organic extracts were washed with 1N NaOH (3×5 mL) and brine (3×5 mL), dried, decanted and stripped to give the free base of (S)-2-(trimethylsilyl)ethyl 2-amino-3-cyclohexylpropyl(methyl)carbamate (3.5 g, 80%). ¹H NMR (400 MHz, CDCl₃): 4.15 (t, J=8.4 Hz, 2H), 3.10 (m, 3H), 2.91 (s, 3H), 1.78-1.56 (m, 5H), 1.50-1.00 (M, 6H), 1.00-0.70 (m, 4H), 0.01 (s, 9H). MS (E/Z): 315 (M+H⁺).

Preparation C

Benzyl (2S,3S)-3-amino-4-cyclohexylbutan-2-ylcarbamate

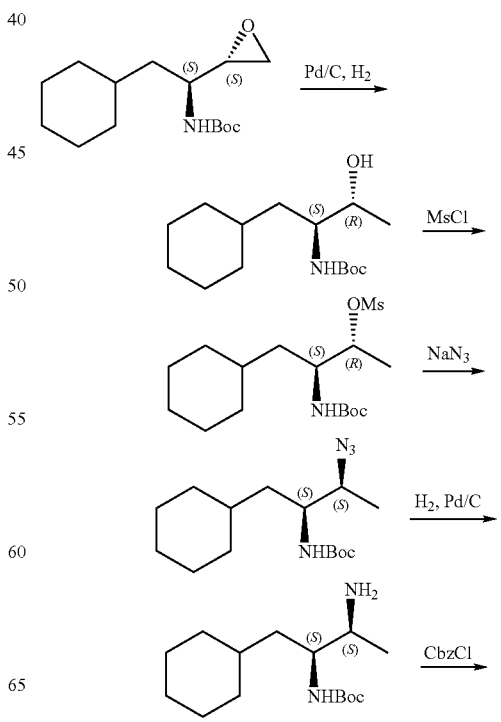

-continued

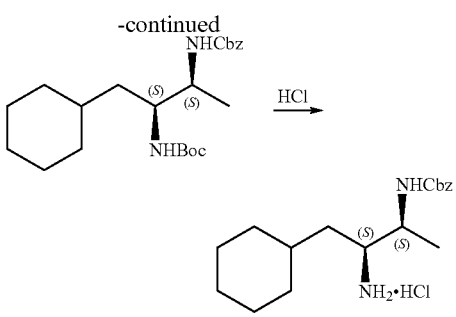

Step 1. Tert-butyl (2S,3R)-1-cyclohexyl-3-hydroxybutan-2-ylcarbamate

To a solution of tert-butyl (S)-2-cyclohexyl-1-((S)-oxiran-2-yl)ethylcarbamate (0.63 g, 2.5 mmol) and triethylamine (0.65 mL, 5 mmol) in methanol (15 mL) was added Pd/C (0.1 g), and the mixture was hydrogenated under 30 psi pressure at rt overnight. The mixture was filtered and the filtrate was concentrated to give tert-butyl (2S,3R)-1-cyclohexyl-3-hydroxybutan-2-ylcarbamate (0.44 g, 70%). $^1$H NMR (400 MHz, CDCl$_3$): 4.48 (brs, 1H), 3.78 (m, 2H), 2.30 (brs, 1H), 1.82 (m, 1H), 1.66 (m, 4h), 1.45 (s, 9H), 1.40-1.00 (m, 6H), 1.10 (d, J=6.4 Hz, 3H), 1.00-0.70 (m, 2H); MS (E/Z): 272 (M+H$^+$).

Step 2. Tert-butyl (2S,3R)-1-cyclohexyl-3-(methanesulfonyloxy)butan-2-ylcarbamate To a solution of tert-butyl (2S,3R)-1-cyclohexyl-3-hydroxybutan-2-ylcarbamate (0.44 g, 1.62 mmol) in dry CH$_2$Cl$_2$ (10 mL) was added Et$_3$N (0.71 g, 7 mmol, 4 eq) at 0 to −5° C. A solution of methanesulfonyl chloride (0.8 g, 7 mmol, 2 eq) in dry CH$_2$Cl$_2$ (5 mL) was added dropwise at the same temperature. The mixture was allowed to warm to rt gradually. TLC showed that the starting material had disappeared. Water (30 mL) was added. The aqueous layer was extracted with CH$_2$Cl$_2$ (3×20 mL). The combined organic layers was washed with 10% aq citric acid, satd aq NaHCO$_3$ and brine, then dried over Na$_2$SO$_4$, filtered and concentrated to give tert-butyl (2S,3R)-1-cyclohexyl-3-(methanesulfonyloxy)butan-2-yl-carbamate (0.46 g, 81%), which was used in the next step without purification.

Step 3. Tert-butyl (2S,3S)-3-azido-1-cyclohexylbutan-2-ylcarbamate tert-Butyl (2S,3R)-1-cyclohexyl-3-(methanesulfonyloxy)butan-2-ylcarbamate (0.46 g, 1.32 mmol) was dissolved into anhydrous DMF (10 mL), solid NaN$_3$ (0.26 g, 4 mmol) was added and the reaction mixture was heated to 80° C. overnight. The reaction mixture was cooled to rt and diluted with EtOAc (100 mL) and water (30 mL). The organic phase was washed with water (3×30 mL), dried over Na$_2$SO$_4$ and evaporated. The residue was separated by chromatography on a silica gel column to give tert-butyl (2S,3S)-3-azido-1-cyclohexylbutan-2-ylcarbamate (0.215 g, 55%). $^1$H NMR (400 MHz, CDCl$_3$): 4.38 (d, J=9.2 Hz, 1H), 3.72 (m, 1H), 3.60 (m, 1H), 1.82 (m, 1H), 1.67 (m, 4h), 1.44 (s, 9H), 1.40-1.00 (m, 61), 1.28 (d, J=6.4 Hz, 3H), 1.00-0.75 (m, 2H); MS (E/Z): 297 (M+H$^+$).

Step 4. Tert-butyl (2S,3S)-3-amino-1-cyclohexylbutan-2-ylcarbamate

A solution of tert-butyl (2S,3S)-3-azido-1-cyclohexylbutan-2-ylcarbamate (0.215 g, 0.73 mmol) in methanol (10 mL) was added to wetted Pd/C (0.1 g) and was hydrogenated with a balloon overnight. The reaction mixture was filtered through a pad of Celite and the solvent was removed to give tert-butyl (2S,3S)-3-amino-1-cyclohexylbutan-2-ylcarbamate (0.153 g, 78%), which was used in the next step without purification.

Step 5. Benzyl (2S,3S)-3-(tert-butoxycarbonyl)amino-4-cyclohexylbutan-2-ylcarbamate To a mixture of tert-butyl (2S,3S)-3-amino-1-cyclohexylbutan-2-ylcarbamate (0.153 g, 0.57 mmol) and Et$_3$N (0.19 mL, 1.42 mmol) in methanol (5 mL) at 0° C. was added dropwise a solution of CBZCl (0.116 g, 0.68 mmol) in methanol (3 mL). The mixture was warmed to rt, stirred 2 h, evaporated to remove methanol, diluted with water (15 mL) and extracted with EtOAc (3×10 mL). The combined organic layers were washed with brine (15 mL), dried and evaporated to give benzyl (2S,3S)-3-(tert-butoxycarbonyl)amino-4-cyclohexylbutan-2-ylcarbamate (0.117 g, 51%) that was used in the next step without further purification. $^1$H NMR (400 MHz, CDCl$_3$): 7.32 (m, 5H), 5.37 (brs, 1H), 5.09 (s, 2H), 4.36 (brs (1H), 3.76 (m, 2H), 1.82 (m, 1H), 1.66 (m, 4H), 1.44 (s, 9H), 1.35-1.10 (m, 6H), 1.07 (d, J=6.4 Hz, 3H), 1.00-0.78 (m, 2H); MS (E/Z): 405 (M+H$^+$).

Step 6. Benzyl (2S,3S)-3-amino-4-cyclohexylbutan-2-ylcarbamate

Benzyl (2S,3S)-3-(tert-butoxycarbonyl)amino-4-cyclohexylbutan-2-ylcarbamate (0.117 g, 0.29 mmol) was dissolved in 2 N HCl in methanol (10 mL, 20 mmol). The mixture was allowed to stir at 40-50° C. for 2 h. The mixture was concentrated in vacuo to give the HCl salt of benzyl (2S,3S)-3-amino-4-cyclohexylbutan-2-ylcarbamate (0.077 g, 78%).

Benzyl (2R,3S)-3-amino-4-cyclohexylbutan-2-ylcarbamate was prepared following the procedure described above starting with (1S,R)-(2-cyclohexyl-1-oxiranyl-ethyl)-carbamic acid tert-butyl ester.

Preparation D

(S)-2-(trimethylsilyl)ethyl 3-amino-5,5-dimethylhexyl(methyl)carbamate

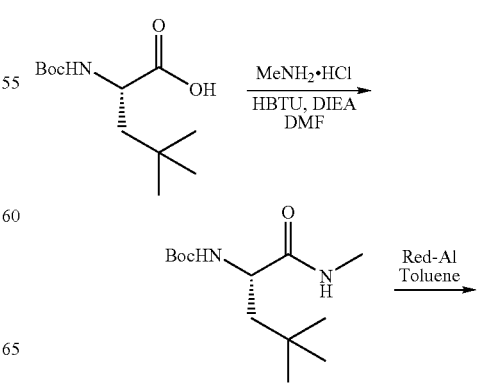

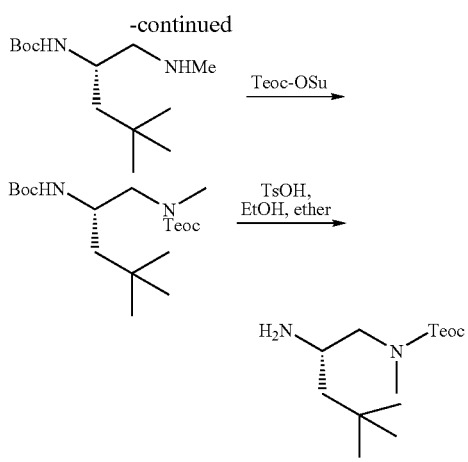

Step 1. tert-Butyl (S)-1-(methylcarbamoyl)-3,3-dimethylbutylcarbamate

To a solution of (S)-2-(t-butoxyaminocarbonylamino)-4,4-dimethylpentanoic acid (1.0 g, 4.08 mmol) and methylamine hydrochloride in DMF (10 mL) was added DIEA (2.1 mL, 12.2 mmol), followed by HBTU (1.55 g, 4.08 mmol). The resulting solution was stirred at rt until no starting material remained (~2 h). The solution was diluted with EtOAc (10 mL), washed with 1 N aq HCl (2×5 mL), sat'd aq NaHCO₃ (10 mL) and brine, and dried over Na₂SO₄. After removal of the solvent, the crude product was purified by flash column chromatography to give tert-butyl (S)-1-(methylcarbamoyl)-3,3-dimethylbutyl carbamate (1.05 g, quant.) as a clear oil. MS m/z 281 (M+Na⁺).

Step 2. tert-Butyl (S)-4,4-dimethyl-1-(methylamino)pentan-2-ylcarbamate

To a solution of tert-butyl (S)-1-(methylcarbamoyl)-3,3-dimethylbutyl carbamate (1.05 g, 4.08 mmol) in toluene (10 mL) at 0° C., there was added Red-Al (65 wt % in toluene, 3.73 mL, 12.2 mmol) dropwise. The solution was warmed to rt slowly and stirred overnight. The reaction was quenched with ice water, filtered through Celite, and solvent was removed to give tert-butyl (S)-4,4-dimethyl-1-(methylamino)pentan-2-ylcarbamate (0.79 g, 79%) as a clear oil. MS m/z 245 (M+H⁺).

Step 3. 2-(Trimethylsilyl)ethyl (S)-2-tert-butylcarboxylamino-4,4-dimethylpentylmethyl carbamate To a solution of tert-butyl (S)-4,4-dimethyl-1-(methylamino)pentan-2-ylcarbamate (0.79 g, 3.24 mmol) in acetone (10 mL) and water (3 mL) was added K₂CO₃ (1.34 g, 9.72 mmol), followed by Teoc-OSu (0.84 g, 3.24 mmol). The resulting mixture was stirred at rt until no starting material remained (~1 h). Acetone was removed in vacuo, and the aqueous residue was extracted with CH₂Cl₂ (4×5 mL), the combined organic layers were concentrated, and the crude residue was purified by flash column chromatography to give 2-(trimethylsilyl)ethyl (S)-2-tert-butylcarboxylamino-4,4-dimethylpentylmethyl carbamate (0.74 g, 59%) as a clear oil. MS m/z 389 (M+H⁺).

Step 4. (S)-2-(trimethylsilyl)ethyl 3-amino-5,5-dimethylhexyl(methyl)carbamate To a solution of 2-(trimethylsilyl)ethyl (S)-2-tert-butylcarboxylamino-4,4-dimethylpentylmethyl carbamate (0.74 g, 1.90 mmol) in ether (7 mL) was added a solution of p-toluenesulfonic acid (0.37 g, 1.92 mmol) in 1.5 mL of ethanol (1.5 mL). Transfer of the p-toluenesulfonic acid was completed with the aid of ether (1 mL). The solution was placed on a rotary evaporator and the ether removed under reduced pressure at rt. Then, with continuing evacuation, the bath temperature was raised to 60-65° C. for 20 min, during which gas evolution was evident. The solid residue of the toluensulfonate salt of (S)-2-(trimethylsilyl)ethyl 3-amino-5,5-dimethylhexyl(methyl)carbamate was used without purification in the next step. MS m/z 289 (M+H⁺).

Preparation E

Benzyl (S)-2-amino-3-(cis-4-fluorocyclohexyl)propylmethylcarbamate

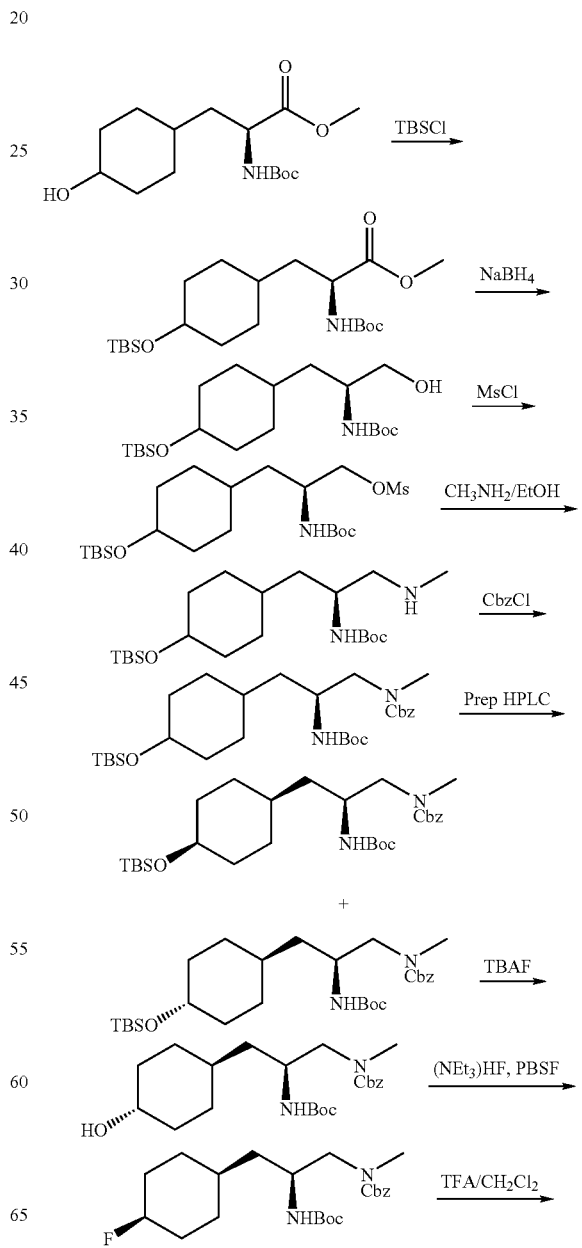

-continued

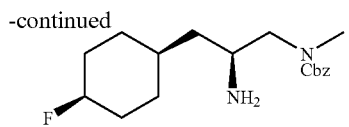

Step 1. tert-butyl (S)-1-(methoxycarbonyl)-2-(4-(t-butyldimethylsilyloxy)cyclohexyl)-ethylcarbamate To a solution of TBSCl (12.7 g, 85 mmol) in dichloromethane (20 mL) was added dropwise a mixture of 2-tert-butoxycarbonylamino-3-(4-hydroxy-cyclohexyl)-propionic acid methyl ester (17 g, 56 mmol) and imidazole (7.68 g, 113 mmol) in dichloromethane (200 mL) at 0° C. After stirring at rt for 5 h, the reaction mixture was washed with water and brine. The organic layer was dried over $Na_2SO_4$ and concentrated to give tert-butyl (S)-1-(methoxycarbonyl)-2-(4-(t-butyldimethylsilyloxy)cyclohexyl)ethylcarbamate (21 g, 91%) that was used in the next step without further purification. $^1$H NMR (CDCl$_3$, 400 MHz) δ 0.08 (d, 6H), 0.89 (d, 9H), 1.45 (s, 9H), 1.51 (m, 4H), 1.58 (m, 1H), 1.68 (t, 4H), 1.85 (d, 1H), 3.71 (d, 3H), 3.91 (m, 1H), 4.34 (m, 1H), 4.86 (m, 1H).

Step 2. (2S)-2-(t-butoxycarbonylamino)-3-(4-(t-butyldimethylsilyloxy)cyclohexyl)propan-1-ol To a solution of tert-butyl (S)-1-(methoxycarbonyl)-2-(4-(t-butyldimethylsilyloxy)-cyclohexyl)ethylcarbamate (25 g, 60 mmol) in EtOH (500 mL) at 0° C. was added NaBH$_4$ (18 g, 480 mmol) in portions. The mixture was stirred for 6 h at rt and then evaporated. The residue was partitioned between water (200 mL) and EtOAc (2×200 mL). The combined organic layers were washed with brine, dried over MgSO$_4$, and evaporated to give (2S)-2-(t-butoxycarbonylamino)-3-(4-(t-butyldimethylsilyloxy)cyclohexyl)propan-1-ol (23 g, yield 98%). $^1$H NMR (CDCl$_3$, 400 MHz) δ 0.08 (d, 6H), 0.89 (d, 9H), 1.30 (m, 4H), 1.40 (t, 2H), 1.45 (s, 9H), 1.61 (m, 1H), 1.58 (m, 1H), 1.68 (t, 4H), 1.85 (d, 1H), 3.50 (m, 1H), 3.65 (m, 1H), 3.73 (m, 1H), 3.91 (s, 1H), 4.53 (s, 1H).

Step 3. (2S)-2-(t-butoxycarbonylamino)-3-(4-(t-butyldimethylsilyloxy)cyclohexyl)-1-methanesulfonyloxypropane To a solution of (2S)-2-(t-butoxycarbonylamino)-3-(4-(t-butyldimethylsilyloxy)-cyclohexyl)propan-1-ol (23 g, 59 mmol) in CH$_2$Cl$_2$ (250 mL) was added Et$_3$N (15 g, 148 mmol). The reaction mixture was cooled to −20° C. and a solution of MsCl (14.9 g, 131 mmol) in CH$_2$Cl$_2$ (40 mL) added dropwise. After returning to rt then stirring for an additional 1 h, at which point TLC showed no starting material, water (100 mL) was added and the mixture was extracted with CH$_2$Cl$_2$ (2×150 mL). The combined organic layers were washed with brine, dried over MgSO$_4$ and evaporated to give crude (2S)-2-(t-butoxycarbonylamino)-3-(4-(t-butyldimethyl-silyloxy)cyclohexyl)-1-methanesulfonyloxypropane (30 g) that was used in the next step without further purification.

Step 4. tert-Butyl (S)-1-(4-(t-butyldimethylsilyloxy)cyclohexyl)-3-(methylamino)propan-2-ylcarbamate A solution of crude (2S)-2-(t-butoxycarbonylamino)-3-(4-(t-butyldimethylsilyloxy)cyclohexyl)-1-methanesulfonyloxypropane (30 g) in methylamine alcohol solution (300 mL) was heated under reflux overnight. The solvent was removed in vacuo and the residue was purified by silica chromatography to obtain tert-butyl (S)-1-(4-(t-butyldimethylsilyloxy)cyclohexyl)-3-(methylamino)propan-2-ylcarbamate as a solid (15 g, 63% for 2 steps). $^1$H NMR (CDCl$_3$, 400 MHz) δ 0.08 (d, 6H), 0.89 (d, 9H), 1.25 (t, 3H), 1.45 (s, 9H), 1.61 (m, 2H), 1.82 (t, 2H), 2.01 (d, 1H), 2.56 (d, 2H), 2.80 (d, 2H), 2.95 (t, 2H), 3.49 (m, 1H), 3.61 (m, 1H), 3.90 (s, 1H), 5.35 (d, 1H), 7.15 (m, 1H).

Step 5. tert-Butyl (S)-1-(4-(t-butyldimethylsilyloxy)cyclohexyl)-3-(N-(benzyloxycarbonyl)-N-methylamino)propan-2-ylcarbamate To a mixture solution of tert-butyl (S)-1-(4-(t-butyldimethylsilyloxy)cyclohexyl)-3-(methylamino)propan-2-ylcarbamate (112 g, 209 mmol) and Et$_3$N (52.8 g, 522 mmol) in CH$_2$Cl$_2$ (1200 mL) was added dropwise a solution of benzyl chloroformate (39 g, 230 mmol) in CH$_2$Cl$_2$ (40 mL) at −20° C. After stirring for an additional 2 h, water (400 mL) was added and the mixture was extracted with CH$_2$Cl$_2$ (2×200 mL). The organic layers were washed with brine, dried over MgSO$_4$, and evaporated. The residue was purified by silica chromatography to afford crude tert-butyl (S)-1-(4-(t-butyldimethylsilyloxy)cyclohexyl)-3-(N-(benzyloxycarbonyl)-N-methylamino)propan-2-ylcarbamate (90 g) as an oil which was a mixture of two isomers. The isomers were separated by preparative HPLC. $^1$H NMR (CDCl$_3$, 400 MHz): δ=0.08 (s, 6H), 0.89 (s, 9H), 1.28 (m, 4H), 1.40 (d, 9H), 1.59 (m, 4H), 2.96 (d, 3H), 3.05 (d, 1H), 3.15 (d, 1H), 3.45 (t, 3H), 3.90 (s, 1H), 5.12 (d, 2H), 7.33 (m, 5H).

Step 6. tert-Butyl (S)-1-(trans-4-hydroxycyclohexyl)-3-(N-(benzyloxycarbonyl)-N-methylamino)propan-2-ylcarbamate tert-Butyl (S)-1-(trans-4-(t-butyldimethylsilyloxy)cyclohexyl)-3-(N-(benzyloxycarbonyl)-N-methylamino)propan-2-ylcarbamate (18 g, 34 mmol) was treated with 4 M nBu$_4$NF/THF (50 mL) at 50° C. for 6 h. Water (30 mL) was added and the mixture was extracted with EtOAc (3×100 mL). The combined organic layers were washed with brine, dried over MgSO$_4$ and evaporated to give crude tert-butyl (S)-1-(trans-4-hydroxycyclohexyl)-3-(N-(benzyloxycarbonyl)-N-methylamino)propan-2-ylcarbamate (9 g, 64%) that was purified by silica chromatography. $^1$H NMR (CDCl$_3$, 400 MHz) δ 1.41 (d, 9H), 1.65 (m, 6H), 1.95 (m, 3H), 2.98 (d, 3H), 3.10 (m, 1H), 3.52 (m, 1H), 3.90 (m, 1H), 5.13 (d, 2H), 7.33 (m, 5H).

Step 7. tert-Butyl (S)-1-(cis-4-fluorocyclohexyl)-3-(N-(benzyloxycarbonyl)-N-methylamino)propan-2-ylcarbamate A mixture of tert-butyl (S)-1-(trans-4-hydroxycyclohexyl)-3-(N-(benzyloxycarbonyl)-N-methylamino)propan-2-ylcarbamate (3 g, 7 mmol), Et$_3$N (12 mL, 88 mmol), NEt$_3$(HF)$_3$ (4.71 mL, 29 mmol) and perfluorobutanesulfonyl fluoride (5.21 mL, 29 mmol) was stirred in THF (70 mL, 1 mmol/10 mL) at 50° C. until HPLC revealed complete conversion. The reaction mixture was quenched with water and extracted with EtOAc (2×100 mL), dried over MgSO$_4$ and evaporated. The residue was then purified by prep HPLC to give tert-butyl (S)-1-(trans-4-fluorocyclohexyl)-3-(N-(benzyloxycarbonyl)-N-methylamino)propan-2-ylcarbamate (1.16 g, 40%) as a white solid. $^1$H NMR (CDCl$_3$, 400 MHz)

δ 1.41 (d, 9H), 1.68 (m, 6H), 1.96 (m, 3H), 2.98 (d, 3H), 3.20 (m, 1H), 3.52 (m, 1H), 3.90 (m, 1H), 5.13 (d, 2H), 7.33 (m, 5H).

Step 8. Benzyl (S)-2-amino-3-(cis-4-fluorocyclohexyl)propylmethylcarbamate

A solution of tert-butyl (S)-1-(trans-4-fluorocyclohexyl)-3-(N-(benzyloxycarbonyl)-N-methylamino)propan-2-ylcarbamate (550 mg, 1.3 mmol) in TFA/CH$_2$Cl$_2$ (20 mL, v/v 20%) was stirred for 1 h at rt, quenched with satd aq NaHCO$_3$ until no further gas evolution was visible and extracted with CH$_2$Cl$_2$ (2×50 mL). The combined organic layers were washed with brine, dried over MgSO$_4$, filtered and condensed under reduced pressure to obtain benzyl (S)-2-amino-3-(cis-4-fluorocyclohexyl)propylmethylcarbamate (400 mg, yield 95%). $^1$H NMR (CDCl$_3$, 400 MHz) δ 1.42 (m, 4H), 1.64 (m, 4H), 2.98 (d, 3H), 3.21 (m, 1H), 3.50 (m, 1H), 3.90 (m, 1H), 5.13 (d, 2H), 7.33 (m, 5H).

Preparation F

Benzyl (S)-2-amino-3-(trans-4-fluorocyclohexyl)propylmethylcarbamate

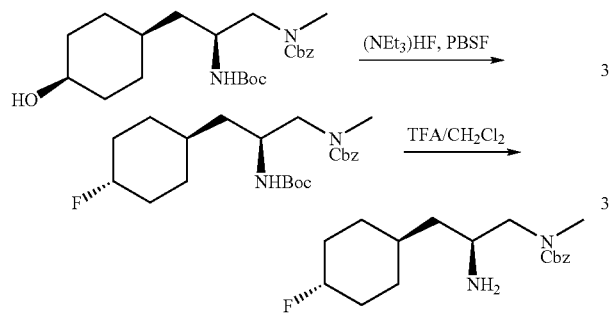

Step 1. Benzyl (S)-2-(t-butoxycarbonylamino)-3-(trans-4-fluorocyclohexyl)propyl-(methyl)carbamate A mixture of benzyl (S)-2-(t-butoxycarbonylamino)-3-(cis-4-hydroxycyclohexyl)-propyl(methyl)carbamate (1 g, 2.38 mmol), base Et$_3$N (5 mL, 28 mmol), a fluoride source NEt$_3$(HF)$_3$ (1.9 mL, 9.52 mmol) and perfluorobutanesulfonyl fluoride (2.1 mL, 9.52 mmol) were stirred in THF (24 mL, 1 mmol/10 mL) in a capped vial or flask at 50° C. until LC revealed complete conversion. The reaction mixture was quenched with water and extracted with EtOAc (2×100 mL), dried over MgSO$_4$, and evaporated. The residue was then purified by preparative HPLC to give benzyl (S)-2-(t-butoxycarbonylamino)-3-(trans-4-fluorocyclohexyl)propyl-(methyl)carbamate (200 mg, 20%) as a white solid.

Step 2. (2-Amino-3-(4-fluoro-cyclohexyl)-propyl)-methyl-carbamic acid benzyl ester A solution of benzyl (S)-2-(t-butoxycarbonylamino)-3-(trans-4-fluorocyclohexyl)-propyl(methyl)carbamate (200 mg, 0.47 mmol) in TFA/CH$_2$Cl$_2$ (15 mL, v/v 20%) was stirred for 1 h at rt, then quenched by addition of sat'd aq NaHCO$_3$ solution until gas evolution ceased. The mixture was extracted with CH$_2$Cl$_2$ (2×50 mL). The combined organic layers were washed with brine, dried over MgSO$_4$, filtered and concentrated under reduced pressure to obtain benzyl (S)-2-amino-3-(trans-4-fluorocyclohexyl)propyl(methyl)carbamate (140 mg, yield 93%). $^1$HNMR (CDCl$_3$, 400 MHz): δ 1.42 (m, 4H), 1.64 (m, 4H), 2.98 (d, 3H), 3.21 (m, 1H), 3.50 (m, 1H), 3.90 (m, 1H), 5.13 (d, 2H), 7.33 (m, 5H).

Preparation G (S)-2-(trimethylsilyl)ethyl 2-amino-3-(3-noradamantyl)propyl(methyl)carbamate

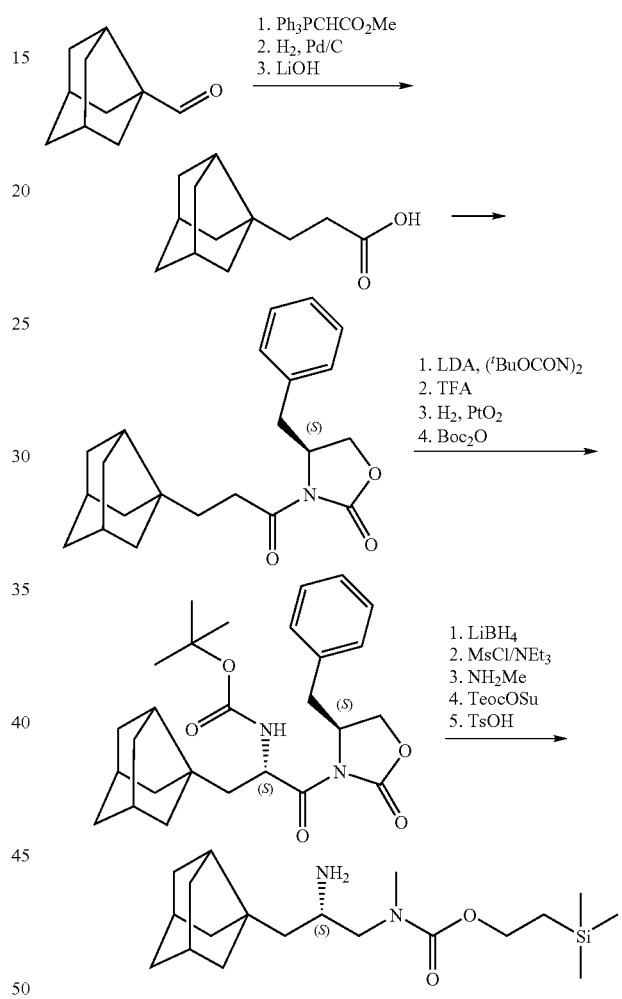

Step 1a-c. 3-(3-noradamantyl)propanoic acid

A 250-mL flask was charged with 3-noradamantylcarboxaldehyde (3.3 g, 22 mol), Ph$_3$PCHCO$_2$Me (9.2 g, 27.5 mmol, 1.25 equiv) and CHCl$_3$ (100 mL). The mixture was heated to reflux for 18 h. The clear solution was allowed to cool to ambient and evaporated. The sticky residue was taken up in 4:1 hexanes/EtOAc (200 mL) and filtered through a pad of silica gel. The pad was washed with additional 4:1 hexanes/EtOAc (200 mL) and the filtrate was evaporated. The product was isolated by flash chromatography on 120 g of silica, eluting with 0-17% EtOAc in hexanes. This afforded (E)-methyl 3-(3-noradamantyl)acrylate (4.13 g, 0.2 mmol, 90%).

A 500-mL pressure bottle was charged with (E)-methyl 3-(3-noradamantyl)acrylate (7.8 g, 37.8 mmol), 10% Pd/C (1.8 g), and (MeOH) 100 mL. The bottle was fitted to a Parr hydrogenation shaker, pressurized to 50 psi with $H_2$, and evacuated. The fill/evacuation procedure was repeated 3×, and the apparatus pressurized with 50 psi $H_2$ and shaken for 3 h. After this time tlc analysis showed no remaining enoate. The mixture was filtered through a pad of celite. The spent catalyst was washed with additional methanol and the combined filtrates were evaporated to yield methyl 3-(3-noradamantyl)propanoate (7.8 g, 37.8 mmol) in quantitative yield.

Methyl 3-(3-noradamantyl)propanoate (7.8 g, 37.8 mmol) was dissolved in THF (150 mL) and the solution was cooled to 0° C. To this was added 1.0 M aqueous LiOH (148 mL). The biphasic reaction mixture was vigorously stirred at 0° C. After 3 h, a homogeneous solution was produced and LC-MS analysis showed no ester remained. The pH of the solution was lowered to ~4 by the dropwise addition of concentrated HCl. The mixture was transferred to a separatory funnel and the layers were separated. The aqueous layer was extracted with EtOAc (4×30 mL). The combined organic layers were dried over $Na_2SO_4$, filtered, and evaporated to afford 3-(3-noradamantyl)propanoic acid (7.15 g, 36.8 mmol) as a tacky solid.

Step 2. (S)-4-benzyl-3-(3-(3-noradamantyl)propanoyl)oxazolidin-2-one 3-(3-Noradamantyl)propanoic acid (7.15 g, 36.8 mmol, 1.0 equiv) was dissolved in THF (70 mL) and the solution was cooled to 0° C. To the stirred solution were added N-methylmorpholine (4.25 mL, 38.7 mmol, 1.05 equiv) and isobutyl chloroformate (4.52 mL, 38.7 mmol, 1.05 equiv). A white precipitate rapidly formed and the mixture containing the 3-(noradamantyl)propanoic(isobutylcarbonic) anhydride was allowed to stir for 0.5 h at 0° C. A separate 500-mL 3-neck flask was charged with S-(−)-4-benzyloxazolidinone (8.5 g, 47.8 mmol, 1.35 equiv) and THF (100 mL). The mixture was cooled to −78° C. and ″BuLi (19.1 mL of a 2.5 M solution) was added over a 10 min period. This was allowed to stir for 0.5 h at −78° C. The first solution was rapidly filtered through a pad of Celite and the resulting clear filtrate transferred via cannula to the solution of the deprotonated oxazolidinone. After stirring for 0.5 h at −78° C. LC-MS analysis showed consumption of the mixed anhydride. The mixture was quenched with brine and allowed to warm to rt. The mixture was transferred to a separatory funnel. The organic layer was separated and evaporated. Flash chromatography (120 g $SiO_2$, O-27% EtOAc in hexanes) afforded (S)-4-benzyl-3-(3-(3-noradamantyl)propanoyl)oxazolidin-2-one.

Step 3a-d. tert-butyl (S)-1-((S)-4-benzyl-2-oxooxazolidin-3-yl)-3-(3-noradamantyl)-1-oxopropan-2-ylcarbamate A solution of LDA was generated by charging an oven-dried 50-mL flask with dry THF (10 mL) and diisopropylamine (152 mg, 1.5 mmol, 1.5 equiv). The mixture was cooled to −0° C. and ″BuLi (2.5 M, 0.6 mL, 1.5 mmol, 1.5 equiv) added dropwise over 5 min. The mixture was stirred for 0.5 h and cooled to −78° C. A solution of (S)-4-benzyl-3-(3-(3-noradamantyl)propanoyl)oxazolidin-2-one (335 mg, 1.0 mmol, 1.0 equiv) in THF (9 mL) was cooled to −78° C. and added to the solution of LDA via cannula. The mixture was allowed to stir for 0.5 h. A separate flask was charged with ′$BuCO_2N$=$NCO_2$′Bu (345 mg, 1.5 mmol, 1.5 equiv) and THF (9 mL) and cooled to −78° C. This solution was transferred to the enolate solution with the aid of a cannula. The resulting mixture was allowed to stir at −78° C. for 0.5 h.

Tlc analysis showed consumption of the starting material. The mixture was quenched with HOAc (0.5 mL), and allowed to warm to rt. The solution was transferred to a separatory funnel and the organic layer was washed with water and brine, dried over $Na_2SO_4$ and filtered. The product was purified by flash chromatography on $SiO_2$, eluting with 0-37% EtOAc in hexanes. This yielded di-tert-butyl 1-((S)-1-((S)-4-benzyl-2-oxooxazolidin-3-yl)-3-(3-noradamantyl)-1-oxopropan-2-yl)hydrazine-1,2-dicarboxylate (477 mg, 0.82 mmol, 82%).

The Boc protected hydrazine was dissolved in 3:1 $CH_2Cl_2$/TFA (20 mL) and stirred for 4 h. LC-MS analysis showed only the presence of the desired product. The mixture was evaporated to afford (S)-4-benzyl-3-((S)-3-(3-noradamantyl)-2-hydrazinylpropanoyl)oxazolidin-2-one as its TFA salt which was used directly in the next step.

The hydrazine TFA salt was dissolved in EtOH (10 mL) of and transferred to a Parr hydrogenation shaker. $PtO_2$ (56 mg, 0.25 mmol, 0.3 equiv) was added and the vessel pressurized to 60 psi with $H_2$, and evacuated. The fill/evacuation procedure was repeated 3 times, and then the apparatus pressurized with 60 psi $H_2$ and shaken for 4 h. After this time the hydrazine was no longer observed in the LC/MS. The mixture was filtered and evaporated to give crude (S)-3-((S)-2-amino-3-cyclopentylpropanoyl)-4-benzyloxazolidin-2-one which was used without purification.

Crude (S)-3-((S)-2-amino-3-cyclopentylpropanoyl)-4-benzyloxazolidin-2-one from the previous step was dissolved in 1:1 acetonitrile/10% aqueous $K_2CO_3$ (20 mL). $Boc_2O$ (327 mg, 1.5 mmol, 1.8 equiv) was added and mixture was stirred for 4 h. LC-MS showed consumption of the free amine. The acetonitrile was removed in vacuo and the product was extracted with EtOAc (2×20 mL). The combined organic extracts were dried over $Na_2SO_4$, filtered, and evaporated. Flash chromatography afforded tert-butyl (S)-1-((S)-4-benzyl-2-oxooxazolidin-3-yl)-3-(3-noradamantyl)-1-oxopropan-2-ylcarbamate (148 mg, 0.32 mmol).

Step 4a-e. (S)-2-(trimethylsilyl)ethyl 2-amino-3-(3-noradainantyl)propyl(methyl)carbamate tert-butyl (S)-1-((S)-4-benzyl-2-oxooxazolidin-3-yl)-3-(3-noradamantyl)-1-oxopropan-2-ylcarbamate (2.0 g, 4.23 mmol) was dissolved in THF and the solution was cooled to 0° C. Methanol (250 μL) was added, followed by a solution of $LiBH_4$ (2.0 M in THF, 8.6 mL, 4.0 equiv). The mixture was allowed to stir at 0° C. until LC-MS analysis indicated that the starting material had been consumed. Excess $LiBH_4$ was quenched by addition of satd aq $NH_4Cl$ and the contents were transferred to a separatory funnel. The layers were separated, the aqueous layer was extracted with EtOAc, and the combined organic layers were washed with brine, dried over $Na_2SO_4$, filtered and evaporated. The protected residue was purified by flash chromatography on silica, eluting with 0-29% EtOAc in hexanes. This afforded (S)-tert-butyl 1-(3-noradamantyl)-3-hydroxypropan-2-ylcarbamate (1.24 g, >98%).

(S)-tert-butyl 1-(3-noradamantyl)-3-hydroxypropan-2-ylcarbamate (75 mg, 0.25 mmol, 1.0 equiv) was dissolved in $CH_2Cl_2$ and cooled to 0° C. Triethylamine (101 mg, 1.0 mmol, 4.0 equiv) was added, followed by methanesulfonyl chloride (58 mg, 0.50 mmol, 2.0 equiv). The mixture was allowed to stir till the starting material was consumed by LC.MS analysis. The mixture was quenched by addition of satd aq $NH_4Cl$ and the contents were transferred to a separatory funnel. The layers were separated and the organic layer was washed with brine, dried over $Na_2SO_4$, filtered, and evaporated to afford (S)-2-(tert-butoxycarbonylamino)-3-(3-noradamantyl)methanesulfonate which was used directly in the next step.

The crude mesylate was dissolved in of 33 wt % methylamine in ethanol (20 mL). The mixture was heated to reflux overnight. The solution was evaporated and the residue was taken up in EtOAc. The solution was washed with saturated NaHCO₃ and brine, and evaporated to afford crude (S)-tert-butyl 1-(3-noradamantyl)-3-(methylamino)propan-2-ylcarbamate which was used directly in the next step.

The crude amine was dissolved in 1:1 acetonitrile/10% aqueous K₂CO₃ (20 mL). TeocOSu (97 mg, 0.375 mmol, 1.5 equiv) was added and mixture was stirred for 4 h. LC-MS showed consumption of the free amine. The acetonitrile was removed in vacuo and the aqueous residue was extracted with EtOAc (2×20 mL). The combined organic extracts were dried over Na₂SO₄, filtered, and evaporated. The product was isolated by flash chromatography on silica eluting with 0-27% EtOAc. (S)-2-(trimethylsilyl)ethyl 2-(t-butoxycarbonylamino)-3-(3-noradamantyl)propyl(methyl)carbamate (36 mg, 0.080 mmol, 32% yield for Steps 4b-d) was isolated.

(S)-2-(trimethylsilyl)ethyl 2-(t-butoxycarbonylamino)-3-(3-noradamantyl)propyl(methyl)carbamate (36 mg, 0.080 mmol, 1.0 equiv) was dissolved in MeOH (5 mL). Toluenesulfonic acid hydrate (16 mg, 0.088 mmol, 1.1 equiv) was added and the solvent was removed at 65° C. under vacuum to afford (S)-2-(trimethylsilyl)ethyl 2-amino-3-(3-noradamantyl)propyl(methyl)carbamate. This material was used without purification.

Preparation H 2-(trimethylsilyl)ethyl (2S)-2-amino-3-(tetrahydro-2H-pyran-2-yl)propylcarbamate

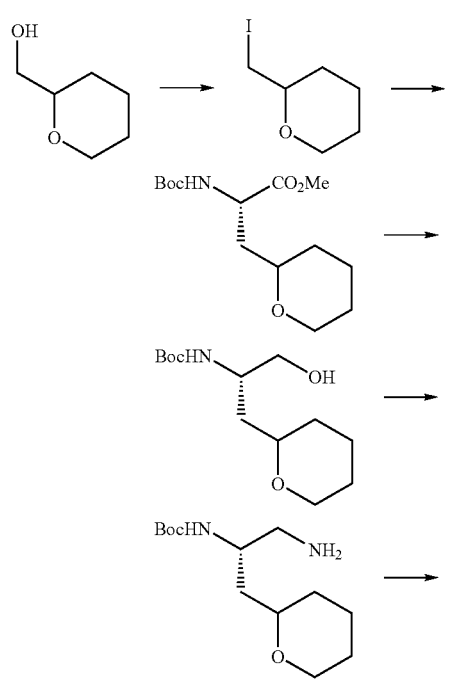

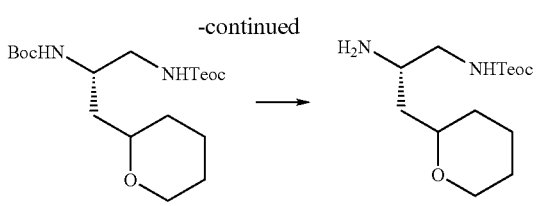

Step 1. 2-(iodomethyl)tetrahydro-2H-pyran

A CH₂Cl₂ solution of (tetrahydro-2H-pyran-2-yl)methanol (7.91 g, 68.1 mmol), Et₃N (14 mL, 102 mmol), and catalytic DMAP was treated with 4-bromobenzenesulfonyl chloride (14.3 g, 74.9 mmol). After 2 h, the reaction was quenched with water. The organic layer was washed with 1M HCl and brine, dried over Na₂SO₄, filtered, and concentrated. The crude material was purified by chromatography on silica gel (EtOAc/Hex) to afford ((tetrahydro-2H-pyran-2-yl)methyl 4-bromobenzenesulfonate as an oil (16 g).

A solution of ((tetrahydro-2H-pyran-2-yl)methyl 4-bromobenzenesulfonate (16 g, 48 mmol) in acetone (250 mL) was treated with sodium iodide (73 g, 48 mmol). The solution was heated at 40° C. for 24 h. The reaction was cooled to rt and the acetone was removed under reduced pressure. The residue was dissolved in hexane and water. The aqueous layer was extracted with hexane three times. The combined organic extracts were dried over Na₂SO₄, filtered and concentrated. The residue was passed through a plug of silica gel, eluting with hexanes several times. After solvent removal, 2-(iodomethyl)tetrahydro-2H-pyran was isolated as an oil (10 g). ¹³C NMR (400 MHz, CDCl₃): 77.2, 68.8, 31.7, 25.6, 23.2, 10.0.

Step 2. (2S)-methyl 2-(tert-butoxycarbonylamino)-3-(tetrahydro-2H-pyran-2-yl)propanoate To a solution of (R)-2,5-dihydro-3,6-dimethoxy-2-isopropylpyrazine in THF at −78° C., n-BuLi (16 mL, 2.5 M in Hexanes) was added dropwise. The mixture was stirred for 1 h and a solution of 2-(iodomethyl)tetrahydro-2H-pyran in THF (6 mL) was added. The reaction flask was transferred to a −20° C. freezer and allowed to stir for 72 h. The reaction was quenched with satd aq NH₄Cl and the aqueous solution was extracted with ether. The combined organic layers were dried over Na₂SO₄. The solvent was removed under reduced pressure and the crude product was purified by chromatography on silica gel (EtOAc/Hex). The product was dissolved in acetonitrile (50 mL) and 2 M aq HCl (50 mL) and stirred at rt for 4 h. The solvent was evaporated and the crude material redissolved in water (100 mL) and THF (100 mL). The solution was chilled to 0° C. and K₂CO₃ (23 g, 166 mmol) was added in portions, followed by addition of di-tert-butyl dicarbonate (22.6 g, 104 mmol). The mixture was allowed to warm rt and stirred for several hours. The aqueous layer was extracted with EtOAc (3 x). The combined organic layers were washed with brine, dried over MgSO₄, filtered, and concentrated. The crude product was purified by chromatography on silica gel (EtOAc/Hex) to afford (2S)-methyl 2-(tert-butoxycarbonylamino)-3-(tetrahydro-2H-pyran-2-yl)propanoate (6.61 g). MS m/z 310 (M+Na).

Step 3. tert-butyl (2S)-1-hydroxy-3-(tetrahydro-2H-pyran-2-yl)propan-2-ylcarbamate (2 S)-methyl 2-(tert-butoxycarbonylamino)-3-(tetrahydro-2H-pyran-2-yl)propanoate (3.88 g, 13.52 mmol) was dissolved in 4 N HCl in dioxane (4 mL). After deprotection was complete the solvent was evaporated. The crude material was redissolved in CH$_2$Cl$_2$ and neutralized with aq NaHCO$_3$. The aqueous layer was extracted with CH$_2$Cl$_2$ (3×). The combined organic layers were dried over Na$_2$SO$_4$, and filtered. After solvent removal, the crude (2S)-methyl 2-amino-3-(tetrahydro-2H-pyran-2-yl)propanoate was used without any further purification. MS m/z 188 (M+1).

At −78° C., (2S)-methyl 2-amino-3-(tetrahydro-2H-pyran-2-yl)propanoate (1.84 g, 7.74 mmol) in THF (16 mL) was treated with lithium aluminum hydride (8 mL, 1 M in THF) at a rate such that the temperature remained below −65° C. The reaction was allowed to warm to rt. Upon completion, the reaction was cooled to 0° C. and quenched by dropwise addition of water, avoiding a rise in temperature above 2° C., the slurry was then stirred for an additional 1 h. The emulsion was dispersed by stirring with 1 M aq NaOH for 30 min, allowing warming to rt. Celite was added and stirred. The slurry was filtered through celite and washed several times with diethyl ether. The filtrate was concentrated to provide (2S)-2-amino-3-(tetrahydro-2H-pyran-2-yl)propan-1-ol as an oil and used without any further purification. A solution of (2S)-2-amino-3-(tetrahydro-2H-pyran-2-yl)propan-1-ol in THF (20 mL) and water (20 mL) was cooled to 0° C. Potassium carbonate (3.2 g, 23.2 mmol) was added, followed by di-tert-butyl dicarbonate (2.2 g, 10.06 mmol). The reaction was subsequently warmed to rt and stirred for 2 h. The aqueous layer was extracted 3 times with EtOAc. The combined organic layers were washed with brine, dried over MgSO$_4$, and filtered. After solvent removal the crude material was purified by chromatography on silica gel (EtOAc/Hex) to afford tert-butyl (2S)-1-hydroxy-3-(tetrahydro-2H-pyran-2-yl)propan-2-ylcarbamate (1.41 g) as an oil. MS m/z 282 (M+Na).

Step 4. 2-(trimethylsilyl)ethyl (2S)-2-amino-3-(tetrahydro-2H-pyran-2-yl)propylcarbamate At 0° C., tert-butyl (2S)-1-hydroxy-3-(tetrahydro-2H-pyran-2-yl)propan-2-ylcarbamate (1.41 g, 5.44 mmol) in CH$_2$Cl$_2$ (50 mL) was treated with Et$_3$N (2.3 mL, 16.3 mmol) followed by methanesulfonyl chloride (1.1 mL, 13.6 mmol). The reaction was allowed to stir for 1 h and quenched with water. The organic layer was washed with satd aq NaHCO$_3$ and brine, dried over Na$_2$SO$_4$, and filtered. After removal of solvent, the crude material was purified using chromatography on silica gel (EtOAc/Hex) to afford (2S)-2-(tert-butoxycarbonylamino)-3-(tetrahydro-2H-pyran-2-yl)propyl methanesulfonate (0.90 g) as a solid. MS m/z 360 (M+Na).

The mesylate (0.90 g, 2.66 mmol) and sodium azide (0.89 g, 13.3 mmol) were dissolved in DMF (30 mL). The mixture was heated at 60° C. for 4 h. The reaction was treated with ice water (100 mL) and extracted with EtOAc (3×). The organic layer was dried over MgSO$_4$ and filtered. The solvent was removed under reduced pressure and the product was used without any further purification. At −78° C., a solution of the azide (~2.66 mmol) in THF (20 mL) was treated with LiAlH$_4$ (3.1 mL, 1M in THF). The reaction was allowed to warm to 0° C. over several hours. The reaction was quenched by the addition of brine at 0° C. Celite was added to the emulsion and stirred for several hours before filtering through a bed of celite. Evaporation of solvent afforded tert-butyl (2S)-1-amino-3-(tetrahydro-2H-pyran-2-yl)propan-2-ylcarbamate which was used without further purification. MS m/z 259 (M+1).

A solution of the amine was dissolved in CH$_2$Cl$_2$ (13 mL) and water (5 mL). The solution was treated with K$_2$CO$_3$ (2.20 g, 15.9 mmol) and 1-[2-trimethylsilyl)ethoxycarbonyloxy]pyrrolidin-2,5-dione (1.24 g, 4.79 mmol). The reaction was stirred for 1 h. The layers were separated and the organic layer was washed with water. After removal of solvent the crude material was redissolved in diethyl ether (2 mL) and ethanol (30 mL). The solution was treated with p-toluenesulfonic acid (0.53 g, 2.71 mmol) and placed on a rotary evaporator with a 60° C. water bath. The solvent was removed. Additional solvent was added and removed as above until complete removal of the Boc group had occurred. The crude material was redissolved in CH$_2$Cl$_2$ and washed with satd aq NaHCO$_3$. The aqueous layer was extracted with CH$_2$Cl$_2$ (3×). The combined organic layers were washed with brine, dried over Na$_2$SO$_4$, and concentrated. The crude product was purified by chromatography on silica gel (10% MeOH/CH$_2$Cl$_2$) to afford 2-(trimethylsilyl)ethyl (2S)-2-amino-3-(tetrahydro-2H-pyran-2-yl)propylcarbamate (0.62 g) as an oil. MS m/z 303 (M+1).

The following compounds were prepared following procedures analogous to those described above:

2-(trimethylsilyl)ethyl (2S)-2-amino-3-(tetrahydro-2H-pyran-4-yl)propylcarbamate using (tetrahydro-2H-pyran-4-yl)methanol in the first step.

Preparation I tert-Butyl (2R,3S)-2-amino-3-cyclohexyl-3-(trimethylsilyloxy)propyl(methyl)carbamate

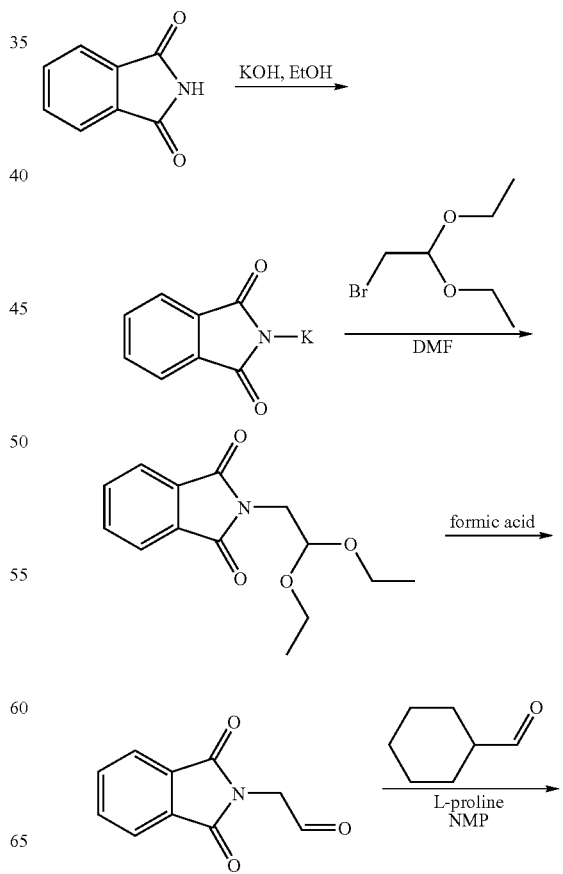

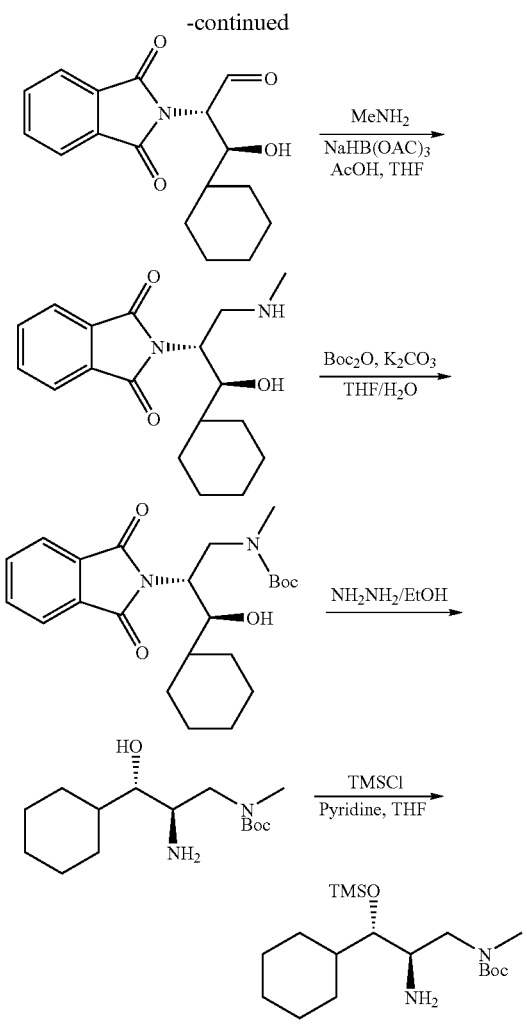

Step 1. Potassium Phthalimide

A three-neck round-bottomed flask fitted with a reflux condenser was charged with phthalimide (80 g, 0.54 mole) and absolute ethanol (1600 mL). The mixture was gently boiled for about 15 min or until no more of the phthalimide dissolved. The hot solution was decanted from any solid into a specially prepared solution of 30.5 g (0.54 mol) of potassium hydroxide. A precipitate of potassium phthalimide separated at once. The mixture was stirred and cooled quickly to rt, and the precipitate was filtered with suction. To the alcoholic mother liquors a second portion of phthalimide (80 g) was added, and the entire process was repeated. The two crops of crystals were combined and washed with acetone (200 mL) to remove any unchanged phthalimide. Air-dried potassium phthalimide was obtained (170 g, 92%).

Step 2. 2-(2,2-diethoxyethyl)isoindoline-1,3-dione

A three-necked round-bottomed flask fitted with an efficient stirrer and a reflux condenser was charged with potassium phthalimide (150 g, 0.81 mol) and 2-bromo-1,1-diethoxy-ethane (196 g, 1.0 mol) and DMF (500 mL). The stirrer was started and the mixture was heated for about 3-4 h in an oil bath maintained at 150° C. The solvent DMF was removed under reduced pressure. The residue was purified by column chromatography to afford pure 2-(2,2-diethoxyethyl)isoindoline-1,3-dione (185 g, yield 87%). $^1$H NMR (400 MHz, MeOD): 1.16 (t, 6H), 3.48-3.60 (m, 2H), 3.68-3.75 (m, 2H), 3.76-3.89 (d, 2H), 4.89 (t, 1H), 7.68-7.75 (m, 2H), 7.85-7.96 (m, 2H). MS (E/Z): 264 (M+H$^+$).

Step 3. 2-(1,3-dioxoisoindolin-2-yl)acetaldehyde 2-(2,2-diethoxyethyl)isoindoline-1,3-dione (40.00 g, 0.15 mol) was dissolved in 85% formic acid (150 mL) and the mixture was stirred for 2 h at rt. After tlc analysis indicated full conversion to the aldehyde (2,4-DNP stain used for visualization), the solvent was removed and the resultant solid was dried at 150 mm torr vacuum to give 2-(1,3-dioxoisoindolin-2-yl)acetaldehyde (27 g, 95%).

Step 4. (2S,3S)-3-cyclohexyl-2-(1,3-dioxoisoindolin-2-yl)-3-hydroxypropanal 2-(1,3-dioxoisoindolin-2-yl)acetaldehyde (2.04 g, 10.7 mmol) was dissolved into a minimal amount of anhydrous N-methylpyrrolidinone (5.0 mL). Heating was required for full dissolution. The solution was cooled to rt and cyclohexanecarboxaldehyde (5.60 g, 50 mmol) was added. The solution was cooled to 0° C. and solid L-proline (0.40 g, 3.4 mmol) was added in one portion. The reaction was stirred for 1 h at 0° C. and the orange mixture was stored in the refrigerator (6° C.) for 36 h. The crude reaction was taken up in 5:1 Et$_2$O/Hexanes (100 mL) and water (20 mL). The layers were separated and the aqueous phase mixture was extracted with 5:1 Et$_2$O/Hexanes (3×10 mL). The combined organic layers were washed with water (5×10 mL) and brine (3×10 mL), dried over Na$_2$SO$_4$, decanted and stripped to give crude (2S, 3S)-3-cyclohexyl-2-(1,3-dioxoisoindolin-2-yl)-3-hydroxypropanal (4.55 g), which was used in the next step without purification.

Step 5. 2-((1S,2R)-1-cyclohexyl-1-hydroxy-3-(methylamino)propan-2-yl)isoindoline-1,3-dione Crude (2S,3S)-3-cyclohexyl-2-(1,3-dioxoisoindolin-2-yl)-3-hydroxypropanal (3.22 g, 10.7 mmol, calculated according to theoretical yield) was dissolved in anhydrous THF (20 mL). The solution was cooled to 0° C. Acetic acid (5.5 mL, 90 mmol), methylamine solution (33% in EtOH, 5.0 mL, 40.0 mmol) and NaHB(OAc)$_3$ (8.80 g, 40.0 mmol) were added sequentially and in single portions. The ice bath was removed and the mixture was stirred for 2 h at rt. The solvent was stripped and the crude 2-((1S,2R)-1-cyclohexyl-1-hydroxy-3-(methylamino)propan-2-yl)isoindoline-1,3-dione (6.45 g) was used directly in the next step.

Step 6. tert-Butyl (2R,3S)-3-cyclohexyl-2-(1,3-dioxoisoindolin-2-yl)-3-hydroxypropyl(methyl)carbamate Crude 2-((1S,2R)-1-cyclohexyl-1-hydroxy-3-(methylamino)propan-2-yl)isoindoline-1,3-dione (3.38 g, 10.7 mmol) was dissolved in THF (20 mL). A solution of K$_2$CO$_3$ (13.8 g, 100 mmol) in water (40 mL) was added followed by Boc$_2$O (10.9 g, 50 mmol). The two phase system was stirred for 1 h at rt. The reaction was extracted with Et$_2$O (2×30 mL). The combined organic extracts were washed with satd aq NaHCO$_3$ (40 mL) and brine, dried over Na$_2$SO$_4$, filtered and concentrated. The residue was purified by column chromatography to give pure tert-butyl (2R,3S)-3-cyclohexyl-2-(1, 3-dioxoisoindolin-2-yl)-3-hydroxypropyl(methyl)carbamate (1.02 g, 22.9%). $^1$H NMR (400 MHz, MeOD): 7.70-7.95

(m, 4H), 4.05-4.50 (m, 3H), 3.20-3.45 (m, 1H), 2.80-2.86 (s, 3H), 1.10-1.80 (m, 11H), 1.00-1.10 (s, 9H). MS (E/Z): 417.3 (M+H⁺).

Step 7. tert-Butyl (2R,3S)-2-amino-3-cyclohexyl-3-hydroxypropyl(methyl)carbamate tert-butyl (2R,3S)-3-cyclohexyl-2-(1,3-dioxoisoindolin-2-yl)-3-hydroxypropyl(methyl)carbamate (500 mg, 1.20 mmol) was dissolved into a minimal volume of EtOH (12 mL) and hydrazine monohydrate (85% in EtOH, 0.35 mL, 6.00 mmol) was added. The solution was heated at 55° C. for 45 min and then the reaction temperature was raised to reflux for 2 h. A white solid formed. The reaction was cooled to rt, Et₂O (50 mL) was added and the reaction was filtered. The filtrate was stripped and the residue was stirred in Et₂O (15 mL) for 1 h and filtered. The filtrate was stripped to afford tert-butyl (2R,3S)-2-amino-3-cyclohexyl-3-hydroxypropyl(methyl)carbamate (300 mg, yield 87%), which was pure enough to use directly in the next step. MS (E/Z): 287 (M+H⁺).

Step 8. tert-Butyl (2R,3S)-2-amino-3-cyclohexyl-3-(trimethylsilyloxy)propyl(methyl)carbamate To a solution of crude tert-butyl (2R,3S)-2-amino-3-cyclohexyl-3-hydroxypropyl(methyl)carbamate (300 mg, 1.05 mmol) in anhydrous THF was added pyridine (846 μL, 10.50 mmol) and TMSCl (663 μL, 5.25 mmol). The mixture was heated to 60° C. and maintained for 20 min, then quenched with satd aq NaHCO₃ (5 mL) and extracted with EtOAc (2×20 mL). The combined organic layers were washed with brine, dried over NaSO₄ and concentrated to afford tert-butyl (2R,3S)-2-amino-3-cyclohexyl-3-(trimethylsilyloxy)propyl (methyl)carbamate (350 mg, yield 93.1%). ¹H NMR (400 MHz, MeOD): 0.13 (s, 9H), 0.80-1.40 (m, 6H), 1.40 (s, 9H), 1.50-2.10 (m, 5H), 2.90 (s, 3H), 3.15-3.50 (m, 4H). MS (E/Z): 359.0 (M+H⁺).

Preparation J (S)-2-(trimethylsilyl)ethyl 2-(t-butoxycarbonylamino)-3-(1-fluorocyclohexyl)propyl(methyl)carbamate

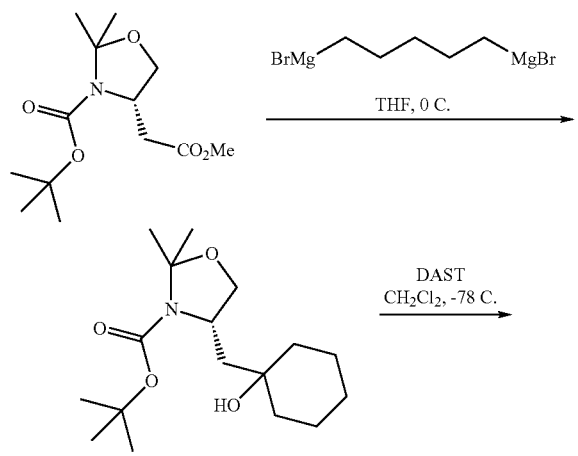

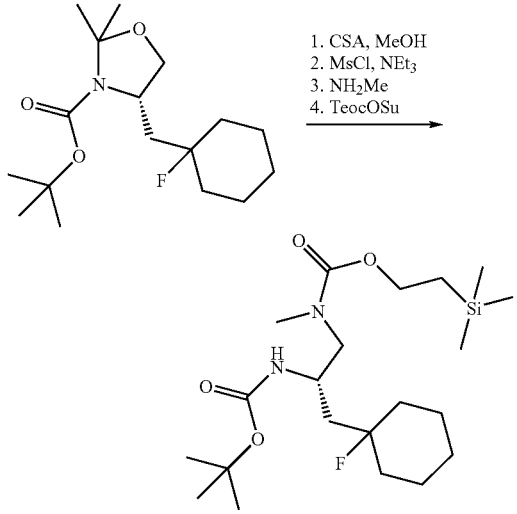

Step 1. (S)-tert-butyl 4-((1-hydroxycyclohexyl)methyl)-2,2-dimethyloxazolidine-3-carboxylate A 250-mL, round-bottom flask was charged with (S)-tert-butyl 4-(2-methoxy-2-oxoethyl)-2,2-dimethyloxazolidine-3-carboxylate (7.0 g, 25.6 mmol) and THF (150 mL). The solution was cooled to 0° C. and a solution of 1,5-bis(brmomagnesio)pentane (0.5 M in THF, 64 mL, 32.6 mmol, 1.25 equiv) was added over a 30 min period with the aid of a syringe pump. After 3 h, LC-MS analysis showed consumption of the starting ester and indicated formation of a ca 4:1 mixture of the desired (S)-tert-butyl 4-((1-hydroxycyclohexyl)methyl)-2,2-dimethyloxazolidine-3-carboxylate and (4S)-tert-butyl 4(2-hydroxyheptyl)-2,2-dimethyloxazolidinone-3-carboxylate. The excess Grignard reagent was quenched with water and the layers were separated. The organic layer was washed with brine, dried over Na₂SO₄, filtered and evaporated. Flash chromatography on silica, eluting with 0-29% EtOAc, afforded (S)-tert-butyl 4-((1-hydroxycyclohexyl)methyl)-2,2-dimethyloxazolidine-3-carboxylate.

Step 2. (S)-tert-butyl 4-((1-fluorocyclohexyl)methyl)-2,2-dimethyloxazolidine-3-carboxylate (S)-tert-Butyl 4-((1-hydroxycyclohexyl)methyl)-2,2-dimethyloxazolidine-3-carboxylate (2.70 g, 8.63 mmol) was dissolved in CH₂Cl₂ and the solution was cooled to −78° C. DAST (2.78 g, 17.2 mmol, 2.0 equiv) was added via syringe and the solution was stirred overnight with concomitant warming to rt. LC-MS showed consumption of the starting alcohol. Satd aq NaHCO₃ was added and the mixture was stirred for 1 h. The layers were separated and the organic layer was washed with brine, dried over Na₂SO₄, and filtered. The resulting solution was treated with m-CPBA (1.5 g, 8.6 mmol) and stirred for 3 h. After this time the olefinic by-products from the fluorination were consumed. The excess m-CPBA was quenched by addition of 10% aq Na₂S₂O₃ (50 mL). The layers were separated and the organic layer was washed with satd aq NaHCO₃ and brine, dried over Na₂SO₄, filtered and evaporated. Flash chromatography on silica, eluting with 0-29% EtOAc in hexanes, afforded (S)-tert-butyl 4-((1-fluorocyclohexyl)methyl)-2,2-dimethyloxazolidine-3-carboxylate (725 mg).

Step 3. (S)-tert-butyl 1-(1-fluorocyclohexyl)-3-hydroxypropan-2-ylcarbamate (S)-tert-butyl 4-((1-fluorocyclohexyl)methyl)-2,2-dimethyloxazolidine-3-carboxylate (1.1 g, 3.50 mmol, 1.0 equiv) was dissolved in methanol (30 mL). To this mixture was added camphorsulfonic acid (202 mg, 0.875 mmol, 0.5 equiv) and the solution was stirred at rt for 3 h. After this time the starting material was consumed. Satd aq NaHCO$_3$ was added and the methanol was removed in vacuo. The aqueous residue was extracted with EtOAc (3×10 mL) and the combined organic extracts were washed with brine, dried over Na$_2$SO$_4$, filtered and evaporated. Flash chromatography on silica, eluting with 0-47% EtOAc in hexanes, afforded (S)-tert-butyl 1-(1-fluorocyclohexyl)-3-hydroxypropan-2-ylcarbamate (275 mg).

Step 4. (S)-2-(tert-butoxycarbonylamino)-3-(1-fluorocyclohexyl)propyl methanesulfonate (S)-tert-butyl 1-(1-fluorocyclohexyl)-3-hydroxypropan-2-ylcarbamate (275 mg, 1.0 mmol, 1.0 equiv) was dissolved in CH$_2$Cl$_2$ and the mixture was cooled to 0° C. To this solution was added methanesulfonyl chloride (230 mg, 2.0 mmol, 2.0 equiv) and triethylamine (304 mg, 3.0 mmol, 3.0 equiv). The mixture was stirred at 0° C. for 0.5 h. After this time LC/MS showed consumption of the starting material. The mixture was transferred to a separatory funnel and 1.0 M aq HCl added. The layers were separated and the organic layer was washed with brine, dried over Na$_2$SO$_4$, filtered and evaporated. The crude (S)-2-(tert-butoxycarbonylamino)-3-(1-fluorocyclohexyl)propyl methanesulfonate was used directly in the next step.

Step 5. (S)-tert-Butyl 1-(1-fluorocyclohexyl)-3-(methylamino)propan-2-ylcarbamate Crude (S)-2-(tert-butoxycarbonylamino)-3-(1-fluorocyclohexyl)propyl methanesulfonate and (n-Bu)$_4$N$^+$T (249 mg, 1.0 mmol) were dissolved in 33% methylamine in ethanol (50 mL). The mixture was heated to 50° C. for 17 h. The solution was cooled to rt and the volatile materials were removed in vacuo. The residue was dissolved in ether, washed with brine, dried over Na$_2$SO$_4$, filtered and evaporated. To afford crude (S)-tert-butyl 1-(1-fluorocyclohexyl)-3-(methylamino)propan-2-ylcarbamate.

Step 6. (S)-2-(trimethylsilyl)ethyl 2-(t-butoxycarbonylamino)-3-(1-fluorocyclohexyl)propyl(methyl) carbamate Crude (S)-tert-butyl 1-(1-fluorocyclohexyl)-3-(methylamino)propan-2-ylcarbamate and TeocOSu (137 mg, 0.5 mmol) were dissolved in 1:1 CH$_3$CN/10% aqueous K$_2$CO$_3$ (20 mL). The mixture was stirred for 2 h. After this time all of the free amine was consumed. The CH$_3$CN was removed in vacuo and the aqueous residue extracted with EtOAc (3×10 mL). The combine organic extracts washed with brine, dried over Na$_2$SO$_4$, filtered and evaporated. Flash chromatography on silica, eluting with 0-27% EtOAc in hexanes, afforded (S)-2-(trimethylsilyl)ethyl 2-(t-butoxycarbonylamino)-3-(1-fluorocyclohexyl)propyl(methyl)carbamate (70 mg).

Preparation K

(S)-tert-butyl 1-(p-nitrophenoxycarbonylamino)-3-cyclohexylpropan-2-ylcarbamate

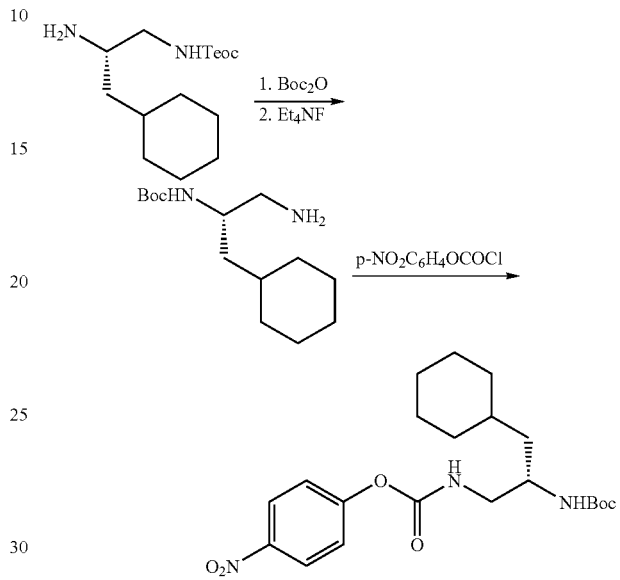

Step 1. (S)-tert-butyl 1-(2-(trimethylsilyl)ethoxycarbonylamino)-3-cyclohexylpropan-2-ylcarbamate To a stirred mixture of (S)-2-(trimethylsilyl)ethyl 2-amino-3-cyclohexylpropylcarbamate (4.61 g, 15.4 mmol), dioxane (50 mL) and 10% aq K$_2$CO$_3$ (50 mL) was added solid Boc$_2$O (3.50 g, 15.4 mmol). The mixture was stirred at rt for 18 h. Dioxane was removed on the rotary evaporator and the aqueous residue was extracted with ether (175 mL). The ether layer was washed with 5% aq HCl (50 mL), satd aq NaHCO$_3$ (50 mL) and brine (50 mL) and dried over MgSO$_4$. Removal of the solvent afforded (S)-tert-butyl 1-(2-(trimethylsilyl)ethoxycarbonyl-amino)-3-cyclohexylpropan-2-ylcarbamate (6.55 g, quant) as a yellow oil.

Step 2. (S)-tert-butyl 1-amino-3-cyclohexylpropan-2-ylcarbamate

To a stirred solution of (S)-tert-butyl 1-(2-(trimethylsilyl)ethoxycarbonylamino)-3-cyclohexylpropan-2-ylcarbamate (6.55 g, 15.4 mmol) in MeCN (100 mL) was added Et$_4$NF (7.5 g, 50 mmol). The mixture was stirred overnight at rt and at 60° C. for 7 h. The mixture was concentrated and the oily residue was taken up in EtOAc (175 mL). The mixture was washed with water (2×50 mL) and brine (50 mL) and dried over Na$_2$SO$_4$. Removal of the solvent afforded (S)-tert-butyl 1-amino-3-cyclohexylpropan-2-ylcarbamate (3.39 g, 80%) as a syrup.

Step 3. (S)-tert-butyl 1-(p-nitrophenoxycarbonylamino)-3-cyclohexylpropan-2-ylcarbamate To a stirred solution of (S)-tert-butyl 1-amino-3-cyclohexylpropan-2-ylcarbamate (0.65 g, 2.54 mmol) in MeCN (20 mL) and THF (5 mL) was added powdered NaHCO$_3$ (0.43 g, 5.08 mmol) followed by a solution of p-nitrophenyl chloroformate (0.51 g, 5.08 mmol) in MeCN (20 mL) dropwise over 10 min. The mixture was stirred at rt for 2 h, filtered through a pad of Celite and concentrated to leave a white solid. This material was purified by chromatography on a 40-g silica cartridge eluted with a gradient from 0-100% EtOAc in hexanes to afford (S)-tert-butyl 1-(p-nitrophenoxycarbonylamino)-3-cyclohexylpropan-2-ylcarbamate (0.67 g, 67%) as an off-white solid.

The following compounds were prepared using procedures analogous to those described above:

tert-butyl (2S)-1-amino-3-(tetrahydro-2H-pyran-2-yl)propan-2-ylcarbamate using 2-(trimethylsilyl)ethyl (2S)-2-amino-3-(tetrahydro-2H-pyran-2-yl)propylcarbamate in Step 1.

Preparation L

4-Nitrophenyl (S)-3-cyclohexyl-1-((2-(trimethylsilyl)ethylcarbamate)methylamino)propan-2-yl)carbamate

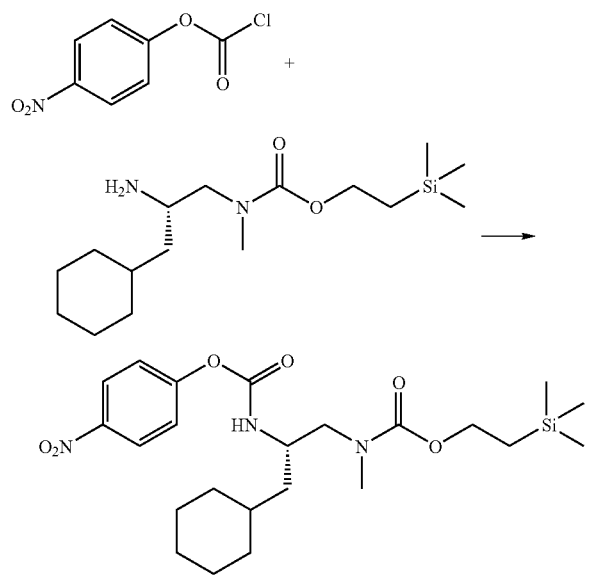

A 100-mL round bottom-flask was charged with diisopropylethylamine (820 mg, 6.34 mmol, 2.0 equiv), 2-(trimethylsilyl)ethyl (S)-2-amino-3-cyclohexylpropylmethylcarbamate (996 mg, 3.17 mmol, 1.0 equiv) and CH$_2$Cl$_2$ (30 mL) The resulting solution was cooled to 0° C. and a solution of 4-nitrophenylchloroformate (733 mg, 3.64 mmol, 1.15 equiv) in CH$_2$Cl$_2$ (20 mL) was added at a rate such that the internal temperature did not rise above 5° C. After 1 h an aliquot was examined by LC-MS which showed no unreacted starting material. The reaction was quenched with water and the layers were separated. The organic layer was washed with of 5% aq K$_2$CO$_3$ (2×40 mL), 0.25 M aq HCl, and brine, dried over Na$_2$SO$_4$ and evaporated. Excess 4-nitrophenyl-chloroformate was removed by flash chromatography on silica, eluting with 0 to 10% methanol in CH$_2$Cl$_2$. This afforded 4-nitrophenyl (S)-3-cyclohexyl-1-((2-(trimethylsilyl)ethylcarbamate)-methylamino)propan-2-yl)carbamate (990 mg, 65%). MS ESI +ve m/z 503 (M+Na$^+$).

Preparation M (S)-2-(trimethylsilyl)ethyl 2-amino-3-cyclohexylpropyl(ethyl)-carbamate

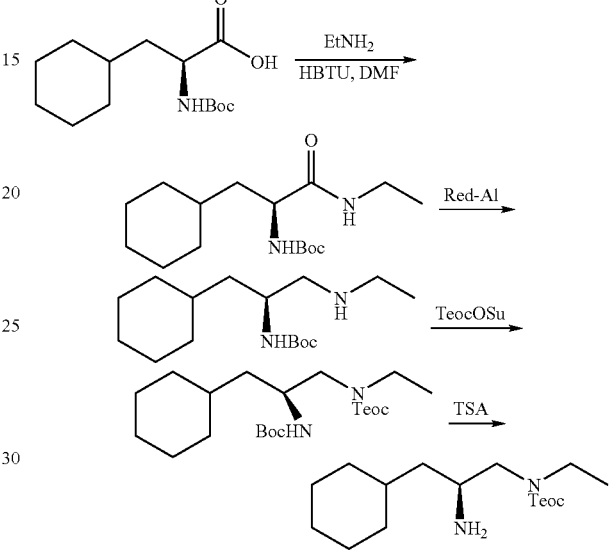

Step 1. (S)-tert-butyl 3-cyclohexyl-1-(ethylamino)-1-oxopropan-2-ylcarbamate

To a solution of (S)-tert-butyl 3-cyclohexyl-1-(methoxy(methyl)amino)-1-oxopropan-2-ylcarbamate (1.17 g, 4.3 mmol) and TEA (2.4 mL, 17.2 mmol) in anhydrous DMF was added 2.0 M EtNH$_2$ solution in EtOH (6.5 mL, 13 mmol), followed by HBTU (1.96 g, 5.2 mmol). The resulting solution was stirred at rt for 3 h. The reaction was concentrated under reduced pressure and the residue dissolved in EtOAc (50 mL). The mixture was then washed with 1 M NaOH (4 times), 1 M HCl (3 times), sat. aq. NaHCO$_3$, brine, dried over Na$_2$SO$_4$ and filtered. The concentrated residue gave (S)-tert-butyl 3-cyclohexyl-1-(ethylamino)-1-oxopropan-2-ylcarbamate (444 mg, 34%). MS ESI +ve m/z 299 (M+H).

Step 2. (S)-tert-butyl 1-cyclohexyl-3-(ethylamino) propan-2-ylcarbamate

To a solution of (S)-tert-butyl 3-cyclohexyl-1-(ethylamino)-1-oxopropan-2-ylcarbamate (444 mg, 1.49 mmol) in anhydrous toluene at 0° C. was added Red-Al (65%, 1.39 g, 1.36 mL, 4.47 mmol) over 20 min. After the addition, the reaction was allowed to stir at rt overnight. The reaction was cooled to 0° C. and quenched with Na$_2$SO$_4$.10H$_2$O. The resulting mixture was stirred for 2-3 h, filtered through Celite, and washed with THF (200 mL). The filtrate was dried and concentrated to give crude product (S)-tert-butyl 1-cyclohexyl-3-(ethylamino)propan-2-ylcarbamate (338 mg, 45% over 2 steps). MS ESI +ve m/z 285 (M+H).

Step 3. (S)-2-(trimethylsilyl)ethyl 2-(N-tert-butoxycarbonyl)amino-3-cyclohexylpropyl(ethyl)carbamate To a solution of (S)-tert-butyl 1-cyclohexyl-3-(ethylamino)propan-2-ylcarbamate (338 mg) and TeocOSu (386 mg, 1.49 mmol) in THF was added TEA (0.6 mL). The resulting solution was stirred at rt for 30 min and evaporated. The residue was purified through chromatography on silica gel to give (S)-2-(trimethylsilyl)ethyl 2-(N-tert-butoxycarbonyl)amino)-3-cyclohexylpropyl-(ethyl)carbamate (287 mg, 45% over 2 steps).

Step 4. (S)-2-(trimethylsilyl)ethyl 2-amino-3-cyclohexylpropyl(ethyl)carbamate To a solution of (S)-2-(trimethylsilyl)ethyl 2-(N-tert-butoxycarbonyl)amino)-3-cyclohexylpropyl(ethyl)carbamate (116 mg, 0.27 mmol) in Et$_2$O (10 mL) was added TSA (51 mg, 0.30 mmol) in EtOH (1 mL). The solvent was removed at rt and heated to 60° C. under vacuum for 30 min to give (S)-2-(trimethylsilyl)ethyl 2-amino-3-cyclohexylpropyl(ethyl)carbamate as a TsOH salt. MS ESI +ve m/z 329 (M+H).

Preparation N

2-(trimethylsilyl)ethyl (2S,3R)-2-amino-1-cyclohexylpentan-3-yl(methyl)carbamate

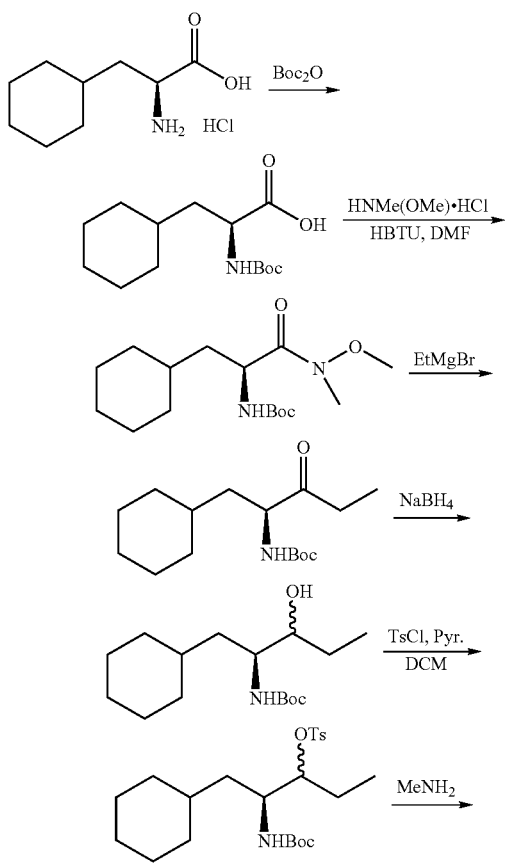

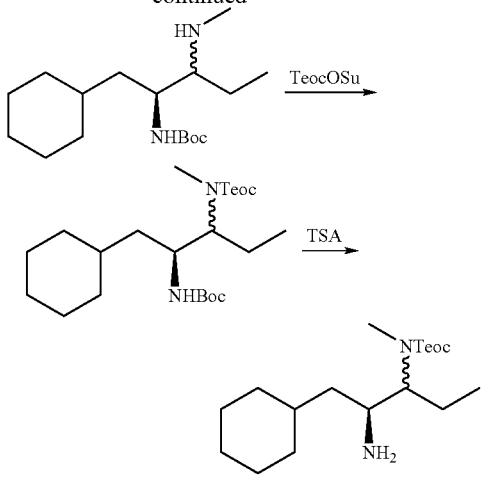

Step 1. (S)-2-(tert-butoxycarbonylamino)-3-cyclohexylpropanoic acid

To a solution of (S)-2-amino-3-cyclohexylpropanoic acid HCl salt (5.00 g, 24.07 mmol) and TEA (15 mL) in THF (150 mL) was added Boc$_2$O (5.51 g, 25.28 mmol). The resulting mixture was stirred at rt overnight. The organic solvent was removed under reduced pressure. The residue was dissolved in EtOAc and washed with 1 M HCl, sat. aq. NaHCO$_3$, 10% citric acid, and brine. The organic layer was dried over Na$_2$SO$_4$, filtered, and concentrated to give (S)-2-(tert-butoxycarbonylamino)-3-cyclohexylpropanoic acid (6.30 g, 96%). MS ESI +ve m/z 272 (M+H).

Step 2. (S)-tert-butyl 3-cyclohexyl-1-(methoxy(methyl)amino)-1-oxopropan-2-ylcarbamate To a solution of (S)-2-(tert-butoxycarbonylamino)-3-cyclohexylpropanoic acid (12.1 g, 44.53 mmol) and N,O-dimethylhydroxylamine hydrochloride (5.62 g, 57.89 mmol) in anhydrous DMF (200 mL) was added TEA (20 mL, 145 mmol), HOBt (6.62 g, 48.98 mmol), HBTU (18.58 g, 48.99 mmol). The suspension was stirred at rt for 2 h and concentrated under reduced pressure. The residue was dissolved in EtOAc (200 mL), washed with 1 M NaOH (3×100 mL), H$_2$O, 1 M HCl (3×100 mL), sat. aq. NaHCO$_3$, brine, and dried over Na$_2$SO$_4$, and filtered. The filtrate was concentrated to give amide (S)-tert-butyl 3-cyclohexyl-1-(methoxy(methyl)amino)-1-oxopropan-2-ylcarbamate (13.04 g, 93%). MS ESI +ve m/z 337 (M+Na).

Step 3. (S)-tert-butyl 1-cyclohexyl-3-oxopentan-2-ylcarbamate

To a solution of (S)-tert-butyl 3-cyclohexyl-1-(methoxy(methyl)amino)-1-oxopropan-2-ylcarbamate (5.23 g, 16.66 mmol) in anhydrous toluene (80 mL) at −20° C. was added EtMgBr (3 M in Et$_2$O, 16.7 mL, 49.97 mmol) slowly. The reaction was allowed to warm to 0° C., and stirred at this temperature for 2 h. The reaction was quenched with 1 M HCl at 0° C. and extracted with EtOAc. The organic phase was washed with sat. aq. NaHCO$_3$, brine, concentrated to give (S)-tert-butyl 1-cyclohexyl-3-oxopentan-2-ylcarbamate. The product was used in the next step without further purification. MS ESI +ve m/z 306 (M+Na).

Step 4. (S)-tert-butyl 1-cyclohexyl-3-hydroxypentan-2-ylcarbamate

To a solution of (S)-tert-butyl 1-cyclohexyl-3-oxopentan-2-ylcarbamate in THF/MeOH (604/15 mL) at 0° C. was carefully added NaBH$_4$ (630 mg, 16.66 mmol). After 20 min, sat. aq. NH$_4$Cl was added to quench the reaction, and extracted with EtOAc, washed with brine, dried over Na$_2$SO$_4$, filtered, and concentrated to give (S)-tert-butyl 1-cyclohexyl-3-hydroxypentan-2-ylcarbamate (4.77 g, 96%, in a ratio of 40:60) as a white solid. MS ESI +ve m/z 286 (M+H).

Step 5. (S)-2-(tert-butoxycarbonylamino)-1-cyclohexylpentan-3-yl 4-methylbenzenesulfonate To a mixture of (S)-tert-butyl 1-cyclohexyl-3-hydroxypentan-2-ylcarbamate (1.067 g, 3.74 mmol), catalytic amount of DMAP, and pyridine (0.651 g, 8.24 mmol) at 0° C. was added TsCl (0.856 g, 4.49 mmol) in CH$_2$Cl$_2$ (4 mL) over 2 min. The resulting solution was stirred at rt overnight. The reaction mixture was diluted with EtOAc, washed with 1 M HCl, sat. aq. NaHCO$_3$, brine, dried over Na$_2$SO$_4$ and filtered. The filtrate was concentrated and purified by on silica gel chromatography to give (S)-2-(tert-butoxycarbonylamino)-1-cyclohexylpentan-3-yl 4-methylbenzenesulfonate as a white solid. MS ESI +ve m/z 462 (M+Na).

Step 6. (S)-tert-butyl 1-cyclohexyl-3-(methylamino)pentan-2-ylcarbamate

A solution of (S)-2-(tert-butoxycarbonylamino)-1-cyclohexylpentan-3-yl 4-methylbenzenesulfonate (640 mg, 1.46 mmol) in 33% MeNH$_2$ (in EtOH) (0.02 M) was heated to 60° C. for 1 h in a pressure sealed vessel. The solvent was removed under reduced pressure to give (S)-tert-butyl 1-cyclohexyl-3-(methylamino)pentan-2-ylcarbamate. MS ESI +ve m/z 299 (M+H).

Step 7. (2S-tert-butyl 1-cyclohexyl-3-(N-methyl-N-(2-(trimethylsilyl)ethoxycarbonyl)amino)pentan-2-ylcarbamate To the solution of (S)-tert-butyl 1-cyclohexyl-3-(methylamino)pentan-2-ylcarbamate in THF (20 mL) was added TeocOSu (398 mg, 1.53 mmol), followed by TEA (0.5 mL). The reaction mixture was stirred for 30 min at rt, and concentrated. The residue was partially purified through chromatography on silica gel to give (2S)-tert-butyl 1-cyclohexyl-3-(N-methyl-N-(2-(trimethylsilyl)ethoxycarbonyl)amino)pentan-2-ylcarbamate. MS ESI +ve m/z 465 (M+Na).

Step 8. (S)-2-(trimethylsilyl)ethyl 2-amino-1-cyclohexylpentan-3-yl(methyl)carbamate The (2S)-tert-butyl 1-cyclohexyl-3-(N-methyl-N-(2-(trimethylsilyl)ethoxycarbonyl)amino)pentan-2-ylcarbamate (137 mg, 0.14 mmol) was dissolved in Et$_2$O (5 mL), anhydrous TSA (24 mg, 0.14 mmol) dissolved in EtOH was added. The solvent was removed in vacuo using a hot bath at 60° C. for 30 min to give (S)-2-(trimethylsilyl)ethyl 2-amino-1-cyclohexylpentan-3-yl(methyl)carbamate. MS ESI +ve m/z 343 (M+H).

Preparation O

2-(trimethylsilyl)ethyl (2S,3R)-2-amino-1-cyclohexylpentan-3-ylcarbamate

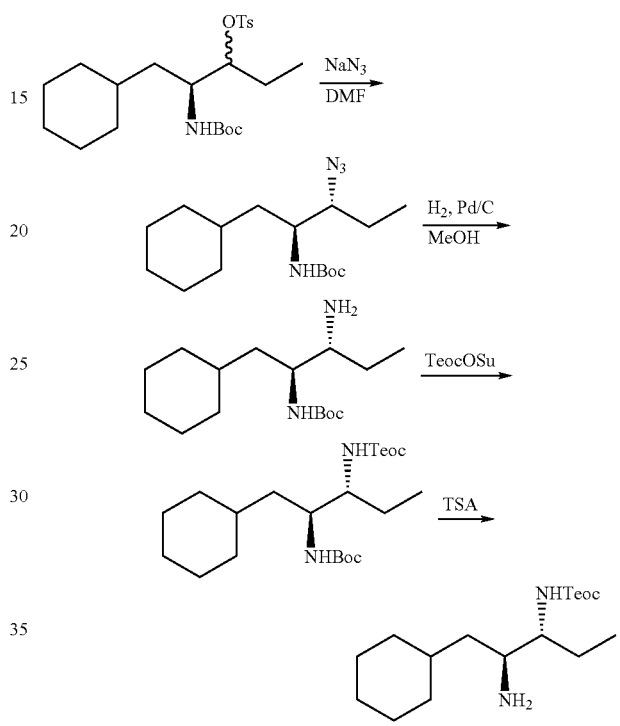

Step 1. tert-butyl (2S,3R)-3-azido-1-cyclohexylpentan-2-ylcarbamate

To a solution of mixture of S-2-(tert-butoxycarbonylamino)-1-cyclohexylpentan-3-yl 4-methylbenzenesulfonate (544 mg, 1.24 mmol) in anhydrous DMF was added NaN$_3$ (241 mg, 3.71 mmol). The resulting solution was heated to 80° C. for 2 h. The reaction was cooled to rt and diluted with EtOAc. The mixture was washed with H$_2$O, brine, dried over Na$_2$SO$_4$ and filtered. The filtrate was concentrated and purified via chromatography on silica gel to give tert-butyl (2S,3R)-3-azido-1-cyclohexylpentan-2-ylcarbamate (second fraction) and (S)-tert-butyl 3-azido-1-cyclohexylpentan-2-ylcarbamate (first fraction) (in a ratio of 40:60 by LC-MS). The mixed fraction was continuously subjected to silica gel chromatography isolate pure tert-butyl (2S,3R)-3-azido-1-cyclohexylpentan-2-ylcarbamate. MS ESI +ve m/z 311 (M+H).

Step 2. tert-butyl (2S,3R)-3-amino-1-cyclohexylpentan-2-ylcarbamate

A solution of tert-butyl (2S,3R)-3-azido-1-cyclohexylpentan-2-ylcarbamate (64 mg, 0.21 mmol) and 10% Pd/C in methanol (20 mL) was hydrogenated at 40 psi for 1 h. The catalyst was filtered off, and the filtrate concentrated to give tert-butyl (2S,3R)-3-amino-1-cyclohexylpentan-2-ylcarbamate (55 mg, 93%). MS ESI +ve m/z 285 (M+H).

Step 3-4. 2-(trimethylsilyl)ethyl (2S,3R)-2-amino-1-cyclohexylpentan-3-ylcarbamate 2-(trimethylsilyl)ethyl (2S,3R)-2-amino-1-cyclohexylpentan-3-ylcarbamate was prepared following procedures analogous to Preparation N, Steps 7-8, using tert-butyl (2S,3R)-3-amino-1-cyclohexylpentan-2-ylcarbamate in Step 7. MS ESI +ve m/z 329 (M+H).

Preparation P (S)-2-(trimethylsilyl)ethyl 2-amino-3-cyclohexyl-2-methylpropylcarbamate

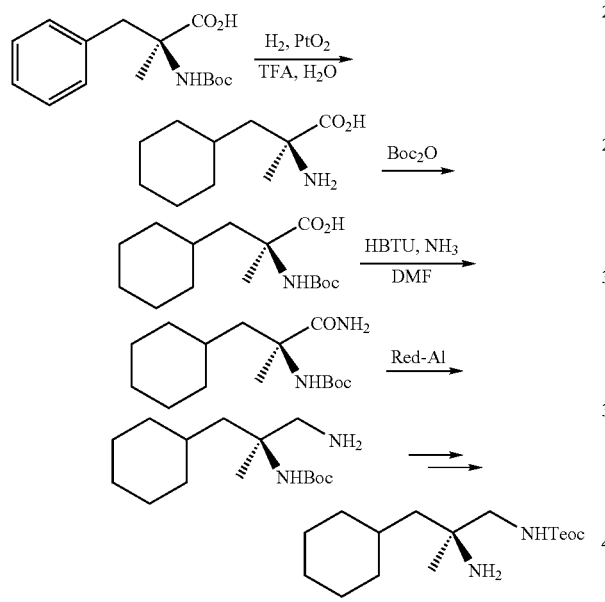

Step 1. (S)-2-amino-3-cyclohexyl-2-methylpropanoic acid (S)-2-(Tert-butoxycarbonylamino)-2-methyl-3-phenylpropanoic acid (1.95 g, 6.98 mmol) was hydrogenated under $H_2$ (50 psi), catalyzed by $PtO_2$ (200 mg), in $TFA/H_2O$ (30/30 mL) overnight. The catalyst was filtered off and concentrated to give (S)-2-amino-3-cyclohexyl-2-methylpropanoic acid in quantitative yield. MS ESI +ve m/z 186 (M+H).

Step 2. (S)-2-(tert-butoxycarbonylamino)-3-cyclohexyl-2-methylpropanoic acid The (S)-2-amino-3-cyclohexyl-2-methylpropanoic acid was dissolved in 1 M NaOH (50 mL) and THF (30 mL), to this stirred solution was added $Boc_2O$ (1.60 g, 7.33 mmol), 2 h later another portion of $Boc_2O$ (3.20 g, 14.66 mmol) was added. The reaction was stirred for another 12 h and extracted with hexane to remove excess $Boc_2O$, the separated aqueous phase was acidified with citric acid and extracted with EtOAc two times. The combined organic phases was washed with brine, and dried over $Na_2SO_4$, filtered, and evaporated to give (S)-2-(tert-butoxycarbonylamino)-3-cyclohexyl-2-methylpropanoic acid (1.99 g, 100%). MS ESI +ve m/z 186 (M+H).

Step 3. (S)-tert-butyl 1-amino-3-cyclohexyl-2-methyl-1-oxopropan-2-ylcarbamate To a solution of (S)-tert-butyl 1-amino-3-cyclohexyl-2-methyl-1-oxopropan-2-ylcarbamate (0.814 g, 2.85 mmol) and TEA (1.2 mL, 8.55 mmol) in anhydrous DMF (30 mL) was added 0.8 M $NH_3$ solution in THF (14 mL), followed by HBTU (1.297 g, 3.42 mmol). The resulting solution was stirred at room temperature for 48 h. Concentrated under reduced pressure to remove most of DMF, the residue was dissolved in EtOAc (50 mL), and washed with 1 M NaOH (3 times), 1 M HCl (3 times), sat. aq. $NaHCO_3$, brine, dried over $Na_2SO_4$ and filtered, and concentrated to give (S)-tert-butyl 1-amino-3-cyclohexyl-2-methyl-1-oxopropan-2-ylcarbamate (811 mg, 100%). The product was used in the next step without further purification. MS ESI +ve m/z 285 (M+H).

Step 4. (S)-tert-butyl 1-amino-3-cyclohexyl-2-methylpropan-2-ylcarbamate (S)-tert-butyl 1-amino-3-cyclohexyl-2-methyl-1-oxopropan-2-ylcarbamate To a solution of (S)-tert-butyl 1-amino-3-cyclohexyl-2-methyl-1-oxopropan-2-ylcarbamate (811 mg, 2.85 mmol) in anhydrous toluene (15 mL) at 0° C. was added Red-Al (65%, 2.66 g, 2.6 mL, 8.55 mmol) within 20 min. After the addition, the reaction was allowed to be stirred at room temperature overnight. The reaction was cooled to 0° C. and quenched with $Na_2SO_4 \cdot 10H_2O$. The resulting mixture was stirred for 2-3 h, filtered through Celite, and washed with THF (200 mL). The filtrate was dried and concentrated to give crude product (S)-tert-butyl 1-cyclohexyl-3-(ethylamino)propan-2-ylcarbamate (860 mg). MS ESI +ve m/z 271 (M+H).

Step 5-6. (S)-2-(trimethylsilyl)ethyl 2-amino-3-cyclohexyl-2-methylpropylcarbamate (S)-2-(trimethylsilyl)ethyl 2-amino-3-cyclohexyl-2-methylpropylcarbamate was obtained using procedures analogous to Preparation M, Steps 3-4, using (S)-tert-butyl 1-cyclohexyl-3-(ethylamino)propan-2-ylcarbamate in Step 3. MS ESI +ve m/z 315 (M+H).

Preparation Q (S)-tert-butyl 2-((tert-butyldimethylsilyloxy)methyl)aziridine-1-carboxylate

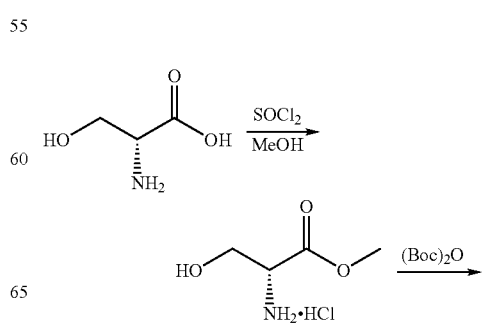

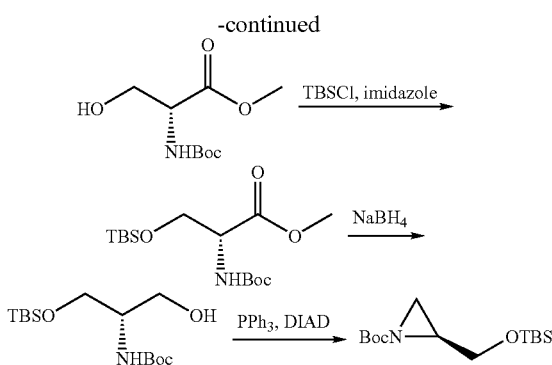

Step 1. (R)-methyl 2-amino-3-hydroxypropanoate hydrochloride salt

To a solution of (R)-2-amino-3-hydroxypropanoic acid (105 g, 1 mol) in methanol (1200 mL) was added thionyl chloride (87.6 mL, 142.8 g, 1.2 mol) dropwise at 0° C. After addition, the reaction mixture was heated at reflux for 12 h. Volatiles were evaporated to give the (R)-methyl 2-amino-3-hydroxypropanoate hydrochloride salt (155 g, yield 100%) as a solid that was used in the next step without further purification. $^1$H NMR (CDCl$_3$, 400 MHz) δ 8.51 (brs, 2H), 4.08 (s, 1H), 3.79 (m, 2H), 3.71 (s, 3H).

Step 2. (R)-methyl 2-(tert-butoxycarbonylamino)-3-hydroxypropanoate

To a stirred suspension of (R)-methyl 2-amino-3-hydroxypropanoate hydrochloride (155 g, 1 mol) in CH$_2$Cl$_2$ (1200 mL) was added DIEA (194 g, 1.5 mol). A solution of Boc$_2$O (218 g, 1 mol) in CH$_2$Cl$_2$ (800 mL) was added dropwise to the above mixture, the reaction mixture was allowed to stir overnight. The solution was washed with 1N aqueous HCl (600 mL), saturated NaHCO$_3$ (500 mL), and brine (500 mL). The solution was then dried, filtered, and evaporated to give (R)-methyl 2-(tert-butoxycarbonylamino)-3-hydroxypropanoate (245 g, yield 96%) as an oil that was used in the next step without further purification. $^1$H NMR (CDCl$_3$, 400 MHz) δ 5.29 (brs, 1H), 4.35 (s, 1H), 3.91 (dd, J=18, 3.2 Hz, 2H), 3.77 (s, 3H), 2.37 (brs, 1H), 1.44 (s, 9H).

Step 3. (R)-methyl 2,2,3,3,10,10-hexamethyl-8-oxo-4,9-dioxa-7-aza-3-silaundecane-6-carboxylate To a solution of (R)-methyl 2-(tert-butoxycarbonylamino)-3-hydroxypropanoate (27.5 g, 0.126 mol) in DMF (250 mL) was added imidazole (25.7 g, 0.378 mol), followed by TBSCl (20.9 g, 0.139 mol) and the reaction mixture stirred for 4 h. The solvents were removed in vacuo and dissolved in EtOAc (300 mL). The solution was washed with saturated NH$_4$Cl (2×100 mL), then with saturated NaHCO$_3$ (100 mL), and brine (100 mL). The organic layer was then dried, filtered, and solvent removed in vacuo to give (R)-methyl 2,2,3,3,10,10-hexamethyl-8-oxo-4,9-dioxa-7-aza-3-silaundecane-6-carboxylate (40 g, yield 95%) as an oil that was used in the next step without further purification. $^1$H NMR (CDCl$_3$, 400 MHz) δ 5.34 (brs, 1H), 4.35 (m, 1H), 4.05 (dd, J=13.2, 3.6 Hz, 1H), 3.82 (dd, J=14, 4.4 Hz, 1H), 1.45 (s, 9H), 3.73 (s, 3H), 0.86 (s, 9H), 0.02 (s, 6H).

Step 4. (S)-tert-butyl 1-(tert-butyldimethylsilyloxy)-3-hydroxypropan-2-ylcarbamate To a solution of (R)-methyl 2,2,3,3,10,10-hexamethyl-8-oxo-4,9-dioxa-7-aza-3-silaundecane-6-carboxylate (40 g, 0.12 mol) in MeOH (500 mL) at 0° C. was added NaBH$_4$ (38 g, 1 mol) in portions. The mixture was stirred for 2 h at rt followed by removal of solvent in vacuo. The residue was partitioned between water (200 mL) and EtOAc (2×200 mL). The organic layers were washed with saturated aqueous NaHCO$_3$ solution, then brine, dried with MgSO$_4$, and evaporated to obtain the alcohol (S)-tert-butyl 1-(tert-butyldimethylsilyloxy)-3-hydroxypropan-2-ylcarbamate (36 g, yield 98%). $^1$H NMR (CDCl$_3$, 400 MHz) δ 5.15 (brs, 1H), 3.78 (m, 2H), 3.68 (m, 2H), 2.25 (brs, 1H), 1.45 (s, 9H), 0.89 (s, 9H), 0.07 (s, 6H).

Step 5. (S)-tert-butyl 1-(tert-butyldimethylsilyloxy)-3-hydroxypropan-2-ylcarbamate To a solution of Ph$_3$P (19.65 g, 75 mmol) dissolved in 9:1 THF/CH$_3$CN (600 mL), cooled to 0° C., DIAD (14.7 mL, 75 mmol) was added dropwise over 15 min. After stirring for 30 min, a solution of (S)-tert-butyl 1-(tert-butyldimethylsilyloxy)-3-hydroxypropan-2-ylcarbamate (15.25 g, 50 mmol) in THF (100 mL) was added dropwise over 15 min. The reaction mixture was allowed to warm to rt and stirred for 24 h. After adding water (100 mL) evaporating volatiles, the residue was further diluted with water (100 mL) and extracted with EtOAc (2×100 mL). The organic layers were washed with saturated aqueous brine, dried with MgSO$_4$, and evaporated, then purified by silica chromatography to provide (S)-tert-butyl 1-(tert-butyldimethylsilyloxy)-3-hydroxypropan-2-ylcarbamate as an oil (7.8 g, yield 54%). $^1$H NMR (CDCl$_3$, 400 MHz) δ 3.82 (dd, J=16.4, 4.4 Hz, 1H), 3.64 (dd, J=16.4, 4.8 Hz, 1H), 2.55 (m, 1H), 2.26 (d, J=6 Hz, 1H), 2.06 (d, J=3.6 Hz, 1H), 1.45 (s, 9H), 0.89 (s, 9H), 0.07 (s, 6H).

Preparation R (S)-benzyl 2-amino-3-cyclopentylpropyl(methyl)carbamate

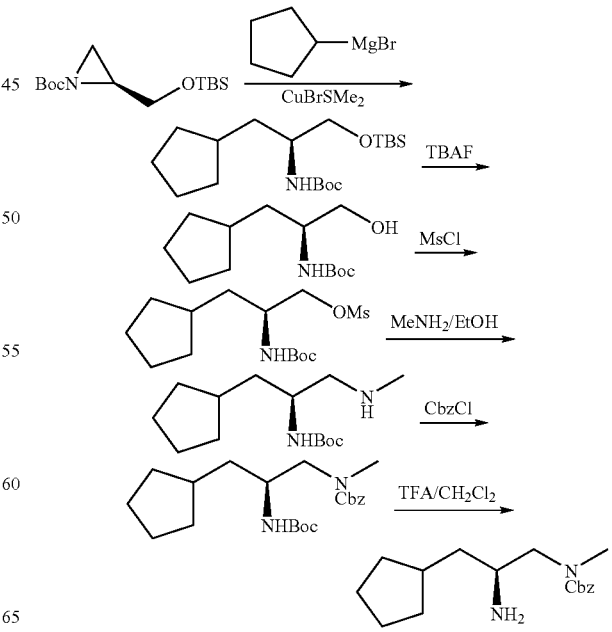

Step 1. (S)-tert-butyl 1-(tert-butyldimethylsilyloxy)-3-cyclopentylpropan-2-ylcarbamate A 100 mL, three-neck round bottom flask was charged with Mg powder (720 mg, 30 mmol), then a solution of cyclopentylbromide (3.73 g, 25 mmol) in THF (25 mL) was added dropwise while a heat gun heated the flask. After stirring for 2 h, most of the Mg was consumed. The cyclopentylmagnesium bromide was added to a suspension of CuBr—SMe$_2$ (307.5 mg, 1.5 mmol) in THF (80 mL) at −78° C., the cuprate was stirred for 30 min and a solution of (S)-tert-butyl 1-(tert-butyldimethylsilyloxy)-3-hydroxypropan-2-ylcarbamate (2.87 g, 10 mmol) in Et$_2$O (30 mL) was added. After stirring for 2 h, the reaction mixture was washed with saturated NaHCO$_3$ (2×20 mL) and brine (30 mL). The organic layer was dried with MgSO$_4$, the solvent evaporated, and the residue purified by silica gel chromatography to obtain (S)-tert-butyl 1-(tert-butyldimethylsilyloxy)-3-cyclopentylpropan-2-ylcarbamate as an oil (2.9 g, yield 81%). $^1$H NMR (CDCl$_3$, 400 MHz) δ 4.60 (brs, 1H), 3.58 (m, 3H), 1.81 (m, 3H), 1.60 (m, 3H), 1.50 (m, 3H), 1.44 (s, 9H), 1.10 (m, 2H), 0.89 (s, 9H), 0.04 (s, 6H).

Step 2. (S)-tert-butyl 1-cyclopentyl-3-hydroxypropan-2-ylcarbamate (S)-tert-butyl 1-(tert-butyldimethylsilyloxy)-3-cyclopentylpropan-2-ylcarbamate (2.9 g, 8.1 mmol) was treated with 1 M Bu$_4$NF/THF (24.3 mL) at 0° C. for 1 h. The reaction was diluted with water (30 mL) and extracted with EtOAc (3×40 mL). The organic layers were washed with saturated aqueous brine, dried over MgSO$_4$, and evaporated to give crude (S)-tert-butyl 1-cyclopentyl-3-hydroxypropan-2-ylcarbamate that was used without further purification. $^1$H NMR (CDCl$_3$, 400 MHz) δ 4.60 (brs, 1H), 3.68 (m, 2H), 3.52 (m, 1H), 1.81 (m, 3H), 1.60 (m, 3H), 1.50 (m, 3H), 1.44 (s, 9H), 1.09 (m, 2H).

Step 3. (S)-2-(tert-butoxycarbonylamino)-3-cyclopentylpropyl methanesulfonate To a solution of (S)-tert-butyl 1-cyclopentyl-3-hydroxypropan-2-ylcarbamate in CH$_2$Cl$_2$ (30 mL) Et$_3$N (3.2 mL, 24.3 mmol) was added. The reaction mixture was cooled to 0° C. followed by dropwise addition of MsCl (1.1 g, 9.7 mmol) in CH$_2$Cl$_2$ (10 mL). After stirring for an additional 2 h, water (30 mL) was added and the mixture was extracted with CH$_2$Cl$_2$ (2×30 mL). The organic layers were washed with saturated aqueous brine, dried over MgSO$_4$, and evaporated to give crude (S)-2-(tert-butoxycarbonylamino)-3-cyclopentylpropyl methanesulfonate that was used in the next step without further purification. $^1$H NMR (CDCl$_3$, 400 MHz) δ 4.59 (brs, 1H), 4.27 (dd, J=10, 3.2 Hz, 1H), 4.17 (dd, J=10, 4 Hz, 1H), 3.86 (m, 1H), 3.02 (s, 3H), 1.81 (m, 3H), 1.60 (m, 3H), 1.50 (m, 3H), 1.46 (s, 9H), 1.09 (m, 2H).

Step 4. (S)-tert-butyl 1-cyclopentyl-3-(methylamino)propan-2-ylcarbamate

A solution of (S)-2-(tert-butoxycarbonylamino)-3-cyclopentylpropyl methanesulfonate in methylamine alcohol solution (30 mL) was heated at reflux overnight. The solvent was removed in vacuo, the residue was purified by silica chromatography to obtain (S)-tert-butyl 1-cyclopentyl-3-(methylamino)propan-2-ylcarbamate as a solid (900 mg, yield 43% for 3 steps). $^1$H NMR (CDCl$_3$, 400 MHz) δ 5.66 (brs, 1H), 3.92 (brs, 1H), 3.17 (m, 1H), 2.90 (m, 1H), 2.69 (s, 3H), 1.81 (m, 3H), 1.60 (m, 3H), 1.49 (m, 3H), 1.44 (s, 9H), 1.10 (m, 2H).

Step 5. (S)-tert-butyl 1-cyclopentyl-3-(N-methyl-N-(2-(trimethylsilyl)ethoxycarbonyl)amino)propan-2-ylcarbamate To a mixture of (S)-tert-butyl 1-cyclopentyl-3-(methylamino)propan-2-ylcarbamate and Et$_3$N (1.5 mL, 10.6 mmol) in CH$_2$Cl$_2$ (10 mL) was added dropwise a solution of CbzCl (720 mg, 4.22 mmol) in CH$_2$Cl$_2$ (5 mL) at 0° C. After stirring for an additional 2 h, water (30 mL) was added and reaction extracted with CH$_2$Cl$_2$ (2×0 mL), the organic layers were washed with saturated aqueous brine, dried over MgSO$_4$, and evaporated, then purified by silica gel chromatography to obtain (S)-tert-butyl 1-cyclopentyl-3-(N-methyl-N-(2-(trimethylsilyl)ethoxycarbonyl)amino)propan-2-ylcarbamate as an oil (550 mg, yield 40%). $^1$H NMR (CDCl$_3$, 400 MHz) δ 7.33 (m, 5H), 5.16 (s, 2H), 4.57 (brs, 1H), 3.83 (brs, 1H), 3.40 (m, 1H), 3.15 (m, 1H), 2.96 (s, 3H), 1.81 (m, 3H), 1.60 (m, 3H), 1.49 (m, 3H), 1.43 (s, 9H), 1.10 (m, 2H).

Step 6. (S)-benzyl 2-amino-3-cyclopentylpropyl(methyl)carbamate

A solution of (S)-tert-butyl 1-cyclopentyl-3-(N-methyl-N-(2-(trimethylsilyl)ethoxycarbonyl)amino)propan-2-ylcarbamate (550 mg) in TFA/CH$_2$Cl$_2$ (10 mL, 20% v/v) was stirred for 2 hrs at 5° C. The reaction was neutralized with saturated aqueous NaHCO$_3$ and extracted with CH$_2$Cl$_2$ (3×30 mL). The combined extracts were washed with saturated brine (30 mL), dried over Na$_2$SO$_4$, and evaporated to give (S)-benzyl 2-amino-3-cyclopentylpropyl(methyl)carbamate (420 mg) that was used without further purification.

Preparation S (S)-2-(trimethylsilyl)ethyl 2-amino-3-cycloheptyl-propyl(methyl)carbamate

Step 1-4. (S)-tert-butyl 1-cycloheptyl-3-(methylamino)propan-2-ylcarbamate (S)-tert-butyl 1-cycloheptyl-3-(methylamino)propan-2-ylcarbamate was obtained following procedures analogous to Preparation R, Steps 1-4, using cyclopentylmagnesium bromide in Step 1. MS ESI +ve m/z 285 (M+H).

Step 5-6. (S)-2-(trimethylsilyl)ethyl 2-amino-3-cycloheptylpropyl(methyl)carbamate (S)-2-(trimethylsilyl)ethyl 2-amino-3-cycloheptylpropyl(methyl)carbamate was prepared from (S)-tert-butyl 1-cycloheptyl-3-(methylamino)propan-2-ylcarbamate using procedures analogous to those described in Preparation M, Steps 3-4. $^1$H NMR (CDCl$_3$, 400 MHz) δ 0.0 (s, 9H), 0.95 (t, 2H), 1.12 (m, 2H), 1.41 (m, 6H), 1.53 (m, 5H), 1.62 (m, 3H), 2.94 (s, 3H), 3.39 (m, 2H), 4.11 (t, 2H). MS ESI +ve m/z 329 (M+H).

The following compounds were prepared following procedures analogous to those described above:
1) (S)-2-(trimethylsilyl)ethyl 2-amino-5,5-dimethylhexyl (methyl)carbamate using neopentylmagnesium chloride in Step 1.
2) (S)-2-(trimethylsilyl)ethyl 2-amino-4,4-dimethylhexyl (methyl)carbamate using (2,2-dimethylbutyl)magnesium bromide in Step 1.
3) (S)-2-(trimethylsilyl)ethyl 2-amino-3-cyclopentylpropyl (methyl)carbamate using cyclopentylmagnesium bromide in Step 1.

Preparation T (S)-2-(trimethylsilyl)ethyl 2-amino-3-(4-methylcyclohexyl)propyl(methyl)carbamate

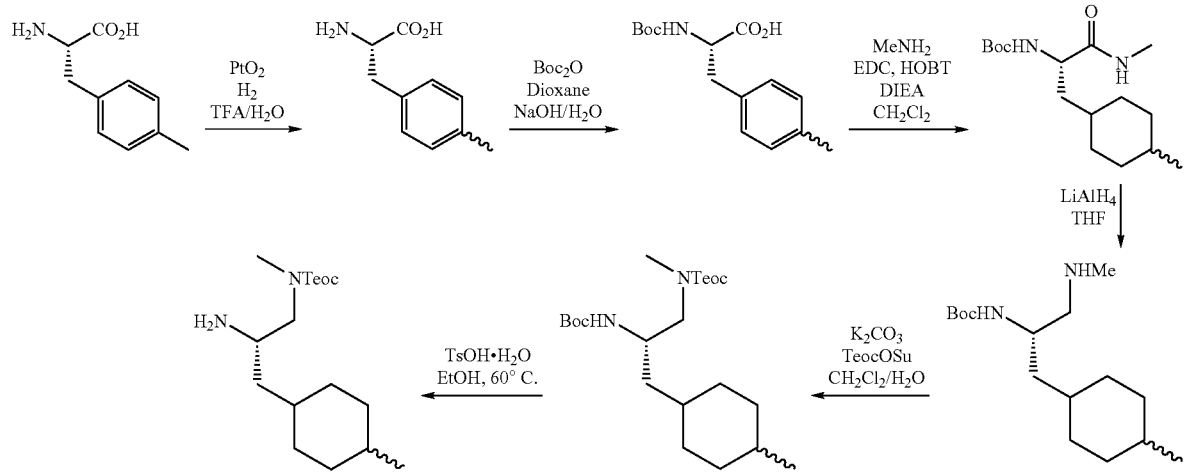

Step 1.
(S)-2-amino-3-(4-methylcyclohexyl)propanoic acid

A 250 mL Parr shaker vessel was charged with 1.0 g (5.6 mmol) of (S)-2-amino-3-p-tolylpropanoic acid, 63 mg (0.28 mmol, 5 mol %) of $PtO_2$, and 10 mL of 1:1 TFA:water. The vessel was placed in a Parr hydrogenation shaker, pressurized to 50 psi, and shaken for 2 d. Analysis of the mixture by LC/MS indicated a ca 1:1 mixture of cis:trans isomers. The contents were filtered through a pad of Celite and the spent catalyst washed with additional water. The clear filtrate was evaporated to afford crude TFA salt of (S)-2-amino-3-(4-methylcyclohexyl)propanoic acid which was used directly in the next step.

Step 2. (S)-2-(tert-butoxycarbonylamino)-3-(4-methylcyclohexyl)propanoic acid The crude TFA salt (S)-2-amino-3-(4-methylcyclohexyl) propanoic acid was dissolved in 20 mL of dioxane and 30 mL of 0.67 M NaOH. The pH of the solution was raised to >14 by addition of solid KOH followed by addition di-tert-butyl dicarbonate (3.03 g, 13.9 mmol, 1.05 equiv). An additional 600 mg of di-tert-butyl dicarbonate was added and the mixture stirred overnight. After this time all the free amine had been consumed. The mixture was cooled to 0° C. and solution pH lowered to <4 by addition of saturated citric acid. The solvent was removed using a rotary evaporator and the product extracted with 5×25 mL of EtOAc. The combined organic extracts were dried over $Na_2SO_4$, filtered and evaporated to yield crude (S)-2-(tert-butoxycarbonylamino)-3-(4-methylcyclohexyl)propanoic acid as a sticky solid which was used without further purification.

Step 3. (S)-tert-butyl 1-(methylamino)-3-(4-methylcyclohexyl)-1-oxopropan-2-ylcarbamate A mixture of (S)-2-(tert-butoxycarbonylamino)-3-(4-methylcyclohexyl)propanoic acid (2.080 g, 7.29 mmol, 1.0 equiv), EDC (3.308 g, 2.37 equiv), HOBT (1.752 g, 1.78 equiv), DIEA (7.6 mL, 6 equiv) and 33% wt. methylamine in EtOH (2.771 g, 4 equiv) in $CH_2Cl_2$ (80 mL) was stirred at rt for 21 h. The solvents were removed in vacuo and 200 mL of 1 N HCl was added. The mixture was extracted three times with EtOAc, washed with brine, and dried over $Na_2SO_4$. After the solvents were removed in vacuo, the residue was purified by reversed-phase HPLC to give 1.0167 g (47%) of (S)-tert-butyl 1-(methylamino)-3-(4-methylcyclohexyl)-1-oxopropan-2-ylcarbamate. MS ESI +ve m/z 321 (M+Na). $^1$H NMR ($CDCl_3$, 400 MHz) δ 6.27 (br s, 1H), 4.91 (br s, 1H), 4.11-4.07 (m, 1H), 2.80, 2.79 (d, J=4.8 Hz, 3H), 1.85-1.20 (m, 21H), 0.88, 0.85 (d, J=6.4 Hz, 3H).

Step 4. (S)-tert-butyl 1-(methylamino)-3-(4-methylcyclohexyl)propan-2-ylcarbamate To a solution of (S)-tert-butyl 1-(methylamino)-3-(4-methylcyclohexyl)-1-oxopropan-2-ylcarbamate (1.0075 g, 3.38 mmol, 1.0 equiv) in THF (40 mL) was added 7 mL (7 mmol, 2.1 equiv) of 1.0 M $LiAlH_4$ in THF at 0° C. under $N_2$. The mixture was stirred at rt for 19 h and then sodium sulfate decahydrate (6.45 g, 20 mmol) was added carefully to quench excess $LiAlH_4$. The mixture was filtered and the solid was washed with ether. After the solvents were removed in vacuo, the crude (S)-tert-butyl 1-(methylamino)-3-(4-methylcyclohexyl)propan-2-ylcarbamate (1.04 g) was used in the next step without further purification. MS ESI +ve m/z 285 (M+H).

Step 5-6. 2-(trimethylsilyl)ethyl (S)-2-amino-3-(4-methylcyclohexyl)-propylmethylcarbamate 2-(trimethylsilyl)ethyl (S)-2-amino-3-(4-methylcyclohexyl)-propylmethylcarbamate was prepared from (S)-tert-butyl 1-(methylamino)-3-(4-methylcyclohexyl)propan-2-ylcarbamate using procedures analogous to those described in Preparation M, Steps 3-4. MS ESI +ve m/z 329 (M+1).

Preparation U 2-(trimethylsilyl)ethyl 2-amino-3-(1-methylcyclohexyl)propyl(methyl)carbamate

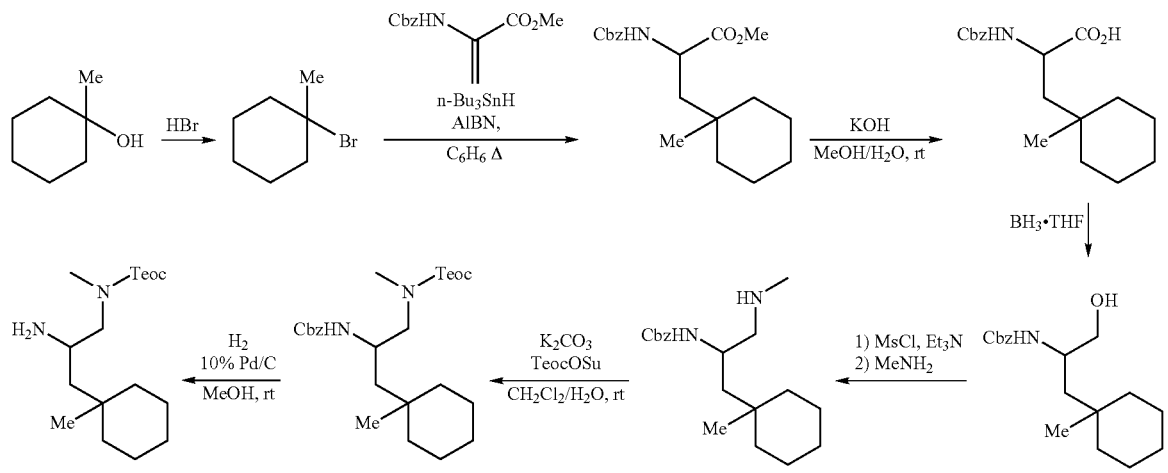

Step 1. 1-bromo-1-methylcyclohexane

A mixture of 16.73 g of 1-methylcyclohexanol and 50 mL of 48 wt. % hydrobromic acid in water was stirred at rt for 3 d. The reaction mixture was extracted with hexanes, washed with brine, and dried over $Na_2SO_4$. The extracts were evaporated under reduced pressure to afford 24.365 g (94%) of 1-bromo-1-methylcyclohexane, which was used in the next step without further purification. $^{13}C$ NMR ($CDCl_3$, 100 MHz) δ 71.78, 43.01, 35.28, 25.18, 23.48.

Step 2. methyl 2-(benzyloxycarbonylamino)-3-(1-methylcyclohexyl)propanoate

A mixture of 1-bromo-1-methylcyclohexane (7.200 g, 3.0 equiv), tributyltin hydride (8 mL, 2.2 equiv), methyl 2-(benzyloxycarbonylamino)acrylate (3.120 g, 13.26 mmol, 1.0 equiv), and 2,2'-azobisisobutyronitrile (0.370 g, 0.17 equiv) in benzene (30 mL) was heated at 100° C. for 6 h. After the reaction mixture was evaporated under reduced pressure, the crude methyl 2-(benzyloxycarbonylamino)-3-(1-methylcyclohexyl)propanoate was used directly in the next step without further purification. MS ESI +ve m/z 356 (M+Na).

Step 3. 2-(benzyloxycarbonylamino)-3-(1-methylcyclohexyl)propanoic acid

A mixture of methyl 2-(benzyloxycarbonylamino)-3-(1-methylcyclohexyl)propanoate, 10.00 g of KOH, 100 mL of MeOH, and 20 mL of water was vigorously stirred at rt for 17 h. After methanol was evaporated under reduced pressure, the residue was diluted with water and extracted with $Et_2O$ (2×). The aqueous phase was treated with 100 mL of 2 NHCl, extracted with EtOAc (3×), and dried over $Na_2SO_4$. The extracts were evaporated under reduced pressure to afford 1.5150 g (36% in two steps) of 2-(benzyloxycarbonylamino)-3-(1-methylcyclohexyl)propanoic acid. MS ESI +ve m/z 320 (M+H).

Step 4. benzyl 1-hydroxy-3-(1-methylcyclohexyl)propan-2-ylcarbamate

A mixture of 0.510 g (1.60 mmol) of 2-(benzyloxycarbonylamino)-3-(1-methylcyclohexyl)propanoic acid, 5 mL of THF, and 10 mL of 1.0 M $BH_3$·THF in THF was stirred at 0° C. for 2 h. The mixture was allowed to warm to rt for 16 h. The reaction mixture was then cooled with an ice bath and quenched with 20 mL of MeOH and 2 mL of HOAc. After the solvents were removed in vacuo, the residue was purified by reversed-phase HPLC to afford 0.3655 g (75%) of benzyl 1-hydroxy-3-(1-methylcyclohexyl)propan-2-ylcarbamate. MS ESI +ve m/z 328 (M+Na).

Step 5. 2-(benzyloxycarbonylamino)-3-(1-methylcyclohexyl)propyl methanesulfonate A mixture of 0.3607 g (1.18 mmol) of benzyl 1-hydroxy-3-(1-methylcyclohexyl)propan-2-ylcarbamate, 0.4 mL (2.87 mmol, 2.43 equiv) of triethylamine, 0.1 mL (1.29 mmol, 1.09 equiv) of methanesulfonyl chloride in $CH_2Cl_2$ (10 mL) was stirred at 0° C. for 1.5 h. The reaction mixture was quenched with ice water, extracted with $CH_2Cl_2$, washed with aqueous $NaHCO_3$, and dried over $Na_2SO_4$. After the solvent was removed in vacuo, the crude 2-(benzyloxycarbonylamino)-3-(1-methylcyclohexyl)propyl methanesulfonate was used directly in the next step without further purification. MS ESI +ve m/z 406 (M+Na).

Step 6. benzyl 1-(methylamino)-3-(1-methylcyclohexyl)propan-2-ylcarbamate

A mixture of 2-(benzyloxycarbonylamino)-3-(1-methylcyclohexyl)propyl methanesulfonate in 16 mL of THF, and 10 mL of 33% wt. methylamine in EtOH was heated at 70° C. for 3 h. After cooling to rt, the reaction mixture was evaporated under reduced pressure. The crude benzyl 1-(methylamino)-3-(1-methylcyclohexyl)propan-2-ylcarbamate was used directly in the next step without further purification. MS ESI +ve m/z 319 (M+H).

Step 7. (S)-tert-butyl 1-(N-methyl-N-(2-(trimethylsilyl)ethoxycarbonyl)amino)-3-(4-methylcyclohexyl)propan-2-ylcarbamate A mixture of benzyl 1-(methylamino)-3-(1-methylcyclohexyl)propan-2-ylcarbamate, obtained as described above, $K_2CO_3$ (5.06 g), TeocOSu (0.80 g, 3.08 mmol, 2.6 equiv), $H_2O$ (20 mL) and $CH_2Cl_2$ (100 mL) was stirred vigorously at rt for 3 h. The reaction mixture was extracted with $CH_2Cl_2$ (2×), and dried over $Na_2SO_4$. After the solvent was removed in vacuo, the residue was purified by reversed-phase HPLC to afford 0.2479 g (45% in three steps) of (S)-tert-butyl 1-(N-methyl-N-(2-(trimethylsilyl)ethoxycarbonyl)amino)-3-(4-methylcyclohexyl)propan-2-ylcarbamate. MS ESI +ve m/z 485 (M+Na).

Step 8. 2-(trimethylsilyl)ethyl 2-amino-3-(1-ethylcyclohexyl)propyl(methyl)carbamate A 250 mL round bottom flask was charged with 0.2479 g (0.54 mmol) of (S)-tert-butyl 1-(N-methyl-N-(2-(trimethylsilyl)ethoxycarbonyl)amino)-3-(4-methylcyclohexyl)propan-2-ylcarbamate, 0.2784 g of 10% Pd/C, and 20 mL of MeOH. The reaction mixture was stirred at rt under a balloon of hydrogen for 5 h. The mixture was then filtered through filter agent, Celite® 545, washed with MeOH. The filtrate was evaporated under reduced pressure to afford 0.1799 g (100%) of 2-(trimethylsilyl)ethyl 2-amino-3-(1-methylcyclohexyl)propyl(methyl)carbamate, which was used in the next step without further purification. MS ESI +ve m/z 329 (M+H).

Preparation V

(S)-2-(trimethylsilyl)ethyl 2-amino-3-(1-adamantyl)propyl(methyl)carbamate (S)-2-(trimethylsilyl)ethyl 2-amino-3-(1-adamantyl)propyl(methyl)carbamate was prepared from tricyclo[3.3.1.13,7]decane-1-propanoic acid using procedures analogous to those described in Preparation G, Steps 2-4 above.

Preparation W tert-butyl 2-amino-3-(bicyclo[2.2.2]octan-1-yl)propyl(methyl)carbamate

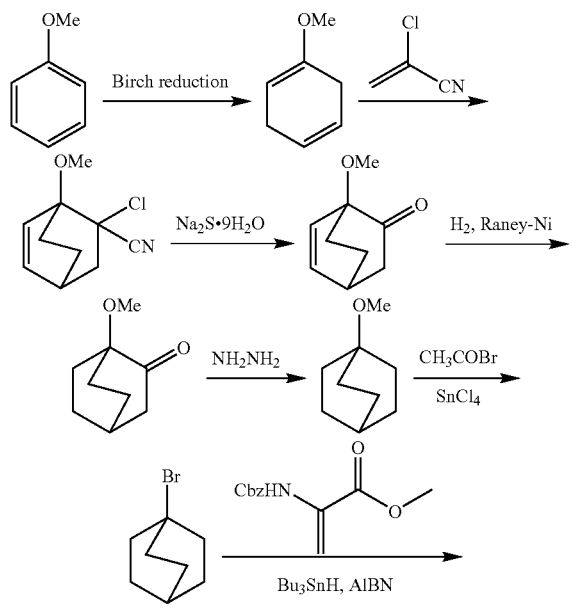

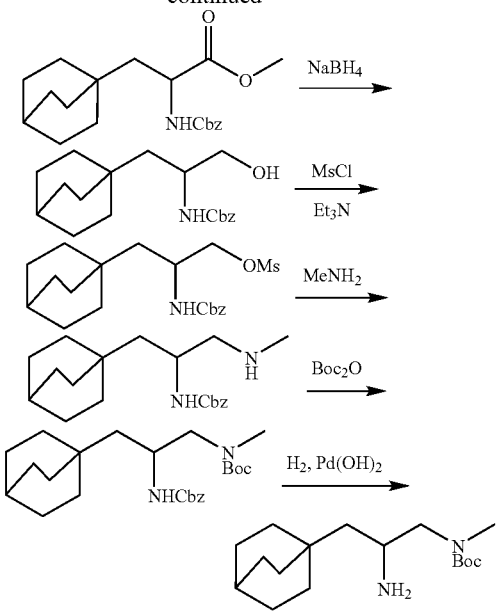

Step 1. 2-chloro-1-methoxybicyclo[2.2.2]oct-5-ene-2-carbonitrile

A solution of 1-methoxy-1,4-cyclohexadiene (15.0 g, 0.14 mol) and 2-chloroacylonitrile (17.5 g, 0.20 mol) in benzene was heated at reflux for 15 h. The solvent was removed, and the residue was purified by column chromatography to afford 2-chloro-1-methoxybicyclo[2.2.2]oct-5-ene-2-carbonitrile (14.0 g, 52%). $^1$H NMR (CDCl$_3$, 400 MHz) δ 6.44-6.23 (m, 2H), 3.51 (s, 3H), 2.69-2.50 (m, 2H), 2.27-1.41 (m, 5H).

Step 2. 1-methoxybicyclo[2.2.2]oct-5-en-2-one

A solution of 2-chloro-1-methoxybicyclo[2.2.2]oct-5-ene-2-carbonitrile (14.0 g, 71 mmol) and Na$_2$S.9H$_2$O (34.0 g, 142 mmol) in ethanol (175 mL) was heated under reflux for 14 h. The solution was poured into H$_2$O and extracted three times with ether. The combined extracts were washed with saturated aqueous NH$_4$Cl solution, H$_2$O, and brine. The organic layer was dried over Na$_2$SO$_4$, concentrated to the residue. The crude product was purified by column chromatography to afford 1-methoxybicyclo[2.2.2]oct-5-en-2-one (5.7 g, 57%). $^1$H NMR (CDCl$_3$, 400 MHz) δ 6.46 (dd, 1H), 6.22 (d, 1H), 3.50 (s, 3H), 2.94 (m, 1H), 2.11 (m, 2H), 1.53-1.92 (m, 4H).

Step 3. 1-methoxybicyclo[2.2.2]octan-2-one

To a solution of 1-methoxybicyclo[2.2.2]oct-5-en-2-one (16.5 g, 0.11 mol) in MeOH (250 mL) was added Raney-Ni (3.3 g). The reaction mixture was stirred at 40° C. and 45 psi under H$_2$ atmosphere for 2-3 h (8.0 g, 40%). The resulting mixture was filtered, the filtrate was concentrated in vacuo to produce 1-methoxybicyclo[2.2.2]octan-2-one (15.0 g, 90%). $^1$H NMR (CDCl$_3$, 400 MHz) δ 3.33 (s, 3H), 2.32 (d, 2H), 2.09 (m, 1H), 1.49-1.95 (m, 8H).

Step 4. 1-methoxybicyclo[2.2.2]octane

To a solution of potassium hydroxide (17 g, 250 mmol) and 85% hydrazine hydrate (11.5 g, 186 mmol) in ethylene glycol (220 mL) was added 1-methoxybicyclo[2.2.2]octan-2-one (11.0 g, 71.4 mmol). The mixture was heated to 195° C. over 1 h and heated for an additional hour. The flask was then fitted for distillation, and approximate 20 mL (two layers) of liquid was collected over a period of 1 h at 195° C. Subsequent dropwise addition of water (215 mL) to the reaction over a period of 3 h afforded a second fraction of distillates (approximately 180 mL). The combined distillates were extracted with ether (3×80 mL), the organic phase was dried over $Na_2SO_4$, and the volatiles were removed to produce 1-methoxybicyclo[2.2.2]octane (4.5 g, 45%) which was used in the next step directly without purification. $^1$H NMR ($CDCl_3$, 400 MHz) δ 3.14 (s, 3H), 1.63-1.59 (m, 6H), 1.58-1.51 (m, 6H), 1.47 (m, 1H).

Step 5. 1-bromobicyclo[2.2.2]octane

To a stirred mixture of 1-methoxybicyclo[2.2.2]octane (4.0 g, 28 mmol) and acetyl bromide (6.2 g, 50.4 mmol) was added 10 drops of stannic chloride at 0° C. After stirring for 0.5 h, the temperature was allowed to rise to 20-25° C. and stirring was continued at the same temperature for 3 h. After cooling to 0° C., water (30 mL) was added and the mixture was stirred for 10 min. Then the mixture was poured into water (150 mL) and extracted with ether (100 mL×3). The ether layers were combined, washed with aqueous sodium bicarbonate and water, and dried over sodium sulfate. The solvent was removed under reduced pressure to produce 1-bromobicyclo[2.2.2]octane (4.0 g, 75%), which was used for next step without purification. $^1$H NMR ($CDCl_3$) δ 2.23 (m, 6H), 1.95 (m, 1H), 1.81-1.63 (m, 6H), 1.52 (m, 1H).

Step 6. methyl 2-(benzyloxycarbonylamino)-3-(bicyclo[2.2.2]octan-1-yl)propanoate methyl 2-(benzyloxycarbonylamino)acrylate (2.05 g, 0.0095 mol, 1 eq.), 1-bromobicyclo[2.2.2]octane (1.8 g, 0.0095 mol, 1 eq.) and AIBN (0.312 g, 0.0019 mol, 0.2 eq.) were dissolved in benzene (30 mL) and heated to reflux. $Bu_3SnH$ (5.53 g, 0.019 mol, 2 eq.) was then added. The resulting mixture was stirred at reflux for 14 hrs. The solvent was removed and the residue was purified via preparative TLC (EtOAc/Petroleum ether=1:9) to give methyl 2-(benzyloxycarbonylamino)-3-(bicyclo[2.2.2]octan-1-yl)propanoate (480 mg, 15%) as a foam. $^1$H NMR ($CDCl_3$, 400 MHz) δ 7.35 (m, 5H), 5.13 (m, 2H), 4.42 (m, 1H), 3.73 (s, 3H), 1.8-1.1 (m, 15H), 1.28 (m, 1H).

Step 7. benzyl 1-(bicyclo[2.2.2]octan-1-yl)-3-hydroxypropan-2-ylcarbamate methyl 2-(benzyloxycarbonylamino)-3-(bicyclo[2.2.2]octan-1-yl)propanoate (720 mg, 2.087 mmol, 1 eq.) was dissolved in 15 mL of MeOH. $NaBH_4$ (631 mg, 16.7 mmol, 8 eq.) was added in portions. The mixture was stirred for 1.5 h. Saturated aq; $NaHSO_3$ (20 mL) was added and the pH of the mixture was adjusted to 7-8 with $NaHSO_3$ (s). The mixture was evaporated and extracted with EtOAc (20 mL×5). The organic phase was combined and evaporated to give benzyl 1-(bicyclo[2.2.2]octan-1-yl)-3-hydroxypropan-2-ylcarbamate as oil, which was used in the next step without further purification. MS ESI +ve m/z 318 (M+H).

Step 8. 2-(benzyloxycarbonylamino)-3-(bicyclo[2.2.2]octan-1-yl)propyl methanesulfonate To a solution of benzyl 1-(bicyclo[2.2.2]octan-1-yl)-3-hydroxypropan-2-ylcarbamate (668 mg, 2.1 mmol, 1 eq.), TEA (638 mg, 6.3 mmol, 3 eq.) in $CH_2Cl_2$ (100 mL) was added dropwise MsCl (289 mg, 2.52 mmol, 1.2 eq.) at 0-5° C. The resulting mixture was stirred for 2 hrs. Then the mixture was poured into water (20 mL) and extracted with $CH_2Cl_2$ (20 mL×4). The organic phase was combined and evaporated to give 2-(benzyloxycarbonylamino)-3-(bicyclo[2.2.2]octan-1-yl)propyl methanesulfonate (1.1 g, crude) as oil, which was used in the next step without further purification.

Step 9. benzyl 1-(bicyclo[2.2.2]octan-1-yl)-3-(methylamino)propan-2-ylcarbamate 2-(benzyloxycarbonylamino)-3-(bicyclo[2.2.2]octan-1-yl)propyl methanesulfonate (830 mg, 2.1 mmol) was dissolved in 15 mL of $NH_2Me$ in MeOH and stirred at 30-40° C. overnight. The mixture was concentrated to give benzyl 1-(bicyclo[2.2.2]octan-1-yl)-3-(methylamino)propan-2-ylcarbamate (1.0 g, crude) as an oil, which was used in the next step without further purification. MS ESI +ve m/z 331 (M+H).

Step 10. benzyl 1-(bicyclo[2.2.2]octan-1-yl)-3-(N-methyl-N-tert-butoxycarbonylamino)propan-2-ylcarbamate To a solution of benzyl 1-(bicyclo[2.2.2]octan-1-yl)-3-(methylamino)propan-2-ylcarbamate (695 mg, 2.1 mmol, 1 eq.) and TEA (636 mg, 6.3 mmol, 3 eq.) in $CH_2Cl_2$ (50 mL) was added dropwise $Boc_2O$ (681 mg, 3.15 mmol, 1.5 eq.). The resulting mixture was stirred overnight. Water (20 mL) was added into the mixture. The mixture was extracted with $CH_2Cl_2$ (20 mL×4) and the organic phase was combined and concentrated. The residue was purified via preparative TLC (EtOAc/Petroleum ether=1:4) to afford benzyl 1-(bicyclo[2.2.2]octan-1-yl)-3-(N-methyl-N-tert-butoxycarbonylamino)propan-2-ylcarbamate (250 mg, 28%) as a white foam. $^1$H NMR ($CDCl_3$, 400 MHz) δ 7.32 (m, 5H), 5.09 (m, 2H), 3.85 (m, 1H), 2.85 (s, 3H), 2.76 (d, 2H), 1.44 (s, 9H), 1.52-1.13 (m, 15H).

Step 11. tert-butyl 2-amino-3-(bicyclo[2.2.2]octan-1-yl)propyl(methyl)carbamate

A mixture of benzyl 1-(bicyclo[2.2.2]octan-1-yl)-3-(N-methyl-N-tert-butoxycarbonylamino)propan-2-ylcarbamate (250 mg, 0.58 mmol) and $Pd(OH)_2$ (20%, 60 mg) in 12 Ml of absolute of MeOH was hydrogenated under 20 psi $H_2$ for 2 h. TLC (EtOAc/Petroleum ether=1:2) indicated the completion of reaction. The mixture was then filtered and evaporated to afford tert-butyl 2-amino-3-(bicyclo[2.2.2]octan-1-yl)propyl(methyl)carbamate (150 mg, 87%) as oil, which was used in the next step without further purification.

Preparation X (±)$_3$-benzyl 7-tert-butyl 3,7-diazabicyclo[4.1.0]heptane-3,7-dicarboxylate

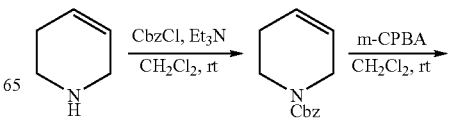

-continued

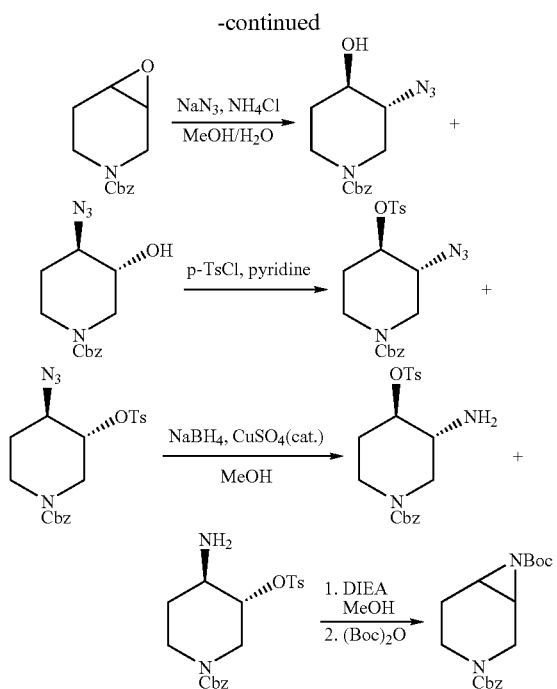

Step 1. Benzyl 5,6-dihydropyridine-1(2H)-carboxylate

A solution of 1,2,3,6-tetrahydropyridine (5.0 g, 60.15 mmol) and triethylamine (16.77 mL, 2 equiv) in CH$_2$Cl$_2$ (50 mL) was cooled to 0° C. (ice-water bath) followed by slow addition of benzyl chloroformate (9.7 mL, 1.1 equiv). After 30 min, the reaction mixture was allowed to warm slowly to rt and stirred for 4 h. The mixture was diluted with ether (300 mL), washed with 5% aq HCl (2×50 mL), satd aq NaHCO$_3$ (40 mL) and brine (40 mL), and dried over Na$_2$SO$_4$. After concentration, benzyl 5,6-dihydropyridine-1(2H)-carboxylate (9.93 g, 78% yield) was left.
MS ESI +ve m/z 218 (M+1).

Step 2. Benzyl 7-oxa-3-azabicyclo[4.1.0]heptane-3-carboxylate

A solution of benzyl 5,6-dihydropyridine-1(2H)-carboxylate (9.93 g, 45.76 mmol) in CH$_2$Cl$_2$ (75 mL) was cooled to 0° C. Solid m-chloroperoxybenzoic acid (77%, 15.38 g, 1.5 equiv) was added. After 10 min, the reaction mixture was warmed slowly to rt. A white precipitate formed after 1 h. The reaction was complete after an additional hour of stirring. The mixture was diluted with ether (300 mL), washed by with 5% aq NaOH (2×40 mL), 25% aq Na$_2$S$_2$O$_3$ solution (3×20 mL) and brine (30 mL), and dried over Na$_2$SO$_4$. After concentration, the residue was purified by flash chromatography to afford benzyl 7-oxa-3-azabicyclo[4.1.0]heptane-3-carboxylate (7.87 g, 74% yield). MS ESI +ve m/z 234 (M+1).

Step 3. trans-benzyl 4-azido-3-hydroxypiperidine-1-carboxylate and trans-benzyl 3-azido-4-hydroxypiperidine-1-carboxylate Benzyl 7-oxa-3-azabicyclo[4.1.0]heptane-3-carboxylate (6.78 g, 29.1 mmol), sodium azide (3.78 g, 2 equiv), and ammonium chloride (1.56 g, 1 equiv) were dissolved in methanol (100 mL) and water (20 mL). The mixture was heated at 65° C. for 18 h. The mixture was cooled to rt and methanol was removed under vacuum. The aqueous residue was extracted with ether (3×120 mL). The combined ether layers were washed with brine (30 mL) and dried over Na$_2$SO$_4$. Concentration afforded a mixture of regioisomers, trans-benzyl 4-azido-3-hydroxypiperidine-1-carboxylate and trans-benzyl 3-azido-4-hydroxypiperidine-1-carboxylate (8.07 g, quant.) which was used without further purification. MS ESI +ve m/z 277 (M+1).

Step 4. trans-benzyl 4-azido-3-(tosyloxy)piperidine-1-carboxylate and trans-benzyl 3-azido-4-(tosyloxy)piperidine-1-carboxylate trans-benzyl 4-azido-3-hydroxypiperidine-1-carboxylate and trans-benzyl 3-azido-4-hydroxypiperidine-1-carboxylate (8.07 g, 29.1 mmol) and pyridine (6 mL, 2.55 equiv) were dissolved in CH$_2$Cl$_2$ (20 mL) and cooled to 0° C. Solid p-TsCl (11.1 g, 2.1 equiv) was added. After 5 min, the reaction mixture was allowed to warm to rt slowly and stirred overnight. The mixture was diluted with ether (300 mL), washed with 5% HCl (3×35 mL), satd aq NaHCO$_3$ (40 mL), brine (30 mL), and dried over Na$_2$SO$_4$. After concentration, the residue was purified by flash chromatography (120 g silica gel column, 0-50% EtOAc in hexanes gradient) to afford a mixture of trans-benzyl 4-azido-3-(tosyloxy)piperidine-1-carboxylate and trans-benzyl 3-azido-4-(tosyloxy)piperidine-1-carboxylate (12.18 g, 97%). MS ESI +ve m/z 431 (M+1).

Step 5. trans-benzyl 4-amino-3-(tosyloxy)piperidine-1-carboxylate and trans-benzyl 3-amino-4-(tosyloxy)piperidine-1-carboxylate To a 0° C. solution of CuSO$_4$.5H$_2$O (642 mg, 0.5 equiv) in methanol (30 mL), NaBH$_4$ (200 mg, 1.05 equiv) was added. To the stirred black suspension was added a solution of trans-benzyl 4-azido-3-(tosyloxy)piperidine-1-carboxylate and trans-benzyl 3-azido-4-(tosyloxy)piperidine-1-carboxylate (2.21 g, 5.14 mmol) in methanol (20 mL). Additional NaBH$_4$ (578 mg, 3 equiv) was added in four portions over the course of 1 h. The reaction mixture was filtered through a pad of Celite and concentrated. The residue was diluted with CH$_2$Cl$_2$ (70 mL), washed with water (15 mL), satd aq NH$_4$Cl solution (2×10 mL), brine (15 mL), and dried over Na$_2$SO$_4$. Concentration afforded trans-benzyl 4-amino-3-(tosyloxy)piperidine-1-carboxylate and trans-benzyl 3-amino-4-(tosyloxy)piperidine-1-carboxylate (1.34 g, 64%). The product was used for the next step without further purification. MS ESI +ve m/z 405 (M+1).

Step 6. (±)$_3$-benzyl 7-tert-butyl 3,7-diaza-bicyclo[4.1.0]heptane-3,7-dicarboxylate The regioisomers, trans-benzyl 4-amino-3-(tosyloxy)piperidine-1-carboxylate and trans-benzyl 3-amino-4-(tosyloxy)piperidine-1-carboxylate, (274 mg, 0.678 mmol) and DIEA (177 µL, 1.5 equiv) were dissolved in methanol (8 mL) and heated to 80° C. for 20 min in a CEM Microwave reactor. The reaction mixture was concentrated and redissolved in CH$_2$Cl$_2$ (10 mL). (Boc)$_2$O (150 mg, 1 equiv) was added and the mixture was stirred overnight at rt. The reaction mixture was concentrated and purified by flash chromatography (40 g silica gel column, 0-45% EtOAc in hexanes gradient) to afford (±)$_3$-benzyl 7-tert-butyl 3,7-diazabicyclo[4.1.0]heptane-3,7-dicarboxylate (227 mg, quant). MS ESI +ve m/z 355 (M+Na).

The following compounds were prepared following procedures analogous to those described above:
1) 3-benzyl 6-tert-butyl 3,6-diaza-bicyclo[3.1.0]hexane-3,6-dicarboxylate using 2,5-dihydro-1H-pyrrole in Step 1.

Preparation Y (±)-(3S,4R)-benzyl 3-amino-4-(cyclobutylmethyl)piperidine-1-carboxylate

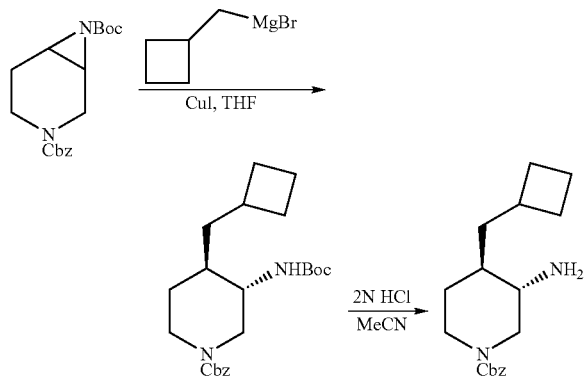

Step 1. (±)-trans-benzyl 3-(tert-butoxycarbonylamino)-4-(cyclobutylmethyl)piperidine-1-carboxylate (±)-3-benzyl 7-tert-butyl 3,7-diaza-bicyclo[4.1.0]heptane-3,7-dicarboxylate (62 mg, 0.187 mmol), CuI (8 mg, 0.2 equiv), and a stirring bar were put in a 100-mL flask. The flask was evacuated and backfilled with $N_2$ gas (3×). Dry THF (5 mL) was added and the mixture was cooled to −40° C. (Cyclobutylmethyl)magnesium bromide in THF (620 µL, 3 equiv., ~0.89 M) was added slowly. After 8 min, the reaction mixture was allowed to warm slowly to rt. After 20 min, the reaction mixture turned black. After stirring a further 2 h the reaction was complete. Satd aq $NH_4Cl$ solution (5 mL) was added to quench the reaction. The reaction mixture was partitioned between EtOAc (50 mL) and satd aq $NH_4Cl$ solution (20 mL). The aqueous layer was extracted with EtOAc (20 mL). The combined EtOAc layers were washed with water (15 mL), brine (15 mL), and dried over $Na_2SO_4$. After concentration, the residue was purified by Gilson to afford (±)-trans-benzyl 3-(tert-butoxycarbonylamino)-4-(cyclobutylmethyl)piperidine-1-carboxylate (14 mg, 19% yield). MS ESI +ve m/z 425 (M+Na).

Step 2. (±)-trans-benzyl 3-amino-4-(cyclobutylmethyl)piperidine-1-carboxylate (±)-trans-benzyl 3-(tert-butoxycarbonylamino)-4-(cyclobutylmethyl)piperidine-1-carboxylate (14 mg, 0.035 mmol)) was dissolved in 1:1 2N aq HCl/acetonitrile (8 mL) and stirred overnight at rt. The reaction mixture was basified with 5% aq NaOH solution to about pH=9. The acetonitrile was removed under vacuum. The aqueous residue was extracted with $CH_2Cl_2$ (3×20 mL). The combined organic layers were washed with brine (10 mL) and dried over $Na_2SO_4$. Concentration afforded (±)-trans-benzyl 3-amino-4-(cyclobutylmethyl)piperidine-1-carboxylate (8.9 mg, 85% yield). The crude product was used in the next step without further purification. MS ESI +ve m/z 303 (M+Na).

The following compounds were prepared following procedures analogous to those described above:
1) (±)-trans-benzyl 3-amino-4-isobutylpyrrolidine-1-carboxylate using (±)-3-benzyl 6-tert-butyl 3,6-diaza-bicyclo[3.1.0]hexane-3,6-dicarboxylate and isobutylmagnesium bromide in Step 1.

Preparation Z 2-(trimethylsilyl)ethyl (S)-2-amino-3-((1s,3R,4S)-3,4-difluorocyclopentyl)propyl-(methyl)carbamate

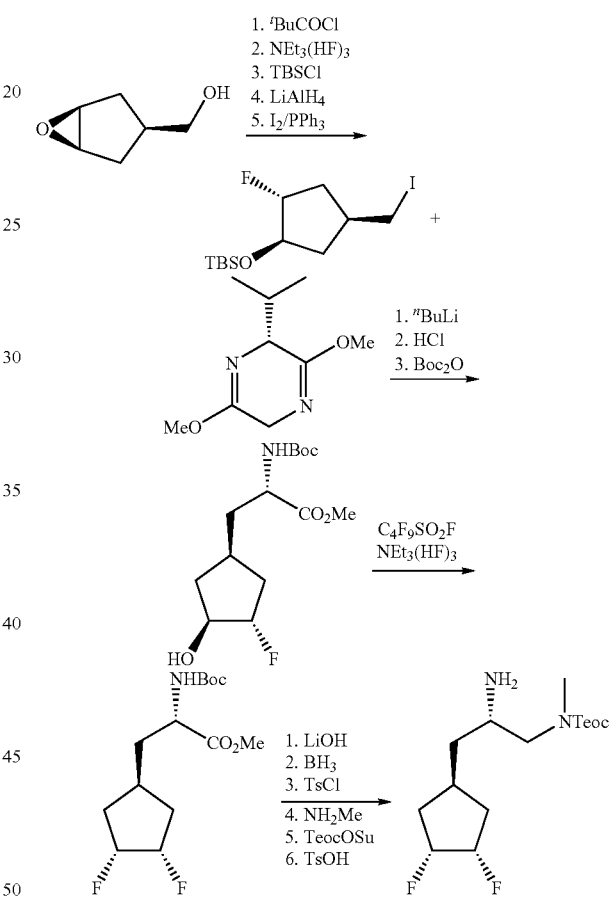

Step 1a-e. (±)-tert-butyl((1r,2R,4S)-2-fluoro-4-(iodomethyl)cyclopentyloxy)dimethylsilane The (1S,3r,5R)-6-oxa-bicyclo[3.1.0]hexan-3-ylmethanol (2.73 g, 24.0 mmol, 1.0 equiv)), NEt$^i$Pr$_2$ (6.8 g, 48.0 mmol, 2.0 equiv) and DMAP (2.9 g, 24 mmol, 1.0 equiv) were dissolved in $CH_2Cl_2$ and the solution cooled to 0° C. Pivaloyl chloride (5.80 g, 48.0 mmol, 2.0 equiv) was added and the mixture stirred for 2 h. The mixture was transferred to a separatory funnel and solution washed with saturated $NH_4Cl$, brine, dried over $Na_2SO_4$, filtered, and evaporated. The crude epoxyester was purified by flash chromatography on silica, eluting with 0-27% EtOAc in hexanes. This affords 4.1 g (86% yield) of the epoxy ester.

The above epoxide (4.1 g, 20.7 mmol) was dissolved in 10 mL of NEt₃(HF)₃ and the mixture heated to 117° C. for 17 h. After this time, the mixture was cooled to ambient temperature and the excess HF quenched by addition of 10% K₂CO₃. The mixture was diluted with EtOAc, and the layers separated. The organic layer was washed with 0.5 M HCl, brine, dried over Na₂SO₄, filtered, and evaporated. The crude fluorohydrin (4.53 g) was used in the next step with no further purification.

The crude fluorohydrin, (4.53 g, >20 mmol), TBSCl (6.23 g, 42 mmol, 2.0 equiv) and imidazole (5.72 g, 84.0 mmol, 4.0 equiv) were dissolved in 10 mL of DMF. The mixture was stirred at ambient temperature for 16 h. After this time the solvent was removed in vacuo. The residue was portioned between Et₂O and water. The layers were separated and the organic layer washed with 0.5 M HCl, brine dried over MgSO₄, filtered, and evaporated. This solution cooled to 0° C. and a solution of LiAlH₄ in THF (1.0 M, 21 mL, 1.0 equiv) added. After 1 h, the excess LiAlH₄ was quenched by drop wise addition of brine and the resulting slurry dispersed by addition of ca 10 g of Celite. The mixture was filtered through a pad of Celite and evaporated to yield 1.20 g (5.2 mmol, 25% yield) of the desired alcohol.

The above alcohol (1.10 g, 4.4 mmol, 1.0 equiv), PPh₃ (1.45 g, 5.5 mmol, 1.25 equiv), and imidazole (1.0 g, 14.7 mmol, 3.3 equiv) were dissolved in THF. Iodine (1.4 g, 5.5 mmol, 1.25 equiv) was added in portions over a 20 min period. The solvent was removed and the mixture filtered through a pad of silica, eluting with Et₂O. The filtrate was evaporated and the iodide purified by flash chromatography on silica, eluting with 0-7% EtOAc in hexanes. This afforded 1.31 g (83% yield) of (±)-tert-butyl((1r,2R,4S)-2-fluoro-4-(iodomethyl)cyclopentyloxy)dimethylsilane.

Step 2a-c. (S)-methyl 2-(tert-butoxycarbonylamino)-3-((1r*,3S*,4S*)-3-fluoro-4-hydroxycyclopentyl)propanoate (R)-2-isopropyl-3,6-dimethoxy-2,5-dihydropyrazine (134 g, 7.24 mmol, 1.5 equiv) was dissolved in 9 mL of THF and the solution cooled to −78° C. A 2.5 M solution of nBuLi (2.9 mL, 7.24 mmol, 1.5 equiv) was added over a 15 min period and the resulting solution stirred for 0.5 h. A solution of (±)-tert-butyl((1r,2R,4S)-2-fluoro-4-(iodomethyl)cyclopentyloxy)dimethylsilane (1.73 g, 4.83 mmol, 1.0 equiv) in THF (9 mL) was added. The mixture was stirred at −78° C. for 2 h, then warmed to −20 and allowed to stir overnight at that temperature. The mixture was quenched with water and the organic layer washed with brine, dried over Na₂SO₄, filtered, and evaporated. The resulting mixture was dissolved in 60 mL of 1:1 CH₃CN: 2.0 M HCl. After stirring for 5 h at ambient temperature the mixture was evaporated and re-dissolved in 30 mL of CH₃CN. To this was added 30 mL of 10% K₂CO₃, followed by 3.3 g (15 mmol, 3.0 equiv) of di-tert-butyl dicarbonate and the mixture rapidly stirred for 1 h. After the time the solution was evaporated. The yellow residue was dissolved in EtOAc and washed with 10% K₂CO₃, 0.5 M HCl, brine, then dried over Na₂SO₄, filtered, and evaporated. The desired protected amino acid was purified by flash chromatography on silica with 0-41% EtOAc. This afforded 1114 mg (3.63 mmol, 75% yield) of (S)-methyl 2-(tert-butoxycarbonylamino)-3-((1 r*,3S*,4S*)-3-fluoro-4-hydroxycyclopentyl)propanoate.

Step 3. (S)-methyl 2-(tert-butoxycarbonylamino)-3-((1s,3R,4S)-3,4-difluorocyclopentyl)propanoate (S)-methyl 2-(tert-butoxycarbonylamino)-3-((1r*,3S*,4S*)-3-fluoro-4-hydroxycyclopentyl)propanoate (798 mg, 2.35 mmol, 1.0 equiv), C₄F₉SO₂F (1425 mg, 4.7 mmol, 2.0 equiv), NEt₃(HF)₃ (1138 mg, 7.1 mmol, 3.0 equiv) and NEt₃ (1427 mg, 14.1 mmol, 6.0 equiv) were dissolved in THF and the mixture allowed to stir at ambient temperature for 19 h. The excess HF was quenched by quenched by addition of 10% K₂CO₃. The mixture was diluted with EtOAc, and the layers separated. The organic layer was washed with 0.5 M HCl, brine, dried over Na₂SO₄, filtered, and evaporated. The difluoride was purified by flash chromatography on silica, eluting with 0-29% EtOAc in hexanes. This afforded 423 mg (1.24 mmol, 53% yield) of pure (S)-methyl 2-(tert-butoxycarbonylamino)-3-((1s,3R,4S)-3,4-difluorocyclopentyl)propanoate.

Step 4a-f. 2-(trimethylsilyl)ethyl (S)-2-amino-3-((1s,3R,4S)-3,4-difluorocyclopentyl)propyl(methyl)carbamate Lithium hydroxide hydrate (48 mg, 1.14 mmol, 3.0 equiv) was dissolved in 1.0 mL of water. This was added to a solution of (S)-methyl 2-(tert-butoxycarbonylamino)-3-((1s,3R,4S)-3,4-difluorocyclopentyl)propanoate (116 mg, 0.379 mmol, 1.0 equiv) in 10 mL of THF. The solution was stirred for 2 h. The mixture was quenched by addition of 10% citric acid (2 mL) and the mixture diluted with water and EtOAc. The layers were separated and the organic layer dried over Na₂SO₄, filtered, and evaporated. The resulting acid was dissolved in THF (10 mL), cooled to 0° C., and borane (1.0 M in THF, 3.0 mL, 8.0 equiv) added. The mixture was stirred at 0° C. for 3 h. The mixture was diluted with EtOAc and 0.25 M HCl added. The layers were separated and the organic layer washed with brine, dried over MgSO₄, filtered through a pad of silica gel, and evaporated. This afforded 88 mg of the desired amino alcohol.

The amino alcohol (88 mg, 0.28 mmol, 1.0 equiv), tosyl chloride (420 mg, 2.21 mmol, 7.9 equiv) and DABCO (50 mg, 0.445 mmol, 1.6 equiv) were dissolved in pyridine and the mixture stirred for 48 h at ambient. The mixture was evaporated and the residue taken up in EtOAc/0.5 M HCl. The layers were separated and the organic layer washed with 0.5 M HCl, brine, dried over Na₂SO₄, filtered, and evaporated. The crude tosylate was purified by flash chromatography on silica, eluting with 0-29% EtOAc in hexanes. The resulting tosylate was used directly in the next step.

The above tosylate and was dissolved in 20 mL of 33% NH₂Me in EtOH. The mixture was heated to 45° C. for 3 h. The mixture was evaporated and the residue dissolved in Et₂O, washed with K₂CO₃, brine, then dried over Na₂SO₄, filtered, and evaporated. The crude amine was used in the next step with no further purification.

The above amine was dissolved in 10 mL of 1:1 acetonitrile/10% aqueous K₂CO₃. TeocOSu (64 mg, 0.275 mmol) was added and mixture stirred for 4 h. The acetonitrile was removed in vacuo and the product extracted with 2×20 mL of EtOAc. The combined organic extracts were dried over Na₂SO₄, filtered, and evaporated. The product was isolated by flash chromatography on silica eluting with 0-29% EtOAc. The protected amine (35 mg, 0.075 mmol, 27% yield for the four steps) was isolated.

(S)-methyl 2-(tert-butoxycarbonylamino)-3-((1s,3R,4S)-3,4-difluorocyclopentyl)propanoate was obtained by following procedures analogous to procedures in Preparation M, Step 4 using tert-butyl (S)-1-((1s,3R,4S)-3,4-difluorocyclopentyl)-3-(N-methyl-N-(2-(trimethylsilyl)ethoxycarbonyl)amino)propan-2-ylcarbamate in Step 4.

Preparation A1 tert-butyl (S)-2-amino-3-((1r,3R,4S)-3,4-difluorocyclopentyl)propyl(methyl)carbamate

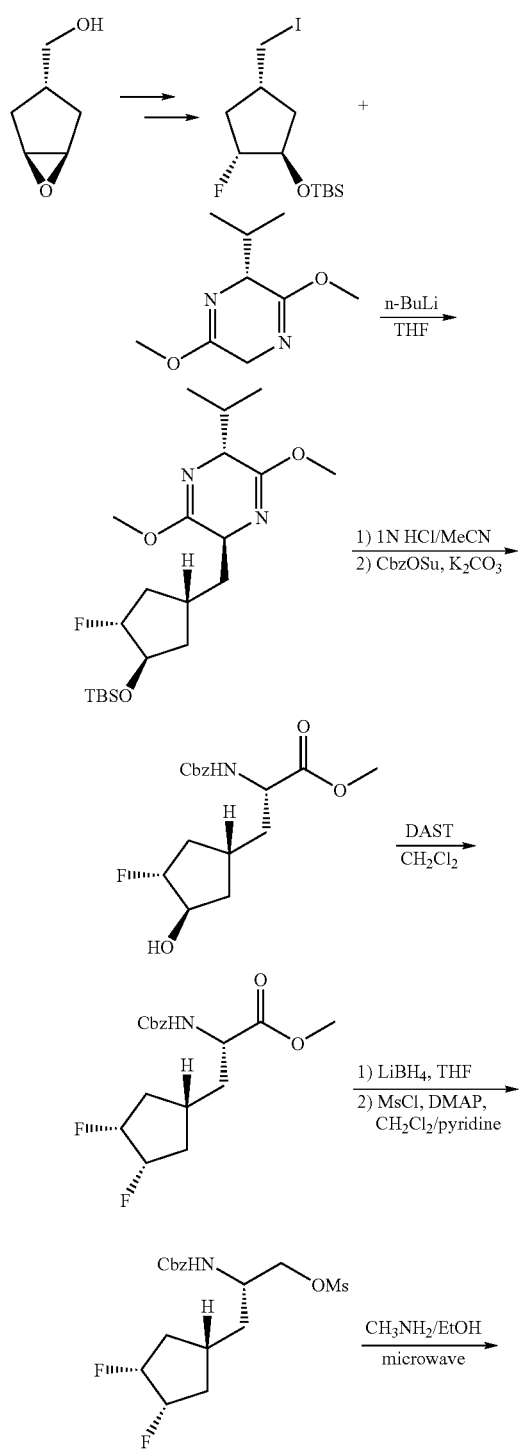

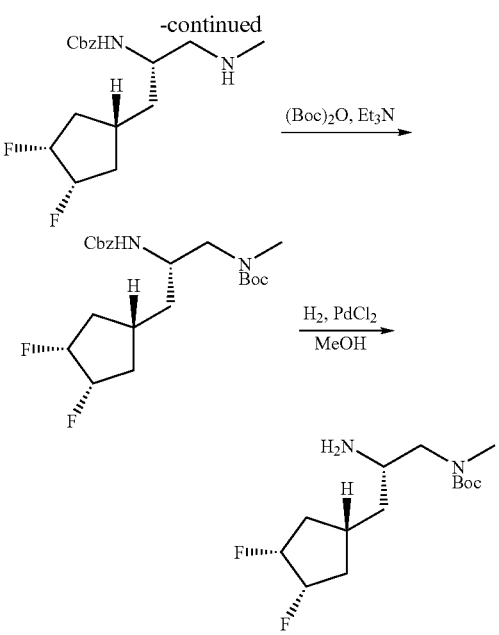

Step 1-5. (±)-tert-butyl((1r,2R,4R)-2-fluoro-4-(iodomethyl)cyclopentyloxy)dimethylsilane (±)-tert-butyl((1r,2R,4R)-2-fluoro-4-(iodomethyl)cyclopentyloxy)dimethylsilane was obtained using procedures analogous to Preparation Z, Steps 1-5, using (1S,3s,5R)-6-oxa-bicyclo[3.1.0]hexan-3-ylmethanol in Step 1.

Step 6. (2S,5R)-2-(((1r*,3R*,4R*)-3-(tert-butyldimethylsilyloxy)-4-fluorocyclopentyl)methyl)-5-isopropyl-3,6-dimethoxy-2,5-dihydropyrazine A solution of (R)-2-isopropyl-3,6-dimethoxy-2,5-dihydropyrazine (1.2 g, 1.5 equiv.) in dry THF (30 mL) was cooled to −78° C. n-BuLi (1.6 M in Hexane, 4.08 mL, 1.5 equiv.) was added dropwise. After stirring 1 h at −78° C., a solution of (±)-tert-butyl((1r,2R,4R)-2-fluoro-4-(iodomethyl)cyclopentyloxy)dimethylsilane (1.56 g, 4.36 mmol) in dry THF (8 mL) was added dropwise. The mixture was stirred another 2 h at −78° C. The mixture was warmed up to rt slowly, quenched by sat. NH$_4$Cl solution (30 mL), extracted by diethyl ether (2×150 mL). The combined organic layers were washed by brine (30 mL), dried over Na$_2$SO$_4$. After filtration and concentration, the residue was purified by ISCO (40 g column, 0~25% EtOAc in Hexanes) to afford (2S,5R)-2-(((1r*,3R*,4R*)-3-(tert-butyldimethylsilyloxy)-4-fluorocyclopentyl)methyl)-5-isopropyl-3,6-dimethoxy-2,5-dihydropyrazine (1.81 g, quant. yield) as a clear oil. MS ESI +ve m/z 415 (M+1).

Step 7. (S)-methyl 2-(benzyloxycarbonylamino)-3-((1r*,3R*,4R*)-3-fluoro-4-hydroxycyclopentyl)propanoate (2S,5R)-2-(((1r*,3R*,4R*)-3-(tert-butyldimethylsilyloxy)-4-fluorocyclopentyl)methyl)-5-isopropyl-3,6-dimethoxy-2,5-dihydropyrazine (500 mg, 1.21 mmol) was dissolved in 1:1 mixture of 1 N HCl solution and acetonitrile (50 mL). The mixture was stirred 3 h at rt, then concentrated. K$_2$CO$_3$ (840 mg, 5 equiv.) and CbzOSu (903 mg, 3 equiv.) were added to the residue, The mixture was dissolved in 1:1 water and acetonitrile (50 mL), stirred overnight at rt. The acetonitrile was removed by evaporation under reduced pressure. The aqueous residue was extracted by EtOAc (3×20 mL). The combined organic layers were washed by brine (20 mL), dried over $Na_2SO_4$. After filtration and concentration, the residue was purified by ISCO (40 g column) to afford 274 mg (67% yield) of (s)-methyl 2-(benzyloxycarbonylamino)-3-((1r*,3R*,4R*)-3-fluoro-4-hydroxycyclopentyl)propanoate. MS ESI +ve m/z 362 (M+Na). $^1$H NMR (CDCl$_3$) δ 7.35 (m, 5H), 5.34 (s, 1H), 5.10 (s, 2H), 4.82 (d, 1H), 4.39-4.19 (m, 2H), 3.73 (s, 3H), 2.43-2.24 (m, 2H), 2.09-1.38 (m, 6H). $^{19}$F NMR (CDCl$_3$) δ −175.92.

Step 8. (S)-methyl 2-(benzyloxycarbonylamino)-3-((1r,3R,4S)-3,4-difluorocyclopentyl)propanoate A solution of (S)-methyl 2-(benzyloxycarbonylamino)-3-((1r*,3R*,4R*)-3-fluoro-4-hydroxycyclopentyl)propanoate (135 mg, 0.398 mmol) in $CH_2Cl_2$ (6 mL) was cooled to −78° C. followed by the slow addition of DAST (100 μL, 2 equiv.). After 1 h, the reaction mixture was warmed up to rt slowly and stirred overnight. Sat. $NaHCO_3$ solution (10 mL) was added to quench the reaction. The mixture was separated. The aqueous phase was extracted by $CH_2Cl_2$ (25 mL). The combined organic layers were concentrated and purified by prep HPLC to afford 55 mg (41% yield) (S)-methyl 2-(benzyloxycarbonylamino)-3-((1r,3R,4S)-3,4-difluorocyclopentyl)propanoate. MS ESI +ve m/z 364 (M+Na). $^1$H NMR (CDCl$_3$) δ 7.35 (m, 5H), 5.33 (d, 1H), 5.10 (s, 2H), 4.89 (m, 1H), 4.76 (m, 1H), 4.37 (td, 1H), 3.74 (s, 3H), 2.30-2.07 (m, 2H), 1.99 (m, 1H), 1.80-1.60 (m, 3H). $^{19}$F NMR (CDCl$_3$) δ −199.81.

Step 9. (S)-2-(benzyloxycarbonylamino)-3-((1r,3R,4S)-3,4-difluorocyclopentyl)propyl methanesulfonate A solution of (S)-methyl 2-(benzyloxycarbonylamino)-3-((1r,3R,4S)-3,4-difluorocyclopentyl)propanoate (218 mg, 0.64 mmol) in dry THF (8 mL) was cooled to 0° C. A 2.0 M $LiBH_4$ solution in THF (640 μL, 2 eq.) was added slowly. After 20 min, the reaction mixture was warmed up to rt slowly. After stirring for 2 hrs, the mixture was cooled to 0° C., quenched by 5% HCl (10 mL), diluted by EtOAc (20 mL). After separation, the aqueous phase was extracted by EtOAc (2×10 mL). The combined organic layers were washed by brine (10 mL), dried over $Na_2SO_4$. After filtration and concentration, the crude product was redissolved in $CH_2Cl_2$ (6 mL) and pyridine (1.5 mL). DMAP (40 mg, 0.5 equiv.) and methylsulfonyl chloride (174 μL, 13.5 equiv.) was added sequentially. After stirring overnight at rt, the mixture was diluted by EtOAc (35 mL), washed by 5% HCl (2×12 mL), sat. $NaHCO_3$ solution (12 mL), brine (10 mL), dried over $Na_2SO_4$. After filtration and concentration, the residue was purified by ISCO (12 g column, 5%-80% EtOAc in Hexanes) to afford 187 mg (75% yield) of (S)-2-(benzyloxycarbonylamino)-3-((1r,3R,4S)-3,4-difluorocyclopentyl)propyl methanesulfonate as a clear oil. MS ESI +ve m/z 393 (M+1). $^1$H NMR (CDCl$_3$) δ 7.34 (m, 5H), 5.09 (s, 2H), 5.01 (m, 1H), 4.83 (d, 2H), 4.20 (m, 2H), 3.94 (m, 1H), 2.96 (s, 3H), 2.46-1.92 (m, 3H), 1.67 (m, 4H).
$^{19}$F NMR (CDCl$_3$) δ −196.74.

Step 10. benzyl (S)-1-((1r,3R,4S)-3,4-difluorocyclopentyl)-3-(N-Methyl-N-tert-butoxycarbonylamino)propan-2-ylcarbamate (S)-2-(benzyloxycarbonylamino)-3-((1r,3R,4S)-3,4-difluorocyclopentyl)propyl methanesulfonate (187 mg, 0.478 mmol), 33% methylamine in ethanol (2 mL) and ethanol (2 mL) were mixed and heated in CEM microwave oven for 20 min at 90° C. The mixture was then concentrated, redissolved in $CH_2Cl_2$ (6 mL). (Boc)$_2$O (200 mg, 2 equiv.) and $Et_3N$ (164 μL, 1 equiv.) were added. The mixture was stirred 3 h at rt. The mixture was then concentrated and the residue was purified by prep HPLC to afford 72 mg (35% yield for 2 steps) of benzyl (S)-1-((1r,3R,4S)-3,4-difluorocyclopentyl)-3-(N-Methyl-N-tert-butoxycarbonylamino)propan-2-ylcarbamate as a clear oil. MS ESI +ve m/z 449 (M+Na).

Step 11. tert-butyl (S)-2-amino-3-((1r,3R,4S)-3,4-difluorocyclopentyl)propyl(methyl)carbamate benzyl (S)-1-((1r,3R,4S)-3,4-difluorocyclopentyl)-3-(N-Methyl-N-tert-butoxycarbonylamino)propan-2-ylcarbamate (72 mg, 0.169 mmol), PdCl$_2$ (catalytic amount, ca 15 mg) were mixed with methanol (20 mL). The mixture was put on Parr hydrogenation shaker for 30 min at 30 psi H$_2$ atmosphere. The mixture was filtered, concentrated to afford 51 mg (quant. yield) crude tert-butyl (S)-2-amino-3-((1r,3R,4S)-3,4-difluorocyclopentyl)propyl(methyl)carbaanate.

Preparation B1

(S)-2-(trimethylsilyl)ethyl 2-amino-3-(4,4-difluorocyclohexyl)propyl(methyl)carbamate

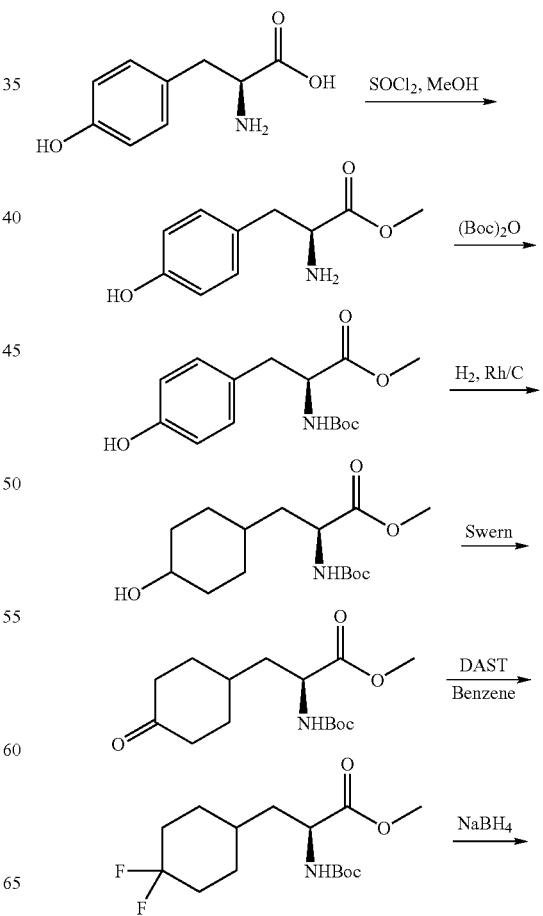

-continued

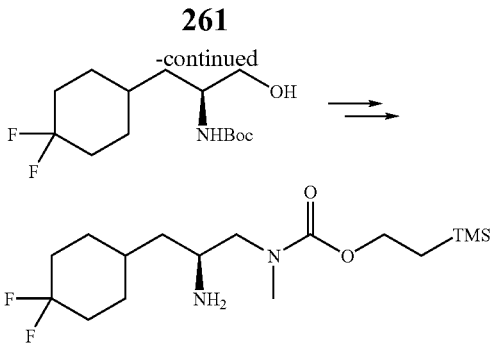

Step 1. L-tyrosine methyl ester

To a solution of L-tyrosine (45.3 g, 0.25 mol) in CH$_3$OH (680 mL), SOCl$_2$ (44.6 g, 0.375 mol) was added dropwise at 0° C. After addition, the mixture was allowed to warm to rt and then refluxed for overnight. The reaction mixture was concentrated to give L-tyrosine methyl ester (49.2 g, 100%), which was used in the next step without purification.

Step 2. L-N-Boc-tyrosine methyl ester

To a solution of Boc$_2$O (60 g, 0.275 mol) in CH$_2$Cl$_2$ (700 mL) was added dropwise to a solution of L-tyrosine methyl ester (49.2 g, 0.25 mol) and Et$_3$N (63.1 g, 0.625 mol) in CH$_2$Cl$_2$ (200 mL) at 0° C. After stirring at rt for 3 h, the mixture was concentrated to give the crude ester, which was purified by column to give pure L-N-Boc-tyrosine methyl ester (68.1 g, 92%). $^1$H NMR (CDCl$_3$, 400 MHz) δ 6.96 (d, 2H), 6.73 (d, 2H), 5.88 (s, 1H), 5.00 (d, 1H), 4.53 (m, 1H), 3.71 (s, 3H), 3.00 (m, 2H), 1.42 (s, 9H). MS ESI +ve m/z 296 (M+1).

Step 3. (S)-methyl 2-(tert-butoxycarbonylamino)-3-(4-hydroxycyclohexyl)propanoate A solution of —N-Boc-tyrosine methyl ester (68.1 g, 0.231 mol) in methanol (1200 mL) was added Rh/C (13.6 g, 5% on wetted carbon) and hydrogenated for overnight at 55-60° C. and under 55 psi. The catalyst was filtered off with Celite and the filtrate was concentrated to give (S)-methyl 2-(tert-butoxycarbonylamino)-3-(4-hydroxycyclohexyl)propanoate (59.5 g, 85.6%) as an oil. $^1$H NMR (CDCl$_3$, 400 MHz) δ 4.90 (m, 1H), 4.34 (m, 1H), 3.97 (m, 1H), 3.72 (s, 3H), 3.52 (m, 1H), 2.00-0.80 (m, 11H), 1.43 (s, 9H). MS ESI +ve m/z 303 (M+1).

Step 4. (S)-methyl 2-(tert-butoxycarbonylamino)-3-(4-oxocyclohexyl)propanoate To a solution of oxalyl dichloride (49.5 g, 0.39 mol) in dry CH$_2$Cl$_2$ (480 mL) was added dropwise a solution of dry DMSO (60.8 g, 0.78 mol) in dry CH$_2$Cl$_2$ (200 mL) at −65° C. for about 0.5-1 hr. Then a solution of (S)-methyl 2-(tert-butoxycarbonylamino)-3-(4-hydroxycyclohexyl)propanoate (59.5 g, 0.197 mol) in dry CH$_2$Cl$_2$ (600 mL) was added dropwise to the above mixture for about 0.5-1 hr. It was allowed to stir for 4-6 hr at −50--30° C. Upon completion of the reaction, 158 mL of Et$_3$N was added dropwise and the mixture was warmed to rt. The solution was added sat. NaHCO$_3$, extracted by EtOAc, washed with H$_2$O, brine, dried over Na$_2$SO$_4$, filtered and concentrated. The residue was purified by flash chromatograph to give (S)-methyl 2-(tert-butoxycarbonylamino)-3-(4-oxocyclohexyl)propanoate (39.5 g, 67%). $^1$H NMR (CDCl$_3$, 400 MHz) δ 5.00 (d, J=8.0H, 1H), 4.39 (m, 1H), 3.74 (s, 3H), 2.40-1.30 (m, 11H), 1.44 (s, 9H). MS ESI +ve m/z 301 (M+1).

Step 5. (S)-methyl 2-(tert-butoxycarbonylamino)-3-(4,4-difluorocyclohexyl)propanoate To a solution of (2-methyl 2-(tert-butoxycarbonylamino)-3-(4-oxocyclohexyl)propanoate (29.9 g, 0.1 mol) in dry benzene (600 mL) was added dropwise the solution of DAST (32.5 g, 0.2 mol) at 0° C. After addition, the mixture was heated to reflux under N$_2$ atmosphere for 2-3 hrs. The mixture was treated with sat. NaHCO$_3$ (400 mL) and EtOAc (300 mL). The aqueous phase was extracted with EtOAc and the combined organic layer was washed with brine (300 mL), dried over Na$_2$SO$_4$, filtered, concentrated in vacuo to give the crude (S)-methyl 2-(tert-butoxycarbonylamino)-3-(4,4-difluorocyclohexyl)propanoate (28.6 g, 89%), which was used in the next step without purification. $^1$H NMR (CDCl$_3$, 400 MHz) δ 4.93 (brs, 1H), 4.35 (m, 1H), 3.74 (s, 3H), 2.30-1.10 (m, 11H), 1.44 (s, 9H). MS ESI +ve m/z 322 (M+1).

Step 6. (S)-tert-butyl 1-(4,4-difluorocyclohexyl)-3-hydroxypropan-2-ylcarbamate To a solution of (S)-methyl 2-(tert-butoxycarbonylamino)-3-(4,4-difluorocyclohexyl)propanoate (28.6 g, 0.089 mol) in EtOH (600 mL) at 0° C. was added NaBH$_4$ (27.1 g, 0.713 mol) in portions while the temperature was maintained at 0-5° C. The mixture was stirred for 2-3 hr at rt and then evaporated. The residue was partitioned between water and EtOAc. The organic layer was washed with H$_2$O and brine, dried over Na$_2$SO$_4$ and evaporated to give (S)-tert-butyl 1-(4,4-difluorocyclohexyl)-3-hydroxypropan-2-ylcarbamate (25.7 g, 99%), which was used in the next step without purification. $^1$H NMR (CDCl$_3$, 400 MHz) δ 4.61 (d, J=7.6 Hz, 1H), 3.70 (m, 1H), 3.50 (m, 1H), 2.45-1.10 (m, 11H), 1.44 (s, 9H). MS ESI +ve m/z 295 (M+1).

Step 7-10. (S)-2-(trimethylsilyl)ethyl 2-amino-3-(4,4-difluorocyclohexyl)propyl(methyl)carbamate (S)-2-(trimethylsilyl)ethyl 2-amino-3-(4,4-difluorocyclohexyl)propyl(methyl)carbamate was obtained using procedures analogous to Preparation S, Steps 3-6, using (S)-tert-butyl 1-(4,4-difluorocyclohexyl)-3-hydroxypropan-2-ylcarbamate in Step 3. $^1$H NMR (CD$_3$OD, 400M Hz) δ 4.17 (t, 2H), 3.15 (m, 1H), 2.93 (s, 3H), 2.61 (dd, 1H), 2.36 (dd, 1H), 2.12-1.16 (m, 11H), 1.00 (t, 2H), 0.04 (s, 9H). MS ESI +ve m/z 351 (M+1).

Preparation C1

2-(trimethylsilyl)ethyl (S)-2-amino-3-((S)-1-methyl-6-oxopiperidin-3-yl)propyl(methyl)carbamate

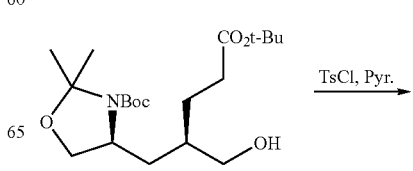

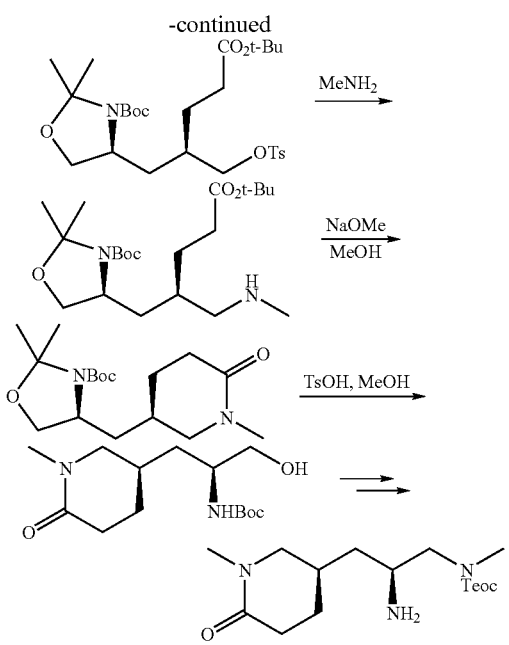

Step 1. (S)-tert-butyl 4-((R)-5-tert-butoxy-5-oxo-2-(tosyloxymethyl)pentyl)-2,2-dimethyloxazolidine-3-carboxylate To a solution of (S)-tert-butyl 4-((R)-5-tert-butoxy-2-(hydroxymethyl)-5-oxopentyl)-2,2-dimethyloxazolidine-3-carboxylate (244 mg, 0.63 mmol) in anhydrous DCM (6 mL) was added pyridine (2 mL) and catalytic amount of DMAP, the solution was chilled to 0° C. TsCl (360 mg, 1.88 mmol) was added and stirred at rt overnight. The reaction mixture was diluted with EtOAc (40 mL) and washed with 1 N HCl (two times, 50 ml+20 ml), followed by H$_2$O, aq. NaHCO$_3$, brine, dried over Na$_2$SO$_4$, and filtered. After evaporation, the residue was purified on silica gel column, eluted with 0-20% EtOAc in hexane to afford (S)-tert-butyl 4-((R)-5-tert-butoxy-5-oxo-2-(tosyloxymethyl)pentyl)-2,2-dimethyloxazolidine-3-carboxylate (317 mg, yield 93%). MS ESI +ve m/z 564 (M+Na).

Step 2. (S)-tert-butyl 4-((R)-5-tert-butoxy-2-((methylamino)methyl)-5-oxopentyl)-2,2-dimethyloxazolidine-3-carboxylate (S)-tert-butyl 4-((R)-5-tert-butoxy-5-oxo-2-(tosyloxymethyl)pentyl)-2,2-dimethyloxazolidine-3-carboxylate (300 mg, 0.55 mmol) was dissolved in 30% MeNH$_2$ in EtOH (60 mL), the solution was heated to 70° C. for 2 h in a pressure sealed vessel. After cooling to rt, the solvent was removed under reduced pressure to give (S)-tert-butyl 4-((R)-5-tert-butoxy-2-((methylamino)methyl)-5-oxopentyl)-2,2-dimethyloxazolidine-3-carboxylate (212 mg, 95%). MS ESI +ve m/z 401 (M+H).

Step 3. (S)-tert-butyl 2,2-dimethyl-4-(((R)-1-methyl-6-oxopiperidin-3-yl)methyl)oxazolidine-3-carboxylate To a solution of (S)-tert-butyl 4-((R)-5-tert-butoxy-2-((methylamino)methyl)-5-oxopentyl)-2,2-dimethyloxazolidine-3-carboxylate (212 mg, 0.53 mmol) in absolute MeOH was added a NaOMe solution in MeOH (33%, 0.4 mL). The resulting solution was stirred for 24 h. The solvent was removed under reduced pressure, the residue was dissolved in EtOAc (50 mL), washed with 1 M HCl, sat. aq. NaHCO$_3$, brine, and dried over Na$_2$SO$_4$, filtered and evaporated to give (S)-tert-butyl 2,2-dimethyl-4-(((R)-1-methyl-6-oxopiperidin-3-yl)methyl)oxazolidine-3-carboxylate (160 mg, 92%). MS ESI +ve m/z 564 (M+Na).

Step 4. tert-butyl (S)-1-hydroxy-3-((R)-1-methyl-6-oxopiperidin-3-yl)propan-2-ylcarbamate To a solution of (S)-tert-butyl 2,2-dimethyl-4-(((R)-1-methyl-6-oxopiperidin-3-yl)methyl)oxazolidine-3-carboxylate (230 mg, 0.70 mmol) in MeOH (10 mL) was added p-TSA (30 mg, 0.17 mmol) and stirred at rt overnight. TEA (1 mL) was added, followed by Boc$_2$O (30 mg). The reaction mixture was stirred for another 30 min. The solvent was removed under vacuum to give crude product tert-butyl (S)-1-hydroxy-3-((R)-1-methyl-6-oxopiperidin-3-yl)propan-2-ylcarbamate, which was used for next step without further purification. MS ESI +ve m/z 287 (M+H).

Step 5-8. 2-(trimethylsilyl)ethyl (S)-2-amino-3-((R)-1-methyl-6-oxopiperidin-3-yl)propyl(methyl)carbamate 2-(trimethylsilyl)ethyl (S)-2-amino-3-((R)-1-methyl-6-oxopiperidin-3-yl)propyl(methyl)carbamate was obtained using procedures analogous to Preparation Z, Steps 4c-4f, using tert-butyl (S)-1-hydroxy-3-((R)-1-methyl-6-oxopiperidin-3-yl)propan-2-ylcarbamate in Step 4c. MS ESI +ve m/z 344 (M+H).

Preparation D1

(S)-2-(trimethylsilyl)ethyl 2-amino-3-(2-oxopiperidin-1-yl)propyl(methyl)carbamate

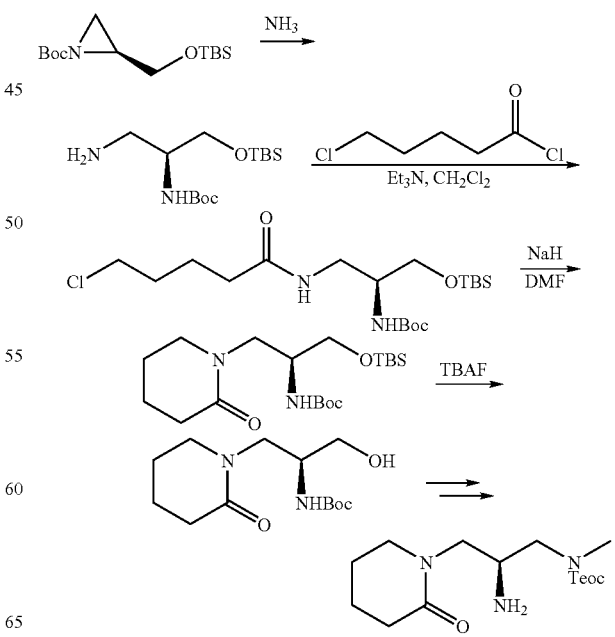

Step 1. (S)-tert-butyl 1-amino-3-(tert-butyldimethyl-silyloxy)propan-2-ylcarbamate A solution of (S)-tert-butyl 2-((tert-butyldimethylsilyloxy)methyl)aziridine-1-carboxylate (5 g, 17.42 mmol) in NH₃/MeOH (50 mL) was stirred at 50-60° C. for 48 h. After the reaction was complete, the mixture was concentrated in vacuo. The residue was purified on silica gel chromatography to afford (S)-tert-butyl 1-amino-3-(tert-butyldimethylsilyloxy)propan-2-ylcarbamate (2.5 g, 47%). ¹H NMR (CDCl₃, 300 MHz) δ 3.67 (m, 3H), 2.88 (d, 2H), 2.71 (s, 3H), 1.44 (s, 9H), 0.88 (s, 9H), 0.0 (s, 6H).

Step 2. (S)-tert-butyl 1-(tert-butyldimethylsilyloxy)-3-(5-chloropentanamido)propan-2-ylcarbamate (S)-tert-butyl 1-amino-3-(tert-butyldimethylsilyloxy)propan-2-ylcarbamate (1 g, 3.29 mmol) was taken up in 10 mL of CH₂Cl₂ and cooled to 0° C. To this was added Et₃N (0.731 g, 7.24 mmol), followed by 5-chloro-pentanoyl chloride (0.557 g, 3.62 mmol). The reaction mixture was allowed to warm to rt and stirred for 4 h. Upon completion of the reaction, satd NaCl solution was added. The organic layer was extracted with EA, dried over Na₂SO₄, and concentrated under reduced pressure. The residue was purified by column to give (S)-tert-butyl 1-(tert-butyldimethylsilyloxy)-3-(5-chloropentanamido)propan-2-ylcarbamate (1.2 g, 86%). ¹H NMR (CDCl₃, 300 MHz) δ 6.31 (s, 1H), 5.04 (d, 1H), 3.65 (m, 3H), 3.53 (m, 2H), 3.40 (m, 2H), 2.18 (t, 2H), 1.78 (m, 4H), 1.43 (s, 9H), 0.88 (s, 9H), 0.0 (s, 6H).

Step 3. (S)-tert-butyl 1-(tert-butyldimethylsilyloxy)-3-(2-oxopiperidin-1-yl)propan-2-ylcarbamate Upon cooling a solution of (S)-tert-butyl 1-(tert-butyldimethylsilyloxy)-3-(5-chloropentanamido)propan-2-ylcarbamate (500 mg, 1.18 mmol) in DMF (10 mL) to 0° C., NaH (52 mg, 1.30 mmol) was added. The reaction mixture was stirred for 4 h. The mixture was taken up in EtOAc, washed with saturated NaCl solution, dried over Na₂SO₄, concentrated under reduced pressure and the crude (S)-tert-butyl 1-(tert-butyldimethylsilyloxy)-3-(2-oxopiperidin-1-yl)propan-2-ylcarbamate was used in next step without purification (370 mg, 81%). ¹H NMR (CDCl₃, 300 MHz) δ 5.25 (d, 1H), 4.04-3.81 (m, 2H), 3.67-3.20 (m, 4H), 2.36 (m, 2H), 1.78 (m, 4H), 1.41 (s, 9H), 0.88 (s, 9H), 0.0 (s, 6H).

Step 4. (S)-tert-butyl 1-hydroxy-3-(2-oxopiperidin-1-yl)propan-2-ylcarbamate To a suspension of (S)-tert-butyl 1-(tert-butyldimethylsilyloxy)-3-(2-oxopiperidin-1-yl)propan-2-ylcarbamate (370 mg, 0.96 mmol) in CH₃CN (3 mL) was added TBAF (750 mg, 2.88 mmol). The reaction mixture was stirred for 1 h at 50-60° C. The reaction mixture was concentrated in vacuo and then EA was added. This solution was washed with brine, water and concentrated again to afford crude (S)-tert-butyl 1-hydroxy-3-(2-oxopiperidin-1-yl)propan-2-ylcarbamate (260 mg 100%), which was used in the next step without further purification.

Step 5-8. (S)-2-(trimethylsilyl)ethyl 2-amino-3-(2-oxopiperidin-1-yl)propyl(methyl)carbamate (S)-2-(trimethylsilyl)ethyl 2-amino-3-(2-oxopiperidin-1-yl)propyl(methyl)carbamate was obtained following procedures analogous to Preparation S, Steps 3-6, using (S)-tert-butyl 1-hydroxy-3-(2-oxopiperidin-1-yl)propan-2-ylcarbamate in Step 3. ¹H NMR (CDCl₃, 300 MHz) δ 4.15 (t, 2H), 3.21-3.37 (m, 7H), 2.94 (s, 3H), 2.39 (m, 2H), 1.80 (m, 4H), 0.99 (t, 2H), 0.0 (s, 9H).

Preparation E1

(R)-tert-butyl 2-amino-3-(2-oxopyrrolidin-1-yl)propyl(methyl)carbamate

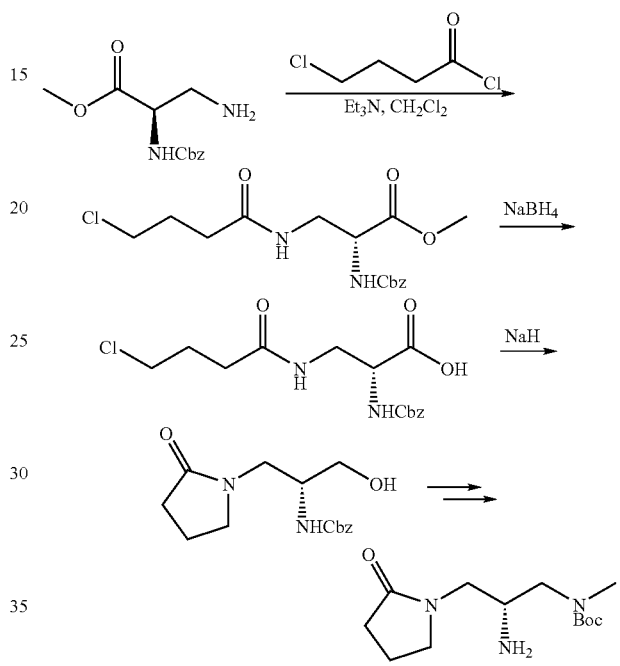

Step 1. (R)-methyl 2-(benzyloxycarbonylamino)-3-(4-chlorobutanamido)propanoate A solution of (R)-methyl 3-amino-2-(benzyloxycarbonylamino)propanoate hydrochloride (4.0 g, 0.014 mol) in methanol (80 mL) was cooled to 0° C. To this mixture was added Et₃N (3.3 g, 31 mmol), followed by 4-chlorobutanoyl chloride (2.3 g, 15.0 mmol). The reaction mixture was allowed to warm to rt and stirred for 4 h. The reaction was quenched with saturated brine (200 mL), the organic layer extracted with CH₂Cl₂, washed with 1N HCl, saturated brine, dried over MgSO₄ and concentrated to give crude (R)-methyl 2-(benzyloxycarbonylamino)-3-(4-chlorobutanamido)propanoate (5.0 g) that was used in the next step without further purification. ¹H NMR (CDCl₃, 400 MHz) δ 7.45-7.35 (m, 5H) 6.01 (s, 1H), 5.84 (d, 1H), 5.11 (d, 2H), 4.42 (t, 5H), 3.68-3.50 (m, 6H), 2.32 (t, 2H), 2.08 (t, 2H).

Step 2. (R)-benzyl 1-(4-chlorobutanamido)-3-hydroxypropan-2-ylcarbamate

To a solution of (R)-methyl 2-(benzyloxycarbonylamino)-3-(4-chlorobutanamido)propanoate (5.0 g, 14 mmol) in 100 mL of anhydrous MeOH was added NaBH₄ (12.9 g, 0.33 mol) and the mixture was stirred at it overnight. The pH of the reaction mixture was adjusted to 8-9 using NaHCO₃, the mixture was evaporated to near dryness, followed by extraction with EtOAc. The organic layer was washed with water, dried over Na₂SO₄, filtered and concentrated to give (R)-benzyl 1-(4-chlorobutanamido)-3-hydroxypropan-2-ylcarbamate (3.9 g, yield 85%) that was used in the next step without further purification. ¹H NMR (CDCl₃, 400 MHz) δ 7.37-7.30 (m, 5H) 5.13 (d, 2H), 3.77 (m, 1H), 3.57 (m, 4H), 2.32 (t, 2H), 2.08 (t, 2H).

Step 3. (R)-benzyl 1-hydroxy-3-(2-oxopyrrolidin-1-yl)propan-2-ylcarbamate

A solution of (R)-benzyl 1-(4-chlorobutanamido)-3-hydroxypropan-2-ylcarbamate (3.9 g, 11.9 mmol) in DMF was cooled to 0° C., followed by the addition of NaH (0.72 g, 17.9 mmol). The mixture was stirred at rt for 4 h. DMF was removed under high vacuum, and the residue was taken up in EtOAc, washed with 1 N HCl, saturated NaHCO₃, NaCl, dried over Na₂SO₄, and concentrated to give the crude product, which was purified by column chromatography to give (R)-benzyl 1-hydroxy-3-(2-oxopyrrolidin-1-yl)propan-2-ylcarbamate (1.1 g, yield 33%). ¹H NMR (CDCl₃, 400 MHz) δ 7.39-7.27 (m, 5H), 5.45 (d, 1H), 5.10 (d, 1H), 4.70 (s, 2H), 3.72 (m, 1H), 3.54-3.40 (m, 4H), 3.20-3.17 (m, 1H), 2.40 (t, 2H), 2.07 (t, 2H).

Step 4-7. (R)-tert-butyl 2-amino-3-(2-oxopyrrolidin-1-yl)propyl(methyl)carbamate (R)-tert-butyl 2-amino-3-(2-oxopyrrolidin-1-yl)propyl(methyl)carbamate was obtained following procedures analogous to Preparation W, Steps 8-11, using (R)-benzyl 1-hydroxy-3-(2-oxopyrrolidin-1-yl)propan-2-ylcarbamate in Step 8. ¹H NMR (CDCl₃, 400 MHz) δ 7.32 (s, 1H), 3.48 (s, 2H), 3.35 (m, 1H), 3.23 (s, 3H), 2.91 (s, 2H), 2.79 (d, 1H), 2.42 (m, 1H), 2.07 (m, 4H), 1.45 (s, 9H).

Preparation F1

(S)-tert-butyl 2,2-dimethyl-4-(((S)-tetrahydrofuran-3-yl)methyl)oxazolidine-3-carboxylate

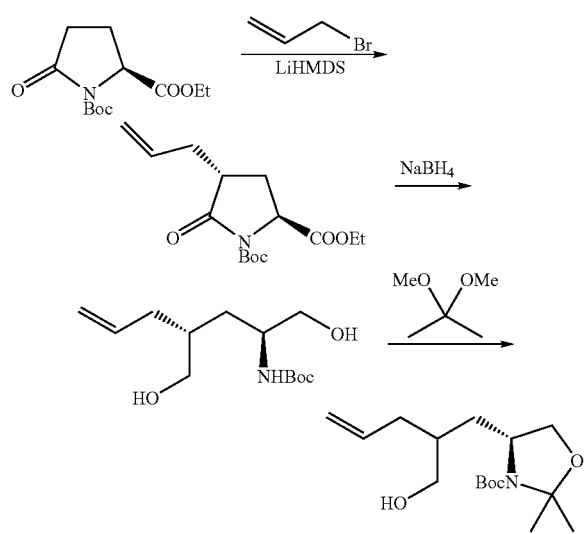

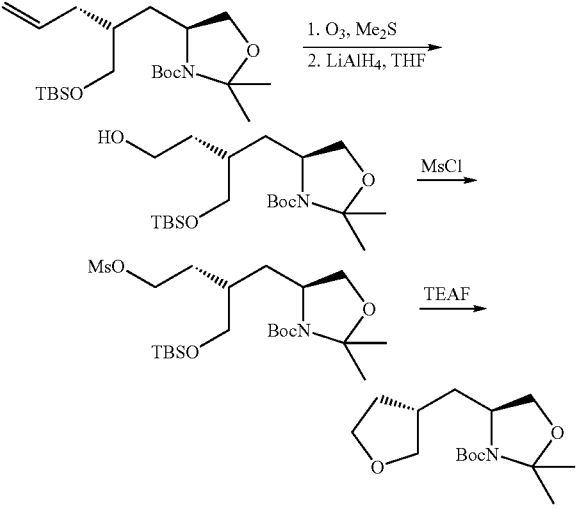

Step 1. (2S,4R)-1-tert-butyl 2-ethyl 4-allyl-5-oxopyrrolidine-1,2-dicarboxylate

To a solution of HMDS in anhydrous THF (200 mL) was added dropwise 2.5 M nBuLi in hexane (130 mL) and the mixture was stirred at −78° C. for 1 h. To a solution of N-Boc pyroglutamic ester (80 g, 0.311 mol) in anhydrous THF (1600 mL) stirred at −78° C. was added to the above solution of lithium hexamethyldisilazide in THF. After the reaction mixture was stirred at −78° C. for 1 hour, 3-bromopropene (38.47 g, 0.318 mol) in THF (200 mL) was added and stirring was continued for 2 h. The reaction mixture was quenched with saturated ammonium chloride solution (600 mL) at −78° C. and extracted with EtOAc (3×500 mL). The combined organic layers were dried over Na₂SO₄, filtered and evaporated to dryness. The crude product was separated by column chromatography to afford (2S,4R)-1-tert-butyl 2-ethyl 4-allyl-5-oxopyrrolidine-1,2-dicarboxylate (15 g, 16%). ¹H NMR (CD₃OD) δ 5.4-5.3 (m, 1H), 5.1-5.0 (m, 2H), 4.6-4.5 (m, 1H), 4.3-4.2 (m, 2H), 2.8-2.6 (m, 2H), 2.2-2.1 (m, 2H), 1.5-1.4 (s, 9H), 1.3-1.2 (t, 3H).

Step 2. tert-butyl (2S,4R)-1-hydroxy-4-(hydroxymethyl)hept-6-en-2-ylcarbamate

To a solution of (2S,4R)-1-tert-butyl 2-ethyl 4-allyl-5-oxopyrrolidine-1,2-dicarboxylate (30 g, 0.1 mol) in MeOH/H₂O (700/70 mL) was added NaBH₄ (25 g, 0.66 mol), the resulting mixture was stirred 1 h at rt and quenched with sat. aq. NH₄Cl (300 mL). The organic solvent was removed under vacuum and extracted with EA (3×250 mL). The combined organic phases were washed with brine (250 mL), dried over anhydrous Na₂SO₄, filtered and evaporated to afford the crude tert-butyl (2S,4R)-1-hydroxy-4-(hydroxymethyl)hept-6-en-2-ylcarbamate (22 g, 85%). It was used for the next step without further purification. ¹H NMR (CD₃OD) δ 5.8-5.7 (m, 1H), 5.1-5.0 (m, 2H), 4.9-4.8 (d, 1H), 3.7-3.5 (m, 4H), 2.2-2.0 (m, 2H), 1.7-1.5 (m, 2H), 1.5-1.4 (s, 9H).

Step 3. (S)-tert-butyl 4-((R)-2-(hydroxymethyl)pent-4-enyl)-2,2-dimethyloxazolidine-3-carboxylate tert-butyl (2S,4R)-1-hydroxy-4-(hydroxymethyl)hept-6-en-2-ylcarbamate (6.8 g, 26.2 mmol) was dissolved in acetone (150 mL) followed by the addition of BF₃.Et₂O (2.62 mmol). The reaction mixture was cooled to 0° C. and 2,2-dimethoxypropane (4.1 g, 39.4 mmol) was added. The resulting mixture was stirred at rt for 1 h, TEA (0.5 mL) was added and stirred for another 5 min before evaporating under reduced pressure. The residue was dissolved in Et₂O (300 mL), washed with 1 N HCl (80 mL), sat. aq. NaHCO₃ (80 mL), brine (80 mL) successively, and dried, filtered, and concentrated under vacuum to give crude (S)-tert-butyl 4-((R)-2-(hydroxymethyl)pent-4-enyl)-2,2-dimethyloxazolidine-3-carboxylate (7.5 g, 96%). It was used for the next step without further purification. ¹H NMR (CD₃OD) δ 1.4-1.5 (m, 13H), 1.5-1.6 (d, 6H), 1.6-1.9 (m, 2H), 2.0-2.1 (m, 1H), 3.3-3.5 (m, 2H), 3.6-3.8 (m, 2H), 3.8-3.9 (m, 2H), 4.1-4.2 (m, 1H), 5.0-5.1 (m, 2H), 5.7-5.8 (m, 1H).

Step 4. (S)-tert-butyl 4-((R)-2-((tert-butyldimethylsilyloxy)methyl)pent-4-enyl)-2,2-dimethyloxazolidine-3-carboxylate To a solution of (S)-tert-butyl 4-((R)-2-(hydroxymethyl)pent-4-enyl)-2,2-dimethyloxazolidine-3-carboxylate (11.5 g, 38.4 mmol), imidazole (7.84 g, 115.2 mmol) and DMAP (234 mg, 1.92 mmol) in CH₂Cl₂ (200 mL) was added a solution of TBSCl (8.68 g, 57.6 mmol) in CH₂Cl₂ (100 mL) dropwise. The reaction mixture was stirred at rt for overnight. Water (100 mL) was added and the aqueous layer was extracted with CH₂Cl₂ (3×100 mL). The combined organic layers was washed with brine (70 mL), then dried over Na₂SO₄, filtered and concentrated to give the crude product, which was purified by column chromatography to afford (S)-tert-butyl 4-((R)-2-((tert-butyldimethylsilyloxy)methyl)pent-4-enyl)-2,2-dimethyloxazolidine-3-carboxylate (9 g, 57%).

Step 5. (S)-tert-butyl 4-((S)-2-((tert-butyldimethylsilyloxy)methyl)-4-hydroxybutyl)-2,2-dimethyloxazolidine-3-carboxylate A solution of (S)-tert-butyl 4-((R)-2-((tert-butyldimethylsilyloxy)methyl)pent-4-enyl)-2,2-dimethyloxazolidine-3-carboxylate (15 g) in dry CH₂Cl₂ (250 mL) was treated with a stream of O₃ until the reaction mixture turned blue at −78° C. The system was then flushed with O₂ to remove excess ozone. Me₂S was added and the mixture was allowed to warm to rt. Solvents were removed in vacuo to give the crude product (12 g). The crude product was dissolved in 250 mL of dry THF. The resulting mixture was cooled to 0° C. before LiAlH₄ was added. After being stirred for 30 min, the reaction was quenched with 40 mL of H₂O followed by 120 mL of 1 N NaOH. The resulting white slurry was filtered through celite, and the clear, colorless filtrate was dried over anhydrous Na₂SO₄. Filtration followed by concentration in vacuo gave the crude product, which was purified by flash column to give the pure product (S)-tert-butyl 4-((S)-2-((tert-butyldimethylsilyloxy)methyl)-4-hydroxybutyl)-2,2-dimethyloxazolidine-3-carboxylate (5.2 g, 340%). ¹H NMR (CDCl₃, 400 MHz) δ 0.06 (s, 6H), 0.89 (s, 9H), 1.46 (s, 12H), 1.50 (m, 3H), 1.53 (m, 3H), 3.09 (m, 1H), 3.49 (m, 2H), 3.50 (m, 2H), 3.7 (m, 2H), 3.90 (m, 1H).

Step 6. (S)-tert-butyl 4-((S)-2-((tert-butyldimethylsilyloxy)methyl)-4-(methylsulfonyloxy)butyl)-2,2-dimethyloxazolidine-3-carboxylate To a solution of (S)-tert-butyl 4-((S)-2-((tert-butyldimethylsilyloxy)methyl)-4-hydroxybutyl)-2,2-dimethyloxazolidine-3-carboxylate and TEA in CH₂Cl₂ at 0° C. was added dropwise a solution of MsCl. The mixture was stirred for 2 h. The mixture was washed with water and dried over Na₂SO₄. The organic phase was distilled off to give the crude product (S)-tert-butyl 4-((S)-2-((tert-butyldimethylsilyloxy)methyl)-4-(methylsulfonyloxy)butyl)-2,2-dimethyloxazolidine-3-carboxylate (6.2 g). ¹H NMR (CDCl₃, 400 MHz) δ 0.06 (s, 6H, 0.89 (s, 9H), 1.46 (s, 12H), 1.50 (s, 3H), 1.53 (m, 3H), 2.94 (s, 3H), 3.49 (m, 2H), 3.50 (m, 2H), 3.7 (m, 2H), 3.9 (m, 1H).

Step 7. (S)-tert-butyl 2,2-dimethyl-4-(((S)-tetrahydrofuran-3-yl)methyl)oxazolidine-3-carboxylate To a solution of (S)-tert-butyl 4-((S)-2-((tert-butyldimethylsilyloxy)methyl)-4-(methylsulfonyloxy)butyl)-2,2-dimethyloxazolidine-3-carboxylate (6.2 g) in 200 mL of THF was added TEAF. The reaction mixture was stirred for 12 h under reflux. The mixture was diluted with EA, washed with water back extracted EA. The combined organic layer was washed with brine, filtered, and concentrated. The crude product was purified by flash column to give the pure product (S)-tert-butyl 2,2-dimethyl-4-(((S)-tetrahydrofuran-3-yl)methyl)oxazolidine-3-carboxylate (2.4 g, 67%).

Preparation G1 tert-butyl (S)-1-hydroxy-3-((R)-oxepan-3-yl)propan-2-ylcarbamate

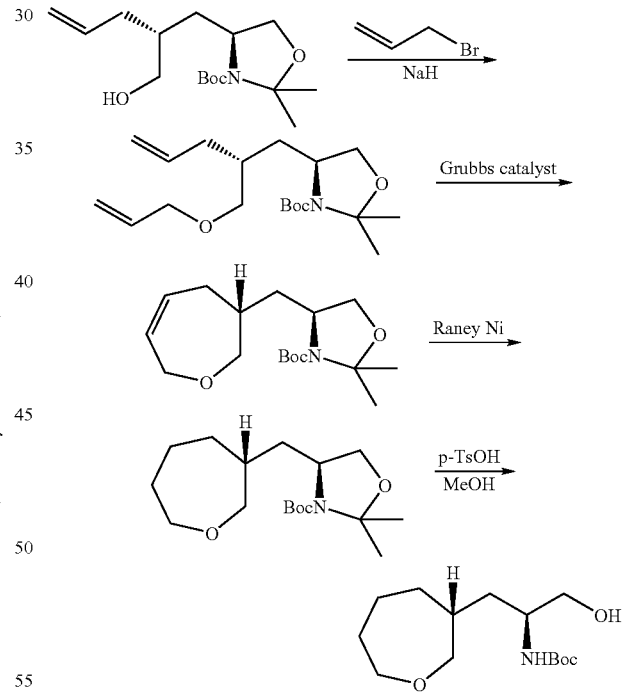

Step 1. (S)-tert-butyl 4-((R)-2-(allyloxymethyl)pent-4-enyl)-2,2-dimethyloxazolidine-3-carboxylate To a solution of (S)-tert-butyl 4-((R)-2-(hydroxymethyl)pent-4-enyl)-2,2-dimethyloxazolidine-3-carboxylate (30 g, 100 mmol, 1 eq) in anhydrous THF (600 mL) was added NaH (60%, 16 g, 400 mmol, 4 eq) in portions at 0° C. The mixture was stirred for 10 min at 0° C., followed by the dropwise addition of allyl bromide (48 g, 400 mmol, 4 eq) over 15 min. After stirring for 30 min at 0° C., the mixture was allowed to warm to rt and stirred for 16 h. The reaction was quenched with aq. NH₄Cl and the mixture was extracted with EA (3×). The combined organic layers were washed with brine, dried over Na₂SO₄, concentrated under reduced pressure to afford the crude product. It was purified by column chromatography on silica gel (PE:EA=100:1→60:1) to give (S)-tert-butyl 4-((R)-2-(allyloxymethyl)pent-4-enyl)-2,2-dimethyloxazolidine-3-carboxylate (26.15 g, 77.0%).

Step 2. (S)-tert-butyl 2,2-dimethyl-4-(((R,Z)-2,3,4,7-tetrahydrooxepin-3-yl)methyl)oxazolidine-3-carboxylate To a solution of (S)-tert-butyl 4-((R)-2-(allyloxymethyl)pent-4-enyl)-2,2-dimethyloxazolidine-3-carboxylate (700 mg, 2.06 mmol, 1 eq) in anhydrous CH₂Cl₂ was added Grubbs catalyst 2$^{nd}$ generation ((1,3-Bis-(2,4,6-trimethylphenyl)-2-imidazolidinylidene)dichloro(phenylmethylene)(tricyclohexylphosphine)ruthenium) (173 mg, 0.21 mol, 0.1 eq). The resulting mixture was stirred and heated to reflux for 4 h. The solvent was removed under reduced pressure to afford the crude product. It was purified by column chromatography on silica gel (PE:EA=100:1) to give (S)-tert-butyl 2,2-dimethyl-4-(((R,Z)-2,3,4,7-tetrahydrooxepin-3-yl)methyl)oxazolidine-3-carboxylate (563 mg, 88%).

Step 3. (S)-tert-butyl 2,2-dimethyl-4-((R)-oxepan-3-ylmethyl)oxazolidine-3-carboxylate The (S)-tert-butyl 2,2-dimethyl-4-(((R,Z)-2,3,4,7-tetrahydrooxepin-3-yl)methyl)oxazolidine-3-carboxylate was dissolved in EtOH, followed by the addition of Raney Ni. The mixture was hydrogenated at rt for 3 h. The catalyst was filtered off and the filtrate was concentrated under reduced pressure to afford (S)-tert-butyl 2,2-dimethyl-4-((R)-oxepan-3-ylmethyl)oxazolidine-3-carboxylate (408 mg, 72%).

Step 4. tert-butyl (S)-1-hydroxy-3-((R)-oxepan-3-yl)propan-2-ylcarbamate

To a solution of (S)-tert-butyl 2,2-dimethyl-4-((R)-oxepan-3-ylmethyl)oxazolidine-3-carboxylate (160 mg, 0.51 mmol) in MeOH (10 mL) was added p-TSA (30 mg, 0.17 mmol) and stirred at rt for 2 h. TEA (1 mL) was added, followed by 1 drop of Boc₂O. The reaction mixture was stirred for another 30 min. The solvent was removed under vacuum to give crude product tert-butyl (S)-1-hydroxy-3-((R)-oxepan-3-yl)propan-2-ylcarbamate, which was used for next step without further purification. MS ESI +ve m/z 296 (M+Na).

Preparation H1 tert-butyl (S)-1-amino-3-((S)-oxepan-3-yl)propan-2-ylcarbamate

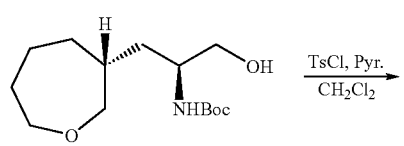

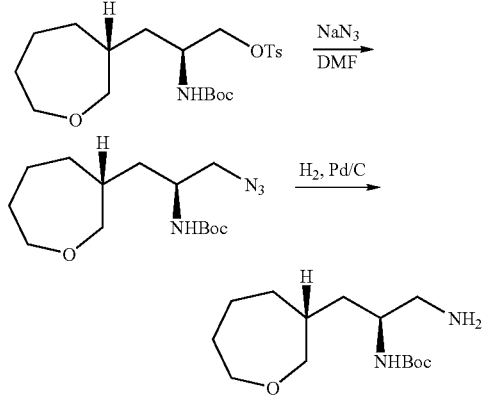

Step 1. (S)-2-(tert-butoxycarbonylamino)-3-((R)-oxepan-3-yl)propyl 4-methylbenzenesulfonate Above crude alcohol was dissolved in pyridine (3 mL), to this stirred solution was added catalytic amount of DMAP and TsCl (117 mg, 0.61 mmol). One hour later another portion of TsCl (30 mg) was added and stirred for another 1.5 h. The reaction was diluted with EtOAc, and washed with 1 M HCl, sat. aq. NaHCO₃, brine, and dried, and filtered, and concentrated to give (S)-2-(tert-butoxycarbonylamino)-3-((R)-oxepan-3-yl)propyl 4-methylbenzenesulfonate. MS ESI +ve m/z 450 (M+Na).

Step 2. tert-butyl (S)-1-azido-3-((S)-oxepan-3-yl)propan-2-ylcarbamate

The solution of NaN₃ (47 mg, 0.72 mmol) and (S)-2-(tert-butoxycarbonylamino)-3-((R)-oxepan-3-yl)propyl 4-methylbenzenesulfonate (103 mmol, 0.24 mmol) in anhydrous DMF was heated to 80° C. for 2 h. After cooling to rt, the reaction was diluted with EtOAc and washed with H₂O, brine, dried over Na₂SO₄, filtered, and concentrated. The residue was purified by chromatography on silica gel to give tert-butyl (S)-1-azido-3-((S)-oxepan-3-yl)propan-2-ylcarbamate. MS ESI +ve m/z 321 (M+Na).

Step 3. tert-butyl (S)-1-amino-3-((S)-oxepan-3-yl)propan-2-ylcarbamate

Above tert-butyl (S)-1-azido-3-((S)-oxepan-3-yl)propan-2-ylcarbamate was hydrogenated under H₂ (40 psi), catalyzed by 10% Pd/C, in MeOH for 1 h. The catalyst was filtered off and concentrated to give tert-butyl (S)-1-amino-3-((S)-oxepan-3-yl)propan-2-ylcarbamate (55 mg, 83% over 2 steps). MS ESI +ve m/z 273 (M+H).

Preparation I1 tert-butyl (S)-1-amino-3-((S)-oxepan-3-yl)propan-2-yl(methyl)carbamate

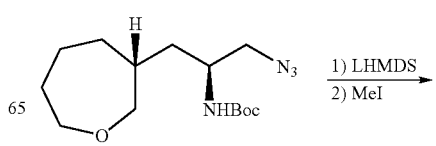

-continued

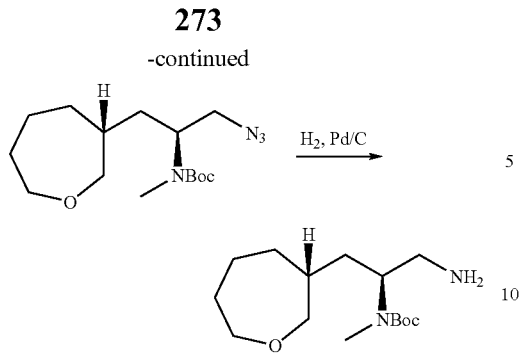

Step 1. tert-butyl (S)-1-azido-3-((S)-oxepan-3-yl) propan-2-yl(methyl)carbamate To a solution of tert-butyl (S)-1-azido-3-((S)-oxepan-3-yl) propan-2-ylcarbamate (83 mg, 0.28 mmol) in anhydrous THF (5 mL) at −78° C. was added 1.0 M LHMDS solution in THF (1.1 mL, 1.12 mmol), then stirred at this temperature for 30 min. To this mixture was added MeI (237 mg, 104 μL, 1.67 mmol), then the temperature was allowed to warm to 0° C., and stand for 12 h and −20° C. The reaction mixture was quenched with saturated aq. NH$_4$Cl, extracted with EtOAc (30 mL), the separated organic phase was washed with H$_2$O (2×10 mL), brine, and dried over Na$_2$SO$_4$, and filtered. The filtrate was concentrated, the resulting slurry was purified through flash chromatography on silica gel (eluted with gradient system, 0-30% EtOAc in hexane) to afford tert-butyl (S)-1-azido-3-((S)-oxepan-3-yl)propan-2-yl(methyl)carbamate. MS ESI +ve m/z 321 (M+Na).

Step 2. tert-butyl (S)-1-amino-3-((S)-oxepan-3-yl) propan-2-yl(methyl)carbamate Above tert-butyl (S)-1-azido-3-((S)-oxepan-3-yl)propan-2-yl(methyl)carbamate was hydrogenated under H$_2$ (40 psi), catalyzed by 10% Pd/C, in MeOH for 1 h. The catalyst was filtered off and concentrated to give tert-butyl (S)-1-amino-3-((S)-oxepan-3-yl)propan-2-ylcarbamate (76.8 mg, 96% over 2 steps). MS ESI +ve m/z 287 (M+H).

Preparation J1

2-(trimethylsilyl)ethyl (S)-2-amino-3-(oxepan-4-yl) propyl(methyl)carbamate

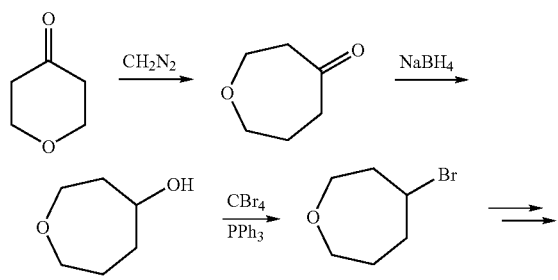

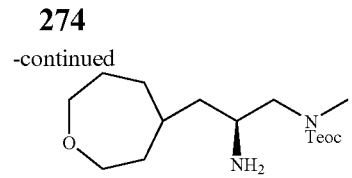

Step 1. oxepan-4-one

A 500 mL 2-neck round-bottomed flask was charged with an addition funnel and distillation apparatus cooled with dry ice-acetone bath. A mixture of KOH (30 g, 0.54 mol), water (50 mL) and carbitol (150 mL) was heated to 70° C., then a solution of N-methyl-N-nitroso-p-toluenesulfonamide (107 g, 0.5 mol) in ether (500 mL) was added dropwise and the ethereal diazomethane solution was collected. To a solution of tetrahydro-pyran-4-one (25 g, 0.25 mol) in ether (150 mL) was added dropwise a solution of 1 M CH$_2$N$_2$ in ether (500 mL) at 0° C. After addition, methanol (125 mL) was added dropwise. Immediately, a brisk evolution of nitrogen ensued. The reaction mixture was allowed to warm to rt and stir for 2 h. The remaining diazomethane was destroyed with a few drops of acetic acid. The solvent was removed under reduced pressure to give the oxepan-4-one (20 g, 70%), which was used for the next step directly without further purification. $^1$H NMR (CDCl$_3$) δ 1.82 (m, 2H), 2.66 (m, 4H), 3.82 (m, 4H).

Step 2. oxepan-4-ol

To a solution of oxepan-4-one (20 g, 0.175 mol) in MeOH (350 mL) was added NaBH$_4$ (13 g, 0.35 mol) while the temperature was lower than 40° C. After addition, the reaction mixture was stirred at rt for 2-3 h. The solvent was removed in vacuo to the residue, which was partitioned between water and EtOAc. The aqueous layer was extracted EtOAc (3×100 mL). The combined organic layers was washed with brine, dried over anhydrous Na$_2$SO$_4$, concentrated in vacuo to afford oxepan-4-ol (13 g, 64%), which was used for the next step directly without further purification. $^1$H NMR (CDCl$_3$) δ 1.45-2.01 (m, 6H), 2.33 (brs, 1H), 3.51-4.03 (m, 5H).

Step 3. 4-bromooxepane

To a solution of oxepan-4-ol (13 g, 0.112 mol) and PPh$_3$ (35 g, 0.134 mol) in CH$_2$Cl$_2$ (250 mL) was added a solution of CBr$_4$ (52 g, 0.157 mol) in CH$_2$Cl$_2$ (200 mL) at 0-5° C. After addition, the reaction mixture was stirred at rt overnight. The solvent was removed under reduced pressure to provide a residue. Ether (300 mL) was added, a white precipitate formed. The solid was filtered off, the filtrate was concentrated in vacuo. The crude product was purified by column chromatography on silica gel to give 4-bromo-oxepane (8.0 g, 40%). $^1$H NMR (CDCl$_3$) δ 1.65 (m, 1H), 1.96 (m, 1H), 2.06-2.33 (m, 4H), 3.55 (m, 1H), 3.72 (m, 3H), 4.41 (m, 1H).

Step 4-9. 2-(trimethylsilyl)ethyl (S)-2-amino-3-(oxepan-4-yl)propyl(methyl)carbamate 2-(trimethylsilyl)ethyl (S)-2-amino-3-(oxepan-4-yl)propyl(methyl)carbamate was obtained following procedures analogous to Preparation S, Steps 1-6, using tert oxepan-4-ylmagnesium bromide in Step 1. $^1$H NMR (CDCl$_3$) δ 0.04 (s, 9H), 1.02 (t, 3H), 1.13-1.53 (m, 8H), 1.61-1.87 (m, 5H), 2.93 (s, 3H), 3.03-3.18 (m, 3H), 3.53-3.81 (m, 4H), 4.16 (m, 2H).

Preparation K1

2,2-dimethyl-4-(((R)-tetrahydro-2H-pyran-3-yl)methyl)oxazolidine

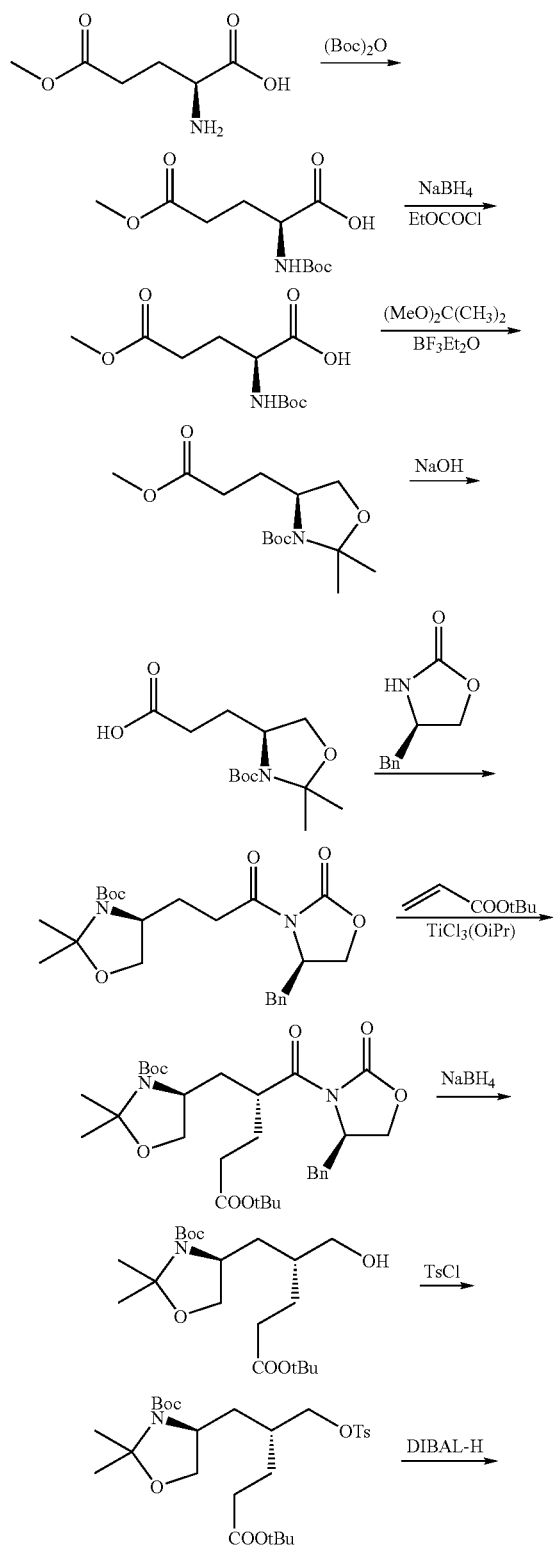

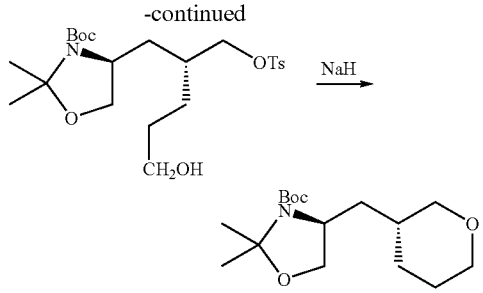

Step 1. (S)-2-(tert-butoxycarbonylamino)-5-methoxy-5-oxopentanoic acid

To a round bottom flask, Et$_3$N (303 g, 3 mol) was added dropwise to a stirred solution of Boc$_2$O (261.6 g, 1.2 mol) and 2-amino-pentanedioic acid 5-methyl ester (161 g, 1 mol) in water (800 ml) and dioxane (800 ml). After 18 hr the solution was extracted with petroleum ether (2×1000 ml) and the aqueous phase was cooled on ice and carefully acidified to pH 3 by slow addition of 10% citric acid solution. The urethane was then extracted into EtOAc (3×1000 ml) and the combined extracts were washed with brine, then dried (Na$_2$SO$_4$), filtered and concentrated under reduced pressure to give (S)-2-(tert-butoxycarbonylamino)-5-methoxy-5-oxopentanoic acid (238 g, 91.2%), which was used without further purification.

Step 2. (1-methyl 4-(tert-butoxycarbonylamino)-5-hydroxypentanoate

To a stirred solution of (S)-2-(tert-butoxycarbonylamino)-5-methoxy-5-oxopentanoic acid (35.2 g, 0.135 mol) in THF (500 mL) at −10° C. was added N-methylmorpholine (15 mL, 0.135 mol) followed by ethyl chloroformate (14.72 g, 0.135 mol). After 10 min, NaBH$_4$ (15.37 g, 0.405 mol) was added in one portion. MeOH (1200 mL) was then added dropwise to the mixture over a period of 20 min at 0° C. The solution was stirred for an additional 20 min and then neutralized with 1M KHSO$_4$. The organic solvent was removed and the aqueous layer was extracted with EtOAc (3×500 ml). The combined organic phases were washed consecutively with 1M KHSO$_4$ (300 mL), H$_2$O (300 mL), 5% aqueous NaHCO$_3$ (300 mL), and dried (Na$_2$SO$_4$). The solvent was evaporated to give a residue, which was purified by column chromatography to give the desired (S)-methyl 4-(tert-butoxycarbonylamino)-5-hydroxypentanoate (24 g, 72%)

Step 3. (S)-tert-butyl 4-(3-methoxy-3-oxopropyl)-2,2-dimethyloxazolidine-3-carboxylate (S)-Methyl 4-(tert-butoxycarbonylamino)-5-hydroxypentanoate (24 g, 97.2 mmol) and isopropenyl methyl ether (88.8 g, 854.6 mmol) was dissolved in acetone (2000 mL) and BF$_3$·Et$_2$O (0.82 mL, 5.84 mmol) was added at rt. The mixture was stirred for 1 hr at rt. The reaction was quenched by addition of Et$_3$N (11.6 mL). The reaction solution was washed with aqueous saturated NaHCO$_3$ (200 mL) and evaporated, and (S)-tert-butyl 4-(3-methoxy-3-oxopropyl)-2,2-dimethyloxazolidine-3-carboxylate (25.1 g, 90%) was obtained as an oil, which was used in the next step without further purification.

Step 4. (S)-3-(3-(tert-butoxycarbonyl)-2,2-dimethyloxazolidin-4-yl)propanoic acid An aqueous solution of sodium hydroxide (195 mL, 4.0 M in H$_2$O, 0.261 mol, 3.0 eq) was added to a solution of (S)-tert-butyl 4-(3-methoxy-3-oxopropyl)-2,2-dimethyloxazolidine-3-carboxylate (25.1 g, 0.087 mol), and the resulting cloudy reaction mixture was stirred at 23° C. for 3.5 hr. The mixture was concentrated under reduced pressure to 50 mL volume and then was partitioned between 0.5 M HCl (360 ml) and EtOAc (2×360 ml). The combined organic layers were dried over Na$_2$SO$_4$ and were filtered. The filtrate was concentrated under reduced pressure to give (s)-3-(3-(tert-butoxycarbonyl)-2,2-dimethyloxazolidin-4-yl)propanoic acid (21.6 g, 91%), which was used without further purification.

Step 5. (S)-tert-butyl 2,2-dimethyl-4-(3-((R)-4-methyl-2-oxooxazolidin-3-yl)-3-oxopropyl)oxazolidine-3-carboxylate A 2000 mL flask was charged with (S)-3-(3-(tert-butoxycarbonyl)-2,2-dimethyloxazolidin-4-yl)propanoic acid (21.6 g, 79 mmol) and 750 mL of dry THF.

The solution was cooled to 0° C., then triethylamine (23.94 g, 237 mmol, 3.0 equiv) and pivaloyl chloride (9.76 mL, 79 mmol, 1.0 equiv) were sequentially added. The solution was stirred for 4 hr at 0° C. After this time (R)-4-benzyl-2-oxazolidinone (13.26 g, 75.2 mmol, 0.95 equiv) and dried LiCl (3.68 g, 86.4 mmol, 1.1 equiv) were added and the reaction was allowed to stir for 13 hr with concomitant warming to ambient temperature. After this time 560 mL of 0.5 M HCl was added, the mixture was transferred to a separatory funnel and the layers were separated. The aqueous layer was extracted with EtOAc (3×370 mL), and the combined organic layers washed with 10% K$_2$CO$_3$ (2×370 mL), and brine (2×370 mL), then dried over Na$_2$SO$_4$, and evaporated. The crude material was purified by flash chromatography, eluting with 0-29% EtOAc in hexanes. This afforded 26.3 g (81%) of (S)-tert-butyl 2,2-dimethyl-4-(3-((R)-4-methyl-2-oxooxazolidin-3-yl)-3-oxopropyl)oxazolidine-3-carboxylate as a clear syrup.

Step 6. (S)-tert-butyl 4-((R)-5-tert-butoxy-2-((R)-4-methyl-2-oxooxazolidine-3-carbonyl)-5-oxopentyl)-2,2-dimethyloxazolidine-3-carboxylate At 0° C., 1.0M TiCl$_4$ in CH$_2$Cl$_2$ solution (8.55 mL, 0.7 eq) was added to CH$_2$Cl$_2$ (100 mL) followed by the addition of 1.0M TiCl(Oi-Pr)$_3$ in hexanes solution (4.28 mL, 0.35 eq) and stirred 5 min DIPEA (2.87 mL, 1.35 eq) was added and stirred 15 min. A solution of (S)-tert-butyl 2,2-dimethyl-4-(3-((R)-4-methyl-2-oxooxazolidin-3-yl)-3-oxopropyl)oxazolidine-3-carboxylate (5.28 g, 12.22 mmol) in CH$_2$Cl$_2$ (50 mL) was added. The reaction mixture was stirred 1 hr at 0° C. To the solution, t-butylacrylate (2.22 mL, 1.25 eq) was added and the mixture was left stirred over 48 hr with concomitant warming to rt. The mixture was concentrated, partitioned between EtOAc (300 mL) and 1% HCl solution (100 mL). The organic layer was washed with sat. NaHCO$_3$ solution (60 mL), brine (60 mL), dried over Na$_2$SO$_4$. After filtration and concentration, the residue was purified by ISCO (120 g column, 0→35% EtOAc in Hexanes gradient) to afford 4.12 g (60%) (S)-tert-butyl 4-((R)-5-tert-butoxy-2-((R)-4-methyl-2-oxooxazolidine-3-carbonyl)-5-oxopentyl)-2,2-dimethyloxazolidine-3-carboxylate as a yellowish solid. MS ESI +ve m/z 583 (M+Na).

Step 7. (S)-tert-butyl 4-((R)-5-tert-butoxy-2-(hydroxymethyl)-5-oxopentyl)-2,2-dimethyloxazolidine-3-carboxylate (S)-tert-Butyl 4-((R)-5-tert-butoxy-2-((R)-4-methyl-2-oxooxazolidine-3-carbonyl)-5-oxopentyl)-2,2-dimethyloxazolidine-3-carboxylate (4.12 g, 7.36 mmol) was dissolved in 4:1 THF and methanol (200 mL) and cooled to 0° C. Sodium borohydride (557 mg, 2 eq) was added slowly. After 10 min, the mixture was warmed up to rt slowly. The mixture was stirred 2 hr at rt. The mixture was concentrated, redissolved in EtOAc (300 mL), washed with 1% HCl solution (100 mL), brine (60 mL), and dried over Na$_2$SO$_4$. After filtration and concentration, the residue was purified by ISCO (40 g column, 10-65% EtOAc in Hexanes gradient, check TLC with Ninhydrin stain) to afford 2.86 g of (S)-tert-butyl 4-((R)-5-tert-butoxy-2-(hydroxymethyl)-5-oxopentyl)-2,2-dimethyloxazolidine-3-carboxylate as a white solid. MS ESI +m/v 410 (M+Na).

Step 8. (S)-tert-butyl 4-((R)-5-tert-butoxy-5-oxo-2-(tosyloxymethyl)pentyl)-2,2-dimethyloxazolidine-3-carboxylate To a solution of (S)-tert-butyl 4-((R)-5-tert-butoxy-2-(hydroxymethyl)-5-oxopentyl)-2,2-dimethyloxazolidine-3-carboxylate (244 mg, 0.63 mmol) in anhydrous DCM (6 mL) was added pyridine (2 mL) and catalytic amount of DMAP, the solution was chilled to 0° C. Tosic chloride (360 mg, 1.88 mmol) was added and stirred at rt overnight. The reaction mixture was diluted with EtOAc (40 mL) and washed with 1 N HCl (2×, 50 ml+20 ml), followed by H$_2$O, aq. NaHCO$_3$, brine, dried over Na$_2$SO$_4$, and filtered. After evaporation of solvent, the residue was purified on silica gel column, eluted with 0-20% EtOAc in hexane to afford (S)-tert-butyl 4-((R)-5-tert-butoxy-5-oxo-2-(tosyloxymethyl)pentyl)-2,2-dimethyloxazolidine-3-carboxylate (317 mg, yield 93%).

Step 9. (S)-tert-butyl 4-((R)-5-hydroxy-2-(tosyloxymethyl)pentyl)-2,2-dimethyloxazolidine-3-carboxylate To a solution of (S)-tert-butyl 4-((R)-5-tert-butoxy-5-oxo-2-(tosyloxymethyl)pentyl)-2,2-dimethyloxazolidine-3-carboxylate (317 mg, 0.58 mmol) in anhydrous DCM (8 mL) at −78° C. under N$_2$ was added DiBAlH (1 M in hexane, 1.75 mL, 1.75 mmol) dropwise. After the addition, the reaction mixture was stirred for another 30 min. The reaction was quenched with MeOH (2 mL), followed by 50% Rochelle's salt aq solution and stirred 2 hr. The resulting solution was extracted with DCM (3×20 mL), the combined organic phases were concentrated and dissolved in THF/MeOH (10 mL, 4/1, v/v), and chilled to 0° C., NaBH$_4$ (11 mg, 0.29 mmol) was added and stirred at this temperature for 30 min. The reaction was quenched by aqueous NH$_4$Cl, then extracted with EtOAc (3×20 mL), the combined organic phases were washed with H$_2$O, brine, and dried over Na$_2$SO$_4$, and filtered, and concentrated to give crude product (S)-tert-butyl 4-((R)-5-hydroxy-2-(tosyloxymethyl)pentyl)-2,2-dimethyloxazolidine-3-carboxylate (255 mg, 92%). It was used without further purification.

Step 10. (S)-tert-butyl 2,2-dimethyl-4-(((R)-tetrahydro-2H-pyran-3-yl)methyl)oxazolidine-3-carboxylate To a solution of (S)-tert-butyl 4-((R)-5-hydroxy-2-(tosyloxymethyl)pentyl)-2,2-dimethyloxazolidine-3-carboxylate (254 mg, 0.54 mmol) in anhydrous DMF (8 mL) at 0° C.

under N₂ was added NaH (43 mg, 1.08 mmol). After stirring at this temperature for 1 hr, the reaction was quenched with aq. NH₄Cl and then evaporated to dryness. The residue was dissolved in EtOAc and H₂O, the separated aqueous phase was extracted with EtOAc. The combined organic phases were washed with H₂O, brine, and dried over Na₂SO₄, filtered, and evaporated. The residue was purified on silica gel column to afford (S)-tert-butyl 2,2-dimethyl-4-(((R)-tetrahydro-2H-pyran-3-yl)methyl)oxazolidine-3-carboxylate (136 mg, 84%).

The following compounds were prepared using procedures analogous to those described above:
1) (S)-tert-butyl 4-((R)-5-(cyclohexyloxy)-5-oxo-2-((R)-2-oxo-4-phenyloxazolidine-3-carbonyl)pentyl)-2,2-dimethyloxazolidine-3-carboxylate using (R)-4-phienyl-2-oxalozolidinone in Step 5 and cyclohexyl acrylate in Step 6.
2) (S)-tert-butyl 4-((R)-5-ethoxy-5-oxo-2-(tosyloxymethyl)pentyl)-2,2-dimethyloxazolidine-3-carboxylate using (R)-4-phenyl-2-oxalozolidinone in Step 5 and using ethyl acrylate in step 6.

Preparation L1

2,2-dimethyl-4-(((R)-tetrahydro-2H-pyran-3-yl)methyl)oxazolidine

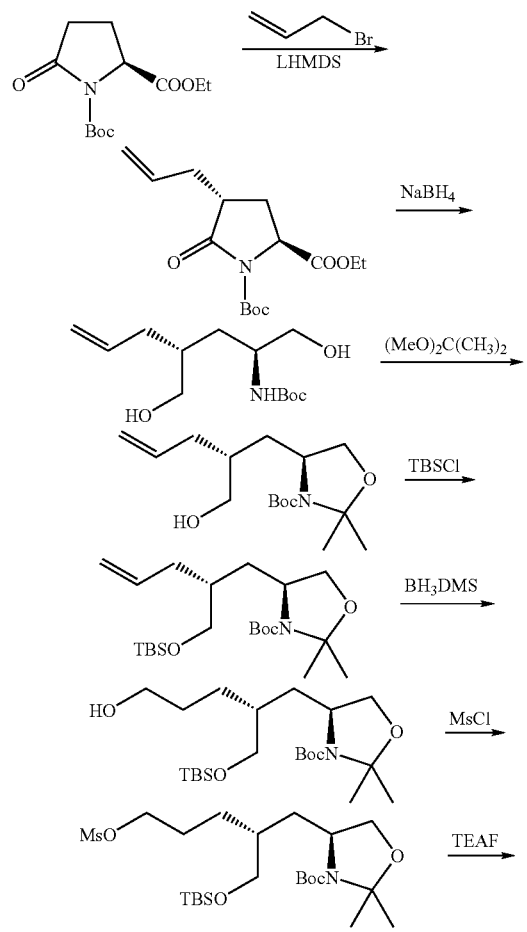

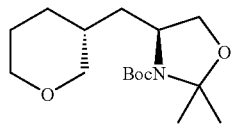

Step 1. (2S,4R)-1-tert-butyl 2-ethyl 4-allyl-5-oxopyrrolidine-1,2-dicarboxylate

To a solution of HMDS in anhydrous THF (200 mL) was added dropwise 2.5 M n-BuLi in hexane (130 mL) and the mixture was stirred at −78° C. for 1 hr. To a solution of (S)-1-tert-butyl 2-ethyl 5-oxopyrrolidine-1,2-dicarboxylate (80 g, 0.311 mol) in anhydrous THF (1600 mL) stirred at −78° C. was added lithium hexamethyldisilazide in THF. After the reaction mixture was stirred at −78° C. for 1 hr, 3-bromopropene (38.47 g, 0.318 mol) in THF (200 mL) was added and stirring was continued for 2 hr. The reaction mixture was quenched with saturated ammonium chloride solution (600 mL) at −78° C. and extracted with EtOAc (3×500 mL). The combined organic layers were dried over Na₂SO₄, filtered and evaporated to dryness. The crude product was separated by column chromatography to afford (2S,4R)-1-tert-butyl 2-ethyl 4-allyl-5-oxopyrrolidine-1,2-dicarboxylate (15 g, 16%).

Step 2. tert-butyl (2S,4R)-1-hydroxy-4-(hydroxymethyl)hept-6-en-2-ylcarbamate

To a solution of (2S,4R)-1-tert-butyl 2-ethyl 4-allyl-5-oxopyrrolidine-1,2-dicarboxylate (30 g, 0.1 mol) in MeOH/H₂O (700/70 mL) was added NaBH₄ (25 g, 0.66 mol), the result mixture was stirred 1 hr at rt and quenched with sat. aq. NH₄Cl (300 mL). The organic solvent was removed under vacuum and extracted with EtOAc (3×250 mL). The combined organic phases were washed with brine (250 mL) and dried over anhydrous Na₂SO₄, filtered and evaporated to afford crude tert-butyl (2S,4R)-1-hydroxy-4-(hydroxymethyl)hept-6-en-2-ylcarbamate (22 g, 85%). It was used in the next step without further purification.

Step 3. (S)-tert-butyl 4-((R)-2-(hydroxymethyl)pent-4-enyl)-2,2-dimethyloxazolidine-3-carboxylate To a solution of tert-butyl (2S,4R)-1-hydroxy-4-(hydroxymethyl)hept-6-en-2-ylcarbamate (6.8 g, 26.2 mmol) in acetone (150 mL), PTSA (0.45 g, 2.62 mmol) was added. The reaction mixture was cooled to −20° C. followed by the addition of 2,2-dimethoxypropane (4.1 g, 39.4 mmol). The resulting mixture was stirred and allowed to warm to rt for 1 hr. TEA (0.5 mL) was then added and stirred for another 5 min. The solvent was removed under reduced pressure. The residue was dissolved in Et₂O (300 mL), washed with 1 N HCl (80 mL), sat. aq. NaHCO₃ (80 mL), brine (80 mL) successively, and dried, filtered, and concentrated under vacuum to give crude (S)-tert-butyl 4-((R)-2-(hydroxymethyl)pent-4-enyl)-2,2-dimethyloxazolidine-3-carboxylate (7.5 g, 96%). It was used without further purification.

Step 4. (S)-tert-butyl 4-((R)-2-((tert-butyldimethylsilyloxy)methyl)pent-4-enyl)-2,2-dimethyloxazolidine-3-carboxylate To a solution of (S)-tert-butyl 4-((R)-2-(hydroxymethyl)pent-4-enyl)-2,2-dimethyloxazolidine-3-carboxylate (11.5 g, 38.4 mmol), imidazole (7.84 g, 115.2 mmol) and DMAP (234 mg, 1.92 mmol) in CH₂Cl₂ (200 mL) was added a solution of TBSCl (8.68 g, 57.6 mmol) in CH₂Cl₂ (100 mL) dropwise. The reaction mixture was stirred at rt for overnight. The reaction was washed with water (100 mL) and the aqueous layer was extracted with CH₂Cl₂ (3×100 mL), the combined organic layers was washed with brine (70 mL), then dried over Na₂SO₄, filtered and concentrated to give the crude product, which was purified by column chromatography to afford (s)-tert-butyl 4-((R)-2-((tert-butyldimethylsilyloxy)methyl)pent-4-enyl)-2,2-dimethyloxazolidine-3-carboxylate (9 g, 57%).

Step 5. (S)-tert-butyl 4-((R)-2-((tert-butyldimethylsilyloxy)methyl)-5-hydroxypentyl)-2,2-dimethyloxazolidine-3-carboxylate A solution of (S)-tert-butyl 4-((R)-2-((tert-butyldimethylsilyloxy)methyl)pent-4-enyl)-2,2-dimethyloxazolidine-3-carboxylate (26 g, 63 mmol) in THF (200 mL) was cooled in an ice-bath, followed by dropwise addition of 10 M BH₃.SMe₂ (6.3 mL). After stirring for 5 hr, 10% NaOH solution (32 mL) followed by 30% H₂O₂ (32 mL) were added carefully. The reaction mixture was stirred at rt for 16 hr. The reaction mixture was diluted with diethyl ether (500 mL) and the aqueous layer was extracted with diethyl ether (3×250 mL). The combined organic layers were washed with brine, dried over Na₂SO₄, filtered and concentrated to give the crude product, which was purified by column chromatography to afford (S)-tert-butyl 4-((R)-2-((tert-butyldimethylsilyloxy)methyl)-5-hydroxypentyl)-2,2-dimethyloxazolidine-3-carboxylate (19.6 g, 72%).

Step 6. (S)-tert-butyl 4-((R)-2-((tert-butyldimethylsilyloxy)methyl)-5-(methylsulfonyloxy)pentyl)-2,2-dimethyloxazolidine-3-carboxylate To a solution of (S)-tert-butyl 4-((R)-2-((tert-butyldimethylsilyloxy)methyl)-5-hydroxypentyl)-2,2-dimethyloxazolidine-3-carboxylate (32 g, 74.2 mmol) and Et₃N (22.5 g, 226 mmol) in CH₂Cl₂ (400 mL) was added a solution of MsCl (10.1 g, 89 mmol) in CH₂Cl₂ (50 mL) at 0-5° C. After addition, the reaction mixture was allowed to warm to rt and stir for 1 hr. The reaction was washed with water (200 mL) and the aqueous layer was extracted with CH₂Cl₂ (3×150 mL). The combined organic layers was washed with 10% citric acid (60 mL), sat. NaHCO₃ (60 mL) and brine (100 mL), then dried over Na₂SO₄, filtered and concentrated to give (S)-tert-butyl 4-((R)-2-((tert-butyldimethylsilyloxy)methyl)-5-(methylsulfonyloxy)pentyl)-2,2-dimethyloxazolidine-3-carboxylate (37.7 g, 100%), which was used in the next step without purification.

Step 7. (S)-tert-butyl 2,2-dimethyl-4-(((R)-tetrahydro-2H-pyran-3-yl)methyl)oxazolidine-3-carboxylate To a solution of (S)-tert-butyl 4-((R)-2-((tert-butyldimethylsilyloxy)methyl)-5-(methylsulfonyloxy)pentyl)-2,2-dimethyloxazolidine-3-carboxylate (37.7 g, 74.2 mmol) in THF (1000 mL) was added tetraethylammonium fluoride hydrate (41 g, 185.5 mmol) in portions. The reaction mixture was stirred under reflux overnight. The mixture was diluted with EtOAc (1000 mL), washed with water (300 mL) and brine (500 mL). The organic phase was dried over Na₂SO₄, filtered and concentrated in vacuo to give the crude product, which was purified by column chromatography to afford (S)-tert-butyl 2,2-dimethyl-4-(((R)-tetrahydro-2H-pyran-3-yl)methyl)oxazolidine-3-carboxylate (12.0 g, 54%).

Preparation M1 tert-butyl (S)-1-hydroxy-3-(tetrahydro-2H-pyran-3-yl)propan-2-ylcarbamate

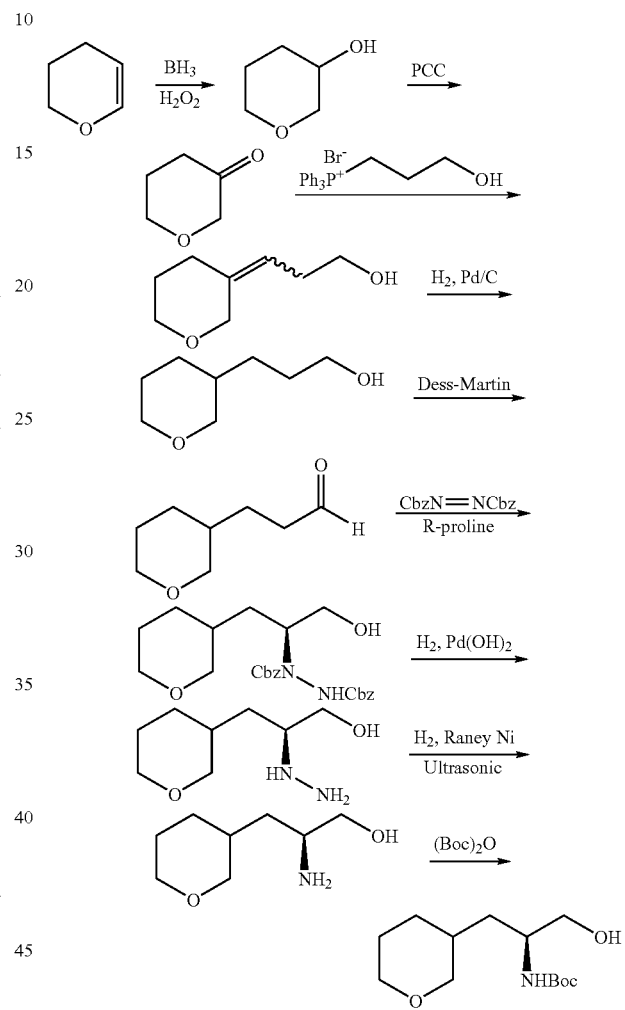

Step 1. tetrahydro-2H-pyran-3-ol

To the solution of 3,4-dihydro-2H-pyran (126 g, 1.5 mol) in dry THF (1350 mL) was added a solution of B₂H₆ in Me₂S (10 M, 75 mL, 0.75 mol) under nitrogen atmosphere at 0° C. The mixture was stirred at this temperature for 3 hr, and then was stirred at 25° C. for another 2 hr. The mixture was warmed to 40-45° C., and was added aq. NaOH (3 N, 390 mL) and H₂O₂ (30%, 270 mL). After stirring for 2 hr, the reaction was quenched by sat. brine. The mixture was filtered, and the filtrate was extracted with EtOAc (3×300 mL). The organic phase was washed with aq. Na₂S₂O₃ (3×100 mL), dried over Na₂SO₄, and concentrated in vacuo to give the crude product, which was purified through column chromatography to give tetrahydro-2H-pyran-3-ol (72.8 g, 48%). ¹H NMR (CD₃OD) δ 3.7-3.6 (m, 4H), 3.6-3.5 (m, 1H), 3.4-3.3 (m, 1H), 1.9-1.7 (m, 2H), 1.6-1.5 (m, 2H),

Step 2. dihydro-2H-pyran-3(4H)-one

To the solution of tetrahydro-2H-pyran-3-ol (30 g, 0.29 mol) in dry CH$_2$Cl$_2$ (900 mL) was added 3 Å molecule series (30 g) and PCC (94.9 g, 0.44 mol). The mixture was stirred at rt overnight. When the reaction was over, the mixture was filtered through celite, dried over Na$_2$SO$_4$, and concentrated in vacuo to give the crude product, which was purified through column chromatography to give dihydro-2H-pyran-3(4H)-one (23 g, 76%). $^1$H NMR (CD$_3$OD) δ 3.9 (s, 2H), 3.8-3.7 (t, 2H), 3.7-3.6 (m, 4H), 2.5-2.4 (m, 2H), 2.0-1.9 (m, 2H).

Step 3. 3-(dihydro-2H-pyran-3(4H)-ylidene)propan-1-ol

To a suspension of the phosphonium salt (69 g, 1.5 eg) in dry THF (1100 mL) at 0° C. under nitrogen atmosphere was added n-BuLi (2.5 M, 111 mL, 0.413 mol). The solution was stirred for 1 hr, followed by addition of dihydro-2H-pyran-3(4H)-one (11.5 g, 0.115 mol). Stirring was continued at rt overnight. The mixture was quenched by sat. aq. NH$_4$Cl, and then filtered. The filtrate was dried over Na$_2$SO$_4$, and concentrated in vacuo to give the crude product, which was purified through column chromatography to give 3-(dihydro-2H-pyran-3(4H)-ylidene)propan-1-ol (11.2 g, 69%). $^1$H NMR (CD$_3$OD) δ 4.2-3.9 (d, 2H), 3.8-3.5 (m, 4H), 2.4-2.2 (m, 4H), 5.3-5.2 (d, 1H), 2.1-1.8 (s, 1H), 1.8-1.6 (m, 2H).

Step 4. 3-(tetrahydro-2H-pyran-3-yl)propan-1-ol

To the solution of compound 3-(dihydro-2H-pyran-3(4H)-ylidene)propan-1-ol (11.2 g, 0.0789 mol) in methanol (200 mL) was added Pd(OH)$_2$/C (1.12 g). The reaction flask was degassed and filled with H$_2$. When the reaction was over, the mixture was filtered through celite, and the filter cake was washed with MeOH (2×10 mL). The combined organic layers were dried over Na$_2$SO$_4$, and concentrated in vacuo to give 3-(tetrahydro-2H-pyran-3-yl)propan-1-ol (10.35 g, yield 91%), which was used for the next step without further purification. $^1$H NMR (CD$_3$OD) δ 3.9-3.8 (m, 1H), 3.7-3.6 (m, 2H), 3.5-3.4 (m, 1H), 3.3 (m, 1H), 3.1-2.9 (t, 1H), 2.6-2.4 (m, 1H), 2.3-1.8 (m, 3H), 1.6-1.4 (m, 4H), 1.3-1.0 (m, 2H).

Step 5. 3-(tetrahydro-2H-pyran-3-yl)propanal

To the solution of 3-(tetrahydro-2H-pyran-3-yl)propan-1-ol (10.35 g, 0.0719 mol) in CH$_2$Cl$_2$ (200 mL) was added Dess-Martin periodinane (61.24 g, 0.1438 mol). The mixture was stirred at rt. When the reaction was over, the solution was poured into Et$_2$O (300 mL) and anhydrous K$_2$CO$_3$ (19.84 g, 0.1438 mol) was added. The mixture was filtered and the filtrate was dried over Na$_2$SO$_4$, and concentrated in vacuo to give the crude product, which was purified through column chromatography to give 3-(tetrahydro-2H-pyran-3-yl)propanal (8.25 g, 80%).

Step 6. dibenzyl 1-((2S)-1-hydroxy-3-(tetrahydro-2H-pyran-3-yl)propan-2-yl)hydrazine-1,2-dicarboxylate To a stirred solution of 3-(tetrahydro-2H-pyran-3-yl)propanal (8.25 g, 0.058 mol) and dibenzyl azodicarboxylate (94%, 12.3 g, 0.041 mol) in MeCN (250 mL) at 0° C. was added (R-proline) (0.47 g, 0.0041 mol). After stirring the mixture at 0° C. for 15 hr, ethanol (100 mL) and NaBH$_4$ (1.56 g, 0.041 mol) was added, and the mixture was stirred at 0° C. for 40 min. The reaction was quenched by slow addition of 10% aqueous citric acid (15 ml), and the whole solution was concentrated in vacuo. This residue was diluted with EtOAc (200 ml), washed with saturated brine (1×50 mL), dried over Na$_2$SO$_4$, and concentrated in vacuo to give the crude product, which was purified through column chromatography to give dibenzyl 1-((2S)-1-hydroxy-3-(tetrahydro-2H-pyran-3-yl)propan-2-yl)hydrazine-1,2-dicarboxylate (14.68 g, 81%).

Step 7. (2S)-2-hydrazinyl-3-(tetrahydro-2H-pyran-3-yl)propan-1-ol

To the solution of 1-((2S)-1-hydroxy-3-(tetrahydro-2H-pyran-3-yl)propan-2-yl)hydrazine-1,2-dicarboxylate (14.68 g, 0.0332 mol) in methanol (250 mL) was added Pd(OH)$_2$/C (1.47 g). The reaction flask was degassed and filled with H$_2$. When the reaction was over, the mixture was filtered through celite, and the filter cake was washed with MeOH (2×20 mL). The combined organic solvent was dried over Na$_2$SO$_4$, and concentrated in vacuo to give (2S)-2-hydrazinyl-3-(tetrahydro-2H-pyran-3-yl)propan-1-ol (5.79 g, 94%), which was used for the next step without purification.

Step 8. (2S)-2-amino-3-(tetrahydro-2H-pyran-3-yl)propan-1-ol

To the solution of (2S)-2-hydrazinyl-3-(tetrahydro-2H-pyran-3-yl)propan-1-ol (5.79 g, 0.033 mol) in MeOH (100 mL) was added Raney Ni. The flask was degassed and equipped with a hydrogen inflated balloon. The flask was dipped into an ultrasound bath filled with water and sonicated for 4 hr at rt until the starting material was completely consumed. The mixture was then filtered through celite, and the filter cake was washed with MeOH (2×30 mL). Removal under reduced pressure gave (2S)-2-amino-3-(tetrahydro-2H-pyran-3-yl)propan-1-ol (5.4 g, 90%).

Step 9. tert-butyl (S)-1-hydroxy-3-(tetrahydro-2H-pyran-3-yl)propan-2-ylcarbamate To a solution of 2-amino-3-(tetrahydro-pyran-3-yl)-propan-1-ol (5.4 g, 0.034 mol) and Et$_3$N (10.23 g, 0.101 mol) in CH$_2$Cl$_2$ (54 mL) at 0° C. was added Boc$_2$O (8.829 g, 0.041 mol). After stirring at rt for 2 h, the mixture was concentrated to give tert-butyl (S)-1-hydroxy-3-(tetrahydro-2H-pyran-3-yl)propan-2-ylcarbamate 9.7 g), which was used for the next reaction without further purification. $^1$H NMR (CD$_3$OD) δ 1.2-1.3 (m, 3H), 1.3-1.5 (m, 10H), 1.6-1.7 (m, 3H), 1.8-1.9 (m, 1H), 2.6-2.7 (s, 1H), 3.0-3.1 (m, 1H), 3.3-3.4 (m, 1H), 3.5-3.7 (m, 3H), 3.8-3.9 (m, 2H), 4.6-4.8 (d, 1H).

The following compound was prepared following procedures analogous to those descried above:

1) tert-butyl (S)-1-hydroxy-3-(tetrahydrofuran-3-yl)propan-2-ylcarbamate using 2,3-dihydrofuran in Step 1 and Dess-Martin Periodiane oxidation in Step 2.
2) (S)-tert-butyl 1-hydroxy-3-(tetrahydro-2H-pyran-4-yl)propan-2-ylcarbamate following Steps 3-9, using tetrahydropyran-4-one in Step 3.

Preparation N1

2-(trimethylsilyl)ethyl (S)-2-amino-3-((R)-tetrahydro-2H-pyran-3-yl)propyl(methyl)carbamate

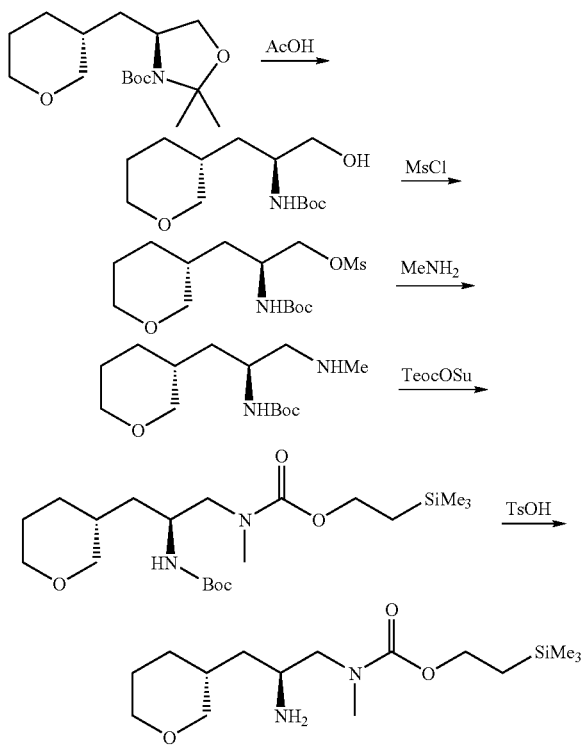

Step 1. tert-butyl (S)-1-hydroxy-3-((R)-tetrahydro-2H-pyran-3-yl)propan-2-ylcarbamate (S)-tert-Butyl-2,2-dimethyl-4-(((R)-tetrahydro-2H-pyran-3-yl)methyl)oxazolidine-3-carboxylate (9 g, 30.1 mmol) was dissolved in 80% CH₃CO₂H (90 ml). The solution was stirred at 50° C. during 1.5 hr and evaporated to dryness at reduced pressure. The residue was dissolved in Et₂O (150 ml) and washed with saturated NaHCO₃ (4×100 mL). The organic layer was dried over Na₂SO₄, filtered, and the solvent removed under reduced pressure to give tert-butyl (S)-1-hydroxy-3-((R)-tetrahydro-2H-pyran-3-yl)propan-2-ylcarbamate (6.2 g, 79.5%) as an oil, which was used in the next step without further purification.

Step 2. (S)-2-(tert-butoxycarbonylamino)-3-((R)-tetrahydro-2H-pyran-3-yl)propyl methanesulfonate To a solution of tert-butyl (S)-1-hydroxy-3-((R)-tetrahydro-2H-pyran-3-yl)propan-2-ylcarbamate (6.2 g, 23.9 mmol) and triethylamine (7.25 g, 71.8 mmol) in CH₂Cl₂ at 0° C. was added mesyl chloride (5.5 g, 47.8 mmol) dropwise. The reaction mixture was stirred at rt until the starting material disappeared. The reaction was quenched with ice-cold water and extracted with CH₂Cl₂ (3×100 ml). The combined organic layers were washed with water (3×50 ml), dried over Na₂SO₄, and concentrated under vacuo to give the (S)-2-(tert-butoxycarbonylamino)-3-((R)-tetrahydro-2H-pyran-3-yl)propyl methanesulfonate (9 g), which was used for the next step without purification.

Step 3. tert-butyl (S)-1-(methylamino)-3-((R)-tetrahydro-2H-pyran-3-yl)propan-2-ylcarbamate To an ethanol solution of MeNH₂ (100 mL) was added tert-butyl (S)-1-(methylamino)-3-((R)-tetrahydro-2H-pyran-3-yl)propan-2-ylcarbamate (9 g, 26.7 mmol). The mixture was stirred at 30-40° C. overnight. When the reaction was complete, the solution was concentrated to afford tert-butyl (S)-1-(methylamino)-3-((R)-tetrahydro-2H-pyran-3-yl)propan-2-ylcarbamate (10 g), which was used for the further reaction without purification.

Step 4. (S)-tert-butyl 1-(N-Methyl-2-(trimethylsilyl)ethoxycarbonylamino)-3-((R)-tetrahydro-2H-pyran-3-yl)propylcarbamate Solid 1-[2-Trimethylsilyl)ethxoycarbonyloxy]pyrrolidin-2,5-dione (9.5 g, 36.7 mmol) was added to a vigorously stirred biphasic solution of the tert-butyl (S)-1-(methylamino)-3-((R)-tetrahydro-2H-pyran-3-yl)propan-2-ylcarbamate (10 g, 36.7 mmol), K₂CO₃ (15.1 g, 110.1 mmol), H₂O (50 mL) and CH₂Cl₂ (100 mL). After the reaction was stirred for 2 hr at rt, the reaction was taken up into 65 mL of CH₂Cl₂. The solution was washed with aq. NaHCO₃ (3×50 mL) and brine (3×50 mL), then dried over Na₂SO₄. The organic layer was concentrated under vacuum to give the crude product, which was purified through column chromatography to give (S)-tert-butyl 1-(N-Methyl-2-(trimethylsilyl)ethoxycarbonylamino)-3-((R)-tetrahydro-2H-pyran-3-yl)propylcarbamate (6 g, 46.2%).

Step 5. 2-(trimethylsilyl)ethyl (S)-2-amino-3-((R)-tetrahydro-2H-pyran-3-yl)propyl(methyl)carbamate To a solution of (S)-tert-butyl 1-(N-Methyl-2-(trimethylsilyl)ethoxycarbonylamino)-3-((R)-tetrahydro-2H-pyran-3-yl)propylcarbamate (6 g, 14.4 mmol) in Et₂O (100 mL) was added a solution of tosic acid (2.8 g, 14.4 mmol) in 13.0 mL of absolute EtOH. This solution was placed on a rotary evaporator and the Et₂O was removed at ambient temp. The flask was then lowered into a 60° C. water bath and the remainder of the solvent was evaporated over 2 hr to afford a white solid. The solid was cooled to rt and dissolved into 80 mL of a mixture of 1:1 EtOH:H₂O. This was washed with 5:1 Hexanes:EA (3×10 mL), basified with 1N NaOH (pH>10), and extracted with Et₂O (3×50 mL). The combined Et₂O extracts were washed with brine (3×5 mL), dried over Na₂SO₄, concentrated under vacuum to give 2-(trimethylsilyl)ethyl (S)-2-amino-3-((R)-tetrahydro-2H-pyran-3-yl)propyl(methyl)carbamate 3.3 g (72%).

The following compound was prepared following procedures analogous to those descried above:
1) 2-(trimethylsilyl)ethyl (S)-2-amino-3-(tetrahydro-2H-pyran-3-yl)propyl(methyl)carbamate following Steps 2-5, using tert-butyl (S)-1-hydroxy-3-(tetrahydro-2H-pyran-3-yl)propan-2-ylcarbamate in Step 2.
2) 2-(trimethylsilyl)ethyl (S)-2-amino-3-(tetrahydrofuran-3-yl)propyl(methyl)carbamate following Steps 2-5, using tert-butyl (S)-1-hydroxy-3-(tetrahydrofuran-3-yl)propan-2-ylcarbamate in Step 2.
3) (S)-2-(trimethylsilyl)ethyl 2-amino-3-(tetrahydro-2H-pyran-4-yl)propyl(methyl)carbamate following Steps 2-5, using (S)-tert-butyl 1-hydroxy-3-(tetrahydro-2H-pyran-4-yl)propan-2-ylcarbamate in Step 2.

4) 2-(trimethylsilyl)ethyl (S)-2-amino-3-((R)-oxepan-3-yl)propyl(methyl)carbamate following Steps 2-5, using tert-butyl (S)-1-hydroxy-3-((R)-oxepan-3-yl)propan-2-ylcarbamate in Step 2.

Preparation O1

2-(trimethylsilyl)ethyl (S)-2-amino-3-((2S,4r,6R)-2,6-dimethyl-tetrahydro-2H-pyran-4-yl)propyl(methyl)carbamate

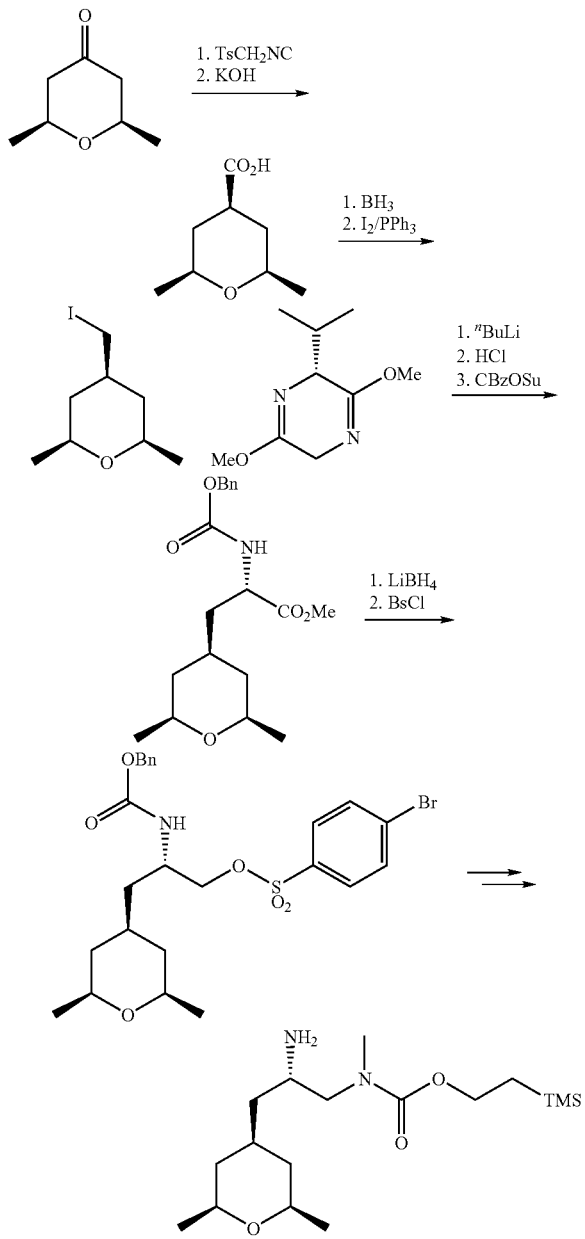

Step 1. (2S,4r,6R)-2,6-dimethyl-tetrahydro-2H-pyran-4-carboxylic acid

A 500 mL round-bottomed equipped with a thermocouple was charged with (2S,6R)-2,6-dimethyl-tetrahydropyran-4-one (10.2 g, 0.08 mol, 1.0 equiv), p-tolylsulphonylmethyl isocyanide (20.2 g, 0.103 mol, 1.3 equiv), $^t$BuOH (10.0 g, 0.135 mol, 1.7 equiv) and DME (300 mL). The mixture was cooled in an ice/brine bath so that the internal temperature was below 0° C., and KO$^t$Bu (22.3 g, 0.199 mol, 2.5 equiv) was added in portions at a rate which maintained the reaction temperature below 10° C. The mixture was heated to 35° C. and allowed to stir for 16 h. After this time the mixture was cooled to ambient and ca 100 mL of Et$_2$O was added. The mixture was filtered through a bed of Celite and the cake washed with additional Et$_2$O. The resulting orange solution was evaporated. The tacky residue was taken up in Et$_2$O and the resulting solution filtered through Celite and evaporated, yielding 10.0 g of the crude nitrile. This material was placed in a flask containing 200 mL of 2.25 M KOH. The mixture was heated to reflux for 17 h. The mixture was then cooled to ambient temperature and transferred to a separatory funnel. The aqueous layer was extracted with 3×50 mL of CH$_2$Cl$_2$ and placed in a flask and cooled to 0° C. The pH was lowered to <2 by addition of concentrated HCl. The resulting slurry was transferred to a separatory funnel and extracted with 4×50 mL of EtOAc. The combined organic fractions were washed with brine, then added to a flask containing ~1 g of activated carbon and the mixture stirred for 1 h. After this time it was filtered through a pad of Celite and evaporated to yield (2S,4r,6R)-2,6-dimethyl-tetrahydro-2H-pyran-4-carboxylic acid as a tan solid.

Step 2. ((2S,4r,6R)-2,6-dimethyl-tetrahydro-2H-pyran-4-yl)methanol

The (2S,4r,6R)-2,6-dimethyl-tetrahydro-2H-pyran-4-carboxylic acid above acid (2.10 g, 13.3 mmol, 1.0 equiv) was dissolved in THF and the solution cooled to 0° C. To this was added a solution of BH$_3$ (1.0 M in THF, 20 mL, 20 mmol, 1.5 equiv). The mixture was stirred for 1.5 h at 0° C. The excess BH$_3$ was quenched by the dropwise addition of saturated NH$_4$Cl. The mixture was transferred to a separatory funnel and the layers separated. The aqueous layer was extracted with 3×20 mL of EtOAc, and the combined organic extracts washed with brine, dried over Na$_2$SO$_4$, filtered, and evaporated. The crude alcohol was purified by flash chromatography on silica, eluting with 0-49% EtOAc. This afforded 1.67 g (87% yield) of ((2S,4r,6R)-2,6-dimethyl-tetrahydro-2H-pyran-4-yl)methanol.

Step 3. (2S,4r,6R)-4-(iodomethyl)-2,6-dimethyl-tetrahydro-2H-pyran

The ((2S,4r,6R)-2,6-dimethyl-tetrahydro-2H-pyran-4-yl)methanol (1.67 g, 11.6 mmol, 1.0 equiv), PPh$_3$ (3.64 g, 13.9 mmol, 1.2 equiv) and imidazole (2.36 g, 34.7 mmol, 3.0 equiv) were dissolved in 67 mL of THF and the solution cooled to 0° C. Iodine (3.67 g, 14.5 mmol, 1.25 equiv) was added in ca 0.5 g portions over a 0.5 h period. After stirring for 1 h an additional 1.62 g of PPh$_3$ and 1.83 g of I2 were added and the mixture stirred for 1 h. The solvent was removed and the mixture filtered through a pad of silica, eluting with Et$_2$O. The filtrate was evaporated and the iodide purified by flash chromatography on silica, eluting with 0-7% EtOAc in hexanes. This afforded 1.69 g (57% yield) of (2S,4r,6R)-4-(iodomethyl)-2,6-dimethyl-tetrahydro-2H-pyran.

Step 4. (S)-methyl 2-(benzyloxycarbonylamino)-3-((2S,4r,6R)-2,6-dimethyl-tetrahydro-2H-pyran-4-yl)propanoate The (R)-2-isopropyl-3,6-dimethoxy-2,5-dihydropyrazine (3.20 g, 17.4 mmol, 2.6 equiv) was dissolved in 70 mL of THF and the solution cooled to −78° C. A 2.5 M solution of "BuLi (10.8 mL, 17.4 mmol, 2.6 equiv) was added over a 15 min period and the resulting solution stirred for 0.5 h. A solution of (2S,4r,6R)-4-(iodomethyl)-2,6-dimethyl-tetrahydro-2H-pyran (1.69 g, 6.56 mmol, 1.0 equiv) was added. The mixture was stirred at −78° C. for 2 h, then warmed to −20° C. and allowed to stir overnight at that temperature. The mixture was quenched with water and the organic layer washed with brine, dried over Na$_2$SO$_4$, filtered, and evaporated. The resulting mixture was dissolved in 300 mL of 1:1 CH$_3$CN: 2.0 M HCl. After stirring for 2 h at ambient temperature the mixture was evaporated and re-dissolved in 100 mL of CH$_3$CN. To this was added 200 mL of 10% K$_2$CO$_3$, followed by 8.5 g (35 mmol, 5.2 equiv) of CBzOSu and the mixture rapidly stirred for 1 h. After the time the solution was evaporated. The yellow residue was dissolved in EtOAc and washed with 10% K$_2$CO$_3$, 0.5 M HCl, brine, then dried over Na$_2$SO$_4$, filtered, and evaporated. The desired protected amino acid was purified by flash chromatography on silica, eluting with 0-29% EtOAc. The (S)-methyl 2-(benzyloxycarbonylamino)-3-((2S,4r,6R)-2,6-dimethyl-tetrahydro-2H-pyran-4-yl)propanoate isolated from this procedure (2.57 g) was contaminated with ca 20% CBzNHCH$_2$CO$_2$Me and was used in subsequent steps.

Step 5. benzyl (S)-1-((2S,4r,6R)-2,6-dimethyl-tetrahydro-2H-pyran-4-yl)-3-hydroxypropan-2-ylcarbamate The (S)-methyl 2-(benzyloxycarbonylamino)-3-((2S,4r,6R)-2,6-dimethyl-tetrahydro-2H-pyran-4-yl)propanoate (2.57 g, 7.4 mmol, 1.0 equiv) and MeOH (0.5 mL) were added to THF (50 mL) and the mixture cooled to 0° C. Solid LiBH$_4$ (481 mg, 22 mmol, 3.0 equiv) was added and the mixture stirred for 2 h. The mixture was allowed to stir at 0° C. until the starting material was consumed by LC/MS analysis. After this time the excess LiBH$_4$ was quenched by addition of saturated NH$_4$Cl and the contents transferred to a separatory funnel. The layers were separated, the aqueous layer was extracted with EtOAc, and the combined organic layers washed with brine, dried over Na$_2$SO$_4$, filtered and evaporated. The benzyl (S)-1-((2S,4r,6R)-2,6-dimethyl-tetrahydro-2H-pyran-4-yl)-3-hydroxypropan-2-ylcarbamate was used in the next step with no further purification.

Step 6. (S)-2-(benzyloxycarbonylamino)-3-((2S,4r,6R)-2,6-dimethyl-tetrahydro-2H-pyran-4-yl)propyl 4-bromobenzenesulfonate The benzyl (S)-1-((2S,4r,6R)-2,6-dimethyl-tetrahydro-2H-pyran-4-yl)-3-hydroxypropan-2-ylcarbamate, DMAP (1.12 g, 9.2 mmol) and NEt$^i$Pr$_2$ (2.1 g, 14.7 mmol) were dissolved in 40 mL of CH$_2$Cl$_2$ and the mixture cooled to 0° C. Brosylchloride (2.35 g, 9.2 mmol) was added the mixture stirred for 2.5 h with warming to ambient temperature. The mixture was quenched by addition of saturated NH$_4$Cl and the mixture transferred to a separatory funnel, and the organic layer was washed with brine, then dried over Na$_2$SO$_4$, filtered, and evaporated. The (S)-2-(benzyloxycarbonylamino)-3-((2S,4r,6R)-2,6-dimethyl-tetrahydro-2H-pyran-4-yl)propyl 4-bromobenzenesulfonate was purified by flash chromatography on silica, eluting with 0-27% EtOAc in hexanes.

Step 7-8. benzyl (S)-1-((2S,4r,6R)-2,6-dimethyl-tetrahydro-2H-pyran-4-yl)-3-(N-methyl-N-(2-trimethylsilylethoxycarbonyl)amino)propan-2-ylcarbamate Benzyl (S)-1-((2S,4r,6R)-2,6-dimethyl-tetrahydro-2H-pyran-4-yl)-3-(N-methyl-N-(2-trimethylsilylethoxycarbonyl)amino)propan-2-ylcarbamate was obtained following procedures analogous to Preparation U, Steps 6-7, using (S)-2-(benzyloxycarbonylamino)-3-((2S,4r,6R)-2,6-dimethyl-tetrahydro-2H-pyran-4-yl)propyl 4-bromobenzenesulfonate in Step 6.

Step 9. 2-(trimethylsilyl)ethyl (S)-2-amino-3-((2S,4r,6R)-2,6-dimethyl-tetrahydro-2H-pyran-4-yl)propyl (methyl)carbamate Benzyl (S)-1-((2S,4r,6R)-2,6-dimethyl-tetrahydro-2H-pyran-4-yl)-3-(N-methyl-N-(2-trimethylsilylethoxycarbonyl)amino)propan-2-ylcarbamate (540 mg, 1.13 mmol) and 10% Pd/C (200 mg) were shaken under 45 psi of H$_2$ for 3 h. After this time LC/MS showed clean removal of the CBz group. The mixture was filtered and evaporated to yield 388 mg of 2-(trimethylsilyl)ethyl (S)-2-amino-3-((2S,4r,6R)-2,6-dimethyl-tetrahydro-2H-pyran-4-yl)propyl(methyl)carbamate.

Preparation P1

(S)-2-(trimethylsilyl)ethyl 2-amino-4-(1-methoxycyclopentyl)butyl(methyl)carbamate

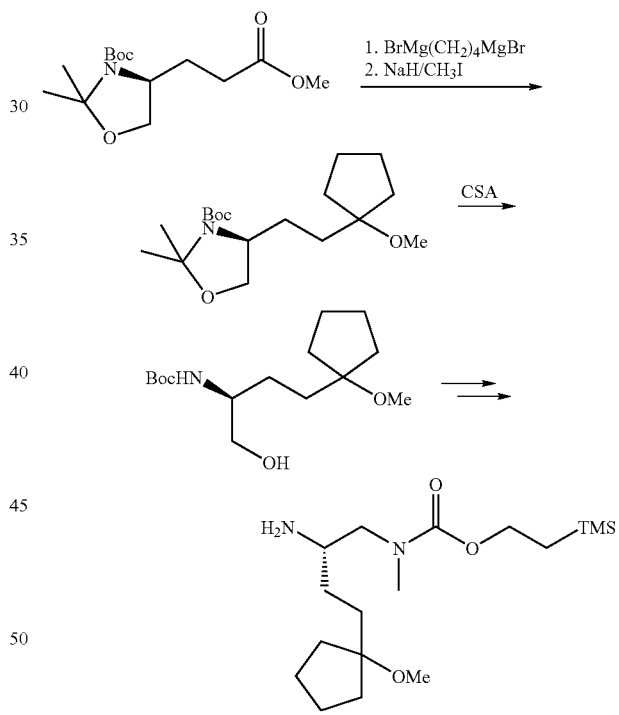

Step 1. (S)-tert-butyl 4-(2-(1-hydroxycyclopentyl)ethyl)-2,2-dimethyloxazolidine-3-carboxylate The (S)-tert-butyl 4-(3-methoxy-3-oxopropyl)-2,2-dimethyloxazolidine-3-carboxylate (1.02 g, 3.55 mmol, 1.0 equiv) was dissolved in 50 mL of THF and cooled to −10° C. A 1.0 M solution of BrMg(CH$_2$)$_4$MgBr (7.1 mL, 2.0 equiv) was added and the mixture stirred for 2 h. After this time a second portion of BrMg(CH$_2$)$_4$MgBr was added and the mixture stirred for 1 h. The mixture was quenched by addition of saturated NH$_4$Cl and the mixture transferred to a separatory funnel, and the organic layer was washed with brine, then dried over Na$_2$SO$_4$, filtered, and evaporated to provide crude (S)-tert-butyl 4-(2-(1-hydroxycyclopentyl)ethyl)-2,2-dimethyloxazolidine-3-carboxylate.

Step 2. (S)-tert-butyl 4-(2-(1-methoxycyclopentyl) ethyl)-2,2-dimethyloxazolidine-3-carboxylate The (S)-tert-butyl 4-(2-(1-hydroxycyclopentyl)ethyl)-2,2-dimethyloxazolidine-3-carboxylate was added to a suspension of NaH (568 mg, 14.2 mmol, 4.0 equiv) and the mixture stirred for 0.5 h. Methyl iodide (2.106 g, 14.2 mmol, 4.0 equiv) was added and the mixture stirred for 48 h at ambient temperature. The excess NaH was quenched by careful addition of water. The mixture was evaporated, and then taken up in EtOAc. The solution was washed with water, then brine and evaporated. The ether was purified by flash chromatography on silica, eluting with 0-41% EtOAc in hexanes. This afforded 1170 mg (3.4 mmol, 95% yield for two steps) of the desired (S)-tert-butyl 4-(2-(1-methoxycyclopentyl)ethyl)-2,2-dimethyloxazolidine-3-carboxylate.

Step 3. (S)-tert-butyl 1-hydroxy-4-(1-methoxycyclopentyl)butan-2-ylcarbamate

The above (S)-tert-butyl 4-(2-(1-methoxycyclopentyl)ethyl)-2,2-dimethyloxazolidine-3-carboxylate (1170 mg, 3.5 mmol, 1.0 equiv) was dissolved in 40 mL of methanol. Camphorsulphonic acid (417 mg, 1.8 mmol, 0.5 equiv) was added and the mixture stirred for 4 h at ambient temperature. The mixture was quenched by addition of ca. 1 mL of NEt$_3$ and the reaction evaporated. The residue was taken up in EtOAc, washed with brine, then dried over MgSO$_4$, filtered through a pad of silica gel, and evaporated. This afforded 1.03 g (3.5 mmol, 100% yield) of the desired (S)-tert-butyl 1-hydroxy-4-(1-methoxycyclopentyl)butan-2-ylcarbamate.

Step 2-5. (s)-2-(trimethylsilyl)ethyl 2-amino-4-(1-methoxycyclopentyl)butyl(methyl)carbamate (S)-2-(trimethylsilyl)ethyl 2-amino-4-(1-methoxycyclopentyl)butyl(methyl)-carbamate was obtained using procedures analogous to Preparation S, Steps 3-6, using (S)-tert-butyl 1-hydroxy-4-(1-methoxycyclopentyl)butan-2-ylcarbamate in Step 3.

Preparation Q1

(S)-benzyl 2-amino-3-(4-oxocyclohexyl)propyl(methyl)carbamate

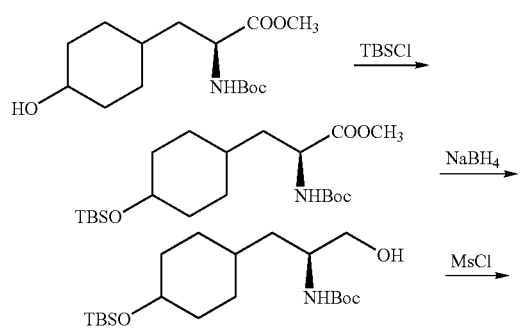

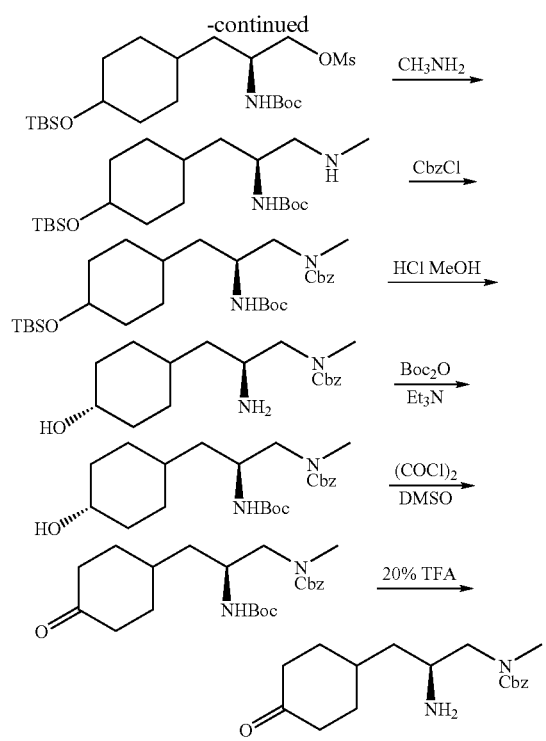

Step 1. (S)-methyl 2-(tert-butoxycarbonylamino)-3-(4-(tert-butyldimethylsilyloxy)cyclohexyl)propanoate To a solution of the (S)-methyl 2-(tert-butoxycarbonylamino)-3-(4-hydroxycyclohexyl)propanoate (96.56 g, 0.32 mol) in CH$_2$Cl$_2$ (500 mL) was added imidazole (43.52 g, 0.64 mol), followed by TBSCl (72 g, 0.48 mol) at 0° C. After addition, the mixture was allowed to stir at rt overnight. The reaction mixture was treated with water and extracted with CH$_2$Cl$_2$. The organic layer was dried over Na$_2$SO$_4$, filtered, and evaporated to give (S)-methyl 2-(tert-butoxycarbonylamino)-3-(4-(tert-butyldimethylsilyloxy)cyclohexyl)propanoate (133 g, yield 100%). $^1$H NMR: (CDCl$_3$, 400 MHz) δ 0.08 (d, 6H), 0.89 (d, 9H), 1.45 (s, 9H), 1.51 (m, 4H), 1.58 (m, 1H), 1.68 (t, 4H), 1.85 (d, 1H), 3.71 (d, 3H), 3.91 (m, 1H), 4.34 (m, 1H), 4.86 (m, 1H).

Step 2. (S)-tert-butyl 1-(4-(tert-butyldimethylsilyloxy)cyclohexyl)-3-hydroxypropan-2-ylcarbamate To a solution of (S)-methyl 2-(tert-butoxycarbonylamino)-3-(4-(tert-butyldimethylsilyloxy)cyclohexyl)propanoate (133 g, 0.32 mol) in 1500 mL methanol was added NaBH$_4$ (73 g, 1.92 mol) at rt. After stirring at rt for 4 h, the solution was evaporated to remove methanol. The remaining solution was treated with water (800 mL), extracted with EtOAc (500 mL×3). The combined organic layers were washed with water (300 mL), dried, filtered, and evaporated to give the desired (S)-tert-butyl 1-(4-(tert-butyldimethylsilyloxy)cyclohexyl)-3-hydroxypropan-2-ylcarbamate (102 g, yield 82%). $^1$H NMR (CDCl$_3$, 400 MHz) δ 0.08 (d, 6H), 0.89 (d, 9H), 1.30 (m, 4H), 1.40 (t, 2H), 1.45 (s, 9H), 1.61 (m, 1H), 1.58 (m, 1H), 1.68 (t, 4H), 1.85 (d, 1H), 3.50 (m, 1H), 3.65 (m, 1H), 3.73 (m, 1H), 3.91 (s, 1H), 4.53 (s, 1H).

Step 3. (S)-2-(tert-butoxycarbonylamino)-3-(4-(tert-butyldimethylsilyloxy)cyclohexyl)propyl methanesulfonate To a solution of (S)-tert-butyl 1-(4-(tert-butyldimethylsilyloxy)cyclohexyl)-3-hydroxypropan-2-ylcarbamate (101.6 g, 0.263 mol) and Et$_3$N (66.3 g, 0.656 mol) in CH$_2$Cl$_2$ (500 mL) was added MsCl (66.1 g, 0.577 mol) at −20° C., which was allowed stir for 1 h at rt. The reaction mixture was treated with water (300 mL) and extracted with CH$_2$Cl$_2$ (3×100 mL). The organic layers dried over Na$_2$SO$_4$ and evaporated give (S)-2-(tert-butoxycarbonylamino)-3-(4-(tert-butyldimethylsilyloxy)cyclohexyl)propyl methanesulfonate (121 g, 99%).

Step 4. (S)-tert-butyl 1-(4-(tert-butyldimethylsilyloxy)cyclohexyl)-3-(methylamino)propan-2-ylcarbamate (S)-2-(tert-butoxycarbonylamino)-3-(4-(tert-butyldimethylsilyloxy)cyclohexyl)propyl methanesulfonate (121 g, 0.26 mol) was dissolved in methylamine alcohol solution (1000 mL), which was heated to 50-60° C. overnight. The solvent was removed and the residue was purified by silica column to give a crude (S)-tert-butyl 1-(4-(tert-butyldimethylsilyloxy)cyclohexyl)-3-(methylamino)propan-2-ylcarbamate (57 g, 55%). $^1$H NMR (CDCl$_3$, 400 MHz) δ 0.08 (d, 6H), 0.89 (d, 9H), 1.25 (t, 3H), 1.45 (s, 9H), 1.61 (m, 2H), 1.82 (t, 2H), 2.01 (d, 1H), 2.56 (d, 2H), 2.80 (d, 2H), 2.95 (t, 2H), 3.49 (m, 1H), 3.61 (m, 1H), 3.90 (s, 1H), 5.35 (d, 1H), 7.15 (m, 1H).

Step 5. (S)-tert-butyl 1-(4-(tert-butyldimethylsilyloxy)cyclohexyl)-3-(N-methyl-N-(benzyloxycarbonyl)amino)propan-2-ylcarbamate To a solution of (S)-tert-butyl 1-(4-(tert-butyldimethylsilyloxy)cyclohexyl)-3-(methylamino)propan-2-ylcarbamate (57 g, 0.142 mol) and Et$_3$N (28.8 g, 0.285 mol) in CH$_2$Cl$_2$ (600 mL) was added CbzCl (26.6 g, 0.156 mol) at −20° C., which was allowed to stir for 1 h at rt. The reaction mixture was treated with water (200 mL) and extracted with CH$_2$Cl$_2$ (3×100 mL). The organic layer was dried over Na$_2$SO$_4$ and evaporated. The residue was separated on a silica column to give the pure isomer (S)-tert-butyl 1-(4-(tert-butyldimethylsilyloxy)cyclohexyl)-3-(N-methyl-N-(benzyloxycarbonyl)amino)propan-2-ylcarbamate (5.5 g) and a fraction with a mixture isomers (33 g, total yield 51%). Mixture isomer: $^1$H NMR (CDCl$_3$, 400 MHz) δ 0.02 (d, 6H), 0.88 (s, 9H), 1.16-1.29 (m, 5H), 1.41 (d, 9H), 1.60 (m, 51H), 1.83 (m, 1H), 2.95 (t, 3H), 3.00-3.40 (m, 1H), 3.49 (m, 1H), 3.89 (m, 2H), 5.11 (s, 2H), 7.34 (m, 5H).

Step 6. (S)-benzyl 2-amino-3-(4-hydroxycyclohexyl)propyl(methyl)carbamate (S)-tert-butyl 1-(4-(tert-butyldimethylsilyloxy)cyclohexyl)-3-(N-methyl-N-(benzyloxycarbonyl)amino)propan-2-ylcarbamate (1.2 g, 2.25 mmol) was dissolved in 2 M HCl MeOH (10 mL) and stirred at 30° C. for 1 hr. The solvent was removed to give the crude (S)-benzyl 2-amino-3-(4-hydroxycyclohexyl)propyl(methyl)carbamate which was used for next step directly.

Step 7. (S)-tert-butyl 1-(4-hydroxycyclohexyl)-3-(N-methyl-N-(benzyloxycarbonyl)amino)propan-2-ylcarbamate (S)-benzyl 2-amino-3-(4-hydroxycyclohexyl)propyl(methyl)carbamate (1.25 g, 3.9 mmol) was dissolved in 10 mL CH$_2$Cl$_2$, Et$_3$N was added, the mixture was cooled to 0° C. and Boc$_2$O in 5 mL of CH$_2$Cl$_2$ was added dropwise. The reaction mixture was stirred at rt for two hr. The mixture was added 50 mL of CH$_2$Cl$_2$ washed with 10% citric acid solution (20 mL) then with saturated NaHCO$_3$, brine, and dried over Na$_2$SO$_4$. After filtration, solvent removal gave (S)-tert-butyl 1-(4-hydroxycyclohexyl)-3-(N-methyl-N-(benzyloxycarbonyl)amino)propan-2-ylcarbamate (1.1 g, 2.62 mmol).

Step 8. (S)-tert-butyl 1-(N-methyl-N-(benzyloxycarbonyl)amino)-3-(4-oxocyclohexyl)propan-2-ylcarbamate A solution of DMSO (0.82 g, 10.47 mmol) in 10 mL of dry CH$_2$Cl$_2$, under protection of N$_2$, was cooled to −78° C., followed by the slow, dropwise addition of oxalyl chloride (0.664 g, 5.23 mmol). After addition the mixture was stirred 2 hr at −65° C., then the solution of (S)-tert-butyl 1-(4-hydroxycyclohexyl)-3-(N-methyl-N-(benzyloxycarbonyl)amino)propan-2-ylcarbamate (1.1 g, 2.62 mmol) was added dropwise. After addition, the mixture was stirred 3 hr at −30° C. The reaction was quenched with Et$_3$N (4 mL) and stirred 10 min, then saturated NaHCO$_3$ (10 mL) was added. The aqueous layer was extracted 3 times with CH$_2$Cl$_2$ (3×20 mL). The CH$_2$Cl$_2$ layer was washed with 10% citric acid solution (20 mL), followed by saturated NaHCO$_3$, brine, then dried over Na$_2$SO$_4$. After filtration, solvent removal gave crude product (1 g), which was purified by preparative TLC to give (S)-tert-butyl 1-(N-methyl-N-(benzyloxycarbonyl)amino)-3-(4-oxocyclohexyl)propan-2-ylcarbamate (500 mg, 1.2 mmol).

Step 9. (S)-benzyl 2-amino-3-(4-oxocyclohexyl)propyl(methyl)carbamate (S)-tert-butyl 1-(N-methyl-N-(benzyloxycarbonyl)amino)-3-(4-oxocyclohexyl)propan-2-ylcarbamate (300 mg, 0.72 mmol) was dissolved in 5 mL of 20% TFA/CH$_2$Cl$_2$ and stirred 1 hr at rt. The solvent was removed to give the crude (S)-benzyl 2-amino-3-(4-oxocyclohexyl)propyl(methyl)carbamate, which was used directly for the next step without further purification.

The following compounds were made analogously to those described above: (S)-benzyl 2-amino-3-(4-hydroxycyclohexyl)propyl(methyl)carbamate, Step 1-Step 6.

Preparation R1

(S)-tert-butyl 1-amino-5-methoxy-4,4-dimethylpentan-2-ylcarbamate

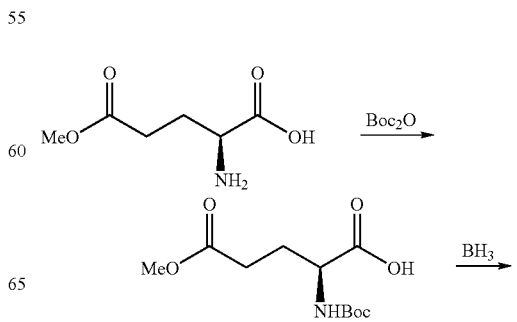

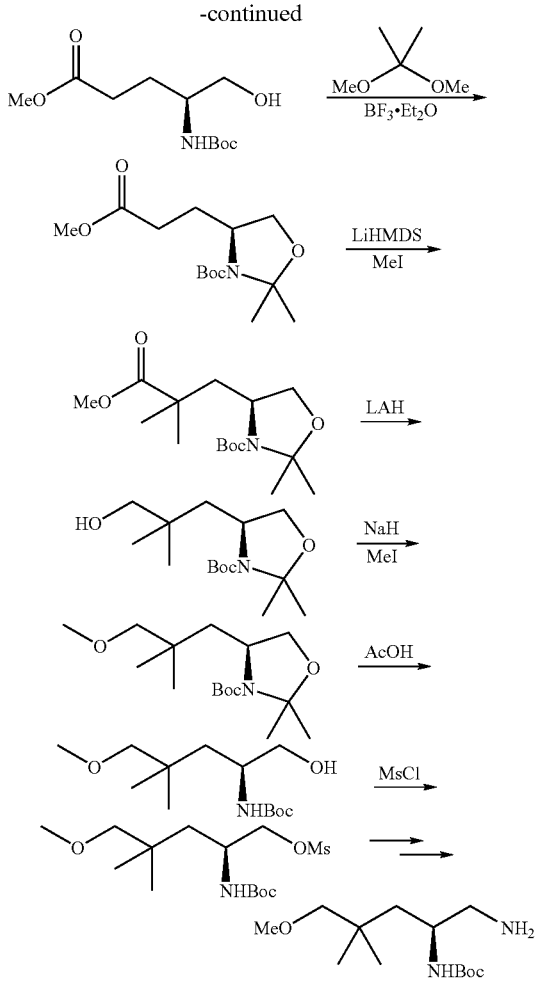

Step 1. (S)-2-(tert-butoxycarbonylamino)-5-methoxy-5-oxopentanoic acid

To a solution of (S)-2-amino-5-methoxy-5-oxopentanoic acid (100 g, 621 mmol) and NaHCO₃ (133.5 g, 1.55 mol) in water (1.6 L) was added a solution of Boc₂O (162.5 g, 745 mmol) in 1,4-dioxane (1.6 L). The mixture was stirred for 32 h at rt and then was filtered and washed with Et₂O (500 mL). The aqueous layer was acidified with 1 N aqueous HCl to pH=2 and was extracted with methylene chloride and propan-2-ol (1:3, 1 L×2). The extract was washed with brine (500 mL), dried over MgSO₄, filtered and concentrated in vacuo to give (S)-2-(tert-butoxycarbonylamino)-5-methoxy-5-oxopentanoic acid (112 g, yield 84%) as an oil that was used in the next step without further purification. $^1$H NMR (CDCl₃, 400 MHz) δ 3.69 (s, 3H), 4.33 (m, 1H), 2.475 (m, 2H), 2.23 (m, 1H), 2.05 (m, 1H), 1.445 (s, 9H).

Step 2. (S)-methyl 4-(tert-butoxycarbonylamino)-5-hydroxypentanoate

To a solution (S)-2-(tert-butoxycarbonylamino)-5-methoxy-5-oxopentanoic acid (26.1 g, 0.1 mol) in THF (500 mL), BH₃.Me₂S (80 mL, 0.8 mmol) was added dropwise at −78° C., then stirred at rt for 3 hrs. The reaction was stopped by careful addition of methanol. After evaporation and three distillations of methanol, the residue was dissolved in EtOAc, washed with 1 M NaHCO₃, and brine. (S)-methyl 4-(tert-butoxycarbonylamino)-5-hydroxypentanoate (12 g, yield 49%) was obtained as an oil that was used in the next step without further purification.

Step 3. (S)-tert-butyl 4-(3-methoxy-3-oxopropyl)-2,2-dimethyloxazolidine-3-carboxylate (S)-methyl 4-(tert-butoxycarbonylamino)-5-hydroxypentanoate (12 g, 48.6 mmol) and isopropenyl methyl ether (44.4 g, 427.3 mmol) was dissolved in acetone (200 mL) and BF₃.Et₂O (0.41 mL, 2.92 mmol) was added at rt and stirred for 1 hour. The reaction was stopped by addition of Et₃N (5.8 mL). The reaction solution was washed with 100 mL of saturated NaHCO₃ and evaporated, and (S)-tert-butyl 4-(3-methoxy-3-oxopropyl)-2,2-dimethyloxazolidine-3-carboxylate (10 g, yield 72%) was obtained as an oil that was used in the next step without further purification.

Step 4. (S)-tert-butyl 4-(3-methoxy-2,2-dimethyl-3-oxopropyl)-2,2-dimethyloxazolidine-3-carboxylate To a −78° C. solution LiHMDS (139.3 mmol) in THF (100 mL) was added a solution of (S)-tert-butyl 4-(3-methoxy-3-oxopropyl)-2,2-dimethyloxazolidine-3-carboxylate (10 g, 34.82 mmol) in THF (50 mL) over 30 min. The mixture was stirred at −78° C. for 1 h, and methyl iodide (24.7 g, 174.1 mmol) was added. Stirring was continued at −78° C. for another 1 h, then the reaction was stirred overnight at rt. The reaction was stopped by addition of saturated NH₄Cl. (S)-tert-butyl 4-(3-methoxy-2,2-dimethyl-3-oxopropyl)-2,2-dimethyloxazolidine-3-carboxylate was obtained by extraction with EtOAc and the residue was purified by column chromatography on silica gel eluting with EtOAc/Petroether (1:50→1:10) to provide the yellow oil (7 g, 63%).

Step 5. (S)-tert-butyl 4-(3-hydroxy-2,2-dimethylpropyl)-2,2-dimethyloxazolidine-3-carboxylate To a solution of (S)-tert-butyl 4-(3-methoxy-2,2-dimethyl-3-oxopropyl)-2,2-dimethyloxazolidine-3-carboxylate (7 g, 22.21 mol) in THF was added with LiAlH₄ (1.27 g, 33.31 mol). The reaction mixture was stirred overnight at rt. Water was added and extracted with EtOAc, dried over Na₂SO₄ and concentrated in vacuo to give the crude product (S)-tert-butyl 4-(3-hydroxy-2,2-dimethylpropyl)-2,2-dimethyloxazolidine-3-carboxylate (6.6 g, 100%) as an oil that was used in the next step without further purification. $^1$H NMR (CDCl₃, 400 MHz) δ 3.69 (m, 4H), 3.32 (m, 1H), 1.82 (m, 1H), 1.54 (s, 3H), 1.48 (s, 9H), 1.42 (s, 3H), 1.22 (m, 1H), 0.91 (m, 3H), 0.72 (s, 2H).

Step 6. (S)-tert-butyl 4-(3-methoxy-2,2-dimethylpropyl)-2,2-dimethyloxazolidine-3-carboxylate To a suspension of NaH (2.76 g, 69 mmol) in DMF (100 mL) was added dropwise a solution of (S)-tert-butyl 4-(3-hydroxy-2,2-dimethylpropyl)-2,2-dimethyloxazolidine-3-carboxylate (6.6 g, 23 mmol) in DMF (150 mL). After the reaction mixture was stirring for 2 h, MeI (6.53 g, 46 mmol) was added dropwise. The mixture was quenched with NH₄Cl (100 mL) and extracted with EtOAc (100 mL×2). The combined organic layers were washed with brine, dried over Na₂SO₄, and concentrated in vacuo. (S)-tert-butyl 4-(3-methoxy-2,2-dimethylpropyl)-2,2-dimethyloxazolidine-3-carboxylate (6.4 g, 93%) was obtained as an oil that was used in the next step without further purification.

Step 7. (S)-tert-butyl 1-hydroxy-5-methoxy-4,4-dimethylpentan-2-ylcarbamate (S)-tert-butyl 4-(3-methoxy-2,2-dimethylpropyl)-2,2-dimethyloxazolidine-3-carboxylate (6.4 g, 21.3 mmol) was dissolved in 70% $CH_3COOH$. The solution was heated to 50-60° C. and stirred for 2 h. The reaction solution was evaporated to give (S)-tert-butyl 1-hydroxy-5-methoxy-4,4-dimethylpentan-2-ylcarbamate (7.8 g, 100%) as an oil that was used in the next step without further purification. $^1H$ NMR ($CDCl_3$, 400 MHz) δ3.69 (m, 3H), 3.32 (s, 3H), 3.01 (m, 2H), 2.11 (s, 7H), 1.48 (m, 10H), 1.23 (m, 22H), 0.91 (m, 18H).

Step 8. (S-2-(tert-butoxycarbonylamino)-5-methoxy-4,4-dimethylpentyl methanesulfonate A solution of (S)-tert-butyl 1-hydroxy-5-methoxy-4,4-dimethylpentan-2-ylcarbamate (7.8 g, 30 mmol) in methylene chloride (150 mL) and $Et_3N$ (10.4 mL, 75 mmol) was cooled to −20° C., MsCl (6.9 g, 60 mmol) was added with fast dropwise addition maintaining the internal temperature at −20° C. The reaction mixture was stirred for 1 h in rt. The reaction was quenched with water (100 mL), extracted with $CH_2Cl_2$ (3×100 mL), washed with water and brine, dried over $Na_2SO_4$ and concentrated in vacuo to give (S)-2-(tert-butoxycarbonylamino)-5-methoxy-4,4-dimethylpentyl methanesulfonate (10.1 g, 100%) as an oil that was used in the next step without further purification.

Step 9-10. (S)-tert-butyl 1-amino-5-methoxy-4,4-dimethylpentan-2-ylcarbamate (S)-tert-butyl 1-amino-5-methoxy-4,4-dimethylpentan-2-ylcarbamate was obtained following procedures analogous to Preparation H1, Steps 2-3, using (S)-2-(tert-butoxycarbonylamino)-5-methoxy-4,4-dimethylpentyl methanesulfonate in Step 2. $^1H$ NMR ($CDCl_3$, 400 MHz) δ 3.69 (m, 1H), 3.48 (s, 1H), 3.32 (m, 3H), 3.11 (m, 2H), 2.61 (m, 2), 1.62 (s, 3H), 1.48 (s, 9H), 1.42 (m, 2H), 0.91 (d, 6H).

Preparation S1

(S)-2-(trimethylsilyl)ethyl 2-amino-5-methoxypentyl (methyl)carbamate (S-2-(trimethylsilyl)ethyl 2-amino-5-methoxypentyl(methyl)carbamate was obtained using procedures analogous to Preparation R1, Steps 5-7, and Preparation S, Steps 3-6 starting with (S)-tert-butyl 4-(3-methoxy-3-oxopropyl)-2,2-dimethyloxazolidine-3-carboxylate in Preparation R1, Step 5.

Preparation T1

(R)-tert-butyl 1-amino-3-phenoxypropan-2-ylcarbamate

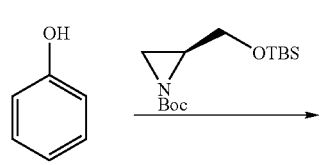

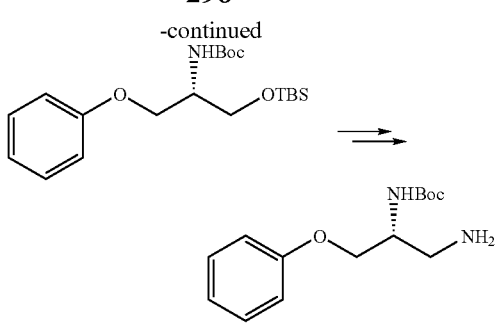

Step 1. ($-tert-butyl 1-(tert-butyldimethylsilyloxy)-3-phenoxypropan-2-ylcarbamate (S)-tert-butyl 2-((tert-butyldimethylsilyloxy)methyl)aziridine-1-carboxylate (5.0 g, 17.4 mmol), phenol (4.92 g, 52.3 mmol), $K_2CO_3$ (24 g, 174 mmol) and 150 mL of acetonenitrile were mixed, and heated to reflux for 48 h. The mixture was filtrated, and the filtrate was concentrated in vacuo. The residue was dissolved in 100 mL of EA, which was washed with water (50 mL×2), brine (50 mL) and dried with $Na_2SO_4$. The solution was concentrated in vacuo to give crude product, which was purified with flash column to give (S)-tert-butyl 1-(tert-butyldimethylsilyloxy)-3-phenoxypropan-2-ylcarbamate (2.0 g, 5.2 mmol, yield 30%) $^1H$ NMR ($CDCl_3$, 400 MHz) δ 0.0 (s, 6H), 0.87 (s, 9H), 1.45 (s, 9H), 3.71 (dd, 1H), 3.85 (dd, 1H), 3.98 (d, 2H), 4.05 (s, 1H), 6.93 (m, 3H), 7.28 (m, 2H). MS ESI +ve m/z 382 (M+1).

Step 2-3. (S)-2-(tert-butoxycarbonylamino)-3-phenoxypropyl methanesulfonate (S)-2-(tert-butoxycarbonylamino)-3-phenoxypropyl methanesulfonate was obtained following procedures analogous to Preparation R, Steps 2-3, using (S)-tert-butyl 1-(tert-butyldimethylsilyloxy)-3-phenoxypropan-2-ylcarbamate in Step 2. MS ESI +ve m/z 345 (M+1).

Steps 4-5. (R)-tert-butyl 1-amino-3-phenoxypropan-2-ylcarbamate (R)-tert-butyl 1-amino-3-phenoxypropan-2-ylcarbamate was obtained following procedures analogous to Preparation H1, Steps 2-3, using (S)-2-(tert-butoxycarbonylamino)-3-phenoxypropyl methanesulfonate in Step 2. MS ESI +ve m/z 267 (M+1).

Preparation U1

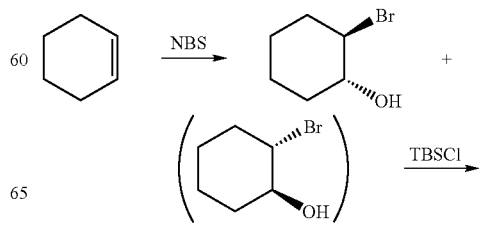

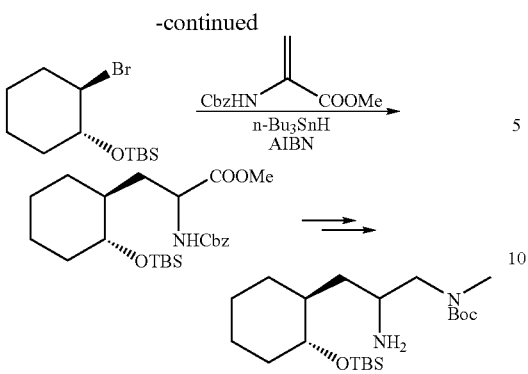

Step 1. (1R*,2R*)-2-bromocyclohexanol

To a solution of cyclohexene (10 g, 0.122 mol) in THF (100 mL) and H₂O (100 mL) was added NBS (31 g, 0.134 mol), the reaction mixture was stirred for 2-3 hours. 20% aqueous solution of KHSO₄ (20 mL) was added and the solution was stirred for 20 minutes. EtOAc was added and the organic layer was separated, which was washed by aqueous Na₂S₂O₃ solution until the solution turned from red to colorless. The organic phase was dried, filtered, and the solvent removed by distillation. The residue (1R*,2R*)-2-bromocyclohexanol (22 g, 85%) was used in the next step without further purification. ¹H NMR (CDCl₃, 400 MHz) δ 1.25-1.40 (m, 3H), 1.60-1.85 (m, 3H), 2.08-2.16 (m, 1H), 2.28-2.48 (m, 1H), 3.53-3.63 (m, 1H), 3.82-3.94 (m, 1H).

Step 2. ((1R*,2R*)-2-bromocyclohexyloxy)(tert-butyl)dimethylsilane

To a solution (1R*,2R*)-2-bromocyclohexanol (27 g, 0.151 mol) of and imidazole (24.9 g, 0.366 mol) in DMF (500 mL) was added TBSCl (24.9 g, 0.166 mol), the reaction mixture was stirred overnight at rt. Water was added and extracted by EtOAc three times. The combined organic layers were dried, filtered, and concentrated to give ((1R*,2R*)-2-bromocyclohexyloxy)(tert-butyl)dimethylsilane (32 g, 72%). ¹H NMR (CDCl₃, 400 MHz) δ 0.05-1.05 (d, 6H), 0.90 (s, 9H), 1.20-1.40 (m, 3H), 1.60-1.85 (m, 3H), 1.98-2.10 (m, 1H), 2.25-2.40 (m, 1H), 3.63-3.73 (m, 1H), 3.85-3.97 (m, 1H).

Step 3. methyl 2-(benzyloxycarbonylamino)-3-((1S*,2R*)-2-(tert-butyldimethylsilyloxy)cyclohexyl)propanoate A benzene solution of ((1R*,2R*)-2-bromocyclohexyloxy)(tert-butyl)dimethylsilane (17.8 g, 0.061 mol), 2-benzyloxycarbonylamino-acrylic acid methyl ester (8 g, 0.037 mol), AIBN (1.22 g, 0.019 mol) was heated to reflux. After 5 minutes, n-Bu₃SnH (19.8 mL, 0.074 mol) was added. The resulting mixture was then stirred at reflux for 14 hours. Solvent was removed under reduced pressure, the residue was purified by column chromatography to give methyl 2-(benzyloxycarbonylamino)-3-((1S*,2R*)-2-(tert-butyldimethylsilyloxy)cyclohexyl)propanoate (6.5 g, 24%).

Step 4-7. benzyl 1-((1S*,2R*)-2-(tert-butyldimethylsilyloxy)cyclohexyl)-3-(N-methyl-(N-tert-butoxycarbonyl)amino)propan-2-ylcarbamate Benzyl 1-((1S*,2R*)-2-(tert-butyldimethylsilyloxy)cyclohexyl)-3-(N-methyl-(N-tert-butoxycarbonyl)amino)propan-2-ylcarbamate was prepared according to procedures analogous to Preparation W, Steps 4-7, using methyl 2-(benzyloxycarbonylamino)-3-(trans-2-(tert-butyldimethylsilyloxy)cyclohexyl)propanoate in Step 4. MS ESI +ve m/z 535 (M+1).

Step 8. tert-butyl 2-amino-3-((1S*,2R*)-2-(tert-butyldimethylsilyloxy)cyclohexyl)propyl(methyl)carbamate To the solution of benzyl 1-((1S*,2R*)-2-(tert-butyldimethylsilyloxy)cyclohexyl)-3-(N-methyl-(N-tert-butoxycarbonyl)amino)propan-2-ylcarbamate (420 mg) in MeOH (8 mL) was added Pd(OH)₂ (1 g) under stream of N₂. The solution was hydrogenated at 0° C. for 1 hour. Pd(OH)₂ was filtered and the filtrate was concentrated to afford the product tert-butyl 2-amino-3-((1S*,2R*)-2-(tert-butyldimethylsilyloxy)cyclohexyl)propyl(methyl)carbamate (300 mg, 95%). ¹H NMR (CD₃OD, 400 MHz) δ 0.05 (s, 6H), 0.88 (d, 9H), 1.10-1.50 (m, 4H), 1.44 (s, 9H), 1.50-1.78 (m, 4H), 1.80-1.98 (m, 1H), 2.80 (s, 3H), 3.10-3.40 (m, 2H), 3.55-3.90 (m, 3H), 5.10 (s, 2H), 7.30-7.40 (m, 5H). MS ESI +ve m/z 401 (M+1).

Preparation V1 tert-butyl (2R,3S)-2-amino-3-cyclopentyl-3-(trimethylsilyloxy)propyl(methyl)-carbamate tert-butyl (2R,3S)-2-amino-3-cyclopentyl-3-(trimethylsilyloxy)propyl(methyl)carbamate was obtained following procedures analogous to Preparation I, Steps 1-8 above, using cyclopentanecarbaldehyde in Step 4.

Preparation D2

(S)-tert-butyl 4-(((R)-6,6-dimethyl-tetrahydro-2H-pyran-3-yl)methyl)-2,2-dimethyloxazolidine-3-carboxylate

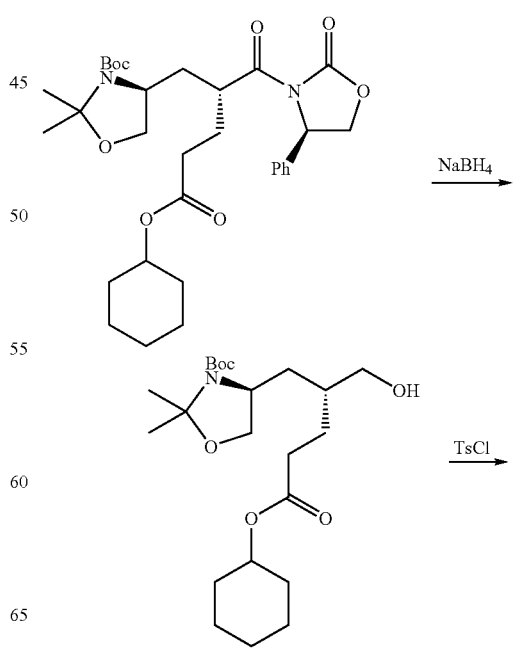

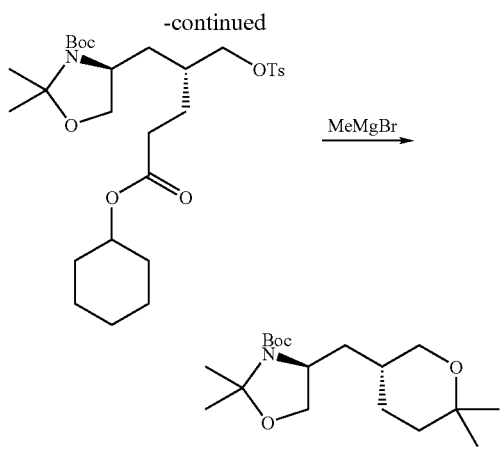

Step 1. (S)-tert-butyl 4-((R)-5-(cyclohexyloxy)-2-(hydroxymethyl)-5-oxopentyl)-2,2-dimethyloxazolidine-3-carboxylate The (S)-tert-butyl 4-((R)-5-(cyclohexyloxy)-5-oxo-2-((R)-2-oxo-4-phenyloxazolidine-3-carbonyl)pentyl)-2,2-dimethyloxazolidine-3-carboxylate (8.12 g, 13.9 mmol, 1.0 equiv) was dissolved in a 4:1 mixture of THF:MeOH (150 mL) and the solution cooled to 0° C. Solid NaBH$_4$ (1.05 g, 27.8 mmol, 2.0 equiv) was added in ca 200 mg portions over a 20 min period. The solution was stirred at 0° C. for 4 h. During this time two additional 500 mg portions of NaBH$_4$ were added. After this time LC/MS analysis showed consumption of the starting material. The excess hydride reagent was quenched by the addition of 10,% citric acid. The mixture was diluted with ca 100 mL of EtOAc and the organic layer separated. The aqueous layer was extracted with additional EtOAc. The combined organic layers were washed with brine, dried over Na$_2$SO$_4$, filtered and evaporated. The alcohol was purified by flash chromatography on silica, (120 g), eluting with 0-41% EtOAc in hexanes. This afforded 5.2 g (90% yield) of (S)-tert-butyl 4-((R)-5-(cyclohexyloxy)-2-(hydroxymethyl)-5-oxopentyl)-2,2-dimethyloxazolidine-3-carboxylate as a clear syrup. MS ESI +ve m/z 436 (M+Na).

Step 2. (S)-tert-butyl 4-((R)-5-(cyclohexyloxy)-5-oxo-2-(tosyloxymethyl)pentyl)-2,2-dimethyloxazolidine-3-carboxylate The (S)-tert-butyl 4-((R)-5-(cyclohexyloxy)-2-(hydroxymethyl)-5-oxopentyl)-2,2-dimethyloxazolidine-3-carboxylate (4.97 g, 12.0 mmol, 1.0 equiv), DMAP (1.47 mg, 12.0 mmol, 1.0 equiv) and tosyl chloride (9.2 g, 48.2 mmol, 4.0 equiv) were dissolved in pyridine (100 mL) and the solution stirred for 18 hr. The pyridine was removed in vacuo and the residue taken up in EtOAc/0.5 M HCl. The layers were separated, and the organic layer washed with 10% K$_2$CO$_3$, brine, dried over Na$_2$SO$_4$, filtered and evaporated. The tosylate was purified by flash chromatography on silica, (12 g), eluting with 0-29% EtOAc in hexanes. This afforded 6.66 g (98% yield) of (S)-tert-butyl 4-((R)-5-(cyclohexyloxy)-5-oxo-2-(tosyloxymethyl)pentyl)-2,2-dimethyloxazolidine-3-carboxylate as a white solid. MS ESI +ve m/z 590 (M+Na).

Step 3. (S)-tert-butyl 4-(((R)-6,6-dimethyl-tetrahydro-2H-pyran-3-yl)methyl)-2,2-dimethyloxazolidine-3-carboxylate The (S)-tert-butyl 4-((R)-5-(cyclohexyloxy)-5-oxo-2-(tosyloxymethyl)pentyl)-2,2-dimethyloxazolidine-3-carboxylate (309 mg, 0.545 mmol, 1.0 equiv) was dissolved in 17 mL of THF and the solution cooled to 0° C. Methylmagnesiumbromide (3.0 M in THF, 1.64 mL, 3.0 equiv) was added via syringe. LC/MS analysis showed ca 15% conversion to the mono-tosylate. An additional 0.55 mL of MeMgBr solution was added and the mixture warmed to ambient and stirred overnight. LC/MS analysis showed complete conversion to the mono-tosylate. The mixture was heated to reflux for 24 hr. After this time, complete conversion to the cyclised product was observed. The mixture was cooled to ambient and quenched with water. The layers were separated and the organic layer washed with brine, dried over Na$_2$SO$_4$, filtered and evaporated. The pyran derivative was purified by flash chromatography on silica, (12 g), eluting with 0-41% EtOAc in hexanes. This afforded 138 g (78% yield) of (S)-tert-butyl 4-(((R)-6,6-dimethyl-tetrahydro-2H-pyran-3-yl)methyl)-2,2-dimethyloxazolidine-3-carboxylate as a clear syrup. MS ESI +ve m/z 350 (M+Na).

Preparation E2

(S)-tert-butyl 4-(((R)-4-oxaspiro[2.5]oct-6-yl)methyl)-2,2-dimethyloxazolidine-3-carboxylate

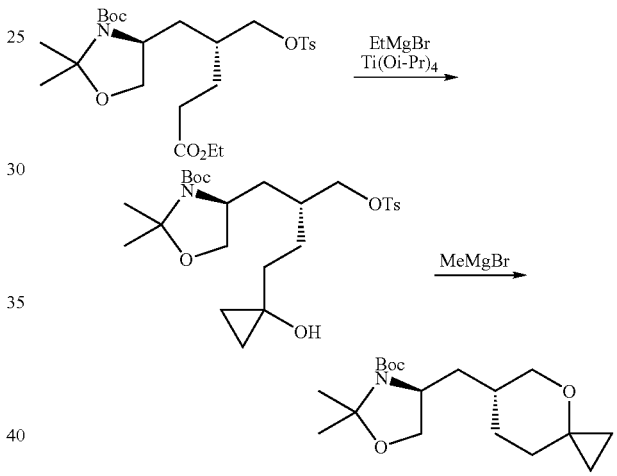

Step 1. (S)-tert-butyl 4-((R)-4-(1-hydroxycyclopropyl)-2-(tosyloxymethyl)butyl)-2,2-dimethyloxazolidine-3-carboxylate (S)-tert-Butyl 4-((R)-5-ethoxy-5-oxo-2-(tosyloxymethyl)pentyl)-2,2-dimethyloxazolidine-3-carboxylate (1.82 g, 3.55 mmol) and Ti(Oi-Pr)$_4$ were dissolved in THF (30 mL) and allowed to stir at ambient temperature. A solution of EtMgBr (3.0 M, 5.91 mL, 17.8 mmol, 5.0 equiv) was added over a 6 hr period via syringe pump and the resulting mixture stirred overnight. The mixture was treated with a 50% solution of Rochelle's salt and diluted with EtOAc. The layers were separated and the aqueous layer extracted with additional EtOAc. The combined organic layers were washed with brine, dried over Na$_2$SO$_4$, filtered and evaporated. The resulting crude (S)-tert-butyl 4-((R)-4-(1-hydroxycyclopropyl)-2-(tosyloxymethyl)butyl)-2,2-dimethyloxazolidine-3-carboxylate was used in the next step with no further purification.

Step 2. (S)-tert-butyl 4-(((R)-4-oxaspiro[2.5]oct-6-yl)methyl)-2,2-dimethyloxazolidine-3-carboxylate The (S)-tert-butyl 4-((R)-4-(1-hydroxycyclopropyl)-2-(tosyloxymethyl)butyl)-2,2-dimethyloxazolidine-3-carboxylate was dissolved in 30 mL of THF and MeMgBr (7.0 mL of a 3.0 M solution, 2.0 equiv) was added and the mixture heated to reflux for 56 hr. After cooling to ambient the mixture was quenched by addition of water and the mixture transferred to a separatory funnel. The layers were separated and the organic layer were washed with brine, dried over Na$_2$SO$_4$, filtered and evaporated. The pyran derivative was purified by flash chromatography on silica (40 g) eluting with 0-29% EtOAc in hexanes. This afforded 1.05 g (91% yield) of (S)-tert-butyl 4-(((R)-4-oxaspiro[2.5]oct-6-yl)methyl)-2,2-dimethyloxazolidine-3-carboxylate. MS ESI +ve m/z 348 (M+Na).

Preparation F2

2-(trimethylsilyl)ethyl (S)-2-amino-3-((R)-6,6-dimethyl-tetrahydro-2H-pyran-3-yl)propyl(methyl)carbamate

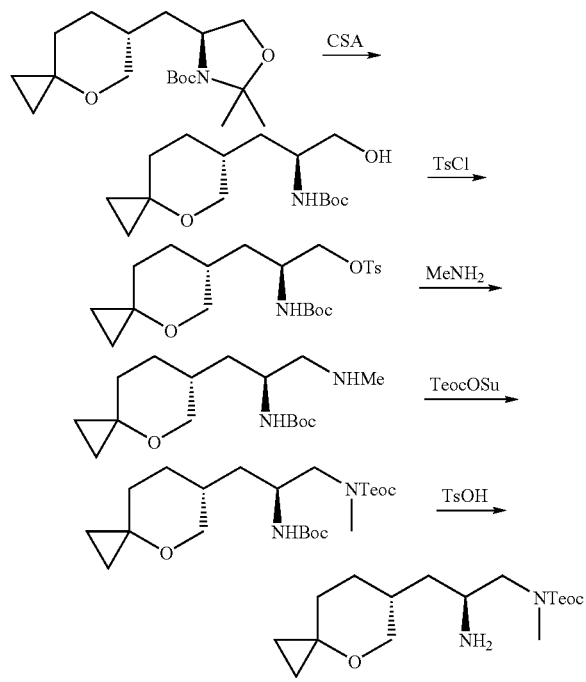

Step 1. tert-butyl (S)-1-((R)-4-oxaspiro[2.5]oct-6-yl)-3-hydroxypropan-2-ylcarbamate The (S)-tert-butyl 4-(((R)-4-oxaspiro[2.5]oct-6-yl)methyl)-2,2-dimethyloxazolidine-3-carboxylate (3.0 g, 9.17 mmol) and camphor sulphonic acid (2.2 g, 9.17 mmol, 1.0 equiv) were dissolved in 200 mL of MeOH and allowed to react at ambient temperature for 3 hr. The mixture was quenched with saturated NaHCO$_3$ solution, the methanol removed in vacuo, and the mixture diluted with EtOAc. The layers were separated and the organic layer washed with brine, dried over Na$_2$SO$_4$, filtered and evaporated. This yielded 1.70 g (65%) of tert-butyl (S)-1-((R)-4-oxaspiro[2.5]oct-6-yl)-3-hydroxypropan-2-ylcarbamate which was used in the next step with no further purification. MS ESI +ve m/z 310 (M+Na).

Step 2. (S)-2-(tert-butoxycarbonylamino)-3-((R)-4-oxaspiro[2.5]oct-6-yl)propyl 4-methylbenzenesulfonate The tert-butyl (S)-1-((R)-4-oxaspiro[2.5]oct-6-yl)-3-hydroxypropan-2-ylcarbamate (1.70 g, 5.92 mmol) and tosyl chloride (4.5 g, 23.7 mmol, 4.0 equiv) were dissolved in pyridine (30 mL) and the mixture stirred at room temperature for 17 hr. The pyridine was removed in vacuo and the residue partitioned between EtOAc and 1.0 M HCl. The layers were separated and the organic layer washed with brine, dried over Na$_2$SO$_4$, filtered and evaporated. The (S)-2-(tert-butoxycarbonylamino)-3-((R)-4-oxaspiro[2.5]oct-6-yl)propyl 4-methylbenzenesulfonate was purified by flash chromatography on silica eluting with 0-29% EtOAc in hexanes. The fractions were evaporated and used directly in the next step. MS ESI +ve m/z 464 (M+Na).

Step 3. tert-butyl (S)-1-((R)-4-oxaspiro[2.5]oct-6-yl)-3-(methylamino)propan-2-ylcarbamate The (S)-2-(tert-butoxycarbonylamino)-3-((R)-4-oxaspiro[2.5]oct-6-yl)propyl 4-methylbenzenesulfonate was dissolved in 100 mL of 33% NH$_2$Me in ethanol. The mixture was heated to 50° C. for 3 hr. After this time LC/MS analysis shows formation of the desired amine. The solution was evaporated and the residue taken up in EtOAc, washed with 10% K$_2$CO$_3$, brine, dried over Na$_2$SO$_4$, filtered and evaporated. The tert-butyl (S)-1-((R)-4-oxaspiro[2.5]oct-6-yl)-3-(methylamino)propan-2-ylcarbamate was used directly in the next step with no further purification. MS ESI +ve m/z 301 (M+1).

Step 4. (S)-tert-butyl 1-(N-Methyl-2-(trimethylsilyl)ethoxycarbonylamino)-3-((R)-4-oxaspiro[2.5]oct-6-yl)propylcarbamate The tert-butyl (S)-1-((R)-4-oxaspiro[2.5]oct-6-yl)-3-(methylamino)propan-2-ylcarbamate was dissolved in 25 mL of acetonitrile and 10% K$_2$CO$_3$ (25 mL) and Teoc-OSu (1.54 g, 5.92 mmol) were subsequently added. The mixture was stirred for 1 hr at ambient temperature. The acetonitrile was removed in vacuo and the mixture diluted with EtOAc. The layers were separated and the organic layer washed with brine, dried over Na$_2$SO$_4$, filtered and evaporated. The tert-butyl (S)-1-((R)-4-oxaspiro[2.5]oct-6-yl)-3-(methylamino)propan-2-ylcarbamate was purified by flash chromatography on silica, eluting with 0-41% EtOAc in hexanes. The fractions staining with ninhydrin were evaporated to yield 1.5 g (60% yield for 3 steps) of (S)-tert-butyl 1-(N-Methyl-2-(trimethylsilyl)ethoxycarbonylamino)-3-((R)-4-oxaspiro[2.5]oct-6-yl) propylcarbamate as a clear syrup. MS ESI +ve m/z 467 (M+Na).

Step 5. 2-(trimethylsilyl)ethyl (S)-2-amino-3-((R)-4-oxaspiro[2.5]oct-6-yl)propyl(methyl)carbamate The (S)-tert-butyl 1-(N-Methyl-2-(trimethylsilyl)ethoxycarbonylamino)-3-((R)-4-oxaspiro[2.5]oct-6-yl)propylcarbamate (250 mg, 0.565 mmol) and tosic acid hydrate (132 mg, 0.694 mmol, 1.22 equiv) were heated to reflux in methanol for 7 h. The solution was then cooled and evaporated. The residue was taken up in EtOAc/10% K$_2$CO$_3$. The layers were separated and the organic layer washed with brine, dried over Na$_2$SO$_4$, filtered and evaporated. The resulting 2-(trimethylsilyl)ethyl (S)-2-amino-3-((R)-4-oxaspiro[2.5]oct-6-yl)propyl(methyl)carbamate was used directly in the next step with no further purification. MS ESI +ve m/z 343 (M+1).

The following compounds were prepared using procedures analogous to those described above:
1) 2-(trimethylsilyl)ethyl (S)-2-amino-3-((R)-6,6-dimethyl-tetrahydro-2H-pyran-3-yl)propyl(methyl)carbamate using (S)-tert-butyl 4-(((R)-6,6-dimethyl-tetrahydro-2H-pyran-3-yl)methyl)-2,2-dimethyloxazolidine-3-carboxylate as in Step 1.

Example 1

(3R)-3-((R)-(3-chlorophenyl)(2-(ethylamino)-2-oxo-ethoxy)methyl)-N—((S)-1-cyclohexyl-3-(methylamino)propan-2-yl)piperidine-1-carboxamide
(I-58A)

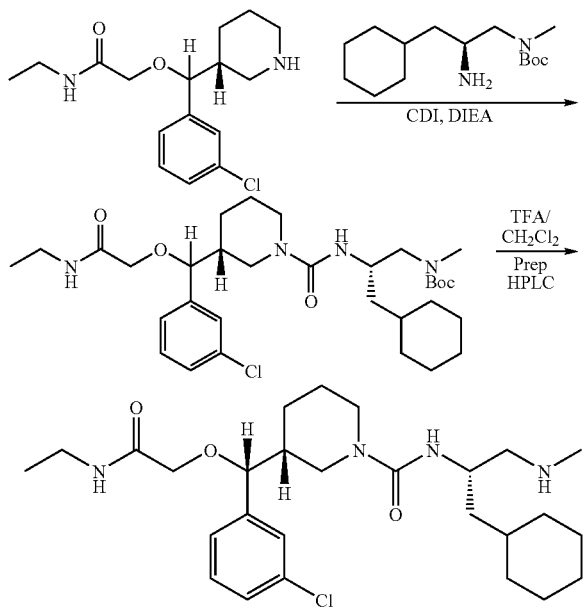

Step 1. tert-Butyl (2S)-2-((3R)-3-((3-chlorophenyl)(2-(ethylamino)-2-oxoethoxy)methyl)piperidine-1-carboxamido)-3-cyclohexylpropyl(methyl)carbamate A solution of (S)-tert-butyl 2-amino-3-cyclohexylpropyl(methyl)carbamate (34.7 mg, 0.129 mmol) in $CH_2Cl_2$ (2 mL) was cooled in an ice-bath and CDI (25 mg, 1.2 mmol) and DIEA (83.2 mg, 0.11 mL, 0.645 mmol) were added. The mixture was stirred at rt for 0.5 h and 2-((3-chlorophenyl)((R)-piperidin-3-yl)methoxy)-N-ethylacetamide (40 mg, 0.129 mmol) was added. The reaction mixture was stirred overnight, washed with brine, dried over $Na_2SO_4$ and concentrated to give crude tert-butyl (2S)-2-((3R)-3-((3-chlorophenyl)(2-(ethylamino)-2-oxoethoxy)methyl)piperidine-1-carboxamido)-3-cyclohexylpropyl(methyl)carbamate (60 mg, yield: 75.6%). MS (E/Z): 607 (M+H$^+$).

Step 2. (R)-3-((R)-(3-chlorophenyl)(2-(ethylamino)-2-oxoethoxy)methyl)-N—((S)-1-cyclohexyl-3-(methylamino)propan-2-yl)piperidine-1-carboxamide To a solution of TFA in $CH_2Cl_2$ (20%, v/v, 5 mL) under stirring was tert-butyl (2S)-2-((3R)-3-((3-chlorophenyl)(2-(ethylamino)-2-oxoethoxy)methyl)piperidine-1-carboxamido)-3-cyclohexylpropyl(methyl)carbamate (60.3 mg, 0.099 mmol). The reaction was followed by tlc (eluting solvent 5:1 petroleum ether/EtOAc). When the reaction was complete, the mixture was washed sequentially with satd aq $NaHCO_3$ and water, dried over $Na_2SO_4$ and concentrated to give the product, which was purified by preparative HPLC to give 3R—[R-(3-chloro-phenyl)-ethylcarbamoylmethoxymethyl]-piperidine-1-carboxylic acid (1S-cyclohexylmethyl-2-methylamino-ethyl)-amide (14 mg). $^1$H NMR (400 MHz, MeOD): 1.30-1.65 (m, 14H), 1.77-1.89 (m, 7H), 2.68 (s, 3H), 2.89-2.97 (m, 2H), 3.03-3.12 (m, 2H), 3.23-3.34 (m, 4H), 3.69-3.84 (m, 3H), 4.08-4.23 (m, 3H), 7.22-7.26 (m, 1H), 7.33-7.41 (m, 3H). MS (E/Z): 507 (M+H$^+$).

The following compounds were prepared using procedures analogous to those described above:

| Cpd. No. | Cpd Name |
| --- | --- |
| I-56a | (3R)-3-((R)-(3-chlorophenyl)(2-(methylamino)-2-oxoethoxy)methyl)-N-((S)-1-cyclohexyl-3-(methylamino)propan-2-yl)piperidine-1-carboxamide |
| I-56b | (3R)-3-((S)-(3-chlorophenyl)(2-(methylamino)-2-oxoethoxy)methyl)-N-((S)-1-cyclohexyl-3-(methylamino)propan-2-yl)piperidine-1-carboxamide |
| I-57a | (R)-3-((S)-(2-amino-2-oxoethoxy)(3-chloro-2-fluorophenyl)methyl)-N-((S)-1-cyclohexyl-3-(methylamino)propan-2-yl)piperidine-1-carboxamide |
| I-58b | (3R)-3-((S)-(3-chlorophenyl)(2-(ethylamino)-2-oxoethoxy)methyl)-N-((S)-1-cyclohexyl-3-(methylamino)propan-2-yl)piperidine-1-carboxamide |
| I-59a | (3R)—N-((2S)-1-cyclohexyl-3-(methylamino)propan-2-yl)-3-((R)-(2,3-difluorophenyl)(2-(ethylamino)-2-oxoethoxy)methyl)piperidine-1-carboxamide |
| I-60a | (R)-3-((R)-(3-chlorophenyl)(2-oxo-2-(propylamino)ethoxy)methyl)-N-((S)-1-cyclohexyl-3-(methylamino)propan-2-yl)piperidine-1-carboxamide |
| I-61a | (R)-3-((R)-(3-chlorophenyl)(2-(isopropylamino)-2-oxoethoxy)methyl)-N-((S)-1-cyclohexyl-3-(methylamino)propan-2-yl)piperidine-1-carboxamide |
| I-62a | (3R)—N-((2S)-1-cyclohexyl-3-(methylamino)propan-2-yl)-3-((R)-(2,3-difluorophenyl)(2-oxo-2-(propylamino)ethoxy)methyl)piperidine-1-carboxamide |
| I-63a | (R)—N-((S)-1-cyclohexyl-3-(methylamino)propan-2-yl)-3-((R)-(2,3-difluorophenyl)(2-(isopropylamino)-2-oxoethoxy)methyl)piperidine-1-carboxamide |
| I-65a | (R)-3-((R)-(3-chlorophenyl)(2-(2-methoxyethylamino)-2-oxoethoxy)methyl)-N-((S)-1-cyclohexyl-3-(methylamino)propan-2-yl)piperidine-1-carboxamide |

-continued

| Cpd. No. | Cpd Name |
|---|---|
| I-66a | (3R)-3-((R)-(3-chlorophenyl)(3-(methylamino)-3-oxopropoxy)methyl)-N-((S)-1-cyclohexyl-3-(methylamino)propan-2-yl)piperidine-1-carboxamide |
| I-67a | (3R)-3-((R)-(3-chlorophenyl)(3-(ethylamino)-3-oxopropoxy)methyl)-N-((S)-1-cyclohexyl-3-(methylamino)propan-2-yl)piperidine-1-carboxamide |
| I-67b | (3R)-3-((S)-(3-chlorophenyl)(3-(ethylamino)-3-oxopropoxy)methyl)-N-((S)-1-cyclohexyl-3-(methylamino)propan-2-yl)piperidine-1-carboxamide |
| I-68a | (3R)-3-((R)-(3-chlorophenyl)(3-oxo-3-(propylamino)propoxy)methyl)-N-((2S)-1-cyclohexyl-3-(methylamino)propan-2-yl)piperidine-1-carboxamide |
| I-69a | (R)-3-((R)-(3-chlorophenyl)(3-(isopropylamino)-3-oxopropoxy)methyl)-N-((S)-1-cyclohexyl-3-(methylamino)propan-2-yl)piperidine-1-carboxamide |
| I-70a | (R)-3-((R)-(3-chloro-2-fluorophenyl)(3-(ethylamino)-3-oxopropoxy)methyl)-N-((S)-1-cyclohexyl-3-(methylamino)propan-2-yl)piperidine-1-carboxamide |
| I-71a | (3R)-3-((S)-5-amino-1-(3-chlorophenyl)-1-hydroxy-5-oxopentyl)-N-((S)-1-cyclohexyl-3-(methylamino)propan-2-yl)piperidine-1-carboxamide |
| I-72a | (3R)-3-((S)-1-(3-chlorophenyl)-1-hydroxy-5-(methylamino)-5-oxopentyl)-N-((S)-1-cyclohexyl-3-(methylamino)propan-2-yl)piperidine-1-carboxamide |
| I-73a | (3R)-3-((S)-1-(3-chlorophenyl)-5-(ethylamino)-1-hydroxy-5-oxopentyl)-N-((S)-1-cyclohexyl-3-(methylamino)propan-2-yl)piperidine-1-carboxamide |

The following compounds were prepared using procedures analogous to those described in Example 1 except $Et_4N^+F^-$ was used to deprotect a Teoc protecting group in Step 2:

1) (R)-3-((R)-(3-chlorophenyl)(2-(ethylamino)-2-oxoethoxy)methyl)-N—((S)-1-(methylamino)-3-((R)-tetrahydro-2H-pyran-3-yl)propan-2-yl)piperidine-1-carboxamide I*—30a
2) (R)-3-((R)-(3-chlorophenyl)(2-(ethylamino)-2-oxoethoxy)methyl)-N—((S)-1-(methylamino)-3-(tetrahydro-2H-pyran-4-yl)propan-2-yl)piperidine-1-carboxamide I*—31a
3) (R)-3-((R)-(3-chlorophenyl)(2-(ethylamino)-2-oxoethoxy)methyl)-N-((2S)-1-(methylamino)-3-((R)-oxepan-3-yl)propan-2-yl)piperidine-1-carboxamide I*—61a
4) methyl 2-((R)-(3-fluorophenyl)((R)-1-((S)-1-((R)-6,6-dimethyl-tetrahydro-2H-pyran-3-yl)-3-(methylamino)propan-2-ylcarbamoyl)piperidin-3-yl)methoxy)ethylcarbamate I*—154a
5) methyl 2-((R)-(3,5-difluorophenyl)((R)-1-((S)-1-((R)-6,6-dimethyl-tetrahydro-2H-pyran-3-yl)-3-(methylamino)propan-2-ylcarbamoyl)piperidin-3-yl)methoxy)ethylcarbamate I*—155a
6) methyl 2-((R)—((R)-1-((S)-1-((R)-6,6-dimethyl-tetrahydro-2H-pyran-3-yl)-3-(methylamino)propan-2-ylcarbamoyl)piperidin-3-yl)(phenyl)methoxy)ethylcarbamate I*156a
7) methyl 2-((R)-(3-chlorophenyl)((R)-1-((S)-1-((R)-6,6-dimethyl-tetrahydro-2H-pyran-3-yl)-3-(methylamino)propan-2-ylcarbamoyl)piperidin-3-yl)methoxy)ethylcarbamate I*—157a
8) methyl 2-((R)-(3-chlorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate I*—158a
9) methyl 2-((R)-(3-fluorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate I*—159a
10) methyl 2-((R)-(3,5-difluorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate I*—160a The following compounds were prepared using procedures analogous to those described in Example 1 except 4 M HCl/dioxane was used to deprotect a Boc protecting group in Step 2:

1) (R)-3-((R)-(3-chlorophenyl)(2-(2-cyano-3-methylguanidino)ethoxy)methyl)-N—((S)-1-cyclohexyl-3-(methylamino)propan-2-yl)piperidine-1-carboxamide I*-126(a)

Example 2

Methyl (S)-4-(2-chloro-3-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate

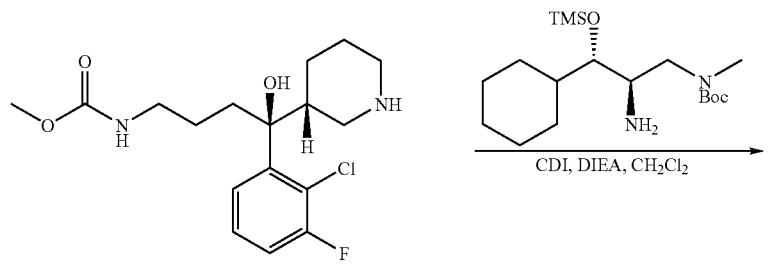

-continued

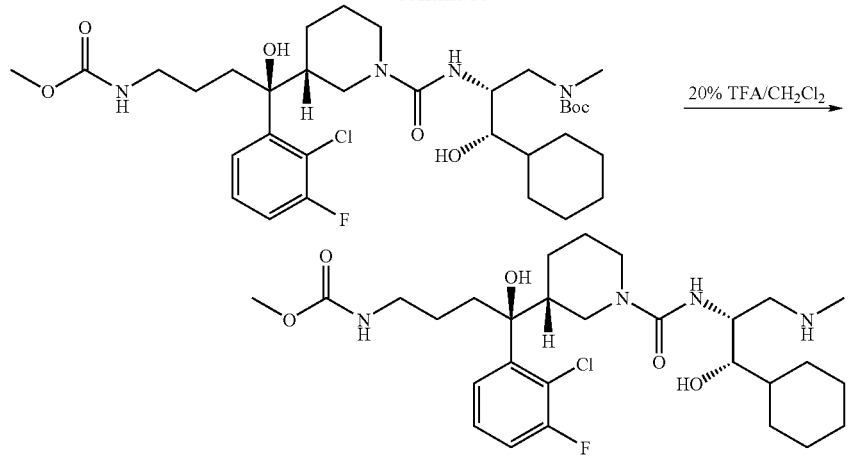

Step 1. Methyl (S)-4-(2-chloro-3-fluorophenyl)-4-((R)-1-((1S,2R)-1-cyclohexyl-1-hydroxy-3-(N-methyl-N-(t-butoxycarbonyl)amino)propan-2-ylcarbamoyl)piperidin-3-yl)-4-hydroxybutylcarbamate To a solution of tert-butyl (2R,3S)-2-amino-3-cyclohexyl-3-(trimethylsilyloxy)propyl(methyl)carbamate (79.8 mg, 0.223 mmol) in anhydrous $CH_2Cl_2$ (2 mL) were added DIEA (190 μL, 1.12 mmol) and CDI (36.2 mg, 0.223 mmol). The mixture was stirred at 0° C. for 45 min, and methyl (S)-4-(2-chloro-3-fluorophenyl)-4-hydroxy-4-((R)-piperidin-3-yl)butylcarbamate (80.0 mg, 0.223 mmol) was added in one portion and the mixture was allowed to warm to rt and stirred overnight. The reaction was quenched with water and extracted with $CH_2Cl_2$ (3×20 mL). The organic extracts were washed with brine and concentrated to give crude product, which was purified by preparative HPLC to afford methyl (S)-4-(2-chloro-3-fluorophenyl)-4-((R)-1-((1S,2R)-1-cyclohexyl-1-hydroxy-3-(N-methyl-N-(t-butoxycarbonyl)amino)propan-2-ylcarbamoyl)piperidin-3-yl)-4-hydroxybutylcarbamate (70 mg, 46.8%). MS (E/Z): 671 (M+H$^+$).

Step 2. Methyl (S)-4-(2-chloro-3-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate (S)-4-(2-chloro-3-fluorophenyl)-4-((R)-1-((1S,2R)-1-cyclohexyl-1-hydroxy-3-(N-methyl-N-(t-butoxycarbonyl)amino)propan-2-ylcarbamoyl)piperidin-3-yl)-4-hydroxybutylcarbamate (70 mg, 0.104 mmol) was cooled to 0° C. and a 20% solution of TFA in $CH_2Cl_2$ (5 mL) was added. The mixture was stirred at 0° C. for about 20 min and quenched with satd aq $NaHCO_3$. The organic layer was separated and the aqueous layer was extracted with $CH_2Cl_2$ (3×). The combined organic layers were washed with brine, then concentrated in vacuo to give crude product, which was purified by preparative HPLC to afford methyl (S)-4-(2-chloro-3-fluorophenyl)-4-((R)-1-((1S,2R)-1-cyclohexyl-1-hydroxy-3-(methylamino)propan-2- ylcarbamoyl)piperidin-3-yl)-4-hydroxybutylcarbamate (50 mg, yield 84%). $^1$H NMR (400 MHz, MeOD): 0.90-1.87 (m, 18H), 1.87-2.08 (m, 2H), 2.10-2.22 (s, 1H), 2.60-2.72 (t, 1H), 2.72 (s, 3H), 2.75-2.85 (t, 1H), 2.90-3.10 (m, 3H), 3.40-3.47 (m, 1H), 3.60 (s, 3H), 3.90-4.05 (d, 1H), 4.05-4.15 (m, 1H), 4.25-4.40 (d, 1H), 7.10-7.20 (s, 1H), 7.32-7.41 (t, 1H), 7.50-7.60 (t, 1H). MS (E/Z): 571.35 (M+H$^+$).

The following compounds were prepared using procedures analogous to those described above:

| Cpd. No. | Cpd Name |
|---|---|
| I-15a | methyl (S)-4-(3-chloro-5-fluorophenyl)-4-((R)-1-((S)-1-cyclohexyl-3-(methylamino)propan-2-ylcarbamoyl)piperidin-3-yl)-4-hydroxybutylcarbamate |
| I-20a | methyl (S)-4-(3-chloro-2-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate |

The following compounds were prepared using procedures analogous to those described above except that the acidic conditions used to remove a Boc group in step 2 were replaced with hydrogenation in the presence of $PdCl_2$ to remove a Cbz protecting group:

| Cpd. No. | Cpd Name |
|---|---|
| I-17a | methyl (S)-4-(2,3-difluorophenyl)-4-((R)-1-((S)-1-((1r,4S)-4-fluorocyclohexyl)-3-(methylamino)propan-2-ylcarbamoyl)piperidin-3-yl)-4-hydroxybutylcarbamate |
| I-22a | methyl (S)-4-(3-chloro-2-fluorophenyl)-4-((R)-1-((S)-1-((1r,4S)-4-fluorocyclohexyl)-3-(methylamino)propan-2-ylcarbamoyl)-piperidin-3-yl)-4-hydroxybutylcarbamate |

The following compounds were prepared using procedures analogous to those described in Example 2:

| Cpd. No. | Cpd Name |
|---|---|
| I*-27a | methyl 2-((R)-((R)-1-((1S,2R)-1-cyclopentyl-1-hydroxy-3-(methylamino)propan-2-ylcarbamoyl)piperidin-3-yl)(3-fluorophenyl)methoxy)ethylcarbamate |

-continued

| Cpd. No. | Cpd Name |
|---|---|
| I*-48a | methyl 2-((R)-((R)-1-((1S,2R)-1-cyclohexyl-1-hydroxy-3-(methylamino)propan-2-ylcarbamoyl)piperidin-3-yl)(3-fluorophenyl)methoxy)ethylcarbamate |
| I*-53a | methyl 2-((R)-((R)-1-((1S,2R)-1-cyclopentyl-1-hydroxy-3-(methylamino)propan-2-ylcarbamoyl)piperidin-3-yl)(5-fluoro-2-methylphenyl)methoxy)ethylcarbamate |
| I*-67a | methyl 2-((R)-(3-chlorophenyl)((R)-1-((1S,2R)-1-cyclopentyl-1-hydroxy-3-(methylamino)propan-2-ylcarbamoyl)piperidin-3-yl)methoxy)ethylcarbamate |
| I*-72a | methyl 2-((R)-((R)-1-((1S,2R)-1-cyclopentyl-1-hydroxy-3-(methylamino)propan-2-ylcarbamoyl)piperidin-3-yl)(2,3-difluorophenyl)methoxy)ethylcarbamate |
| I*-100a | methyl 2-((R)-(3-chlorophenyl)((R)-1-((1S,2R)-1-cyclohexyl-1-hydroxy-3-(methylamino)propan-2-ylcarbamoyl)piperidin-3-yl)methoxy)ethylcarbamate |
| I*-107a | methyl 2-((R)-(5-chloro-2-methylphenyl)((R)-1-((1S,2R)-1-cyclopentyl-1-hydroxy-3-(methylamino)propan-2-ylcarbamoyl)piperidin-3-yl)methoxy)ethylcarbamate |
| I*-112a | methyl 2-((R)-((R)-1-((1S,2R)-1-cyclohexyl-1-hydroxy-3-(methylamino)propan-2-ylcarbamoyl)piperidin-3-yl)(3,5-difluorophenyl)methoxy)ethylcarbamate I*-112a |
| I*-138a | methyl 2-((R)-(3-chloro-2-fluorophenyl)((R)-1-((1S,2R)-1-cyclohexyl-1-hydroxy-3-(methylamino)propan-2-ylcarbamoyl)piperidin-3-yl)methoxy)ethylcarbamate |

The following compounds were prepared using procedures analogous to those described in Example 2 except Et$_4$N$^+$F$^-$ was used to deprotect a Teoc protecting group in Step 2:

1) methyl (S)-4-(3-fluorophenyl)-4-hydroxy-4-((3R)-1-((S)-1-(methylamino)-3-(tetrahydro-2H-pyran-3-yl)propan-2-ylcarbamoyl)piperidin-3-yl)butylcarbamate I*-54a
2) methyl (S)-4-(3-chloro-2-fluorophenyl)-4-hydroxy-4-((3R)-1-((S)-1-(methylamino)-3-(tetrahydro-2H-pyran-3-yl)propan-2-ylcarbamoyl)piperidin-3-yl)butylcarbamate I*-139a
3) methyl (S)-4-(3-chloro-2-fluorophenyl)-4-hydroxy-4-((R)-1-((S)-1-(methylamino)-3-((R)-tetrahydro-2H-pyran-3-yl)propan-2-ylcarbamoyl)piperidin-3-yl)butylcarbamate I*-142a Example 3

Methyl 2-((R)—((R)-1-((S)-1-cyclohexyl-3-(methylamino)propan-2-ylcarbamoyl)piperidin-3-yl)(3-fluorophenyl)methoxy)ethylcarbamate

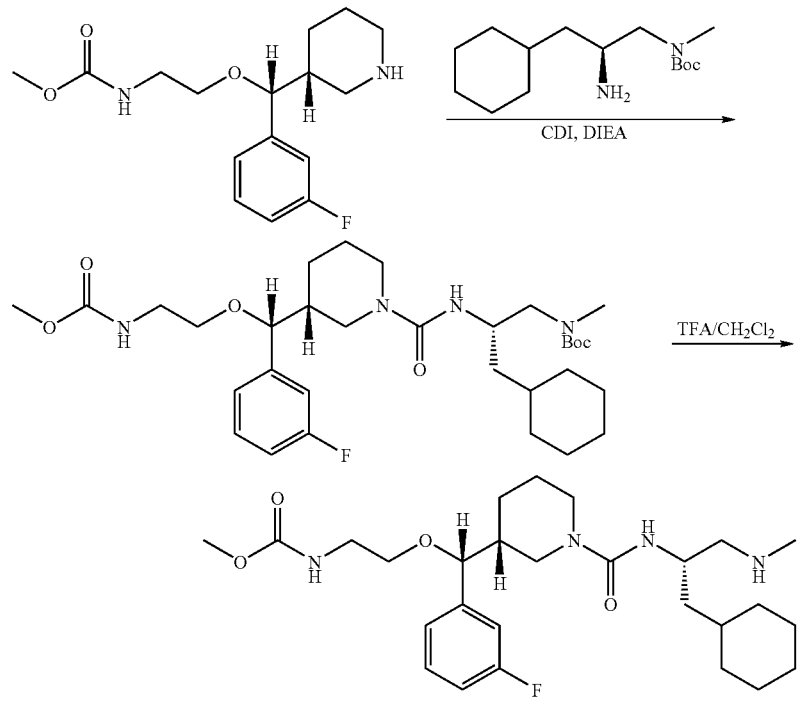

Step 1. Methyl 2-((R)—((R)-1-((S)-1-cyclohexyl-3-(N-methyl-N-(t-butoxycarbonyl)amino)propan-2-ylcarbamoyl)piperidin-3-yl)(3-fluorophenyl)methoxy)ethylcarbamate To a solution of tert-butyl (S)-2-amino-3-cyclohexylpropylmethylcarbamate (65 mg, 0.24 mmol) and CDI (40 mg, 0.24 mmol) in anhydrous $CH_2Cl_2$ (5 mL) cooled in an ice bath was added DIEA (104 mg, 0.81 mmol). After addition, the mixture was stirred for 1 h at 0° C., a solution of methyl 2-((R)-(3-fluorophenyl)((R)-piperidin-3-yl)methoxy)ethylcarbamate (50 mg, 0.16 mmol) in anhydrous $CH_2Cl_2$ (5 mL) was added dropwise. The reaction mixture was allowed to warm to rt and stirred overnight. After the reaction was complete, the solvent was removed in vacuo. The product was purified by preparative tlc to afford the desired isomer of methyl 2-((R)—((R)-1-((S)-1-cyclohexyl-3-(N-methyl-N-(t-butoxycarbonyl)amino)propan-2-ylcarbamoyl)piperidin-3-yl)(3-fluorophenyl)methoxy)ethylcarbamate (50 mg, 52% yield). MS (E/Z): 607 (M+H$^+$).

Step 2. Methyl 2-((R)—((R)-1-((S)-1-cyclohexyl-3-(methylamino)propan-2-ylcarbamoyl)piperidin-3-yl)(3-fluorophenyl)methoxy)ethylcarbamate A mixture of methyl 2-((R)—((R)-1-((S)-1-cyclohexyl-3-(N-methyl-N-(t-butoxycarbonyl)amino)propan-2-ylcarbamoyl)piperidin-3-yl)(3-fluorophenyl)methoxy)ethylcarbamate (20 mg, 0.03 mmol) and a 20% solution of TFA in $CH_2Cl_2$ (2 mL) were stirred for about 1 h at rt until the reaction was complete. The solvent was removed by evaporation and the crude product was purified by preparative HPLC to afford methyl 2-((R)—((R)-1-((S)-1-cyclohexyl-3-(methylamino)propan-2-ylcarbamoyl)piperidin-3-yl)(3-fluorophenyl)methoxy)ethylcarbamate (7.5 mg, 44% yield). $^1$H-NMR (400 MHz, CD$_3$OD): 0.90 (m, 1H), 1.04 (m, 1H), 1.11-1.45 (m, 8H), 1.51 (m, 1H), 1.71 (m, 7H), 2.71 (s, 3H), 2.91 (m, 2H), 3.06 (m, 1H), 3.23 (m, 3H), 3.61 (s, 3H), 3.81 (m, 1H), 4.07 (m, 2H), 7.03 (m, 2H), 7.09 (m, 1H), 7.36 (m, 1H). MS (E/Z): 507 (M+H$^+$).

The following compounds were prepared using procedures analogous to those described above:

| Cpd. No. | Cpd Name |
| --- | --- |
| I-1a | methyl (S)-4-((R)-1-((S)-1-cyclohexyl-3-(methylamino)propan-2-ylcarbamoyl)piperidin-3-yl)-4-(2-fluorophenyl)-4-hydroxybutylcarbamate |
| I-2a | methyl (S)-4-(3-chloro-2-fluorophenyl)-4-((R)-1-((S)-4,4-dimethyl-1-(methylamino)pentan-2-ylcarbamoyl)piperidin-3-yl)-4-hydroxybutylcarbamate |
| I-3a | methyl (S)-4-((R)-1-((S)-1-cyclohexyl-3-(methylamino)propan-2-ylcarbamoyl)piperidin-3-yl)-4-(3,5-dimethylphenyl)-4-hydroxybutylcarbamate |
| I-4a | methyl (S)-4-((R)-1-((S)-1-cyclohexyl-3-(methylamino)propan-2-ylcarbamoyl)piperidin-3-yl)-4-(3-fluoro-5-methylphenyl)-4-hydroxybutylcarbamate |
| I-5a | methyl (S)-4-((R)-1-((S)-1-cyclohexyl-3-(methylamino)propan-2-ylcarbamoyl)piperidin-3-yl)-4-(2-fluoro-5-methylphenyl)-4-hydroxybutylcarbamate |
| I-6a | methyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate |
| I-7a | methyl (S)-4-((R)-1-((S)-1-cyclohexyl-3-(methylamino)propan-2-ylcarbamoyl)piperidin-3-yl)-4-(2,3-difluorophenyl)-4-hydroxybutylcarbamate |
| I-7b | methyl (R)-4-((R)-1-((S)-1-cyclohexyl-3-(methylamino)propan-2-ylcarbamoyl)piperidin-3-yl)-4-(2,3-difluorophenyl)-4-hydroxybutylcarbamate |
| I-8a | methyl (S)-4-((R)-1-((S)-1-cyclohexyl-3-(methylamino)propan-2-ylcarbamoyl)piperidin-3-yl)-4-(3,5-difluorophenyl)-4-hydroxybutylcarbamate |
| I-11a | ethyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate |
| I-12a | methyl (S)-4-((R)-1-((1S,2R)-1-cyclohexyl-1-hydroxy-3-(methylamino)propan-2-ylcarbamoyl)piperidin-3-yl)-4-(2,3-difluorophenyl)-4-hydroxybutylcarbamate |
| I-13a | methyl (S)-4-(3-chloro-2-fluorophenyl)-4-((R)-1-((S)-1-cyclohexyl-3-(methylamino)propan-2-ylcarbamoyl)piperidin-3-yl)-4-hydroxybutylcarbamate |
| I-14a | methyl (S)-4-(2-chloro-3-fluorophenyl)-4-((R)-1-((S)-1-cyclohexyl-3-(methylamino)propan-2-ylcarbamoyl)piperidin-3-yl)-4-hydroxybutylcarbamate |
| I-16a | methyl (S)-4-((R)-1-((2S,3R)-3-amino-1-cyclohexylbutan-2-ylcarbamoyl)piperidin-3-yl)-4-(3-chloro-2-fluorophenyl)-4-hydroxybutylcarbamate |
| I-35a | methyl 2-((R)-(3-chlorophenyl)((R)-1-((S)-1-cyclohexyl-3-(methylamino)propan-2-ylcarbamoyl)piperidin-3-yl)methoxy)ethylcarbamate |
| I-37a | methyl 2-((R)-((3R)-1-((2S)-1-cyclohexyl-3-(methylamino)propan-2-ylcarbamoyl)piperidin-3-yl)(2,3-difluorophenyl)methoxy)ethylcarbamate |
| I-41a | ethyl 2-((R)-(3-chlorophenyl)((R)-1-((S)-1-cyclohexyl-3-(methylamino)propan-2-ylcarbamoyl)piperidin-3-yl)methoxy)ethylcarbamate |
| I-43a | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate |
| I-43b | methyl 2-((3-chloro-2-fluorophenyl)(1-((S)-1-cyclohexyl-3-(methylamino)propan-2-ylcarbamoyl)piperidin-3-yl)methoxy)ethylcarbamate |
| I-44a | methyl 2-((R)-(3-chloro-5-fluorophenyl)((R)-1-((S)-1-cyclohexyl-3-(methylamino)propan-2-ylcarbamoyl)piperidin-3-yl)methoxy)ethylcarbamate |
| I-45a | methyl 2-((R)-(3-chlorophenyl)((R)-1-((S)-1-(trans-4-fluorocyclohexyl)-3-(methylamino)propan-2-ylcarbamoyl)piperidin-3-yl)methoxy)ethylcarbamate |
| I-46b | methyl 2-((1R)-(3-chlorophenyl)((3R)-1-(1-(1-fluorocyclohexyl)-3-(methylamino)propan-2-ylcarbamoyl)piperidin-3-yl)methoxy)ethylcarbamate |
| I-48a | methyl 2-((S)-(3-chloro-2-fluorophenyl)((R)-4-((S)-1-cyclohexyl-3-(methylamino)propan-2-ylcarbamoyl)morpholin-2-yl)methoxy)ethylcarbamate |
| I-49a | ethyl 2-((R)-(3-chloro-2-fluorophenyl)((3R)-1-((2S)-1-cyclohexyl-3-(methylamino)propan-2-ylcarbamoyl)piperidin-3-yl)methoxy)ethylcarbamate |
| I-50a | methyl 2-((1R)-(3-chloro-2-fluorophenyl)((3R)-1-(1-(1-fluorocyclohexyl)-3-(methylamino)propan-2-ylcarbamoyl)piperidin-3-yl)methoxy)ethylcarbamate |
| I-51a | methyl 2-((R)-(3-chloro-2-fluorophenyl)((R)-1-((S)-1-(trans-4-fluorocyclohexyl)-3-(methylamino)propan-2-ylcarbamoyl)piperidin-3-yl)methoxy)ethylcarbamate |
| I-75a | (R)-3-((R)-(3-chlorophenyl)(4-oxohexyloxy)methyl)-N-((S)-1-cyclohexyl-3-(methylamino)propan-2-yl)piperidine-1-carboxamide |

The following compounds were prepared using procedures analogous to those described in Example 3:

| Cpd. No. | Cpd Name |
| --- | --- |
| I*-4a | methyl 2-((R)-((R)-1-((S)-1-amino-3-cyclohexylpropan-2-ylcarbamoyl)piperidin-3-yl)(3-fluorophenyl)methoxy)ethylcarbamate I*-4a |
| I*-18a | methyl 2-((R)-((R)-1-((S)-1-cyclohexyl-3-(methylamino)propan-2-ylcarbamoyl)piperidin-3-yl)(m-tolyl)methoxy)ethylcarbamate I*-18a |
| I*-40a | methyl 2-((R)-((R)-1-((S)-1-cyclohexyl-3-(methylamino)propan-2-ylcarbamoyl)piperidin-3-yl)(5-fluoro-2-methylphenyl)methoxy)ethylcarbamate I*-40a |
| I*-63a | methyl 2-((R)-((R)-1-((S)-1-cyclohexyl-3-(methylamino)propan-2-ylcarbamoyl)piperidin-3-yl)(2,5-difluorophenyl)methoxy)ethylcarbamate I*-63a |
| I*-64a | methyl 2-((R)-((R)-1-((S)-1-cyclohexyl-3-(methylamino)propan-2-ylcarbamoyl)piperidin-3-yl)(3,5-difluorophenyl)methoxy)ethylcarbamate I*-64a |
| I*-65a | methyl 2-((R)-((R)-1-((S)-1-cyclohexyl-3-(methylamino)propan-2-ylcarbamoyl)piperidin-3-yl)(3,4-difluorophenyl)methoxy)ethylcarbamate I*-65a |
| I*-66a | methyl 2-((S)-(3-chlorophenyl)((R)-4-((S)-1-cyclohexyl-3-(methylamino)propan-2-ylcarbamoyl)morpholin-2-yl)methoxy)ethylcarbamate I*-66a |
| I*-85a | methyl 2-((R)-(5-chloro-2-methylphenyl)((R)-1-((S)-1-cyclohexyl-3-(methylamino)propan-2-ylcarbamoyl)piperidin-3-yl)methoxy)ethylcarbamate I*-85a |
| I*-91a | methyl 2-((R)-(3-chlorophenyl)((R)-1-((S)-1-cyclohexyl-3-(methylamino)propan-2-ylcarbamoyl)azepan-3-yl)methoxy)ethylcarbamate I*-91a |
| I*-92a | methyl 2-((S)-(3-chlorophenyl)((R)-1-((S)-1-cyclohexyl-3-(methylamino)propan-2-ylcarbamoyl)azepan-3-yl)methoxy)ethylcarbamate I*-92a |
| I*-96a | methyl 2-((R)-((R)-1-((S)-1-cyclohexyl-3-(methylamino)propan-2-ylcarbamoyl)piperidin-3-yl)(2,3-difluoro-6-methylphenyl)methoxy)ethylcarbamate I*-96a |
| I*-97a | methyl 2-((R)-((S)-1-((S)-1-cyclohexyl-3-(methylamino)propan-2-ylcarbamoyl)piperidin-3-yl)(2,3-difluoro-6-methylphenyl)methoxy)ethylcarbamate I*-97a |
| I*-115a | methyl 2-((R)-(2,3-difluoro-6-methylphenyl)(1-((S)-1-(methylamino)-3-(tetrahydro-2H-pyran-4-yl)propan-2-ylcarbamoyl)piperidin-3-yl)methoxy)ethylcarbamate I*-115a |
| I*-116a | methyl 2-((5-chloro-2-fluorophenyl)((R)-1-((S)-1-cyclohexyl-3-(methylamino)propan-2-ylcarbamoyl)piperidin-3-yl)methoxy)ethylcarbamate I*-116a |
| I*-117a | methyl 2-((R)-(5-chloro-2-fluorophenyl)((R)-1-((S)-1-cyclohexyl-3-(methylamino)propan-2-ylcarbamoyl)piperidin-3-yl)methoxy)ethylcarbamate I*-117a |
| I*-118a | methyl 2-((R)-(3-chloro-4-fluorophenyl)((R)-1-((S)-1-cyclohexyl-3-(methylamino)propan-2-ylcarbamoyl)piperidin-3-yl)methoxy)ethylcarbamate I*-118a |
| I*-119a | methyl 2-((R)-((R)-1-((S)-1-cyclohexyl-3-(methylamino)propan-2-ylcarbamoyl)piperidin-3-yl)(3,4,5-trifluorophenyl)methoxy)ethylcarbamate I*-119a |
| I*-128a | (R)-3-((R)-(3-chlorophenyl)(2-(thiazol-2-ylamino)ethoxy)methyl)-N-((S)-1-cyclohexyl-3-(methylamino)propan-2-yl)piperidine-1-carboxamide I*-128a |
| I*-129a | methyl 2-((R)-((3R)-1-(1-(bicyclo[2.2.2]octan-1-yl)-3-(methylamino)propan-2-ylcarbamoyl)piperidin-3-yl)(3-chlorophenyl)methoxy)ethylcarbamate I*-129a |
| I*-136a | methyl 2-((R)-((R)-1-((S)-1-cyclohexyl-3-(methylamino)propan-2-ylcarbamoyl)piperidin-3-yl)(3-(trifluoromethyl)phenyl)methoxy)ethylcarbamate I*-136a |

The following compounds were prepared using procedures analogous to those described in Example 3 except Et$_4$N$^+$F$^-$ was used to deprotect a Teoc protecting group in Step 2:

| Cpd. No. | Cpd Name |
| --- | --- |
| I*-6a | methyl 2-((R)-(3-fluorophenyl)((3R)-1-((S)-1-(methylamino)-3-(tetrahydrofuran-3-yl)propan-2-ylcarbamoyl)piperidin-3-yl)methoxy)ethylcarbamate |

| Cpd. No. | Cpd Name |
|---|---|
| I*-7a | methyl 2-((R)-((R)-1-((S)-4,4-dimethyl-1-(methylamino)hexan-2-ylcarbamoyl)piperidin-3-yl)(3-fluorophenyl)methoxy)ethylcarbamate |
| I*-20a | methyl 2-((R)-((R)-1-((S)-1-(methylamino)-3-(tetrahydro-2H-pyran-4-yl)propan-2-ylcarbamoyl)piperidin-3-yl)(m-tolyl)methoxy)ethylcarbamate |
| I*-26a | methyl 2-((R)-(3-fluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-34a | methyl 2-((R)-(3-chlorophenyl)((R)-1-((S)-4,4-dimethyl-1-(methylamino)hexan-2-ylcarbamoyl)piperidin-3-yl)methoxy)ethylcarbamate |
| I*-36a | methyl 2-((R)-(3,5-dimethylphenyl)((R)-1-((S)-1-(methylamino)-3-(tetrahydro-2H-pyran-4-yl)propan-2-ylcarbamoyl)piperidin-3-yl)methoxy)ethylcarbamate |
| I*-37a | methyl 2-((R)-(2,5-dimethylphenyl)((R)-1-((S)-1-(methylamino)-3-(tetrahydro-2H-pyran-4-yl)propan-2-ylcarbamoyl)piperidin-3-yl)methoxy)ethylcarbamate |
| I*-39a | methyl 2-((R)-((R)-1-((S)-1-cycloheptyl-3-(methylamino)propan-2-ylcarbamoyl)piperidin-3-yl)(3-fluorophenyl)methoxy)ethylcarbamate |
| I*-46a | methyl 2-((R)-(3-fluorophenyl)((R)-1-((R)-1-(methylamino)-3-(2-oxopiperidin-1-yl)propan-2-ylcarbamoyl)piperidin-3-yl)methoxy)ethylcarbamate |
| I*-47a | methyl 2-((R)-(3-fluorophenyl)((3R)-1-((S)-1-(methylamino)-3-(oxepan-4-yl)propan-2-ylcarbamoyl)piperidin-3-yl)methoxy)ethylcarbamate |
| I*-49a | methyl 2-((R)-(2-fluoro-5-methylphenyl)((R)-1-((S)-1-(methylamino)-3-(tetrahydro-2H-pyran-4-yl)propan-2-ylcarbamoyl)piperidin-3-yl)methoxy)ethylcarbamate |
| I*-50a | methyl 2-((R)-(5-fluoro-2-methylphenyl)((R)-1-((S)-1-(methylamino)-3-(tetrahydro-2H-pyran-4-yl)propan-2-ylcarbamoyl)piperidin-3-yl)methoxy)ethylcarbamate |
| I*-52a | methyl 2-((R)-(3-fluoro-5-methylphenyl)((R)-1-((S)-1-(methylamino)-3-(tetrahydro-2H-pyran-4-yl)propan-2-ylcarbamoyl)piperidin-3-yl)methoxy)ethylcarbamate |
| I*-56a | methyl 2-((R)-(3-fluorophenyl)((R)-1-((S)-1-(methylamino)-3-((R)-tetrahydro-2H-pyran-3-yl)propan-2-ylcarbamoyl)azepan-3-yl)methoxy)ethylcarbamate |
| I*-60a | methyl 2-((R)-(5-chloro-2-methylphenyl)((R)-1-((S)-1-cyclopentyl-3-(methylamino)propan-2-ylcarbamoyl)piperidin-3-yl)methoxy)ethylcarbamate |
| I*-62a | methyl 2-((R)-(3-chlorophenyl)((R)-1-((R)-1-(methylamino)-3-(2-oxopyrrolidin-1-yl)propan-2-ylcarbamoyl)piperidin-3-yl)methoxy)ethylcarbamate |
| I*-69a | methyl 2-((R)-(2,5-difluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-70a | methyl 2-((R)-(3,5-difluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-71a | methyl 2-((R)-(2,3-difluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-75a | methyl 2-((S)-(3-chlorophenyl)((R)-4-((S)-1-(methylamino)-3-(tetrahydro-2H-pyran-4-yl)propan-2-ylcarbamoyl)morpholin-2-yl)methoxy)ethylcarbamate |
| I*-77a | methyl 2-((R)-((R)-1-((S)-1-((2S,4r,6R)-2,6-dimethyl-tetrahydro-2H-pyran-4-yl)-3-(methylamino)propan-2-ylcarbamoyl)piperidin-3-yl)(3-fluorophenyl)methoxy)ethylcarbamate |
| I*-78a | methyl 2-((R)-(3-fluorophenyl)((R)-1-((S)-4-(1-methoxycyclopentyl)-1-(methylamino)butan-2-yl-carbamoyl)piperidin-3-yl)methoxy)ethylcarbamate |
| I*-84a | methyl 2-((R)-(3-chlorophenyl)((R)-1-((S)-1-cycloheptyl-3-(methylamino)propan-2-ylcarbamoyl)piperidin-3-yl)methoxy)ethylcarbamate |
| I*-93a | methyl 2-((R)-(3-chlorophenyl)((R)-1-((R)-1-(methylamino)-3-(2-oxopiperidin-1-yl)propan-2-yl-carbamoyl)piperidin-3-yl)methoxy)ethylcarbamate |
| I*-98a | methyl 2-((R)-(3-chlorophenyl)((R)-1-((S)-1-(methylamino)-3-((R)-oxepan-4-yl)propan-2-yl-carbamoyl)piperidin-3-yl)methoxy)ethylcarbamate |
| I*-99a | methyl 2-((R)-(3-chlorophenyl)((R)-1-((S)-1-(methylamino)-3-((S)-oxepan-4-yl)propan-2-ylcarbamoyl)piperidin-3-yl)methoxy)ethylcarbamate |
| I*-101a | methyl 2-((R)-(5-chloro-2-methylphenyl)((R)-1-((S)-1-(methylamino)-3-(tetrahydro-2H-pyran-4-yl)propan-2-ylcarbamoyl)piperidin-3-yl)methoxy)ethylcarbamate |

-continued

| Cpd. No. | Cpd Name |
|---|---|
| I*-108a | methyl 2-((R)-(3-chlorophenyl)((R)-1-((S)-1-(methylamino)-3-(tetrahydro-2H-pyran-4-yl)propan-2-ylcarbamoyl)azepan-3-yl)methoxy)ethylcarbamate |
| I*-121a | methyl 2-((R)-(3-chloro-5-fluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-123a | methyl 2-((R)-((3R)-1-((S)-1-(3-noradamantyl)-3-(methylamino)propan-2-ylcarbamoyl)piperidin-3-yl)(3-fluorophenyl)methoxy)ethylcarbamate |
| I*-125a | methyl 2-((R)-(3-chlorophenyl)((R)-1-((S)-1-((1s,3R,4S)-3,4-difluorocyclopentyl)-3-(methylamino)propan-2-ylcarbamoyl)piperidin-3-yl)methoxy)ethylcarbamate |
| I*-132a | methyl 2-((R)-(3-chlorophenyl)((R)-1-((S)-1-((2S,4r,6R)-2,6-dimethyl-tetrahydro-2H-pyran-4-yl)-3-(methylamino)propan-2-ylcarbamoyl)piperidin-3-yl)methoxy)ethylcarbamate |
| I*-134a | methyl 2-((R)-(3,5-difluorophenyl)((R)-1-((S)-4-(1-methoxycyclopentyl)-1-(methylamino)butan-2-ylcarbamoyl)piperidin-3-yl)methoxy)ethylcarbamate |
| I*-135a | methyl 2-((R)-(3-chloro-2-fluorophenyl)((R)-1-((S)-1-cycloheptyl-3-(methylamino)propan-2-ylcarbamoyl)piperidin-3-yl)methoxy)ethylcarbamate |
| I*-137a | methyl 2-((R)-(3-chloro-2-fluorophenyl)((3R)-1-((S)-1-(methylamino)-3-(oxepan-4-yl)propan-2-ylcarbamoyl)piperidin-3-yl)methoxy)ethylcarbamate |
| I*-144a | methyl 2-((R)-((R)-1-((S)-1-(methylamino)-3-(tetrahydro-2H-pyran-4-yl)propan-2-ylcarbamoyl)piperidin-3-yl)(3-(trifluoromethyl)phenyl)methoxy)ethylcarbamate |
| I*-145a | methyl 2-((R)-((R)-1-((S)-1-(1-adamantyl)-3-(methylamino)propan-2-ylcarbamoyl)piperidin-3-yl)(3-fluorophenyl)methoxy)ethylcarbamate |
| I*-148a | methyl 2-((R)-(3-chloro-2,4-difluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I*-149a | methyl 2-((R)-((R)-1-((S)-1-(3-noradamantyl)-3-(methylamino)propan-2-ylcarbamoyl)piperidin-3-yl)(2,5-difluorophenyl)methoxy)ethylcarbamate |
| I*-150a | methyl 2-((R)-1-(3-chlorophenyl)-1-((R)-1-((S)-1-cyclohexyl-3-(methylamino)propan-2-ylcarbamoyl)piperidin-3-yl)butoxy)ethylcarbamate |
| I*-152a | methyl 2-((R)-((R)-1-((S)-1-(1-adamantyl)-3-(methylamino)propan-2-ylcarbamoyl)piperidin-3-yl)(2,5-difluorophenyl)methoxy)ethylcarbamate |

The following compounds were prepared using procedures analogous to those described in Example 3 except H₂ and Pd/C or Pd(OH)₂ was used to deprotect a Cbz protecting group in Step 2:

1) methyl 2-((R)—((R)-1-((S)-1-cyclopentyl-3-(methylamino)propan-2-ylcarbamoyl)piperidin-3-yl)(3-fluorophenyl)methoxy)ethylcarbamate I*-5a
2) methyl 2-((R)—((R)-1-((S)-1-cyclopentyl-3-(methylamino)propan-2-ylcarbamoyl)piperidin-3-yl)(5-fluoro-2-methylphenyl)methoxy)ethylcarbamate I*-24a
3) methyl 2-((R)-(3-chlorophenyl)((R)-1-((S)-1-cyclopentyl-3-(methylamino)propan-2-ylcarbamoyl)piperidin-3-yl)methoxy)ethylcarbamate I*-29a
4) methyl 2-((R)-(3-fluorophenyl)((R)-1-((S)-1-(4-hydroxycyclohexyl)-3-(methylamino)propan-2-ylcarbamoyl)piperidin-3-yl)methoxy)ethylcarbamate I*-51a
5) methyl 2-((R)-(3-chlorophenyl)((R)-1-((S)-1-(methylamino)-3-(4-oxocyclohexyl)propan-2-ylcarbamoyl)piperidin-3-yl)methoxy)ethylcarbamate I*-80a
6) methyl 2-((R)-(3-chlorophenyl)((R)-1-((S)-1-(4-hydroxycyclohexyl)-3-(methylamino)propan-2-ylcarbamoyl)piperidin-3-yl)methoxy)ethylcarbamate I*-102a The following compounds were prepared using procedures analogous to those described in Example 3 except 20% TFA/CH₂Cl₂ (V/V) was used to deprotect a Teoc protecting group in Step 2:

| Cpd. No. | Cpd Name |
|---|---|
| I*-9a | methyl 2-((R)-((R)-1-((S)-1-cyclohexyl-3-(methylamino)propan-2-ylcarbamoyl)piperidin-3-yl)(thiophen-2-yl)methoxy)ethylcarbamate |
| I*-12a | methyl 2-((S)-((R)-1-((S)-1-cyclohexyl-3-(methylamino)propan-2-ylcarbamoyl)piperidin-3-yl)(thiazol-2-yl)methoxy)ethylcarbamate |
| I*-13a | methyl 2-((R)-((R)-1-((S)-1-cyclohexyl-3-(methylamino)propan-2-ylcarbamoyl)piperidin-3-yl)(thiazol-2-yl)methoxy)ethylcarbamate |
| I*-15a | methyl 2-((R)-((R)-1-((S)-1-(methylamino)-3-(tetrahydro-2H-pyran-4-yl)propan-2-ylcarbamoyl)piperidin-3-yl)(thiophen-2-yl)methoxy)ethylcarbamate |
| I*-16a | methyl 2-((S)-((R)-1-((S)-1-(methylamino)-3-(tetrahydro-2H-pyran-4-yl)propan-2-ylcarbamoyl)piperidin-3-yl)(thiophen-2-yl)methoxy)ethylcarbamate |
| I*-32a | methyl 2-((R)-((R)-1-((S)-1-cyclohexyl-3-(methylamino)propan-2-ylcarbamoyl)piperidin-3-yl)(4-methylthiazol-2-yl)methoxy)ethylcarbamate |
| I*-33a | methyl 2-((S)-((R)-1-((S)-1-cyclohexyl-3-(methylamino)propan-2-ylcarbamoyl)piperidin-3-yl)(4-methylthiazol-2-yl)methoxy)ethylcarbamate |

Example 4

Methyl (S)-4-((R)-1-((S)-2-amino-3-cyclohexylpropylcarbamoyl)piperidin-3-yl)-4-(3-chloro-2-fluorophenyl)-4-hydroxybutylcarbamate (I-9A)

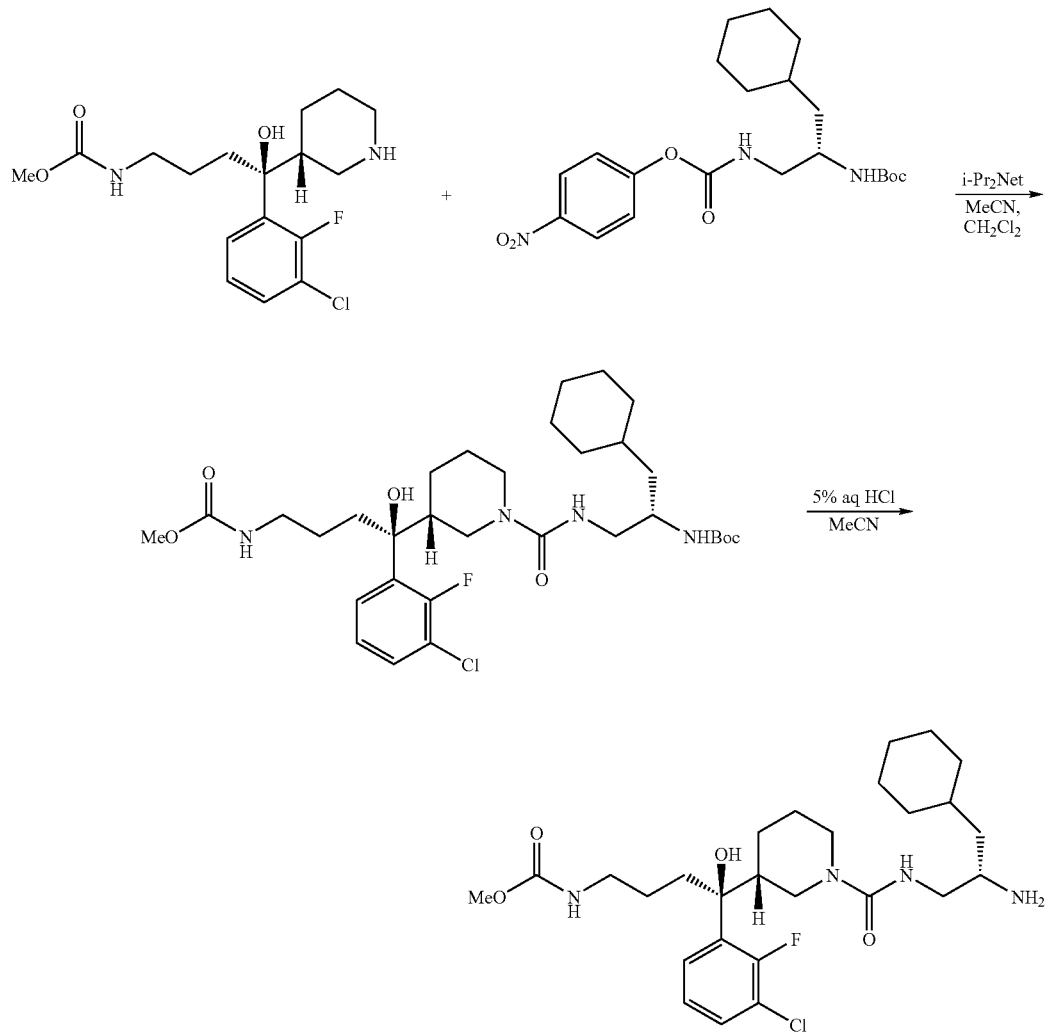

Step 1. Methyl (S)-4-((R)-1-((S)-2-(t-butoxycarbonylamino)-3-cyclohexylpropylcarbamoyl)piperidin-3-yl)-4-(3-chloro-2-fluorophenyl)-4-hydroxybutylcarbamate To a stirred suspension of the HCl salt of methyl (S)-4-(3-chloro-2-fluorophenyl)-4-hydroxy-4-((R)-piperidin-3-yl)butylcarbamate (31.6 mg, 0.08 mmol) and (S)-4-nitrophenyl 2-(t-butoxycarbonylamino)-3-cyclohexylpropylcarbamate (45 mg, 0.105 mmol) in MeCN (1 mL) and CH$_2$Cl$_2$ (1 mL) was added DIEA (80 µL, 0.45 mmol). The mixture was stirred at rt for 3 d, diluted with ether (90 mL), washed with 5% aq HCl (20 mL), IM aq NaOH (20 mL) and brine (20 mL), and dried over MgSO$_4$. Removal of the solvent left a white solid (61 mg) which was applied to a 2-g silica SPE cartridge. The cartridge was eluted sequentially with 0, 25, 50, 75 and 100% EtOAc in hexanes (15 mL of each) to afford five fractions. Fractions 4 and 5 were pooled and concentrated to afford methyl (S)-4-((R)-1-((S)-2-(t-butoxycarbonylamino)-3-cyclohexylpropylcarbamoyl)piperidin-3-yl)-4-(3-chloro-2-fluorophenyl)-4-hydroxybutylcarbamate (35 mg) as an oil.

Step 2. Methyl (S)-4-((R)-1-((S)-2-amino-3-cyclohexylpropylcarbamoyl)piperidin-3-yl)-4-(3-chloro-2-fluorophenyl)-4-hydroxybutylcarbamate Methyl (S)-4-((R)-1-((S)-2-(t-butoxycarbonylamino)-3-cyclohexylpropylcarbamoyl)piperidin-3-yl)-4-(3-chloro-2-fluorophenyl)-4-hydroxybutylcarbamate (35 mg, 0.055 mmol) was dissolved in MeCN (5 mL) and 5% aq HCl (5 mL) was added. The mixture was stirred at rt for 2 d. Solid K$_2$CO$_3$ was added and, after stirring for 1 h, MeCN was recovered on the rotary evaporator. The aqueous residue was extracted with CH$_2$Cl$_2$ (2×50 mL) and the combined organic extracts were washed with brine and dried over Na$_2$SO$_4$. Removal of the solvent left a white solid which was purified by preparative HPLC to afford methyl (S)-4-((R)-1-((S)-2-amino-3-cyclohexylpropylcarbamoyl)piperidin-3-yl)-4-(3-chloro-2-fluorophenyl)-4-hydroxybutylcarbamate as its TFA salt (28 mg).

The following compounds were prepared using procedures analogous to those described above:

| Cpd. No. | Cpd Name |
|---|---|
| I-10a | methyl (4S)-4-((3R)-1-((2S)-2-amino-3-(tetrahydro-2H-pyran-2-yl)propylcarbamoyl)piperidin-3-yl)-4-(3-chloro-2-fluorophenyl)-4-hydroxybutylcarbamate |
| I-19a | methyl (S)-4-((R)-1-((S)-2-amino-3-cyclohexylpropylcarbamoyl)piperidin-3-yl)-4-(3-chloro-2,4-difluorophenyl)-4-hydroxybutylcarbamate |
| I-39a | methyl 2-((R)-((R)-1-((S)-2-amino-3-cyclohexylpropylcarbamoyl)piperidin-3-yl)(3-chloro-2-fluorophenyl)methoxy)ethylcarbamate |

The following compounds were prepared using procedures analogous to those described in Example 4 except 20% TFA/CH$_2$Cl$_2$ (V/V) was used to deprotect a Boc protecting group in Step 2:

| Cpd. No. | Cpd Name |
|---|---|
| I*-28a | methyl 2-((R)-((R)-1-((S)-2-amino-3-((R)-oxepan-3-yl)propylcarbamoyl)piperidin-3-yl)(3-fluorophenyl)methoxy)ethylcarbamate |
| I*-58a | methyl 2-((R)-((R)-1-((S)-2-amino-3-((R)-oxepan-3-yl)propylcarbamoyl)piperidin-3-yl)(5-fluoro-2-methylphenyl)methoxy)ethylcarbamate |
| I*-68a | methyl 2-((R)-((R)-1-((S)-2-amino-3-((R)-oxepan-3-yl)propylcarbamoyl)piperidin-3-yl)(3-chlorophenyl)methoxy)ethylcarbamate |
| I*-73a | methyl 2-((R)-((R)-1-((S)-2-amino-3-((R)-oxepan-3-yl)propylcarbamoyl)piperidin-3-yl)(3,5-difluorophenyl)methoxy)ethylcarbamate |
| I*-109a | methyl 2-((R)-((R)-1-((S)-2-amino-3-((R)-oxepan-3-yl)propylcarbamoyl)piperidin-3-yl)(5-chloro-2-methylphenyl)methoxy)ethylcarbamate |
| I*-122a | methyl 2-((R)-((R)-1-((S)-2-amino-3-((R)-oxepan-3-yl)propylcarbamoyl)piperidin-3-yl)(3-chloro-5-fluorophenyl)methoxy)ethylcarbamate |

The following compounds were prepared using procedures analogous to those described in Example 4 except 20% TFA/CH$_2$Cl$_2$ (V/V) was used to deprotect Teoc protecting group in Step 2:

| Cpd. No. | Cpd Name |
|---|---|
| I*-110a | methyl 2-((R)-(3-chlorophenyl)((R)-1-((S)-2-(methylamino)-3-((R)-oxepan-3-yl)propylcarbamoyl)piperidin-3-yl)methoxy)ethylcarbamate |
| I*-133a | methyl 2-((R)-(5-chloro-2-methylphenyl)((R)-1-((S)-2-(methylamino)-3-((R)-oxepan-3-yl)propylcarbamoyl)piperidin-3-yl)methoxy)ethylcarbamate |
| I*-143a | methyl 2-((R)-(3-chloro-5-fluorophenyl)((R)-1-((S)-2-(methylamino)-3-((R)-oxepan-3-yl)propylcarbamoyl)piperidin-3-yl)methoxy)ethylcarbamate |

The following compound was prepared using procedures analogous to those described in Example 4:
methyl 2-((R)-(3-chlorophenyl)((R)-1-((S)-1-((1r,3S,4R)-3,4-difluorocyclopentyl)-3-(methylamino)propan-2-ylcarbamoyl)piperidin-3-yl)methoxy)ethylcarbamate Example 5

Methyl (S)-4-(3-chloro-2,4-difluorophenyl)-4-((R)-1-((S)-1-cyclohexyl-3-(methylamino)propan-2-ylcarbamoyl)piperidin-3-yl)-4-hydroxybutylcarbamate (I-23a)

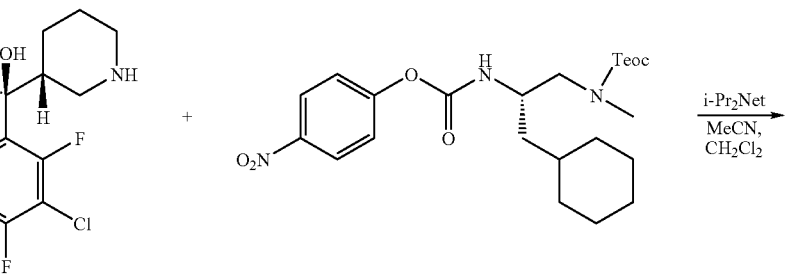

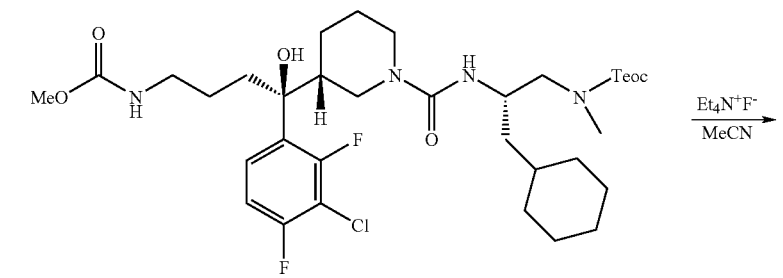

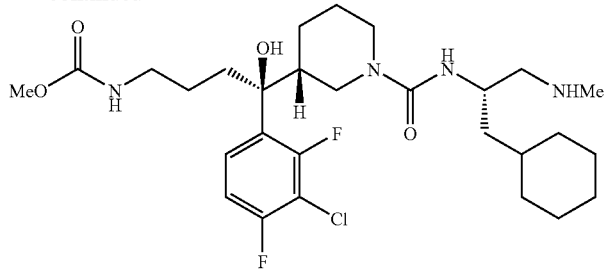

Step 1. Methyl (S)-4-(3-chloro-2,4-difluorophenyl)-4-((R)-1-((S)-1-cyclohexyl-3-(N-methyl-N-(2-(trimethylsilyl)ethoxycarbonyl)amino)propan-2-ylcarbamoyl)piperidin-3-yl)-4-hydroxybutylcarbamate To a stirred solution of methyl (S)-4-(3-chloro-2,4-difluorophenyl)-4-hydroxy-4-((R)-piperidin-3-yl)butylcarbamate (25 mg, 0.066 mmol) and 4-nitrophenyl (S)-3-cyclohexyl-1-((2-(trimethylsilyl)ethylcarbamate)methylamino)propan-2-yl)carbamate (42 mg, 0.088 mmol) in MeCN (1 mL) and $CH_2Cl_2$ (1 mL) was added DIEA (0.06 mL, 0.34 mmol). The mixture was stirred at rt for 3 d, diluted with ether (90 mL), washed with 5% aq HCl (20 mL), 1M aq NaOH (20 mL) and brine (20 mL), and dried over $MgSO_4$. Removal of the solvent left a white solid (61 mg) which was applied to a 2-g silica SPE cartridge. The cartridge was eluted sequentially with 0, 25, 50, 75 and 100% EtOAc in hexanes (15 mL of each) to afford five fractions. Fractions 3, 4 and 5 were pooled and concentrated to afford methyl (S)-4-(3-chloro-2,4-difluorophenyl)-4-((R)-1-((S)-cyclohexyl-3-(N-methyl-N-(2-(trimethylsilyl)ethoxycarbonyl)amino)propan-2-ylcarbamoyl) piperidin-3-yl)-4-hydroxybutylcarbamate (48 mg, quant) as an oil.

Step 2. Methyl (S)-4-(3-chloro-2,4-difluorophenyl)-4-((R)-1-((S)-1-cyclohexyl-3-(methylamino)propan-2-ylcarbamoyl)piperidin-3-yl)-4-hydroxybutylcarbamate To a stirred solution of methyl (S)-4-(3-chloro-2,4-difluorophenyl)-4-((R)-1-((S)-1-cyclohexyl-3-(N-methyl-N-(2-(trimethylsilyl)ethoxycarbonyl)amino)propan-2-ylcarbamoyl)piperidin-3-yl)-4-hydroxybutylcarbamate (48 mg, 0.066 mmol) in MeCN (2 mL) was added $Et_4N^+F^-$ (200 mg, 1.3 mmol). The resulting solution was stirred at rt for 2 d and submitted directly to preparative HPLC to afford the TFA salt of methyl (S)-4-(3-chloro-2,4-difluorophenyl)-4-((R)-1-((S)-1-cyclohexyl-3-(methylamino)propan-2-ylcarbamoyl) piperidin-3-yl)-4-hydroxybutylcarbamate (34 mg, 74%) as a syrup.

The following compounds were prepared using procedures analogous to those described above:

| Cpd. No. | Cpd Name |
|---|---|
| I-18A | methyl (4S)-4-(3-chloro-2-fluorophenyl)-4-hydroxy-4-((3R)-1-(1-(methylamino)-3-(tetrahydro-2H-pyran-4-yl)propan-2-ylcarbamoyl)piperidin-3-yl)butylcarbamate |
| I-30A | methyl 2-((R)-(3-chlorophenyl)((R)-1-((S)-4,4-dimethyl-1-(methylamino)pentan-2-ylcarbamoyl)piperidin-3-yl)methoxy)ethylcarbamate |
| I-32A | methyl 2-((R)-((R)-1-((S)-1-amino-3-cyclohexylpropan-2-ylcarbamoyl)piperidin-3-yl)(3-chlorophenyl)methoxy)ethylcarbamate |
| I-34A | methyl 2-((1R)-((3R)-1-((2S)-1-amino-3-(tetrahydro-2H-pyran-2-yl)propan-2-ylcarbamoyl)piperidin-3-yl)(3-chlorophenyl)methoxy)ethylcarbamate |
| I-38A | methyl 2-((R)-(3-chlorophenyl)((R)-1-((S)-1-(methylamino)-3-(tetrahydro-2H-pyran-4-yl)propan-2-ylcarbamoyl)piperidin-3-yl)methoxy)ethylcarbamate |
| I-38B | methyl 2-((R)-(3-chlorophenyl)((R)-1-((R)-1-methylamino)-3-(tetrahydro-2H-pyran-4-yl)propan-2-ylcarbamoyl)piperidin-3-yl)methoxy)ethylcarbamate |
| I-42A | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate |
| I-46A | methyl 2-((R)-(3-chlorophenyl)((R)-1-((S)-1-(1-fluorocyclohexyl)-3-(methylamino)propan-2-ylcarbamoyl)piperidin-3-yl)methoxy)ethylcarbamate |
| I-47A | methyl 2-((R)-(3-chloro-2-fluorophenyl)((R)-1-((S)-1-(methylamino)-3-(tetrahydro-2H-pyran-4-yl)propan-2-ylcarbamoyl)piperidin-3-yl)methoxy)ethylcarbamate |
| I-47B | methyl 2-((R)-(3-chloro-2-fluorophenyl)((R)-1-((R)-1-(methylamino)-3-(tetrahydro-2H-pyran-4-yl)propan-2-ylcarbamoyl)piperidin-3-yl)methoxy)ethylcarbamate |
| I-52A | methyl 2-((R)-(3-chlorophenyl)((R)-1-((S)-1-(3-noradamantyl)-3-(methylamino)propan-2-ylcarbamoyl)piperidin-3-yl)methoxy)ethylcarbamate |
| I-64A | (3R)-3-((R)-(3-chloro-2-fluorophenyl)(2-(ethylamino)-2-oxoethoxy)methyl)-N-((2S)-1-cyclohexyl-3-(methylamino)propan-2-yl)piperidine-1-carboxamide |
| I-64B | (3R)-3-((3-chloro-2-fluorophenyl)(2-(ethylamino)-2-oxoethoxy)methyl)-N-((2S)-1-cyclohexyl-3-(methylamino)propan-2-yl)piperidine-1-carboxamide |
| I-74A | (R)-3-((S)-1-(3-chlorophenyl)-4-formamido-1-hydroxybutyl)-N-((S)-1-cyclohexyl-3-(methylamino)propan-2-yl)piperidine-1-carboxamide |
| I-76A | (3R)-3-((S)-1-(3-chlorophenyl)-1-hydroxy-6-oxoheptyl)-N-((S)-1-cyclohexyl-3-(methylamino)propan-2-yl)piperidine-1-carboxamide |

The following compounds were prepared using procedures analogous to those described above except that the $Et_4N^+F^-$ used to remove a Teoc group in step 2 were replaced with hydrogenation in the presence of $PdCl_2$ to remove a Cbz protecting group:

| Cpd. No. | Cpd Name |
|---|---|
| I-36A | methyl 2-((R)-((R)-1-((2S,3R)-3-amino-1-cyclohexylbutan-2-ylcarbamoyl)piperidin-3-yl)(3-chlorophenyl)methoxy)ethylcarbamate |

The following compounds were prepared using procedures analogous to those described in Example 5:

| Cpd. No. | Cpd Name |
|---|---|
| I*-81a | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate |
| I*-82a | methyl 2-((R)-(3-chlorophenyl)((R)-1-((2S,3R)-1-cyclohexyl-3-(methylamino)butan-2-ylcarbamoyl)piperidin-3-yl)methoxy)ethylcarbamate |
| I*-103a | methyl 2-((R)-1-(3-chlorophenyl)-1-((R)-1-((S)-1-(methylamino)-3-(tetrahydro-2H-pyran-4-yl)propan-2-ylcarbamoyl)piperidin-3-yl)ethoxy)ethylcarbamate |

| Cpd. No. | Cpd Name |
|---|---|
| I*-151a | methyl 2-((R)-1-(3-chlorophenyl)-1-((3R)-1-((S)-1-(3-noradamantyl)-3-(methylamino)propan-2-ylcarbamoyl)piperidin-3-yl)ethoxy)ethylcarbamate |

The following compounds were prepared using procedures analogous to those described in Example 5 except 20% TFA/CH$_2$Cl$_2$ (V/V) was used to deprotect Boc protecting group in Step 2:

I*-120a—methyl 2-((R)—((R)-1-((S)-1-(4,4-difluorocyclohexyl)-3-(methylamino)propan-2-ylcarbamoyl)piperidin-3-yl)(3-fluorophenyl)methoxy)ethylcarbamate The following compounds were prepared using procedures analogous to those described in Example 5 except H$_2$ and PdCl$_2$ was used to deprotect Cbz protecting group in Step 2:

I*-11a—methyl 2-((R)-(3-chlorophenyl)((R)-1-((3R*,4S*)-4-isobutylpyrrolidin-3-ylcarbamoyl)piperidin-3-yl)methoxy)ethylcarbamate I*-44a—methyl 2-((R)-(3-chlorophenyl)((R)-1-((3S*,4R*)-4-(cyclobutylmethyl)piperidin-3-ylcarbamoyl)piperidin-3-yl)methoxy)ethylcarbamate The following compounds were prepared using procedures analogous to those described in Example 5 except 20% TPA/CH$_2$Cl$_2$ (V/V) was used to deprotect Teoc protecting group in Step 2:

| Cpd. No. | Cpd Name |
|---|---|
| I*-1a | methyl 2-((R)-(3-chlorophenyl)((R)-1-((S)-5-methoxy-1-(methylamino)pentan-2-ylcarbamoyl)piperidin-3-yl(methoxy)ethylcarbamate |
| I*-17a | methyl 2-((R)-(3-fluorophenyl)((R)-1-((S)-5-methoxy-1-(methylamino)pentan-2-ylcarbamoyl)piperidin-3-yl)methoxy)ethylcarbamate |
| I*-22a | methyl (S)-4-((S)-1-((S)-1-cyclohexyl-3-(methylamino)propan-2-ylcarbamoyl)piperidin-3-yl)-4-(3-fluorophenyl)butylcarbamate |
| I*-23a | methyl (R)-4-((S)-1-((S)-1-cyclohexyl-3-(methylamino)propan-2-ylcarbamoyl)piperidin-3-yl)-4-(3-fluorophenyl)butylcarbamate |
| I*-41a | methyl 2-((R)-((R)-1-((S)-1-cyclohexyl-3-(ethylamino)propan-2-ylcarbamoyl)piperidin-3-yl)(3-fluorophenyl)methoxy)ethylcarbamate |
| I*-42a | methyl 2-((R)-(3-fluorophenyl)((R)-1-((R)-1-(methylamino)-3-(1-methylcyclohexyl)propan-2-ylcarbamoyl)piperidin-3-yl)methoxy)ethylcarbamate |
| I*-43a | methyl 2-((R)-(3-fluorophenyl)((R)-1-((S)-1-(methylamino)-3-(1-methylcyclohexyl)propan-2-ylcarbamoyl)piperidin-3-yl)methoxy)ethylcarbamate |
| I*-55a | methyl 2-((R)-(3-fluorophenyl)((R)-1-((S)-1-(methylamino)-3-((R)-oxepan-3-yl)propan-2-ylcarbamoyl)piperidin-3-yl)methoxy)ethylcarbamate |
| I*-59a | methyl 2-((R)-((R)-1-((S)-1-amino-3-cyclohexyl-2-methylpropan-2-ylcarbamoyl)piperidin-3-yl)(3-chlorophenyl)methoxy)ethylcarbamate |
| I*-76a | methyl 2-((R)-(3-fluorophenyl)((R)-1-((S)-1-((R)-1-methyl-6-oxopiperidin-3-yl)-3-(methylamino)propan-2-ylcarbamoyl)piperidin-3-yl)methoxy)ethylcarbamate |
| I*-79a | methyl 2-((R)-(5-fluoro-2-methylphenyl)((R)-1-((S)-1-(methylamino)-3-((R)-oxepan-3-yl)propan-2-ylcarbamoyl)piperidin-3-yl)methoxy)ethylcarbamate |
| I*-83a | methyl 2-((R)-((R)-1-((2S,3R)-3-amino-1-cyclohexylpentan-2-ylcarbamoyl)piperidin-3-yl)(3-chlorophenyl)methoxy)ethylcarbamate |
| I*-86a | methyl 2-((R)-(3-chlorophenyl)((R)-1-((S)-1-(methylamino)-3-(4-methylcyclohexyl)propan-2-ylcarbamoyl)piperidin-3-yl)methoxy)ethylcarbamate |
| I*-88a | methyl 2-((R)-(3-chlorophenyl)((R)-1-((S)-1-cyclohexyl-3-(ethylamino)propan-2-ylcarbamoyl)piperidin-3-yl)methoxy)ethylcarbamate |

| Cpd. No. | Cpd Name |
|---|---|
| I*-89a | methyl 2-((R)-(3-chlorophenyl)((R)-1-((R)-1-(methylamino)-3-(1-methylcyclohexyl)propan-2-ylcarbamoyl)piperidin-3-yl)methoxy)ethylcarbamate |
| I*-90a | methyl 2-((R)-(3-chlorophenyl)((R)-1-((S)-1-(methylamino)-3-(1-methylcyclohexyl)propan-2-ylcarbamoyl)piperidin-3-yl)methoxy)ethylcarbamate |
| I*-94a | methyl 2-((R)-(3,5-difluorophenyl)((R)-1-((R)-1-(methylamino)-3-(1-methylcyclohexyl)propan-2-ylcarbamoyl)piperidin-3-yl)methoxy)ethylcarbamate |
| I*-95a | methyl 2-((R)-(3,5-difluorophenyl)((R)-1-((S)-1-(methylamino)-3-(1-methylcyclohexyl)propan-2-ylcarbamoyl)piperidin-3-yl)methoxy)ethylcarbamate |
| I*-106a | methyl 2-((R)-(3-chlorophenyl)((R)-1-((S)-1-(methylamino)-3-((R)-oxepan-3-yl)propan-2-ylcarbamoyl)piperidin-3-yl)methoxy)ethylcarbamate |
| I*-113a | methyl 2-((R)-(3,5-difluorophenyl)((R)-1-((S)-1-(methylamino)-3-((R)-oxepan-3-yl)propan-2-ylcarbamoyl)piperidin-3-yl)methoxy)ethylcarbamate 1 |
| I*-131a | methyl 2-((R)-(3-chlorophenyl)((R)-1-((S)-1-((R)-1-methyl-6-oxopiperidin-3-yl)-3-(methylamino)propan-2-ylcarbamoyl)piperidin-3-yl)methoxy)ethylcarbamate |
| I*-140a | methyl 2-((R)-(3-chloro-2-fluorophenyl)((R)-1-((S)-1-(methylamino)-3-((R)-oxepan-3-yl)propan-2-ylcarbamoyl)piperidin-3-yl)methoxy)ethylcarbamate |
| I*-141a | methyl 2-((R)-(3-chloro-5-fluorophenyl)((R)-1-((S)-1-(methylamino)-3-((R)-oxepan-3-yl)propan-2-ylcarbamoyl)piperidin-3-yl)methoxy)ethylcarbamate |
| I*-146a | methyl 2-((R)-(3-chlorophenyl)((R)-1-((S)-1-(4,4-difluorocyclohexyl)-3-(methylamino)propan-2-ylcarbamoyl)piperidin-3-yl)methoxy)ethylcarbamate |
| I*-147a | methyl 2-((R)-((R)-1-((S)-1-(4,4-difluorocyclohexyl)-3-(methylamino)propan-2-ylcarbamoyl)piperidin-3-yl)(3,5-difluorophenyl)methoxy)ethylcarbamate |
| I*-153a | methyl 2-((R)-(3-chloro-5-fluorophenyl)((R)-1-((S)-1-(4,4-difluorocyclohexyl)-3-(methylamino)propan-2-ylcarbamoyl)piperidin-3-yl)methoxy)ethylcarbamate |

Example 6

2-((R)-(3-Chlorophenyl)((R)-1-((S)-1-cyclohexyl-3-(methylamino)propan-2-ylcarbamoyl)piperidin-3-yl)methoxy)ethyl carbamate (1-53A)

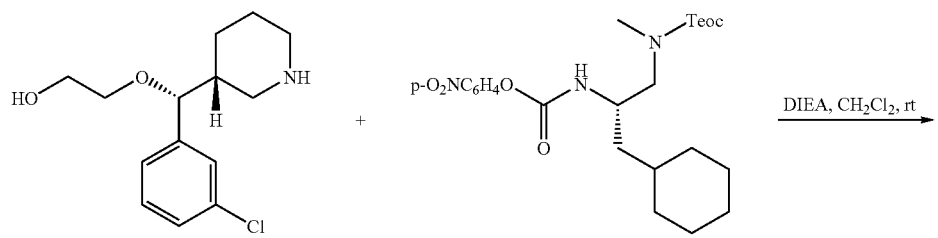

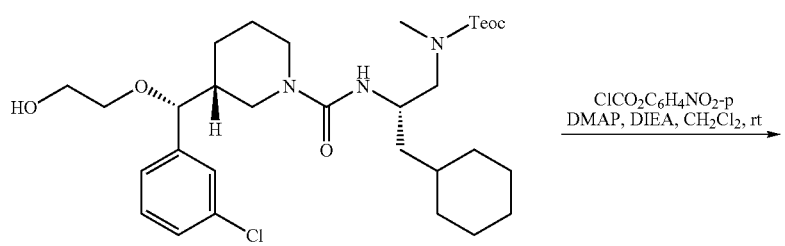

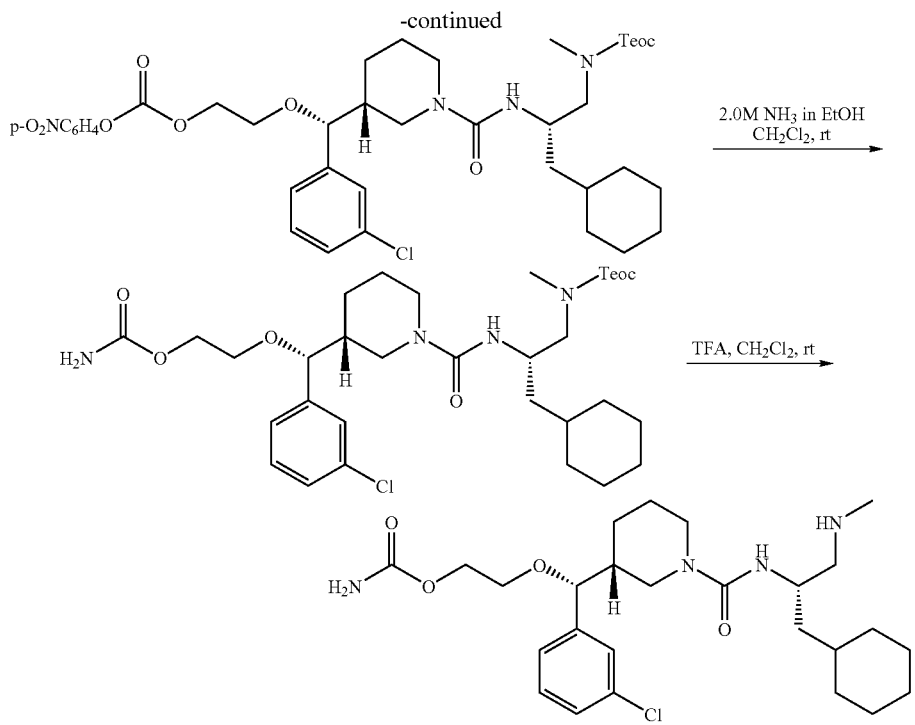

Step 1. 2-(trimethylsilyl)ethyl (S)-2-((R)-3-((R)-(3-chlorophenyl)(2-hydroxyethoxy)methyl)piperidine-1-carboxamido)-3-cyclohexylpropyl(methyl)carbamate A mixture of the HCl salt of 2-((R)-(3-chlorophenyl)((R)-piperidin-3-yl)methoxy)ethanol, (S)-4-nitrophenyl 1-cyclohexyl-3-(2-(trimethylsilyl)ethoxycarbonylmethylamino)propan-2-ylcarbamate (0.3724 g, 0.78 mmol, 1.3 equiv), and DIEA (2 mL, 12 mmol, 20 equiv) in $CH_2Cl_2$ was stirred at rt for 17 h. After the solvents were removed in vacuo, the residue was purified by reversed-phase HPLC (Phenomenex® Luna 5μ C18(2) 100 A, 250×21.20 mm, 5 micron, 70%→90% $CH_3CN/H_2O$, 0.1% $CF_3COOH$ over 8 min and then 90% $CH_3CN/H_2O$, 0.1% $CF_3COOH$ over 7 min, flow rate 25 mL/min) to give 0.1880 g (51% in 3 steps) of 2-(trimethylsilyl)ethyl (S)-2-((R)-3-((R)-(3-chlorophenyl)(2-hydroxyethoxy)methyl)piperidine-1-carboxamido)-3-cyclohexylpropyl(methyl)carbamate. LC-MS (3 min) $t_R$=2.52 min, m/z 612, 610 (MH$^+$).

Step 2. 2-(trimethylsilyl)ethyl (S)-2-((R)-3-((R)-(3-chlorophenyl)(2-((4-nitrophenoxy)carbonyloxy)ethoxy)methyl)piperidine-1-carboxamido)-3-cyclohexylpropyl(methyl)carbamate A mixture of 2-(trimethylsilyl)ethyl (S)-2-((R)-3-((R)-(3-chlorophenyl)(2-hydroxyethoxy)methyl)piperidine-1-carboxamido)-3-cyclohexylpropyl(methyl)carbamate (0.1880 g, 0.3 mmol, 1.0 equiv), DMAP (0.150 g, 1.2 mmol, 4 equiv), DIEA (1 mL, 6 mmol, 20 equiv), and 4-nitrophenyl chloroformate (0.1346 g, 0.67 mmol, 2.2 equiv) in $CH_2Cl_2$ (6 mL) was stirred at rt for 24 h. The reaction mixture was directly used in the next step without further purification. LC-MS (3 min) $t_R$=2.68 min, m/z 777, 775 (MH$^+$).

Step 3. 2-((R)-(3-chlorophenyl)((R)-1-((S)-1-cyclohexyl-3-(2-(trimethylsilyl)ethoxycarbonylmethylamino)propan-2-ylcarbamoyl)piperidin-3-yl)methoxy)ethyl carbamate A solution of 2-(trimethylsilyl)ethyl (S)-2-((R)-3-((R)-(3-chlorophenyl)(2-((4-nitrophenoxy)carbonyloxy)ethoxy)methyl)piperidine-1-carboxamido)-3-cyclohexylpropyl(methyl)carbamate in $CH_2Cl_2$ (1 mL, ca. 0.044 mmol), obtained as described above, and 2.0 M $NH_3$ in EtOH (4 mL) was stirred at rt for 19 h. After the solvents were removed in vacuo, the residue was purified by reversed-phase HPLC (Phenomenex® Luna 5μ C18(2) 100 A, 250×21.20 mm, 5 micron, 70%→90% $CH_3CN/H_2O$, 0.1% $CF_3COOH$ over 8 min and then 90% $CH_3CN/H_2O$, 0.1% $CF_3COOH$ over 6 min, flow rate 25 mL/min) to give of 2-((R)-(3-chlorophenyl)((R)-1-((S)-1-cyclohexyl-3-(2-(trimethylsilyl)ethoxycarbonylmethylamino)propan-2-ylcarbamoyl)piperidin-3-yl)methoxy)ethyl carbamate (0.0250 g, 87%). LC-MS (3 min) $t_R$=2.36 min, m/z 655, 653 (MH$^+$).

Step 4. 2-((R)-(3-chlorophenyl)((R)-1-((S)-1-cyclohexyl-3-(methylamino)propan-2-ylcarbamoyl)piperidin-3-yl)methoxy)ethyl carbamate A mixture of 2-((R)-(3-chlorophenyl)((R)-1-((S)-1-cyclohexyl-3-(2-(trimethylsilyl)ethoxycarbonylmethylamino)propan-2-ylcarbamoyl)piperidin-3-yl)methoxy)ethyl carbamate (0.0250 g, 0.038 mmol) and trifluoroacetic acid (1 mL) in $CH_2Cl_2$ (5 mL) was stirred at rt for 3 h. After the solvents were removed in vacuo, the residue was purified by reversed-phase HPLC (Phenomenex® Luna 5μ C18(2) 100 A, 250×21.20 mm, 5 micron, 10%→90% $CH_3CN/H_2O$, 0.1% $CF_3COOH$ over 13 min, flow rate 25 mL/min) to give 2-((R)-(3-chlorophenyl)((R)-1-((S)-1-cyclohexyl-3-(methylamino)propan-2-ylcarbamoyl)piperidin-3-yl)methoxy)ethyl carbamate as its TFA salt (0.0205 g, 86%). LC-MS (3 min)

$t_R$=1.49 min, m/z 511, 509 (MH$^+$); $^1$H NMR (400 MHz, CD$_3$OD) δ 7.28-7.12 (m, 4H), 4.20 (d, J=13.2 Hz, 1H), 4.11-3.99 (m, 3H), 3.95 (d, J=8.8 Hz, 1H), 3.87 (d, J=13.2 Hz, 1H), 3.40-3.28 (m, 2H), 2.96 (dd, J=12.6, 3.2 Hz, 1H), 2.84 (dd, J=12.6, 10.2 Hz, 1H), 2.73-2.63 (m, 2H), 2.61 (s, 3H), 1.71-0.75 (m, 18H).

The following compounds were prepared using procedures analogous to those described above:

| Cpd. No. | Cpd Name |
|---|---|
| I-54a | 2-((R)-(3-chlorophenyl)((R)-1-((S)-1-cyclohexyl-3-(methylamino)propan-2-ylcarbamoyl)piperidin-3-yl)methoxy)ethyl methylcarbamate |
| I-55a | 2-((R)-(3-chlorophenyl)((R)-1-((S)-1-cyclohexyl-3-(methylamino)propan-2-ylcarbamoyl)piperidin-3-yl)methoxy)ethyl ethylcarbamate |

The following compounds were prepared using procedures analogous to those described above except that (R)-(3-chlorophenyl)((R)-piperidin-3-yl)methanol was used in Step 1:

| Cpd. No. | Cpd Name |
|---|---|
| I-26a | (R)-(3-chlorophenyl)((R)-1-((S)-1-cyclohexyl-3-(methylamino)propan-2-ylcarbamoyl)piperidin-3-yl)methyl carbamate |
| I-27a | (R)-(3-chlorophenyl)((R)-1-((S)-1-cyclohexyl-3-(methylamino)propan-2-ylcarbamoyl)piperidin-3-yl)methyl methylcarbamate |
| I-28a | (R)-(3-chlorophenyl)((R)-1-((S)-1-cyclohexyl-3-(methylamino)propan-2-ylcarbamoyl)piperidin-3-yl)methyl ethylcarbamate |
| I-28b | (S)-(3-chlorophenyl)((R)-1-((S)-1-cyclohexyl-3-(methylamino)propan-2-ylcarbamoyl)piperidin-3-yl)methyl ethylcarbamate |
| I-29b | (R)-(3-chlorophenyl)((R)-1-((S)-1-cyclohexyl-3-(methylamino)propan-2-ylcarbamoyl)piperidin-3-yl)methyl butylcarbamate |
| I-29b | (S)-(3-chlorophenyl)((R)-1-((S)-1-cyclohexyl-3-(methylamino)propan-2-ylcarbamoyl)piperidin-3-yl)methyl butylcarbamate |

Example 7

Methyl (S)-4-acetamido-4-(3-chlorophenyl)-4-((R)-1-((S)-1-cyclohexyl-3-(methylamino)propan-2-ylcarbamoyl)piperidin-3-yl)butylcarbamate (I-24A)

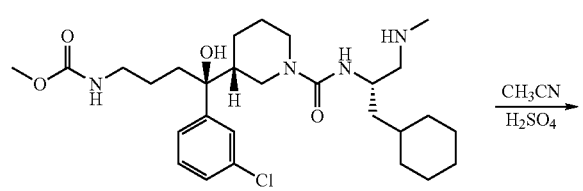

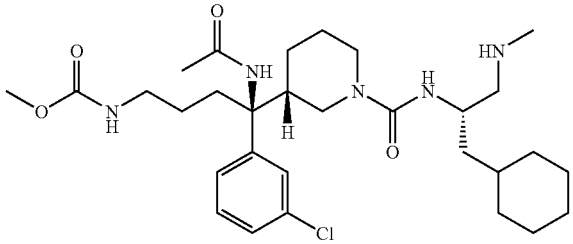

A mixture of the fumarate salt of methyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate (0.0658 g), acetonitrile (8 mL), and conc H$_2$SO$_4$ (20 drops) was stirred at rt for 4 d. The mixture was neutralized with DIEA and the solvent was removed in vacuo. The crude product was purified by reversed-phase HPLC (Phenomenex® Luna 5µ C18(2) 100 A, 250×21.20 mm, 5 micron, 10%→90% CH$_3$CN/H$_2$O, 0.1% CF$_3$COOH over 13 min, flow rate 25 mL/min) to give the TFA salt of methyl (S)-4-acetamido-4-(3-chlorophenyl)-4-((R)-1-((S)-1-cyclohexyl-3-(methylamino)propan-2-ylcarbamoyl)piperidin-3-yl)butylcarbamate (0.0062 g) and the TFA salt of methyl (R)-4-acetamido-4-(3-chlorophenyl)-4-((R)-1-((S)-1-cyclohexyl-3-(methylamino)propan-2-ylcarbamoyl)piperidin-3-yl)butylcarbamate (0.0192 g).

Data for the TFA salt of methyl (S)-4-acetamido-4-(3-chlorophenyl)-4-((R)-1-((S)-1-cyclohexyl-3-(methylamino)propan-2-ylcarbamoyl)piperidin-3-yl)butylcarbamate: LC-MS (3 min) $t_R$=1.40 min, m/z 578, 580 (MH$^+$); $^1$H NMR (400 MHz, CD$_3$OD) δ 7.88 (s, 1H), 7.26-7.14 (m, 4H), 4.11 (d, J=12.0 Hz, 1H), 4.04-3.97 (m, 1H), 3.78 (d, J=12.3 Hz, 1H), 3.52 (s, 3H), 3.03-2.96 (m, 3H), 2.89 (dd, J=12.6, 10.2 Hz, 1H), 2.62 (s, 3H), 1.98 (s, 3H), 2.39-0.73 (m, 24H).

Data for TFA salt of methyl (R)-4-acetamido-4-(3-chlorophenyl)-4-((R)-1-((S)-1-cyclohexyl-3-(methylamino)propan-2-ylcarbamoyl)piperidin-3-yl)butylcarbamate: LC-MS (3 min) $t_R$=1.36 min, m/z 578, 580 (MH$^+$); $^1$H NMR (400 MHz, CD$_3$OD) δ 7.79 (s, 1H), 7.24-7.12 (m, 4H), 4.05-3.99 (m, 2H), 3.83 (d, J=12.6 Hz, 1H), 3.51 (s, 3H), 3.07-2.94 (m, 3H), 2.83 (dd, J=12.6, 10.0 Hz, 1H), 2.60 (s, 3H), 1.93 (s, 3H), 2.37-0.74 (m, 24H).

The following compounds were prepared using procedures analogous to those described above:

| Cpd. No. | Cpd Name |
|---|---|
| I-25a | methyl (S)-4-(3-chlorophenyl)-4-((R)-1-((S)-1-cyclohexyl-3-(methylamino)propan-2-ylcarbamoyl)piperidin-3-yl)-4-propionamidobutylcarbamate |
| I-25b | methyl (R)-4-(3-chlorophenyl)-4-((R)-1-((S)-1-cyclohexyl-3-(methylamino)propan-2-ylcarbamoyl)piperidin-3-yl)-4-propionamidobutylcarbamate |

Example 8

I*-19a—methyl 2-((R)—((R)-1-((1S,2R)-1-cyclo-hexyl-1-hydroxy-3-(methylamino)propan-2-ylcar-bamoyl)piperidin-3-yl)(phenyl)methoxy)ethylcarbamate

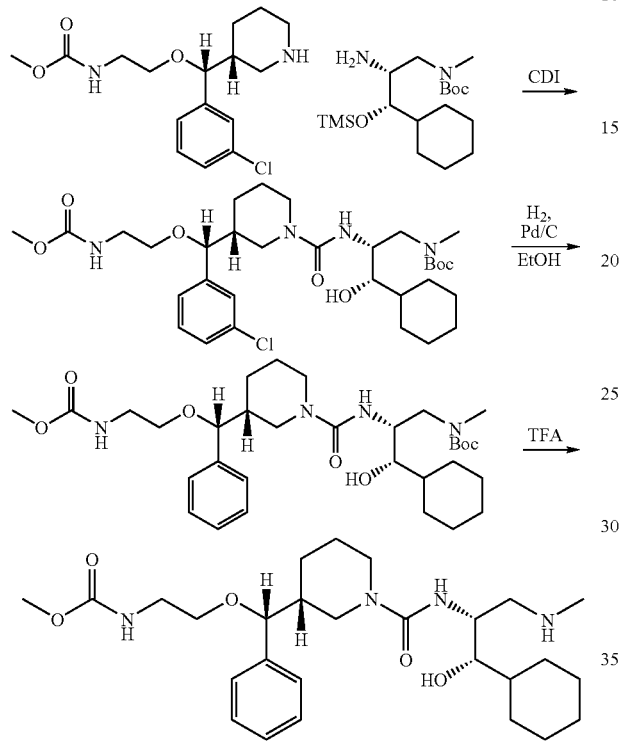

Step 1. methyl 2-((R)-(3-chlorophenyl)((R)-1-((1S,2R)-1-cyclohexyl-1-hydroxy-3-(N-methyl-N-(tert-butoxycarbonyl)amino)propan-2-ylcarbamoyl)piperidin-3-yl)methoxy)ethylcarbamate methyl 2-((R)-(3-chlorophenyl)((R)-1-((1S,2R)-1-cyclohexyl-1-hydroxy-3-(N-methyl-N-(tert-butoxycarbonyl)amino)propan-2-ylcarbamoyl)piperidin-3-yl)methoxy)ethylcarbamate was obtained using procedures analogous to Example 2, Step 1, using methyl 2-((R)-phenyl((R)-piperidin-3-yl)methoxy)ethylcarbamate in Step 1.

Step 2. methyl 2-((R)—((R)-1-((1S,2R)-1-cyclohexyl-1-hydroxy-3-(N-methyl-N-(tert-butoxycarbonyl)amino)propan-2-ylcarbamoyl)piperidin-3-yl)(phenyl)methoxy)ethylcarbamate A solution of methyl 2-((R)-(3-chlorophenyl)((R)-1-((1S,2R)-1-cyclohexyl-1-hydroxy-3-(N-methyl-N-(tert-butoxycarbonyl)amino)propan-2-ylcarbamoyl)piperidin-3-yl)methoxy)ethylcarbamate (5 mg, 0.008 mmol) in EtOH (2 mL) was stirred with 10% Pd/C (5 mg) under $H_2$ overnight. The mixture was filtered thru Celite. After removal of solvent in vacuo, the residue was used directly in the next step.

Step 3. methyl 2-((R)—((R)-1-((1S,2R)-1-cyclohexyl-1-hydroxy-3-(methylamino)propan-2-ylcarbamoyl)piperidin-3-yl)(phenyl)methoxy)ethylcarbamate A solution of methyl 2-((R)—((R)-1-((1S,2R)-1-cyclohexyl-1-hydroxy-3-(N-methyl-N-(tert-butoxycarbonyl)amino)propan-2-ylcarbamoyl)piperidin-3-yl)(phenyl)methoxy)ethylcarbamate in 20% (V/V) $CH_2Cl_2$ (1 mL) was stirred for 1 h. The solution was evaporated under reduced pressure and the residue purified via prep HPLC to afford methyl 2-((R)—((R)-1-((1S,2R)-1-cyclohexyl-1-hydroxy-3-(methylamino)propan-2-ylcarbamoyl)piperidin-3-yl)(phenyl)methoxy)ethylcarbamate (1.01 mg).

Example 9

I*-38a—methyl 2-((R)—((R)-1-((R)-2-amino-3-phenoxypropylcarbamoyl)piperidin-3-yl)(3-chlorophenyl)methoxy)ethylcarbamate

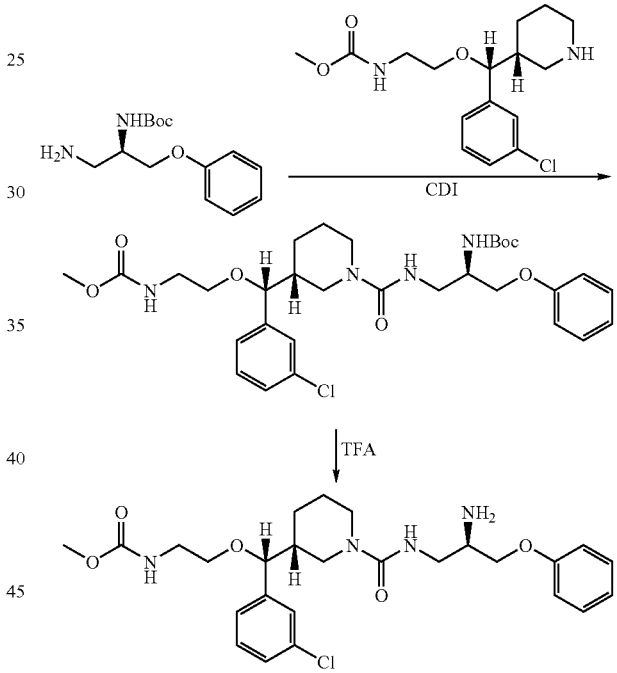

Step 1. methyl 2-((R)—((R)-1-((R)-2-(N-tertbutoxycarbonyl)amino-3-phenoxypropylcarbamoyl)piperidin-3-yl)(3-chlorophenyl)methoxy)ethylcarbamate DIEA (66 mg, 0.52 mmol) was added to a solution of (R)-tert-butyl 1-amino-3-phenoxypropan-2-ylcarbamate (68.7 mg, 0.26 mmol) in 2 mL of anhydrous dichloromethane at 0° C. After the mixture stirred for 1.5 h, a solution of methyl 2-((R)-(3-chlorophenyl)((R)-piperidin-3-yl)methoxy)ethylcarbamate (84 mg, 0.26 mol) in 2 mL of anhydrous dichloromethane was added. The reaction mixture was stirred overnight. The reaction mixture concentrated in vacuo to remove the solvent, and the residue was purified by preparative TLC to get crude methyl 2-((R)—((R)-1-((R)-2-(N-tertbutoxycarbonyl)amino-3-phenoxypropylcarbamoyl)piperidin-3-yl)(3-chlorophenyl)methoxy)ethylcarbamate (152 mg), which was used in the next step without further purification.

Step 2. methyl 2-((R)—((R)-1-((R)-2-amino-3-phenoxypropylcarbamoyl)piperidin-3-yl)(3-chlorophenyl)methoxy)ethylcarbamate 20% TFA solution in CH$_2$Cl$_2$ (2 mL) was added to methyl 2-((R)—((R)-1-((R)-2-(N-tertbutoxycarbonyl)amino-3-phenoxypropylcarbamoyl)piperidin-3-yl)(3-chlorophenyl)methoxy)ethylcarbamate (150 mg, 0.24 mmol) at 0° C. The reaction was stirred for 1 h and concentrated in vacuo. The residue was purified by preparative HPLC to get methyl 2-((R)—((R)-1-((R)-2-amino-3-phenoxypropylcarbamoyl)piperidin-3-yl)(3-chlorophenyl)methoxy)ethylcarbamate (70 mg, 56%).

The following compounds were prepared using procedures analogous to those described above except hydrogen gas was used.

I*-35A—methyl 2-((R)—((R)-1-((S)-2-amino-5-methoxy-4,4-dimethylpentylcarbamoyl)piperidin-3-yl)(3-chlorophenyl)methoxy)ethylcarbamate I*-14a—methyl 2-((R)—((R)-1-((S)-2-amino-5-methoxy-4,4-dimethylpentylcarbamoyl)piperidin-3-yl)(3-fluorophenyl)methoxy)ethylcarbamate

Example 10

I*-8a—methyl 2-((R)-(3-chlorophenyl)((R)-1-((S)-5,5-dimethyl-1-(methylamino)hexan-9-ylcarbamoyl)piperidin-3-yl)methoxy)ethylcarbamate

Step 1. (S)-prop-1-en-2-yl 5,5-dimethyl-1-(N-methyl-N-(trimethylsilylethoxycarbonyl)amino)hexan-2-ylcarbamate (S)-2-(trimethylsilyl)ethyl 2-amino-5,5-dimethylhexyl(methyl)carbamate (34 mg, 0.113 mmol, 1.0 equiv) and K$_2$CO$_3$ (50 mg, 0.362 mmol, 3.0 equiv) were added CH$_2$Cl$_2$ and the solution cooled to 0° C. Isopropenylchloroformate (41 mg, 0.339 mmol, 3.0 equiv) was added and the mixture warmed to ambient temperature and stirred for 3 h. The solution was filtered, evaporated and residual solvent removed in vacuo to afford (1-prop-1-en-2-yl 5,5-dimethyl-1-(N-methyl-N-(trimethylsilylethoxycarbonyl)amino)hexan-2-ylcarbamate and used without further purification.

Step 2. methyl 2-((R)-(3-chlorophenyl)((R)-1-((S)-5,5-dimethyl-1-(N-methyl-N-(2-trimethylsilylethoxycarbonyl)amino)hexan-2-ylcarbamoyl)piperidin-3-yl)methoxy)ethylcarbamate The resulting (S)-prop-1-en-2-yl 5,5-dimethyl-1-(N-methyl-N-(2-trimethylsilylethoxycarbonyl)amino)hexan-2-ylcarbamate was dissolved in THF (5 mL) and methyl 2-((R)-(3-chlorophenyl)((R)-piperidin-3-yl)methoxy)ethylcarbamate (40 mg, 0.1227 mmol, 1.1 equiv) added and the mixture heated to 50° C. overnight. After completion of the reaction, the solution was washed with 0.5 M HCl, brine,

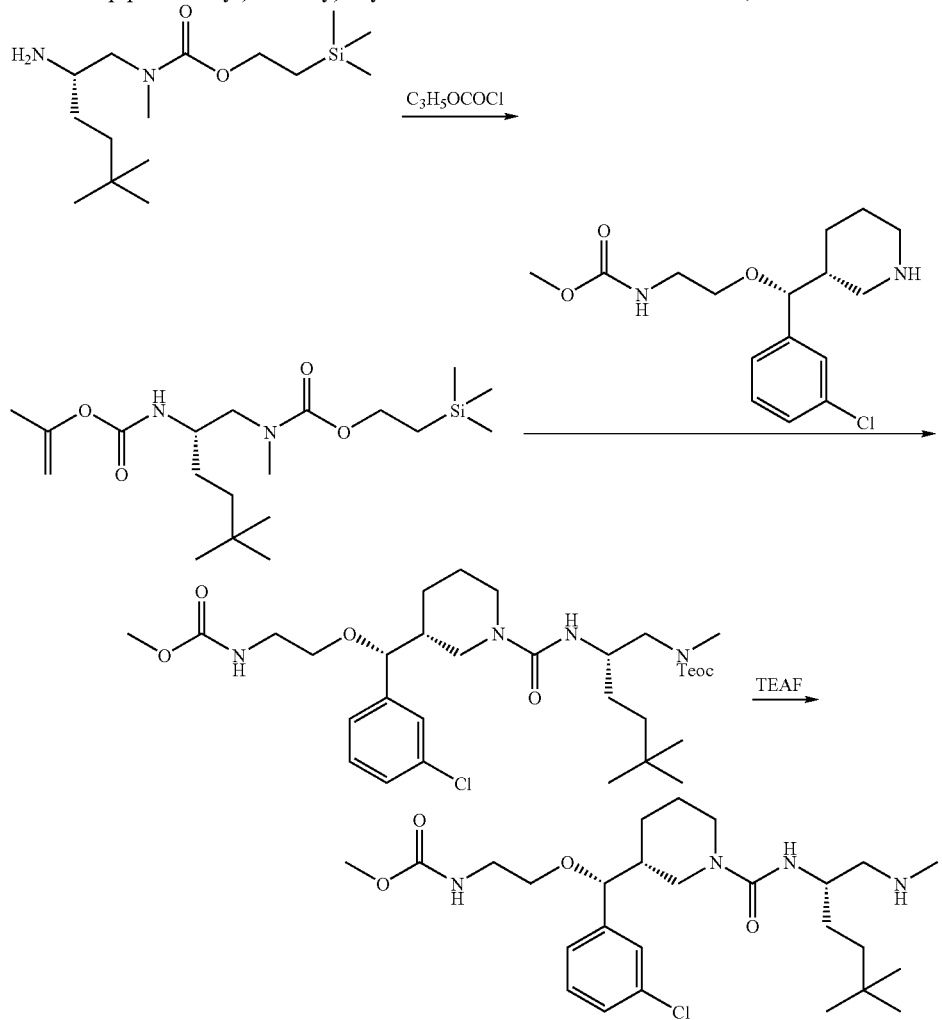

then dried over Na$_2$SO$_4$, filtered, and evaporated to afford crude methyl 2-((R)-(3-chlorophenyl)((R)-1-((S)-5,5-dimethyl-1-(N-methyl-N-(2-trimethylsilylethoxycarbonyl)amino)hexan-2-ylcarbamoyl)piperidin-3-yl)methoxy)ethylcarbamate which was taken directly to the next step.

Step 3. methyl 2-((R)-(3-chlorophenyl)((R)-1-((S-5,5-dimethyl-1-(methylamino)hexan-2-ylcarbamoyl)piperidin-3-yl)methoxy)ethylcarbamate Methyl 2-((R)-(3-chlorophenyl)((R)-1-((S)-5,5-dimethyl-1-(N-methyl-N-(2-trimethylsilylethoxycarbonyl)amino)hexan-2-ylcarbamoyl)piperidin-3-yl)methoxy)ethylcarbamate was dissolved in CH$_3$CN and treated with 75 mg (0.504 mmol, 4.5 equiv) of TEAF and the mixture heated to 55° C. for 3 h. The solution was evaporated and purified by prep HPLC to afford methyl 2-((R)-(3-chlorophenyl)((R)-1-((S)-5,5-dimethyl-1-(methylamino)hexan-2-ylcarbamoyl)piperidin-3-yl)methoxy)ethylcarbamate.

Example 11

I*-130a—methyl 2-((R)-(3-chlorophenyl)((R)-1-((2S,3R)-1-cyclohexyl-3-(methylamino)pentan-2-ylcarbamoyl)piperidin-3-yl)methoxy)ethylcarbamate Step 1. methyl 2-((R)-(3-chlorophenyl)((R)-1-((2S,3R)-1-cyclohexyl-3-(methyl((2-(trimethylsilyl)ethoxy)carbonyl)amino)pentan-2-ylcarbamoyl)piperidin-3-yl)methoxy)ethylcarbamate To a solution of 4-nitrophenolchloroformate (14 mg, 0.068 mmol) and 2-(trimethylsilyl)ethyl (2S,3R)-2-amino-1-cyclohexylpentan-3-yl(methyl)carbamate (23 mg, 0.068 mmol) in anhydrous DCM was added TEA (12 µL, 0.88 mmol). The resulting solution was stirred at room temperature for 5 min. A solution of methyl 2-((R)-(3-chlorophenyl)((R)-piperidin-3-yl)methoxy)ethylcarbamate (26 mg, 0.82 mmol) in DCM (2 mL) was added, followed by TEA (0.5 mL), then stirred for another 30 min. The solvent was removed in vacuo, the slurry was purified through preparative HPLC to afford methyl 2-((R)-(3-chlorophenyl)((R)-1-((2S,3R)-1-cyclohexyl-3-(methyl((2-(trimethylsilyl)ethoxy)carbonyl)amino)pentan-2-ylcarbamoyl)piperidin-3-yl)methoxy)ethylcarbamate (17 mg). MS ESI +ve m/z 695 (M+H).

Step 2. methyl 2-((R)-(3-chlorophenyl)((R)-1-((2S,3R)-1-cyclohexyl-3-(methylamino)pentan-2-ylcarbamoyl)piperidin-3-yl)methoxy)ethylcarbamate Methyl 2-((R)-(3-chlorophenyl)((R)-1-((2S,3R)-1-cyclohexyl-3-(methyl((2-(trimethylsilyl)ethoxy)carbonyl)amino)

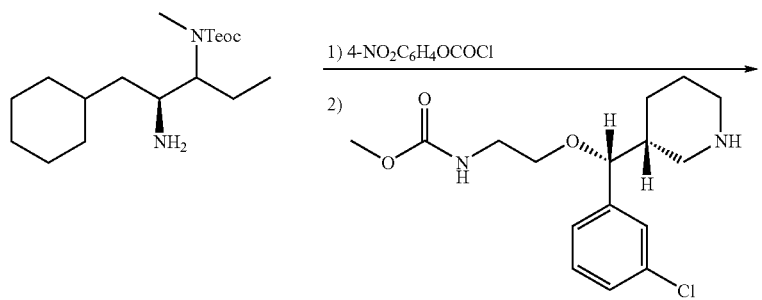

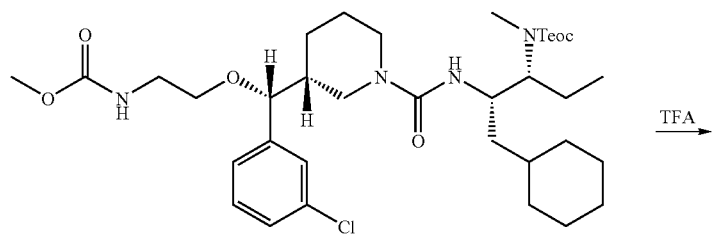

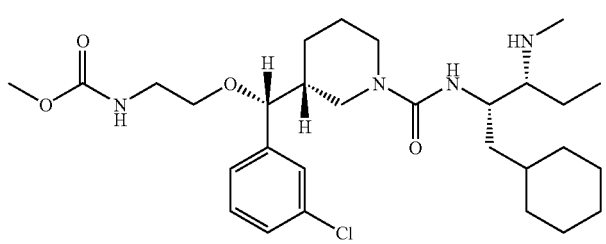

pentan-2-ylcarbamoyl)piperidin-3-yl)methoxy)ethylcarbamate (17 mg) was dissolved in DCM/TFA (4/1 mL) and stirred for 30 min. After concentrated, the slurry was purified through preparative HPLC to afford methyl 2-((R)-(3-chlorophenyl)((R)-1-((2S,3R)-1-cyclohexyl-3-(methylamino)pentan-2-ylcarbamoyl)piperidin-3-yl)methoxy)ethylcarbamate TFA salt (11.9 mg).

Example 12

I*-114a—methyl 2-((R)—((R)-1-((S)-1-cyclohexyl-3-(methylamino)propan-2-ylcarbamoyl)piperidin-3-yl)(3,5-difluoro-2-hydroxyphenyl)methoxy)ethylcarbamate

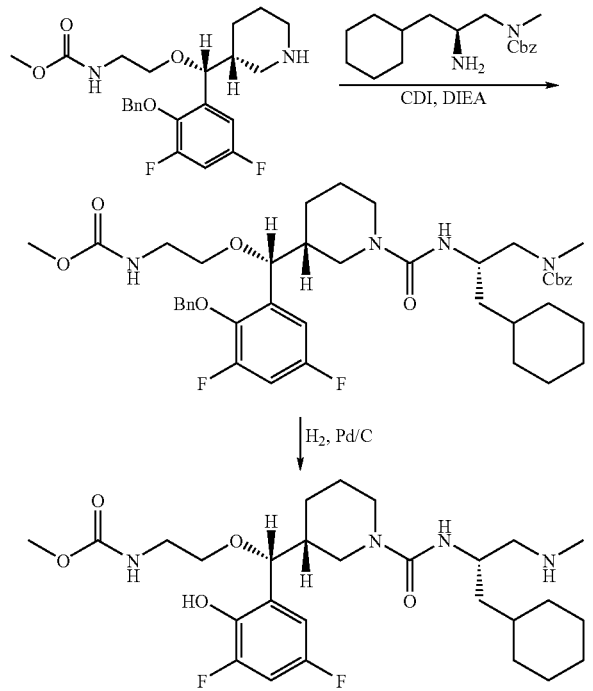

Step 1. methyl 2-((R)—((R)-1-((S)-1-cyclohexyl-3-(N-methyl-N-(tert-butoxycarbonyl)amino)propan-2-ylcarbamoyl)piperidin-3-yl)(3,5-difluoro-2-hydroxyphenyl)methoxy)ethylcarbamate Methyl 2-((R)—((R)-1-((S)-1-cyclohexyl-3-(N-methyl-N-(tert-butoxycarbonyl)amino)propan-2-ylcarbamoyl)piperidin-3-yl)(3,5-difluoro-2-hydroxyphenyl)methoxy)ethylcarbamate was obtained following procedures analogous to Example 3, Step 1, using methyl 2-((R)-(2-(benzyloxy)-3,5-difluorophenyl)((R)-piperidin-3-yl)methoxy)ethylcarbamate and (S)-benzyl 2-amino-3-cyclohexylpropyl(methyl)carbamate in Step 1.

Step 2. methyl 2-((R)—((R)-1-((S)-1-cyclohexyl-3-(methylamino)propan-2-ylcarbamoyl)piperidin-3-yl)(3,5-difluoro-2-hydroxyphenyl)methoxy)ethylcarbamate methyl 2-((R)—((R)-1-((S)-1-cyclohexyl-3-(N-methyl-N-(tert-butoxycarbonyl)amino)propan-2-ylcarbamoyl)piperidin-3-yl)(3,5-difluoro-2-hydroxyphenyl)methoxy)ethylcarbamate (100 mg, 0.131 mmol) was dissolved in MeOH (1 mL) and Pd/C (20 mg) was added to it. The reaction mixture was stirred in 30 psi at room temperature for 2 h. The suspension was filtered and the filtrate was concentrated in vacuo. The residue was purified by preparative HPLC to afford methyl 2-((R)—((R)-1-((S)-1-cyclohexyl-3-(methylamino)propan-2-ylcarbamoyl)piperidin-3-yl)(3,5-difluoro-2-hydroxyphenyl)methoxy)ethylcarbamate (20 mg, 28%).

Example 13

I*-2a—methyl 2-((R)—((R)-1-((±)-1-cyclohexyl-3-(methylamino)propan-2-ylcarbamoyl)piperidin-3-yl)(phenyl)methoxy)ethylcarbamate

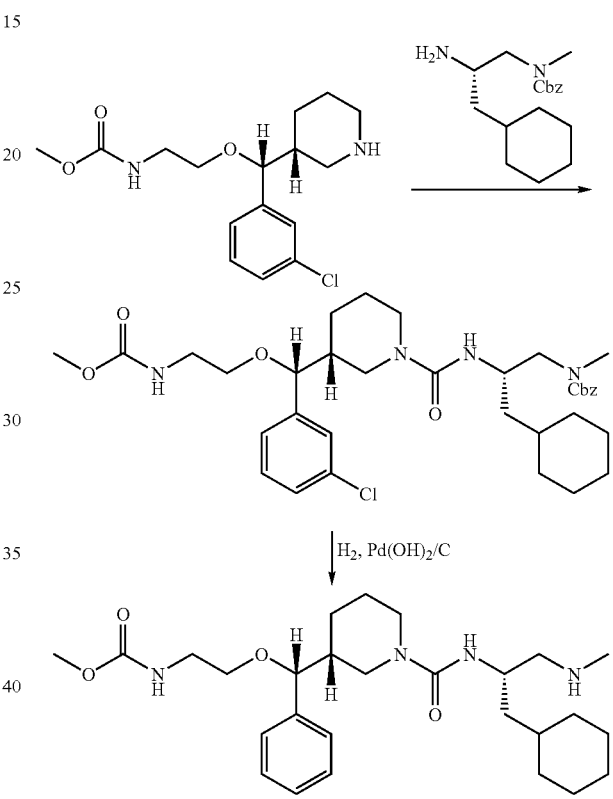

Step 1. methyl 2-((R)—((R)-1-((S)-1-cyclohexyl-3-(N-methyl-N-(benzyloxycarbonyl)amino)propan-2-ylcarbamoyl)piperidin-3-yl)(phenyl)methoxy)ethylcarbamate methyl 2-((R)—((R)-1-((S)-1-cyclohexyl-3-(N-methyl-N-(benzyloxycarbonyl)amino)propan-2-ylcarbamoyl)piperidin-3-yl)(phenyl)methoxy)ethylcarbamate was obtained by using procedures analogous to Example 3, Step 1, methyl 2-((R)-(3-chlorophenyl)((R)-piperidin-3-yl)methoxy)ethylcarbamate and (S)-benzyl 2-amino-3-cyclohexylpropyl(methyl)carbamate in Step 1.

Step 2. methyl 2-((R)—((R)-1-((S)-1-cyclohexyl-3-(methylamino)propan-2-ylcarbamoyl)piperidin-3-yl)(phenyl)methoxy)ethylcarbamate A 100 mL flask was charged with methyl 2-((R)—((R)-1-((S)-1-cyclohexyl-3-(N-methyl-N-(benzyloxycarbonyl)amino)propan-2-ylcarbamoyl)piperidin-3-yl)(phenyl)methoxy)ethylcarbamate (230 mg, 0.35 mmol) and Pd(OH)$_2$ (45 mg) dissolved in MeOH (35 mL) under H$_2$ and stirred for 1 hr. After completion of the reaction, the mixture was filtered. The solution was evaporated to give the crude product (120 mg), which was purified by preparative HPLC to obtain the target molecule (50.2 mg, 29%).

Example 14

I*-105a—methyl 2-((R)-(3-chlorophenyl)((R)-1-((S)-1-((1R,2S)-2-hydroxycyclohexyl)-3-(methylamino)propan-2-ylcarbamoyl)piperidin-3-yl)methoxy)ethylcarbamate

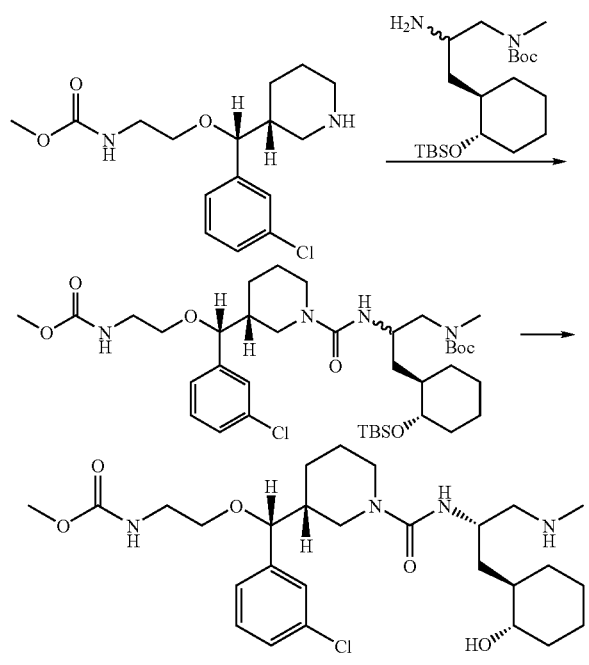

Step 1. methyl 2-((R)-(3-chlorophenyl)((R) 1-(1-((1R*,2S*)-2-hydroxycyclohexyl)-3-(N-methyl-N-(tert-butoxycarbonyl)amino)propan-2-ylcarbamoyl) piperidin-3-yl)methoxy)ethylcarbamate Methyl 2-((R)-(3-chlorophenyl)((R)-1-(1-((1R*,2S*)-2-hydroxycyclohexyl)-3-(N-methyl-N-(tert-butoxycarbonyl) amino)propan-2-ylcarbamoyl)piperidin-3-yl)methoxy)ethylcarbamate was obtained following procedures analogous to Example 3, Step 1, using methyl 2-((R)-(3-chlorophenyl) ((R)-piperidin-3-yl)methoxy)ethylcarbamate and tert-butyl 2-amino-3-((1R,2S)-2-(tert-butyldimethylsilyloxy)cyclohexyl)propyl(methyl)carbamate in Step 1.

Step 2. methyl 2-((R)-(3-chlorophenyl)((R)-1-((S)-1-((1R*,2S*)-2-hydroxycyclohexyl)-3-(methylamino) propan-2-ylcarbamoyl)piperidin-3-yl)methoxy)ethylcarbamate methyl 2-((R)-(3-chlorophenyl)((R)-1-(1-((1R*,2S*)-2-hydroxycyclohexyl)-3-yl)methoxy)ethylcarbamate (30 mg, 0.04 mmol) was dissolved in a solution of HCL/CH$_3$OH (3 mL, 2 M). The reaction mixture was stirred at room temperature for 1 h. After the reaction was completed the product was concentrated in vacuo and purified via preparative HPLC to afford the desired product methyl 2-((R)-(3-chlorophenyl) ((R)-1-((S)-1-((1R*,2S*)-2-hydroxycyclohexyl)-3-(methylamino)propan-2-ylcarbamoyl)piperidin-3-yl)methoxy)ethylcarbamate (3 mg, 14%) and side product I*-104a—methyl 2-((R)-(3-chlorophenyl)((R)-1-((R)-1-((1R*,2S*)-2-hydroxycyclohexyl)-3-(methylamino)propan-2-ylcarbamoyl) piperidin-3-yl)methoxy)ethylcarbamate (4.5 mg, 21%).

Example 15

I*-127a—methyl 2-((R)-(3-chlorophenyl)((R)-1-(N'-cyano-N—((S)-1-cyclohexyl-3-(methylamino)propan-2-yl)carbamimidoyl)piperidin-3-yl)methoxy) ethylcarbamate

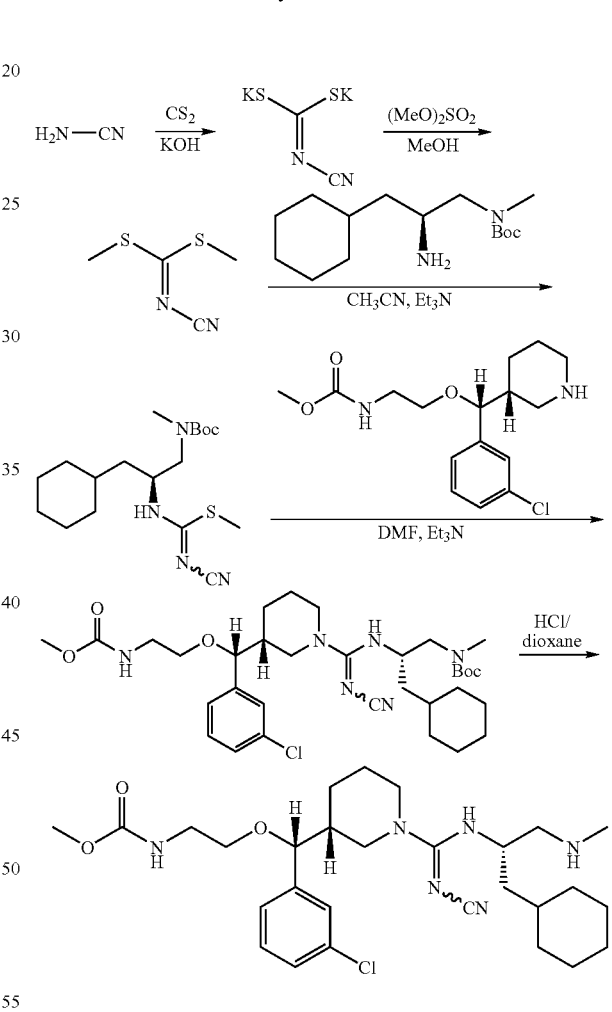

Step 1. Potassium Cyanocarbonimidodithioate

To a mixture of amine cyanamide (21 g, 0.5 mol) and carbon disulfide (58.5 g, 46 mL, 0.77 mol) in anhydrous EtOH (62.5 mL) was added dropwise a solution of potassium hydroxide (56.2 g, 1 mol) in EtOH (210 mL) at −2-0° C. The mixture was kept at the same temperature for 3 hours. The precipitate was then filtered, washed with cold EtOH, and dried to afford potassium cyanocarbonimidodithioate (68 g, 70%).

Step 2. Dimethyl Cyanocarbonimidodithioate

To a mixture of potassium cyanocarbonimidodithioate (19.4 g, 0.1 mmol) in 100 mL of methanol and 150 mL of water was added dropwise dimethyl sulfate (15.1 g, 0.12 mol). The mixture was left to stand overnight at rt. The precipitate was separated and recrystallized from IPA-isopropyether to give dimethyl cyanocarbonimidodithioate (11 g, 75%).

Step 3. (S)-tert-butyl 2-((cyanoimino)(methylthio) methylamino)-3-cyclohexylpropyl(methyl)carbamate To a solution of (S)-tert-butyl 2-amino-3-cyclohexylpropyl (methyl)carbamate (1.08 g, 4 mmol) in CH$_3$CN (15 mL) and Et$_3$N (3 mL) was added dimethyl cyanocarbonimidodithioate (642 mg, 4.4 mmol). The mixture was heated to reflux for 4 h. The reaction mixture was concentrated to give the residue, which was purified by column to give (S)-tert-butyl 2-((cyanoimino)(methylthio)methylamino)-3-cyclohexylpropyl (methyl)carbamate (450 mg, 31%).

Step 4. methyl 2-((R)-(3-chlorophenyl)((R)-1-(N'-cyano-N—((S)-1-cyclohexyl-3-(N-met yl-N-(tert-butoxycarbonyl)amino)propan-2-yl)carbamimidoyl) piperidin-3-yl)methoxy)ethylcarbamate To a solution of (S)-tert-butyl 2-((cyanoimino)(methylthio)methylamino)-3-cyclohexylpropyl(methyl)carbamate (200 mg, 0.543 mmol) in DMF (8 mL) and Et$_3$N (0.5 mL) was added methyl 2-((R)-(3-chlorophenyl)((R)-piperidin-3-yl) methoxy)ethylcarbamate (178 mg, 0.543 mmol). The mixture was heated at 100-110° C. for 48 h. The reaction mixture was diluted with ethyl acetate (100 mL), washed with water (30 mL×4), dried over Na$_2$SO$_4$ and concentrated to give the residue, which was purified by column to give methyl 2-((R)-(3-chlorophenyl)((R)-1-(N'-cyano-N—((S)-1-cyclohexyl-3-(N-methyl-N-(tert-butoxycarbonyl)amino)propan-2-yl)carbamimidoyl)piperidin-3-yl)methoxy)ethylcarbamate (8 mg, 2%).

Step 5. methyl 2-((R)-(3-chlorophenyl)((R)-1-(N'-cyano-N—((S)-1-cyclohexyl-3-(methylamino)propan-2-yl)carbamimidoyl)piperidin-3-yl)methoxy) ethylcarbamate The methyl 2-((R)-(3-chlorophenyl)((R)-1-(N'-cyano-N—((S)-1-cyclohexyl-3-(N-methyl-N-(tert-butoxycarbonyl)amino)propan-2-yl)carbamimidoyl)piperidin-3-yl) methoxy)ethylcarbamate (8 mg, 0.0124 mmol) was dissolved in a solution of 4 N HCl/dioxane (5 mL). The reaction mixture was stirred at rt for 1 h and then concentrated in vacuo. The residue was purified by preparative HPLC to afford the product (4 mg, 59%).

Example 16

I*-11a—methyl 2-((R)-(3-chlorophenyl)((R)-1-((S)-1-cyclohexyl-3-(methylamino)propan-2-ylcarbamothioyl)piperidin-3-yl)methoxy)ethylcarbamate

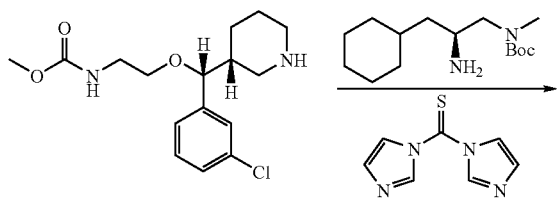

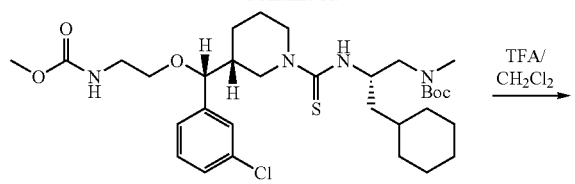

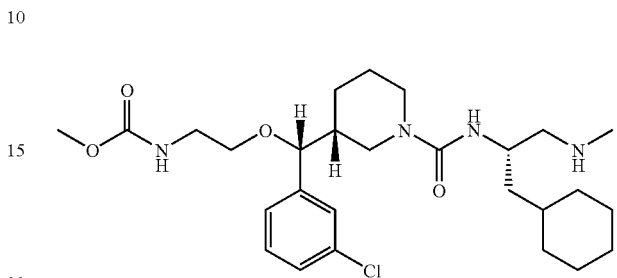

Step 1. methyl 2-((R)-(3-chlorophenyl)((R)-1-((S)-1-cyclohexyl-3-(N-methyl-N-(tert-butoxycarbonyl) amino)propan-2-ylcarbamothioyl)piperidin-3-yl) methoxy)ethylcarbamate To a solution of (S)-tert-butyl 2-amino-3-cyclohexylpropyl (methyl)carbamate (326 mg, 1 mmol), DIEA (258 mg, 2 mmol) and methyl 2-((R)-(3-chlorophenyl)((R)-piperidin-3-yl)methoxy)ethylcarbamate (270 mg, 1 mmol) in ethyl acetate (6 mL) was added dropwise a solution of di-imidazol-1-yl-methanethione (194 mg, 1 mmol) in ethyl acetate (4 mL) at 0-5° C. After addition, the mixture was allowed to warm to room temperature for 3-4 h, the mixture was washed with water (20 mL) and brine (20 ml), the organic layer was dried over Na$_2$SO$_4$, filtered and concentrated in vacuo to give the residue, which was purified by preparative TLC to afford methyl 2-((R)-(3-chlorophenyl)((R)-1-((S)-1-cyclohexyl-3-(N-methyl-N-(tert-butoxycarbonyl)amino)propan-2-ylcarbamothioyl)piperidin-3-yl)methoxy)ethylcarbamate. MS ESI +ve m/z 638 (M+H).

Step 2. methyl 2-((R)-(3-chlorophenyl)((R)-1-((S)-1-cyclohexyl-3-(methylamino)propan-2-ylcarbamothioyl)piperidin-3-yl)methoxy)ethylcarbamate methyl 2-((R)-(3-chlorophenyl)((R)-1-((S)-1-cyclohexyl-3-(N-methyl-N-(tert-butoxycarbonyl)amino)propan-2-ylcarbamothioyl)piperidin-3-yl)methoxy)ethylcarbamate (640 mg, 0.1 mmol) was dissolved in a solution of 20% (V/V) TFA/CH$_2$Cl$_2$ (5 mL). The reaction mixture was stirred at room temperature for 1 h, a solution of saturated sodium bicarbonate was added dropwise to adjust the pH to 7-8. The resulting mixture was extracted with CH$_2$Cl$_2$ (3×15 mL), washed with brine, dried over Na$_2$SO$_4$, concentrated in vacuo. The residue was purified by preparative HPLC to afford methyl 2-((R)-(3-chlorophenyl)((R)-1-((S)-1-cyclohexyl-3-(methylamino)propan-2-ylcarbamothioyl)piperidin-3-yl)methoxy)ethylcarbamate (10 mg, 19%).

Example 17

I*-10a—methyl 2-((S)-cyclohexyl((R)-1-((S)-1-cyclohexyl-3-(methylamino)propan-2-ylcarbamoyl)piperidin-3-yl)methoxy)ethylcarbamate

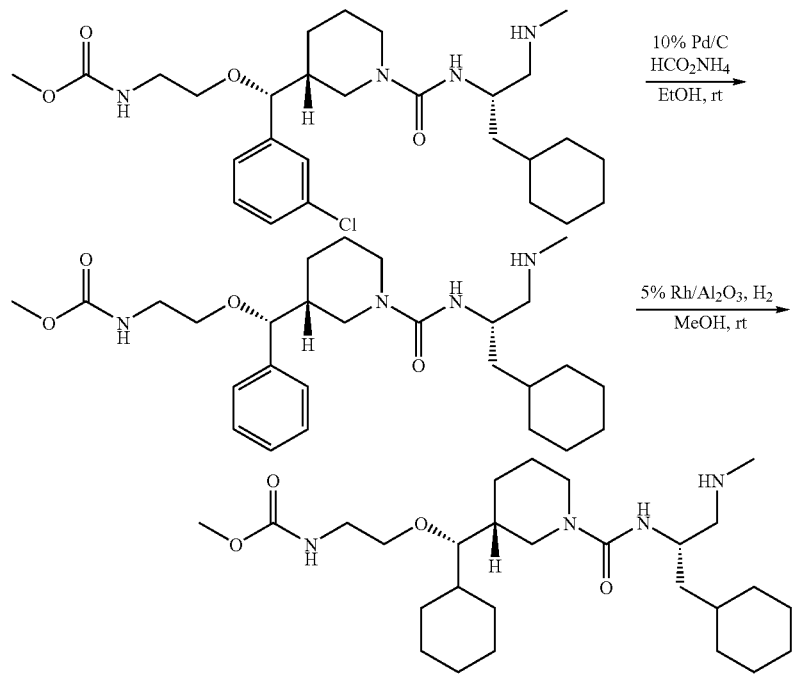

Step 1. methyl 2-((R)—((R)-1-((S)-1-cyclohexyl-3-(methylamino)propan-2-ylcarbamoyl)piperidin-3-yl)(phenyl)methoxy)ethylcarbamate A mixture of fumarate salt (0.120 g) of methyl 2-((R)-(3-chlorophenyl)((R)-1-((S)-1-cyclohexyl-3-(methylamino)propan-2-ylcarbamoyl)piperidin-3-yl)methoxy)ethylcarbamate, $HCO_2NH_4$ (1.200 g), and 10% Pd/C (0.150 g) in MeOH was stirred at rt for 3 d. The mixture was filtered off precipitates through Celite® 545 and washed with MeOH. After the solvent was evaporated under reduced pressure, the crude methyl 2-((R)—((R)-1-((S)-1-cyclohexyl-3-(methylamino)propan-2-ylcarbamoyl)piperidin-3-yl)(phenyl)methoxy)ethylcarbamate was directly used in the next step without further purification. MS ESI +ve m/z 489 (M+H).

Step 2. methyl 2-((S)-cyclohexyl((R)-1-((S)-1-cyclohexyl-3-(methylamino)propan-2-ylcarbamoyl)piperidin-3-yl)methoxy)ethylcarbamate A 250 mL Parr shaker vessel was charged with methyl 2-((R)—((R)- 1-((S)-1-cyclohexyl-3-(methylamino)propan-2-ylcarbamoyl)piperidin-3-yl)(phenyl)methoxy)ethylcarbamate, 0.1595 g of 5% $Rh/Al_2O_3$, and MeOH. The vessel was placed in a Parr hydrogenation shaker and pressurized to 60 psi. After the reaction vessel was shook for 27 h, the contents were filtered through HPLC filter and washed with MeOH. The filtrate was evaporated under reduced pressure and the residue was purified by reversed-phase to give the TFA salt of methyl 2-((S)-cyclohexyl((R)-1-((S)-1-cyclohexyl-3-(methylamino)propan-2-ylcarbamoyl)piperidin-3-yl)methoxy)ethylcarbamate. MS ESI +ve m/z 495 (M+H). $^1$H NMR ($CD_3OD$, 400 MHz) δ 4.04-3.89 (m, 3H), 3.53 (s, 3H), 3.58-2.64 (m, 9H), 2.60 (s, 3H), 1.72-0.77 (m, 29H).

Example 18

I*-57a—methyl 2-((1R)-(2-fluorophenyl)((3R)-1-(1-(methylamino)-3-((R)-oxepan-3-yl)propan-2-ylcarbamoyl)piperidin-3-yl)methoxy)ethylcarbamate

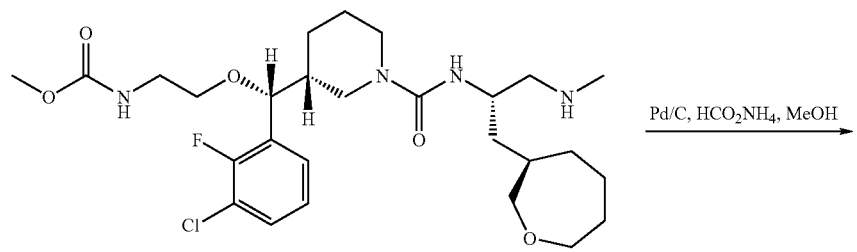

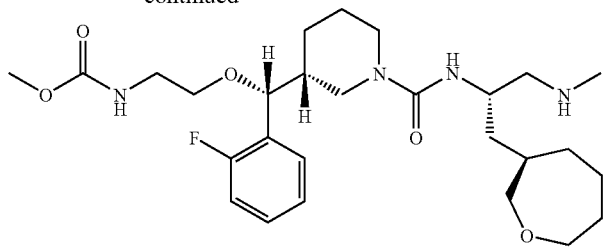

Step 1. methyl 2-((1R)-(2-fluorophenyl)((3R)-1-(1-(methylamino)-3-((R)-oxepan-3-yl)propan-2-ylcarbamoyl)piperidin-3-yl)methoxy)ethylcarbamate To a solution of methyl 2-((1R)-(3-chloro-2-fluorophenyl)((3R)-1-(1-(methylamino)-3-((R)-oxepan-3-yl)propan-2-ylcarbamoyl)piperidin-3-yl)methoxy)ethylcarbamate TFA salt (12 mg, 0.018 mmol) in MeOH (5 mL) was added HCO$_2$NH$_4$ (1.2 g) and 10% Pd/C (50 mg). The mixture was stirred for 1 h at rt. The catalyst was filtered off and concentrated, the residue was purified on preparative HPLC to give methyl 2-((1R)-(2-fluorophenyl)((3R)-1-(1-(methylamino)-3-((R)-oxepan-3-yl)propan-2-ylcarbamoyl)piperidin-3-yl)methoxy)ethylcarbamate as a TFA salt (1.84 mg, 16%).

The following compounds were prepared using procedures analogous to those described above except hydrogen gas was used:

I*-21a—Methyl 2-((R)—((R)-1-((S)-1-(methylamino)-3-((R)-oxepan-3-yl)propan-2-ylcarbamoyl)piperidin-3-yl)(phenyl)methoxy)ethylcarbamate following Example 18, Step 1, using methyl 2-((R)-(3-chlorophenyl)((R)-1-((S)-1-(methylamino)-3-((R)-oxepan-3-yl)propan-2-ylcarbamoyl)piperidin-3-yl)methoxy)ethylcarbamate I*-74a—methyl 2-((R)-((3R)-1-((S)-1-(3-noradamantyl)-3-(methylamino)propan-2-ylcarbamoyl)piperidin-3-yl)(phenyl)methoxy)ethylcarbamate following Example 18, Step 1, using methyl 2-((R)-(3-chlorophenyl)((R)-1-((S)-1-(3-noradamantyl)-3-(methylamino)propan-2-ylcarbamoyl)piperidin-3-yl)methoxy)ethylcarbamate.

Example 19

I*-3a—methyl 2-((R)—((R)-1-((S)-4-(methylamino)-3-(tetrahydro-2H-pyran-4-yl)propan-2-ylcarbamoyl)piperidin-3-yl)(phenyl)methoxy)ethylcarbamate

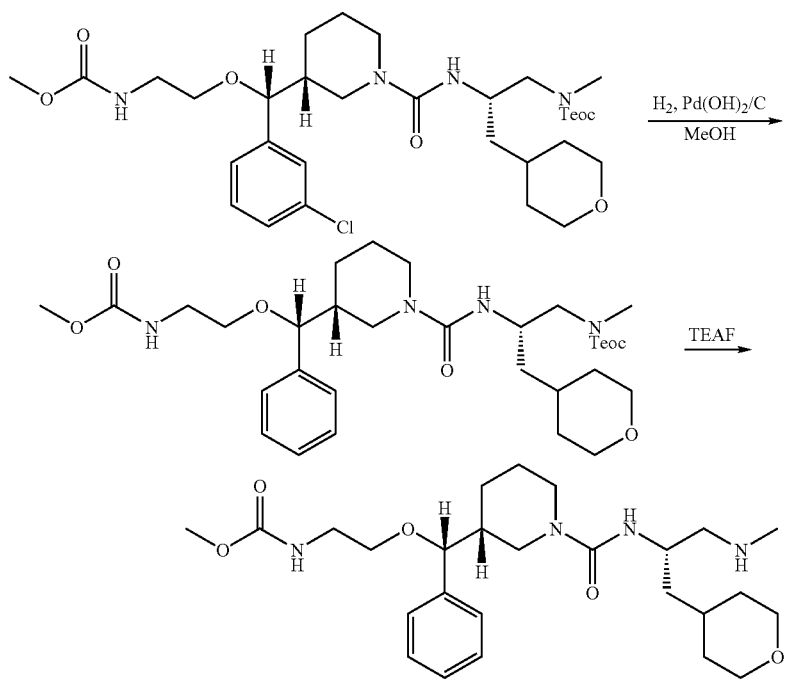

Step 1. methyl 2-((R)—((R)-1-((S)-1-(N-methyl-N-(2-(trimethylsilyl)ethoxycarbonyl)amino)-3-(tetrahydro-2H-pyran-4-yl)propan-2-ylcarbamoyl)piperidin-3-yl)(phenyl)methoxy)ethylcarbamate A 50 mL flask was charged with methyl 2-((R)-(3-chlorophenyl)((R)-1-((S)-1-(N-methyl-N-(2-(trimethylsilyl)ethoxycarbonyl)amino)-3-(tetrahydro-2H-pyran-4-yl)propan-2-ylcarbamoyl)piperidin-3-yl)methoxy)ethylcarbamate (100 mg, 0.15 mmol) and Pd(OH)$_2$ (20 mg) dissolved in MeOH (5 mL) under H$_2$. After stirring for 0.5 hr, the mixture was filtered, evaporated to give crude methyl 2-((R)—((R)-

1-((S)-1-(N-methyl-N-(2-(trimethylsilyl)ethoxycarbonyl)amino)-3-(tetrahydro-2H-pyran-4-yl)propan-2-ylcarbamoyl)piperidin-3-yl)(phenyl)methoxy)ethylcarbamate (20 mg, 21%), which was used without further purification.

Step 2. methyl 2-((R)—((R)-1-((S)-1-(methylamino)-3-(tetrahydro-2H-pyran-4-yl)propan-2-ylcarbamoyl)piperidin-3-yl)(phenyl)methoxy)ethylcarbamate In a round bottom flask methyl 2-((R)—((R)-1-((S)-1-(N-methyl-N-(2-(trimethylsilyl)ethoxycarbonyl)amino)-3-(tetrahydro-2H-pyran-4-yl)propan-2-ylcarbamoyl)piperidin-3-yl)(phenyl)methoxy)ethylcarbamate (20 mg, 0.03 mmol) and TEAF (15 mg, 0.07 mmol) was dissolved in a 15 mL of in MeCN. The solution was allowed to stir at reflux for 1 h. The mixture was concentrated in vacuo and purified by preparative HPLC to give methyl 2-((R)—((R)-1-((S)-1-(methylamino)-3-(tetrahydro-2H-pyran-4-yl)propan-2-ylcarbamoyl)piperidin-3-yl)(phenyl)methoxy)ethylcarbamate (6.24 mg, 42%).

Example 20

I*-45a—(R)-3-((R)-(3-chlorophenyl)(4-(methylamino)-4-oxobutoxy)methyl)-N—((S)-1-cyclohexyl-3-(methylamino)propan-2-yl)piperidine-1-carboxamide

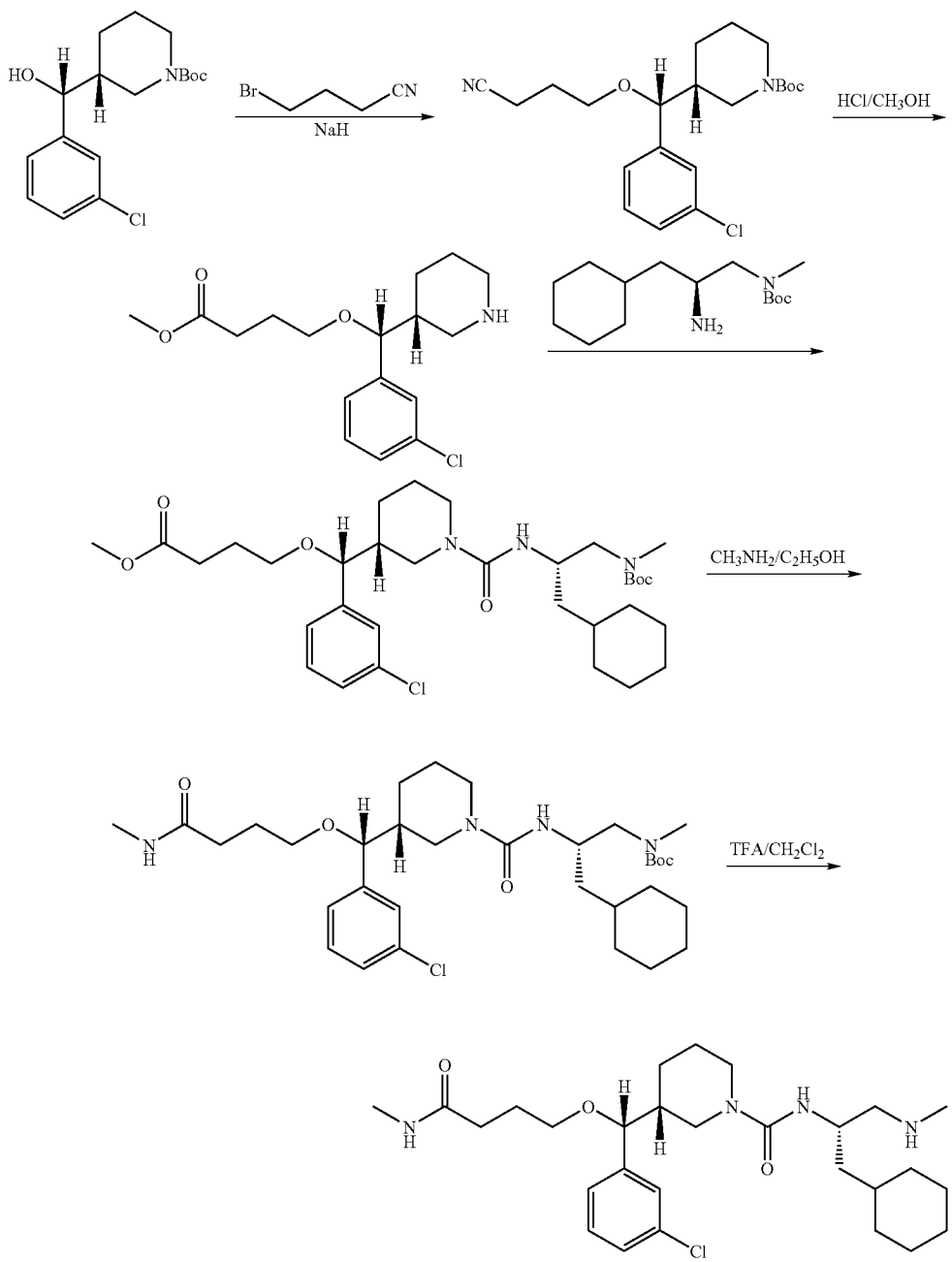

Step 1. (R)-tert-butyl 3-((R)-(3-chlorophenyl)(3-cyanopropoxy)methyl)piperidine-1-carboxylate To a suspension of NaH (763 mg, 19.1 mmol) and (R)-tert-butyl 3-((R)-(3-chlorophenyl)(hydroxy)methyl)piperidine-1-carboxylate (1.55 g, 4.77 mmol) in $CH_3CN$ (20 mL) at 0-5° C. was added dropwise a solution of 4-bromobutyronitrile (3.17 g, 21.5 mmol) in $CH_3CN$ (5 mL), the reaction mixture was stirred for overnight at rt. The reaction mixture was poured into saturated aqueous $NH_4Cl$, ethyl acetate (50 mL) was added. The organic layer was washed with water (3×20 mL) and brine, dried over $Na_2SO_4$, filtered and concentrated in vacuo. The residue was purified by preparative HPLC to afford (R)-tert-butyl 3-((R)-(3-chlorophenyl)(3-cyanopropoxy)methyl)piperidine-1-carboxylate (0.44 g, 21% yield). $^1$H NMR ($CD_3OD$, 400 MHz) δ 7.38-7.28 (m, 3H), 7.22 (m, 1H), 4.22 (m, 1H), 4.02 (d, 1H), 3.86 (d, 1H), 3.34 (m, 2H), 2.77 (q, 2H), 2.56 (t, 2H), 1.62 (m, 1H), 1.59 (m, 1H), 1.43 (s, 9H), 1.35-1.25 (m, 3H), 1.12 (d, 1H).

Step 2. methyl 4-((R)-(3-chlorophenyl)((R)-piperidin-3-yl)methoxy)butanoate (R)-tert-butyl 3-((R)-(3-chlorophenyl)(3-cyanopropoxy)methyl)piperidine-1-carboxylate (200 mg, 0.51 mmol) was dissolved in 20 mL of $CH_3OH$, and HCl was bubbled into the mixture over 30 min at −78° C. The mixture was stirred at rt overnight, then under reflux for another 6 hr. The solvent was removed and the residue was treated with sat. $NaHCO_3$, the mixture was extracted with ethyl acetate (20 mL). The organic layers was dried over $NaSO_4$ and evaporated to give the crude methyl 4-((R)-(3-chlorophenyl)((R)-piperidin-3-yl)methoxy)butanoate, which was used in the next step without further purification (75 mg, 46% yield). $^1$H NMR ($CDCl_3$, 400 MHz) δ 7.35 (m, 3H), 7.25 (m, 1H), 3.56 (m, 3H), 3.31-3.25 (m, 5H), 2.96 (m, 2H), 2.41 (m, 2H), 2.02 (m, 1H), 1.84 (m, 2H), 1.60 (m, 1H), 1.38-1.19 (m, 2H), 0.95 (d, 1H).

Step 3. methyl 4-((R)—((R)-1-((S)-1-(tert-butoxycarbonyl(methyl)amino)-3-cyclohexylpropan-2-ylcarbamoyl)piperidin-3-yl)(3-chlorophenyl)methoxy)butanoate To a solution of (S)-tert-butyl 2-amino-3-cyclohexylpropyl(methyl)carbamate (165 mg, 0.61 mmol) and DIEA (3 mL) in anhydrous $CH_2Cl_2$ (10 mL) was added CDI (98 mg, 0.61 mmol) with ice bath. After addition, the mixture was stirred for 1 h at 0° C., followed by the addition of methyl 4-((R)-(3-chlorophenyl)((R)-piperidin-3-yl)methoxy)butanoate (165 mg, 0.51 mmol) in anhydrous $CH_2Cl_2$ (2 mL). The reaction mixture was allowed to warm to rt and stirred overnight. The reaction mixture was washed with water (10 mL) and the aqueous layer extracted with $CH_2Cl_2$ (15 mL×2), the combined organic layers was washed with saturated brine, dried over $Na_2SO_4$, filtered, then evaporated to give a residue, which was purified via preparative TLC to afford methyl 4-((R)—((R)-1-((S)-1-(tert-butoxycarbonyl(methyl)amino)-3-cyclohexylpropan-2-ylcarbamoyl)piperidin-3-yl)(3-chlorophenyl)methoxy)butanoate (70 mg, 22% yield). $^1$H NMR ($CD_3OD$, 400 MHz) δ 7.34-7.28 (m, 3H), 7.19 (t, 1H), 4.25 (d, 1H), 4.11 (d, 1H), 3.95 (m, 2H), 3.64 (t, 3H), 3.27 (m, 1H), 3.10 (m, 1H), 2.87 (s, 2H), 2.69 (m, 2H), 2.43 (t, 1H), 1.84 (t, 2H), 1.72-1.52 (m, 6H), 1.45 (d, 9H), 1.39-1.22 (m, 10H), 1.14 (d, 1H), 0.97 (d, 2H), 0.85 (t, 1H).

Step 4. tert-butyl (S)-2-((R)-3-((R)-(3-chlorophenyl)(4-(methylamino)-4-oxobutoxy)methyl)piperidine-1-carboxamido)-3-cyclohexylpropyl(methyl)carbamate methyl 4-((R)—((R)-1-((S)-1-(tert-butoxycarbonyl(methyl)amino)-3-cyclohexylpropan-2-ylcarbamoyl)piperidin-3-yl)(3-chlorophenyl)methoxy)butanoate (70 mg, 0.11 mmol) was dissolved in the $CH_3NH_2/C_2H_5OH$ (20 mL), which was stirred at rt overnight. After the reaction was completed, the solvent was removed in vacuo. The product was purified via preparative TLC to afford tert-butyl (S)-2-((R)-3-((R)-(3-chlorophenyl)(4-(methylamino)-4-oxobutoxy)methyl)piperidine-1-carboxamido)-3-cyclohexylpropyl(methyl)carbamate (50 mg, 71% yield), which was used immediately in the next step.

Step 5. (R)-3-((R)-(3-chlorophenyl)(4-(methylamino)-4-oxobutoxy)methyl)-N—((S)-1-cyclohexyl-3-(methylamino)propan-2-yl)piperidine-1-carboxamide tert-butyl (S)-2-((R)-3-((R)-(3-chlorophenyl)(4-(methylamino)-4-oxobutoxy)methyl)piperidine-1-carboxamido)-3-cyclohexylpropyl(methyl)carbamate (50 mg, 0.08 mmol) was dissolved in a solution of 20% (V/V) $TFA/CH_2Cl_2$ (10 mL). The reaction mixture was stirred at rt for 1 h, a solution of saturated sodium bicarbonate was added dropwise to adjust pH=7-8. The resulting mixture was extracted with $CH_2Cl_2$ (3×15 mL), washed with brine, dried over $Na_2SO_4$, and concentrated in vacuo. The residue was purified by preparative HPLC to afford (R)-3-((R)-(3-chlorophenyl)(4-(methylamino)-4-oxobutoxy)methyl)-N—((S)-1-cyclohexyl-3-(methylamino)propan-2-yl)piperidine-1-carboxamide (3.30 mg, yield 8%). $^1$H NMR ($CD_3OD$, 400 MHz) δ 7.30-7.34 (m, 3H), 7.20 (d, 1H), 4.30 (d, 1H), 4.05 (m, 1H), 3.97 (m, 2H), 2.76 (m, 3H), 2.69 (s, 3H), 2.53 (s, 3H), 2.27 (m, 3H), 1.83 (m, 3H), 1.71 (m, 5H), 1.13-1.28 (m, 10H), 0.89 (m, 4H).

Example 21

I*-25a—(R)-3-((R)-1-(3-chlorophenyl)-1-(2-(methylamino)-2-oxoethoxy)ethyl)-N—((S)-1-cyclohexyl-3-(methylamino)propan-2-yl)piperidine-1-carboxamide

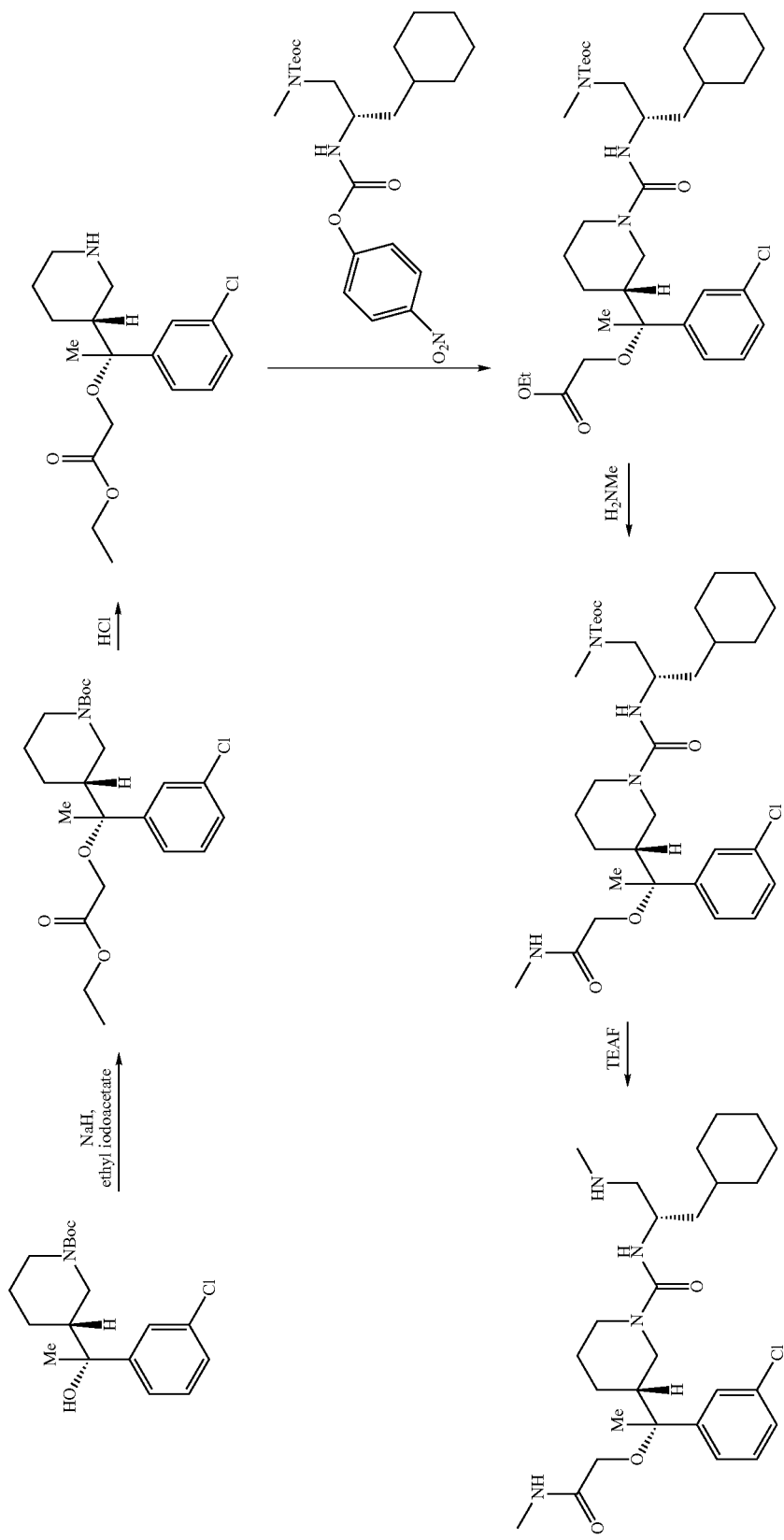

Step 1. (R)-tert-butyl 3-((R)-1-(3-chlorophenyl)-1-(2-ethoxy-2-oxoethoxy)ethyl)piperidine-1-carboxylate A mixture of (R)-tert-butyl 3-((R)-1-(3-chlorophenyl)-1-hydroxyethyl)piperidine-1-carboxylate (0.4395 g, 1.29 mmol), 60% NaH (1.320 g, 33 mmol), and ethyl iodoacetate (5.237 g, 24.5 mmol) in THF (20 mL) was heated at 90° C. for 18 h and then cooled to rt. The reaction mixture was then quenched with saturated brine and extracted with ethyl acetate (3×), dried over $Na_2SO_4$. After the solvent was evaporated under reduced pressure, the crude product was purified by reversed-phase HPLC to afford 0.0775 g (14%) of (R)-tert-butyl 3-((R)-1-(3-chlorophenyl)-1-(2-ethoxy-2-oxoethoxy)ethyl)piperidine-1-carboxylate. MS ESI +ve m/z 450 (M+Na).

Step 2. ethyl 2-((R)-1-(3-chlorophenyl)-1-((R)-piperidin-3-yl)ethoxy)acetate A mixture of (R)-tert-butyl 3-((R)-1-(3-chlorophenyl)-1-(2-ethoxy-2-oxoethoxy)ethyl)piperidine-1-carboxylate (0.0580 g, 0.136 mmol), 2 NHCl (50 mL), and $CH_3CN$ (50 mL) was vigorously stirred at rt for 24 h. After the reaction mixture was evaporated under reduced pressure, the crude product ethyl 2-((R)-1-(3-chlorophenyl)-1-((R)-piperidin-3-yl)ethoxy)acetate was directly used in the next step without further purification. MS ESI +ve m/z 328 (M+H).

Step 3. ethyl 2-((R)-1-(3-chlorophenyl)-1-((R)-1-((S)-1-cyclohexyl-3-(methyl((2-(trimethylsilyl)ethoxy)carbonyl)amino)propan-2-ylcarbamoyl)piperidin-3-yl)ethoxy)acetate A mixture of ethyl 2-((R)-1-(3-chlorophenyl)-1-((R)-piperidin-3-yl)ethoxy)acetate, (S)-4-nitrophenyl 1-cyclohexyl-3-(methyl((2-(trimethylsilyl)ethoxy)carbonyl)amino)propan-2-ylcarbamate (0.096 g, 0.20 mmol), and DIPEA (1 mL) in $CH_2Cl_2$ was stirred at rt for 24 h. After the reaction mixture was evaporated under reduced pressure, the crude product was purified by reversed-phase HPLC to afford 0.0425 g (47% in two steps) of ethyl 2-((R)-1-(3-chlorophenyl)-1-((R)-1-((S)-1-cyclohexyl-3-(methyl((2-(trimethylsilyl)ethoxy)carbonyl)amino)propan-2-ylcarbamoyl)piperidin-3-yl)ethoxy)acetate. MS ESI +ve m/z 668 (M+H).

Step 4. 2-(trimethylsilyl)ethyl (S)-2-((R)-3-((R)-1-(3-chlorophenyl)-1-(2-(methylamino)-2-oxoethoxy)ethyl)piperidine-1-carboxamido)-3-cyclohexylpropyl (methyl)carbamate A mixture of ethyl 2-((R)-1-(3-chlorophenyl)-1-((R)-1-((S)-1-cyclohexyl-3-(methyl((2-(trimethylsilyl)ethoxy)carbonyl)amino)propan-2-ylcarbamoyl)piperidin-3-yl)ethoxy)acetate (0.0185 g) and 33% wt. methylamine in ethyl alcohol (10 mL) was stirred at rt for 3 d. After the reaction mixture was evaporated under reduced pressure, the crude product was purified by reversed-phase HPLC to afford 0.0035 g of 2-(trimethylsilyl)ethyl (S)-2-((R)-3-((R)-1-(3-chlorophenyl)-1-(2-(methylamino)-2-oxoethoxy)ethyl)piperidine-1-carboxamido)-3-cyclohexylpropyl(methyl)carbamate. MS ESI +ve m/z 653 (M+H).

Step 5. (R)-3-((R)-1-(3-chlorophenyl)-1-(2-(methylamino)-2-oxoethoxy)ethyl)-N—((S)-1-cyclohexyl-3-(methylamino)propan-2-yl)piperidine 1-carboxamide A mixture of 2-(trimethylsilyl)ethyl (S)-2-((R)-3-((R)-1-(3-chlorophenyl)-1-(2-(methylamino)-2-oxoethoxy)ethyl)piperidine-1-carboxamido)-3-cyclohexylpropyl(methyl)carbamate (0.0035 g) and 0.5 M $Et_4NF$ in $CH_3CN$ (6 mL) was heated at 80° C. for 1.5 h and then stirred at rt overnight. After the solvent was removed in vacuo, the residue was purified by reversed-phase HPLC to give TFA salt of (R)-3-((R)-1-(3-chlorophenyl)-1-(2-(methylamino)-2-oxoethoxy)ethyl)-N—((S)-1-cyclohexyl-3-(methylamino)propan-2-yl)piperidine-1-carboxamide. MS ESI +ve m/z 509 (M+H). $^1$H NMR ($CD_3OD$, 400 MHz) δ 7.31-7.14 (m, 4H), 4.17 (s, 2H), 4.20-3.98 (m, 3H), 3.02 (dd, J=12.6, 3.2 Hz, 1H), 2.89 (dd, J=12.3, 10.5 Hz, 1H), 2.65 (s, 3H), 2.38 (s, 3H), 1.41 (s, 3H), 2.69-0.83 (m, 20H).

Example 22

I*-87a—methyl 1-((R)-(3-chlorophenyl)((R)-1-((S)-1-cyclohexyl-3-(methylaminopropan-2-ylcarbamoyl)piperidin-3-yl)methoxy)propan-2-ylcarbamate

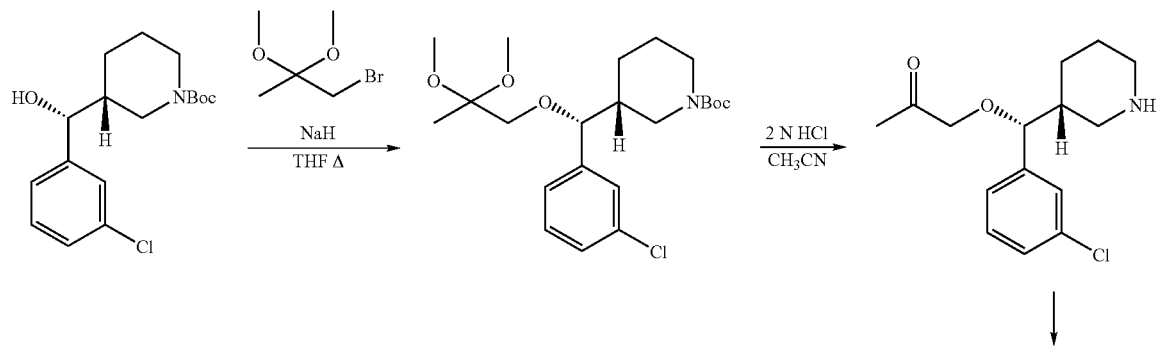

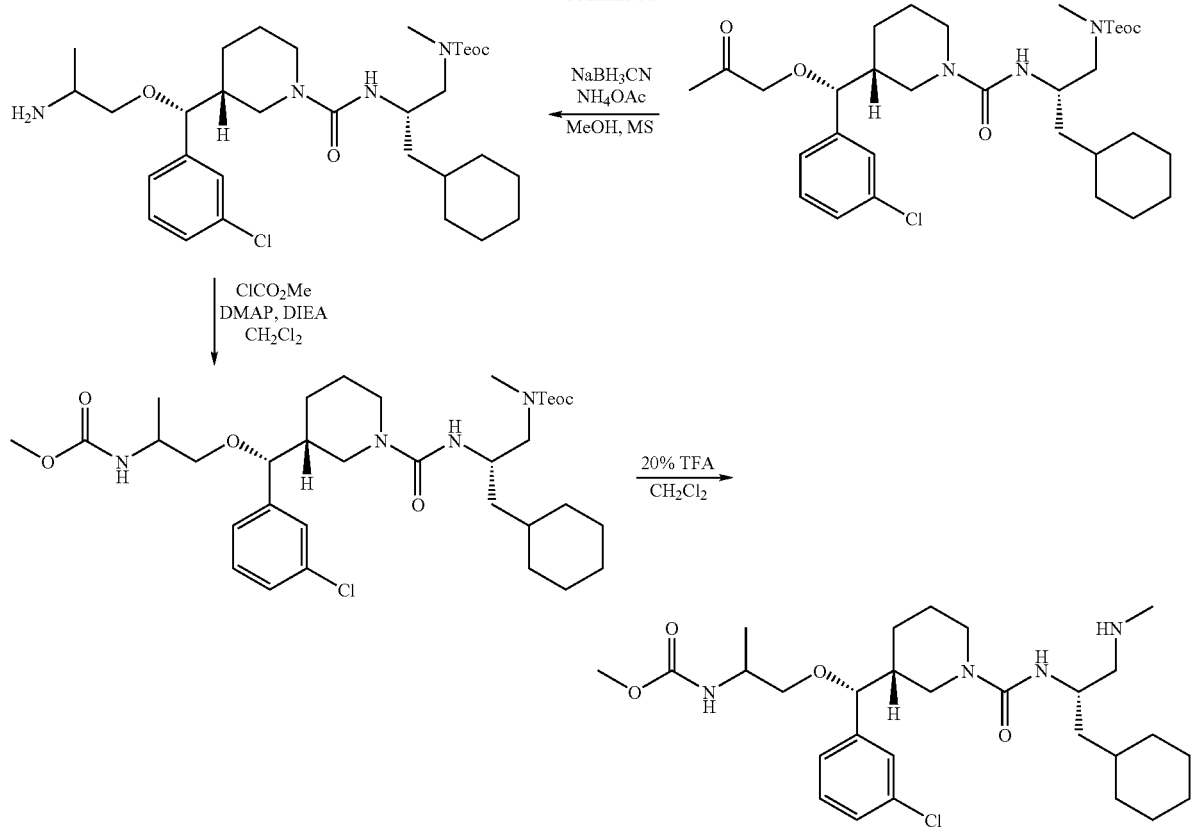

Step 1. (R)-tert-butyl 3-((R)-(3-chlorophenyl)(2,2-dimethoxypropoxy)methyl)piperidine-1-carboxylate A mixture of (R)-tert-butyl 3-((R)-(3-chlorophenyl)(hydroxy)methyl)piperidine-1-carboxylate (0.2234 g, 0.68 mmol), 60% NaH (1.460 g, 36.5 mmol), and 1-bromo-2,2-dimethoxypropane (7.760 g, 42.4 mmol) in THF (20 mL) was heated at 80° C. for 3 d and then cooled to rt. The reaction mixture was then quenched with water, extracted with ethyl acetate (3×), and dried over Na₂SO₄. After the solvent was evaporated under reduced pressure, the crude product (R)-tert-butyl 3-((R)-(3-chlorophenyl)(2,2-dimethoxypropoxy)methyl)piperidine-1-carboxylate was directly used in the next step without further purification.

Step 2. 1-((R)-(3-chlorophenyl)((R)-piperidin-3-yl)methoxy)propan-2-one

A mixture of (R)-tert-butyl 3-((R)-(3-chlorophenyl)(2,2-dimethoxypropoxy)methyl)piperidine-1-carboxylate, obtained as described above, 2 N HCl (100 mL) and CH₃CN (100 mL) was vigorously stirred at rt for 22 h. After the reaction mixture was evaporated under reduced pressure, the crude 1-((R)-(3-chlorophenyl)((R)-piperidin-3-yl)methoxy)propan-2-one was directly used in the next step without further purification. MS ESI +ve m/z 284 (M+H).

Step 3. 2-(trimethylsilyl)ethyl (S)-2-((R)-3-((R)-(3-chlorophenyl)(2-oxopropoxy)methyl)piperidine-1-carboxamido)-3-cyclohexylpropyl(methyl)carbamate A mixture of 1-((R)-(3-chlorophenyl)((R)-piperidin-3-yl)methoxy)propan-2-one, obtained as described above, (S)-4-nitrophenyl 1-cyclohexyl-3-(methyl((2-(trimethylsilyl)ethoxy)carbonyl)amino)propan-2-ylcarbamate (0.390 g, 0.81 mmol), and DIPEA (2.5 mL) in CH₂Cl₂ was stirred at rt for 16 h. After the reaction mixture was evaporated under reduced pressure, the crude product was purified by reversed-phase HPLC to afford 0.0487 g (11.4% in three steps) of 2-(trimethylsilyl)ethyl (S)-2-((R)-3-((R)-(3-chlorophenyl)(2-oxopropoxy)methyl)piperidine-1-carboxamido)-3-cyclohexylpropyl(methyl)carbamate. MS ESI +ve m/z 624 (M+H).

Step 4. 2-(trimethylsilyl)ethyl (2S)-2-((3R)-3-((1R)-(2-aminopropoxy)(3-chlorophenyl)methyl)piperidine-1-carboxamido)-3-cyclohexylpropyl(methyl)carbamate A mixture of 2-(trimethylsilyl)ethyl (S)-2-((R)-3-((R)-(3-chlorophenyl)(2-oxopropoxy)methyl)piperidine-1-carboxamido)-3-cyclohexylpropyl(methyl)carbamate (0.0487 g, 0.078 mmol, 1.0 equiv), NaBH₃CN (0.0296 g, 0.471 mmol, 6.0 equiv), NH₄OAc (0.2550 g, 3.31 mmol, 42 equiv), and 4 Å molecular sieves (0.0555 g) in MeOH (1 mL) was stirred at rt for 22 h. The reaction mixture was diluted with MeOH and filtered through filter agent, Celite® 545. The filtrate was evaporated under reduced pressure to afford 0.2405 g of crude 2-(trimethylsilyl)ethyl (2S)-2-((3R)-3-((1R)-(2-aminopropoxy)(3-chlorophenyl)methyl)piperidine-1-carboxamido)-3-cyclohexylpropyl(methyl)carbamate, which was used in the next step without further purification. MS ESI +ve m/z 625 (M+H).

Step 5. 2-(trimethylsilyl)ethyl (S)-2-((R)-3-((R)-(2-(methoxycarbonylamino)propoxy)(3-chlorophenyl)methyl)piperidine-1-carboxamido)-3-cyclohexylpropyl(methyl)carbamate A mixture of crude 2-(trimethylsilyl)ethyl (2S)-2-((3R)-3-((1R)-(2-aminopropoxy)(3-chlorophenyl)methyl)piperidine-1-carboxamido)-3-cyclohexylpropyl(methyl)carbamate (0.1340 g), obtained as, described above, DMAP (0.151 g), DIPEA (2 mL), and methyl chloroformate (0.483 g) in CH$_2$Cl$_2$ was stirred at rt for 2 d. After the reaction mixture was evaporated under reduced pressure, the crude product was purified by reversed-phase HPLC to give 2-(trimethylsilyl)ethyl (S)-2-((R)-3-((R)-(2-(methoxycarbonylamino)propoxy)(3-chlorophenyl)methyl)piperidine-1-carboxamido)-3-cyclohexylpropyl(methyl)carbamate. MS ESI +ve m/z 705 (M+Na).

Step 6. methyl 1-((R)-(3-chlorophenyl)((R)-1-((S)-1-cyclohexyl-3-(methylamino)propan-2-ylcarbamoyl)piperidin-3-yl)methoxy)propan-2-ylcarbamate A mixture of 2-(trimethylsilyl)ethyl (S)-2-((R)-3-((R)-(2-(methoxycarbonylamino)propoxy)(3-chlorophenyl)methyl)piperidine-1-carboxamido)-3-cyclohexylpropyl(methyl)carbamate and TFA (2 mL) in CH$_2$Cl$_2$ (5 mL) was stirred at rt for 3 h. After the reaction mixture was evaporated under reduced pressure, the crude product was purified by reversed-phase HPLC to give TFA salt of methyl 1-((R)-(3-chlorophenyl)((R)-1-((S)-1-cyclohexyl-3-(methylamino)propan-2-ylcarbamoyl)piperidin-3-yl)methoxy)propan-2-ylcarbamate. MS ESI +ve m/z 539 (M+H).

General Synthetic Schemes for Compounds of Formula (XL)

The compounds of Formula (XL) of present invention can be synthesized by coupling a pyran intermediate represented by the following structure:

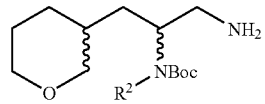

with a piperidine intermediate represented by the following structure:

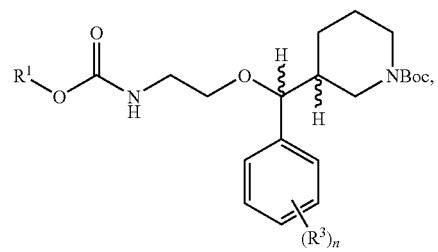

described in the following scheme:

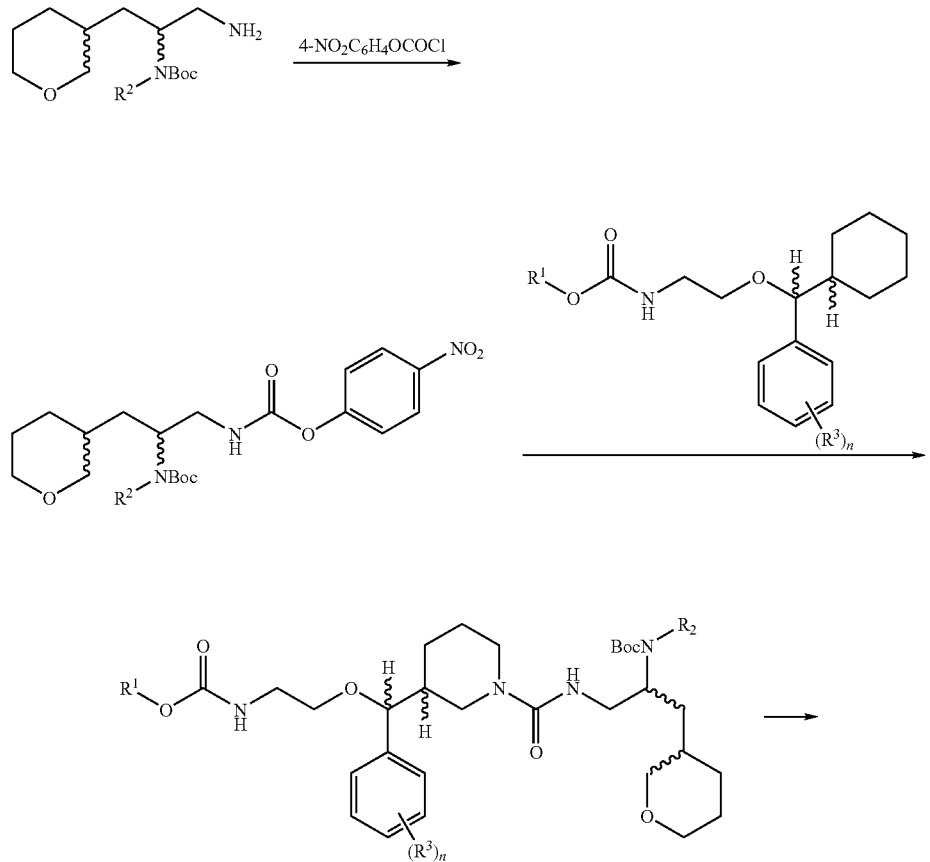

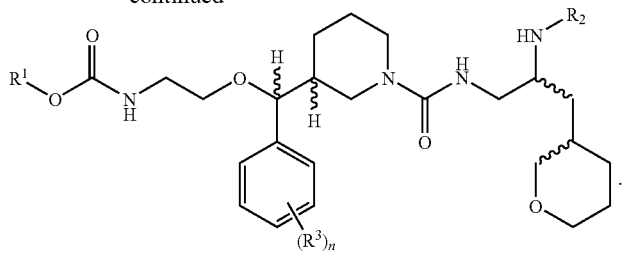
Preparation of the Pyran Intermediate from Glutamic Ester
The pyran intermediate can be prepared from glutamic ester using the following synthetic scheme:
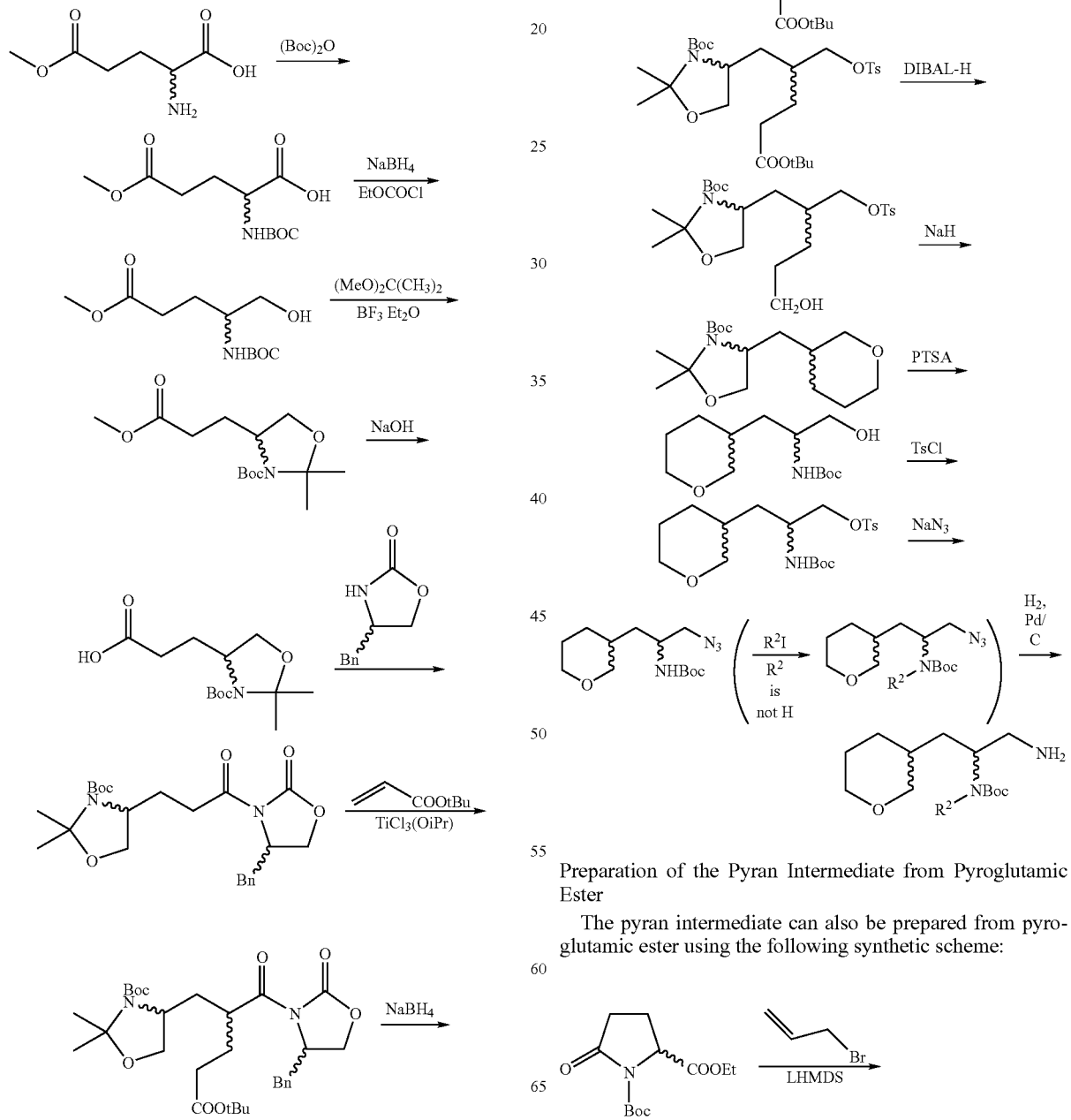
Preparation of the Pyran Intermediate from Pyroglutamic Ester
The pyran intermediate can also be prepared from pyroglutamic ester using the following synthetic scheme:

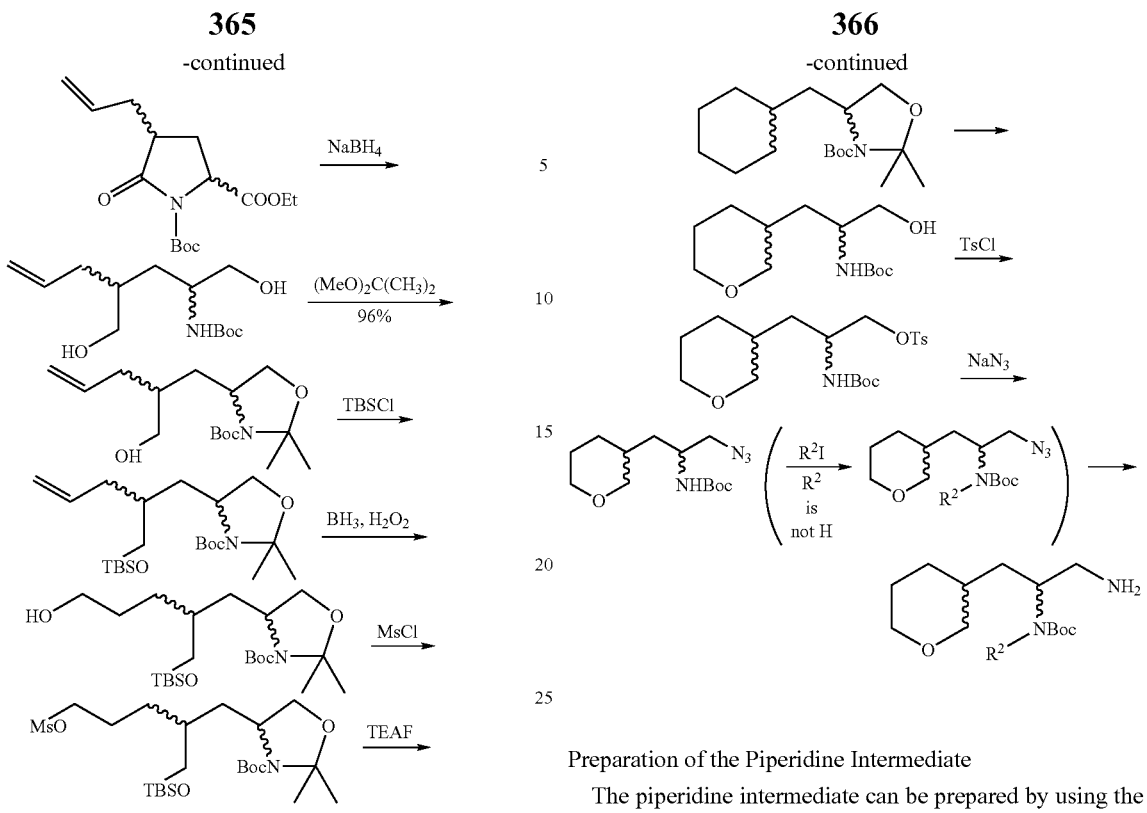
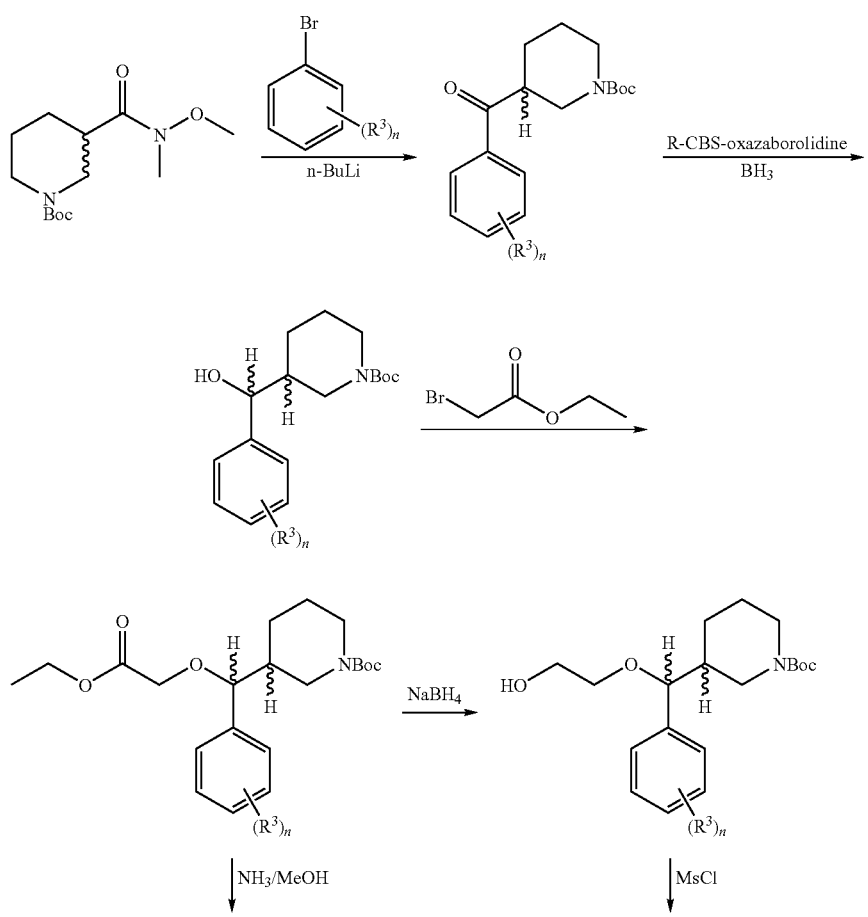
Preparation of the Piperidine Intermediate
The piperidine intermediate can be prepared by using the following synthetic scheme.

-continued
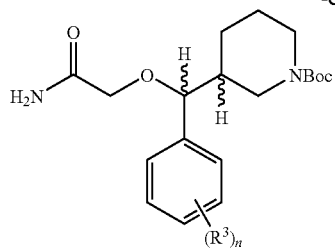
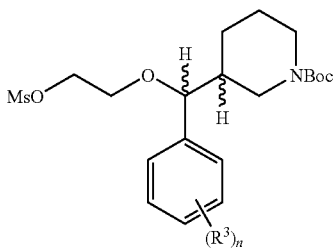
↓ Red-Al
↓ NaN₃
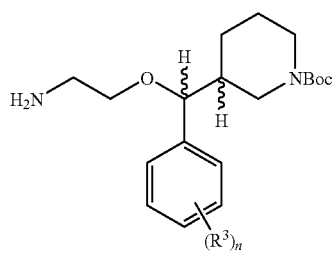
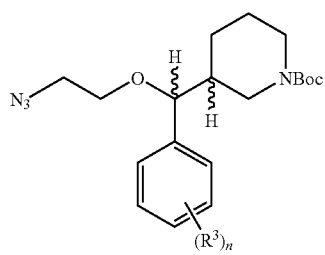
← H₂, Pd(OH)₂
↓ R¹—O—C(O)—Cl
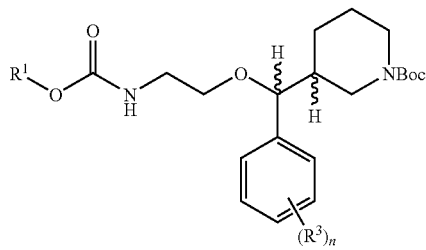
Alternatively, the piperidine intermediate can be prepared using the following synthetic scheme:
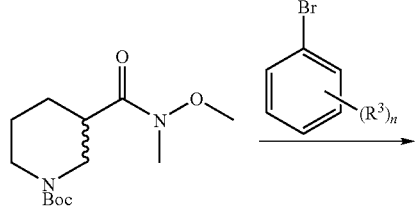
-continued
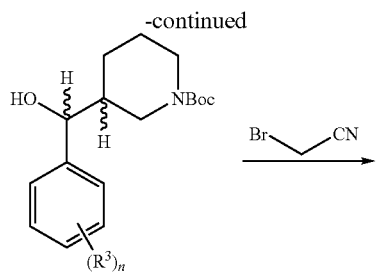
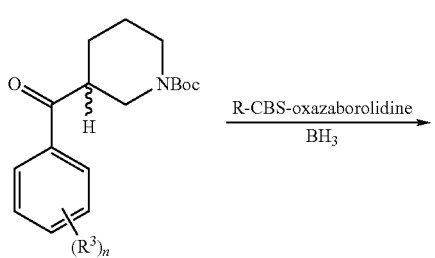
R-CBS-oxazaborolidine
BH₃
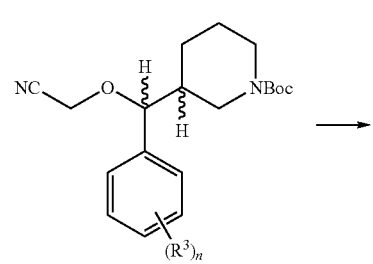

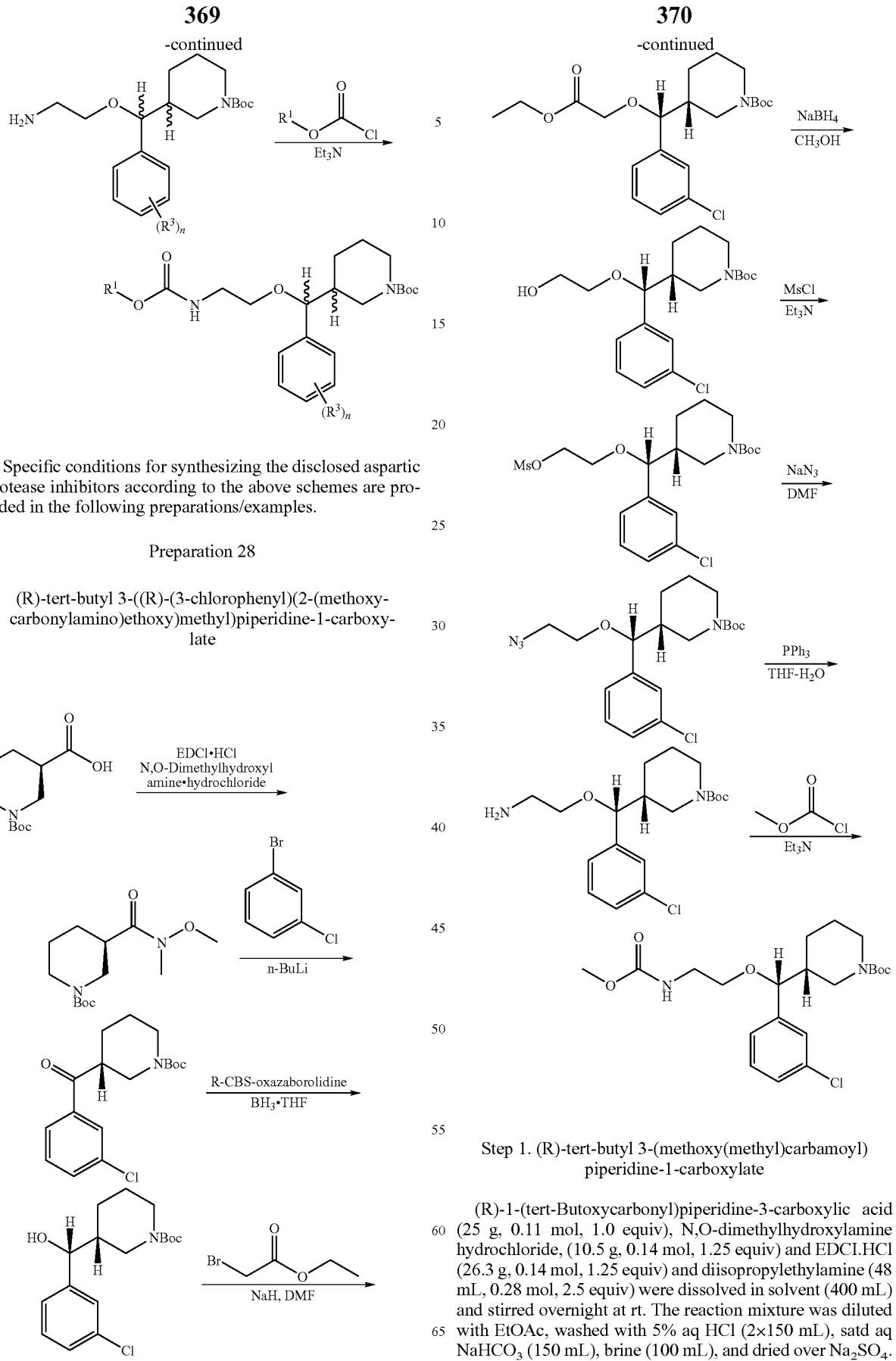
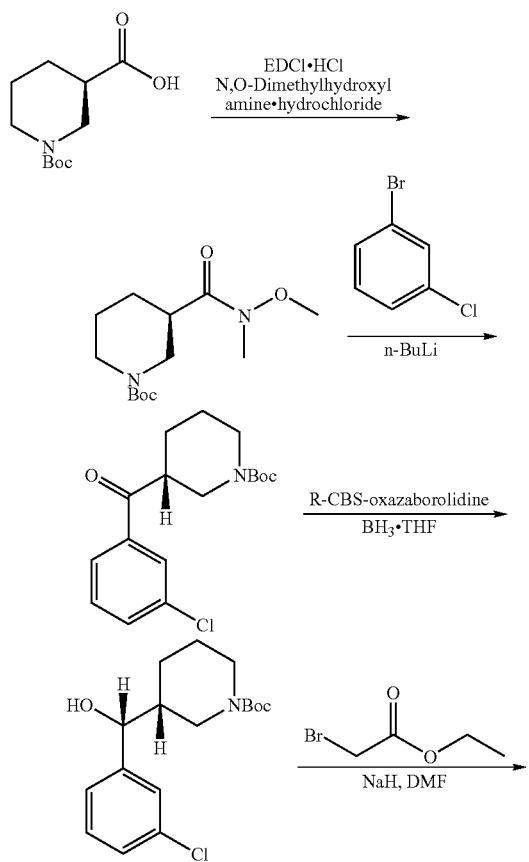

Specific conditions for synthesizing the disclosed aspartic protease inhibitors according to the above schemes are provided in the following preparations/examples.

Preparation 28

(R)-tert-butyl 3-((R)-(3-chlorophenyl)(2-(methoxycarbonylamino)ethoxy)methyl)piperidine-1-carboxylate Step 1. (R)-tert-butyl 3-(methoxy(methyl)carbamoyl)piperidine-1-carboxylate (R)-1-(tert-Butoxycarbonyl)piperidine-3-carboxylic acid (25 g, 0.11 mol, 1.0 equiv), N,O-dimethylhydroxylamine hydrochloride, (10.5 g, 0.14 mol, 1.25 equiv) and EDCI.HCl (26.3 g, 0.14 mol, 1.25 equiv) and diisopropylethylamine (48 mL, 0.28 mol, 2.5 equiv) were dissolved in solvent (400 mL) and stirred overnight at rt. The reaction mixture was diluted with EtOAc, washed with 5% aq HCl (2×150 mL), satd aq NaHCO₃ (150 mL), brine (100 mL), and dried over Na₂SO₄. Concentration afforded (R)-tert-butyl 3-(methoxy(methyl)

carbamoyl)piperidine-1-carboxylate (24.42 g, 82%) as a clear oil. The crude product was used for next step without further purification. MS ESI +ve m/z 295 (M+Na). $^1$H NMR (CDCl$_3$) δ 4.19-4.00 (m, 2H), 3.77 (m, 3H), 3.12 (s, 3H), 2.79 (m, 2H), 2.64 (m, 1H), 1.89 (m, 1H), 1.71-1.52 (m, 2H), 1.51-1.33 (m, 10H).

Step 2. (R)-tert-butyl 3-(3-chlorobenzoyl)piperidine-1-carboxylate

To a solution of 1-bromo-3-chlorobenzene (100 g, 0.52 mol) in anhydrous THF (550 mL) at −78° C. under nitrogen was added dropwise a solution of 2.5 M n-BuLi in hexane (210 mL, 0.52 mol). After stirring for 1 hr at −78° C., a solution of (R)-tert-butyl 3-(methoxy(methyl)carbamoyl)piperidine-1-carboxylate (120 g, 0.44 mol) in anhydrous THF (500 mL) was added dropwise. After addition, the reaction mixture was allowed to warm to rt and stirred for 2 hr. The mixture was quenched with saturated NH$_4$Cl solution (500 mL) and extracted with EtOAc (3×400 mL). The combined organic layers were washed with brine, dried over Na$_2$SO$_4$ and concentrated in vacuo to give the crude (R)-tert-butyl 3-(3-chlorobenzoyl)piperidine-1-carboxylate (178 g), which was used immediately for next step without purification.

Step 3. (R)-tert-butyl 3-((R)-(3-chlorophenyl)(hydroxy)methyl)piperidine-1-carboxylate To a solution of (R)-tert-butyl 3-(3-chlorobenzoyl)piperidine-1-carboxylate (178 g, 0.55 mol) in anhydrous THF (600 mL) at −15° C. under nitrogen was added dropwise a solution of 1 M R-CBS-oxazaborolidine in toluene (82 mL, 82 mmol, 0.15 eq). After stirring for 1 hr at −15° C., a solution of 10 M BH$_3$ in THF (60 mL, 0.60 mol, 1.1 eq) was added dropwise. After addition, the reaction mixture was stirred for 2 hr at −15° C. Methanol (400 mL) was added dropwise carefully at −15° C. The solvent was removed under reduced pressure, the residue was purified by column chromatography on silica gel eluting with AcOEt/hexane (1:30→1:15) to provide the light yellow oil (95 g, HPLC purity≧70%, isomer ratio≧3:1). The mixture was dissolved in EtOAc till the alcohol was just dissolved (about 5 mL/1 g), the solvent was removed on the rotary evaporator until a few crystals appeared. The solution was cooled to rt slowly and stood for 1-2 hr. To the above solution was added hexane (about 300 mL) and then filtered, the crystals were washed with cool hexane and re-crystallized from AcOEt-hexane twice to afford the pure isomer (R)-tert-butyl 3-((R)-(3-chlorophenyl)(hydroxy)methyl)piperidine-1-carboxylate (20 g, ee≧99%).

Step 4. (R)-tert-butyl 3-((R)-(3-chlorophenyl)(2-ethoxy-2-oxoethoxy)methyl)piperidine-1-carboxylate To a suspension of NaH (7.44 g, 161 mmol) in anhydrous DMF (50 mL) at 0-5° C. was added dropwise a solution of (R)-tert-butyl 3-((R)-(3-chlorophenyl)(hydroxy)methyl)piperidine-1-carboxylate (17.45 g, 54 mmol) in anhydrous DMF (100 mL), the reaction mixture was stirred for 1 hr at rt. A solution of ethyl bromoacetate (17.82 g, 11.87 mL, 107 mmol) in anhydrous DMF (100 mL) was added dropwise to the above mixture at 0-5° C. After addition, the reaction mixture was stirred for 2-3 hr at rt. The reaction mixture was poured into saturated aqueous NH$_4$Cl and EtOAc (1000 mL) was added. The organic layer was washed with water (3×200 mL) and brine, dried over Na$_2$SO$_4$, filtered and concentrated in vacuo. The residue was purified on silica gel chromatography to afford (R)-tert-butyl 3-((R)-(3-chlorophenyl)(2-ethoxy-2-oxoethoxy)methyl)piperidine-1-carboxylate (14 g, 64% yield).

Step 5. (R)-tert-butyl 3-((R)-(3-chlorophenyl)(2-hydroxyethoxy)methyl)piperidine-1-carboxylate To a solution of (R)-tert-butyl 3-((R)-(3-chlorophenyl)(2-ethoxy-2-oxoethoxy)methyl)piperidine-1-carboxylate (14 g, 34 mmol) in MeOH (200 mL) was added NaBH$_4$ (10.35 g, 272 mmol) in portions while the temperature was lower than 40° C. After addition, the mixture was stirred at rt for 2-3 hr. The solvent was removed in vacuo to provide a residue which was partitioned between water and EtOAc. The organic layer was washed with H$_2$O and brine, dried over Na$_2$SO$_4$ and evaporated to give the crude (R)-tert-butyl 3-((R)-(3-chlorophenyl)(2-hydroxyethoxy)methyl)piperidine-1-carboxylate (12.50 g), which was used in the next step without purification.

Step 6. (R)-tert-butyl 3-((R)-(3-chlorophenyl)(2-(methylsulfonyloxy)ethoxy)methyl)piperidine-1-carboxylate To a solution of (R)-tert-butyl 3-((R)-(3-chlorophenyl)(2-hydroxyethoxy)methyl)piperidine-1-carboxylate (12.50 g, 34 mmol) in dry CH$_2$Cl$_2$ (150 mL) was added Et$_3$N (13.74 g, 18.3 mL, 136 mmol, 4 eq) at −5-0° C. Then a solution of MsCl (7.75 g, 5.16 mL, 68 mmol, 2 eq) in dry CH$_2$Cl$_2$ (50 mL) was added dropwise at the same temperature. After addition, it was allowed to warm to rt gradually. Upon reaction completion water (100 mL) was added. The aqueous layer was extracted with CH$_2$Cl$_2$ (3×80 mL), the combined organic layers was washed with 10% citric acid, sat. NaHCO$_3$ and brine, then dried over Na$_2$SO$_4$, filtered and concentrated to give (R)-tert-butyl 3-((R)-(3-chlorophenyl)(2-(methylsulfonyloxy)ethoxy)methyl)piperidine-1-carboxylate (15 g), which was used in the next step without purification.

Step 7. (R)-tert-butyl 3-((R)-(2-azidoethoxy)(3-chlorophenyl)methyl)piperidine-1-carboxylate (R)-tert-butyl 3-((R)-(3-chlorophenyl)(2-(methylsulfonyloxy)ethoxy)methyl)piperidine-1-carboxylate (15 g, 34 mmol) was dissolved into anhydrous DMF (150 mL), solid NaN$_3$ (6.7 g, 102 mmol, 3 eq) was added and the reaction mixture was heated to 80° C. for overnight. The reaction mixture was cooled to rt and then was added with EtOAc (500 mL), the organic phase was washed with water (3×100 mL) and brine (2×80 mL), dried over Na$_2$SO$_4$ and concentrated in vacuo to provide crude (R)-tert-butyl 3-((R)-(2-azidoethoxy)(3-chlorophenyl)methyl)piperidine-1-carboxylate (13.3 g), which was used for next step without purification.

Step 8. (R)-tert-butyl 3-((R)-(2-aminoethoxy)(3-chlorophenyl)methyl)piperidine-1-carboxylate (R)-tert-butyl 3-((R)-(2-azidoethoxy)(3-chlorophenyl) methyl)piperidine-1-carboxylate (13.3 g, 33.8 mmol) was dissolved in THF/H$_2$O (20:1, 180 mL/9 mL), triphenylphosphine (36.0 g, 135 mmol) was added in portions. The reaction mixture was stirred overnight at rt. The solvent was removed under reduced pressure to the residue, which was purified on silica gel chromatography to afford (R)-tert-butyl 3-((R)-(2-aminoethoxy)(3-chlorophenyl)methyl)piperidine-1-carboxylate (10.4 g, purity: HPLC=75%).

Step 9. (R)-tert-butyl 3-((R)-(3-chlorophenyl)(2-(methoxycarbonylamino)ethoxy)methyl)piperidine-1-carboxylate To a solution of (R)-tert-butyl 3-((R)-(2-aminoethoxy)(3-chlorophenyl)methyl)piperidine-1-carboxylate (7.7 g, 21 mmol, HPLC=75%) and DMAP (1.27 g, 10 mmol, 0.5 eq) in dry $CH_2Cl_2$ (120 mL), $Et_3N$ (6.38 g, 8.45 mL, 63 mmol) was added. The resulting mixture was cooled to 0-5° C. under ice-water bath, a solution of methyl chloroformate (8.1 mL, 104.5 mmol, 5 eq) in dry $CH_2Cl_2$ (50 mL) was added dropwise. After addition, the reaction mixture was stirred for 1-2 hr at 0-5° C. The reaction was quenched with water (80 mL). The aqueous layer was extracted with $CH_2Cl_2$ (3×50 mL), the combined organic layers were washed with 10% citric acid (2×80 mL) and brine, then dried over $Na_2SO_4$, filtered and concentrated to the crude product, which was purified by preparative HPLC to afford (R)-tert-butyl 3-((R)-(3-chlorophenyl)(2-(methoxycarbonylamino)ethoxy)methyl)piperidine-1-carboxylate (4.4 g, HPLC≧98%, the total yield for five steps is 41%).

The following compounds were prepared following procedures analogous to those described above:
1) (R)-tert-butyl 3-((R)-(3,5-difluorophenyl)(2-(methoxycarbonylamino)ethoxy)methyl)piperidine-1-carboxylate using (3,5-difluorophenyl)lithium in Step 2.

Alternatively, (R)-tert-butyl 3-((R)-(2-aminoethoxy)(3-chlorophenyl)methyl)piperidine-1-carboxylate can be prepared by the following procedures:

overnight at room temperature. The solvent was removed under reduced pressure to give (R)-tert-butyl 3-((R)-(2-amino-2-oxoethoxy)(3-chlorophenyl)methyl)piperidine-1-carboxylate (902 mg, 100%), which was used for the next step without further purification. MS ESI +ve m/z 383 (M+H)$^+$.

Step 2: Preparation of (R)-tert-butyl 3-((R)-(2-aminoethoxy)(3-chlorophenyl)methyl)-piperidine-1-carboxylate To a solution of (R)-tert-butyl 3-((R)-(2-amino-2-oxoethoxy)(3-chlorophenyl)methyl)piperidine-1-carboxylate (902 mg, 2.36 mmol) in anhydrous toluene (30 mL) at 0° C. was added Red-Al® (65% solution in toluene, 1.4 mL, 7.07 mmol) slowly over 10 min. After the addition, the solution was stirred overnight at room temperature. The reaction was cooled to 0° C. and quenched with $Na_2SO_4 \cdot 10H_2O$. The resulting mixture was stirred for 2-3 h, filtered through Celite®, and washed with THF (200 mL). The filtrate was dried and concentrated to give crude product (R)-tert-butyl 3-((R)-(2-aminoethoxy)(3-chlorophenyl)methyl)piperidine-1-carboxylate (776 mg, 89%). MS ESI +ve m/z 369 (M+H)$^+$.

Preparation 29

(R)-tert-butyl 3-((R)-(5-fluoro-2-methylphenyl)(2-(methoxycarbonylamino)ethoxy)methyl)piperidine-1-carboxylate

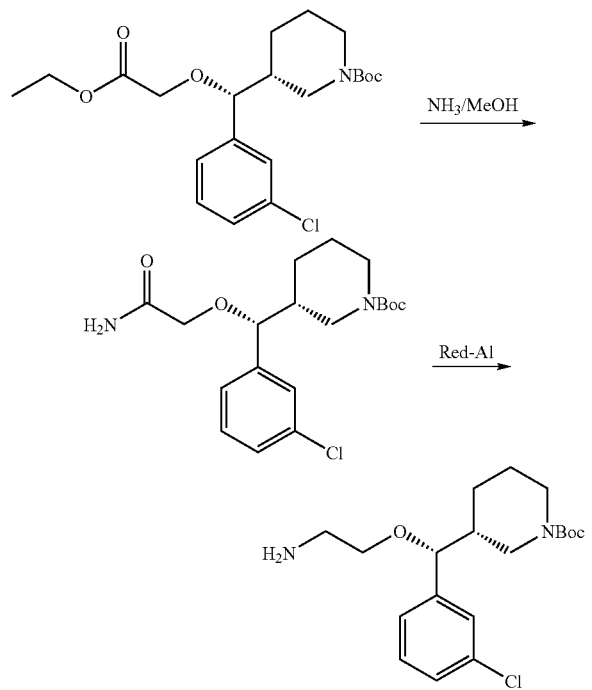

Step 1: Preparation of (R)-tert-butyl 3-((R)-(2-amino-2-oxoethoxy)(3-chlorophenyl)methyl)-piperidine-1-carboxylate (R)-tert-Butyl 3-((R)-(3-chlorophenyl)(2-ethoxy-2-oxoethoxy)methyl)-piperidine-1-carboxylate (0.971 g, 2.36 mmol) was dissolved in 7 M $NH_3$/MeOH (20 mL), and stirred

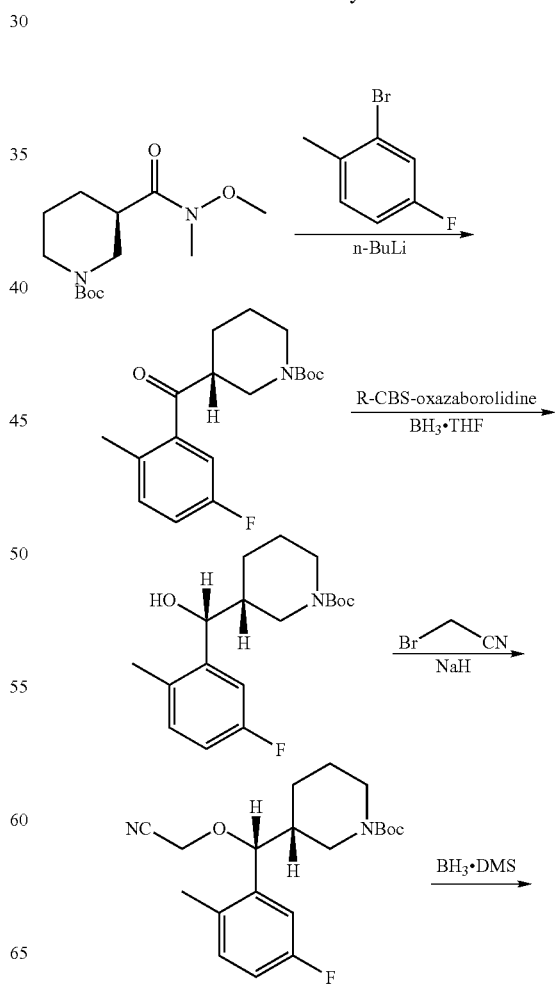

-continued

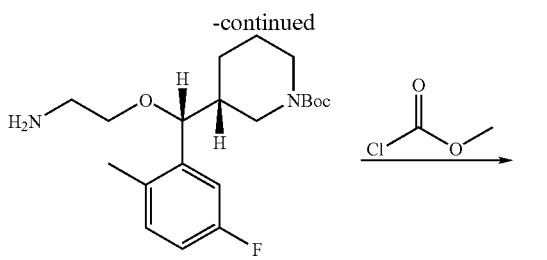

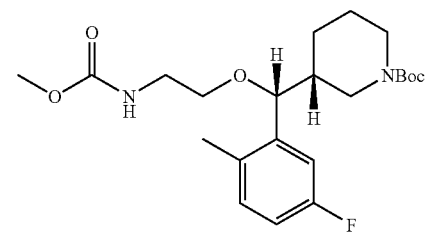

Step 1. (R)-tert-butyl 3-(5-fluoro-2-methylbenzoyl)piperidine-1-carboxylate

To a solution of 2-bromo-4-fluoro-1-methylbenzene (10.6 g, 0.056 mol) in anhydrous THF (150 mL) at −78° C. under nitrogen was added dropwise a solution of 2.5 M n-BuLi in hexane (22 mL, 0.056 mol). After stirring for 1 hr at −78° C., a solution of (R)-tert-butyl 3-(methoxy(methyl)carbamoyl)piperidine-1-carboxylate (10 g, 0.037 mol) in anhydrous THF (120 mL) was added dropwise, After addition, the reaction mixture was allowed to warm to rt and stirred for 2 hr. The mixture was quenched with saturated NH$_4$Cl (100 mL) solution and extracted with EtOAc (3×80 mL). The combined organic layers were washed with brine, dried over Na$_2$SO$_4$ and concentrated in vacuo to provide crude (R)-tert-butyl 3-(5-fluoro-2-methylbenzoyl)piperidine-1-carboxylate (10.5 g, yield 88%), which was used in the next step without purification.

Step 2. (R)-tert-butyl 3-((R)-(5-fluoro-2-methylphenyl)(hydroxy)methyl)piperidine-1-carboxylate To a solution of (R)-tert-butyl 3-(5-fluoro-2-methylbenzoyl)piperidine-1-carboxylate (10.5 g, 0.0336 mol) in anhydrous THF (150 mL) at −15° C. under nitrogen was added dropwise a solution of 1 M R-CBS-oxazaborolidine in toluene (3 mL, 3 mmol, 0.09 eq). After stirring for 1 hr at −15° C., a solution of 10 M BH$_3$ in THF (17 mL, 0.0336 mol, 1 eq) was added dropwise. After addition, the reaction mixture was stirred for 2 hr at −15° C. Methanol (80 mL) was added dropwise carefully at −15° C. The solvent was removed under reduced pressure, the residue was purified by column chromatography on silica gel eluting with AcOEt/hexane (1:30→1:15) to provide the light yellow oil (95 g, HPLC≧70%, ratio≧3:1). The mixture was dissolved in a minimum volume of EtOAc, the solvent was removed on the rotary evaporator until crystals appeared. The solution was cooled to rt and stood for 1-2 h. To the solution was added hexane and then filtered, the crystals were washed with cool hexane and re-crystallized an additional two times to afford the pure isomer (R)-tert-butyl 3-((R)-(5-fluoro-2-methylphenyl)(hydroxy)methyl)piperidine-1-carboxylate (3.2 g, ee≧99%). $^1$H NMR (CDCl$_3$) δ 7.1 (m, 2H), 6.85 (m, 1H), 4.7 (m, 1H), 2.3 (s, 3H), 1.45 (s, 9H), 1.25 (m, 4H).

Step 3. (R)-tert-butyl 3-((R)-(cyanomethoxy)(5-fluoro-2-methylphenyl)methyl)piperidine-1-carboxylate To a solution of (R)-tert-butyl 3-((R)-(5-fluoro-2-methylphenyl)(hydroxy)methyl)piperidine-1-carboxylate (1.2 g, 0.0037 mol) in MeCN (20 mL), NaH (0.27 g, 0.011 mol) was added at 0° C. The mixture was stirred for 1 hr followed by cooling to −40° C. and adding bromoacetonitrile (1.3 g, 0.011 mol) in portions. The mixture was stirred for 0.5 hour at −20° C. The reaction was quenched with H$_2$O. The mixture was extracted with CH$_2$Cl$_2$. The organic layer was dried by Na$_2$SO$_4$, concentrate to get the target molecule (R)-tert-butyl 3-((R)-(cyanomethoxy)(5-fluoro-2-methylphenyl)methyl)piperidine-1-carboxylate (1.2 g, 90%).

Step 4. (R)-tert-butyl 3-((R)-(2-aminoethoxy)(5-fluoro-2-methylphenyl)methyl)piperidine-1-carboxylate A solution of (R)-tert-butyl 3-((R)-(cyanomethoxy)(5-fluoro-2-methylphenyl)methyl)piperidine-1-carboxylate (1.8 g, 0.005 mol) in anhydrous THF (20 ml) was heated to reflux under nitrogen. A solution of BH$_3$.Me$_2$S in THF was added dropwise and stirring was continued under reflux overnight. When the resulting solution was cooled to rt, MeOH was added dropwise to quench the reaction. After evaporation of the solution, the crude product was purified by column chromatography to afford (R)-tert-butyl 3-((R)-(2-aminoethoxy)(5-fluoro-2-methylphenyl)methyl)piperidine-1-carboxylate (1.2 g, yield 66%).

Step 5. (R)-tert-butyl 3-((R)-(5-fluoro-2-methylphenyl)(2-(methoxycarbonylamino)ethoxy)methyl)piperidine-1-carboxylate To a solution of (R)-tert-butyl 3-((R)-(2-aminoethoxy)(5-fluoro-2-methylphenyl)methyl)piperidine-1-carboxylate (3.1 g, 8.5 mmol) and DMAP (0.54 g) in dry CH$_2$Cl$_2$ (45 mL), Et$_3$N (2.58 g, 3.6 mL) was added. The resulting mixture was cooled to 0-5° C. under ice-water bath, a solution of methyl chloroformate (4.0 g, 43 mmol, 5 eq) in dry CH$_2$Cl$_2$ (50 mL) was added dropwise. After addition, the reaction mixture was stirred for 1-2 h at 0-5° C. The reaction was quenched with water (50 mL). The aqueous layer was extracted with CH$_2$Cl$_2$ (3×30 mL), the combined organic layers were washed with 10% citric acid (2×50 mL) and brine, then dried over Na$_2$SO$_4$, filtered and concentrated to the crude product, which was purified by preparative HPLC to afford (R)-tert-butyl 3-((R)-(5-fluoro-2-methylphenyl)(2-(methoxycarbonylamino)ethoxy)methyl)piperidine-1-carboxylate (400 mg, HPLC≧98%). $^1$H NMR (CDCl$_3$) δ 7.2 (m, 1H), 7.1 (m, 1H), 6.9 (m, 1H), 4.4 (m, 1H), 4.1 (m, 1H), 3.7 (m, 1H), 3.6 (s, 3H), 3.2 (m, 2H), 2.9 (m, 2H), 2.3 (s, 3H), 1.75 (m, 1H), 1.6 (m, 1H), 1.4 (s, 9H), 1.25 (m, 2H).

Preparation 30

(R)-tert-butyl 3-((R)-(3-chloro-5-fluorophenyl)(2-(methoxycarbonylamino)ethoxy)methyl)piperidine-1-carboxylate

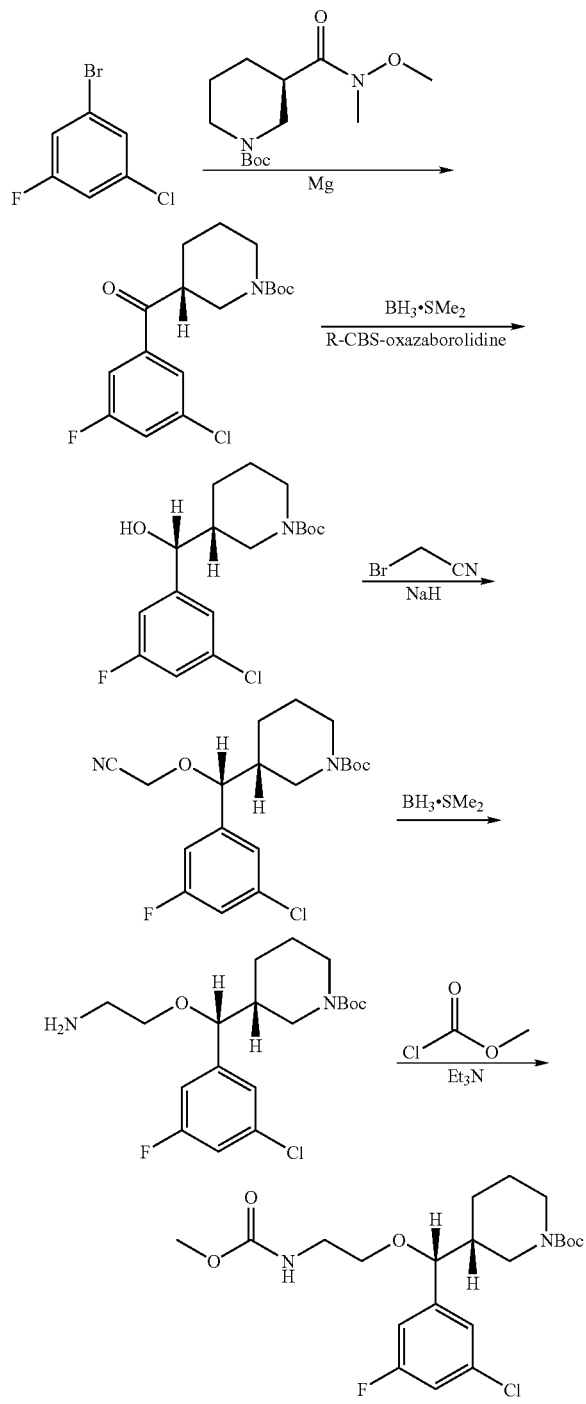

Step 1. (R)-tert-butyl 3-(3-chloro-5-fluorobenzoyl)piperidine-1-carboxylate

In a 2 L three-necked bottle flushed with $N_2$, Mg (26.5 g, 1.1 mol) was warmed to 50° C., 1-bromo-3-chloro-5-fluorobenzene (157 g, 0.75 mol) solution in anhydrous THF (1 L) was added dropwise, then the mixture was stirred at r.t. for 2 hr. To a solution of (R)-tert-butyl 3-(methoxy(methyl)carbamoyl)piperidine-1-carboxylate (120 g, 0.441 mol) in anhydrous THF (1.1 L) at −78° C. under nitrogen was added dropwise the above Grignard reagent. The reaction mixture was allowed to warm to rt and stirred for 2 h. The mixture was quenched with saturated $NH_4Cl$ solution (500 mL) and extracted with EtOAc (3×400 mL). The combined organic layer was washed with brine, dried over $Na_2SO_4$ and concentrated in vacuo to give (R)-tert-butyl 3-(3-chloro-5-fluorobenzoyl)piperidine-1-carboxylate (163 g), which was used immediately without further purification.

Step 2. (R)-tert-butyl 3-((R)-(3-chloro-5-fluorophenyl)(hydroxy)methyl)piperidine-1-carboxylate A mixture of 10 M $H_3B.S_2Me$ in THF (47.7 mL, 0.477 mol) and 1 M R-CBS-oxazaborolidine in toluene (72 mL, 0.072 mol) were dissolved in 100 mL anhydrous THF and cooled to −15° C. (R)-tert-butyl 3-(3-chloro-5-fluorobenzoyl)piperidine-1-carboxylate in 400 mL anhydrous THF was added dropwise to the above solution and stirred at −15° C. for 2 hr. The reaction was quenched with methanol (500 mL). The solvent was removed under reduced pressure and the residue was purified by column chromatography. The product was re-crystallized three times with EtOAc/Hexanes to give (R)-tert-butyl 3-((R)-(3-chloro-5-fluorophenyl)(hydroxy)methyl)piperidine-1-carboxylate (55 g, 0.156 mol). $^1$H NMR ($CDCl_3$, 400 MHz) δ7.10 (s, 1H), 7.04-6.90 (dd, 2H), 4.46-4.30 (d, 1H), 4.05-2.40 (m, 5H), 1.74 (s, 1H), 1.60 (s, 1H), 1.53-1.31 (m, 11H), 1.30-1.14 (m, 1H).

Step 3. (R)-tert-butyl 3-((R)-(3-chloro-5-fluorophenyl)(cyanomethoxy)methyl)piperidine-1-carboxylate A solution of (R)-tert-butyl 3-((R)-(3-chloro-5-fluorophenyl)(hydroxy)methyl)piperidine-1-carboxylate (55 g, 0.156 mol) in acetonitrile (1.2 L) was cooled to 0° C., NaH (19.2 g, 0.48 mol, 60% in oil) was added in portions, then the mixture was stirred at rt for 1 hr. The mixture was cooled to −20° C. and bromoacetonitrile (57.7 g, 0.48 mol) was added dropwise. After 0.5 hr, additional NaH (19.2 g, 0.48 mol, 60% in oil) and bromoacetonitrile (57.7 g, 0.48 mol) was added. TLC showed 80% of the starting material was reacted. The reaction was quenched with saturated $NH_4Cl$ solution (200 mL), water (1 L) was added. Acetonitrile was removed by reduced pressure, $CH_2Cl_2$ (1 L) was added, the aqueous layer was back extracted with $CH_2Cl_2$ (3×500 mL), dried over $Na_2SO_4$ and concentrated in vacuo to give the crude (R)-tert-butyl 3-((R)-(3-chloro-5-fluorophenyl)(cyanomethoxy)methyl)piperidine-1-carboxylate (90 g), which was used for the next step without further purification.

Step 4. (R)-tert-butyl 3-((R)-(2-aminoethoxy)(3-chloro-5-fluorophenyl)methyl)piperidine-1-carboxylate A solution of (R)-tert-butyl 3-((R)-(3-chloro-5-fluorophenyl)(cyanomethoxy)methyl)piperidine-1-carboxylate (90 g) in anhydrous THF (1.3 L), under protection of $N_2$, was heated to reflux followed by the dropwise addition of 10 M H₃B.SMe₂ in THF (70 mL, 0.7 mol). The mixture was stirred at reflux overnight. The reaction was quenched with MeOH (500 mL) and the solvent removed in vacuo, the residue was purified by column chromatography to give (R)-tert-butyl 3-((R)-(2-aminoethoxy)(3-chloro-5-fluorophenyl)methyl) piperidine-1-carboxylate (24 g, 0.062 mol).

Step 5. (R)-tert-butyl 3-((R)-(3-chloro-5-fluorophenyl)(2-(methoxycarbonylamino)ethoxy)methyl)piperidine-1-carboxylate A solution of (R)-tert-butyl 3-((R)-(2-aminoethoxy)(3-chloro-5-fluorophenyl)methyl)piperidine-1-carboxylate (24 g, 0.062 mol) in dry CH₂Cl₂ (300 mL) and Et₃N (31.4 g, 43 mL) was cooled to 0° C. in ice-water bath, a solution of methyl chloroformate (11.8 g, 0.124 mol) in dry CH₂Cl₂ (100 mL) was added dropwise. After addition, the reaction mixture was stirred for 1-2 h at 0-5° C. Water (200 mL) was added to quench the reaction. The aqueous layer was extracted with CH₂Cl₂ (3×100 mL), the combined organic layers were washed with 10% citric acid (2×80 mL) and brine, then dried over Na₂SO₄, filtered and concentrated to give the crude product, which was purified by column chromatography to give (R)-tert-butyl 3-((R)-(3-chloro-5-fluorophenyl)(2-(methoxycarbonylamino)ethoxy)methyl)piperidine-1-carboxylate (19 g, 0.043 mol). ¹H NMR (CD₃OD) δ 7.17 (s, 1H), 7.16-7.08 (m, 1H), 7.07-7.00 (m, 1H), 4.20-4.00 (m, 2H), 3.90-3.78 (d, 1H), 3.61 (s, 3H), 3.28-3.20 (m, 2H), 2.92-2.68 (dd, 2H), 1.52-1.74 (m, 2H), 1.42 (s, 9H), 1.35-1.10 (m, 3H).

Preparation 31

(R)-tert-butyl 3-((R)-(3-fluorophenyl)(2-(methoxycarbonylamino)ethoxy)methyl)piperidine-1-carboxylate

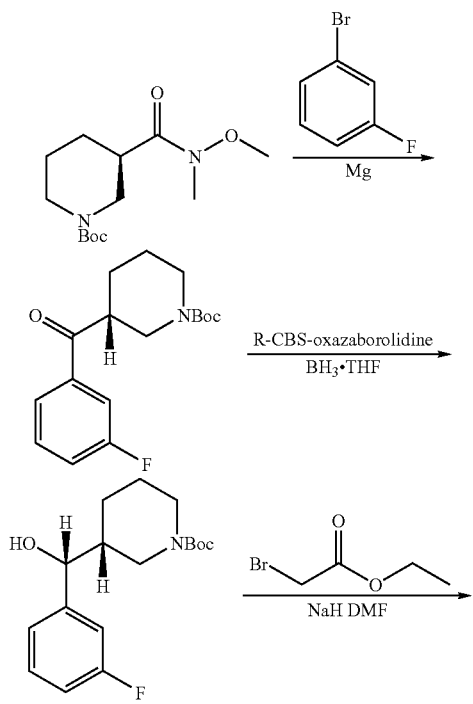

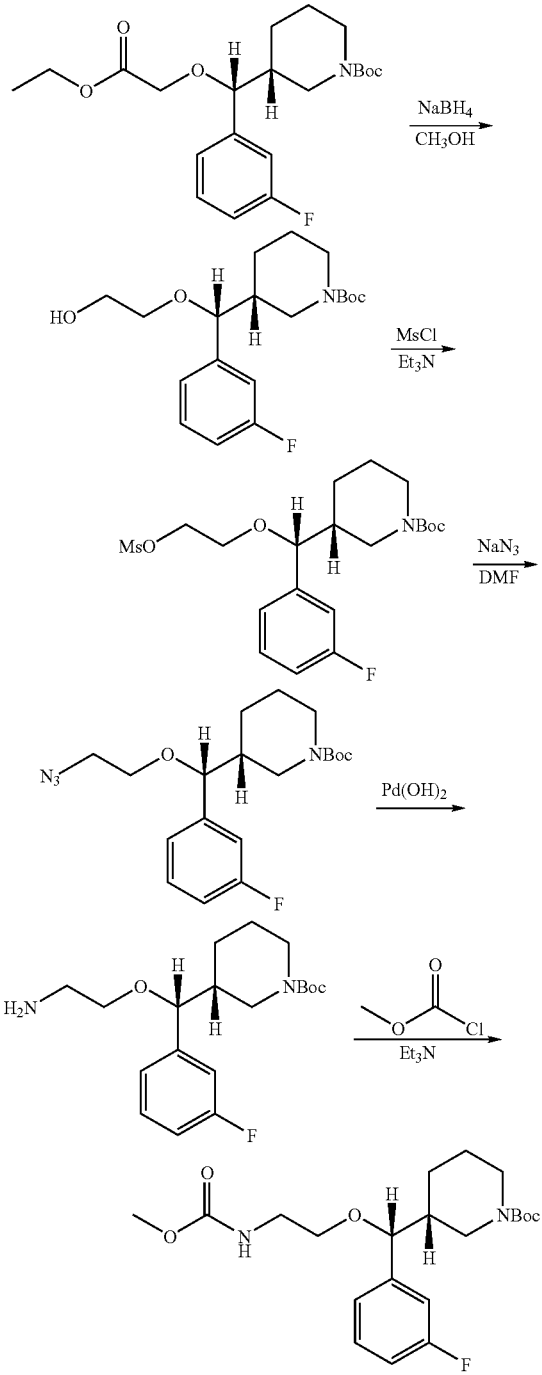

Step 1. (R)-tert-butyl 3-(3-fluorobenzoyl)piperidine-1-carboxylate

A solution of 1-bromo-3-fluoro-benzene (57.7 g, 0.33 mol) in anhydrous THF (480 mL) was added dropwise to Mg (10.6 g, 0.44 mol) at rt under nitrogen. The mixture was stirred at 50-60° C. for 1 hr. The resulting Grignard reagent was used for the next step. The Grignard reagent was added dropwise to a solution of (R)-tert-butyl 3-(methoxy(methyl)carbamoyl) piperidine-1-carboxylate (60 g, 0.22 mol) in anhydrous THF (600 mL) at −78° C. under nitrogen. After addition, the mixture was allowed to stir at rt for 1.5 hr. The mixture was quenched with saturated NH$_4$Cl solution (300 mL) and extracted with EtOAc (3×200 mL). The combined organic layers were washed with brine, dried over Na$_2$SO$_4$ and concentrated in vacuo to give crude (R)-tert-butyl 3-(3-fluorobenzoyl)piperidine-1-carboxylate (67.5 g, 100%), which was used immediately in the next step without purification.

Step 2. (R)-tert-butyl 3-((R)-(3-fluorophenyl)(hydroxy)methyl)piperidine-1-carboxylate To a solution of 1 M R-CBS-oxazaborolidine in toluene (33 mL, 33 mmol, 0.15 eq) and 10 M BH$_3$ in THF (22 mL, 0.22 mol, 1.0 eq) at −15° C. under nitrogen was added dropwise a solution of (R)-tert-butyl 3-(3-fluorobenzoyl)piperidine-1-carboxylate (67.5 g, 0.22 mol) in anhydrous THF (300 mL). After addition, the reaction mixture was stirred for 1 hr at rt. Methanol (200 mL) was added dropwise carefully at 0° C. The solvent was removed under reduced pressure to provide the crude product. The crude product was dissolved in EtOAc until the alcohol was just dissolved (about 5 mL/1 g), the solvent was removed on the rotary evaporator until a few crystals appeared. To the above solution was added petroleum ether (about 300 mL) under stirring, which was allowed to stir at rt for 2 hr and then filtered, the crystals were washed with petroleum ether and re-crystallized to afford the pure R)-tert-butyl 3-((R)-(3-fluorophenyl)(hydroxy)methyl)piperidine-1-carboxylate (26 g, 39%).

Step 3. (R)-tert-butyl 3-((R)-(2-ethoxy-2-oxoethoxy)(3-fluorophenyl)methyl)piperidine-1-carboxylate To a suspension of NaH (4.8 g, 120 mmol) in THF (400 mL) at 0-5° C. was added dropwise a solution of (R)-tert-butyl 3-((R)-(2-ethoxy-2-oxoethoxy)(3-fluorophenyl)methyl)piperidine-1-carboxylate (30.9 g, 100 mmol) in anhydrous THF (100 mL), the reaction mixture was stirred for 1 hr at rt. A solution of ethyl bromoacetate (20.04 g, 13.40 mL, 120 mmol) in anhydrous THF (100 mL) was added dropwise to the above mixture, and the reaction was heated to reflux for 3-5 hr. The reaction mixture was poured into saturated aqueous NH$_4$Cl, then extracted with EtOAc (3×100 mL). The organic layer was washed with water (3×100 mL) and brine, dried over Na$_2$SO$_4$, filtered and concentrated in vacuo to afford crude (R)-tert-butyl 3-((R)-(2-ethoxy-2-oxoethoxy)(3-fluorophenyl)methyl)piperidine-1-carboxylate (29.88 g 76%), which was used for next step without purification.

Step 4. (R)-tert-butyl 3-((R)-(3-fluorophenyl)(2-hydroxyethoxy)methyl)piperidine-1-carboxylate To a solution of (R)-tert-butyl 3-((R)-(2-ethoxy-2-oxoethoxy)(3-fluorophenyl)methyl)piperidine-1-carboxylate (29.88 g, 75.9 mmol) in MeOH (300 mL) was added NaBH$_4$ (23 g, 605.2 mmol) in portions while the temperature was lower than 40° C. After addition, the mixture was stirred at rt for 2-3 hr. The solvent was removed in vacuo to give a residue which was partitioned between water and EtOAc. The organic layer was washed with H$_2$O and brine, dried over Na$_2$SO$_4$, filtered and concentrated in vacuo. The residue was purified on silica gel chromatography to afford (R)-tert-butyl 3-((R)-(3-fluorophenyl)(2-hydroxyethoxy)methyl)piperidine-1-carboxylate (11 g, 41%).

Step 5. (R)-tert-butyl 3-((R)-(3-fluorophenyl)(2-(methylsulfonyloxy)ethoxy)methyl)piperidine-1-carboxylate To a solution of (R)-tert-butyl 3-((R)-(3-fluorophenyl)(2-hydroxyethoxy)methyl)piperidine-1-carboxylate (11 g, 31.16 mmol) in dry CH$_2$Cl$_2$ (140 mL) was added Et$_3$N (12.60 g, 16.68 mL, 124.65 mmol, 4 eq) at −5-0° C. Then a solution of MsCl (7.1 g, 4.72 mL, 62.32 mmol, 2 eq) in dry CH$_2$Cl$_2$ (40 mL) was added dropwise at the same temperature. After addition, it was allowed to warm to rt gradually. Water (100 mL) was added. The aqueous layer was extracted with CH$_2$Cl$_2$ (3×80 mL), the combined organic layers was washed with 10% citric acid, sat. NaHCO$_3$ and brine, then dried over Na$_2$SO$_4$, filtered and concentrated to give (R)-tert-butyl 3-((R)-(3-fluorophenyl)(2-(methylsulfonyloxy)ethoxy)methyl)piperidine-1-carboxylate (13.8 g), which was used in the next step without purification.

Step 6. (R)-tert-butyl 3-((R)-(2-azidoethoxy)(3-fluorophenyl)methyl)piperidine-1-carboxylate (R)-tert-Butyl 3-((R)-(3-fluorophenyl)(2-(methylsulfonyloxy)ethoxy)methyl)piperidine-1-carboxylate (13.8 g, 32 mmol) was dissolved into anhydrous DMF (150 mL), solid NaN$_3$ (6.1 g, 96 mmol, 3 eq) was added and the reaction mixture was heated to 80° for overnight. The reaction mixture was cooled to rt and then was added with EtOAc (500 mL), the organic phase was washed with water (3×100 mL) and brine (2×80 mL), dried over Na$_2$SO$_4$ and concentrated in vacuo to give crude (R)-tert-butyl 3-((R)-(2-azidoethoxy)(3-fluorophenyl)methyl)piperidine-1-carboxylate (12 g), which was used in the next step without further purification.

Step 7. (R)-tert-butyl 3-((R)-(2-aminoethoxy)(3-fluorophenyl)methyl)piperidine-1-carboxylate A suspension of (R)-tert-butyl 3-((R)-(2-azidoethoxy)(3-fluorophenyl)methyl)piperidine-1-carboxylate (12 g, 31.75 mmol) and Pd(OH)$_2$/C (1.2 g) in MeOH (240 ml) was stirred under H$_2$ for 1 hr. The mixture was filtered and evaporated under reduced pressure to give desired (R)-tert-butyl 3-((R)-(2-aminoethoxy)(3-fluorophenyl)methyl)piperidine-1-carboxylate (10 g).

Step 8. (R)-tert-butyl 3-((R)-(3-fluorophenyl)(2-(methoxycarbonylamino)ethoxy)methyl)piperidine-1-carboxylate To a solution of (R)-tert-butyl 3-((R)-(2-aminoethoxy)(3-fluorophenyl)methyl)piperidine-1-carboxylate (10 g, 28.41 mmol) and DMAP (1.8 g, 14.21 mmol, 0.5 eq) in dry CH$_2$Cl$_2$ (150 mL), Et$_3$N (8.62 g, 11.42 mL, 85.23 mmol) was added. The resulting mixture was cooled to 0-5° C. under ice-water bath, a solution of methyl chloroformate (10.95 mL, 142.05 mmol, 5 eq) in dry CH$_2$Cl$_2$ (60 mL) was added dropwise. After addition, the reaction mixture was stirred for 1-2 hr at 0-5° C. Water (80 mL) was added to quench the reaction. The aqueous layer was extracted with CH$_2$Cl$_2$ (3×50 mL), the combined organic layers were washed with 10% citric acid (2×80 mL) and brine, then dried over Na$_2$SO$_4$, filtered and concentrated to the crude product, which was purified by silica gel to afford (R)-tert-butyl 3-((R)-(3-fluorophenyl)(2-(methoxycarbonylamino)ethoxy)methyl)piperidine-1-carboxylate (11.3 g, 97%).

Preparation 32

(R)-tert-butyl 3-((R)-(5-chloro-2-methylphenyl)(2-(methoxycarbonylamino)ethoxy)methyl)piperidine-1-carboxylate

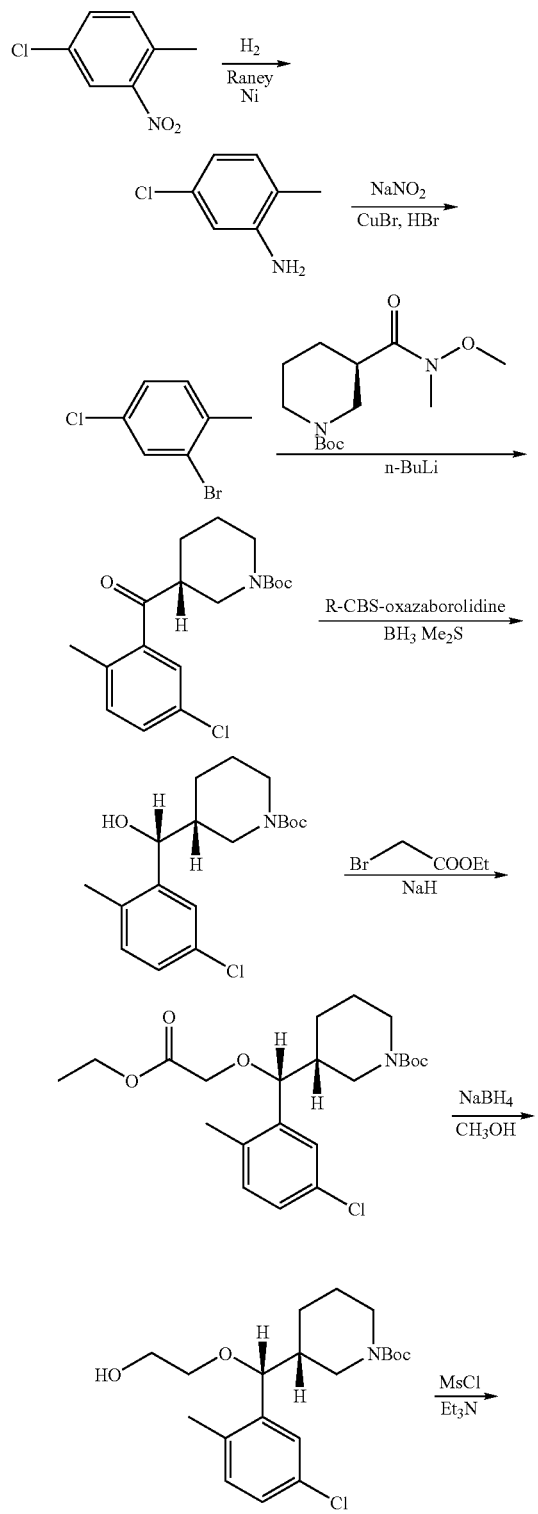

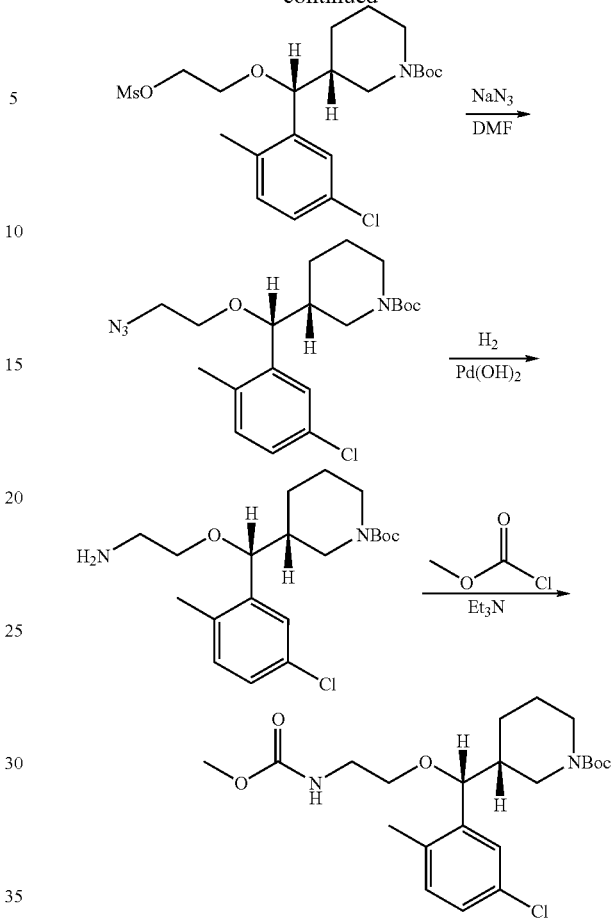

Step 1. 5-chloro-2-methylbenzenamine

A 2 L flask was charged the solution of 4-chloro-1-methyl-2-nitrobenzene (60 g, 0.35 mol) in MeOH (1 L), Raney Ni was added, the air in flask was replaced three times with $H_2$, the mixture was stirred for 3 hr at rt. The solution was filtered and concentrated. The residue was dissolved in $CH_2Cl_2$ (500 mL), and the solution was washed with brine, dried over $Na_2SO_4$. Solvent removal gave 5-chloro-2-methylbenzenamine (50 g, 0.35 mol). $^1$H NMR (CDCl$_3$, 400 MHz) δ 7.02-6.93 (d, 2H), 6.70-6.60 (d, 2H), 3.67 (s, 2H), 2.14 (s, 3H).

Step 2. 2-bromo-4-chloro-1-methylbenzene 5-chloro-2-methylbenzenamine (50 g, 0.355 mol) was dissolved in HBr solution (1.5 M, 100 mL) and cooled to 0° C., a solution of NaNO$_2$ (27.6 g, 0.4 mol) in water (200 mL) was added dropwise. After addition, the mixture was stirred for 1 hr. In another flask CuBr (30 g, 0.21 mol) was added to HBr solution (1.5 M, 30 mL) and heated to 60° C., then the mixture was added to the above solution. The mixture was heated to reflux for 1 hr then cooled to rt. The reaction was quenched with water (500 mL), the aqueous layer was extracted 3 times with $CH_2Cl_2$, dried over Na$_2$SO$_4$, solvent removal and purification by column chromatography afforded 2-bromo-4-chloro-1-methylbenzene (53 g, 0.26 mol). $^1$H NMR (CDCl$_3$, 400 MHz) δ 7.53 (s, 1H), 7.20-7.10 (m, 2H), 2.36 (s, 3H).

Step 3. (R)-tert-butyl 3-(5-chloro-2-methylbenzoyl)piperidine-1-carboxylate

To a solution of 2-bromo-4-chloro-1-methylbenzene (53 g, 0.26 mol) in anhydrous THF (600 mL) at −78° C. under nitrogen was added dropwise a solution of 2.5 M n-BuLi in hexane (103 mL, 0.26 mol). After stirring for 1 hr at −78° C., a solution of the (R)-tert-butyl 3-(methoxy(methyl)carbamoyl)piperidine-1-carboxylate (67 g, 0.246 mol) in anhydrous THF (300 mL) was added dropwise. After addition, the reaction mixture was allowed to warm to rt and stirred for 2 hr. The mixture was quenched with saturated $NH_4Cl$ solution (500 mL) and extracted with EtOAc (3×400 mL). The combined organic layers were washed with brine, dried over $Na_2SO_4$ and concentrated in vacuo to give crude (R)-tert-butyl 3-(5-chloro-2-methylbenzoyl)piperidine-1-carboxylate (86 g), which was used immediately in the next step without purification.

Step 4. (R)-tert-butyl 3-((R)-(5-chloro-2-methylphenyl)(hydroxy)methyl)piperidine-1-carboxylate A mixture of 10 M $BH_3.Me_2S$ in THF (25.4 mL, 0.254 mol) and 1 M R-CBS-oxazaborolidine in toluene (38 mL, 0.038 mol) were dissolved in 100 mL anhydrous THF and cooled to −15° C. (R)-tert-butyl 3-(5-chloro-2-methylbenzoyl)piperidine-1-carboxylate in 200 mL anhydrous THF was added dropwise to the above solution and stirred at −15° C. for 2 hr. The reaction was quenched with methanol (300 mL). The solvent was removed under reduced pressure, and the residue was purified by column chromatography to give (R)-tert-butyl 3-((R)-(5-chloro-2-methylphenyl)(hydroxy)methyl)piperidine-1-carboxylate (32 g), which contained 30% isomer.

Step 5. (R)-tert-butyl 3-((R)-(5-chloro-2-methylphenyl)(2-ethoxy-2-oxoethoxy)methyl)piperidine-1-carboxylate To a suspension of NaH (5.64 g, 0.141 mol) in the mixed solvent of DMF (70 mL) and THF (70 mL) at −25° C. was added dropwise a solution of (R)-tert-butyl 3-((R)-(5-chloro-2-methylphenyl)(hydroxy)methyl)piperidine-1-carboxylate (16 g, 47 mmol) in anhydrous THF (100 mL), the reaction mixture was stirred for 1 hr at rt. A solution of ethyl bromoacetate (15.6 g, 94 mmol) in anhydrous THF (70 mL) was added dropwise to the above mixture at −10−−5° C. After addition, the reaction mixture was stirred for 2-3 hr at rt. The reaction was quenched with saturated $NH_4Cl$ solution (100 mL) and EtOAc (500 mL) was added. The organic layer was washed with water (5×50 mL) and brine, dried over $Na_2SO_4$, filtered and concentrated in vacuo. The residue was purified by column chromatography to afford (R)-tert-butyl 3-((R)-(5-chloro-2-methylphenyl)(2-ethoxy-2-oxoethoxy)methyl)piperidine-1-carboxylate (8 g, 18.8 mmol).

Step 6. (R)-tert-butyl 3-((R)-(5-chloro-2-methylphenyl)(2-hydroxyethoxy)methyl)piperidine-1-carboxylate To a solution of (R)-tert-butyl 3-((R)-(5-chloro-2-methylphenyl)(2-ethoxy-2-oxoethoxy)methyl)piperidine-1-carboxylate (8 g, 18.8 mmol) in MeOH (300 mL) was added $NaBH_4$ (5.6 g, 0.15 mol) in portions while the temperature was lower than 40° C. After addition, the mixture was stirred overnight. The solvent was removed in vacuo to the residue, which was partitioned between water and EtOAc. The organic layer was washed with $H_2O$ and brine, dried over $Na_2SO_4$ and evaporated to give crude (R)-tert-butyl 3-((R)-(5-chloro-2-methylphenyl)(2-hydroxyethoxy)methyl)piperidine-1-carboxylate (7 g), which was used in the next step without purification.

Step 7. (R)-tert-butyl 3-((R)-(5-chloro-2-methylphenyl)(2-(methylsulfonyloxy)ethoxy)methyl)piperidine-1-carboxylate To a solution of (R)-tert-butyl 3-((R)-(5-chloro-2-methylphenyl)(2-hydroxyethoxy)methyl)piperidine-1-carboxylate (7 g, 18.3 mmol) in dry $CH_2Cl_2$ (100 mL) was added $Et_3N$ (54 g, 10 mL, 0.73 mmol) at −5-0° C. Then a solution of MsCl (4.2 g, 36.5 mmol) in dry $CH_2Cl_2$ (50 mL) was added dropwise at the same temperature. After addition, it was allowed to warm to rt gradually. The reaction mixture was washed with 10% citric acid solution (30 mL), $NaHCO_3$ and brine, then dried over $Na_2SO_4$, filtered and concentrated to give (R)-tert-butyl 3-((R)-(5-chloro-2-methylphenyl)(2-(methylsulfonyloxy)ethoxy)methyl)piperidine-1-carboxylate (8.4 g), which was used in the next step without purification.

Step 8. (R)-tert-butyl 3-((R)-(2-azidoethoxy)(5-chloro-2-methylphenyl)methyl)piperidine-1-carboxylate (R)-tert-butyl 3-((R)-(5-chloro-2-methylphenyl)(2-(methylsulfonyloxy)ethoxy)methyl)piperidine-1-carboxylate (8.4 g, 18.3 mmol) was dissolved in anhydrous DMF (150 mL), solid $NaN_3$ (3.56 g, 54.8 mmoL) was added and the reaction mixture was heated to 60° C. for overnight. The reaction mixture was cooled to rt and diluted with EtOAc (500 mL), the organic phase was washed with water (5×50 mL) and brine (100 mL), dried over $Na_2SO_4$ and concentrated in vacuo to give (R)-tert-butyl 3-((R)-(2-azidoethoxy)(5-chloro-2-methylphenyl)methyl)piperidine-1-carboxylate (7 g).

Step 9. (R)-tert-butyl 3-((R)-(2-aminoethoxy)(5-chloro-2-methylphenyl)methyl)piperidine-1-carboxylate (R)-tert-butyl 3-((R)-(2-azidoethoxy)(5-chloro-2-methylphenyl)methyl)piperidine-1-carboxylate (7 g, 17.1 mmoL) was dissolved in EtOAc (300 mL), 0.8 g of $Pd(OH)_2$ was added and the air in bottle was replaced 3 times with $H_2$, the reaction was stirred at rt for 3 hr. The solution was filtered and concentrated to give (R)-tert-butyl 3-((R)-(2-aminoethoxy)(5-chloro-2-methylphenyl)methyl)piperidine-1-carboxylate (6.2 g), which was used in the next step without further purification.

Step 10. (R)-tert-butyl 3-((R)-(5-chloro-2-methylphenyl)(2-(methoxycarbonylamino)ethoxy)methyl)piperidine-1-carboxylate To a solution of (R)-tert-butyl 3-((R)-(2-aminoethoxy)(5-chloro-2-methylphenyl)methyl)piperidine-1-carboxylate (6.2 g, 16.2 mmol) and DMAP (0.2 g, 1.62 mmol) in dry $CH_2Cl_2$ (70 mL), $Et_3N$ (8 g, 81 mmol) was added. The resulting mixture was cooled to 0-5° C. in ice-water bath, a solution of methyl chloroformate (3.1 g, 32.4 mmol) in dry $CH_2Cl_2$ (30 mL) was added dropwise. After addition, the reaction mixture was stirred for 1-2 hr at 0-5° C. The reaction was quenched with water. The aqueous layer was extracted with $CH_2Cl_2$ (3×30 mL), the combined organic layers were washed with brine, then dried over $Na_2SO_4$, filtered and concentrated to give the crude product, which was firstly purified by column chromatography and then by preparative HPLC to give (R)-tert-butyl 3-((R)-(5-chloro-2-methylphenyl)(2-(methoxycarbonylamino)ethoxy)methyl)piperidine-1-carboxylate (1.5 g). $^1$H NMR (CD$_3$OD, 400 MHz) δ 7.30 (s, 1H), 7.20-7.10 (d, 2H), 4.81 (s, 1H), 4.46-4.30 (d, 1H), 4.29-4.15 (d, 1H), 3.95-3.83 (d, 1H), 3.62 (s, 3H), 3.30 (s, 4H), 2.90-2.65 (dd, 2H), 2.30 (s, 3H), 1.70 (s, 1H), 1.59 (s, 1H), 1.41 (s, 9H), 1.35-1.20 (m, 3H).

Preparation W1

2,2-dimethyl-4-(((R)-tetrahydro-2H-pyran-3-yl)methyl)oxazolidine

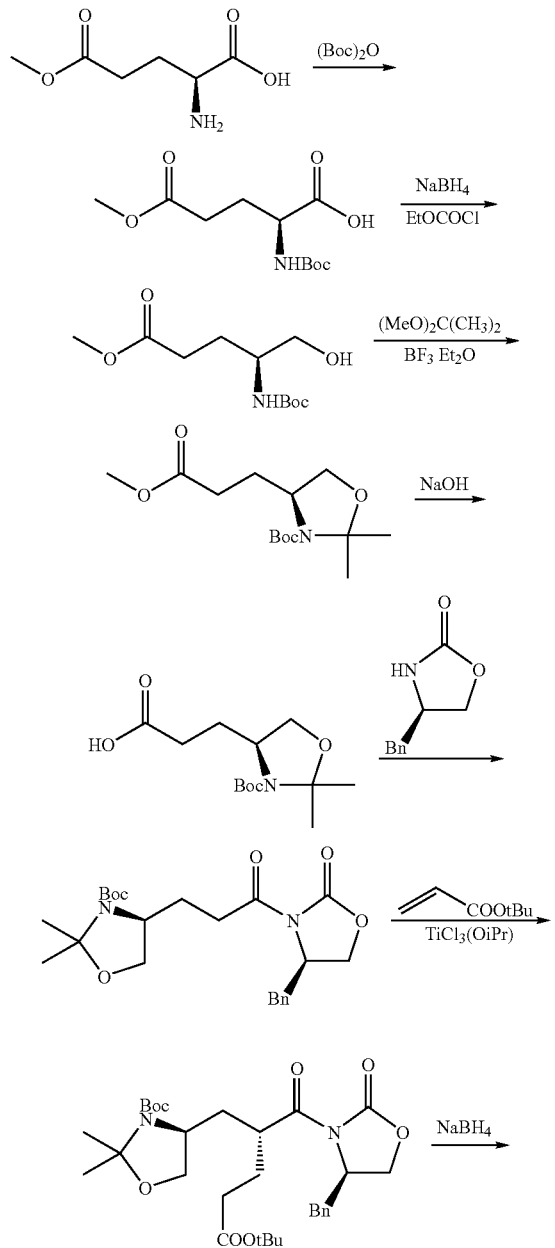

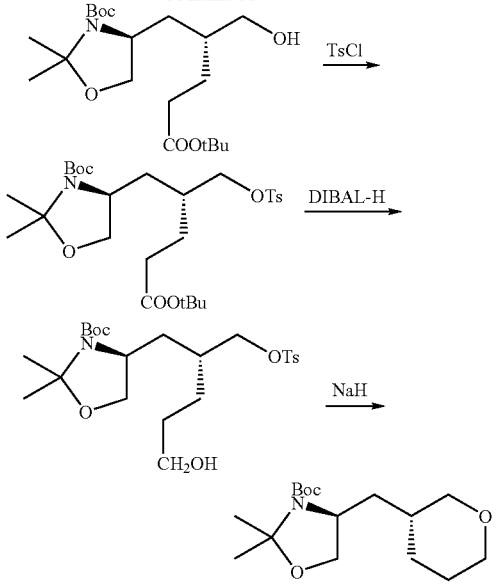

Step 1. (S)-2-(tert-butoxycarbonylamino)-5-methoxy-5-oxopentanoic acid

To a round bottom flask, Et$_3$N (303 g, 3 mol) was added dropwise to a stirred solution of Boc$_2$O (261.6 g, 1.2 mol) and 2-amino-pentanedioic acid 5-methyl ester (161 g, 1 mol) in water (800 ml) and dioxane (800 ml). After 18 hr the solution was extracted with petroleum ether (2×1000 ml) and the aqueous phase was cooled on ice and carefully acidified to pH 3 by slow addition of 10% citric acid solution. The urethane was then extracted into EtOAc (3×1000 ml) and the combined extracts were washed with brine, then dried (Na$_2$SO$_4$), filtered and concentrated under reduced pressure to give (S)-2-(tert-butoxycarbonylamino)-5-methoxy-5-oxopentanoic acid (238 g, 91.2%), which was used without further purification.

Step 2. (S)-methyl 4-(tert-butoxycarbonylamino)-5-hydroxypentanoate

To a stirred solution of (S)-2-(tert-butoxycarbonylamino)-5-methoxy-5-oxopentanoic acid (35.2 g, 0.135 mol) in THF (500 mL) at −10° C. was added N-methylmorpholine (15 mL, 0.135 mol) followed by ethyl chloroformate (14.72 g, 0.135 mol). After 10 min, NaBH$_4$ (15.37 g, 0.405 mol) was added in one portion. MeOH (1200 mL) was then added dropwise to the mixture over a period of 20 min at 0° C. The solution was stirred for an additional 20 min and then neutralized with 1M KHSO$_4$. The organic solvent was removed and the aqueous layer was extracted with EtOAc (3×500 ml). The combined organic phases were washed consecutively with 1M KHSO$_4$ (300 mL), H$_2$O (300 mL), 5% aqueous NaHCO$_3$ (300 mL), and dried (Na$_2$SO$_4$). The solvent was evaporated to give a residue, which was purified by column chromatography to give the desired (S)-methyl 4-(tert-butoxycarbonylamino)-5-hydroxypentanoate (24 g, 72%)

Step 3. (S)-tert-butyl 4-(3-methoxy-3-oxopropyl)-2,2-dimethyloxazolidine-3-carboxylate (S)-methyl 4-(tert-butoxycarbonylamino)-5-hydroxypentanoate (24 g, 97.2 mmol) and isopropenyl methyl ether (88.8 g, 854.6 mmol) was dissolved in acetone (2000 mL) and BF$_3$·Et$_2$O (0.82 mL, 5.84 mmol) was added at rt. The mixture was stirred for 1 hr at rt. The reaction was quenched by addition of Et$_3$N (11.6 mL). The reaction solution was washed with aqueous saturated NaHCO$_3$ (200 mL) and evaporated, and (S)-tert-butyl 4-(3-methoxy-3-oxopropyl)-2,2-dimethyloxazolidine-3-carboxylate (25.1 g, 90%) was obtained as an oil, which was used in the next step without further purification.

Step 4. (S)-3-(3-(tert-butoxycarbonyl)-2,2-dimethyloxazolidin-4-yl)propanoic acid An aqueous solution of sodium hydroxide (195 mL, 4.0 M in H$_2$O, 0.261 mol, 3.0 eq) was added to a solution of (S)-tert-butyl 4-(3-methoxy-3-oxopropyl)-2,2-dimethyloxazolidine-3-carboxylate (25.1 g, 0.087 mol), and the resulting cloudy reaction mixture was stirred at 23° C. for 3.5 hr. The mixture was concentrated under reduced pressure to ~50 mL volume and then was partitioned between 0.5 M HCl (360 ml) and EtOAc (2×360 ml). The combined organic layers were dried over Na$_2$SO$_4$ and were filtered. The filtrate was concentrated under reduced pressure to give (S)-3-(3-(tert-butoxycarbonyl)-2,2-dimethyloxazolidin-4-yl)propanoic acid (21.6 g, 91%), which was used without further purification.

Step 5. (S)-tert-butyl 2,2-dimethyl-4-(3-((R)-4-methyl-2-oxooxazolidin-3-yl)-3-oxopropyl)oxazolidine-3-carboxylate A 2000 mL flask was charged with (S)-3-(3-(tert-butoxycarbonyl)-2,2-dimethyloxazolidin-4-yl)propanoic acid (21.6 g, 79 mmol) and 750 mL of dry THF. The solution was cooled to 0° C., then triethylamine (23.94 g, 237 mmol, 3.0 equiv) and pivaloyl chloride (9.76 mL, 79 mmol, 1.0 equiv) were sequentially added. The solution was stirred for 4 hr at 0° C. After this time (R)-4-benzyl-2-oxalozolidinone (13.26 g, 75.2 mmol, 0.95 equiv) and dried LiCl (3.68 g, 86.4 mmol, 1.1 equiv) were added and the reaction was allowed to stir for 13 hr with concomitant warming to ambient temperature. After this time 560 mL of 0.5 M HCl was added, the mixture was transferred to a separatory funnel and the layers were separated. The aqueous layer was extracted with EtOAc (3×370 mL), and the combined organic layers washed with 10% K$_2$CO$_3$ (2×370 mL), and brine (2×370 mL), then dried over Na$_2$SO$_4$, and evaporated. The crude material was purified by flash chromatography, eluting with 0-29% EtOAc in hexanes. This afforded 26.3 g (81%) of (S)-tert-butyl 2,2-dimethyl-4-(3-((R)-4-methyl-2-oxooxazolidin-3-yl)-3-oxopropyl)oxazolidine-3-carboxylate as a clear syrup.

Step 6. (S)-tert-butyl 4-((R)-5-tert-butoxy-2-((R)-4-methyl-2-oxooxazolidine-3-carbonyl)-5-oxopentyl)-2,2-dimethyloxazolidine-3-carboxylate At 0° C., 1.0M TiCl$_4$ in CH$_2$Cl$_2$ solution (8.55 mL, 0.7 eq) was added to CH$_2$Cl$_2$ (100 mL) followed by the addition of 1.0M TiCl(Oi-Pr)$_3$ in hexanes solution (4.28 mL, 0.35 eq) and stirred 5 min DIPEA (2.87 mL, 1.35 eq) was added and stirred 15 min. A solution of (S)-tert-butyl 2,2-dimethyl-4-(3-((R)-4-methyl-2-oxooxazolidin-3-yl)-3-oxopropyl)oxazolidine-3-carboxylate (5.28 g, 12.22 mmol) in CH$_2$Cl$_2$ (50 mL) was added. The reaction mixture was stirred 1 hr at 0° C. To the solution, t-butylacrylate (2.22 mL, 1.25 eq) was added and the mixture was left stirred over 48 hr with concomitant warming to rt. The mixture was concentrated, partitioned between EtOAc (300 mL) and 1% HCl solution (100 mL). The organic layer was washed with sat. NaHCO$_3$ solution (60 mL), brine (60 mL), dried over Na$_2$SO$_4$. After filtration and concentration, the residue was purified by ISCO (120 g column, 0→35% EtOAc in Hexanes gradient) to afford 4.12 g (60%) (S)-tert-butyl 4-((R)-5-tert-butoxy-2-((R)-4-methyl-2-oxooxazolidine-3-carbonyl)-5-oxopentyl)-2,2-dimethyloxazolidine-3-carboxylate as a yellowish solid. MS ESI +ve m/z 583 (M+Na).

Step 7. (S)-tert-butyl 4-((R)-5-tert-butoxy-2-(hydroxymethyl)-5-oxopentyl)-2,2-dimethyloxazolidine-3-carboxylate (S)-tert-butyl 4-((R)-5-tert-butoxy-2-((R)-4-methyl-2-oxooxazolidine-3-carbonyl)-5-oxopentyl)-2,2-dimethyloxazolidine-3-carboxylate (4.12 g, 7.36 mmol) was dissolved in 4:1 THF and methanol (200 mL) and cooled to 0° C. Sodium borohydride (557 mg, 2 eq) was added slowly. After 10 min., the mixture was warmed up to rt slowly. The mixture was stirred 2 hr at rt. The mixture was concentrated, redissolved in EtOAc (300 mL), washed with 1% HCl solution (100 mL), brine (60 mL), and dried over Na$_2$SO$_4$. After filtration and concentration, the residue was purified by ISCO (40 g column, 10-65% EtOAc in Hexanes gradient, check TLC with Ninhydrin stain) to afford 2.86 g of (S)-tert-butyl 4-((R)-5-tert-butoxy-2-(hydroxymethyl)-5-oxopentyl)-2,2-dimethyloxazolidine-3-carboxylate as a white solid. MS ESI +m/v 410 (M+Na).

Step 8. (S)-tert-butyl 4-((R)-5-tert-butoxy-5-oxo-2-(tosyloxymethyl)pentyl)-2,2-dimethyloxazolidine-3-carboxylate To a solution of (S)-tert-butyl 4-((R)-5-tert-butoxy-2-(hydroxymethyl)-5-oxopentyl)-2,2-dimethyloxazolidine-3-carboxylate (244 mg, 0.63 mmol) in anhydrous DCM (6 mL) was added pyridine (2 mL) and catalytic amount of DMAP, the solution was chilled to 0° C. Tosic chloride (360 mg, 1.88 mmol) was added and stirred at rt overnight. The reaction mixture was diluted with EtOAc (40 mL) and washed with 1 N HCl (2×, 50 ml+20 ml), followed by H$_2$O, aq. NaHCO$_3$, brine, dried over Na$_2$SO$_4$, and filtered. After evaporation of solvent, the residue was purified on silica gel column, eluted with 0-20% EtOAc in hexane to afford (S)-tert-butyl 4-((R)-5-tert-butoxy-5-oxo-2-(tosyloxymethyl)pentyl)-2,2-dimethyloxazolidine-3-carboxylate (317 mg, yield 93%).

Step 9. (S)-tert-butyl 4-((R)-5-hydroxy-2-(tosyloxymethyl)pentyl)-2,2-dimethyloxazolidine-3-carboxylate To a solution of (S)-tert-butyl 4-((R)-5-tert-butoxy-5-oxo-2-(tosyloxymethyl)pentyl)-2,2-dimethyloxazolidine-3-carboxylate (317 mg, 0.58 mmol) in anhydrous DCM (8 mL) at −78° C. under N$_2$ was added DiBAlH (1 M in hexane, 1.75 mL, 1.75 mmol) dropwise. After the addition, the reaction mixture was stirred for another 30 min. The reaction was quenched with MeOH (2 mL), followed by 50% Rochelle's salt aq-solution and stirred 2 hr. The resulting solution was extracted with DCM (3×20 mL), the combined organic phases were concentrated and dissolved in THF/MeOH (10 mL, 4/1, v/v), and chilled to 0° C., NaBH$_4$ (11 mg, 0.29 mmol) was added and stirred at this temperature for 30 min. The reaction was quenched by aqueous NH$_4$Cl, then extracted with EtOAc (3×20 mL), the combined organic phases were washed with H$_2$O, brine, and dried over Na$_2$SO$_4$, and filtered, and concentrated to give crude product (S)-tertbutyl 4-((R)-5-hydroxy-2-(tosyloxymethyl)pentyl)-2,2-dimethyloxazolidine-3-carboxylate (255 mg, 92%). It was used without further purification.

Step 10. (S)-tert-butyl 2,2-dimethyl-4-(((R)-tetrahydro-2H-pyran-3-yl)methyl)oxazolidine-3-carboxylate To a solution of (S)-tert-butyl 4-((R)-5-hydroxy-2-(tosyloxymethyl)pentyl)-2,2-dimethyloxazolidine-3-carboxylate (254 mg, 0.54 mmol) in anhydrous DMF (8 mL) at 0° C. under $N_2$ was added NaH (43 mg, 1.08 mmol). After stirred at this temperature for 1 hr, the reaction was quenched with aq. $NH_4Cl$ and then evaporated to dryness. The residue was dissolved in EtOAc and $H_2O$, the separated aqueous phase was extracted with EtOAc. The combined organic phases were washed with $H_2O$, brine, and dried over $Na_2SO_4$, filtered, and evaporated. The residue was purified on silica gel column to afford (S)-tert-butyl 2,2-dimethyl-4-(((R)-tetrahydro-2H-pyran-3-yl)methyl)oxazolidine-3-carboxylate (136 mg, 84%).

Preparation X1

2,2-dimethyl-4-(((R)-tetrahydro-2H-pyran-3-yl)methyl)oxazolidine

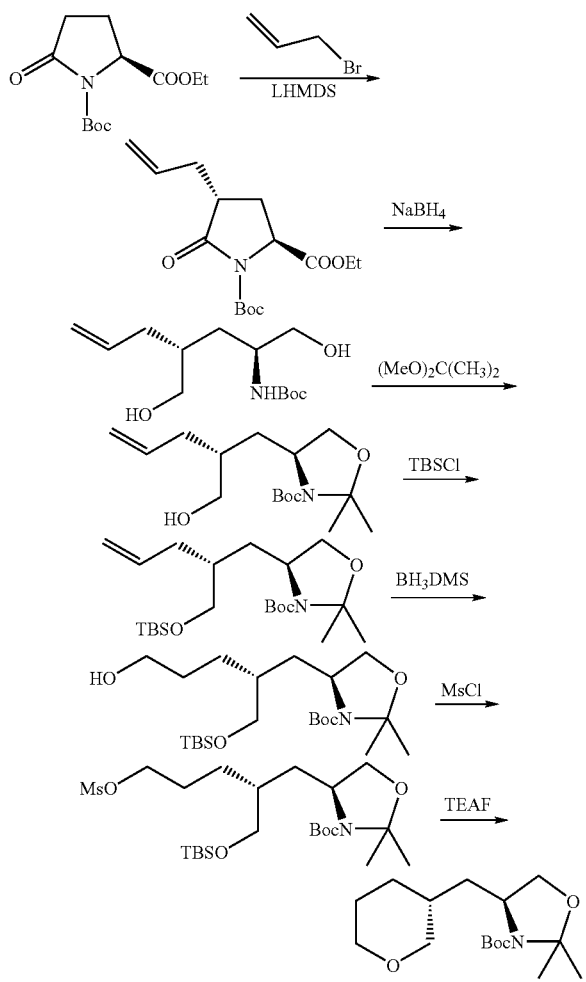

Step 1. (2S,4R)-1-tert-butyl 2-ethyl 4-allyl-5-oxopyrrolidine-1,2-dicarboxylate To a solution of HMDS in anhydrous THF (200 mL) was added dropwise 2.5 M n-BuLi in hexane (130 mL) and the mixture was stirred at −78° C. for 1 hr. To a solution of (S)-1-tert-butyl 2-ethyl 5-oxopyrrolidine-1,2-dicarboxylate (80 g, 0.311 mol) in anhydrous THF (1600 mL) stirred at −78° C. was added lithium hexamethyldisilazide in THF. After the reaction mixture was stirred at −78° C. for 1 hr, 3-bromopropene (38.47 g, 0.318 mol) in THF (200 mL) was added and stirring was continued for 2 hr. The reaction mixture was quenched with saturated ammonium chloride solution (600 mL) at −78° C. and extracted with EtOAc (3×500 mL). The combined organic layers were dried over $Na_2SO_4$, filtered and evaporated to dryness. The crude product was separated by column chromatography to afford (2S,4R)-1-tert-butyl 2-ethyl 4-allyl-5-oxopyrrolidine-1,2-dicarboxylate (15 g, 16%).

Step 2. tert-butyl (2S,4R)-1-hydroxy-4-(hydroxymethyl)hept-6-en-2-ylcarbamate To a solution of (2S,4R)-1-tert-butyl 2-ethyl 4-allyl-5-oxopyrrolidine-1,2-dicarboxylate (30 g, 0.1 mol) in MeOH/$H_2O$ (700/70 mL) was added $NaBH_4$ (25 g, 0.66 mol), the result mixture was stirred 1 hr at rt and quenched with sat. aq. $NH_4Cl$ (300 mL). The organic solvent was removed under vacuum and extracted with EtOAc (3×250 mL). The combined organic phases were washed with brine (250 mL) and dried over anhydrous $Na_2SO_4$, filtered and evaporated to afford crude tert-butyl (2S,4R)-1-hydroxy-4-(hydroxymethyl)hept-6-en-2-ylcarbamate (22 g, 85%). It was used in the next step without further purification.

Step 3. (S)-tert-butyl 4-((R)-2-(hydroxymethyl)pent-4-enyl)-2,2-dimethyloxazolidine-3-carboxylate To a solution of tert-butyl (2S,4R)-1-hydroxy-4-(hydroxymethyl)hept-6-en-2-ylcarbamate (6.8 g, 26.2 mmol) in acetone (150 mL), PTSA (0.45 g, 2.62 mmol) was added. The reaction mixture was cooled to −20° C. followed by the addition of 2,2-dimethoxypropane (4.1 g, 39.4 mmol). The resulting mixture was stirred and allowed to warm to rt for 1 hr. TEA (0.5 mL) was then added and stirred for another 5 min. The solvent was removed under reduced pressure. The residue was dissolved in $Et_2O$ (300 mL), washed with 1 N HCl (80 mL), sat. aq. $NaHCO_3$ (80 mL), brine (80 mL) successively, and dried, filtered, and concentrated under vacuum to give crude (S)-tert-butyl 4-((R)-2-(hydroxymethyl)pent-4-enyl)-2,2-dimethyloxazolidine-3-carboxylate (7.5 g, 96%). It was used without further purification.

Step 4. (S)-tert-butyl 4-((R)-2-((tert-butyldimethylsilyloxy)methyl)pent-4-enyl)-2,2-dimethyloxazolidine-3-carboxylate To a solution of (S)-tert-butyl 4-((R)-2-(hydroxymethyl)pent-4-enyl)-2,2-dimethyloxazolidine-3-carboxylate (11.5 g, 38.4 mmol), imidazole (7.84 g, 115.2 mmol) and DMAP (234 mg, 1.92 mmol) in $CH_2Cl_2$ (200 mL) was added a solution of TBSCl (8.68 g, 57.6 mmol) in $CH_2Cl_2$ (100 mL) dropwise. The reaction mixture was stirred at rt for overnight. The reaction was washed with water (100 mL) and the aqueous layer was extracted with $CH_2Cl_2$ (3×100 mL), the combined organic layers was washed with brine (70 mL), then dried over $Na_2SO_4$, filtered and concentrated to give the crude product, which was purified by column chromatography to afford (S)-tert-butyl 4-((R)-2-((tert-butyldimethylsilyloxy)methyl)pent-4-enyl)-2,2-dimethyloxazolidine-3-carboxylate (9 g, 57%).

Step 5. (S)-tert-butyl 4-((R)-2-((tert-butyldimethylsilyloxy)methyl)-5-hydroxypentyl)-2,2-dimethyloxazolidine-3-carboxylate A solution of (S)-tert-butyl 4-((R)-2-((tert-butyldimethylsilyloxy)methyl)pent-4-enyl)-2,2-dimethyloxazolidine-3-carboxylate (26 g, 63 mmol) in THF (200 mL) was cooled in an ice-bath, followed by dropwise addition of 10 M $BH_3 \cdot SMe_2$ (6.3 mL). After stirring for 5 hr, 10% NaOH solution (32 mL) followed by 30% $H_2O_2$ (32 mL) were added carefully. The reaction mixture was stirred at rt for 16 hr. The reaction mixture was diluted with diethyl ether (500 mL) and the aqueous layer was extracted with diethyl ether (3×250 mL). The combined organic layers were washed with brine, dried over $Na_2SO_4$, filtered and concentrated to give the crude product, which was purified by column chromatography to afford (S)-tert-butyl 4-((R)-2-((tert-butyldimethylsilyloxy)methyl)-5-hydroxypentyl)-2,2-dimethyloxazolidine-3-carboxylate (19.6 g, 72%).

Step 6. (S)-tert-butyl 4-((R)-2-((tert-butyldimethylsilyloxy)methyl)-5-(methylsulfonyloxy)pentyl)-2,2-dimethyloxazolidine-3-carboxylate To a solution of (S)-tert-butyl 4-((R)-2-((tert-butyldimethylsilyloxy)methyl)-5-hydroxypentyl)-2,2-dimethyloxazolidine-3-carboxylate (32 g, 74.2 mmol) and $Et_3N$ (22.5 g, 226 mmol) in $CH_2Cl_2$ (400 mL) was added a solution of MsCl (10.1 g, 89 mmol) in $CH_2Cl_2$ (50 mL) at 0-5° C. After addition, the reaction mixture was allowed to warm to rt and stir for 1 hr. The reaction was washed with water (200 mL) and the aqueous layer was extracted with $CH_2Cl_2$ (3×150 mL). The combined organic layers was washed with 10% citric acid (60 mL), sat. $NaHCO_3$ (60 mL) and brine (100 mL), then dried over $Na_2SO_4$, filtered and concentrated to give (S)-tert-butyl 4-((R)-2-((tert-butyldimethylsilyloxy)methyl)-5-(methylsulfonyloxy)pentyl)-2,2-dimethyloxazolidine-3-carboxylate (37.7 g, 100%), which was used in the next step without purification.

Step 7. (S)-tert-butyl 2,2-dimethyl-4-(((R)-tetrahydro-2H-pyran-3-yl)methyl)oxazolidine-3-carboxylate To a solution of (S)-tert-butyl 4-((R)-2-((tert-butyldimethylsilyloxy)methyl)-5-(methylsulfonyloxy)pentyl)-2,2-dimethyloxazolidine-3-carboxylate (37.7 g, 74.2 mmol) in THF (1000 mL) was added tetraethylammonium fluoride hydrate (41 g, 185.5 mmol) in portions. The reaction mixture was stirred under reflux overnight. The mixture was diluted with EtOAc (1000 mL), washed with water (300 mL) and brine (500 mL). The organic phase was dried over $Na_2SO_4$, filtered and concentrated in vacuo to give the crude product, which was purified by column chromatography to afford (S)-tert-butyl 2,2-dimethyl-4-(((R)-tetrahydro-2H-pyran-3-yl)methyl)oxazolidine-3-carboxylate (12.0 g, 54%).

Preparation Y1 tert-butyl (S)-1-amino-3-((R)-tetrahydro-2H-pyran-3-yl)propan-2-ylcarbamate

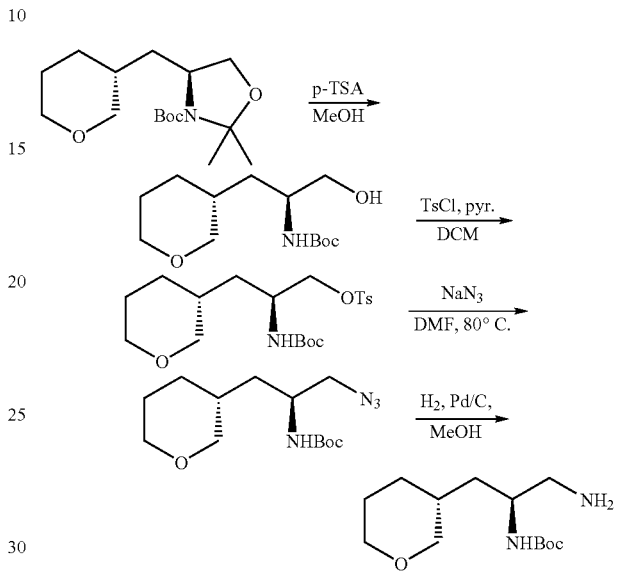

Step 1. Preparation of tert-butyl (S)-1-hydroxy-3-((R)-tetrahydro-2H-pyran-3-yl)propan-2-ylcarbamate To a solution of (S)-tert-butyl 2,2-dimethyl-4-(((R)-tetrahydro-2H-pyran-3-yl)methyl)oxazolidine-3-carboxylate (643 mg, 2.15 mmol) in MeOH (10 mL) was added p-TSA (37 mg, 0.22 mmol), then the solution was stirred at rt for 12 hr. TEA (2 mL) was added, followed by $Boc_2O$ (46 mg, 0.21 mmol). After the addition the reaction solution was stirred for another 30 min. The organic solvent was removed under reduced pressure to give the crude product tert-butyl (S)-1-hydroxy-3-((R)-tetrahydro-2H-pyran-3-yl)propan-2-ylcarbamate. It was used in the next step without further purification. MS ESI +ve m/z 260 (M+1).

Step 2. Preparation of (S)-2-(tert-butoxycarbonylamino)-3-((R)-tetrahydro-2H-pyran-3-yl)propyl 4-methylbenzenesulfonate The above crude product tert-butyl (S)-1-hydroxy-3-((R)-tetrahydro-2H-pyran-3-yl)propan-2-ylcarbamate was dissolved in anhydrous DCM (22 mL). To this solution was added pyridine (2 mL) and TsCl (1.230 g, 6.45 mmol). After stirred at rt for 4 hr, another batch of pyridine (3 mL) and TsCl (0.700 g, 3.67 mmol) was added and stirred for another 12 hr. The reaction mixture was diluted with EtOAc (80 mL), washed with 1 N HCl (75 mL), followed by $H_2O$ (2×30 mL), saturated aq. $NaHCO_3$, brine, and dried over anhydrous $Na_2SO_4$, and filtered, and concentrated under reduced pressure. The resulted slurry was purified through flash chromatography on silica gel (eluted with gradient system: 0-35% EtOAc in hexane) to afford (S)-2-(tert-butoxycarbonylamino)-3-((R)-tetrahydro-2H-pyran-3-yl)propyl 4-methylbenzenesulfonate, 670 mg, yield 75% for two steps. MS ESI +ve m/z 436 (M+Na).

Step 3. tert-butyl (S)-1-azido-3-((R)-tetrahydro-2H-pyran-3-yl)propan-2-ylcarbamate The solution of (S)-2-(tert-butoxycarbonylamino)-3-((R)-tetrahydro-2H-pyran-3-yl)propyl 4-methylbenzenesulfonate (132 mg, 0.32 mmol) and NaN$_3$ (62 mg, 0.95 mmol) in anhydrous DMF was heated to 80° C. under N$_2$ atmosphere for 1.5 hr, cooled to rt and diluted with EtOAc, and washed with H$_2$O (3×20 mL), followed by brine, and dried over anhydrous Na$_2$SO$_4$, and filtered, and concentrated under reduced pressure. The resulted slurry was purified through flash chromatography on silica gel (eluted with gradient system: 0-30% EtOAc in hexane) to afford tert-butyl (S)-1-azido-3-((R)-tetrahydro-2H-pyran-3-yl)propan-2-ylcarbamate 58 mg, yield 64%. MS ESI +ve m/z 307 (M+Na).

Step 4: tert-butyl (S)-1-amino-3-((R)-tetrahydro-2H-pyran-3-yl)propan-2-ylcarbamate Hydrogenation of tert-butyl (S)-1-azido-3-((R)-tetrahydro-2H-pyran-3-yl)propan-2-ylcarbamate (146 mg, 0.51 mmol) was carried out in MeOH (10 mL), 10% Pd/C (25 mg) under 40 psi of H$_2$ for 2 h. After filtration 114 mg of tert-butyl (S)-1-amino-3-((R)-tetrahydro-2H-pyran-3-yl)propan-2-ylcarbamate was obtained, yield 86%. MS ESI +ve m/z 259 (M+H).

Preparation Z1 tert-butyl (S)-1-amino-3-((R)-tetrahydro-2H-pyran-3-yl)propan-2-yl(methyl)carbamate

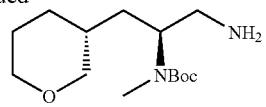

Step 1. tert-butyl (S)-1-azido-3-((R)-tetrahydro-2H-pyran-3-yl)propan-2-yl(methyl)carbamate To a solution of tert-butyl (S)-1-azido-3-((R)-tetrahydro-2H-pyran-3-yl)propan-2-ylcarbamate (30 mg, 0.11 mmol) in anhydrous THF (4 mL) at −78° C. was added 1.0 M LHMDS solution in THF (253 µL, 0.25 mmol), then stirred at this temperature for 30 min. To this mixture was added MeI (125 µL, 0.22 mmol), then the temperature was allowed to warm to 0° C., and stand for 12 hr in the refrigerator. The reaction mixture was quenched with saturated aq. NH$_4$Cl, extracted with EtOAc (30 mL), the separated organic phase was washed with H$_2$O (2×10 mL), brine, and dried (Na$_2$SO$_4$), and filtered. The filtrate was concentrated, the resulting slurry was purified through flash chromatography on silica gel (eluted with gradient system, 0-30% EtOAc in hexane) to afford tert-butyl (S)-1-azido-3-((R)-tetrahydro-2H-pyran-3-yl)propan-2-yl(methyl)carbamate 31 mg, yield 100%. MS ESI +ve m/z 321 (M+Na).

Step 2. tert-butyl (S)-1-amino-3-((R)-tetrahydro-2H-pyran-3-yl)propan-2-yl(methyl)carbamate Hydrogenation of (S)-1-azido-3-((R)-tetrahydro-2H-pyran-3-yl)propan-2-yl(methyl)carbamate (62 mg, 0.51 mmol) was carried out in EtOAc (20 mL), 10% Pd/C (15 mg) under 40 psi of H$_2$ for 2 h. After filtration 52 mg of tert-butyl (S)-1-amino-3-((R)-tetrahydro-2H-pyran-3-yl)propan-2-ylcarbamate was obtained, yield 91%. MS ESI +ve m/z 273 (M+H).

Example 28 methyl 2-((R)—((R)-1-((S)-2-amino-3-((R)-tetrahydro-2H-pyran-3-yl)propylcarbamoyl)piperidin-3-yl)(3-chlorophenyl)methoxy)ethylcarbamate

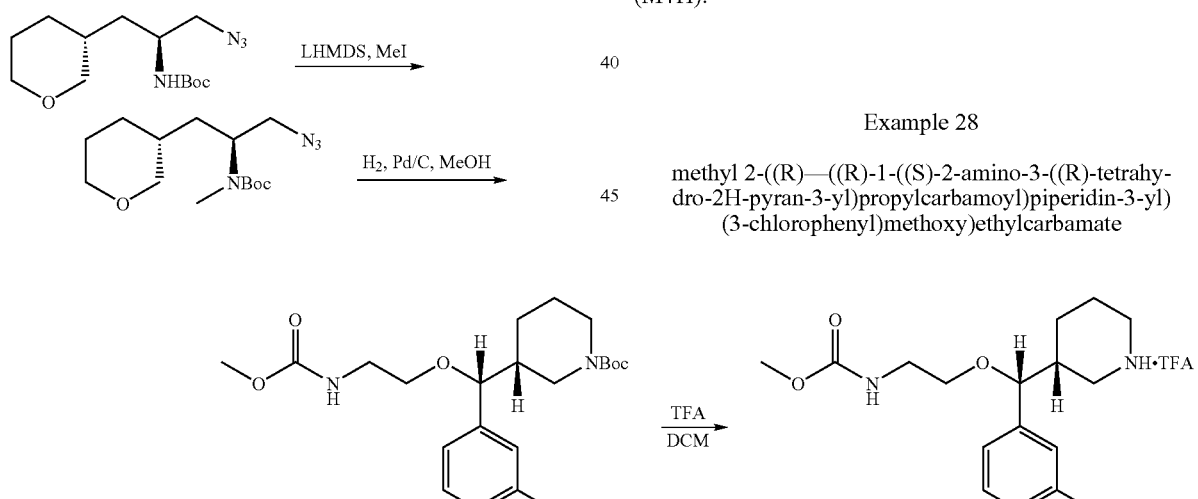

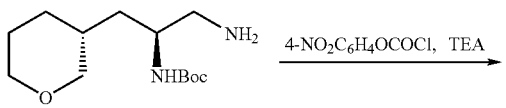

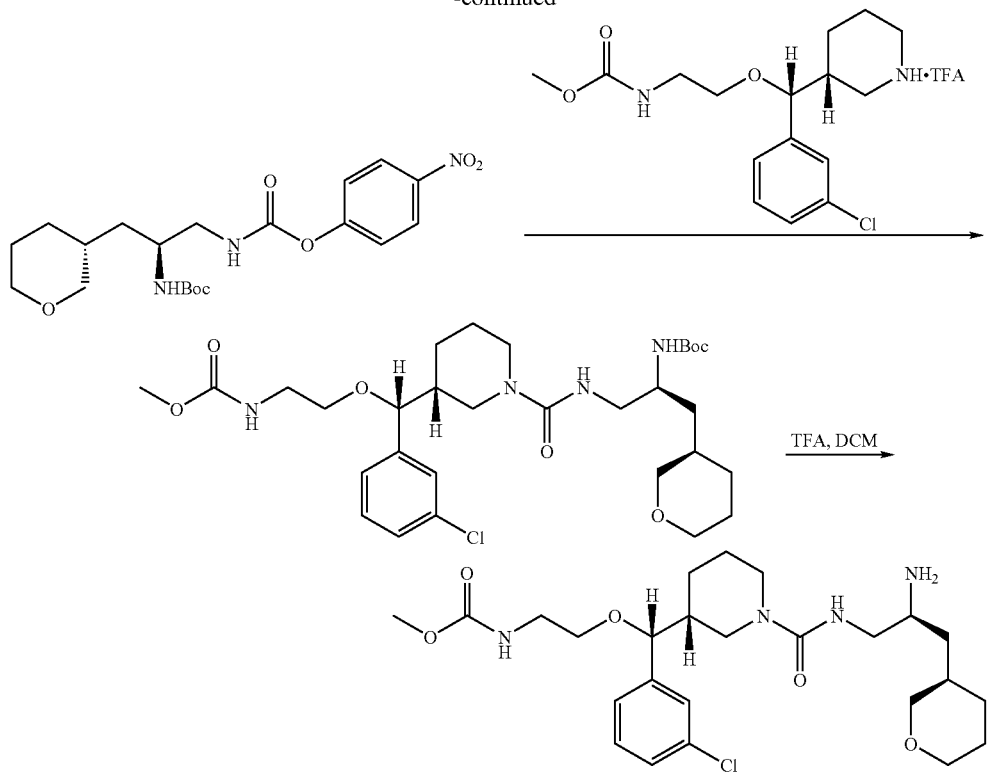

Step 1. methyl 2-((R)-(3-chlorophenyl)((R)-piperidin-3-yl)methoxy)ethylcarbamate.TFA salt The solution of (R)-tert-butyl 3-((R)-(3-chlorophenyl)(2-(methoxycarbonylamino)ethoxy)methyl)piperidine-1-carboxylate (2.247 g, 5.26 mmol) in mixed solvent of DCM/TFA (24 mL, 3:1, v/v) was stirred at rt for 30 min. The solvents were removed in vacuo to produce 2-((R)-(3-chlorophenyl)((R)-piperidin-3-yl)methoxy)ethylcarbamate TFA salt in quantitative yield. MS ESI +ve m/z 327 (M+H).

Step 2. (4-nitrophenyl) (s)-2-(N-(tert-butoxycarbonyl)amino)-3-((R)-tetrahydro-2H-pyran-3-yl)propylcarbamate To a solution of tert-butyl (S)-1-amino-3-((R)-tetrahydro-2H-pyran-3-yl)propan-2-ylcarbamate (20.8 mg, 0.081 mmol) in anhydrous DCM (9 mL) was added 4-nitrophenyl chloroformate (17.1 mg, 0.085 mmol), followed by TEA (12.2 mg, 17 µL, 0.12 mmol). The resulting solution was stirred at rt for 5 min (monitored by LC-MS) and diluted to 12 mL. An aliquot of the carbamate mixture solution (2 mL) was used for the next step without purification.

Step 3. 2-((R)—((R)-1-((S)-2-(Boc-amino)-3-((R)-tetrahydro-2H-pyran-3-yl)propylcarbamoyl)piperidin-3-yl)(3-chlorophenyl)methoxy)ethylcarbamate To (4-nitrophenyl) (S)-2-(N-(tert-butoxycarbonyl)amino)-3-((R)-tetrahydro-2H-pyran-3-yl)propylcarbamate solution (2 mL, 0.013 mmol) was added 2-((R)-(3-chlorophenyl)((R)-piperidin-3-yl)methoxy)ethylcarbamate TFA salt (7.0 mg, 0.016 mmol), followed by excess TEA (0.3 mL). The mixture was stirred for 30 min, then the solvent was removed in vacuo. The resulting oil was purified on preparative HPLC to give methyl 2-((R)—((R)-1-((S)-2-(Boc-amino)-3-((R)-tetrahydro-2H-pyran-3-yl)propylcarbamoyl)piperidin-3-yl)(3-chlorophenyl)methoxy)ethylcarbamate 5 mg, yield 63%. MS ESI +ve m/z 611 (M+H).

Step 4. methyl 2-((R)—((R)-1-((S)-2-amino-3-((R)-tetrahydro-2H-pyran-3-yl)propylcarbamoyl)piperidin-3-yl)(3-chlorophenyl)methoxy)ethylcarbamate TFA salt The 2-((R)—((R)-1-((S)-2-(Boc-amino)-3-((R)-tetrahydro-2H-pyran-3-yl)propylcarbamoyl)piperidin-3-yl)(3-chlorophenyl)methoxy)ethylcarbamate (5 mg, 0.008 mmol) was dissolved in DCM/TFA (3/1 mL). The solution was stirred for 30 min and concentrated. The crude mixture was purified on preparative HPLC to afford 2-((R)—((R)-1-((S)-2-amino-3-((R)-tetrahydro-2H-pyran-3-yl)propylcarbamoyl)piperidin-3-yl)(3-chlorophenyl)methoxy)ethylcarbamate TFA salt 2.8 mg, yield 54%. $^1$H NMR (CD$_3$OD) δ 7.36-7.32 (m, 3H), 7.23 (d, J=7.6 Hz, 1H), 4.20 (br d, J=13.6 Hz, 1H), 4.04 (d, J=8.8 Hz, 1H), 3.89-3.78 (m, 3H), 3.64 (s, 3H), 3.48-3.42 (m, 2H), 3.37 (m, 1H), 3.28-3.24 (m, 5H), 3.15 (dd, J=10.8, 9.2 Hz, 1H), 2.92 (m, 2H), 1.97 (m, 1H), 1.78 (m, 2H), 1.68-1.54 (m, 4H), 1.45-1.07 (m, 5H). MS ESI +ve m/z 511 (M+H).

The following compounds of Formula (XL) were prepared following procedures analogous to those described above:
1) methyl 2-((R)—((R)-1-((S)-2-amino-3-((R)-tetrahydro-2H-pyran-3-yl)propylcarbamoyl)piperidin-3-yl)(3-fluorophenyl)methoxy)ethylcarbamate using trifluoroacetic acid salt of methyl 2-((R)-(3-fluorophenyl)((R)-piperidin-3-yl)methoxy)ethylcarbamate in Step 2.
2) methyl 2-((R)—((R)-1-((S)-2-amino-3-((R)-tetrahydro-2H-pyran-3-yl)propylcarbamoyl)piperidin-3-yl)(3-chloro-5-fluorophenyl)methoxy)ethylcarbamate using trifluoroacetic acid salt of methyl 2-((R)-(3-chloro-5-fluorophenyl)((R)-piperidin-3-yl)methoxy)ethylcarbamate in Step 2.

3) methyl 2-((R)—((R)-1-((S)-2-amino-3-((R)-tetrahydro-2H-pyran-3-yl)propylcarbamoyl)piperidin-3-yl)(3,5-difluorophenyl)methoxy)ethylcarbamate using trifluoroacetic acid salt of methyl 2-((R)-(3,5-difluorophenyl)((R)-piperidin-3-yl)methoxy)ethylcarbamate in Step 2.
4) methyl 2-((R)—((R)-1-((S)-2-amino-3-((R)-tetrahydro-2H-pyran-3-yl)propylcarbamoyl)piperidin-3-yl)(5-chloro-2-methylphenyl)methoxy)ethylcarbamate using trifluoroacetic acid salt of methyl 2-((R)-(5-chloro-2-methylphenyl)((R)-piperidin-3-yl)methoxy)ethylcarbamate in Step 2.

with a piperidine intermediate represented by the following structure:

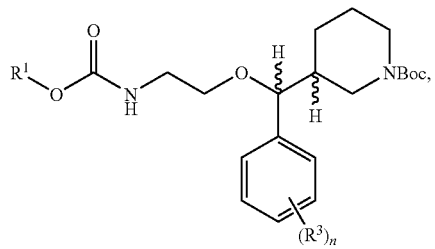

described in the following scheme:

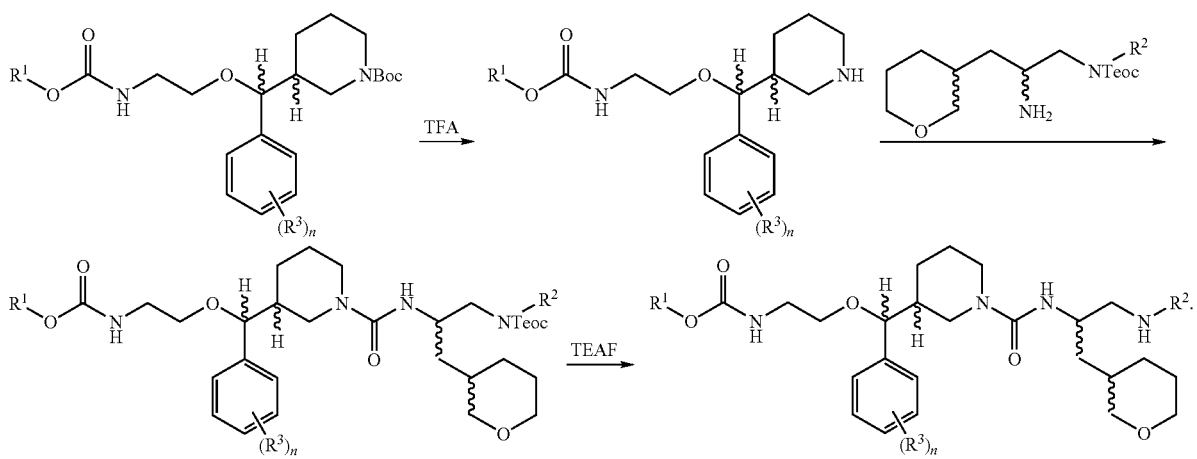

5) methyl 2-((R)—((R)-1-((S)-2-amino-3-((R)-tetrahydro-2H-pyran-3-yl)propylcarbamoyl)piperidin-3-yl)(5-fluoro-2-methylphenyl)methoxy)ethylcarbamate using trifluoroacetic acid salt of methyl 2-((R)-(5-fluoro-2-methylphenyl)((R)-piperidin-3-yl)methoxy)ethylcarbamate in Step 2.
6) methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate using tert-butyl (S)-1-amino-3-((R)-tetrahydro-2H-pyran-3-yl)propan-2-yl(methyl)carbamate in Step 1.
7) methyl 2-((R)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate using tert-butyl (S)-1-amino-3-((R)-tetrahydro-2H-pyran-3-yl)propan-2-yl(methyl)carbamate in Step 1 and trifluoroacetic acid salt of methyl 2-((R)-(5-chloro-2-methylphenyl)((R)-piperidin-3-yl)methoxy)ethylcarbamate in Step 2.

General Synthetic Schemes for Compounds of Formula (L)

The compounds of present invention can be synthesized by coupling a pyran intermediate represented by the following structure:

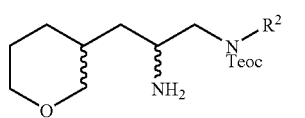

Preparation of the Pyran Intermediate from Glutamic Ester

The pyran intermediate can be prepared from glutamic ester using the following synthetic scheme:

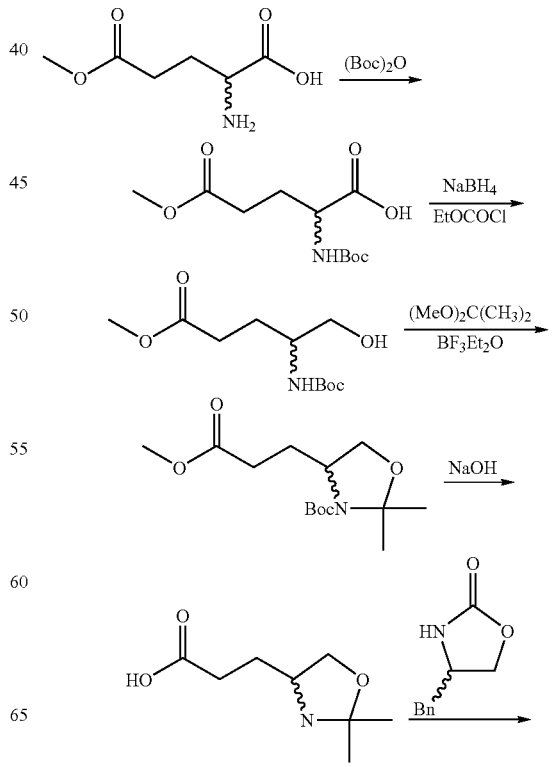

401
-continued
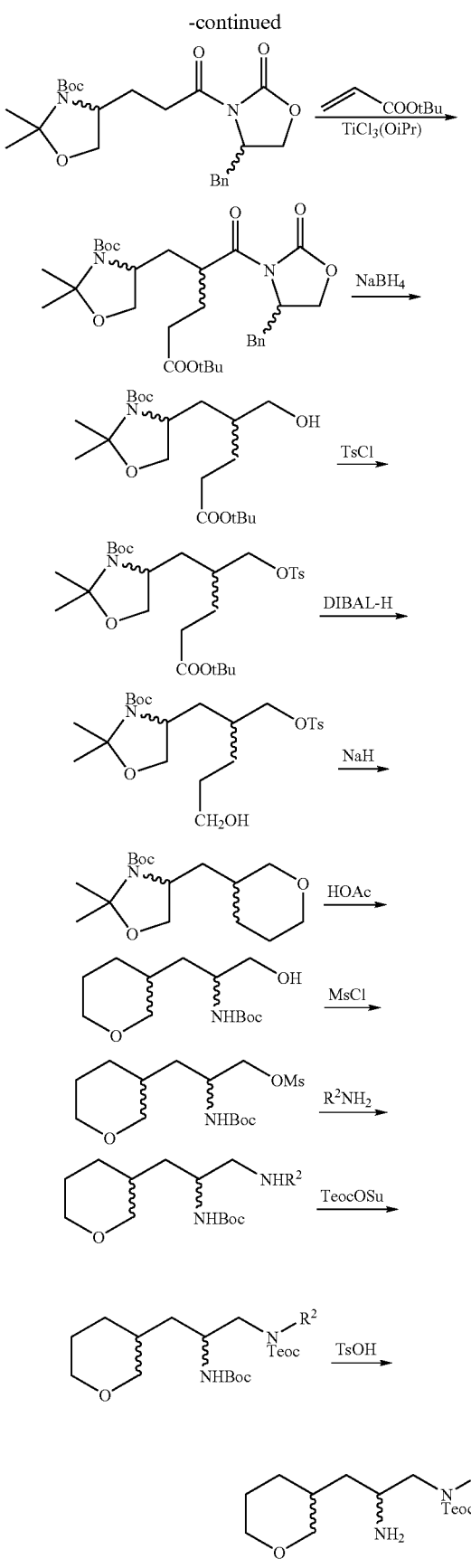
402
Preparation of the Pyran Intermediate from Pyroglutamic Ester
The pyran intermediate can also be prepared from pyroglutamic ester using the following synthetic scheme:
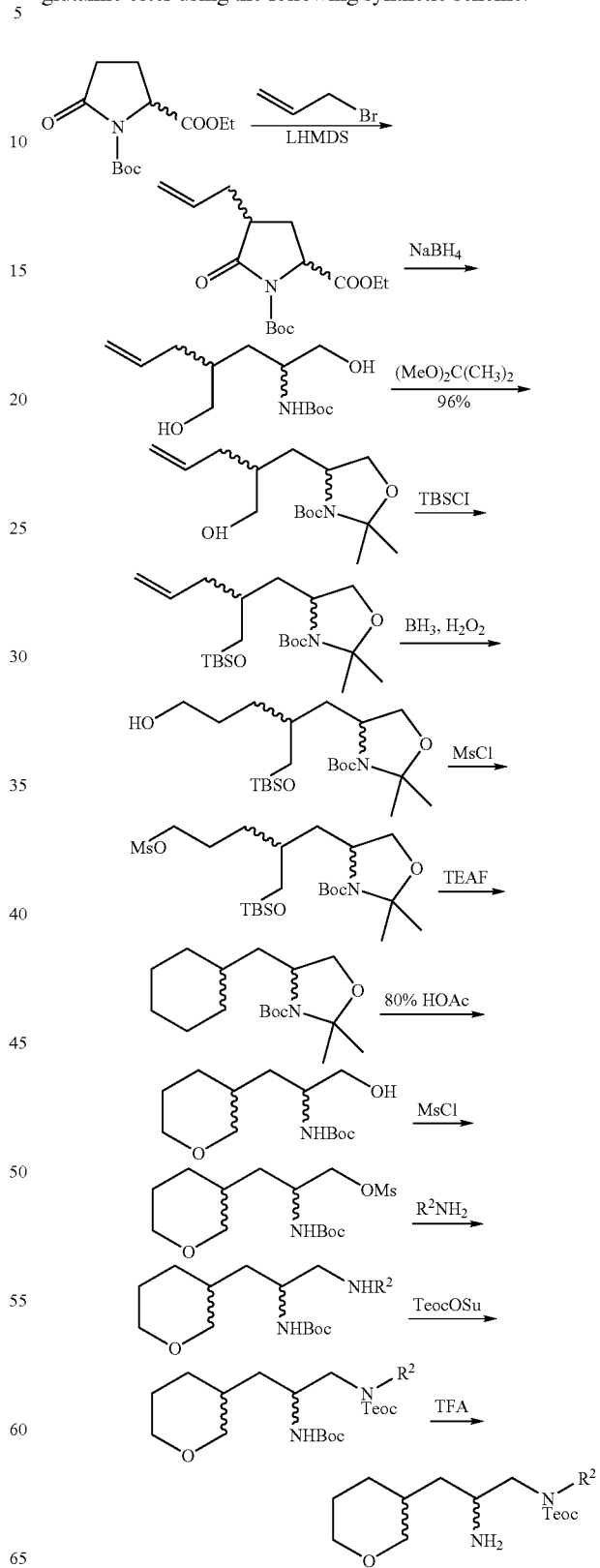

Preparation of the Piperidine Intermediate
The piperidine intermediate can be prepared by using the following synthetic scheme.
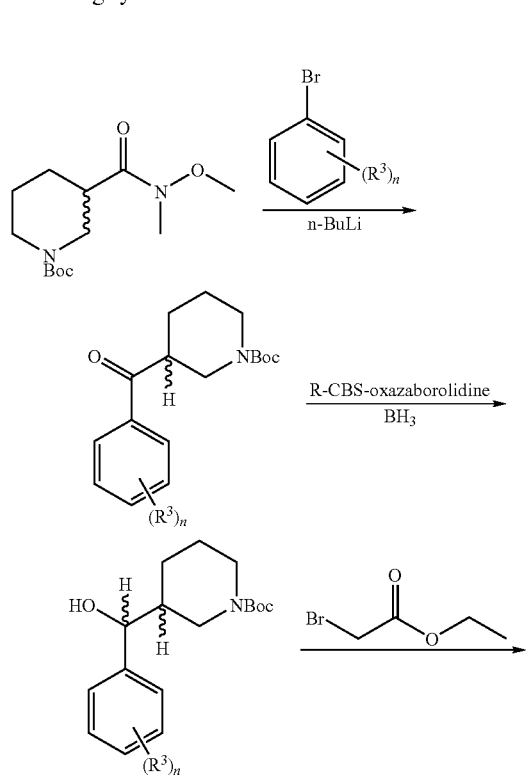
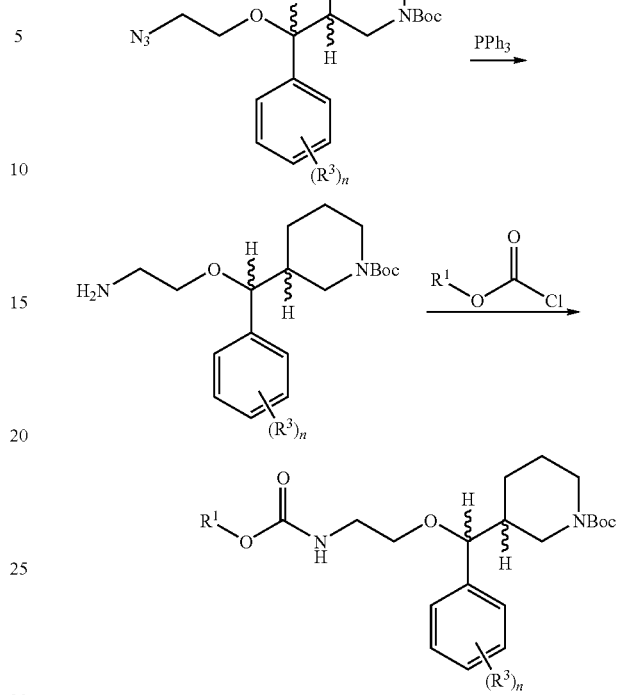
Alternatively, the piperidine intermediate can be prepared using the following synthetic scheme:
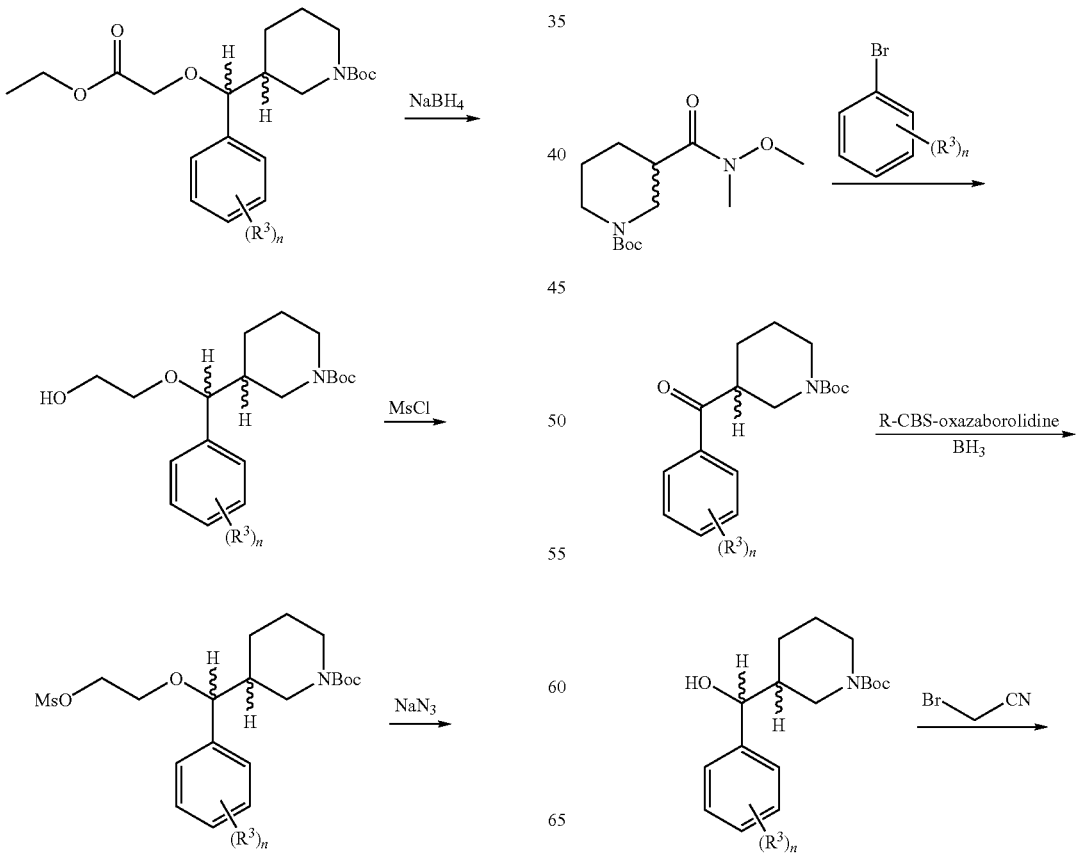

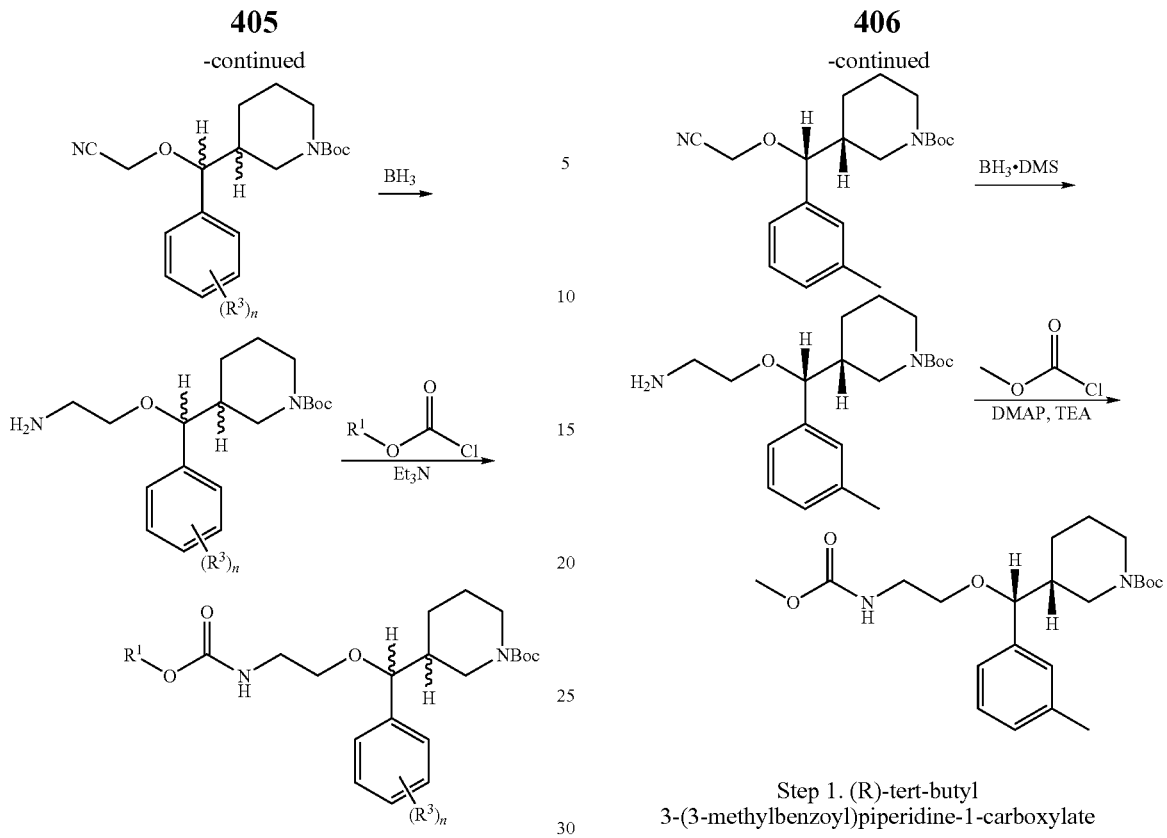

Specific conditions for synthesizing the disclosed aspartic protease inhibitors according to the above schemes are provided in the examples below.

Preparation 33

(R)-tert-butyl 3-((R)-(2-(methoxycarbonylamino)ethoxy)(m-tolyl)methyl)piperidine-1-carboxylate

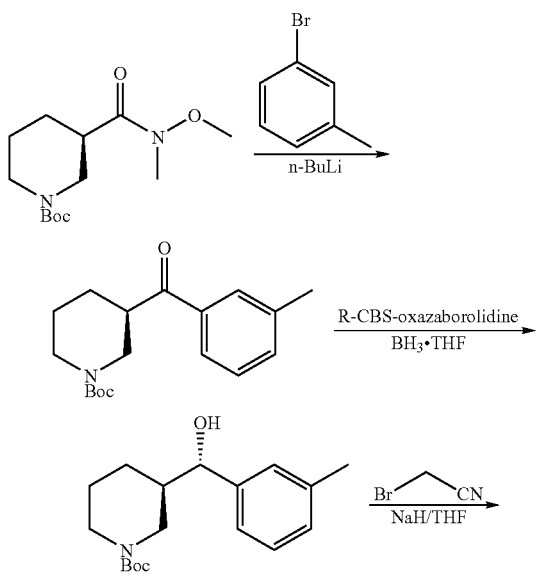

Step 1. (R)-tert-butyl 3-(3-methylbenzoyl)piperidine-1-carboxylate

To a solution of 1-bromo-3-methylbenzene (88.4 g, 0.52 mol) in anhydrous THF (550 mL) at −78° C. under nitrogen was added dropwise a solution of 2.5 M n-BuLi in hexane (210 mL, 0.52 mol). After stirring for 1 hr at −78° C., a solution of (R)-tert-butyl 3-((R)-(2-(methoxycarbonylamino)ethoxy)(m-tolyl)methyl)piperidine-1-carboxylate (120 g, 0.44 mol) in anhydrous THF (500 mL) was added dropwise. After addition, the reaction mixture was allowed to warm to rt and stirred for 2 hr. The mixture was quenched with saturated NH$_4$Cl solution (500 mL) and extracted with EtOAc (3×400 mL). The combined organic layers were washed with brine, dried over Na$_2$SO$_4$ and concentrated in vacuo to give crude (R)-tert-butyl 3-(3-methylbenzoyl)piperidine-1-carboxylate (168 g), which was used immediately for next step without purification.

Step 2. (R)-tert-butyl 3-((S)-hydroxy(m-tolyl)methyl)piperidine-1-carboxylate To a solution of (R)-tert-butyl 3-(3-methylbenzoyl)piperidine-1-carboxylate (168 g, 0.55 mol) in anhydrous THF (600 mL) at −15° C. under nitrogen was added dropwise a solution of 1 M R-CBS-oxazaborolidine in toluene (82 mL, 82 mmol, 0.15 eq). After stirring for 1 hr at −15° C., a solution of 10 M BH$_3$ in THF (60 mL, 0.60 mol, 1.1 eq) was added dropwise. After addition, the reaction mixture was stirred for 2 hr at −15° C. TLC indicated the starting material was disappeared. Methanol (400 mL) was added dropwise carefully at −15° C. The solvent was removed under reduced pressure, the residue was purified by column chromatography on silica gel eluting with EtOAc/hexane (1:30→1:15) to provide the light yellow oil (95 g, HPLC≧70%, ratio≧3:1). The mixture was dissolved in EtOAc until the alcohol was just dissolved (about 5 mL/1 g), the solvent was removed on the rotary evaporator until a few crystals appeared. The solution was cooled to rt slowly and stood for 1-2 hr. To the above solution was added hexane (about 300 mL) and then filtered, the crystals were washed with cool hexane and re-crystallized two more times to afford the pure isomer (R)-tert-butyl 3-((S)-hydroxy(m-tolyl)methyl)piperidine-1-carboxylate (20 g, ee≧99%).

Step 3. (R)-tert-butyl 3-((R)-(cyanomethoxy)(m-tolyl)methyl)piperidine-1-carboxylate To a solution of (R)-tert-butyl 3-((S)-hydroxy(n-tolyl)methyl)piperidine-1-carboxylate (30.5 g, 0.1 mol) in MeCN (300 mL), NaH (12 g, 0.3 mol) was added at 0° C. The mixture was stirred for 1 hr at rt. The mixture was cooled to −40° C., then bromoacetonitrile (35.7 g, 0.3 mol) was added in portions. The mixture was stirred for 0.5 hr at −20° C. continually. The reaction was quenched with sat. $NH_4Cl$. The mixture was extracted with $CH_2Cl_2$. The organic layer was dried over $Na_2SO_4$, concentrated. Crude (R)-tert-butyl 3-((R)-(cyanomethoxy)(m-tolyl)methyl)piperidine-1-carboxylate was used for the next step without purification.

Step 4. (R)-tert-butyl 3-((R)-(2-aminoethoxy)(m-tolyl)methyl)piperidine-1-carboxylate (R)-tert-Butyl 3-((R)-(cyanomethoxy)(m-tolyl)methyl)piperidine-1-carboxylate (20 g, 0.04 mol) was dissolved in anhydrous THF (300 mL), and the solution was heated to reflux under nitrogen. A solution of $BH_3 \cdot Me_2S$ (12 mL, 0.12 mol) in THF was added dropwise, and stirring was continued under reflux overnight. The resulting solution was cooled to rt and MeOH was added dropwise to quench the excess borane. After evaporation of the solution, the crude (R)-tert-butyl 3-((R)-(2-aminoethoxy)(m-tolyl)methyl)piperidine-1-carboxylate was obtained and used without further purification.

Step 5. (R)-tert-butyl 3-((R)-(2-(methoxycarbonylamino)ethoxy)(m-tolyl)methyl)piperidine-1-carboxylate To a solution of (R)-tert-butyl 3-((R)-(2-aminoethoxy)(m-tolyl)methyl)piperidine-1-carboxylate and DMAP in anhydrous $CH_2Cl_2$, $Et_3N$ was added. The resulting mixture was cooled to 0-5° C. under ice-water bath, a solution of methyl chloroformate in anhydrous $CH_2Cl_2$ was added dropwise. After addition, the reaction mixture was stirred for 1-2 hr at 0-5° C. Water was added to quench the reaction. The aqueous layer was extracted with $CH_2Cl_2$, the combined organic layers were washed with 10% citric acid and brine, then dried over $Na_2SO_4$, filtered and concentrated to the crude product, which was purified by preparative TLC to afford (R)-tert-butyl 3-((R)-(2-(methoxycarbonylamino)ethoxy)(m-tolyl)methyl)piperidine-1-carboxylate.

Preparation 34

(R)-tert-butyl 3-((R)-(3-chloro-4-fluorophenyl)(2-(methoxycarbonylamino)ethoxy)methyl)piperidine-1-carboxylate

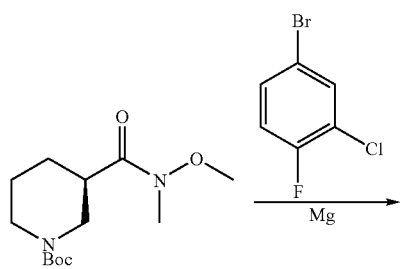

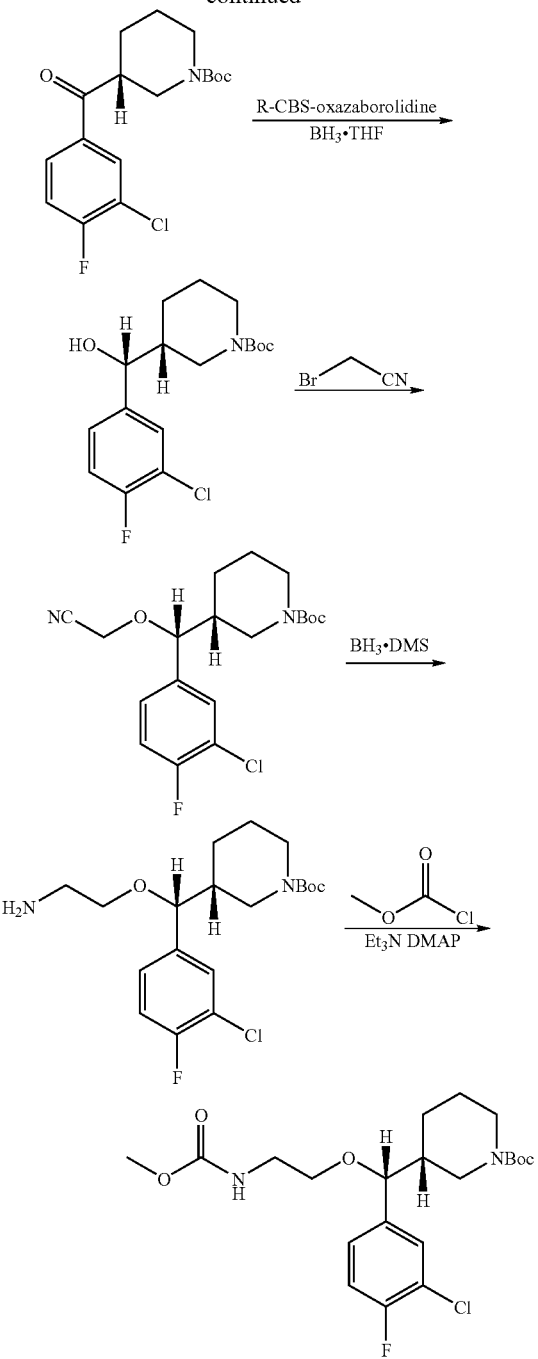

Step 1. (R)-tert-butyl 3-(3-chloro-4-fluorobenzoyl)piperidine-1-carboxylate

A solution of 4-bromo-2-chloro-1-fluoro-benzene (31.3 g, 0.15 mol) in anhydrous THF (150 mL) was added dropwise to Mg (4.8 g, 0.2 mol) in THF (50 mL) at rt under nitrogen. The mixture was stirred at 50-60° C. for 1 hr at which time most of the magnesium was consumed. The resulting Grignard reagent was used for the next step. The Grignard reagent was added dropwise to a solution of (R)-tert-butyl 3-(methoxy(methyl)carbamoyl)piperidine-1-carboxylate (27.2 g, 0.1 mol) in anhydrous THF (300 mL) at −78° C. under nitrogen.

After addition, the mixture was allowed to stir at rt for 1.5 hr. The mixture was quenched with saturated NH$_4$Cl solution (300 mL) and extracted with EtOAc (3×200 mL). The combined organic layers were washed with brine, dried over Na$_2$SO$_4$ and concentrated in vacuo to give crude (R)-tert-butyl 3-(3-chloro-4-fluorobenzoyl)piperidine-1-carboxylate (31.5 g, 92%), which was used immediately for next step without purification.

Step 2. (R)-tert-butyl 3-((R)-(3-chloro-4-fluorophenyl)(hydroxy)methyl)piperidine-1-carboxylate To a solution of 1 M R-CBS-oxazaborolidine in toluene (13.8 mL, 13.8 mmol, 0.15 eq) and 10 M BH$_3$ in THF (9.2 mL, 92.4 mmol, 1.0 eq) at −15° C. under nitrogen was added dropwise a solution of (R)-tert-butyl 3-(3-chloro-4-fluorobenzoyl)piperidine-1-carboxylate (31.5 g, 92.4 mmol) in anhydrous THF (300 mL). After addition, the reaction mixture was stirred for 1 hr at rt. Methanol (200 mL) was added dropwise carefully at 0° C. The solvent was removed under reduced pressure to provide the crude product. The crude product was dissolved in EtOAc till the alcohol was just dissolved (about 5 mL/1 g), the solvent was removed on the rotary evaporator until a few crystals appeared. To the above solution was added petroleum ether (about 300 mL) under stirring, which was allowed to stir at rt for 2 hr and then filtered, the crystals were washed with petroleum ether and re-crystallized 6 times to afford the (R)-tert-butyl 3-((R)-(3-chloro-4-fluorophenyl)(hydroxy)methyl)piperidine-1-carboxylate (10 g, 32%, 93% e.e.). $^1$H NMR (CD$_3$OD, 400 MHZ) δ 7.44 (d, 1H), 7.25 (d, 1H), 7.20 (t, 1H), 4.34 (d, 1H), 4.20 (s, 1H), 3.93 (d, 1H), 2.68 (m, 2H), 1.62 (m, 2H), 1.41 (s, 9H), 1.32 (m, 2H), 1.21 (m, 1H).

Step 3. (R)-tert-butyl 3-((R)-(3-chloro-4-fluorophenyl)(cyanomethoxy)methyl)piperidine-1-carboxylate To a solution of (R)-tert-butyl 3-((R)-(3-chloro-4-fluorophenyl)(hydroxy)methyl)piperidine-1-carboxylate (5.1 g, 15 mmol) in CH$_3$CN (150 mL), NaH (1.8 g, 45 mmol) was added at 0° C. The mixture was stirring for 1 hour. Then the mixture was cooled to −40° C., the bromoacetonitrile (5.4 g, 45 mmol) was added dropwise. The mixture was allowed to warm to 0° C. gradually. The addition of NaH and bromoacetonitrile was repeated three times. The mixture was quenched with H$_2$O and exacted with CH$_2$Cl$_2$. The organic layer was dried over Na$_2$SO$_4$ and concentrate to get the crude (R)-tert-butyl 3-((R)-(3-chloro-4-fluorophenyl)(cyanomethoxy)methyl)piperidine-1-carboxylate (6.5 g, 100%).

Step 4. (R)-tert-butyl 3-((R)-(2-aminoethoxy)(3-chloro-4-fluorophenyl)methyl)piperidine-1-carboxylate (R)-tert-Butyl 3-((R)-(3-chloro-4-fluorophenyl)(cyanomethoxy)methyl)piperidine-1-carboxylate (2.28 g, 6 mmol) was dissolved in anhydrous THF (50 mL), and the solution was heated to reflux under nitrogen. A solution of 10 M of BH$_3$.Me$_2$S (1.8 mL, 18 mmol) in THF was added dropwise and stirring was continued under reflux overnight. The resulting solution was cooled to 0° C., CH$_3$OH was added dropwise to quench the reaction. Evaporation of the solvent led to crude (R)-tert-butyl 3-((R)-(2-aminoethoxy)(3-chloro-4-fluorophenyl)methyl)piperidine-1-carboxylate (2 g, yield 87%), which was used in the next step without further purification.

Step 5. (R)-tert-butyl 3-((R)-(3-chloro-4-fluorophenyl)(2-(methoxycarbonylamino)ethoxy)methyl)piperidine-1-carboxylate To a solution of (R)-tert-butyl 3-((R)-(2-aminoethoxy)(3-chloro-4-fluorophenyl)methyl)piperidine-1-carboxylate (1 g, 2.6 mmol) and DMAP (79 mg, 0.62 mmol) in dry CH$_2$Cl$_2$ (20 mL), Et$_3$N (657 mg, 6.5 mmol) was added. The resulting mixture was cooled to 0-5° C. under ice-water bath, a solution of methyl chloroformate (1.22 g, 13 mmol, 5 eq) was added dropwise. After addition, the reaction mixture was stirred for 1-2 hr at rt. Water (20 mL) was added to quench the reaction. The aqueous layer was extracted with CH$_2$Cl$_2$ (3×20 mL), the combined organic layers were dried over Na$_2$SO$_4$, filtered and concentrated to give the crude product, which was purified by preparative HPLC to afford (R)-tert-butyl 3-((R)-(3-chloro-4-fluorophenyl)(2-(methoxycarbonylamino)ethoxy)methyl)piperidine-1-carboxylate (50 mg, yield 4.3%). $^1$H NMR (CDCl$_3$, 400 MHz) δ 7.27 (m, 1H), 7.12 (m, 2H), 4.30 (s, 1H), 3.91 (d, 2H), 3.66 (s, 3H), 3.10-3.40 (m, 5H), 2.90 (m, 1H), 1.75 (s, 1H), 1.55 (d, 1H), 1.46 (s, 9H), 1.33 (m, 2H), 1.04 (m, 1H).

The following compounds were prepared following procedures analogous to those described above:

1) (R)-tert-butyl 3-((R)-(5-fluoro-2-methylphenyl)(2-(methoxycarbonylamino)ethoxy)methyl)piperidine-1-carboxylate using (5-fluoro-2-methylphenyl)magnesium bromide in Step 1.
2) (R)-tert-butyl 3-((R)-(3-chloro-5-fluorophenyl)(2-(methoxycarbonylamino)ethoxy)methyl)piperidine-1-carboxylate using (3-chloro-5-fluorophenyl)magnesium bromide in Step 1.

Preparation 35

(R)-tert-butyl 3-((R)-(3-chloro-5-fluorophenyl)(2-(ethoxycarbonylamino)ethoxy)methyl)piperidine-1-carboxylate

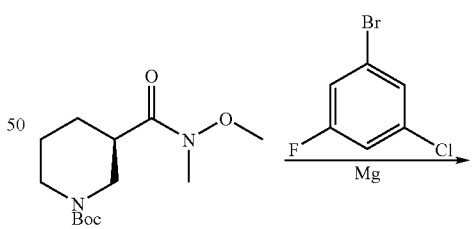

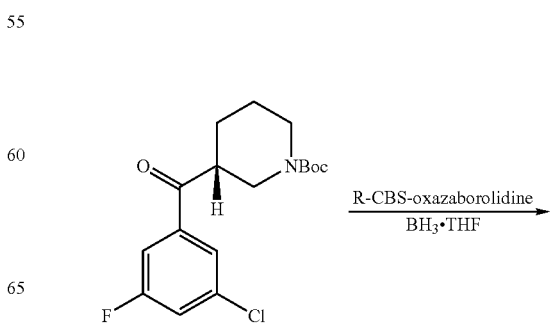

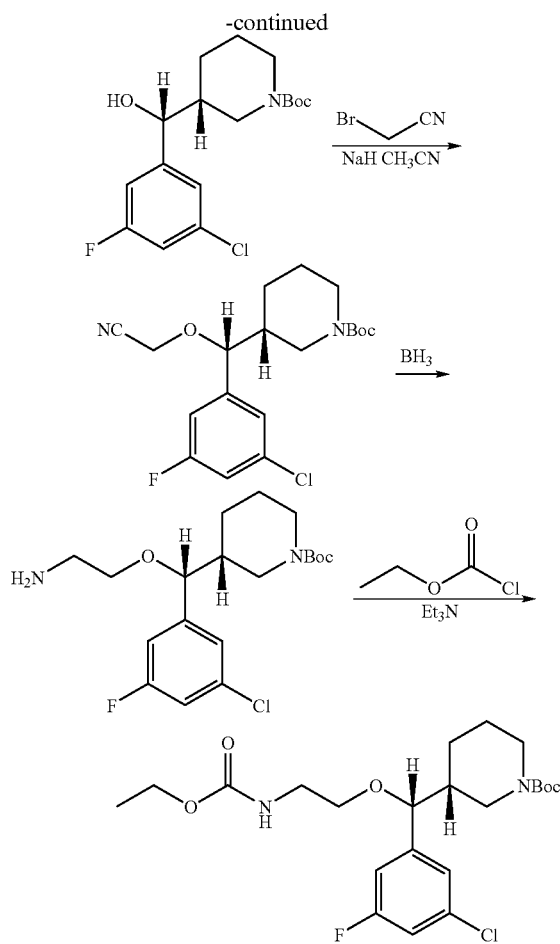

Step 1. (R)-tert-butyl 3-(3-chloro-5-fluorobenzoyl)piperidine-1-carboxylate

A solution of 1-bromo-3-chloro-5-fluoro-benzene (31.5 g, 0.15 mol) in anhydrous THF (120 mL) was added dropwise to the Mg (5.4 g, 0.22 mol) at rt under nitrogen. The mixture was stirred at 50-60° C. for 1 hr until most of the magnesium was consumed. The resulting Grignard reagent was used for the next step. The Grignard reagent was added dropwise to a solution of (R)-tert-butyl 3-(methoxy(methyl)carbamoyl)piperidine-1-carboxylate (20.4 g, 0.075 mol) in anhydrous THF (200 mL) at −78° C. under nitrogen. After addition, the mixture was allowed to stir at rt for 1.5 hr. The mixture was quenched with saturated NH$_4$Cl solution (300 mL) and extracted with EtOAc (3×200 mL). The combined organic layers were washed with brine, dried over Na$_2$SO$_4$ and concentrated in vacuo to give crude (R)-tert-butyl 3-(3-chloro-5-fluorobenzoyl)piperidine-1-carboxylate (25 g, 98%), which was used in the next step without further purification.

Step 2. (R)-tert-butyl 3-((R)-(3-chloro-5-fluorophenyl)(hydroxy)methyl)piperidine-1-carboxylate To a solution of 1 M R-CBS-oxazaborolidine in toluene (11 mL, 11 mmol, 0.15 eq) and 10 M BH$_3$ in THF (7.3 mL, 73 mmol, 1.0 eq) at −15° C. under nitrogen was added dropwise a solution of (R)-tert-butyl 3-(3-chloro-5-fluorobenzoyl)piperidine-1-carboxylate (25 g, 73 mmol) in anhydrous THF (50 mL). After addition, the reaction mixture was stirred for 1 hr at rt. Methanol (100 mL) was added dropwise carefully at 0° C. The solvent was removed under reduced pressure to provide the crude product. The crude product was dissolved in EtOAc until the alcohol was just dissolved (about 5 mL/1 g), the solvent was removed on the rotary evaporator until a few crystals appeared. To the above solution was added petroleum ether (about 300 mL) under stirring, which was allowed to stir at rt for 2 hr and then filtered, the crystals were washed with petroleum ether and re-crystallized a few more times to afford pure (R)-tert-butyl 3-((R)-(3-chloro-5-fluorophenyl)(hydroxy)methyl)piperidine-1-carboxylate (9.2 g, 37%). $^1$H NMR (DMSO, 400 MHz): δ 7.44 (d, 1H), 7.38 (s, 1H), 7.30 (d, 1H), 4.48 (t, 1H), 4.20 (brs, 1H), 3.98 (d, 1H), 2.73 (s, 2H), 1.70 (s, 2H), 1.48 (s, 10H), 1.36-1.39 (m, 2H).

Step 3. (R)-tert-butyl 3-((R)-(3-chloro-5-fluorophenyl)(cyanomethoxy)methyl)piperidine-1-carboxylate To a solution of (R)-tert-butyl 3-((R)-(3-chloro-5-fluorophenyl)(hydroxy)methyl)piperidine-1-carboxylate (3.5 g, 10.2 mmol) in CH$_3$CN (140 mL), NaH (1.2 g, 30.6 mmol) was added at 0° C. The mixture was stirred for 1 hr. Then the mixture was cooled to −20° C., bromoacetonitrile (3.6 g, 30.6 mmol) was added dropwise. The mixture was allowed warm to 0° C. gradually. Another batch of NaH and bromoacetonitrile was added in the same manner. The mixture was quenched with H$_2$O and extracted with CH$_2$Cl$_2$. The organic layer was dried over Na$_2$SO$_4$ and concentrate to give the crude (R)-tert-butyl 3-((R)-(3-chloro-5-fluorophenyl)(cyanomethoxy)methyl)piperidine-1-carboxylate (4.4 g, 100%).

Step 4. (R)-tert-butyl 3-((R)-(2-aminoethoxy)(3-chloro-5-fluorophenyl)methyl)piperidine-1-carboxylate (R)-tert-Butyl 3-((R)-(3-chloro-5-fluorophenyl)(cyanomethoxy)methyl)piperidine-1-carboxylate (4.4 g, 10.2 mmol, crude) was dissolved in anhydrous THF (60 mL), and the solution was heated to reflux under nitrogen. A solution of 10 M of BH$_3$.Me$_2$S (3 mL, 30.6 mmol) in THF was added dropwise and stirring was continued under reflux overnight. The resulting solution was cooled to 0° C., CH$_3$OH was added dropwise to quench the reaction. Evaporation of the solvent to give the crude product, which was purified by silica column to give (R)-tert-butyl 3-((R)-(2-aminoethoxy)(3-chloro-5-fluorophenyl)methyl)piperidine-1-carboxylate (1.1 g, yield 28%), which was used in the next step without further purification.

Step 5. (R)-tert-butyl 3-((R)-(3-chloro-5-fluorophenyl)(2-(ethoxycarbonylamino)ethoxy)methyl)piperidine-1-carboxylate To a solution of (R)-tert-butyl 3-((R)-(2-aminoethoxy)(3-chloro-5-fluorophenyl)methyl)piperidine-1-carboxylate (1.1 g, 2.85 mmol) in dry CH$_2$Cl$_2$ (20 mL), Et$_3$N (2 mL) was added. The resulting mixture was cooled to 0-5° C. under ice-water bath, a solution of ethyl chloroformate (615 mg, 5.7 mmol) in dry CH$_2$Cl$_2$ (2 mL) was added dropwise. After addition, the reaction mixture was stirred for 1-2 hr at rt. Water (20 mL) was added to quench the reaction. The aqueous layer was extracted with CH$_2$Cl$_2$ (3×20 mL), the combined organic layers were dried over Na$_2$SO$_4$, filtered and concentrated to give the crude (R)-tert-butyl 3-((R)-(3-chloro-5-fluorophenyl)(2-(ethoxycarbonylamino)ethoxy)methyl)piperidine-1-carboxylate (1.3 mg, 100%). $^1$H NMR (CD$_3$OD, 400 MHz) δ 7.01 (d, 2H), 6.87 (d, 1H), 4.32 (m, 2H), 4.09 (m, 2H), 3.92 (m, 2H), 3.33 (m, 5H), 1.75 (s, 1H), 1.55 (m, 1H), 1.43 (s, 9H), 1.34 (m, 2H), 1.23 (t, 3H), 1.09 (t, 1H).

Preparation 36

(R)-tert-butyl 3-((R)-(2-(methoxycarbonylamino)ethoxy)(phenyl)methyl)piperidine-1-carboxylate

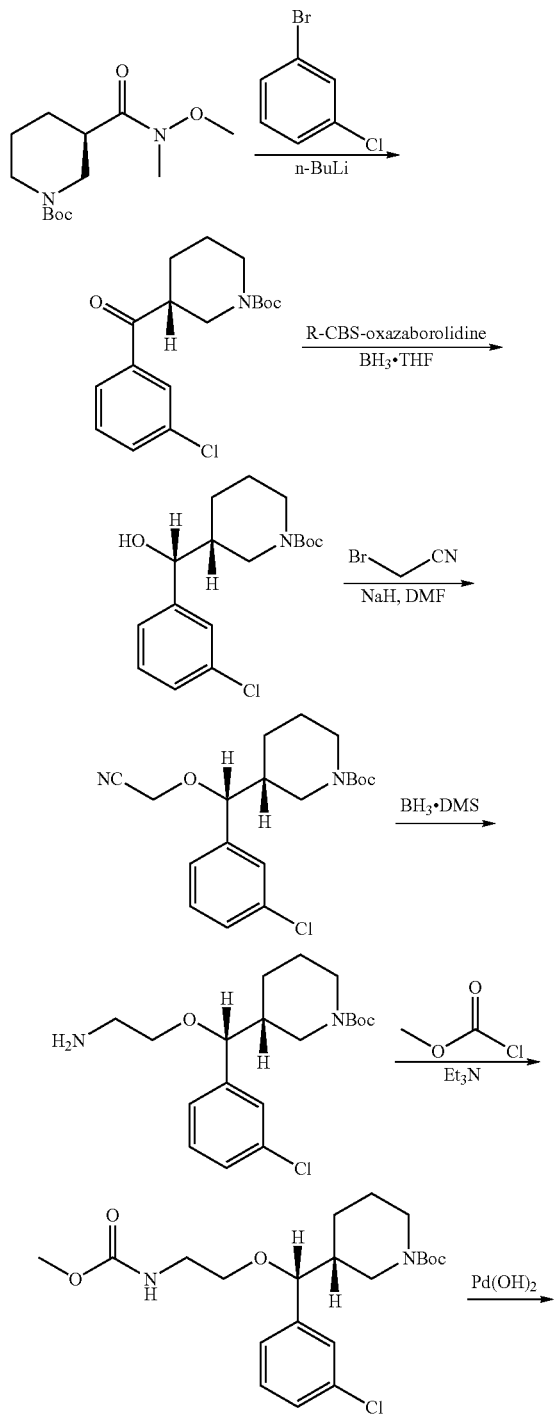

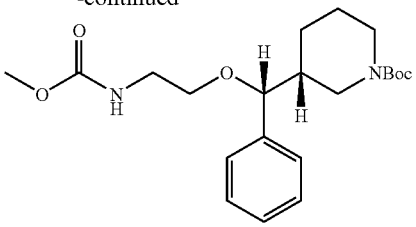

Step 1. (R)-tert-butyl 3-(3-chlorobenzoyl)piperidine-1-carboxylate

To a solution of 1-bromo-3-chlorobenzene (100 g, 0.52 mol) in anhydrous THF (550 mL) at −78° C. under nitrogen was added dropwise a solution of 2.5 M n-BuLi in hexane (210 mL, 0.52 mol). After stirring for 1 hr at −78° C., a solution of (R)-tert-butyl 3-(methoxy(methyl)carbamoyl)piperidine-1-carboxylate (120 g, 0.44 mol) in anhydrous THF (500 mL) was added dropwise. After addition, the reaction mixture was allowed to warm to rt and stirred for 2 hr. The mixture was quenched with saturated $NH_4Cl$ solution (500 mL) and extracted with EtOAc (3×400 mL). The combined organic layers were washed with brine, dried over $Na_2SO_4$ and concentrated in vacuo to give crude (R)-tert-butyl 3-(3-chlorobenzoyl)piperidine-1-carboxylate (178 g), which was used immediately for next step without purification.

Step 2. (R)-tert-butyl 3-((R)-(3-chlorophenyl)(hydroxy)methyl)piperidine-1-carboxylate To a solution of (R)-tert-butyl 3-(3-chlorobenzoyl)piperidine-1-carboxylate (178 g, 0.55 mol) in anhydrous THF (600 mL) at −15° C. under nitrogen was added dropwise a solution of 1 M R-CBS-oxazaborolidine in toluene (82 mL, 82 mmol, 0.15 eq). After stirring for 1 hr at −15° C., a solution of 10 M $BH_3$ in THF (60 mL, 0.60 mol, 1.1 eq) was added dropwise. After addition, the reaction mixture was stirred for 2 hr at −15° C. Methanol (400 mL) was added dropwise carefully at −15° C. The solvent was removed under reduced pressure, the residue was purified by column chromatography on silica gel eluting with EtOAc/hexane (1:30→1:15) to provide the light yellow oil (95 g, HPLC≧70%, ratio≧3:1). The mixture was dissolved in EtOAc until the alcohol was just dissolved (about 5 mL/1 g), the solvent was removed on the rotary evaporator until a few crystals appeared. The solution was cooled to rt slowly and stood for 1-2 hr. To the above solution was added hexane (about 300 mL) and then filtered, the crystals were washed with cool hexane and re-crystallized an additional two times to afford the pure (R)-tert-butyl 3-((R)-(3-chlorophenyl)(hydroxy)methyl)piperidine-1-carboxylate (20 g, ee≧99%).

Step 3. (R)-tert-butyl 3-((R)-(3-chlorophenyl)(cyanomethoxy)methyl)piperidine-1-carboxylate To a solution of (R)-tert-butyl 3-((R)-(3-chlorophenyl)(hydroxy)methyl)piperidine-1-carboxylate (32.5 g, 0.1 mol) in MeCN (325 mL), NaH (12 g, 0.3 mol) was added at 0° C. The mixture was stirred for 1 hr at rt. The mixture was cooled to −40° C., then bromoacetonitrile (35.7 g, 0.3 mol) was added in portions. The mixture was stirred for 0.5 hr at −20° C. After the reaction was complete it was quenched with sat. $NH_4Cl$. The mixture was extracted with $CH_2Cl_2$. The organic layer was dried over $Na_2SO_4$, concentrated. Crude (R)-tert-butyl 3-((R)-(3-chlorophenyl)(cyanomethoxy)methyl)piperidine-1-carboxylate was used for the next step without further purification.

Step 4. (R)-tert-butyl 3-((R)-(2-aminoethoxy)(3-chlorophenyl)methyl)piperidine-1-carboxylate (R)-tert-Butyl 3-((R)-(3-chlorophenyl)(cyanomethoxy)methyl)piperidine-1-carboxylate (23 g, 0.04 mol) was dissolved in anhydrous THF (300 mL), and the solution was heated to reflux under nitrogen. A solution of $BH_3 \cdot Me_2S$ (12 mL, 0.12 mol) in THF was added dropwise, and stirring was continued at reflux overnight. The resulting solution was cooled to rt and MeOH was added dropwise to quench the reaction. After evaporation of the solution, the crude (R)-tert-butyl 3-((R)-(2-aminoethoxy)(3-chlorophenyl)methyl)piperidine-1-carboxylate was obtained which was used for the next step without purification.

Step 5. (R)-tert-butyl 3-((R)-(3-chlorophenyl)(2-(methoxycarbonylamino)ethoxy)methyl)piperidine-1-carboxylate To a solution of (R)-tert-butyl 3-((R)-(2-aminoethoxy)(3-chlorophenyl)methyl)piperidine-1-carboxylate (7.7 g, 21 mmol) and DMAP (1.27 g, 10 mmol, 0.5 eq) in dry $CH_2Cl_2$ (120 mL), $Et_3N$ (6.38 g, 8.45 mL, 63 mmol) was added. The resulting mixture was cooled to 0-5° C. under ice-water bath, a solution of methyl chloroformate (9.88 g, 8.1 mL, 104.5 mmol, 5 eq) in dry $CH_2Cl_2$ (50 mL) was added dropwise. After addition, the reaction mixture was stirred for 1-2 hr at 0-5° C. The reaction was quenched with water (80 mL). The aqueous layer was extracted with $CH_2Cl_2$ (3×50 mL), the combined organic layers were washed with 10% citric acid (2×80 mL) and brine, then dried over $Na_2SO_4$, filtered and concentrated to the crude product, which was purified by preparative HPLC to afford (R)-tert-butyl 3-((R)-(3-chlorophenyl)(2-(methoxycarbonylamino)ethoxy)methyl)piperidine-1-carboxylate (4.4 g, the total yield for five steps is 41%).

Step 6. (R)-tert-butyl 3-((R)-(2-(methoxycarbonylamino)ethoxy)(phenyl)methyl)piperidine-1-carboxylate To a solution of (R)-tert-butyl 3-((R)-(3-chlorophenyl)(2-(methoxycarbonylamino)ethoxy)methyl)piperidine-1-carboxylate (3 g, 7.04 mmol) in MeOH (60 mL) was added wet $Pd(OH)_2/C$ (300 mg). The reaction mixture was stirred under 50 of hydrogen psi at 50° C. for 3 hr. The suspension was filtered and the filtrate was concentrated hydrogen in vacuo. The crude product was purified by preparative HPLC to afford (R)-tert-butyl 3-((R)-(2-(methoxycarbonylamino)ethoxy)(phenyl)methyl)piperidine-1-carboxylate (1.4 g, 51%). $^1$H NMR (CD$_3$OD) δ 7.40-7.22 (m, 5H), 4.20 (m, 1H), 4.01 (m, 1H), 3.81 (m, 1H), 3.6 (s, 3H), 3.27 (m, 3H), 2.84 (m, 2H), 1.8-1.5 (m, 2H), 1.45 (s, 9H). MS ESI +ve m/z 393 (M+1).

Preparation A2

The following compounds were prepared using procedures analogous to those described above in PREPARATION W1:
1) (S)-tert-butyl 4-((R)-5-(cyclohexyloxy)-5-oxo-2-((R)-2-oxo-4-phenyloxazolidine-3-carbonyl)pentyl)-2,2-dimethyloxazolidine-3-carboxylate using (R)-4-phenyl-2-oxalozolidinone in Step 5 and cyclohexyl acrylate in Step 6.
2) (S)-tert-butyl 4-((R)-5-ethoxy-5-oxo-2-(tosyloxymethyl)pentyl)-2,2-dimethyloxazolidine-3-carboxylate using (R)-4-phenyl-2-oxalozolidinone in Step 5 and using ethyl acrylate in step 6.
3) (S)-benzyl 2,2-dimethyl-4-(((R)-tetrahydro-2H-pyran-3-yl)methyl)oxazolidine-3-carboxylate using benzyl chloroformate in Step 1.

Preparation B2 tert-butyl (S)-1-hydroxy-3-(tetrahydro-2H-pyran-3-yl)propan-2-ylcarbamate

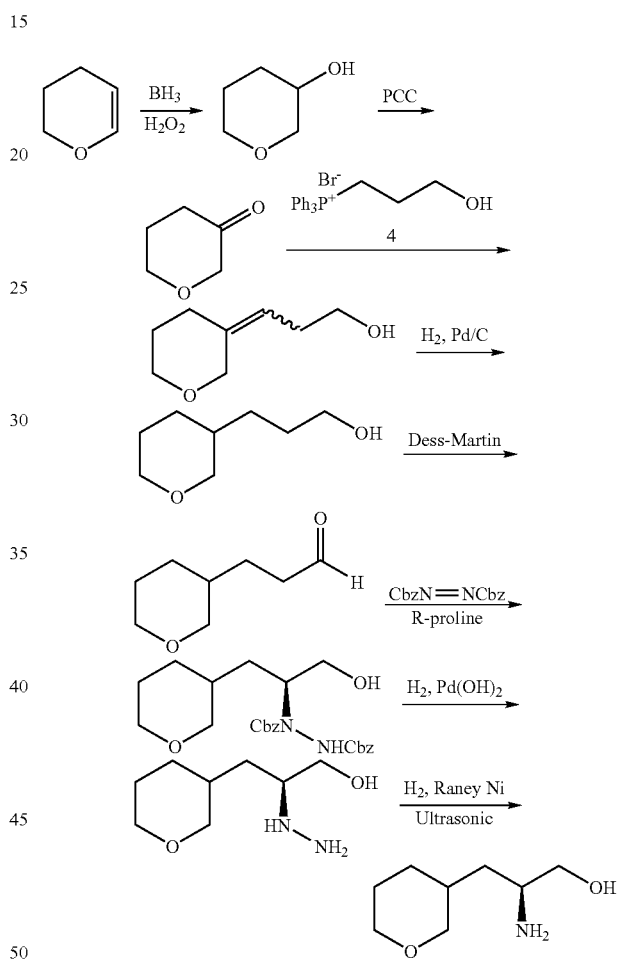

Step 1. tetrahydro-2H-pyran-3-ol

To the solution of 3,4-dihydro-2H-pyran (126 g, 1.5 mol) in dry THF (1350 mL) was added a solution of $B_2H_6$ in $Me_2S$ (10 M, 75 mL, 0.75 mol) under nitrogen atmosphere at 0° C. The mixture was stirred at this temperature for 3 hr, and then was stirred at 25° C. for another 2 hr. The mixture was warmed to 40-45° C., and was added aq. NaOH (3 N, 390 mL) and $H_2O_2$ (30%, 270 mL). After stirring for 2 hr, the reaction was quenched by sat. brine. The mixture was filtered, and the filtrate was extracted with EtOAc (3×300 mL). The organic phase was washed with aq. $Na_2S_2O_3$ (3×100 mL), dried over $Na_2SO_4$, and concentrated in vacuo to give the crude product, which was purified through column chromatography to give tetrahydro-2H-pyran-3-ol (72.8 g, 48%). ¹H NMR (CD₃OD) δ 3.7-3.6 (m, 4H), 3.6-3.5 (m, 1H), 3.4-3.3 (m, 1H), 1.9-1.7 (m, 2H), 1.6-1.5 (m, 2H), Step 2. dihydro-2H-pyran-3(4H)-one To the solution of tetrahydro-2H-pyran-3-ol (30 g, 0.29 mol) in dry CH₂Cl₂ (900 mL) was added 3 Å molecule series (30 g) and PCC (94.9 g, 0.44 mol). The mixture was stirred at rt overnight. When the reaction was over, the mixture was filtered through celite, dried over Na₂SO₄, and concentrated in vacuo to give the crude product, which was purified through column chromatography to give dihydro-2H-pyran-3(4H)-one (23 g, 76%). ¹H NMR (CD₃OD) δ 3.9 (s, 2H), 3.8-3.7 (t, 2H), 3.7-3.6 (m, 4H), 2.5-2.4 (m, 2H), 2.0-1.9 (m, 2H).

Step 3. 3-(dihydro-2H-pyran-3(4H)-ylidene)propan-1-ol

To a suspension of the phosphonium salt (69 g, 1.5 eg) in dry THF (1100 mL) at 0° C. under nitrogen atmosphere was added n-BuLi (2.5 M, 111 mL, 0.413 mol). The solution was stirred for 1 hr, followed by addition of dihydro-2H-pyran-3(4H)-one (11.5 g, 0.115 mol). Stirring was continued at rt overnight. The mixture was quenched by sat. aq. NH₄Cl, and then filtered. The filtrate was dried over Na₂SO₄, and concentrated in vacuo to give the crude product, which was purified through column chromatography to give 3-(dihydro-2H-pyran-3(4H)-ylidene)propan-1-ol (11.2 g, 69%). ¹H NMR (CD₃OD): δ 4.2-3.9 (d, 2H), 3.8-3.5 (m, 4H), 2.4-2.2 (m, 4H), 5.3-5.2 (d, 1H), 2.1-1.8 (s, 1H), 1.8-1.6 (m, 2H).

Step 4. 3-(tetrahydro-2H-pyran-3-yl)propan-1-ol

To the solution of compound 3-(dihydro-2H-pyran-3(4H)-ylidene)propan-1-ol (11.2 g, 0.0789 mol) in methanol (200 mL) was added Pd(OH)₂/C (1.12 g). The reaction flask was degassed and filled into H₂. Stirring was continued until the starting material disappeared. When the reaction was over, the mixture was filtered through celite, and the filter cake was washed with MeOH (2×10 mL). The combined organic layers were dried over Na₂SO₄, and concentrated in vacuo to give 3-(tetrahydro-2H-pyran-3-yl)propan-1-ol (10.35 g, yield 91%), which was used for the next step without purification. ¹H NMR (CD₃OD) δ 3.9-3.8 (m, 1H), 3.7-3.6 (m, 2H), 3.5-3.4 (m, 1H), 3.3 (m, 1H), 3.1-2.9 (t, 1H), 2.6-2.4 (m, 1H), 2.3-1.8 (m, 3H), 1.6-1.4 (m, 4H), 1.3-1.0 (m, 2H).

Step 5. 3-(tetrahydro-2H-pyran-3-yl)propanal

To the solution of 3-(tetrahydro-2H-pyran-3-yl)propan-1-ol (10.35 g, 0.0719 mol) in CH₂Cl₂ (200 mL) was added Dess-Martin periodinane (61.24 g, 0.1438 mol). The mixture was stirred at rt. When the reaction was over, the solution was poured into Et₂O (300 mL) and anhydrous K₂CO₃ (19.84 g, 0.1438 mol) was added. The mixture was filtered. The filtrate was dried over Na₂SO₄, and concentrated in vacuo to give the crude product, which was purified through column chromatography to give 3-(tetrahydro-2H-pyran-3-yl)propanal (8.25 g, 80%).

Step 6. dibenzyl 1-((2S)-1-hydroxy-3-(tetrahydro-2H-pyran-3-yl)propan-2-yl)hydrazine-1,2-dicarboxylate To a stirred solution of 3-(tetrahydro-2H-pyran-3-yl)propanal (8.25 g, 0.058 mol) and dibenzyl azodicarboxylate (94%, 12.3 g, 0.041 mol) in MeCN (250 mL) at 0° C. was added (R-proline) (0.47 g, 0.0041 mol). After stirring the mixture at 0° C. for 15 hr. ethanol (100 mL) and NaBH₄ (1.56 g, 0.041 mol) was added, and the mixture was stirred at 0° C. for 40 min. The reaction was quenched by slow addition of 10% aqueous citric acid (15 ml), and the whole solution was concentrated in vacuo. This residue was diluted with EtOAc (200 ml), washed with saturated brine (1×50 mL), dried over Na₂SO₄, and concentrated in vacuo to give the crude product, which was purified through column chromatography to give dibenzyl 1-((2S)-1-hydroxy-3-(tetrahydro-2H-pyran-3-yl)propan-2-yl)hydrazine-1,2-dicarboxylate (14.68 g, 81%).

Step 7. (2S)-2-hydrazinyl-3-(tetrahydro-2H-pyran-3-yl)propan-1-ol

To the solution of 1-((2S)-1-hydroxy-3-(tetrahydro-2H-pyran-3-yl)propan-2-yl)hydrazine-1,2-dicarboxylate (14.68 g, 0.0332 mol) in methanol (250 mL) was added Pd(OH)₂/C (1.47 g). The reaction flask was degassed and filled into H₂. Stirring was continued until the starting material disappeared. When the reaction was over, the mixture was filtered through celite, and the filter cake was washed with MeOH (2×20 mL). The combined organic solvent was dried over Na₂SO₄, and concentrated in vacuo to give (2S)-2-hydrazinyl-3-(tetrahydro-2H-pyran-3-yl)propan-1-ol (5.79 g, 94%), which was used for the next step without purification.

Step 8. (2S)-2-amino-3-(tetrahydro-2H-pyran-3-yl)propan-1-ol

To the solution of (2S)-2-hydrazinyl-3-(tetrahydro-2H-pyran-3-yl)propan-1-ol (5.79 g, 0.033 mol) in MeOH (100 mL) was added Raney Ni. The flask was degassed and equipped with a hydrogen-inflated balloon. The flask was dipped into an ultrasound bath filled with water and sonicated for 4 hr at rt until the starting material was completely consumed. The mixture was then filtered through celite, and the filter cake was washed with MeOH (2×30 mL). Removal under reduced pressure gave (2S)-2-amino-3-(tetrahydro-2H-pyran-3-yl)propan-1-ol (5.4 g, 90%).

Preparation C2

2-(trimethylsilyl)ethyl (S)-2-amino-3-((R)-tetrahydro-2H-pyran-3-yl)propyl(methyl)carbamate

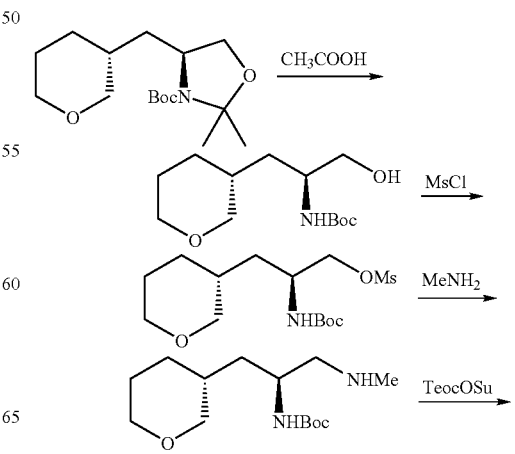

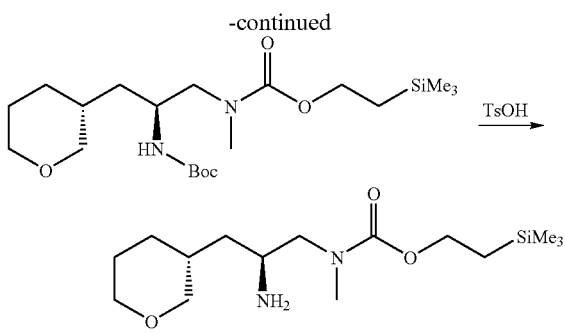

Step 1. tert-butyl (S)-1-hydroxy-3-((R)-tetrahydro-2H-pyran-3-yl)propan-2-ylcarbamate (S)-tert-Butyl-2,2-dimethyl-4-(((R)-tetrahydro-2H-pyran-3-yl)methyl)oxazolidine-3-carboxylate (9 g, 30.1 mmol) was dissolved in 80% aq CH$_3$CO$_2$H (90 ml). The solution was stirred at 50° C. during 1.5 hr and evaporated to dryness at reduced pressure. The residue was dissolved in Et$_2$O (150 ml) and washed with saturated NaHCO$_3$ (4×100 mL). The organic layer was dried over Na$_2$SO$_4$, filtered, and the solvent removed under reduced pressure to give tert-butyl (S)-1-hydroxy-3-((R)-tetrahydro-2H-pyran-3-yl)propan-2-ylcarbamate (6.2 g, 79.5%) as an oil, which was used in the next step without further purification.

Step 2. (S)-2-(tert-butoxycarbonylamino)-3-((R)-tetrahydro-2H-pyran-3-yl)propyl methanesulfonate To a solution of tert-butyl (S)-1-hydroxy-3-((R)-tetrahydro-2H-pyran-3-yl)propan-2-ylcarbamate (6.2 g, 23.9 mmol) and triethylamine (7.25 g, 71.8 mmol) in CH$_2$Cl$_2$ at 0° C. was added mesyl chloride (5.5 g, 47.8 mmol) dropwise. The reaction mixture was stirred at rt until the starting material disappeared. The reaction was quenched with ice-cold water and extracted with CH$_2$Cl$_2$ (3×100 ml). The combined organic layers were washed with water (3×50 ml), dried over Na$_2$SO$_4$, and concentrated under vacuo to give the (S)-2-(tert-butoxycarbonylamino)-3-((R)-tetrahydro-2H-pyran-3-yl)propyl methanesulfonate (9 g), which was used for the next step without purification.

Step 3. tert-butyl (S)-1-(methylamino)-3-((R)-tetrahydro-2H-pyran-3-yl)propan-2-ylcarbamate To an ethanol solution of MeNH$_2$ (100 mL) was added tert-butyl (S)-1-(methylamino)-3-((R)-tetrahydro-2H-pyran-3-yl)propan-2-ylcarbamate (9 g, 26.7 mmol). The mixture was stirred at 30-40° C. overnight. When the reaction was complete, the solution was concentrated to afford tert-butyl (S)-1-(methylamino)-3-((R)-tetrahydro-2H-pyran-3-yl)propan-2-ylcarbamate (10 g), which was used for the further reaction without purification.

Step 4. (S)-tert-butyl 1-(N-Methyl-2-(trimethylsilyl)ethoxycarbonylamino)-3-((R)-tetrahydro-2H-pyran-3-yl)propylcarbamate Solid 1-[2-Trimethylsilyl)ethoxycarbonyloxy]pyrrolidin-2,5-dione (9.5 g, 36.7 mmol) was added to a vigorously stirred biphasic solution of the tert-butyl (S)-1-(methylamino)-3-((R)-tetrahydro-2H-pyran-3-yl)propan-2-ylcarbamate (10 g, 36.7 mmol), K$_2$CO$_3$ (15.1 g, 110.1 mmol), H$_2$O (50 mL) and CH$_2$Cl$_2$ (100 mL). After the reaction was stirred for 2 hr at rt, the reaction was taken up into 65 mL of CH$_2$Cl$_2$. The solution was washed with aq. NaHCO$_3$ (3×50 mL) and brine (3×50 mL), then dried over Na$_2$SO$_4$. The organic layer was concentrated under vacuum to give the crude product, which was purified through column chromatography to give (S)-tert-butyl 1-(N-Methyl-2-(trimethylsilyl)ethoxycarbonylamino)-3-((R)-tetrahydro-2H-pyran-3-yl)propylcarbamate (6 g, 46.2%).

Step 5. 2-(trimethylsilyl)ethyl (S)-2-amino-3-((R)-tetrahydro-2H-pyran-3-yl)propyl(methyl)carbamate To a solution of (S)-tert-butyl 1-(N-Methyl-2-(trimethylsilyl)ethoxycarbonylamino)-3-((R)-tetrahydro-2H-pyran-3-yl)propylcarbamate (6 g, 14.4 mmol) in Et$_2$O (100 mL) was added a solution of tosic acid (2.8 g, 14.4 mmol) in 13.0 mL of absolute EtOH. This solution was placed on a rotary evaporator and the Et$_2$O was removed at ambient temp. The flask was then lowered into a 60° C. water bath and the remainder of the solvent was evaporated over 2 hr to afford a white solid. The solid was cooled to rt and dissolved into 80 mL of a mixture of 1:1 EtOH:H$_2$O. This was washed with 5:1 Hexanes:EA (3×10 mL), basified with 1N NaOH (pH>10), and extracted with Et$_2$O (3×50 mL). The combined Et$_2$O extracts were washed with brine (3×5 mL), dried over Na$_2$SO$_4$, concentrated under vacuum to give 2-(trimethylsilyl)ethyl (S)-2-amino-3-((R)-tetrahydro-2H-pyran-3-yl)propyl(methyl)carbamate 3.3 g (72%).

The following compound was prepared following procedures analogous to those descried above:

1) 2-(trimethylsilyl)ethyl (S)-2-amino-3-(tetrahydro-2H-pyran-3-yl)propyl(methyl)carbamate using tert-butyl (S)-1-hydroxy-3-(tetrahydro-2H-pyran-3-yl)propan-2-ylcarbamate in Step 2.

Example 29 methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate

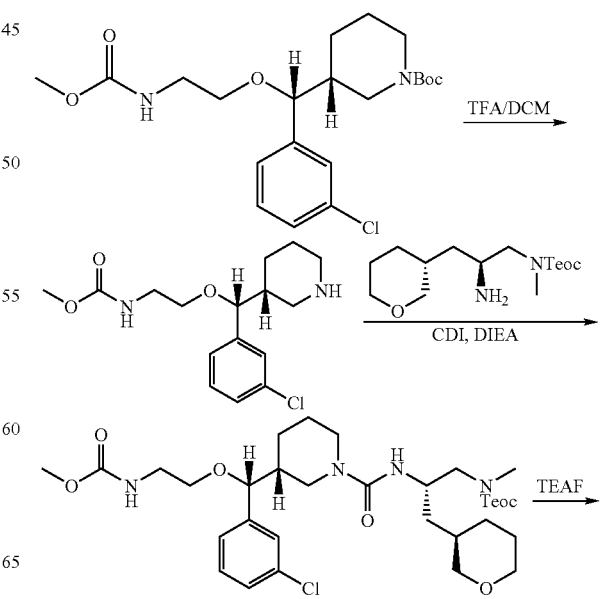

-continued

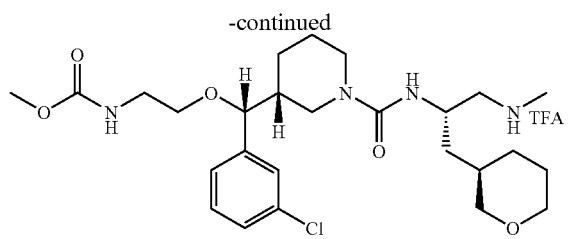

Step 1. methyl 2-((R)-(3-chlorophenyl)((R)-piperidin-3-yl)methoxy)ethylcarbamate (R)-tert-Butyl 3-((R)-(3-chlorophenyl)(2-(methoxycarbonylamino)ethoxy)methyl)piperidine-1-carboxylate (4.86 g, 11.4 mmol) was dissolved in a solution of 20% (V/V) TFA/CH$_2$Cl$_2$ (10 mL). The reaction mixture was stirred at rt for 1 hr. The solvent was removed in vacuo to afford methyl 2-((R)-(3-chlorophenyl)((R)-piperidin-3-yl)methoxy)ethylcarbamate as TFA salt (4.8 g, 100%), which was used for the next step directly without purification.

Step 2. methyl 2-((R)-(3-chlorophenyl)((R)-1-((S)-1-(N-Methyl-2-(trimethylsilyl)ethoxycarbonylamino)-3-((R)-tetrahydro-2H-pyran-3-yl)propan-2-ylcarbamoyl)piperidin-3-yl)methoxy)ethylcarbamate At 0° C., to a solution of 2-(trimethylsilyl)ethyl (S)-2-amino-3-((R)-tetrahydro-2H-pyran-3-yl)propyl(methyl)carbamate (1.9 g, 6 mmol) and DIPEA (3.87 g, 30 mmol) in anhydrous CH$_2$Cl$_2$ (20 mL) was added CDI (1.26 g, 7.8 mmol). After addition, the mixture was stirred for 1 hr at 0° C., followed by addition of methyl 2-((R)-(3-chlorophenyl)((R)-piperidin-3-yl)methoxy)ethylcarbamate as TFA salt (2.8 g, 6.6 mmol) in anhydrous CH$_2$Cl$_2$ (20 mL). The reaction mixture was allowed to warm to rt and stirred overnight. After the reaction was completed, the solvent was removed in vacuo. The product was purified by column chromatography on silica gel eluting with petroleum ether/EtOAc (5:1→2:1) to afford methyl 2-((R)-(3-chlorophenyl)((R)-1-((S)-1-(N-Methyl-2-(trimethylsilyl)ethoxycarbonylamino)-3-((R)-tetrahydro-2H-pyran-3-yl)propan-2-ylcarbamoyl)piperidin-3-yl)methoxy)ethylcarbamate (3.0 g, 75% yield).

Step 3. methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate.trifluoroacetic acid salt Methyl 2-((R)-(3-chlorophenyl)((R)-1-((S)-1-(N-Methyl-2-(trimethylsilyl)ethoxycarbonylamino)-3-((R)-tetrahydro-2H-pyran-3-yl)propan-2-ylcarbamoyl)piperidin-3-yl)methoxy)ethylcarbamate (2.9 g, 4.34 mmol) and TEAF (1.42 g, 9.6 mmol) was dissolved in CH$_3$CN (40 mL). The reaction mixture was heated under reflux for 20 min. Then the mixture was concentrated in vacuo. The residue was purified by preparative HPLC to afford methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate as TFA salt (2.23 g, 83%).

The following compounds were prepared using procedures analogous to those described above:
1) methyl 2-((R)—((R)-1-((S)-1-(methylamino)-3-(tetrahydro-2H-pyran-3-yl)propan-2-ylcarbamoyl)piperidin-3-yl)(m-tolyl)methoxy)ethylcarbamate
2) methyl 2-((R)-(3-chloro-4-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate
3) ethyl 2-((R)-(3-chloro-5-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate
4) methyl 2-((R)-(5-chloro-2-methylphenyl)((R)-1-((S)-1-(methylamino)-3-((R)-tetrahydro-2H-pyran-3-yl)propan-2-ylcarbamoyl)piperidin-3-yl)methoxy)ethylcarbamate

Example 30 methyl 2-((R)-(3-chloro-5-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate

Step 1. (4-nitrophenyl) (S)-1-(N-methyl-N-(trimethylsilylethoxycarbonyl)amino)-3-((R)-tetrahydro-2H-pyran-3-yl)propan-2-ylcarbamate A solution of 2-(trimethylsilyl)ethyl (S)-2-amino-3-((R)-tetrahydro-2H-pyran-3-yl)propyl(methyl)carbamate (0.7350 g, 2.32 mmol, 1.0 equiv, ~7% diastereomeric impurities) in CH$_3$CN (50 mL) was treated with 4-nitrophenyl chloroformate (0.4950 g, 2.45 mmol, 1.05 equiv) and 0.600 g (7.14 mmol, 3 equiv) of NaHCO$_3$. The reaction was stirred at rt for 3 hr. The mixture was filtered using Celite® 545. The filtrate was evaporated under reduced pressure to afford 1.1647 g (100%) of (4-nitrophenyl) (S)-1-(N-methyl-N-(trimethylsilylethoxycarbonyl)amino)-3-((R)-tetrahydro-2H-pyran-3-yl)propan-2-ylcarbamate, which was used in the next step without further purification. MS ESI +ve m/z 504 (M+Na).

Step 2. methyl 2-((R)-(3-chloro-5-fluorophenyl)((R)-1-((S)-1-(N-Methyl-2-(trimethylsilyl)ethoxycarbonylamino)-3-((R)-tetrahydro-2H-pyran-3-yl)propan-2-ylcarbamoyl)piperidin-3-yl)methoxy)ethylcarbamate A mixture of (R)-tert-butyl 3-((R)-(3-chloro-5-fluorophenyl)(2-(methoxycarbonylamino)ethoxy)methyl)piperidine-1-carboxylate (0.1915 g, 0.43 mmol) in TFA (4 mL) and CH$_2$Cl$_2$ (6 mL) was stirred at rt for 2 hr. After the solvents were removed in vacuo, the TFA salt of methyl 2-((R)-(3-chloro-5-fluorophenyl)((R)-piperidin-3-yl)methoxy)ethylcarbamate was directly used in the next step without further purification. MS ESI +ve m/z 345, 347 (M+1).

A mixture of TFA salt of methyl 2-((R)-(3-chloro-5-fluorophenyl)((R)-piperidin-3-yl)methoxy)ethylcarbamate (0.43 mmol, 1.0 equiv), (4-nitrophenyl)(S)-1-(N-methyl-N-(trimethylsilylethoxycarbonyl)amino)-3-((R)-tetrahydro-2H-pyran-3-yl)propan-2-ylcarbamate (0.2710 g, 0.56 mmol, 1.3 equiv), and DIEA (4 mL) in CH$_2$Cl$_2$ was stirred at rt for 19 hr. After the solvents were removed in vacuo, the crude product was purified by reversed-phase HPLC (Phenomenex® Luna 5μ C18(2) 100 A, 250×21.20 mm, 5 micron, 70%→90% CH$_3$CN/H$_2$O, 0.1% CF$_3$CO$_2$H over 8 min and then 90% CH$_3$CN/H$_2$O, 0.1% CF$_3$CO$_2$H over 2 min, flow rate 25 mL/min) to afford 0.2840 g (96%) the product as a mixture of diastereoisomers. MS ESI +ve m/z 687, 689 (M+1). The mixture was further separated by chiral HPLC (CHIRALPAK AD-H, 1 cm ⌀×25 cm, 10% IPA in hexane with 0.025% diethylamine, flow rate 4 mL/min) to give four fractions in the ratio of 49.8 (t$_R$=11.00 min): 4.8 (t$_R$=12.77 min): 43.3 (t$_R$=13.97 min): 2.1 (t$_R$=16.23 min). Among them, the two major fractions [methyl 2-((R)-(3-chloro-5-fluorophenyl)((R)-1-((S)-1-(N-Methyl-2-(trimethylsilyl)ethoxycarbonylamino)-3-((S)-tetrahydro-2H-pyran-3-yl)propan-2-ylcarbamoyl)piperidin-3-yl)methoxy)ethylcarbamate (11 min) and methyl 2-((R)-(3-chloro-5-fluorophenyl)((R)-1-((S)-1-(N-Methyl-2-(trimethylsilyl)ethoxycarbonylamino)-3-((R)-tetrahydro-2H-pyran-3-yl)propan-2-ylcarbamoyl)piperidin-3-yl)methoxy)ethylcarbamate (13.97 min), were assigned S configurations at the amine chiral center and other two minor fractions [methyl 2-((R)-(3-chloro-5-fluorophenyl)((3R)-1-((R)-1-(N-Methyl-2-(trimethylsilyl)ethoxycarbonylamino)-3-(tetrahydro-2H-pyran-3-yl)propan-2-ylcarbamoyl)piperidin-3-yl)methoxy)ethylcarbamate Isomer 1 (12.77 min) and methyl 2-((R)-(3-chloro-5-fluorophenyl)((3R)-1-((R)-1-(N-Methyl-2-(trimethylsilyl)ethoxycarbonylamino)-3-(tetrahydro-2H-pyran-3-yl)propan-2-ylcarbamoyl)piperidin-3-yl)methoxy)ethylcarbamate Isomer 2 (16.23 min), were assigned R configurations at the amine chiral center based on stereoselective synthesis of this diamine. The chiral center at 3-pyran portion was finally determined by asymmetric synthesis of the third fraction. For the two minor fractions, however, the chiral centers at 3-pyran portion were not confirmed by asymmetric synthesis.

Step 3. methyl 2-((R)-(3-chloro-5-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate A solution of methyl 2-((R)-(3-chloro-5-fluorophenyl)((R)-1-((S)-1-(N-Methyl-2-(trimethylsilyl)ethoxycarbonylamino)-3-((R)-tetrahydro-2H-pyran-3-yl)propan-2-ylcarbamoyl)piperidin-3-yl)methoxy)ethylcarbamate (0.0948 g) in TFA (5 mL) and CH$_2$Cl$_2$ (10 mL) was stirred at rt for 2.5 hr. After the solvents were removed in vacuo, the crude product was purified by reversed-phase HPLC (Phenomenex® Luna 5μ C18(2) 100 A, 250×21.20 mm, 5 micron, 10%→90% CH$_3$CN/H$_2$O, 0.1% CF$_3$CO$_2$H over 13 min, flow rate 25 mL/min) to give 0.0928 g of TFA salt of methyl 2-((R)-(3-chloro-5-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate.

The methyl 2-((R)-(3-chloro-5-fluorophenyl)((R)-1-((S)-1-(methylamino)-3-((S)-tetrahydro-2H-pyran-3-yl)propan-2-ylcarbamoyl)piperidin-3-yl)methoxy)ethylcarbamate, methyl 2-((R)-(3-chloro-5-fluorophenyl)((3R)-1-((R)-1-(methylamino)-3-(tetrahydro-2H-pyran-3-yl)propan-2-ylcarbamoyl)piperidin-3-yl)methoxy)ethylcarbamate Isomer 1, and methyl 2-((R)-(3-chloro-5-fluorophenyl)((3R)-1-((R)-1-(methylamino)-3-(tetrahydro-2H-pyran-3-yl)propan-2-ylcarbamoyl)piperidin-3-yl)methoxy)ethylcarbamate Isomer 2 was prepared as above.

The following compounds were prepared using procedures analogous to those described above:

1) methyl 2-((R)-(3,5-difluorophenyl)((R)-1-((S)-1-(methylamino)-3-((S)-tetrahydro-2H-pyran-3-yl)propan-2-ylcarbamoyl)piperidin-3-yl)methoxy)ethylcarbamate
2) methyl 2-((R)-(3,5-difluorophenyl)((R)-1-((S)-1-(methylamino)-3-((R)-tetrahydro-2H-pyran-3-yl)propan-2-ylcarbamoyl)piperidin-3-yl)methoxy)ethylcarbamate
3) methyl 2-((R)-(5-fluoro-2-methylphenyl)((R)-1-((S)-1-(methylamino)-3-((S)-tetrahydro-2H-pyran-3-yl)propan-2-ylcarbamoyl)piperidin-3-yl)methoxy)ethylcarbamate
4) methyl 2-((R)-(5-fluoro-2-methylphenyl)((R)-1-((S)-1-(methylamino)-3-((R)-tetrahydro-2H-pyran-3-yl)propan-2-ylcarbamoyl)piperidin-3-yl)methoxy)ethylcarbamate
5) methyl 2-((R)-(3-chlorophenyl)((R)-1-((S)-1-(methylamino)-3-((S)-tetrahydro-2H-pyran-3-yl)propan-2-ylcarbamoyl)piperidin-3-yl)methoxy)ethylcarbamate Example 31 methyl 2-((R)-(3-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate and methyl 2-((R)-(3-fluorophenyl)((R)-1-((S)-1-(methylamino)-3-((S)-tetrahydro-2H-pyran-3-yl)propan-2-ylcarbamoyl)piperidin-3-yl)methoxy)ethylcarbamate

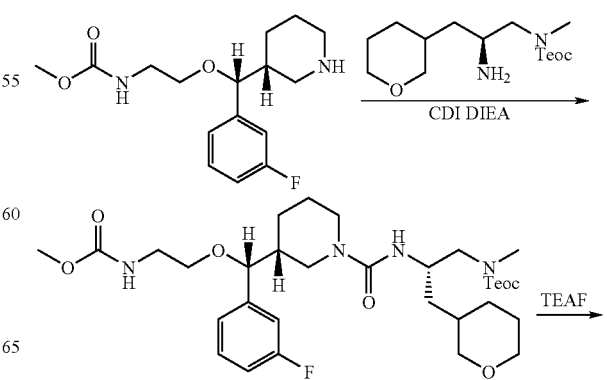

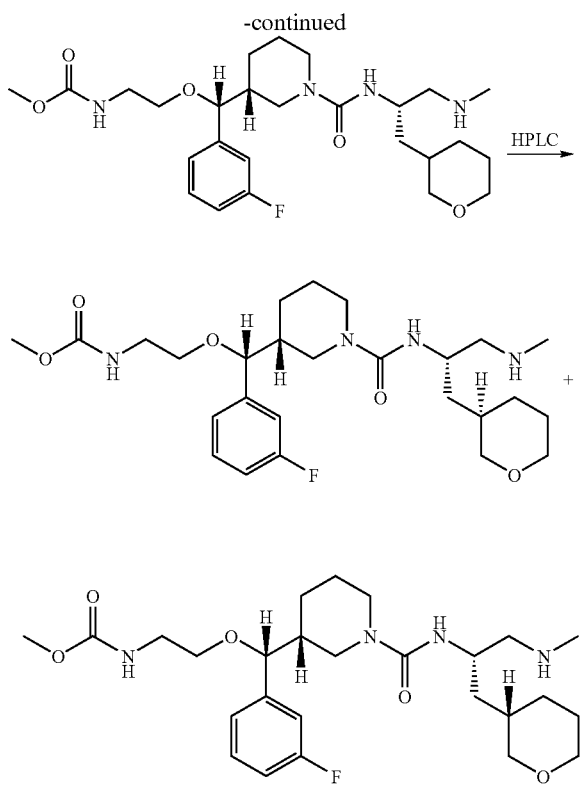

Step 1. methyl 2-((R)-(3-fluorophenyl)((3R)-1-((S)-1-(N-Methyl-2-(trimethylsilyl)ethoxycarbonylamino)-3-(tetrahydro-2H-pyran-3-yl)propan-2-ylcarbamoyl)piperidin-3-yl)methoxy)ethylcarbamate To a solution of 2-(trimethylsilyl)ethyl (S)-2-amino-3-(tetrahydro-2H-pyran-3-yl)propyl(methyl)carbamate (300 mg, 0.95 mmol) and CDI (154 mg, 0.95 mmol) in anhydrous CH$_2$Cl$_2$ (20 mL), DIEA (612 mg, 4.7 mmol) was added with ice bath. After addition, the mixture was stirred for 1 h at 0° C., then was added to a solution of {2-[(3-fluoro-phenyl)-piperidin-3-yl-methoxy]-ethyl}-carbamic acid methyl ester (245 mg, 0.79 mmol) in anhydrous CH$_2$Cl$_2$ (25 mL). The reaction mixture was allowed to warm to rt and stirred overnight. After the reaction was completed, the solvent was removed in vacuo. The product was purified by preparative TLC to afford methyl 2-((R)-(3-fluorophenyl)((3R)-1-((S)-1-(N-Methyl-2-(trimethylsilyl)ethoxycarbonylamino)-3-(tetrahydro-2H-pyran-3-yl)propan-2-ylcarbamoyl)piperidin-3-yl)methoxy)ethylcarbamate (258 mg, 50% yield).

Step 2. methyl 2-((R)-(3-fluorophenyl)((3R)-1-((S)-1-(methylamino)-3-(tetrahydro-2H-pyran-3-yl)propan-2-ylcarbamoyl)piperidin-3-yl)methoxy)ethylcarbamate A solution of methyl 2-((R)-(3-fluorophenyl)((3R)-1-((S)-1-(N-Methyl-2-(trimethylsilyl)ethoxycarbonylamino)-3-(tetrahydro-2H-pyran-3-yl)propan-2-ylcarbamoyl)piperidin-3-yl)methoxy)ethylcarbamate (258 mg, 0.40 mmol) in MeCN (25 mL) was treated with TEAF (192 mg, 0.87 mmol) and allowed to stir under reflux for 1 h. The mixture was concentrated in vacuo and purified by preparative HPLC to give methyl 2-((R)-(3-fluorophenyl)((3R)-1-((S)-1-(methylamino)-3-(tetrahydro-2H-pyran-3-yl)propan-2-ylcarbamoyl)piperidin-3-yl)methoxy)ethylcarbamate as trifluoroacetic acid salt. (162 mg, 81% yield).

Step 3. methyl 2-((R)-(3-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate and methyl 2-((R)-(3-fluorophenyl)((R)-1-((S)-1-(methylamino)-3-((S)-tetrahydro-2H-pyran-3-yl)propan-2-ylcarbamoyl)piperidin-3-yl)methoxy)ethylcarbamate A solution of methyl 2-((R)-(3-fluorophenyl)((3R)-1-((S)-1-(methylamino)-3-(tetrahydro-2H-pyran-3-yl)propan-2-ylcarbamoyl)piperidin-3-yl)methoxy)ethylcarbamate as trifluoroacetic acid salt in CH$_2$Cl$_2$ (5 mL) was washed with 1 M NaOH (2 mL, 2×). The aqueous layer was extracted with CH$_2$Cl$_2$ (1 mL, 3×) and the combined organic fractions were washed with water, brine, and dried over sodium sulfate. The filtrate was evaporated to afford the free base. The crude product was separated via chiral HPLC (CHIRALPAK AD-H, 1 cm ⌀×25 cm, 10% IPA in hexane with 0.025% diethylamine, flow rate 4 mL/min) to afford two isomers, methyl 2-((R)-(3-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate (78.57 mg, $t_R$=20.70 min) and methyl 2-((R)-(3-fluorophenyl)((R)-1-((S)-1-(methylamino)-3-((S)-tetrahydro-2H-pyran-3-yl)propan-2-ylcarbamoyl)piperidin-3-yl)methoxy)ethylcarbamate (90.9 mg, $t_R$=29.63 min).

Step 4. methyl 2-((R)-(3-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate fumaric acid salt An ethanol solution of methyl 2-((R)-(3-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate (71.2 mg, 0.14 mmol) was treated with fumaric acid (16.3 mg, 0.14 mmol). The solvent was removed in vacuo and the residue re-dissolved in water. The solution was frozen using a dry ice-acetone bath and placed on a lypholizer to afford methyl 2-((R)-(3-fluorophenyl)((R)-1-((S)-1-(methylamino)-3-((R)-tetrahydro-2H-pyran-3-yl)propan-2-ylcarbamoyl)piperidin-3-yl)methoxy)ethylcarbamate fumaric acid salt (87.46 mg) as a white solid.

Step 5. methyl 2-((R)-(3-fluorophenyl)((R)-1-((S)-1-(methylamino)-3-((S)-tetrahydro-2H-pyran-3-yl)propan-2-ylcarbamoyl)piperidin-3-yl)methoxy)ethylcarbamate fumaric acid salt An ethanol solution of methyl 2-((R)-(3-fluorophenyl)((R)-1-((S)-1-(methylamino)-3-((S)-tetrahydro-2H-pyran-3-yl)propan-2-yl carbamoyl)piperidin-3-yl)methoxy)ethylcarbamate (87.2 mg, 0.17 mmol) was treated with fumaric acid (19.8 mg, 0.17 mmol). The solvent was removed in vacuo and the residue re-dissolved in water. The solution was frozen using a dry ice-acetone bath and placed on a lypholizer to afford methyl 2-((R)-(3-fluorophenyl)((R)-1-((S)-1-(methylamino)-3-((S)-tetrahydro-2H-pyran-3-yl)propan-2-ylcarbamoyl)piperidin-3-yl)methoxy)ethylcarbamate fumaric acid salt (106.8 mg) as a white solid.

Example 32 methyl 2-((R)—((R)-1-((S)-1-(methylamino)-3-((R)-tetrahydro-2H-pyran-3-yl)propan-2-ylcarbamoyl)piperidin-3-yl)(phenyl)methoxy)ethylcarbamate

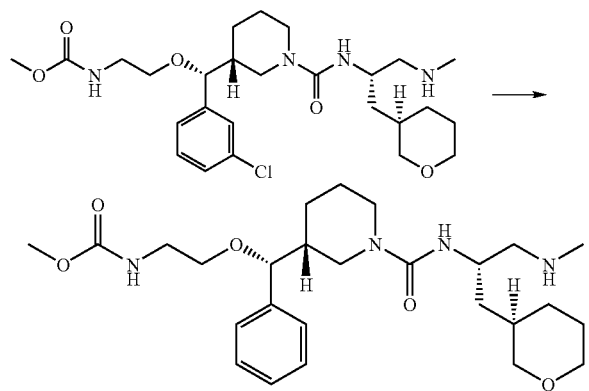

Step 1. methyl 2-((R)—((R)-1-((S)-1-(methylamino)-3-((R)-tetrahydro-2H-pyran-3-yl)propan-2-ylcarbamoyl)piperidin-3-yl)(phenyl)methoxy)ethylcarbamate A mixture of methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate (0.0027 g), HCO$_2$NH$_4$ (0.7350 g), and 10% Pd/C (0.0545 g) in MeOH was stirred at rt for 3 hr. The mixture was filtered off precipitates through filter agent, Celite® 545 and washed with MeOH. After the solvent was evaporated under reduced pressure, the crude product was purified by reversed-phase HPLC (Phenomenex® Luna 5μ C18(2) 100 A, 250×21.20 mm, 5 micron, 10%→90% CH$_3$CN/H$_2$O, 0.1% CF$_3$COOH over 13 min, flow rate 25 mL/min) to give TFA salt of methyl 2-((R)—((R)-1-((S)-1-(methylamino)-3-((R)-tetrahydro-2H-pyran-3-yl)propan-2-ylcarbamoyl)piperidin-3-yl)(phenyl)methoxy)ethylcarbamate. MS ESI +ve m/z 491 (M+1).

Example 33 methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate fumaric acid salt

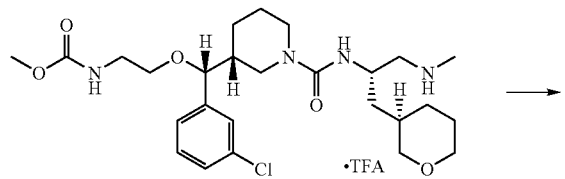

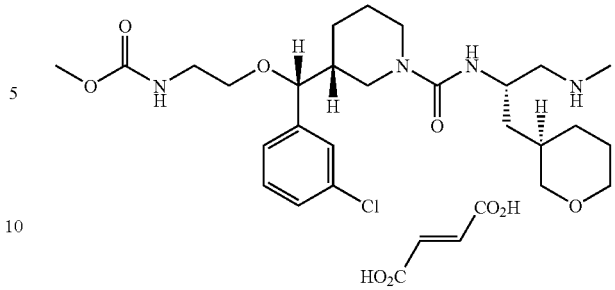

Step 1. methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate The TFA salt of methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate (2.2300 g, 3.49 mmol) was treated with 10 mL of 1 N NaOH. The mixture was extracted with CH$_2$Cl$_2$ (4×) and dried over K$_2$CO$_3$. After the solvent was removed in vacuo, the residue was dissolved into Et$_2$O and filtered through HPLC filter. The filtrate was evaporated under reduced pressure and the residue was dried in vacuo to give 1.6806 g (3.20 mmol, 92%) methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate as free base. $^1$H NMR (CD$_3$OD, 400 MHz) δ 7.27-7.13 (m, 4H), 4.05 (br d, J=13.5 Hz, 1H), 3.92 (d, J=9.1 Hz, 1H), 3.89-3.83 (m, 2H), 3.79-3.70 (m, 2H), 3.53 (s, 3H), 3.32-3.26 (m, 1H), 3.18-3.13 (m, 4H), 3.01 (dd, J=10.8, 10.0 Hz, 1H), 2.88-2.75 (m, 2H), 2.53-2.44 (m, 2H), 2.29 (s, 3H), 1.78-1.47 (m, 6H), 1.30-1.03 (m, 6H).

Step 2. methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate fumaric acid salt The free base of methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate (1.6806 g, 3.20 mmol) and fumaric acid (0.3713 g, 3.20 mmol) were dissolved into EtOH and the solution was evaporated under reduced pressure. The residue was dissolved into H$_2$O, frozen in a dry ice-acetone bath, and dried by lyophilization to provide fumarate salt of methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate as a white powder. $^1$H NMR (CD$_3$OD, 400 MHz) δ 7.27-7.13 (m, 4H), 6.59 (s, 1.76H), 4.04 (br d, J=12.0 Hz, 1H), 3.99-3.96 (m, 1H), 3.92 (d, J=9.1 Hz, 1H), 3.82-3.73 (m, 3H), 3.53 (s, 3H), 3.35-3.28 (m, 1H), 3.18-3.12 (m, 4H), 3.03 (dd, J=10.8, 10.0 Hz, 1H), 2.97 (dd, J=12.6, 3.5 Hz, 1H), 2.93-2.78 (m, 3H), 2.62 (s, 3H), 1.79-1.48 (m, 6H), 1.45-1.02 (m, 6H).

Example 34 methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate L-tartaric acid salt

Step 1. methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate L-tartaric acid salt The free base of methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate (0.28 g, 0.53 mmol) and L-tartaric acid (84.4 mg, 0.56 mmol, 99.5%) were dissolved in ethanol (5 mL) to give a clear solution. The solvent was removed in vacuo to dryness, and the residue was redissolved in 95% ethanol:MeCN (3:97 v/v) (10.5 mL) at 35° C. A seed crystal was added and the resulting solution was stirred at 35° C. for 2 hr, then cooled to rt slowly, and stirred for 48 hr. The resulting white crystal was filtered and washed with MeCN (2×5 mL) to give 1:1 L-tartrate of methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate (0.31 g, 84%). Selected $^1$H NMR (CD$_3$OD, 400 MHz), δ: 7.36 (m, 3H), 7.22 (d, 1H), 4.40 (s, 2H), 4.18-4.00 (m, 3H), 3.86 (m, 3H), 3.62 (s, 3H), 3.40 (m, 1H), 3.24 (m, 3H), 3.18-2.84 (m, 5H), 2.72 (s, 3H), 1.90-1.08 (m, 12H); mp=122-127° C. MS ESI +ve m/z 525 (M+1).

X-ray powder diffraction of two batches of 1:1 methyl 2-((R)-(3-chlorophenyl)((R)-1-((S)-1-(methylamino)-3-((R)-tetrahydro-2H-pyran-3-yl)propan-2-ylcarbamoyl)piperidin-3-yl)methoxy)ethylcarbamate L-tartaric acid salt is shown in FIG. 1.

The following are aspartic protease inhibitors of the invention. Compound names were generated with the assistance of ChemDraw® versions 8.0 and 9.0 (CambridgeSoft Corporation, 100 CambridgePark Drive, Cambridge, Mass. 02140 USA). When the stereochemistry at a chiral center is not defined in the compound name this indicates that the sample prepared contained a mixture of isomers at this center.

| | Table of Compound of Formula (I*) | | |
|---|---|---|---|
| I*-1a | methyl 2-((R)-(3-chlorophenyl)((R)-1-((S)-5-methoxy-1-(methylamino)pentan-2-ylcarbamoyl)piperidin-3-yl)methoxy)ethylcarbamate | | |
| I*-2a | methyl 2-((R)-((R)-1-((S)-1-cyclohexyl-3-(methylamino)propan-2-ylcarbamoyl)piperidin-3-yl)(phenyl)methoxy)ethylcarbamate | 2.21  489 (M + 1) | 0.89 (m, 1H), 1.04 (m, 1H), 2.70 (s, 3H), 3.62 (s, 3H), 3.85 (m, 1H), 4.00 (m, 1H), 4.15 (m, 2H), 7.31 (m, 5H) |
| I*-3a | methyl 2-((R)-((R)-1-((S)-1-(methylamino)-3-(tetrahydro-2H-pyran-4-yl)propan-2-ylcarbamoyl)piperidin-3-yl)(phenyl)methoxy)ethylcarbamate | 1.77  491 (M + 1) | 2.65 (s, 3H), 3.06 (m, 1H), 3.61 (s, 3H), 4.16 (m, 2H), 7.32 (m, 5H) |
| I*-4a | methyl 2-((R)-((R)-1-((S)-1-amino-3-cyclohexylpropan-2-ylcarbamoyl)piperidin-3-yl)(3-fluorophenyl)methoxy)ethylcarbamate | 2.18  493 (M + 1) | 0.95 (m, 2H), 3.60 (s, 3H), 3.85 (m, 1H), 6.91 (m, 3H), 7.35 (m, 1H) |
| I*-5a | methyl 2-((R)-((R)-1-((S)-1-cyclopentyl-3-(methylamino)propan-2-ylcarbamoyl)piperidin-3-yl)(3-fluorophenyl)methoxy)ethylcarbamate | 2.15  493 (M + 1) | 1.17 (m, 3H), 1.84 (m, 3H), 2.71 (s, 3H), 2.92 (m, 3H), 3.10 (m, 1H), 3.61 (s, 3H), 3.85 (m, 1H), 4.05 (m, 2H), 4.17 (m, 1H), 7.06 (m, 3H), 7.35 (m, 1H) |
| I*-6a | methyl 2-((R)-(3-fluorophenyl)((3R)-1-((S)-1-(methylamino)-3-(tetrahydrofuran-3-yl)propan-2-ylcarbamoyl)piperidin-3-yl)methoxy)ethylcarbamate | 1.65  495 (M + 1) | 0.89 (m, 1H), 2.10 (m, 1H), 2.30 (m, 1H), 2.72 (s, 3H), 3.11 (m, 1H), 3.61 (s, 3H), 4.19 (m, 1H), 7.06 (m, 3H), 7.46 (m, 1H) |
| I*-7a | methyl 2-((R)-((R)-1-((S)-4,4-dimethyl-1-(methylamino)hexan-2-ylcarbamoyl)piperidin-3-yl)(3-fluorophenyl)methoxy)ethylcarbamate | 2.00  495 (M + 1) | 0.86 (t, 3H), 0.92 (s, 6H), 2.70 (s, 3H), 3.60 (s, 3H), 3.85 (m, 1H), 4.10 (m, 2H), 7.03 (m, 3H), 7.35 (m, 1H) |

-continued

| Table of Compound of Formula (I*) | | | | |
|---|---|---|---|---|
| I*-8a | methyl 2-((R)-((R)-1-((S)-5,5-dimethyl-1-(methylamino)hexan-2-ylcarbamoyl)piperidin-3-yl)(3-fluorophenyl)methoxy)ethylcarbamate | 1.51 | 495 (M + 1) | 7.36 (m, 1H), 7.09 (d, 1H), 7.04 (m, 2H), 4.05 (d, 1H), 3.62 (s, 3H), 2.72 (s, 3H), 0.93 (s, 9H), |
| I*-9a | methyl 2-((R)-((R)-1-((S)-1-cyclohexyl-3-(methylamino)propan-2-ylcarbamoyl)piperidin-3-yl)(thiophen-2-yl)methoxy)ethylcarbamate | 2.17 | 495 (M + 1) | 1.81-1.86 (m, 6H), 2.80 (s, 3H), 3.7 (s, 3H), 4.23 (m, 2H), 4.40 (d, 1H), 7.10 (m, 2H), 7.50 (d, 1H) |
| I*-10a | methyl 2-((S)-cyclohexyl((R)-1-((S)-1-cyclohexyl-3-(methylamino)propan-2-ylcarbamoyl)piperidin-3-yl)methoxy)ethylcarbamate | 1.71 | 495 (M + 1) | 4.04-3.89 (m, 3H), 3.53 (s, 3H), 3.58-2.64 (m, 9H), 2.60 (s, 3H), 1.72-0.77 (m, 29H). |
| I*-11a | methyl 2-((R)-(3-chlorophenyl)((R)-1-((3R*,4S*)-4-isobutylpyrrolidin-3-ylcarbamoyl)piperidin-3-yl)methoxy)ethylcarbamate | 1.48 | 495 (M+) | 7.36-7.15 (m, 3H), 4.19 (d, 1H), 3.79 (t, 1H), 3.62 (s, 3H), 2.88 (m, 3H), 2.44 (m, 2H), 1.18 (t, 1H), 0.94 (m, 6H). |
| I*-12a | methyl 2-((S)-((R)-1-((S)-1-cyclohexyl-3-(methylamino)propan-2-ylcarbamoyl)piperidin-3-yl)(thiazol-2-yl)methoxy)ethylcarbamate | 1.87 | 496 (M + 1) | 1.58 (m, 25H), 2.71 (s, 3H), 3.01 (m, 4H), 3.47 (m, 2H), 3.62 (s, 3H), 3.78 (m, 1H), 4.11 (m, 2H), 4.47 (d, 1H), 7.65 (d, 1H), 7.79 (d, 1H), |
| I*-13a | methyl 2-((R)-((R)-1-((S)-1-cyclohexyl-3-(methylamino)propan-2-ylcarbamoyl)piperidin-3-yl)(thiazol-2-yl)methoxy)ethylcarbamate | 1.84 | 496 (M + 1) | 1.48 (m, 30H), 2.71 (s, 3H), 3.01 (m, 5H), 3.52 (m, 2H), 3.62 (s, 3H), 3.74 (m, 2H), 4.11 (m, 1H), 4.60 (d, 1H), 7.65 (d, 1H), 7.79 (d, 1H), |
| I*-14a | methyl 2-((R)-((R)-1-((S)-2-amino-5-methoxy-4,4-dimethylpentylcarbamoyl)piperidin-3-yl)(3-fluorophenyl)methoxy)ethylcarbamate | 1.95 | 497 (M + 1) | 0.97 (d, 6H), 1.15 (m, 1H), 1.54 (m, 1H), 1.75 (b, 1H), 2.81-2.98 (m, 2H), 3.62 (s, 3H), 3.75 (d, 2H), 4.06 (d, 1H), 4.19 (d, 1H), 6.97-7.11 (m, 3H), 7.45 (m, 1H) |
| I*-15a | methyl 2-((R)-((R)-1-((S)-1-(methylamino)-3-(tetrahydro-2H-pyran-4-yl)propan-2-ylcarbamoyl)piperidin-3-yl)(thiophen-2-yl)methoxy)ethylcarbamate | 1.68 | 497 (M + 1) | 2.72 (s, 3H), 3.07 (m, 1H), 3.62 (s, 3H), 3.91 (m, 4H), 4.32 (m, 1H), 7.00 (m, 2H), 7.41 (m, 1H) |
| I*-16a | methyl 2-((S)-((R)-1-((S)-1-(methylamino)-3-(tetrahydro-2H-pyran-4-yl)propan-2-ylcarbamoyl)piperidin-3-yl)(thiophen-2-yl)methoxy)ethylcarbamate | 1.57 | 497 (M + 1) | 1.10-1.49 (m, 7H), 1.55-1.90 (m, 7H), 2.60-2.73 (d, 4H), 3.65 (s, 2H), 7.01 (m, 2H), 7.40 (m, 1H) |
| I*-17a | methyl 2-((R)-(3-fluorophenyl)((R)-1-((S)-5-methoxy-1-(methylamino)pentan-2-ylcarbamoyl)piperidin-3-yl)methoxy)ethylcarbamate | | | |
| I*-18a | methyl 2-((R)-((R)-1-((S)-1-cyclohexyl-3-(methylamino)propan-2-ylcarbamoyl)piperidin-3-yl)(m-tolyl)methoxy)ethylcarbamate | 2.15 | 503 (M + 1) | 2.31 (s, 3H), 2.70 (s, 3H), 3.05 (m, 1H), 3.60 (s, 3H), 3.85 (m, 1H), 3.95 (m, 1H), 4.14 (m, 2H), 7.05 (m, 3H), 7.20 (m, 1H) |

-continued

| | Table of Compound of Formula (I*) | | | |
|---|---|---|---|---|
| I*-19a | methyl 2-((R)-((R)-1-((1S,2R)-1-cyclohexyl-1-hydroxy-3-(methylamino)propan-2-ylcarbamoyl)piperidin-3-yl)(phenyl)methoxy)ethylcarbamate | 1.47 | 505 (M + 1) | 7.37-7.25 (m), 7.17 (m), 3.62 (s), 2.73 (s) |
| I*-20a | methyl 2-((R)-((R)-1-((S)-1-(methylamino)-3-(tetrahydro-2H-pyran-4-yl)propan-2-ylcarbamoyl)piperidin-3-yl)(m-tolyl)methoxy)ethylcarbamate | 1.47 | 505 (M + 1) | 2.34 (s, 3H), 2.72 (s, 3H), 3.09 (m, 1H), 3.62 (s, 3H), 3.94 (m, 4H), 4.18 (m, 2H), 7.07 (m, 3H), 7.24 (m, 1H) |
| I*-21a | methyl 2-((R)-((R)-1-((S)-1-(methylamino)-3-((R)-oxepan-3-yl)propan-2-ylcarbamoyl)piperidin-3-yl)(phenyl)methoxy)ethylcarbamate | 1.32 | 505 (M + H) | 7.37-7.27 (m, 5H), 4.18-4.00 (m, 3H), 3.85 (brd, J = 12.4 Hz, 1H), 3.77-3.67 (m, 3H), 3.62 (s, 3H), 3.44 (dd, J = 12.4, 7.6 Hz, 1H), 3.28-3.21 (m, 4H), 3.08 (dd, J = 12.8, 3.2 Hz, 1H), 3.00-2.85 (m, 3H), 2.71 (s, 3H), 1.88-1.28 (m, 13H), 1.15 (m, 1H). |
| I*-22a | methyl (S)-4-((S)-1-((S)-1-cyclohexyl-3-(methylamino)propan-2-ylcarbamoyl)piperidin-3-yl)-4-(3-fluorophenyl)butylcarbamate | 1.63 | 505 (M + 1) | 7.24-7.19 (m, 1H), 6.91-6.82 (m, 3H), 3.95-3.89 (m, 1H), 3.81 (d, J = 12.9 Hz, 1H), 3.54 (d, J = 12.9 Hz, 1H), 3.49 (s, 3H), 2.93-2.88 (m, 3H), 2.74 (dd, J = 12.6, 10.3 Hz, 1H), 2.64-2.57 (m, 1H), 2.56 (s, 3H), 2.36-2.30 (m, 2H), 2.02-0.74 (m, 22H). |
| I*-23a | methyl (R)-4-((S)-1-((S)-1-cyclohexyl-3-(methylamino)propan-2-ylcarbamoyl)piperidin-3-yl)-4-(3-fluorophenyl)butylcarbamate | 1.67 | 505 (M + 1) | 7.24-7.18 (m, 1H), 6.87-6.78 (m, 3H), 4.07-3.98 (m, 2H), 3.77 (d, J = 13.5 Hz, 1H), 3.49 (s, 3H), 2.61 (s, 3H), 2.99-2.33 (m, 7H), 1.84-0.79 (m, 22H). |
| I*-24a | methyl 2-((R)-((R)-1-((S)-1-cyclopentyl-3-(methylamino)propan-2-ylcarbamoyl)piperidin-3-yl)(5-fluoro-2-methylphenyl)methoxy)ethylcarbamate | 2.21 | 507 (M + 1) | 1.00-1.50 (m, 7H), 1.51-1.95 (m, 10H), 2.30 (s, 3H), 2.70 (s, 3H), 3.63 (s, 3H), 3.92 (d, 1H), 4.25 (d, 1H), 4.35 (d, 1H), 6.91 (m, 1H), 7.08 (m, 1H), 7.18 (t, 1H) |
| I*-25a | R)-3-((R)-1-(3-chlorophenyl)-1-(2-(methylamino)-2-oxoethoxy)ethyl)-N-((S)-1-cyclohexyl-3-(methylamino)propan-2-yl)piperidine-1-carboxamide | 1.53 | 507 (M+) | 7.31-7.14 (m, 4H), 4.17 (s, 2H), 4.20-3.98 (m, 3H), 3.02 (dd, J = 12.6, 3.2 Hz, 1H), 2.89 (dd, J = 12.3, 10.5 Hz, 1H), 2.65 (s, 3H), 2.38 (s, 3H), 1.41 (s, 3H), 2.69-0.83 (m, 20H). |
| I*-26a | methyl 2-((R)-(3-fluorophenyl)((R)-1-((S)-1-(methylamino)-3-(tetrahydro-2H-pyran-4-yl)propan-2-ylcarbamoyl)piperidin-3-yl)methoxy)ethylcarbamate | 1.72 | 509 (M + 1) | 2.70 (s, 3H), 3.07 (m, 1H), 3.61 (s, 3H), 3.91 (m, 3H), 4.05 (m, 1H), 4.15 (m, 2H), 7.05 (m, 3H), 7.35 (m, 1H) |

-continued

| Table of Compound of Formula (I*) | | | | |
|---|---|---|---|---|
| I*-27a | methyl 2-((R)-((R)-1-((1S,2R)-1-cyclopentyl-1-hydroxy-3-(methylamino)propan-2-yl)carbamoyl)piperidin-3-yl)(3-fluorophenyl)methoxy)ethylcarbamate | 1.37 | 509 (M + 1) | 7.39-7.34, (m), 7.10-7.02 (m), 4.16 (d), 3.62 (s), 3.54 (t), 2.72 (s) |
| I*-28a | methyl 2-((R)-((R)-1-((S)-2-amino-3-((R)-oxepan-3-yl)propylcarbamoyl)piperidin-3-yl)(3-fluorophenyl)methoxy)ethylcarbamate | 1.26 | 509 (M + H) | 7.36 (m, 1H), 7.11-7.00 (m, 3H), 4.18 (brd, J = 13.6 Hz, 1H), 4.04 (d, J = 8.8 Hz, 1H), 3.79-3.65 (m, 5H), 3.62 (s, 3H), 3.44 (m, 2H), 3.33-3.22 (m, 5H), 2.91 (m, 2H), 1.89-1.29 (m, 13H), 1.15 (m, 1H). |
| I*-29a | methyl 2-((R)-(3-chlorophenyl)((R)-1-((S)-1-cyclopentyl-3-(methylamino)propan-2-ylcarbamoyl)piperidin-3-yl)methoxy)ethylcarbamate | 2.25 | 509 (M+) | 2.71 (s, 3H), 2.90 (m, 3H), 3.10 (m, 1H), 3.62 (s, 3H), 3.85 (m, 1H), 4.03 (m, 2H), 4.15 (m, 1H), 7.20 (m, 1H), 7.33 (m, 3H) |
| I*-30a | (R)-3-((R)-(3-chlorophenyl)(2-(ethylamino)-2-oxoethoxy)methyl)-N-((S)-1-(methylamino)-3-((R)-tetrahydro-2H-pyran-3-yl)propan-2-yl)piperidine-1-carboxamide | 1.76 | 509 (M+) | 1.48 (m, 17H) 2.71 (s, 3H) 3.01 (m, 7H) 3.42 (m, 1H) 3.62 (s, 3H) 3.84 (m, 8H) 7.32 (m, 4H) |
| I*-31a | (R)-3-((R)-(3-chlorophenyl)(2-(ethylamino)-2-oxoethoxy)methyl)-N-((S)-1-(methylamino)-3-(tetrahydro-2H-pyran-4-yl)propan-2-yl)piperidine-1-carboxamide | 1.83 | 509 (M+) | 1.48 (m, 15H) 2.73 (s, 3H) 3.28 (m, 9H) 3.98 (m, 8H) 7.37 (m, 4H) |
| I*-32a | methyl 2-((R)-((R)-1-((S)-1-cyclohexyl-3-(methylamino)propan-2-ylcarbamoyl)piperidin-3-yl)(4-methylthiazol-2-yl)methoxy)ethylcarbamate | 1.88 | 510 (M + 1) | 1.48 (m, 19H) 2.41 (m, 7H) 2.98 (m, 2H) 3.47 (m, 5H) 3.62 (s, 3H) 3.78 (m, 1H) 4.11 (m, 2H) 4.47 (d, 1H) 7.18 (s, 1H) |
| I*-33a | methyl 2-((S)-((R)-1-((S)-1-cyclohexyl-3-(methylamino)propan-2-ylcarbamoyl)piperidin-3-yl)(4-methylthiazol-2-yl)methoxy)ethylcarbamate | 1.84 | 510 (M + 1) | 1.48 (m, 20H) 2.47 (m, 9H) 2.82 (m, 2H) 3.47 (m, 8H) 3.49 (d, 1H) 7.11 (m, 1H) |
| I*-34a | methyl 2-((R)-(3-chlorophenyl)((R)-1-((S)-4,4-dimethyl-1-(methylamino)hexan-2-ylcarbamoyl)piperidin-3-yl)methoxy)ethylcarbamate | 2.15 | 511 (M+) | 0.85 (t, 3H), 0.92 (s, 6H), 2.70 (s, 3H), 3.61 (s, 3H), 3.85 (m, 1H), 7.17 (m, 1H), 7.30 (m, 3H) |
| I*-35a | methyl 2-((R)-((R)-1-((S)-2-amino-5-methoxy-4,4-dimethylpentylcarbamoyl)piperidin-3-yl)(3-chlorophenyl)methoxy)ethylcarbamate | 2.05 | 513 (M+) | 0.91 (d, 6H), 2.80 (m, 2H), 3.55 (s, 3H), 3.75 (d, 1H), 3.95 (d, 1H), 4.15 (d, 1H), 7.15 (d, 1H), 7.20-7.30 (m, 3H) |
| I*-36a | methyl 2-((R)-(3,5-dimethylphenyl)((R)-1-((S)-1-(methylamino)-3-(tetrahydro-2H-pyran-4-yl)propan-2-ylcarbamoyl)piperidin-3-yl)methoxy)ethylcarbamate | 1.97 | 519 (M + 1) | 1.57-1.80 (m, 6H), 2.30 (s, 6H), 2.70 (s, 3H), 3.75-4.00 (m, 4H), 6.87 (s, 2H), 6.95 (s, 1H) |

| | Table of Compound of Formula (I*) | | | |
|---|---|---|---|---|
| I*-37a | methyl 2-((R)-(2,5-dimethylphenyl)((R)-1-((S)-1-(methylamino)-3-(tetrahydro-2H-pyran-4-yl)propan-2-ylcarbamoyl)piperidin-3-yl)methoxy)ethylcarbamate | 1.95 | 519 (M + 1) | 1.31 (m, 7H), 1.65 (m, 6H), 2.29 (s, 6H), 2.72 (s, 3H), 3.07 (m, 4H), 3.26 (m, 4H), 3.42 (m, 3H), 3.62 (s, 3H), 3.95 (m, 3H), 4.30 (m, 3H), 7.02 (m, 3H), |
| I*-38a | methyl 2-((R)-((R)-1-((R)-2-amino-3-phenoxypropylcarbamoyl)piperidin-3-yl)(3-chlorophenyl)methoxy)ethylcarbamate | 1.92 | 519 (M+) | 1.15 (m, 1H), 1.30 (m, 2H), 1.61 (m, 1H), 1.75 (m, 1H), 2.90 (m, 2H), 3.24 (m, 3H), 3.54 (m, 2H), 3.60 (s, 3H), 3.74 (m, 2H), 4.00 (d, 1H), 4.20 (m, 3H), 7.00 (m, 3H), 7.20 (m, 1H), 7.31 (m 5H) |
| I*-39a | methyl 2-((R)-((R)-1-((S)-1-cycloheptyl-3-(methylamino)propan-2-ylcarbamoyl)piperidin-3-yl)(3-fluorophenyl)methoxy)ethylcarbamate | 2.14 | 521 (M + 1) | 2.71 (s, 3H), 3.07 (m, 1H) 3.25 (m, 3H), 3.62 (s, 3H), 3.89 (m, 1H), 4.11 (m, 3H), 7.05 (m, 3H), 7.35 (m, 1H) |
| I*-40a | methyl 2-((R)-((R)-1-((S)-1-cyclohexyl-3-(methylamino)propan-2-ylcarbamoyl)piperidin-3-yl)(5-fluoro-2-methylphenyl)methoxy)ethylcarbamate | 2.31 | 521 (M + 1) | 0.95 (m, 2H), 2.30 (s, 3H), 2.70 (s, 3H), 3.61 (s, 3H), 3.95 (m, 1H), 4.10 (m, 1H), 4.25 (m, 1H), 4.35 (m, 1H), 6.90 (m, 1H), 7.03 (m, 1H), 7.17 (m, 1H) |
| I*-41a | methyl 2-((R)-((R)-1-((S)-1-cyclohexyl-3-(ethylamino)propan-2-ylcarbamoyl)piperidin-3-yl)(3-fluorophenyl)methoxy)ethylcarbamate | 1.71 | 521 (M + 1) | 7.37 (m, 1H), 7.11-7.01 (m, 3H)), 4.18-4.08 (m, 2H), 4.04 (d, J = 8.4 Hz, 1H), 3.88 (brd, J = 13.2 Hz, 1H), 3.62 (s, 3H), 3.34-2.83 (m, 14H), 1.83-0.88 (m 21H) |
| I*-42a | methyl 2-((R)-(3-fluorophenyl)((R)-1-((R)-1-(methylamino)-3-(1-methylcyclohexyl)propan-2-ylcarbamoyl)piperidin-3-yl)methoxy)ethylcarbamate | 1.55 | 521 (M + 1) | 7.30-7.24 (m, 1H), 7.01-6.91 (m, 3H), 4.33 (d, J = 13.2 Hz, 1H), 4.14-4.10 (m, 1H), 3.93 (d, J = 8.8 Hz, 1H), 3.70 (d, J = 13.2 Hz, 1H), 3.52 (s, 3H), 2.61 (s, 3H), 3.20-2.53 (m, 8H), 1.62-1.03 (m, 17H), 0.87 (s, 3H). |
| I*-43a | methyl 2-((R)-(3-fluorophenyl)((R)-1-((S)-1-(methylamino)-3-(1-methylcyclohexyl)propan-2-ylcarbamoyl)piperidin-3-yl)methoxy)ethylcarbamate | 1.55 | 521 (M + 1) | 7.30-7.25 (m, 1H), 6.99-6.91 (m, 3H), 4.13 (m, 1H), 4.00 (d, J = 12.6 Hz, 1H), 3.95 (d, J = 8.2 Hz, 1H), 3.77 (d, J = 10.8 Hz, 1H), 3.53 (s, 3H), 3.23-2.74 (m, 8H), 2.61 (s, 3H), 1.62-1.07 (m, 17H), 0.87 (s, 3H). |
| I*-44a | methyl 2-((R)-(3-chlorophenyl)((R)-1-((3S*,4R*)-4-(cyclobutylmethyl)piperidin-3-ylcarbamoyl)piperidin-3-yl)methoxy)ethylcarbamate | 1.56 | 521 (M+) | 7.31 (m, 3H), 7.21 (m, 1H), 4.24 (dd, 1H), 4.02 (d, 1H), 3.83 (dd, 1H), 3.68 (t, 1H), 3.62 (s, 3H), 2.88 (t, 2H), 2.41 (m, 1H), 1.42 (q, 1H), 1.20 (q, 1H). |

| | Table of Compound of Formula (I*) | | | |
|---|---|---|---|---|
| I*-45a | R)-3-((3R)-(3-chlorophenyl)(4-(methylamino)-4-oxobutoxy)methyl)-N-((S)-1-cyclohexyl-3-(methylamino)propan-2-yl)piperidine-1-carboxamide | 2.24 | 521 (M+) | 2.30 (m, 3H), 2.53 (s, 3H), 2.70 (s, 3H), 2.75 (m, 3H), 3.95 (m, 2H), 4.28 (m, 1H), 5.48 (s, 1H), 7.20 (m, 1H), 7.30 (m, 3H) |
| I*-46a | methyl 2-((R)-(3-fluorophenyl)((R)-1-((R)-1-(methylamino)-3-(2-oxopiperidin-1-yl)propan-2-ylcarbamoyl)piperidin-3-yl)methoxy)ethylcarbamate | 1.24 | 522 (M + 1) | 7.64 (m, 1H), 7.07 (m, 3H), 4.33 (m, 1H), 4.22 (m, 1H), 3.62 (s, 3H), 2.73 (s, 3H), 2.43 (m, 2H) |
| I*-47a | methyl 2-((R)-(3-fluorophenyl)((3R)-1-((S)-1-(methylamino)-3-(oxepan-4-yl)propan-2-ylcarbamoyl)piperidin-3-yl)methoxy)ethylcarbamate | 1.72 | 523 (M + 1) | 2.71 (s, 3H), 3.08 (m, 1H), 3.22 (m, 3H), 3.60 (s, 3H), 3.90 (m, 1H), 7.05 (m, 3H), 7.48 (m, 1H) |
| I*-48a | methyl 2-((R)-((R)-1-((1S,2R)-1-cyclohexyl-1-hydroxy-3-(methylamino)propan-2-ylcarbamoyl)piperidin-3-yl)(3-fluorophenyl)methoxy)ethylcarbamate | 2.01 | 523 (M + 1) | 2.72 (s, 3H), 3.46 (m, 1H), 3.61 (s, 3H), 3.86 (m, 1H), 7.06 (m, 3H), 7.35 (m, 1H) |
| I*-49a | methyl 2-((R)-(2-fluoro-5-methylphenyl)((R)-1-((S)-1-(methylamino)-3-(tetrahydro-2H-pyran-4-yl)propan-2-ylcarbamoyl)piperidin-3-yl)methoxy)ethylcarbamate | 1.94 | 523 (M + 1) | 2.32 (s, 3H), 2.72 (s, 3H), 2.93 (m, 2H), 3.08 (m, 2H), 3.60 (s, 3H), 3.80 (m, 1H), 3.93 (s, 2H), 4.40 (m, 1H), 6.95 (m, 1H), 7.11 (m, 2H) |
| I*-50a | methyl 2-((R)-(5-fluoro-2-methylphenyl)((R)-1-((S)-1-(methylamino)-3-(tetrahydro-2H-pyran-4-yl)propan-2-ylcarbamoyl)piperidin-3-yl)methoxy)ethylcarbamate | 1.87 | 523 (M + 1) | 2.31 (s, 3H), 2.67 (s, 3H), 3.08 (m, 1H), 3.62 (s, 3H), 3.93 (m, 3H), 6.90 (m, 1H), 7.04 (m, 1H), 7.17 (m, 1H) |
| I*-51a | methyl 2-((R)-(3-fluorophenyl)((R)-1-((S)-1-(4-hydroxycyclohexyl)-3-(methylamino)propan-2-ylcarbamoyl)piperidin-3-yl)methoxy)ethylcarbamate | 1.66 | 523 (M + 1) | 0.95 (m, 1H), 2.71 (s, 3H), 2.91 (m, 3H), 3.07 (m, 1H), 3.49 (m, 1H), 3.62 (s, 3H), 3.86 (m, 1H), 4.03 (m, 1H), 4.14 (m, 2H), 7.02 (m, 2H), 7.10 (m, 1H), 7.37 (m, 1H) |
| I*-52a | methyl 2-((R)-(3-fluoro-5-methylphenyl)((R)-1-((S)-1-(methylamino)-3-(tetrahydro-2H-pyran-4-yl)propan-2-ylcarbamoyl)piperidin-3-yl)methoxy)ethylcarbamate | 1.89 | 523 (M + 1) | 1.55-1.80 (m, 6H), 2.37 (s, 3H), 2.72 (s, 3H), 3.65 (s, 3H), 6.78-6.94 (m, 3H) |
| I*-53a | methyl 2-((R)-((R)-1-((1S,2R)-1-cyclopentyl-1-hydroxy-3-(methylamino)propan-2-ylcarbamoyl)piperidin-3-yl)(5-fluoro-2-methylphenyl)methoxy)ethylcarbamate | 2.05 | 523 (M + 1) | 1.92 (m, 16H), 2.31 (s, 3H), 2.73 (s, 3H), 3.24 (m, 8H), 3.58 (m, 1H), 3.65 (s, 3H), 3.79 (m, 1H), 4.09 (m, 2H), 4.44 (d, 1H), 7.13 (m, 3H), |
| I*-54a | methyl (S)-4-(3-fluorophenyl)-4-hydroxy-4-((3R)-1-((S)-1-(methylamino)-3-(tetrahydro-2H-pyran-3-yl)propan-2-ylcarbamoyl)piperidin-3-yl)butylcarbamate | 1.33 | 523 (M + 1) | 1.92 (m, 17H), 2.55 (m, 2H), 2.71 (s, 3H), 3.08 (m, 5H), 3.41 (m, 1H), 3.58 (s, 3H), 4.06 (m, 5H), 6.94 (m, 1H), 7.17 (d, 1H), 7.13 (m, 1H), |

| | Table of Compound of Formula (I*) | | | |
|---|---|---|---|---|
| I*-55a | methyl 2-((R)-(3-fluorophenyl)((R)-1-((S)-1-(methylamino)-3-((R)-oxepan-3-yl)propan-2-ylcarbamoyl)piperidin-3-yl)methoxy)ethylcarbamate | 1.32 | 523 (M + 1) | 7.36 (m, 1H), 7.11-7.01 (m, 3H), 4.13-4.03 (m, 3H), 3.85 (brd, J = 13.2 Hz, 1H), 3.87-3.71 (m, 3H), 3.62 (s, 3H), 3.43 (dd, J = 12.4, 7.6 Hz, 1H), 3.28-3.20 (m, 4H), 3.08 (dd, J = 13.2, 3.2 Hz, 1H), 3.00-2.85 (m, 3H), 2.71 (s, 3H), 1.88-1.29 (m, 13H), 1.17 (m, 1H). |
| I*-56a | methyl 2-((R)-(3-fluorophenyl)((R)-1-((S)-1-(methylamino)-3-((R)-tetrahydro-2H-pyran-3-yl)propan-2-ylcarbamoyl)azepan-3-yl)methoxy)ethylcarbamate | 1.841 | 523 (M + 1) | 1.10 (m, 1H), 2.75 (s, 3H), 3.64 (s, 3H), 3.90 (m, 1H), 4.01 (m, 1H), 4.14 (m, 2H), 7.10 (m, 3H), 7.38 (m, 1H) |
| I*-57a | methyl 2-((R)-(2-fluorophenyl)((R)-1-((S)-1-(methylamino)-3-((R)-oxepan-3-yl)propan-2-ylcarbamoyl)piperidin-3-yl)methoxy)ethylcarbamate | 1.32 | 523 (M + 1) | 7.40 (m, 1H), 7.33 (m, 1H), 7.21 (t, J = 7.6 Hz, 1H), 7.08 (t, J = 7.6 Hz, 1H), 4.45 (d, J = 8.8 Hz, 1H), 4.08 (m, 2H), 3.79-3.66 (m, 4H), 3.62 (s, 3H), 3.45 (dd, J = 12.4, 7.2 Hz, 1H), 3.31-3.25 (m, 4H), 3.10-3.06 (m, 2H), 3.00-2.89 (m, 2H), 2.71 (s, 3H), 2.32 (s, 3H), 1.83-1.39 (m, 13H), 1.25 (m, 1H) |
| I*-58a | methyl 2-((R)-((R)-1-((S)-2-amino-3-((R)-oxepan-3-yl)propylcarbamoyl)piperidin 3-yl)(5-fluoro-2-methylphenyl)methoxy)ethylcarbamate | 1.35 | 523 (M + 1) | 7.18 (d, J = 6.8 Hz, 1H), 7.10 (m, 1H), 6.95 (dd, J = 10.0, 8.4, 1H), 4.39 (d, J = 8.8 Hz, 1H), 4.14 (brd, J = 12.4 Hz, 1H), 3.79-3.65 (m, 5H), 3.62 (s, 3H), 3.44 (m, 2H), 3.34-3.24 (m, 5H), 3.01-2.92 (m, 2H), 2.32 (s, 3H), 1.88-1.56 (m, 9H), 1.50-1.34 (m, 4H), 1.20 (m, 1H) |
| I*-59a | methyl 2-((R)-((R)-1-((S)-1-amino-3-cyclohexyl-2-methylpropan-2-ylcarbamoyl)piperidin-3-yl)(3-chlorophenyl)methoxy)ethylcarbamate | 1.72 | 524 (M + H) | 7.37-7.29 (m, 3H), 7.21 (dd, J = 7.2, 1.2 Hz, 1H), 4.27 (brd, J = 14.0 Hz, 1H), 4.01 (d, J = 8.8 Hz, 1H), 3.81 (brd, J = 12.4 Hz, 1H), 3.62 (s, 3H), 3.33-3.24 (m, 4H), 2.94 (d, J = 12.8 Hz, 1H), 2.86 (m, 1H), 1.99 (dd, J = 14.4, 6.4 Hz, 1H), 1.76-1.62 (m, H), 1.46 (m, 1H), 1.32 (s, 3H), 1.36-1.00 (m, 8H) |
| I*-60a | methyl 2-((R)-(5-chloro-2-methylphenyl)((R)-1-((S)-1-cyclopentyl-3-(methylamino)propan-2-ylcarbamoyl)piperidin-3-yl)methoxy)ethylcarbamate | 2.30 | 523 (M+) | 1.92 (m, 17H), 2.31 (s, 3H), 2.71 (s, 3H), 3.09 (m, 8H), 3.62 (s, 3H), 4.30 (m, 4H), 7.16 (m, 2H), 7.27 (m, 1H), |

-continued

| | Table of Compound of Formula (I*) | | | |
|---|---|---|---|---|
| I*-61a | R)-3-((R)-(3-chlorophenyl)(2-(ethylamino)-2-oxoethoxy)methyl)-N-((2S)-1-(methylamino)-3-((R)-oxepan-3-yl)propan-2-yl)piperidine-1-carboxamide | 1.88 | 523 (M+) | 1.48 (m, 18H) 2.71 (s, 3H) 3.01 (m, 6H) 3.48 (m, 1H) 3.62 (m, 6H) 4.11 (m, 3H) 7.31 (m, 4H) |
| I*-62a | methyl 2-((R)-(3-chlorophenyl)((R)-1-((R)-1-(methylamino)-3-(2-oxopyrrolidin-1-yl)propan-2-ylcarbamoyl)piperidin-3-yl)methoxy)ethylcarbamate | 1.82 | 546 (M + Na − 1) | 1.05-1.20 (m, 1H), 1.27-1.40 (m, 2H), 2.05-2.17 (m, 2H), 2.71 (s, 3H), 3.62 (s, 3H), 1.14 (d, 1H), 7.22 (d, 1H), 7.30-7.40 (m, 3H) |
| I*-63a | methyl 2-((R)-((R)-1-((S)-1-cyclohexyl-3-(methylamino)propan-2-ylcarbamoyl)piperidin-3-yl)(2,5-difluorophenyl)methoxy)ethylcarbamate | 2.08 | 525 (M + 1) | 0.98 (m, 2H), 2.71 (s, 3H), 2.92 (m, 2H), 3.07 (m, 2H), 3.61 (s, 3H), 3.81 (m, 1H), 4.10 (m, 2H), 4.45 (d, 1H), 7.10 (m, 3H) |
| I*-64a | methyl 2-((R)-((R)-1-((S)-1-cyclohexyl-3-(methylamino)propan-2-ylcarbamoyl)piperidin-3-yl)(3,5-difluorophenyl)methoxy)ethylcarbamate | 2.24 | 525 (M + 1) | 0.98 (m, 2H), 2.70 (s, 3H), 3.06 (m, 1H), 3.61 (s, 3H), 3.87 (m, 1H), 4.10 (m, 3H), 6.90 (m, 3H) |
| I*-65a | methyl 2-((R)-((R)-1-((S)-1-cyclohexyl-3-(methylamino)propan-2-ylcarbamoyl)piperidin-3-yl)(3,4-difluorophenyl)methoxy)ethylcarbamate | 2.08 | 525 (M + 1) | 2.70 (s, 3H), 3.08 (m, 1H), 3.23 (m, 3H), 3.60 (s, 3H), 3.85 (m, 1H), 4.01 (m, 1H), 4.15 (m, 2H), 7.06 (m, 1H), 7.21 (m, 2H) |
| I*-66a | methyl 2-((S)-(3-chlorophenyl)((R)-4-((S)-1-cyclohexyl-3-(methylamino)propan-2-ylcarbamoyl)morpholin-2-yl)methoxy)ethylcarbamate | 2.16 | 525 (M+) | 1.6-1.8 (m, 5H), 2.65 (s, 3H), 2.8-2.9 (m, 2H), 3.6 (m, 3H), 4.0-4.1 (m, 2H), 4.25 (d, 1H), 7.2-7.35 (m, 4H) |
| I*-67a | methyl 2-((R)-(3-chlorophenyl)((R)-1-((1S,2R)-1-cyclopentyl-1-hydroxy-3-(methylamino)propan-2-ylcarbamoyl)piperidin-3-yl)methoxy)ethylcarbamate | 2.05 | 525 (M+) | 2.67 (s, 3H), 3.60 (s, 3H), 3.68 (d, 1H), 7.15 (d, 1H), 7.20-7.35 (m, 3H) |
| I*-68a | methyl 2-((R)-((R)-1-((S)-2-amino-3-((R)-oxepan-3-yl)propylcarbamoyl)piperidin-3-yl)(3-chlorophenyl)methoxy)ethylcarbamate | 1.35 | 526 (M + H) | 7.36-7.29 (m, 3H), 7.21 (d, J = 7.2 Hz, 1H), 4.18 (brd, J = 12.4 Hz, 1H), 4.02 (d, J = 8.8 Hz, 1H), 3.79-3.65 (m, 5H), 3.62 (s, 3H), 3.45 (m, 2H), 3.33-3.22 (m, 5H), 2.90 (m, 2H), 1.87-1.31 (m, 13H), 1.17 (m, 1H). |
| I*-69a | methyl 2-((R)-(2,5-difluorophenyl)((R)-1-((S)-1-(methylamino)-3-(tetrahydro-2H-pyran-4-yl)propan-2-ylcarbamoyl)piperidin-3-yl)methoxy)ethylcarbamate | 1.78 | 527 (M + 1) | 2.70 (s, 3H), 2.94 (m, 2H), 3.07 (m, 2H), 3.61 (s, 3H), 4.11 (m, 1H), 4.46 (d, 1H), 7.10 (m, 3H) |
| I*-70a | methyl 2-((R)-(3,5-difluorophenyl)((R)-1-((S)-1-(methylamino)-3-(tetrahydro-2H-pyran-4-yl)propan-2-ylcarbamoyl)piperidin-3-yl)methoxy)ethylcarbamate | 1.76 | 527 (M + 1) | 2.70 (s, 3H), 3.07 (m, 1H), 3.61 (s, 3H), 3.94 (m, 3H), 6.90 (m, 3H) |

-continued

Table of Compound of Formula (I*)

| | | | |
|---|---|---|---|
| I*-71a | methyl 2-((R)-(2,3-difluorophenyl)((R)-1-((S)-1-(methylamino)-3-(tetrahydro-2H-pyran-4-yl)propan-2-ylcarbamoyl)piperidin-3-yl)methoxy)ethylcarbamate | | 1.79 (m, 1H), 2.72 (s, 3H), 3.08 (m, 2H), 3.62 (s, 3H), 3.80 (m, 1H), 3.93 (m, 2H), 4.14 (m, 2H), 4.45 (d, 1H), 7.21 (m, 3H) |
| I*-72a | methyl 2-((R)-((R)-1-((1S,2R)-1-cyclopentyl-1-hydroxy-3-(methylamino)propan-2-ylcarbamoyl)piperidin-3-yl)(2,3-difluorophenyl)methoxy)ethylcarbamate | 1.94 527 (M + 1) | 2.02 (m, 1H), 2.72 (s, 3H), 3.55 (t, 1H), 3.62 (s, 3H), 4.47 (d, 1H), 7.15-7.26 (m, 3H) |
| I*-73a | methyl 2-((R)-((R)-1-((S)-2-amino-3-((R)-oxepan-3-yl)propylcarbamoyl)piperidin-3-yl)(3,5-difluorophenyl)methoxy)ethylcarbamate | 1.30 527 (M + H) | 6.93-6.86 (m, 3H), 4.16 (brd, J = 12.4 Hz, 1H), 4.05 (d, J = 8.8 Hz, 1H), 3.78-3.65 (m, 5H), 3.62 (s, 3H), 3.44 (m, 2H), 3.34-3.26 (m, 5H), 2.94-2.84 (m, 2H), 2.32 (s, 3H), 1.87-1.57 (m, 9H), 1.49-1.34 (m, 4H), 1.19 (m, 1H) |
| I*-74a | methyl 2-((R)-((3R)-1-((S)-1-(3-noradamantyl)-3-(methylamino)propan-2-ylcarbamoyl)piperidin-3-yl)(phenyl)methoxy)ethylcarbamate | 1.62 527 (M + 1) | 7.36-7.24 (m, 5H), 4.24 (m, 1H), 3.62 (s, 3H), 2.72 (s, 3H), 2.21 (m, 2H) |
| I*-75a | methyl 2-((S)-(3-chlorophenyl)((R)-4-((S)-1-(methylamino)-3-(tetrahydro-2H-pyran-4-yl)propan-2-ylcarbamoyl)morpholin-2-yl)methoxy)ethylcarbamate | 1.70 527 (M+) | 1.52-176 (m, 4H), 2.70 (s, 3H), 3.65 (s, 3H), 4.33 (m, 1H), 7.20-7.40 (m, 4H) |
| I*-76a | methyl 2-((R)-(3-fluorophenyl)((R)-1-((S)-1-((R)-1-methyl-6-oxopiperidin-3-yl)-3-(methylamino)propan-2-ylcarbamoyl)piperidin-3-yl)methoxy)ethylcarbamate | 1.10 536 (M + H) | 7.37 (m, 1H), 7.07-7.02 (m, 3H), 4.23 (d, J = 13.2 Hz, 1H), 4.11 (m, 1H), 4.02 (d, J = 8.4 Hz, 1H), 3.90 (d, J = 13.2 Hz, 1H), 3.62 (s, 3H), 3.39 (m, 1H), 3.33-3.21 (m, 4H), 3.13-2.95 (m, 3H), 2.92 (s, 3H), 2.88-2.81 (m, 2H), 2.73 (s, 3H), 2.45-2.36 (m, 2H), 2.02 (m, 1H), 1.88 (m, 1H), 1.68-1.50 (m, 5H), 1.38-1.13 (m, 3H). |
| I*-77a | methyl 2-((R)-((R)-1-((S)-1-((2S,4r,6R)-2,6-dimethyl-tetrahydro-2H-pyran-4-yl)-3-(methylamino)propan-2-ylcarbamoyl)piperidin-3-yl)(3-fluorophenyl)methoxy)ethylcarbamate | 1.36 537 (M + H) | 7.37 (m, 1H), 7.09 (d, 1H), 7.04 (m, 2H), 3.62 (s, 3H), 3.49 (m, 2H), 2.72 (s, 3H), 1.17 (m, 7H) |
| I*-78a | methyl 2-((R)-(3-fluorophenyl)((R)-1-((S)-4-(1-methoxycyclopentyl)-1-(methylamino)butan-2-ylcarbamoyl)piperidin-3-yl)methoxy)ethylcarbamate | 1.38 536 (M + H) | 7.37 (m, 1H), 7.06 (m, 3H), 4.28 (d, 1H), 3.62 (s, 3H), 2.72 (s, 3H), |

-continued

| Table of Compound of Formula (I*) | | | | |
|---|---|---|---|---|
| I*-79a | methyl 2-((R)-(5-fluoro-2-methylphenyl)((R)-1-((S)-1-(methylamino)-3-((R)-oxepan-3-yl)propan-2-ylcarbamoyl)piperidin-3-yl)methoxy)ethylcarbamate | 1.38 | 537 (M + H) | 7.19 (m, 1H), 7.11 (m, 1H), 6.95 (m, 1H), 4.39 (d, J = 9.6 Hz, 1H), 4.08 (m, 2H), 3.83-3.66 (m, 4H), 3.62 (s, 3H), 3.45 (dd, J = 12.4, 7.2 Hz, 1H), 3.34-3.25 (m, 4H), 3.10-3.13 (m, 2H), 2.96-2.89 (m, 2H), 2.71 (s, 3H), 2.32 (s, 3H), 1.83-1.20 (m, 14H) |
| I*-80a | methyl 2-((R)-(3-chlorophenyl)((R)-1-((S)-1-(methylamino)-3-(4-oxocyclohexyl)propan-2-ylcarbamoyl)piperidin-3-yl)methoxy)ethylcarbamate | 1.90 | 559 (M + Na) | 1.00-1.50 (m, 9H), 1.51-1.80 (m, 5H), 2.15 (m, 2H), 2.72 (s, 3H), 3.10 (m, 1H), 3.65 (s, 3H), 3.90 (m, 1H), 7.21 (d, 1H), 7.30-7.40 (m, 3H) |
| I*-81a | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate | 1.66 | 537 (M+) | 7.30-7.18 (m, 4H), 4.16 (d, J = 13.2 Hz, 1H), 4.10-4.04 (m, 1H), 3.99 (d, J = 12.9 Hz, 1H), 3.57 (s, 3H), 3.35-2.53 (m, 8H), 2.63 (s, 3H), 1.45 (s, 3H), 1.76-0.79 (m, 18H). |
| I*-82a | methyl 2-((R)-(3-chlorophenyl)((R)-1-((2S,3R)-1-cyclohexyl-3-(methylamino)butan-2-ylcarbamoyl)piperidin-3-yl)methoxy)ethylcarbamate | 1.68 | 538 (M + H) | 7.37-7.30 (m, 3H), 7.21 (dd, J = 7.2, 1.6 Hz, 1H), 4.20-4.17 (m, 2H), 4.01 (d, J = 8.8 Hz, 1H), 3.89 (brd, J = 10.8 Hz, 1H), 3.62 (s, 3H), 3.36-3.13 (m, 5H), 2.99 (dd, J = 13.2, 10 Hz, 1H), 2.89 (m, 1H), 2.73 (s, 3H), 1.81-0.88 (m 21H) |
| I*-83a | methyl 2-((R)-((R)-1-((2S,3R)-3-amino-1-cyclohexylpentan-2-ylcarbamoyl)piperidin-3-yl)(3-chlorophenyl)methoxy)ethylcarbamate | 1.69 | 538 (M + H) | 7.37-7.31 (m, 3H), 7.21 (d, J = 7.2, Hz, 1H)), 4.18 (d, J = 12.8 Hz, 1H), 4.07 (d, J = 10.8 Hz 1H), 4.01 (d, J = 9.2 Hz, 1H), 3.87 (brd, J = 12.0 Hz, 1H), 3.62 (s, 3H), 3.50-3.20 (m, 5H), 3.09 (m, 1H) 2.99-2.85 (m, 2H), 1.81-0.88 (m 24H) |
| I*-84a | methyl 2-((R)-(3-chlorophenyl)((R)-1-((S)-1-cycloheptyl-3-(methylamino)propan-2-ylcarbamoyl)piperidin-3-yl)methoxy)ethylcarbamate | 2.25 | 537 (M+) | 2.71 (s, 3H), 3.06 (m, 1H), 3.62 (s, 3H), 7.20 (m, 1H), 7.32 (m, 3H) |
| I*-85a | methyl 2-((R)-(5-chloro-2-methylphenyl)((R)-1-((S)-1-cyclohexyl-3-(methylamino)propan-2-ylcarbamoyl)piperidin-3-yl)methoxy)ethylcarbamate | 2.35 | 537 (M+) | 2.32 (s, 3H), 2.70 (s, 3H), 3.07 (m, 1H), 3.63 (s, 3H), 3.95 (m, 1H), 4.12 (m, 1H), 4.31 (m, 2H), 7.16 (m, 2H), 7.31 (m, 1H) |

-continued

| Table of Compound of Formula (I*) | | | | |
|---|---|---|---|---|
| I*-86a | methyl 2-((R)-(3-chlorophenyl)((R)-1-((S)-1-(methylamino)-3-(4-methylcyclohexyl)propan-2-ylcarbamoyl)piperidin-3-yl)methoxy)ethylcarbamate | 1.69 | 537 (M+) | 7.29-7.12 (m, 4H), 4.09-4.00 (m, 2H), 3.94 (d, J = 8.8 Hz, 1H), 3.80-3.77 (m, 1H), 3.54 (s, 3H), 3.17-2.75 (m, 8H), 2.63 (s, 3H), 1.73-0.93 (m, 17H), 0.86, 0.83 (d, J = 6.6 Hz, 3H). |
| I*-87a | methyl 1-((R)-(3-chlorophenyl)((R)-1-((S)-1-cyclohexyl-3-(methylamino)propan-2-ylcarbamoyl)piperidin-3-yl)methoxy)propan-2-ylcarbamate | 1.67 | 537 (M+) | |
| I*-88a | methyl 2-((R)-(3-chlorophenyl)((R)-1-((S)-1-cyclohexyl-3-(ethylamino)propan-2-ylcarbamoyl)piperidin-3-yl)methoxy)ethylcarbamate | 1.78 | 538 (M + H) | 7.37-7.30 (m, 3H), 7.21 (d, J = 7.2 Hz, 1H), 4.18-4.08 (m, 2H), 4.02 (d, J = 8.8 Hz, 1H), 3.89 (brd, J = 12.4 Hz, 1H), 3.62 (s, 3H), 3.34-2.82 (m, 10H), 1.81-0.88 (m 21H) |
| I*-89a | methyl 2-((R)-(3-chlorophenyl)((R)-1-((R)-1-(methylamino)-3-(1-methylcyclohexyl)propan-2-ylcarbamoyl)piperidin-3-yl)methoxy)ethylcarbamate | 1.57 | 537 (M+) | 7.27-7.11 (m, 4H), 4.33 (d, J = 12.9 Hz, 1H), 4.15-4.11 (m, 1H), 3.92 (d, J = 8.8 Hz, 1H), 3.71 (d, J = 12.9 Hz, 1H), 3.53 (s, 3H), 2.61 (s, 3H), 3.20-2.53 (m, 8H), 1.63-1.03 (m, 17H), 0.87 (s, 3H). |
| I*-90a | methyl 2-((R)-(3-chlorophenyl)((R)-1-((S)-1-(methylamino)-3-(1-methylcyclohexyl)propan-2-ylcarbamoyl)piperidin-3-yl)methoxy)ethylcarbamate | 1.57 | 537 (M) | 7.28-7.10 (m, 4H), 4.14 (m, 1H), 4.02 (d, J = 13.8 Hz, 1H), 3.94 (d, J = 8.5 Hz, 1H), 3.78 (d, J = 11.4 Hz, 1H), 3.54 (s, 3H), 3.16-2.74 (m, 8H), 2.62 (s, 3H), 1.63-1.08 (m, 17H), 0.88 (s, 3H). |
| I*-91a | methyl 2-((R)-(3-chlorophenyl)((R)-1-((S)-1-cyclohexyl-3-(methylamino)propan-2-ylcarbamoyl)azepan-3-yl)methoxy)ethylcarbamate | 1.636 | 537 (M+) | 2.73 (s, 3H), 3.04 (m, 4H), 3.62 (s, 3H), 4.09 (m, 1H), 4.21 (m, 1H), 7.21 (m, 1H), 7.33 (m, 3H) |
| I*-92a | methyl 2-((S)-(3-chlorophenyl)((R)-1-((S)-1-cyclohexyl-3-(methylamino)propan-2-ylcarbamoyl)azepan-3-yl)methoxy)ethylcarbamate | 1.588 | 537 (M+) | 2.03 (m, 1H), 2.70 (s, 3H), 3.02 (m, 3H), 3.63 (s, 3H), 4.17 (m, 1H), 4.31 (m, 1H), 7.30 (m, 4H) |
| I*-93a | methyl 2-((R)-(3-chlorophenyl)((R)-1-((R)-1-(methylamino)-3-(2-oxopiperidin-1-yl)propan-2-ylcarbamoyl)piperidin-3-yl)methoxy)ethylcarbamate | 1.91 | 538 (M+) | 2.71 (S, 3H), 3.65 (s, 3H), 4.00 (d, 1H), 4.21 (d, 1H), 7.23 (m, 1H), 7.31 (m, 3H) |
| I*-94a | methyl 2-((R)-(3,5-difluorophenyl)((R)-1-((R)-1-(methylamino)-3-(1-methylcyclohexyl)propan-2-ylcarbamoyl)piperidin-3-yl)methoxy)ethylcarbamate | 1.57 | 539 (M + 1) | 6.83-6.76 (m, 3H), 4.30 (d, J = 12.9 Hz, 1H), 4.14-4.10 (m, 1H), 3.96 (d, J = 8.2 Hz, 1H), 3.71 (d, J = 14.3 Hz, 1H), 3.52 (s, 3H), 2.60 (s, 3H), 3.23-2.51 (m, 8H), 1.62-1.05 (m, 17H), 0.86 (s, 3H). |

-continued

| | Table of Compound of Formula (I*) | | | |
|---|---|---|---|---|
| I*-95a | methyl 2-((R)-(3,5-difluorophenyl)((R)-1-((S)-1-(methylamino)-3-(1-methylcyclohexyl)propan-2-ylcarbamoyl)piperidin-3-yl)methoxy)ethylcarbamate | 1.57 | 539 (M + 1) | 6.81-6.77 (m, 3H), 4.14-4.09 (m, 1H), 4.00-3.96 (m, 2H), 3.78 (d, J = 12.0 Hz, 1H), 3.53 (s, 3H), 3.25-2.71 (m, 8H), 2.61 (s, 3H), 1.60-1.11 (m, 17H), 0.86 (s, 3H). |
| I*-96a | methyl 2-((R)-((R)-1-((S)-1-cyclohexyl-3-(methylamino)propan-2-ylcarbamoyl)piperidin-3-yl)(2,3-difluoro-6-methylphenyl)methoxy)ethylcarbamate | 2.23 | 539 (M + 1) | 1.58 (m, 22H), 2.19 (m, 1H), 2.41 (s, 3H), 2.71 (s, 3H), 3.01 (m, 4H), 3.62 (s, 3H), 3.78 (m, 1H), 4.18 (m, 2H), 4.59 (m, 1H), 7.02 (m, 2H), |
| I*-97a | methyl 2-((R)-((S)-1-((S)-1-cyclohexyl-3-(methylamino)propan-2-ylcarbamoyl)piperidin-3-yl)(2,3-difluoro-6-methylphenyl)methoxy)ethylcarbamate | 2.23 | 539 (M + 1) | 1.58 (m, 20H), 2.19 (m, 1H), 2.41 (s, 3H), 2.71 (s, 3H), 3.01 (m, 4H), 3.16 (s, 3H), 3.33 (m, 1H), 4.18 (m, 1H), 4.51 (m, 2H), 7.02 (m, 2H), |
| I*-98a | methyl 2-((R)-(3-chlorophenyl)((R)-1-((S)-1-(methylamino)-3-((R)-oxepan-4-yl)propan-2-ylcarbamoyl)piperidin-3-yl)methoxy)ethylcarbamate | | | 7.36-7.29 (m), 7.21 (d), 4.20 (d), 3.86 (d), 3.62 (s), 2.83 (q), 2.68 (d), 2.45 (s) |
| I*-99a | methyl 2-((R)-(3-chlorophenyl)((R)-1-((S) 1-(methylamino)-3-((S)-oxepan-4-yl)propan-2-ylcarbamoyl)piperidin-3-yl)methoxy)ethylcarbamate | | | 7.36-7.29 (m), 7.21 (d), 3.62 (s), 2.88-2.79 (m), 2.65 (m), 2.43 (s) |
| I*-100a | methyl 2-((R)-(3-chlorophenyl)((R)-1-((1S,2R)-1-cyclohexyl-1-hydroxy-3-(methylamino)propan-2-ylcarbamoyl)piperidin-3-yl)methoxy)ethylcarbamate | 1.49 | 539 (M+) | 7.37-7.31 (m), 7.21-7.20 (d), 4.17 (d), 4.09 (m), 4.02 (d), 3.62 (s), 2.72 (s) |
| I*-101a | methyl 2-((R)-(5-chloro-2-methylphenyl)((R)-1-((S)-1-(methylamino)-3-(tetrahydro-2H-pyran-4-yl)propan-2-ylcarbamoyl)piperidin-3-yl)methoxy)ethylcarbamate | 1.52 | 539 (M+) | 2.34 (s, 3H), 2.70 (s, 3H), 3.10 (m, 2H), 3.62 (s, 3H), 3.95 (m, 3H) |
| I*-102a | methyl 2-((R)-(3-chlorophenyl)((R)-1-((S)-1-(4-hydroxycyclohexyl)-3-(methylamino)propan-2-ylcarbamoyl)piperidin-3-yl)methoxy)ethylcarbamate | 1.78 | 539 (M+) | 1.0-1.5 (m, 10H), 1.59 (m, 2H), 1.74 (m, 3H), 1.98 (m, 2H), 2.7 (s, 3H), 3.6 (s, 3H), 4.0 (d, 1H), 7.2 (m, 1H), 7.3-7.35 (m, 3H), |
| I*-103a | methyl 2-((R)-1-(3-chlorophenyl)-1-((R)-1-((S)-1-(methylamino)-3-(tetrahydro-2H-pyran-4-yl)propan-2-ylcarbamoyl)piperidin-3-yl)ethoxy)ethylcarbamate | 1.30 | 539 (M+) | 7.27-7.16 (m, 4H), 4.15 (d, J = 13.2 Hz, 1H), 4.09-4.04 (m, 1H), 3.94 (d, J = 12.0 Hz, 1H), 3.89-3.83 (m, 2H), 3.55 (s, 3H), 2.62 (s, 3H), 3.40-2.86 (m, 8H), 2.61-2.52 (m, 2H), 1.43 (s, 3H), 1.63-1.12 (m, 12H). |
| I*-104a | methyl 2-((R)-(3-chlorophenyl)((R)-1-((R)-1-((1R*,2S*)-2-hydroxycyclohexyl)-3-(methylamino)propan-2-ylcarbamoyl)piperidin-3-yl)methoxy)ethylcarbamate | 2.02 | 539 (M+) | 2.70 (s, 3H), 3.65 (s, 3H), 3.75-3.90 (m, 2H), 7.20 (m, 1H), 7.35 (m, 3H) |

-continued

| Table of Compound of Formula (I*) | | | |
|---|---|---|---|
| I*-105a | methyl 2-((R)-(3-chlorophenyl)((R)-1-((S)-1-((1R*,2S*)-2-hydroxycyclohexyl)-3-(methylamino)propan-2-ylcarbamoyl)piperidin-3-yl)methoxy)ethylcarbamate | 2.06  539 (M+) | 2.72 (s, 3H), 3.65 (s, 3H), 4.15 (d, 1H), 7.21 (m, 1H), 7.30-7.40 (m, 3H) |
| I*-106a | methyl 2-((R)-(3-chlorophenyl)((R)-1-((S)-1-(methylamino)-3-((R)-oxepan-3-yl)propan-2-ylcarbamoyl)piperidin-3-yl)methoxy)ethylcarbamate | 1.39  540 (M + 1) | 7.36-7.23 (m, 3H), 7.22 (d, J = 7.8 Hz, 1H), 4.16-4.01 (m, 3H), 3.85 (brd, J = 12.8 Hz, 1H), 3.78-3.71 (m, 3H), 3.62 (s, 3H), 3.43 (dd, J = 12.4, 7.6 Hz, 1H), 3.28-3.22 (m, 4H), 3.08 (dd, J = 12.8, 3.2 Hz, 1H), 3.00-2.85 (m, 3H), 2.71 (s, 3H), 1.88-1.30 (m, 13H), 1.17 (m, 1H). |
| I*-107a | methyl 2-((R)-(5-chloro-2-methylphenyl)((R)-1-((1S,2R)-1-cyclopentyl-1-hydroxy-3-(methylamino)propan-2-ylcarbamoyl)piperidin-3-yl)methoxy)ethylcarbamate | 2.16  539 (M+) | 1.58 (m, 15H), 2.31 (s, 3H), 2.71 (s, 3H), 2.84 (m, 2H), 3.17 (m, 5H), 3.56 (m, 1H), 3.62 (s, 3H), 3.99 (m, 2H), 4.29 (m, 2H), 7.17 (m, 2H), 7.31 (d, 1H), |
| I*-108a | methyl 2-((R)-(3-chlorophenyl)((R)-1-((S)-1-(methylamino)-3-(tetrahydro-2H-pyran-4-yl)propan-2-ylcarbamoyl)azepan-3-yl)methoxy)ethylcarbamate | 1.94  539 (M+) | 2.73 (s, 3H), 3.07 (m, 2H), 3.63 (s, 3H), 3.94 (m, 2H), 4.10 (m, 1H), 4.23 (m, 1H) |
| I*-109a | methyl 2-((R)-((R)-1-((S)-2-amino-3-((R)-oxepan-3-yl)propylcarbamoyl)piperidin-3-yl)(5-chloro-2-methylphenyl)methoxy)ethylcarbamate | 1.38  540 (M + 1) | 7.30 (d, J = 3.2 Hz, 1H), 7.19-7.13 (m, 2H), 4.33-4.26 (m, 2H), 3.86-3.65 (m, 5H), 3.62 (s, 3H), 3.47-3.42 (m, 2H), 3.34-3.20 (m, 5H), 2.90-2.80 (m, 2H), 2.32 (s, 3H), 1.89-1.56 (m, 9H), 1.49-1.20 (m, 5H). |
| I*-110a | methyl 2-((R)-(3-chlorophenyl)((R)-1-((S)-2-(methylamino)-3-((R)-oxepan-3-yl)propylcarbamoyl)piperidin-3-yl)methoxy)ethylcarbamate | 1.36  540 (M + 1) | 7.37-7.30 (m, 3H), 7.21 (d, J = 7.2 Hz, 1H), 4.20 (brd, J = 13.2 Hz, 1H), 4.02 (d, J = 8.8 Hz, 1H), 3.81-3.67 (m, 5H), 3.62 (s, 3H), 3.58 (m, 1H), 3.44 (dd J = 12.4, 7.2 Hz, 1H), 3.34-3.22 (m, 5H), 2.94-2.85 (m, 2H), 2.75 (s, 3H), 1.88-1.52 (m, 10H), 1.39-1.29 (m, 3H), 1.16 (m, 1H) |
| I*-111a | methyl 2-((R)-(3-chlorophenyl)((R)-1-((S)-1-cyclohexyl-3-(methylamino)propan-2-ylcarbamothioyl)piperidin-3-yl)methoxy)ethylcarbamate | 2.52  539 (M + 1) | 0.90 (m, 1H), 1.05 (m, 1H), 2.72 (s, 3H), 3.05 (m, 2H), 3.62 (s, 3H), 4.02 (d, 1H), 4.70 (m, 2H), 5.13 (m, 1H), 7.20 (m, 1H), 7.32 (m, 3H) |

-continued

Table of Compound of Formula (I*)

| | | | | |
|---|---|---|---|---|
| I*-112a | methyl 2-((R)-((R)-1-((1S,2R)-1-cyclohexyl-1-hydroxy-3-(methylamino)propan-2-ylcarbamoyl)piperidin-3-yl)(3,5-difluorophenyl)methoxy)ethylcarbamate | 2.09 | 541 (M+) | 2.66 (s, 3H), 2.90 (m, 2H), 3.05 (m, 1H), 3.44 (m, 1H), 3.62 (s, 3H), 3.87 (m, 1H), 6.90 (m, 3H) |
| I*-113a | methyl 2-((R)-(3,5-difluorophenyl)((R)-1-((S)-1-(methylamino)-3-((R)-oxepan-3-yl)propan-2-ylcarbamoyl)piperidin-3-yl)methoxy)ethylcarbamate | 1.39 | 541 (M + 1) | 6.95-6.86 (m, 3H), 4.12-4.05 (m, 3H), 3.85 (brd, J = 12.0 Hz, 1H), 3.78-3.71 (m, 3H), 3.62 (s, 3H), 3.41 (dd, J = 12.4, 7.6 Hz, 1H), 3.34-3.20 (m, 4H), 3.07 (dd, J = 12.8, 3.2 Hz, 1H), 2.99-2.85 (m, 3H), 2.71 (s, 3H), 1.84-1.34 (m, 13H), 1.22 (m, 1H). |
| I*-114a | methyl 2-((R)-((R)-1-((S)-1-cyclohexyl-3-(methylamino)propan-2-ylcarbamoyl)piperidin-3-yl)(3,5-difluoro-2-hydroxyphenyl)methoxy)ethylcarbamate | 1.93 | 541 (M + 1) | 1.58 (m, 19H), 2.19 (d, 2H), 2.71 (s, 3H), 3.13 (m, 7H), 3.42 (m, 2H), 3.62 (s, 3H), 3.78 (m, 1H), 4.26 (m, 2H), 4.59 (m, 1H) 6.88 (m, 2H), |
| I*-115a | methyl 2-((R)-(2,3-difluoro-6-methylphenyl)(1-((S)-1-(methylamino)-3-(tetrahydro-2H-pyran-4-yl)propan-2-ylcarbamoyl)piperidin-3-yl)methoxy)ethylcarbamate | 1.75 | 541 (M + 1) | 1.48 (m, 11H) 2.17 (m, 1H) 2.40 (s, 3H) 2.71 (s, 3H) 3.01 (m, 6H) 3.48 (m, 2H) 3.62 (s, 3H) 3.89 (m, 3H) 4.19 (m, 2H) 4.60 (m, 2H) 7.03 (m, 2H) |
| I*-116a | methyl 2-((5-chloro-2-fluorophenyl)((R)-1-((S)-1-cyclohexyl-3-(methylamino)propan-2-ylcarbamoyl)piperidin-3-yl)methoxy)ethylcarbamate | 2.16 | 541 (M+) | 2.70 (s, 3H), 2.79 (m, 1H), 2.91 (m, 2H), 3.07 (m, 1H), 3.23 (m, 2H), 3.62 (s, 3H), 3.80 (m, 1H), 4.12 (m, 1H), 4.42 (d, 1H), 7.10 (m, 1H), 7.32 (m, 1H), 7.40 (m, 1H) |
| I*-117a | methyl 2-((R)-(5-chloro-2-fluorophenyl)((R)-1-((S)-1-cyclohexyl-3-(methylamino)propan-2-ylcarbamoyl)piperidin-3-yl)methoxy)ethylcarbamate | 2.30 | 541 (M+) | 2.71 (s, 3H), 2.90 (m, 2H), 3.05 (m, 2H), 3.61 (s, 3H), 3.80 (m, 1H), 4.10 (m, 2H), 4.41 (m, 1H), 7.10 (m, 1H), 7.35 (m, 2H) |
| I*-118a | methyl 2-((R)-(3-chloro-4-fluorophenyl)((R)-1-((S)-1-cyclohexyl-3-(methylamino)propan-2-ylcarbamoyl)piperidin-3-yl)methoxy)ethylcarbamate | 2.44 | 541 (M+) | 1.66-1.84 (m, 6H), 2.70 (s, 3H), 3.65 (s, 3H), 3.87 (d, 1H), 7.25 (d, 2H), 7.40 (d, 1H) |
| I*-119a | methyl 2-((R)-((R)-1-((S)-1-cyclohexyl-3-(methylamino)propan-2-ylcarbamoyl)piperidin-3-yl)(3,4,5-trifluorophenyl)methoxy)ethylcarbamate | 2.14 | 543 (M + 1) | 2.70 (s, 3H), 3.05 (d, 1H), 3.62 (s, 3H), 3.89 (m, 1H), 4.10 (m, 3H), 7.08 (m, 2H) |
| I*-120a | methyl 2-((R)-((R)-1-((S)-1-(4,4-difluorocyclohexyl)-3-(methylamino)propan-2-ylcarbamoyl)piperidin-3-yl)(3-fluorophenyl)methoxy)ethylcarbamate | 1.42 | 543 (M + 1) | 7.34-7.28 (m, 1H), 7.04-6.95 (m, 3H), 4.15 (d, J = 12.9 Hz, 1H), 4.09-4.03 (m, 1H), 3.99 (d, J = 8.5 Hz, 1H), 3.83 (d, J = 12.3 Hz, 1H), 3.56 (s, 3H), 3.29-2.74 (m, 8H), 2.66 (s, 3H), 1.99-1.11 (m, 16H). |

-continued

| Table of Compound of Formula (I*) | | | | |
|---|---|---|---|---|
| I*-121a | methyl 2-((R)-(3-chloro-5-fluorophenyl)((R)-1-((S)-1-(methylamino)-3-(tetrahydro-2H-pyran-4-yl)propan-2-ylcarbamoyl)piperidin-3-yl)methoxy)ethylcarbamate | 1.80 | 543 (M+) | 2.70 (s, 3H), 3.08 (m, 1H), 3.61 (s, 3H), 7.01 (m, 1H), 7.16 (m, 2H) |
| I*-122a | methyl 2-((R)-((R)-1-((S)-2-amino-3-((R)-oxepan-3-yl)propylcarbamoyl)piperidin-3-yl)(3-chloro-5-fluorophenyl)methoxy)ethylcarbamate | 1.36 | 544 (M + 1) | 7.16-7.13 (m, 2H), 7.03 (d, J = 7.6 Hz, 1H), 4.17 (brd, J = 11.2 Hz, 1H), 4.05 (d, J = 8.8 Hz, 1H), 3.78-3.65 (m, 5H), 3.62 (s, 3H), 3.44 (d, J = 12.4, 6.8 Hz, 2H), 3.34-3.26 (m, 5H), 2.94-2.84 (m, 2H), 1.87-1.56 (m, 9H), 1.49-1.34 (m, 4H), 1.19 (m, 1H). |
| I*-123a | methyl 2-((R)-((3R)-1-((S)-1-(3-noradamantyl)-3-(methylamino)propan-2-ylcarbamoyl)piperidin-3-yl)(3-fluorophenyl)methoxy)ethylcarbamate | 1.63 | 545 (M + 1) | 7.36 (q, 1H), 7.05 (m, 3H0, 4.25 (m, 1H0, 3.63 (s, 3H), 2.72 (s, 3H), 2.21 (m, 1H). |
| I*-124a | methyl 2-((R)-(3-chlorophenyl)((R)-1-((S)-1-((1r,3S,4R)-3,4-difluorocyclopentyl)-3-(methylamino)propan-2-ylcarbamoyl)piperidin-3-yl)methoxy)ethylcarbamate | 1.38 | 545 (M+) | 7.33 (m, 3H), 7.21 (d, 1H), 4.93 (m, 1H), 4.81 (m, 1H), 4.20 (d, 1H), 3.87 (d, 1H), 3.62 (s, 3H), 3.23 (s, 3H), 3.10 (dd, 1H), 2.71 (s, 3H), 2.19 (m, 2H), 2.04 (m, 1H), 1.18 (q, 1H). |
| I*-125a | methyl 2-((R)-(3-chlorophenyl)((R)-1-((S)-1-((1s,3R,4S)-3,4-difluorocyclopentyl)-3-(methylamino)propan-2-ylcarbamoyl)piperidin-3-yl)methoxy)ethylcarbamate | 1.38 | 546 (M + 1) | 7.36 (m, 3H), 7.25 (d, 1H), 5.04 (d of m, 2H), 3.63 (s, 3H), 2.76 (s, 3H) |
| I*-126a | (R)-3-((R)-(3-chlorophenyl)(2-(2-cyano-3-methylguanidino)ethoxy)methyl)-N-((S)-1-cyclohexyl-3-(methylamino)propan-2-yl)piperidine-1-carboxamide | 2.24 | 546 (M+) | 0.95 (m, 2H), 1.55 (m, 2H), 2.67 (s, 3H), 2.79 (s, 3H), 2.94 (m, 2H), 3.85 (m, 1H), 4.05 (m, 2H), 4.16 (m, 1H), 7.21 (m, 1H), 7.35 (m, 3H) |
| I*-127a | methyl 2-((R)-(3-chlorophenyl)((R)-1-(N'-cyano-N-((S)-1-cyclohexyl-3-(methylamino)propan-2-yl)carbamimidoyl)piperidin-3-yl)methoxy)ethylcarbamate | 2.27 | 547 (M+) | 0.95 (m, 4H), 2.70 (s, 3H), 2.95 (m, 3H), 3.61 (d, 3H), 4.06 (m, 2H), 4.30 (m, 2H), 7.20 (m, 1H), 7.33 (m, 2H) |
| I*-128a | (R)-3-((R)-(3-chlorophenyl)(2-(thiazol-2-ylamino)ethoxy)methyl)-N-((S)-1-cyclohexyl-3-(methylamino)propan-2-yl)piperidine-1-carboxamide | 1.95 | 548 (M+) | 0.95 (m, 2H), 2.72 (s, 3H), 2.91 (m, 1H), 3.07 (m, 2H), 3.50 (m, 3H), 3.96 (m, 1H), 4.15 (m, 2H), 6.79 (d, 1H), 7.19 (m, 2H), 7.32 (m, 3H) |
| I*-129a | methyl 2-((R)-((3R)-1-(1-(bicyclo[2.2.2]octan-1-yl)-3-(methylamino)propan-2-ylcarbamoyl)piperidin-3-yl)(3-chlorophenyl)methoxy)ethylcarbamate | 2.39 | 549 (M+) | 1.30-1.50 (m, 10H), 1.52-1.80 (m, 10H), 2.70 (s, 3H), 3.65 (s, 3H), 4.05 (d, 1H), 4.41 (d, 1H), 7.22 (m, 1H), 7.30-7.40 (m, 3H) |

-continued

| Table of Compound of Formula (I*) | | | | |
|---|---|---|---|---|
| I*-130a | methyl 2-((R)-(3-chlorophenyl)((R)-1-((2S,3R)-1-cyclohexyl-3-(methylamino)pentan-2-ylcarbamoyl)piperidin-3-yl)methoxy)ethylcarbamate | 1.75 | 552 (M + 1) | 7.37-7.31 (m, 3H), 7.21 (m, 1H)), 4.20-4.13 (m, 2H), 4.02 (d, J = 8.8 Hz 1H), 3.88 (brd, J = 12.0 Hz, 1H), 3.63 (s, 3H), 3.36-3.21 (m, 5H), 3.01 (m, 3H), 2.80 (s, 3H), 1.83-0.88 (m 24H) |
| I*-131a | methyl 2-((R)-(3-chlorophenyl)((R)-1-((S)-1-((R)-1-methyl-6-oxopiperidin-3-yl)-3-(methylamino)propan-2-ylcarbamoyl)piperidin-3-yl)methoxy)ethylcarbamate | 1.18 | 553 (M + 1) | 7.37-7.29 (m, 3H), 7.17 (d, J = 7.2 Hz, 1H), 4.23 (d, J = 12.4 Hz, 1H), 4.11 (m, 1H), 4.01 (d, J = 8.8 Hz, 1H), 3.91 (d, J = 12.8 Hz, 1H), 3.62 (s, 3H), 3.39 (dd, J = 12.0, 4.0 Hz, 1H), 3.26-3.21 (m, 4H), 3.13-2.95 (m, 3H), 2.92 (s, 3H), 2.90-2.81 (m, 2H), 2.73 (s, 3H), 2.45-2.32 (m, 2H), 2.01 (m, 1H), 1.88 (m, 1H), 1.71-1.49 (m, 5H), 1.38-1.12 (m, 3H). |
| I*-132a | methyl 2-((R)-(3-chlorophenyl)((R)-1-((S)-1-((2S,4r,6R)-2,6-dimethyl-tetrahydro-2H-pyran-4-yl)-3-(methylamino)propan-2-ylcarbamoyl)piperidin-3-yl)methoxy)ethylcarbamate | 1.43 | 554 (M + 1) | 7.33 (m, 3H), 7.20 (d, 1H), 3.38 (m, 2H), 3.62 (s, 3H), 2.71 (s, 3H), 1.17 (m, 7H), 0.84 (d of q, 2H) |
| I*-133a | methyl 2-((R)-(5-chloro-2-methylphenyl)((R)-1-((S)-2-(methylamino)-3-((R)-oxepan-3-yl)propylcarbamoyl)piperidin-3-yl)methoxy)ethylcarbamate | 1.41 | 554 (M + 1) | 7.30 (d, J = 1.6 Hz, 1H), 7.19-7.13 (m, 2H), 4.33-4.27 (m, 2H), 3.88-3.68 (m, 5H), 3.62 (s, 3H), 3.58 (m, 1H), 3.44 (m, 1H), 3.33-3.20 (m, 5H), 2.89-2.80 (m, 2H), 2.75 (s, 3H), 2.32 (s, 3H), 1.88-1.51 (m, 10H), 1.37-1.23 (m, 4H) |
| I*-134a | methyl 2-((R)-(3,5-difluorophenyl)((R)-1-((S)-4-(1-methoxycyclopentyl)-1-(methylamino)butan-2-ylcarbamoyl)piperidin-3-yl)methoxy)ethylcarbamate | 1.41 | 555 (M + 1) | 6.96 (m, 3H), 4.18 (d, 1H), 4.04 (d, 1H), 3.62 (s, 3H), 3.15 (s, 3H), 2.72 (s, 3H) |
| I*-135a | methyl 2-((R)-(3-chloro-2-fluorophenyl)((R)-1-((S)-1-cycloheptyl-3-(methylamino)propan-2-ylcarbamoyl)piperidin-3-yl)methoxy)ethylcarbamate | 2.24 | 555 (M+) | 2.71 (s, 3H), 2.92 (m, 2H), 3.06 (m, 2H), 3.62 (s, 3H), 3.81 (m, 1H), 4.09 (m, 2H), 4.47 (d, 1H), 7.20 (m, 1H), 7.32 (m, 1H), 7.44 (m, 1H) |
| I*-136a | methyl 2-((R)-((R)-1-((S)-1-cyclohexyl-3-(methylamino)propan-2-ylcarbamoyl)piperidin-3-yl)(3-(trifluoromethyl)phenyl)methoxy)ethylcarbamate | 1.69 | 556 (M+) | 1.48 (m, 20H) 2.71 (s, 3H) 2.97 (m, 8H) 3.62 (s, 3H) 3.71 (m, 1H) 3.87 (m, 1H) 4.16 (m, 3H) 7.59 (m, 4H) |
| I*-137a | methyl 2-((R)-(3-chloro-2-fluorophenyl)((3R)-1-((S)-1-(methylamino)-3-(oxepan-4-yl)propan-2-ylcarbamoyl)piperidin-3-yl)methoxy)ethylcarbamate | 1.84 | 557 (M+) | 2.71 (s, 3H), 3.61 (s, 2H), 4.12 (m, 2H), 4.45 (d, 1H), 7.21 (m, 1H), 7.41 (m, 2H) |

-continued

| | Table of Compound of Formula (I*) | | | |
|---|---|---|---|---|
| I*-138a | methyl 2-((R)-(3-chloro-2-fluorophenyl)((R)-1-((1S,2R)-1-cyclohexyl-1-hydroxy-3-(methylamino)propan-2-ylcarbamoyl)piperidin-3-yl)methoxy)ethylcarbamate | 1.49 | 558 (M + 1) | 7.42 (t), 7.33 (t), 7.19 (t), 4.45 (d), 3.61 (s), 2.71 (s) |
| I*-139a | methyl (S)-4-(3-chloro-2-fluorophenyl)-4-hydroxy-4-((3R)-1-((S)-1-(methylamino)-3-(tetrahydro-2H-pyran-3-yl)propan-2-ylcarbamoyl)piperidin-3-yl)butylcarbamate | 1.85 | 557 (M+) | 1.92 (m, 17H), 2.64 (m, 1H), 2.29 (s, 3H), 3.09 (m, 6H), 3.41 (m, 1H), 3.58 (s, 3H), 4.15 (m, 5H), 7.34 (t, 1H), 7.49 (t, 1H), 7.54 (m, 1H), |
| I*-140a | methyl 2-((R)-(3-chloro-2-fluorophenyl)((R)-1-((S)-1-(methylamino)-3-((R)-oxepan-3-yl)propan-2-ylcarbamoyl)piperidin-3-yl)methoxy)ethylcarbamate | 1.41 | 558 (M + 1) | 7.43 (td, J = 8.8, 1.6 Hz, 1H), 7.36 (td, J = 6.0, 1.6 Hz, 1H), 7.21-7.01 (t, J = 7.6 Hz, 1H), 4.45 (d, J = 8.8 Hz, 1H), 4.08 (m, 2H), 3.81 (m, 1H), 3.76-3.65 (m, 3H), 3.62 (s, 3H), 3.45 (dd, J = 12.4, 7.6 Hz, 1H), 3.33-3.26 (m, 4H), 3.10-3.06 (m, 2H), 3.95-2.85 (m, 2H), 2.71 (s, 3H), 1.85-1.39 (m, 13H), 1.27 (m, 1H) |
| I*-141a | methyl 2-((R)-(3-chloro-5-fluorophenyl)((R)-1-((S)-1-(methylamino)-3-((R)-oxepan-3-yl)propan-2-ylcarbamoyl)piperidin-3-yl)methoxy)ethylcarbamate | 1.42 | 556 (M + 1) | 7.18-7.13 (m, 2H), 7.05 (d, J = 9.2 Hz, 1H), 4.12-4.04 (m, 3H), 3.85 (brd, J = 13.2 Hz, 1H), 3.78-3.71 (m, 3H), 3.62 (s, 3H) 3.41 (dd, J = 12.8, 7.6 Hz, 1H), 3.34-3.23 (m, 4H), 3.07 (dd, J = 13.2, 3.2 Hz, 1H), 2.97-2.89 (m, 3H), 2.71 (s, 3H), 1.88-1.19 (m, 14H) |
| I*-142a | methyl (S)-4-(3-chloro-2-fluorophenyl)-4-hydroxy-4-((R)-1-((S)-1-(methylamino)-3-((R)-tetrahydro-2H-pyran-3-yl)propan-2-ylcarbamoyl)piperidin-3-yl)butylcarbamate | 1.78 | 557 (M+) | 1.00 (m, 1H), 1.95 (m, 3H), 2.72 (s, 3H), 2.80 (m, 1H), 3.44 (m, 1H), 3.60 (s, 3H), 4.36 (m, 1H), 7.15 (m, 1H), 7.38 (m, 1H), 7.52 (m, 1H) |
| I*-143a | methyl 2-((R)-(3-chloro-5-fluorophenyl)((R)-1-((S)-2-(methylamino)-3-((R)-oxepan-3-yl)propylcarbamoyl)piperidin-3-yl)methoxy)ethylcarbamate | 1.40 | 558 (M + H) | 7.17-7.13 (m, 2H), 7.03 (d, J = 8.8 Hz, 1H), 4.18 (d, J = 11.2 Hz, 1H), 4.05 (d, J = 8.4 Hz, 1H) 3.80-3.68 (m, 5H), 3.62 (s, 3H), 3.56 (d, J = 14.4 Hz, 1H), 3.44 (d, J = 12.4, 7.2 Hz, 1H), 3.34-3.21 (m, 5H), 2.94-2.83 (m, 2H), 2.74 (s, 3H), 2.32 (s, 3H), 1.88-1.53 (m, 10H), 1.37-1.33 (m, 3H), 1.19 (m, 1H) |

-continued

| Table of Compound of Formula (I*) | | | |
|---|---|---|---|
| I*-144a | methyl 2-((R)-((R)-1-((S)-1-(methylamino)-3-(tetrahydro-2H-pyran-4-yl)propan-2-ylcarbamoyl)piperidin-3-yl)(3-(trifluoromethyl)phenyl)methoxy)ethylcarbamate | 1.94 559 (M + 1) | 1.12-1.47 (m, 6H), 1.52-1.70 (m, 6H), 2.70 (s, 3H), 3.62 (s, 3H), 3.82-3.96 (m, 3H), 7.50-7.69 (m, 4H) |
| I*-145a | methyl 2-((R)-((R)-1-((S)-1-(1-adamantyl)-3-(methylamino)propan-2-ylcarbamoyl)piperidin-3-yl)(3-fluorophenyl)methoxy)ethylcarbamate | 1.68 559 (M + 1) | 7.36 (q, 1H), 7.04 (m, 3H), 4.21 (m, 1H), 3.63 (s, 3H), 2.70 (2, 3H) |
| I*-146a | methyl 2-((R)-(3-chlorophenyl)((R)-1-((S)-1-(4,4-difluorocyclohexyl)-3-(methylamino)propan-2-ylcarbamoyl)piperidin-3-yl)methoxy)ethylcarbamate | 1.45 559 (M+) | 7.31-7.14 (m, 4H), 4.16 (d, J = 13.5 Hz, 1H), 4.08-4.03 (m, 1H), 3.96 (d, J = 8.5 Hz, 1H), 3.83 (d, J = 12.0 Hz, 1H), 3.56 (s, 3H), 3.27-2.74 (m, 8H), 2.66 (s, 3H), 2.00-1.10 (m, 16H). |
| I*-147a | methyl 2-((R)-((R)-1-((S)-1-(4,4-difluorocyclohexyl)-3-(methylamino)propan-2-ylcarbamoyl)piperidin-3-yl)(3,5-difluorophenyl)methoxy)ethylcarbamate | 1.47 561 (M + 1) | 6.87-6.80 (m, 3H), 4.13 (d, J = 12.0 Hz, 1H), 4.08-4.03 (m, 1H), 4.01 (d, J = 8.2 Hz, 1H), 3.83 (d, J = 13.2 Hz, 1H), 3.56 (s, 3H), 3.31-2.74 (m, 8H), 2.65 (s, 3H), 1.99-1.12 (m, 16H). |
| I*-148a | methyl 2-((R)-(3-chloro-2,4-difluorophenyl)((R)-1-((S)-1-(methylamino)-3-(tetrahydro-2H-pyran-4-yl)propan-2-ylcarbamoyl)piperidin-3-yl)methoxy)ethylcarbamate | 1.98 561 (M+) | 1.62 (m, 12H), 2.71 (s, 6H), 3.01 (m, 4H), 3.39 (m, 3H), 3.81 (m, 3H), 4.12 (m, 2H), 4.42 (d, 1H), 7.18 (t, 1H), 7.38 (m, 1H), |
| I*-149a | methyl 2-((R)-((R)-1-((S)-1-(3-noradamantyl)-3-(methylamino)propan-2-ylcarbamoyl)piperidin-3-yl)(2,5-difluorophenyl)methoxy)ethylcarbamate | 1.64 563 (M + 1) | 7.10 (m, 3H), 4.24 (m, 1H0, 3.63 (s, 3H), 2.72 (s, 3H). |
| I*-150a | methyl 2-((R)-1-(3-chlorophenyl)-1-((R)-1-((S)-1-cyclohexyl-3-(methylamino)propan-2-ylcarbamoyl)piperidin-3-yl)butoxy)ethylcarbamate | 2.48 565 (M+) | 0.80-0.98 (m, 6H), 1.17-1.58 (m, 10H), 1.60-1.85 (m, 7H), 1.90-2.34 (m, 5H), 2.37-2.49 (m, 1H), 2.70 (s, 3H), 3.65 (s, 3H), 3.95 (d, 1H), 4.11 (d, 2H), 7.20-7.30 (m, 3H), 7.40 (s, 1H) |
| I*-151a | methyl 2-((R)-1-(3-chlorophenyl)-1-((3R)-1-((S)-1-(3-noradamantyl)-3-(methylamino)propan-2-ylcarbamoyl)piperidin-3-yl)ethoxy)ethylcarbamate | 1.73 575 (M+) | 7.27-7.14 (m, 4H), 4.18-4.15 (m, 2H), 4.03 (d, J = 12.6 Hz, 1H), 3.55 (s, 3H), 2.62 (s, 3H), 3.30-2.48 (m, 8H), 1.42 (s, 3H), 2.18-1.15 (m, 20H). |
| I*-152a | methyl 2-((R)-((R)-1-((S)-1-(1-adamantyl)-3-(methylamino)propan-2-ylcarbamoyl)piperidin-3-yl)(2,5-difluorophenyl)methoxy)ethylcarbamate | 1.68 577 (M + 1) | 7.10 (m, 3H), 4.45 (d, 1H), 4.22 (m, 1H0, 3.96 (d, 1H), 3.63 (s, 3H), 2.70 (s, 3H), 1.96 (bs, 3H) |

-continued

| Table of Compound of Formula (I*) | | | | |
|---|---|---|---|---|
| I*-153a | methyl 2-((R)-(3-chloro-5-fluorophenyl)((R)-1-((S)-1-(4,4-difluorocyclohexyl)-3-(methylamino)propan-2-ylcarbamoyl)piperidin-3-yl)methoxy)ethylcarbamate | 1.52 | 577 (M+) | 7.10-7.07 (m, 2H), 6.97-6.95 (m, 1H), 4.14 (d, J = 13.2 Hz, 1H), 4.09-4.03 (m, 1H), 4.00 (d, J = 8.2 Hz, 1H), 3.83 (d, J = 12.3 Hz, 1H), 3.57 (s, 3H), 3.31-2.75 (m, 8H), 2.66 (s, 3H), 1.99-1.14 (m, 16H). |
| I*-154a | methyl 2-((R)-(3-fluorophenyl)((R)-1-((S)-1-((R)-6,6-dimethyl-tetrahydro-2H-pyran-3-yl)-3-(methylamino)propan-2-ylcarbamoyl)piperidin-3-yl)methoxy)ethylcarbamate | 1.36 | 536 (M+) | 7.38-7.34, m, 1H; 7.12-7.01 m, 3H; 3.62, s, 3H; 2.71, s, 3H; 1.21, s, 6H |
| I*-155a | methyl 2-((R)-(3,5-difluorophenyl)((R)-1-((S)-1-((R)-6,6-dimethyl-tetrahydro-2H-pyran-3-yl)-3-(methylamino)propan-2-ylcarbamoyl)piperidin-3-yl)methoxy)ethylcarbamate | 1.35 | 555 (M+) | 6.90 (m, 3H), 3.62 (s, 3H), 2.71 (s, 3H), 1.20 (s, 6H) |
| I*-156a | methyl 2-((R)-((R)-1-((S)-1-((R)-6,6-dimethyl-tetrahydro-2H-pyran-3-yl)-3-(methylamino)propan-2-ylcarbamoyl)piperidin-3-yl)(phenyl)methoxy)ethylcarbamate | 1.35 | 518 (M+) | 7.37-7.28, m, 5H; 3.62, s, 3H; 2.72, s, 3H; 1.21, s, 6H |
| I*-157a | methyl 2-((R)-((R)-1-((S)-1-((R)-6,6-dimethyl-tetrahydro-2H-pyran-3-yl)-3-(methylamino)propan-2-ylcarbamoyl)piperidin-3-yl)(phenyl)methoxy)ethylcarbamate | 1.41 | 553 (M+) | 7.35-7.30 m, 3H 7.23, ap d, 1H; 3.63 s, 3H; 2.71, s, 3H; 1.21, s, 6H |
| I*-158a | methyl 2-((R)-(3-chlorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate | 1.44 | 551 (M+) | 7.36-7.26, m, 4H; 3.64, s, 3H; 2.73, s, 3H; 0.80 m, 1H; 0.63, m, 1H; 0.52, m, 1H; 0.41, m, 1H |
| I*-159a | methyl 2-((R)-(3-fluorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate | 1.35 | 535 (M+) | 7.36, m, 1H; 7.15-7.0, m, 3H; 3.62, s, 3H; 2.72, s, 3H; 0.79, m, 1H; 0.62, m, 1H; 0.51, m, 1H; 0.40, m, 1H |
| I*-160a | methyl 2-((R)-(3,5-difluorophenyl)((R)-1-((S)-1-((R)-4-oxaspiro[2.5]octan-6-yl)-3-(methylamino)propan-2-ylcarbamoyl)piperidin-3-yl)methoxy)ethylcarbamate | 1.41 | 553 (M+) | 6.98, m, 2H; 6.88, m, 1H; 3.63, s, 3H; 2.72, s, 3H; 0.80, m, 1H; 0.61, m, 1H; 0.51, m, 1H; 0.40, m, 1H |

| Table of Compounds Formula (I) | | | | | |
|---|---|---|---|---|---|
| Cpd. No. | Cpd Name | Example | LC-MS (3 min) $t_R$ (min) | Mass observed | Selected 1H NMR |
| I-1a | methyl (S)-4-((R)-1-((S)-1-cyclohexyl-3-(methylamino)propan-2-ylcarbamoyl)piperidin-3-yl)-4-(2-fluorophenyl)-4-hydroxybutylcarbamate | 3.1 | | 521 | 0.90 (m, 1H), 1.96 (m, 2H), 2.15 (m, 1H), 2.62 (m, 1H), 2.70 (s, 3H), 2.87 (m, 2H), 3.01 (m, 3H), 3.56 (s, 3H), 3.98 (d, 1H), 4.14 (m, 1H), 4.32 (d, 1H), 7.00 (m, 1H), 7.14 (m, 1H), 7.26 (m, 1H), 7.58 (m, 1H) |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-2a | methyl (S)-4-(3-chloro-2-fluorophenyl)-4-((R)-1-((S)-4,4-dimethyl-1-(methylamino)pentan-2-ylcarbamoyl)piperidin-3-yl)-4-hydroxybutylcarbamate | 3.1 | | 529 | 0.99 (s, 9H), 2.14 (m, 1H), 2.62 (m, 1H), 2.71 (s, 3H), 3.59 (s, 3H), 4.02 (d, 1H), 4.24 (m, 1H), 4.34 (d, 1H), 7.14 (m, 1H), 7.36 (m, 1H), 7.52 (m, 1H) |
| I-3a | methyl (S)-4-((R)-1-((S)-1-cyclohexyl-3-(methylamino)propan-2-ylcarbamoyl)piperidin-3-yl)-4-(3,5-dimethylphenyl)-4-hydroxybutylcarbamate | 3.1 | | 531 | 0.92 (m, 1H), 1.02 (m, 1H), 2.28 (s, 6H), 2.54 (m, 2H), 2.71 (s, 3H), 3.60 (s, 3H), 3.98 (d, 1H), 4.14 (m, 1H), 4.23 (d, 1H), 6.86 (s, 1H), 6.97 (s, 2H) |
| I-4a | methyl (S)-4-((R)-1-((S)-1-cyclohexyl-3-(methylamino)propan-2-ylcarbamoyl)piperidin-3-yl)-4-(3-fluoro-5-methylphenyl)-4-hydroxybutylcarbamate | 3.1 | | 535 | 0.88 (m, 1H), 1.06 (m, 1H), 2.34 (s, 3H), 2.54 (m, 2H), 2.70 (s, 3H), 3.59 (s, 3H), 3.96 (d, 1H), 4.12 (m, 1H), 4.26 (d, 1H), 6.76 (d, 1H), 6.94 (d, 1H), 6.97 (s, 1H) |
| I-5a | methyl (S)-4-((R)-1-((S)-1-cyclohexyl-3-(methylamino)propan-2-ylcarbamoyl)piperidin-3-yl)-4-(2-fluoro-5-methylphenyl)-4-hydroxybutylcarbamate | 3.1 | | 535 | 1.02 (m, 1H), 1.15 (m, 2H), 2.24 (m, 1H), 2.44 (s, 3H), 2.74 (m, 1H), 2.82 (s, 3H), 2.92 (m, 2H), 3.71 (s, 3H), 4.12 (d, 1H), 4.14 (m, 1H), 4.43 (d, 1H), 6.98 (m, 1H), 7.16 (m, 1H), 7.50 (m, 1H) |
| I-6a | methyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate | 3.1 | 1.43 | 538, 540 | 7.34-7.33 (m, 1H), 7.24-7.12 (m, 3H), 4.19 (d, J = 12.9 Hz, 1H), 4.07-4.00 (m, 1H), 3.88 (d, J = 11.7 Hz, 1H), 3.50 (s, 3H), 2.99-2.93 (m, 3H), 2.83 (dd, J = 12.6, 10.2 Hz, 1H), 2.61 (s, 3H), 2.48-2.39 (m, 2H), 1.92-0.76 (m, 22H). |
| I-7a | methyl (S)-4-((R)-1-((S)-1-cyclohexyl-3-(methylamino)propan-2-ylcarbamoyl)piperidin-3-yl)-4-(2,3-difluorophenyl)-4-hydroxybutylcarbamate | 3.1 | | 539 | 0.88 (m, 1H), 2.14 (m, 1H), 2.69 (s, 3H), 3.58 (s, 3H), 3.96 (m, 1H), 4.14 (m, 1H), 4.38 (m, 1H), 7.13 (m, 2H), 7.46 (m, 1H) |
| I-7b | methyl (R)-4-((R)-1-((S)-1-cyclohexyl-3-(methylamino)propan-2-ylcarbamoyl)piperidin-3-yl)-4-(2,3-difluorophenyl)-4-hydroxybutylcarbamate | 3.1 | | 539 | 0.88 (m, 1H), 2.18 (m, 1H), 2.69 (s, 3H), 3.58 (s, 3H), 3.86 (d, 1H), 4.16 (m, 1H), 4.95 (d, 1H), 7.12 (m, 2H), 7.35 (m, 1H) |
| I-8a | methyl (S)-4-((R)-1-((S)-1-cyclohexyl-3-(methylamino)propan-2-ylcarbamoyl)piperidin-3-yl)-4-(3,5-difluorophenyl)-4-hydroxybutylcarbamate | 3.1 | | 539 | 0.92 (m, 2H), 2.54 (m, 2H), 2.70 (s, 3H), 2.92 (m, 1H), 3.60 (s, 3H), 3.94 (d, 1H), 4.14 (m, 1H), 4.28 (d, 1H), 6.80 (m, 1H), 6.99 (m, 2H) |
| I-9a | methyl (S)-4-((R)-1-((S)-2-amino-3-cyclohexylpropylcarbamoyl)piperidin-3-yl)-4-(3-chloro-2-fluorophenyl)-4-hydroxybutylcarbamate | 4 | 1.41 | 541 | 2.18 (m, 1H), 2.67 (m, 2H), 3.55 (s, 3H), 3.87 (d, 1H), 4.39 (d, 1H), 7.11 (m, 1H), 7.36 (m, 1H), 7.51 (m, 1H) |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-10a | methyl (4S)-4-((3R)-1-((2S)-2-amino-3-(tetrahydro-2H-pyran-2-yl)propylcarbamoyl)piperidin-3-yl)-4-(3-chloro-2-fluorophenyl)-4-hydroxybutylcarbamate | 4.1 | 1.36 | 543 | 7.51 (m), 7.36 (m), 7.13 (m), 6.81 (br s), 4.39 (d), 3.97 (br m), 3.85 (br m), 3.25 (ap d), 2.68 (br m) |
| I-11a | ethyl (S)-4-(3-chlorophenyl)-4-((R)-1-((S)-1-cyclohexyl-3-(methylamino)propan-2-ylcarbamoyl)piperidin-3-yl)-4-hydroxybutylcarbamate | 3.1 | 1.48 | 551, 553 | 7.35-7.34 (m, 1H), 7.24-7.12 (m, 3H), 4.20 (d, J = 13.2 Hz, 1H), 4.08-4.01 (m, 1H), 3.94 (q, J = 7.1 Hz, 2H), 3.88 (d, J = 14.4 Hz, 1H), 2.99-2.92 (m, 3H), 2.84 (dd, J = 12.6, 10 Hz, 1H), 2.61 (s, 3H), 2.49-2.39 (m, 2H), 1.11 (t, J = 7.0 Hz, 3H), 1.92-0.76 (m, 22H). |
| I-12a | methyl (S)-4-((R)-1-((1S,2R)-1-cyclohexyl-1-hydroxy-3-(methylamino)propan-2-ylcarbamoyl)piperidin-3-yl)-4-(2,3-difluorophenyl)-4-hydroxybutylcarbamate | 3.1 | | 555 | 1.98 (m, 2H), 2.16 (m, 1H), 2.66 (m, 1H), 2.73 (s, 3H), 3.05 (m, 3H), 3.46 (m, 1H), 3.64 (s, 3H), 3.96 (m, 1H), 4.13 (m, 1H), 4.42 (m, 1H), 7.15 (m, 2H), 7.36 (m, 1H) |
| I-13a | methyl (S)-4-(3-chloro-2-fluorophenyl)-4-((R)-1-((S)-1-cyclohexyl-3-(methylamino)propan-2-ylcarbamoyl)piperidin-3-yl)-4-hydroxybutylcarbamate | 3.1 | | 555 | 2.16 (m, 1H), 2.71 (s, 3H), 3.59 (s, 3H), 3.98 (d, 1H), 4.16 (m, 1H), 4.34 (d, 1H), 7.14 (m, 1H), 7.37 (m, 1H), 7.53 (m, 1H) |
| I-14a | methyl (S)-4-(2-chloro-3-fluorophenyl)-4-((R)-1-((S)-1-cyclohexyl-3-(methylamino)propan-2-ylcarbamoyl)piperidin-3-yl)-4-hydroxybutylcarbamate | 3.1 | | 555 | 0.92 (m, 1H), 2.48 (m, 1H), 2.70 (s, 3H), 3.58 (s, 3H), 3.98 (d, 1H), 4.14 (m, 1H), 4.42 (d, 1H), 7.14 (m, 1H), 7.31 (m, 1H), 7.60 (m, 1H) |
| I-15a | methyl (S)-4-(3-chloro-5-fluorophenyl)-4-((R)-1-((S)-1-cyclohexyl-3-(methylamino)propan-2-ylcarbamoyl)piperidin-3-yl)-4-hydroxybutylcarbamate | 2.1 | | 555 | 0.88 (m, 1H), 1.03 (m, 1H), 2.54 (m, 2H), 2.70 (s, 3H), 2.94 (m, 1H), 3.05 (m, 3H), 3.60 (s, 3H), 3.96 (d, 1H), 4.13 (m, 1H), 4.28 (d, 1H), 7.08 (m, 2H), 7.23 (m, 1H) |
| I-16a | methyl (S)-4-((R)-1-((2S,3R)-3-amino-1-cyclohexylbutan-2-ylcarbamoyl)piperidin-3-yl)-4-(3-chloro-2-fluorophenyl)-4-hydroxybutylcarbamate | 3.1 | | | |
| I-17a | methyl (S)-4-(2,3-difluorophenyl)-4-((R)-1-((S)-1-((1r,4S)-4-fluorocyclohexyl)-3-(methylamino)propan-2-ylcarbamoyl)piperidin-3-yl)-4-hydroxybutylcarbamate | 2.2 | | 557 | 1.78 (m, 1H), 2.72 (s, 3H), 3.58 (s, 3H), 3.90 (m, 1H), 4.13 (m, 1H), 4.42 (m, 2H), 7.13 (m, 2H), 7.35 (m, 1H) |
| I-18a | methyl (4S)-4-(3-chloro-2-fluorophenyl)-4-hydroxy-4-((3R)-1-(1-(methylamino)-3-(tetrahydro-2H-pyran-4-yl)propan-2-ylcarbamoyl)piperidin-3-yl)butylcarbamate | 5.1 | 1.27 | 557, 559 | 2.70 (s, 3H), 3.58 (s, 3H), 7.15 (m, 1H), 7.38 (m, 1H), 7.53 (m, 1H) |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-19a | methyl (S)-4-((R)-1-((S)-2-amino-3-cyclohexylpropylcarbamoyl)piperidin-3-yl)-4-(3-chloro-2,4-difluorophenyl)-4-hydroxybutylcarbamate | 4.1 | 1.48 | 559 | 2.18 (m, 1H), 2.65 (m, 2H), 3.56 (s, 3H), 3.87 (d, 1H), 4.39 (d, 1H), 7.09 (m, 1H), 7.56 (m, 1H) |
| I-20a | methyl (S)-4-(3-chloro-2-fluorophenyl)-4-((R)-1-((1S,2R)-1-cyclohexyl-1-hydroxy-3-(methylamino)propan-2-ylcarbamoyl)piperidin-3-yl)-4-hydroxybutylcarbamate | 2.1 | | 571 | 2.15 (m, 1H), 2.64 (m, 1H), 2.72 (s, 3H), 3.04 (m, 3H), 3.44 (m, 1H), 3.58 (s, 3H), 3.96 (d, 1H), 4.12 (m, 1H), 4.32 (d, 1H), 7.15 (m, 1H), 7.37 (m, 1H), 7.54 (m, 1H) |
| I-21a | methyl (S)-4-(2-chloro-3-fluorophenyl)-4-((R)-1-((1S,2R)-1-cyclohexyl-1-hydroxy-3-methylamino)(propan-2-ylcarbamoyl)piperidin-3-yl)-4-hydroxybutylcarbamate | 2 | | 571 | 2.48 (m, 1H), 2.64 (m, 2H), 2.72 (s, 3H), 3.05 (m, 3H), 3.43 (m, 1H), 3.58 (s, 3H), 3.96 (d, 1H), 4.12 (m, 1H), 4.34 (d, 1H), 7.15 (m, 1H), 7.28 (m, 1H), 7.58 (m, 1H) |
| I-22a | methyl (S)-4-(3-chloro-2-fluorophenyl)-4-((R)-1-((S)-1-((1r,4S)-4-fluorocyclohexyl)-3-(methylamino)propan-2-ylcarbamoyl)piperidin-3-yl)-4-hydroxybutylcarbamate | 2.2 | | 573 | 1.79 (m, 1H), 2.65 (m, 1H), 2.70 (s, 3H), 2.82 (m, 1H), 3.59 (s, 3H), 3.97 (m, 1H), 4.14 (m, 1H), 4.35 (m, 1H), 4.46 (m, 1H), 7.12 (m, 1H), 7.37 (m, 1H), 7.52 (m, 1H) |
| I-23a | methyl (S)-4-(3-chloro-2,4-difluorophenyl)-4-((R)-1-((S)-1-cyclohexyl-3-(methylamino)propan-2-ylcarbamoyl)piperidin-3-yl)-4-hydroxybutylcarbamate | 5 | 1.53 | 573 | 2.13 (m, 1H), 2.62 (m, 1H), 2.70 (s, 3H), 3.59 (s, 3H), 3.99 (d, 1H), 4.15 (m, 1H), 4.32 (d, 1H), 7.09 (m, 1H), 7.58 (m, 1H) |
| I-24a | methyl (S)-4-acetamido-4-(3-chlorophenyl)-4-((R)-1-((S)-1-cyclohexyl-3-(methylamino)propan-2-ylcarbamoyl)piperidin-3-yl)butylcarbamate | 7 | 1.4 | 578, 580 | 7.88 (s, 1H), 7.26-7.14 (m, 4H), 4.11 (d, J = 12.0 Hz, 1H), 4.04-3.97 (m, 1H), 3.78 (d, J = 12.3 Hz, 1H), 3.52 (s, 3H), 3.03-2.96 (m, 3H), 2.89 (dd, J = 12.6, 10.2 Hz, 1H), 2.62 (s, 3H), 1.98 (s, 3H), 2.39-0.73 (m, 24H). |
| I-25a | methyl (S)-4-(3-chlorophenyl)-4-((R)-1-((S)-1-cyclohexyl-3-(methylamino)propan-2-ylcarbamoyl)piperidin-3-yl)-4-propionamidobutylcarbamate | 7.1 | 1.42 | 592, 594 | 7.78 (s, 1H), 7.31-7.18 (m, 4H), 4.13 (d, J = 13.2 Hz, 1H), 4.08-4.02 (m, 1H), 3.84 (d, J = 14.0 Hz, 1H), 3.56 (s, 3H), 3.07-2.89 (m, 4H), 2.67 (s, 3H), 2.31 (q, J = 7.5 Hz, 2H), 1.11 (t, J = 7.6 Hz, 3H), 2.43-0.74 (m, 24H). |
| I-25b | methyl (R)-4-(3-chlorophenyl)-4-((R)-1-((S)-1-cyclohexyl-3-(methylamino)propan-2-ylcarbamoyl)piperidin-3-yl)-4-propionamidobutylcarbamate | 7.1 | 1.41 | 592, 594 | 7.69 (s, 1H), 7.24-7.12 (m, 4H), 4.10-3.98 (m, 2H), 3.83 (d, J = 12.0 Hz, 1H), 3.50 (s, 3H), 3.07-2.81 (m, 4H), 2.60 (s, 3H), 2.21 (q, J = 7.6 Hz, 2H), 1.03 (t, J = 7.6 Hz, 3H), 2.37-0.75 (m, 24H). |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-26a | (R)-(3-chlorophenyl) ((R)-1-((S)-1-cyclohexyl-3-(methylamino)propan-2-ylcarbamoyl) piperidin-3-yl) methyl carbamate | 6.2 | 1.42 | 465, 467 | 7.29-7.16 (m, 4H), 5.32 (d, J = 8.5 Hz, 1H), 4.05-4.00 (m, 1H), 3.89 (d, J = 13.5 Hz, 1H), 3.62 (d, J = 13.2 Hz, 1H), 3.00-2.79 (m, 4H), 2.62 (s, 3H), 1.90-0.78 (m, 18H). |
| I-27a | (R)-(3-chlorophenyl)((R)-1-((S)-1-cyclohexyl-3-(methylamino)propan-2-ylcarbamoyl) piperidin-3-yl)methyl methylcarbamate | 6.2 | 1.49 | 479, 481 | 7.28-7.14 (m, 4H), 5.32 (d, J = 7.9 Hz, 1H), 4.04-3.99 (m, 1H), 3.95 (d, J = 12.3 Hz, 1H), 3.69 (d, J = 13.5 Hz, 1H), 2.98-2.74 (m, 4H), 2.61 (s, 3H), 2.58 (s, 3H), 1.85-0.78 (m, 18H). |
| I-28a | (R)-(3-chlorophenyl) ((R)-1-((S)-1-cyclohexyl-3-(methylamino)propan-2-ylcarbamoyl) piperidin-3-yl)methyl ethylcarbamate | 6.2 | | 493 | 0.90 (m, 2H), 1.07 (t, 3H), 2.70 (s, 3H), 3.77 (m, 1H), 4.05 (m, 2H), 5.40 (d, 1H), 7.25 (m, 1H), 7.33 (m, 3H) |
| I-28b | (S)-(3-chlorophenyl) ((R)-1-((S)-1-cyclohexyl-3-(methylamino)propan-2-ylcarbamoyl) piperidin-3-yl)methyl ethylcarbamate | 6.2 | | 493 | 0.91 (m, 2H), 1.08 (t, 3H), 2.70 (s, 3H), 3.08 (m, 3H), 3.78 (m, 1H), 4.05 (m, 2H), 5.40 (d, 1H), 7.25 (m, 1H), 7.33 (m, 3H) |
| I-29a | (R)-(3-chlorophenyl) ((R)-1-((S)-1-cyclohexyl-3-(methylamino) propan-2-ylcarbamoyl) piperidin-3-yl)methyl butylcarbamate | 6.2 | | 521 | 0.89 (m, 4H), 2.70 (s, 3H), 2.90 (m, 3H), 3.05 (m, 3H), 3.79 (m, 1H), 4.06 (m, 2H), 5.39 (d, 1H), 7.32 (m, 1H), 7.33 (m, 3H) |
| I-29b | (S)-(3-chlorophenyl) ((R)-1-(S)-1-cyclohexyl (-3-(methylamino) propan-2-ylcarbamoyl) piperidin-3-yl)methyl butylcarbamate | 6.2 | | 521 | 0.92 (m, 5H), 2.70 (s, 3H), 2.89 (m, 3H), 3.79 (m, 1H), 4.04 (m, 2H), 5.39 (d, 1H), 7.21 (m, 1H), 7.33 (m, 3H) |
| I-30a | methyl 2-((R)-(3-chlorophenyl)((R)-1-((S)-4,4-dimethyl-1-(methylamino)pentan-2-ylcarbamoyl) piperidin-3-yl) methoxy)ethylcarbamate | 5.1 | | | |
| I-31a | methyl 2-((R)-((R)-1-((S)-1-cyclohexyl-3-(methylamino)propan-2-ylcarbamoyl) piperidin-3-yl)(3-fluorophenyl) methoxy)ethylcarbamate | 3 | | 507 | 0.95 (m, 2H), 2.71 (s, 3H), 3.04 (m, 1H), 3.25 (m, 3H), 3.60 (s, 3H), 3.88 (m, 1H), 4.12 (m, 3H), 7.03 (m, 3H), 7.37 (m, 1H) |
| I-32a | methyl 2-((R)-((R)-1-((S)-1-amino-3-cyclohexylpropan-2-ylcarbamoyl)piperidin-3-yl)(3-chlorophenyl) methoxy)ethylcarbamate | 5.1 | | | |
| I-34a | methyl 2-((1R)-((3R)-1-((2S)-1-amino-3-(tetrahydro-2H-pyran-2-yl)propan-2-ylcarbamoyl)piperidin-3-yl)(3-chlorophenyl) methoxy)ethylcarbamate | 5.1 | | | |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-35a | methyl 2-((R)-(3-chlorophenyl)((R)-1-((S)-1-cyclohexyl-3-(methylamino)propan-2-ylcarbamoyl)piperidin-3-yl)methoxy)ethylcarbamate | 3.1 | | 523 | 0.95 (m, 2H), 2.71 (s, 3H), 3.24 (m, 3H), 3.62 (s, 3H), 3.87 (m, 1H), 4.01 (m, 1H), 4.13 (m, 2H), 7.20 (m, 1H), 7.32 (m, 3H) |
| I-36a | methyl 2-((R)-((R)-1-((2S,3R)-3-amino-1-cyclohexylbutan-2-ylcarbamoyl)piperidin-3-yl)(3-chlorophenyl)methoxy)ethylcarbamate | 5.2 | | | |
| I-37a | methyl 2-((R)-((3R)-1-((2S)-1-cyclohexyl-3-(methylamino)propan-2-ylcarbamoyl)piperidin-3-yl)(2,3-difluorophenyl)methoxy)ethylcarbamate | 3.1 | | 525 | 0.90 (m, 1H), 1.03 (m, 1H), 1.53 (m, 1H), 2.71 (s, 3H), 3.62 (s, 3H), 3.81 (m, 1H), 4.11 (m, 2H), 4.48 (m, 1H), 7.19 (m, 3H) |
| I-38a | methyl 2-((R)-(3-chlorophenyl)((R)-1-((S)-1-(methylamino)-3-(tetrahydro-2H-pyran-4-yl)propan-2-ylcarbamoyl)piperidin-3-yl)methoxy)ethylcarbamate | 5.1 | | | |
| I-38b | methyl 2-((R)-(3-chlorophenyl)((R)-1-((R)-1-(methylamino)-3-(tetrahydro-2H-pyran-4-yl)propan-2-ylcarbamoyl)piperidin-3-yl)methoxy)ethylcarbamate | 5.1 | | | |
| I-39a | methyl 2-((R)-((R)-1-((S)-2-amino-3-cyclohexylpropylcarbamoyl)piperidin-3-yl)(3-chloro-2-fluorophenyl)methoxy)ethylcarbamate | 4.1 | 1.53 | 527 | 2.97 (m, 12H), 3.61 (s, 3H), 4.12 (d, 1H), 4.43 (d, 1H), 7.10 (m, 1H), 7.35 (m, 1H), 7.42 (m, 1H) |
| I-41a | ethyl 2-((R)-(3-chlorophenyl)((R)-1-((S)-1-cyclohexyl-3-(methylamino)propan-2-ylcarbamoyl)piperidin-3-yl)methoxy)ethylcarbamate | 3.1 | | 537 | 0.90 (m, 1H), 1.03 (m, 1H), 1.21 (t, 3H), 2.71 (s, 3H), 2.91 (m, 3H), 3.06 (m, 1H), 3.89 (m, 1H), 7.21 (m, 1H), 7.32 (m, 3H) |
| I-42a | methyl 2-((R)-1-(3-chlorophenyl)-1-((R)-1-((S)-1-cyclohexyl-3-(methylamino)propan-2-ylcarbamoyl)piperidin-3-yl)ethoxy)ethylcarbamate | 5.1 | | | |
| I-43a | methyl 2-((R)-(3-chloro-2-fluorophenyl)((R)-1-((S)-1-cyclohexyl-3-(methylamino)propan-2-ylcarbamoyl)piperidin-3-yl)methoxy)ethylcarbamate | 3.1 | 1.59 | 541 | 7.42 (t), 7.35 (t), 7.20 (t), 4.46 (d), 4.07 (m), 4.45 (d), 4.07 (m), 3.79 (d), 3.61 (s), 3.25 (s), 3.02 (t), 2.91 (t), 2.62 (d), 2.42 (s). |
| I-43b | methyl 2-((3-chloro-2-fluorophenyl)(1-((S)-1-cyclohexyl-3-(methylamino)propan-2-ylcarbamoyl)piperidin-3-yl)methoxy)ethylcarbamate | 3.1 | 1.62 | 541 | 7.42 (t), 7.35 (m), 7.19 (t), 4.45 (d), 4.22 (d), 4.06 (br s), 3.75 (d), 3.60 (s), 3.24 (m), 2.88 (m), 2.61 (m), 2.40 (s). |

| Cpd. No. | Cpd Name | Example | LC-MS (3 min) $t_R$ (min) | Mass observed | Selected 1H NMR |
|---|---|---|---|---|---|
| I-44a | methyl 2-((R)-(3-chloro-5-fluorophenyl)((R)-1-((S)-1-cyclohexyl-3-(methylamino)propan-2-ylcarbamoyl)piperidin-3-yl)methoxy)ethylcarbamate | 3.1 | | 541 | 0.98 (m, 2H), 2.71 (s, 3H), 2.90 (m, 2H), 3.06 (m, 1H), 3.26 (m, 3H), 3.62 (s, 3H), 3.87 (m, 1H), 4.10 (m, 3H), 7.01 (m, 1H), 7.14 (m, 2H) |
| I-45a | methyl 2-((R)-(3-chlorophenyl)((R)-1-((S)-1-(trans-4-fluorocyclohexyl)-3-(methylamino)propan-2-ylcarbamoyl)piperidin-3-yl)methoxy)ethylcarbamate | 3.1 | | | |
| I-46a | methyl 2-((R)-(3-chlorophenyl)((R)-1-((S)-1-(1-fluorocyclohexyl)-3-(methylamino)propan-2-ylcarbamoyl)piperidin-3-yl)methoxy)ethylcarbamate | 5.1 | 1.55 | 540 | 7.32 (m, 3H), 7.20 ("d", 1H), 3.62 (s, 3H), 2.72 (s, 3H) |
| I-46b | methyl 2-((1R)-(3-chlorophenyl)((3R)-1-(1-(1-fluorocyclohexyl)-3-(methylamino)propan-2-ylcarbamoyl)piperidin-3-yl)methoxy)ethylcarbamate | 3.1 | | 541 | 1.14 (m, 1H), 2.71 (s, 3H), 3.27 (m, 3H), 3.62 (s, 3H), 3.79 (m, 1H), 4.12 (d, 1H), 4.30 (m, 2H), 7.21 (m, 1H), 7.32 (m, 3H) |
| I-47a | methyl 2-((R)-(3-chloro-2-fluorophenyl)((R)-1-((S)-1-(methylamino)-3-(tetrahydro-2H-pyran-4-yl)propan-2-ylcarbamoyl)piperidin-3-yl)methoxy)ethylcarbamate | 5.1 | 1.32 | 543 | 7.45 (q), 7.35 (q), 7.23 (q), 4.47 (m), 4.13 (m), 3.94 (d), 3.82 (d), 3.64 (s), 3.27 (s), 3.08 (m), 2.96 (m), 2.73 (m) |
| I-47b | methyl 2-((R)-(3-chloro-2-fluorophenyl)((R)-1-((R)-1-(methylamino)-3-(tetrahydro-2H-pyran-4-yl)propan-2-ylcarbamoyl)piperidin-3-yl)methoxy)ethylcarbamate | 5.1 | 1.33 | 543 | 7.44 (q), 7.36 (q), 7.22, 4.48 (m), 4.33 (d), 4.17 (br m), 3.93 (m), 3.79 (m), 3.63 (s), 3.10 (m), 2.97 (m), 2.80 (m), 2.72 (d) |
| I-48a | methyl 2-((S)-(3-chloro-2-fluorophenyl)((R)-4-((S)-1-cyclohexyl-3-(methylamino)propan-2-ylcarbamoyl)morpholin-2-yl)methoxy)ethylcarbamate | 3.1 | | | |
| I-49a | ethyl 2-((R)-(3-chloro-2-fluorophenyl)((3R)-1-((2S)-1-cyclohexyl-3-(methylamino)propan-2-ylcarbamoyl)piperidin-3-yl)methoxy)ethylcarbamate | 3.1 | | 555 | 0.98 (m, 2H), 1.21 (t, 3H), 2.71 (s, 3H), 2.95 (m, 2H), 3.04 (m, 2H), 3.24 (m, 2H), 3.82 (m, 1H), 4.48 (m, 1H), 7.21 (m, 1H), 7.35 (m, 1H), 7.43 (m, 1H) |
| I-50a | methyl 2-((1R)-(3-chloro-2-fluorophenyl)((3R)-1-(1-(1-fluorocyclohexyl)-3-(methylamino)propan-2-ylcarbamoyl)piperidin-3-yl)methoxy)ethylcarbamate | 3.1 | | 559 | 2.64 (s, 3H), 3.53 (s, 3H), 3.69 (m, 1H), 4.23 (m, 2H), 4.48 (m, 1H), |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-51a | methyl 2-((R)-(3-chloro-2-fluorophenyl)((R)-1-((S)-1-(trans-4-fluorocyclohexyl)-3-(methylamino)propan-2-ylcarbamoyl)piperidin-3-yl)methoxy)ethylcarbamate | 3.1 | 1.41 | 559 | 7.42 (m), 7.33 (m), 7.21 (m), 4.46 (m), 4.35 (m), 4.16 (m), 3.82 (m), 3.62 (s), 3.05 (m), 2.91 (m), 2.70 (d) |
| I-52a | methyl 2-((R)-(3-chlorophenyl)((R)-1-((S)-1-(3-noradamantyl)-3-(methylamino)propan-2-ylcarbamoyl)piperidin-3-yl)methoxy)ethylcarbamate | 5.1 | 1.65 | 561 | 7.31 (m, 3H), 7.19 ("d", 1H), 4.12 (m, 2H), 4.02 ("d", 1H), 3.87 ("d", 1H), 3.62 (s, 3H), 2.37 (s, 3H) |
| I-53a | 2-((R)-(3-chlorophenyl)((R)-1-((S)-1-cyclohexyl-3-(methylamino)propan-2-ylcarbamoyl)piperidin-3-yl)methoxy)ethylcarbamate | 6 | 1.49 | 509, 511 | 7.28-7.12 (m, 4H), 4.20 (d, J = 13.2 Hz, 1H), 4.11-3.99 (m, 3H), 3.95 (d, J = 8.8 Hz, 1H), 3.87 (d, J = 13.2 Hz, 1H), 3.40-3.28 (m, 2H), 2.96 (dd, J = 12.6, 3.2 Hz, 1H), 2.84 (dd, J = 12.6, 10.2 Hz, 1H), 2.73-2.63 (m, 2H), 2.61 (s, 3H), 1.71-0.75 (m, 18H). |
| I-54a | 2-((R)-(3-chlorophenyl)((R)-1-((S)-1-cyclohexyl-3-(methylamino)propan-2-ylcarbamoyl)piperidin-3-yl)methoxy)ethylmethylcarbamate | 6.1 | 1.48 | 523, 525 | 7.30-7.14 (m, 4H), 4.22 (d, J = 11.7 Hz, 1H), 4.09-4.00 (m, 3H), 3.98 (d, J = 8.5 Hz, 1H), 3.88 (d, J = 13.5 Hz, 1H), 3.43-3.33 (m, 2H), 2.99 (dd, J = 12.6, 3.2 Hz, 1H), 2.85 (dd, J = 12.6, 10.2 Hz, 1H), 2.75-2.66 (m, 2H), 2.634 (s, 3H), 2.628 (s, 3H), 1.73-0.79 (m, 18H). |
| I-55a | 2-((R)-(3-chlorophenyl)((R)-1-((S)-1-cyclohexyl-3-(methylamino)propan-2-ylcarbamoyl)piperidin-3-yl)methoxy)ethylethylcarbamate | 6.1 | 1.55 | 537, 539 | 7.29-7.13 (m, 4H), 4.21 (d, J = 12.9 Hz, 1H), 4.07-4.00 (m, 3H), 3.97 (d, J = 8.5 Hz, 1H), 3.86 (d, J = 13.5 Hz, 1H), 3.41-3.32 (m, 2H), 3.04 (q, J = 7.0 Hz, 2H), 2.98 (dd, J = 12.7, 2.8 Hz, 1H), 2.85 (dd, J = 12.0, 10.5 Hz, 1H), 2.74-2.65 (m, 2H), 2.62 (s, 3H), 1.03 (t, J = 7.0 Hz, 3H), 1.72-0.78 (m, 18H). |
| I-56a | (3R)-3-((R)-(3-chlorophenyl)(2-(methylamino)-2-oxoethoxy)methyl)-N-((S)-1-cyclohexyl-3-(methylamino)propan-2-yl)piperidine-1-carboxamide | 1.1 | | 493 | 0.95 (m, 2H), 2.70 (s, 3H), 2.78 (s, 3H), 2.96 (m, 2H), 3.05 (m, 2H), 3.70 (m, 3H), 4.12 (m, 3H), 7.26 (m, 1H), 7.37 (m, 3H) |
| I-56b | (3R)-3-((S)-(3-chlorophenyl)(2-(methylamino)-2-oxoethoxy)methyl)-N-((S)-1-cyclohexyl-3-(methylamino)propan-2-yl)piperidine-1-carboxamide | 1.1 | | 493 | 0.90 (m, 2H), 2.66 (s, 3H), 2.78 (s, 3H), 2.89 (m, 1H), 3.01 (m, 1H), 3.77 (m, 3H), 3.86 (m, 1H), 4.07 (m, 1H), 4.24 (m, 1H), 7.26 (m, 1H), 7.37 (m, 3H) |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-57a | (R)-3-((S)-(2-amino-2-oxoethoxy)(3-chloro-2-fluorophenyl)methyl)-N-((S)-1-cyclohexyl-3-(methylamino)propan-2-yl)piperidine-1-carboxamide | 1.1 | | 497 | 1.83 (m, 1H), 2.71 (s, 3H), 2.96 (m, 1H), 3.06 (m, 1H), 3.21 (m, 1H), 4.12 (m, 2H), 4.58 (d, 2H), 7.25 (m, 1H), 7.48 (m, 1H), 7.50 (m, 1H) |
| I-58a | (3R)-3-((R)-(3-chlorophenyl)(2-(ethylamino)-2-oxoethoxy)methyl)-N-((S)-1-cyclohexyl-3-(methylamino)propan-2-yl)piperidine-1-carboxamide | 1 | | 507 | 1.12 (t, 3H), 2.70 (s, 3H), 2.95 (m, 2H), 3.06 (m, 2H), 3.75 (m, 3H), 4.15 (m, 3H), 7.25 (m, 1H), 7.38 (m, 3H) |
| I-58b | (3R)-3-((S)-(3-chlorophenyl)(2-(ethylamino)-2-oxoethoxy)methyl)-N-((S)-1-cyclohexyl-3-(methylamino)propan-2-yl)piperidine-1-carboxamide | 1.1 | | 507 | 1.11 (t, 3H), 2.66 (s, 3H), 3.00 (m, 1H), 3.76 (m, 3H), 3.88 (m, 1H), 4.06 (m, 1H), 4.24 (m, 1H), 7.27 (m, 1H), 7.37 (m, 3H) |
| I-59a | (3R)—N-((2S)-1-cyclohexyl-3-(methylamino)propan-2-yl)-3-((R)-(2,3-difluorophenyl)(2-(ethylamino)-2-oxoethoxy)methyl)piperidine-1-carboxamide | 1.1 | | 509 | 0.92 (m, 2H), 1.07 (t, 3H), 1.92 (m, 1H), 2.65 (s, 3H), 3.19 (m, 3H), 3.68 (m, 3H), 4.08 (m, 2H), 4.50 (m, 1H), 7.18 (m, 3H) |
| I-60a | (R)-3-((R)-(3-chlorophenyl)(2-oxo-2-(propylamino)ethoxy)methyl)-N-((S)-1-cyclohexyl-3-(methylamino)propan-2-yl)piperidine-1-carboxamide | 1.1 | | 521 | 2.71 (t, 3H), 2.71 (s, 3H), 2.94 (m, 2H), 3.06 (m, 2H), 3.17 (m, 2H), 7.23 (m, 1H), 7.36 (m, 3H) |
| I-61a | (R)-3-((R)-(3-chlorophenyl)(2-(isopropylamino)-2-oxoethoxy)methyl)-N-((S)-1-cyclohexyl-3-(methylamino)propan-2-yl)piperidine-1-carboxamide | 1.1 | | | |
| I-62a | (3R)—N-((2S)-1-cyclohexyl-3-(methylamino)propan-2-yl)-3-((R)-(2,3-difluorophenyl)(2-oxo-2-(propylamino)ethoxy)methyl)piperidine-1-carboxamide | 1.1 | | 523 | 0.92 (m, 3H), 1.52 (m, 3H), 2.00 (m, 1H), 2.71 (s, 3H), 3.01 (m, 3H), 3.19 (m, 3H0, 3.76 (m, 3H), 4.15 (m, 2H), 4.55 (m, 1H), 7.24 (m, 3H) |
| I-63a | (R)—N-((S)-1-cyclohexyl-3-(methylamino)propan-2-yl)-3-((R)-(2,3-difluorophenyl)(2-(isopropylamino)-2-oxoethoxy)methyl)piperidine-1-carboxamide | 1.1 | | 523 | 0.97 (m, 2H), 1.13 (m, 6H), 2.70 (s, 3H), 3.98 (m, 1H), 4.15 (m, 2H), 4.52 (d, 1H), 7.20 (m, 3H) |
| I-64a | (3R)-3-((R)-(3-chloro-2-fluorophenyl)(2-(ethylamino)-2-oxoethoxy)methyl)-N-((2S)-1-cyclohexyl-3-(methylamino)propan-2-yl)piperidine-1-carboxamide | 5.1 | | 525 | 7.47 (m), 7.37 (m), 7.23 (m), 7.55 (m), 4.11 (m), 3.75 (m), 3.24 (m), 3.05 (m), 2.92 (s), 2.70 (s) |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-64b | (3R)-3-((3-chloro-2-fluorophenyl)(2-(ethylamino)-2-oxoethoxy)methyl)-N-((2S)-1-cyclohexyl-3-(methylamino)propan-2-yl)piperidine-1-carboxamide | 5.1 | | 525 | 7.47 (m), 7.37 (m), 7.23 (m), 7.55 (m), 4.11 (m), 3.75 (m), 3.24 (m), 3.05 (m), 2.92 (s), 2.70 (s) |
| I-65a | (R)-3-((R)-(3-chlorophenyl)(2-(2-methoxyethylamino)-2-oxoethoxy)methyl)-N-((S)-1-cyclohexyl-3-(methylamino)propan-2-yl)piperidine-1-carboxamide | 1.1 | | 537 | 0.95 (m, 2H), 2.71 (s, 3H), 2.93 (m, 2H), 3.05 (m, 2H), 3.36 (s, 3H), 3.40 (m, 2H), 3.45 (m, 2H), 4.15 (m, 3H), 7.24 (m, 1H), 7.36 (m, 3H) |
| I-66a | (3R)-3-((R)-(3-chlorophenyl)(3-(methylamino)-3-oxopropoxy)methyl)-N-((S)-1-cyclohexyl-3-(methylamino)propan-2-yl)piperidine-1-carboxamide | 1.1 | | 507 | 0.89 (m, 1H), 0.98 (m, 1H), 2.40 (m, 2H), 2.52 (s, 3H), 2.72 (s, 3H), 3.50 (m, 2H), 3.84 (m, 1H), 4.10 (m, 3H), 4.20 (m, 1H), 7.32 (m, 3H) |
| I-67a | (3R)-3-((R)-(3-chlorophenyl)(3-(ethylamino)-3-oxopropoxy)methyl)-N-((S)-1-cyclohexyl-3-(methylamino)propan-2-yl)piperidine-1-carboxamide | 1.1 | | 521 | 0.89 (m, 1H), 0.96 (m, 1H), 1.11 (m, 3H), 2.40 (m, 2H), 2.70 (s, 3H), 2.85 (m, 2H), 3.00 (m, 2H), 3.20 (m, 2H), 3.50 (m, 2H), 3.83 (m, 1H), 4.05 (m, 1H), 4.16 (m, 2H), 7.20 (m, 1H), 7.31 (m, 3H) |
| I-67b | (3R)-3-((S)-(3-chlorophenyl)(3-(ethylamino)-3-oxopropoxy)methyl)-N-((S)-1-cyclohexyl-3-(methylamino)propan-2-yl)piperidine-1-carboxamide | 1.1 | | 521 | 0.86 (m, 1H), 0.94 (m, 1H), 1.12 (m, 5H), 1.72 (m, 7H), 1.89 (m, 1H), 2.39 (m, 2H), 2.66 (s, 3H), 2.87 (m, 1H), 3.02 (m, 1H), 3.20 (m, 2H), 3.53 (m, 2H), 3.70 (m, 1H), 3.90 (m, 1H), 4.07 (m, 1H), 4.16 (m, 2H), 7.20 (m, 1H), 7.30 (m, 3H) |
| I-68a | (3R)-3-((R)-(3-chlorophenyl)(3-oxo-3-(propylamino)propoxy)methyl)-N-((2S)-1-cyclohexyl-3-(methylamino)propan-2-yl)piperidine-1-carboxamide | 1.1 | | 535 | 0.93 (t, 3H), 1.51 (m, 3H), 2.41 (m, 2H), 2.70 (s, 3H), 3.14 (m, 2H), 3.51 (m, 2H), 3.82 (m, 1H), 4.05 (m, 1H), 4.14 (m, 2H), 7.19 (m, 1H), 7.31 (m, 3H) |
| I-69a | (R)-3-((R)-(3-chlorophenyl)(3-(isopropylamino)-3-oxopropoxy)methyl)-N-((S)-1-cyclohexyl-3-(methylamino)propan-2-yl)piperidine-1-carboxamide | 1.1 | | 535 | 1.13 (d, 6H), 2.38 (m, 2H), 3.78 (m, 3H), 3.80 (m, 2H), 4.10 (m, 4H), 7.20 (m, 1H), 7.32 (m, 3H) |
| I-70a | (R)-3-((R)-(3-chloro-2-fluorophenyl)(3-(ethylamino)-3-oxopropoxy)methyl)-N-((S)-1-cyclohexyl-3-(methylamino)propan-2-yl)piperidine-1-carboxamide | 1.1 | | 539 | 0.97 (m, 3H), 1.13 (t, 3H), 2.39 (m, 2H), 2.70 (s, 3H), 3.18 (m, 2H), 3.51 (m, 2H), 3.72 (m, 1H), 4.15 (m, 2H), 4.46 (d, 1H), 7.20 (m, 1H), 7.32 (m, 1H), 7.42 (m, 1H) |

-continued

Table of Compounds Formula (I)

| Cpd. No. | Cpd Name | Example | LC-MS (3 min) $t_R$ (min) | Mass observed | Selected 1H NMR |
|---|---|---|---|---|---|
| I-71a | (3R)-3-((S)-5-amino-1-(3-chlorophenyl)-1-hydroxy-5-oxopentyl)-N-((S)-1-cyclohexyl-3-(methylamino)propan-2-yl)piperidine-1-carboxamide | 1.1 | | 507 | 0.99 (m, 2H), 2.18 (m, 2H), 2.55 (m, 2H), 2.71 (s, 3H), 2.96 (m, 1H), 3.06 (m, 2H), 4.07 (m, 1H), 4.25 (m, 2H), 7.27 (m, 3H), 7.44 (m, 1H) |
| I-72a | (3R)-3-((S)-1-(3-chlorophenyl)-1-hydroxy-5-(methylamino)-5-oxopentyl)-N-((S)-1-cyclohexyl-3-(methylamino)propan-2-yl)piperidine-1-carboxamide | 1.1 | | 521 | 0.98 (m, 2H), 2.13 (m, 2H), 2.69 (s, 3H), 2.71 (s, 3H), 2.96 (m, 1H), 3.05 (m, 1H), 4.06 (m, 1H), 4.21 (m, 2H), 7.26 (m, 3H), 7.45 (m, 1H) |
| I-73a | (3R)-3-((S)-1-(3-chlorophenyl)-5-(ethylamino)-1-hydroxy-5-oxopentyl)-N-((S)-1-cyclohexyl-3-(methylamino)propan-2-yl)piperidine-1-carboxamide | 1.1 | | 535 | 0.89 (m, 2H), 1.08 (t, 3H), 2.12 (m, 2H), 2.60 (m, 2H), 2.70 (s, 3H), 2.96 (m, 1H), 3.06 (m, 1H), 3.16 (m, 2H), 4.08 (m, 1H), 4.24 (m, 2H), 7.26 (m, 3H), 7.43 (m, 1H) |
| I-74a | (R)-3-((S)-1-(3-chlorophenyl)-4-formamido-1-hydroxybutyl)-N-((S)-1-cyclohexyl-3-(methylamino)propan-2-yl)piperidine-1-carboxamide | 5.1 | 1.32 | 507, 509 | 7.90 (s, 1H), 7.35-7.34 (m, 1H), 7.25-7.13 (m, 3H), 4.21 (d, J = 13.2 Hz, 1H), 4.08-4.01 (m, 1H), 3.88 (d, J = 12.9 Hz, 1H), 3.08 (t, J = 7.0 Hz, 2H), 2.98 (dd, J = 12.7, 3.4 Hz, 1H), 2.86 (dd, J = 12.6, 10 Hz, 1H), 2.62 (s, 3H), 2.50-2.42 (m, 2H), 1.93-0.76 (m, 22H). |
| I-75a | (R)-3-((R)-1-(3-chlorophenyl)(4-oxohexyloxy)methyl)-N-((S)-1-cyclohexyl-3-(methylamino)propan-2-yl)piperidine-1-carboxamide | 3.1 | | 520 | 0.89 (m, 1H), 1.00 (t, 3H), 2.48 (m, 4H), 2.70 (s, 3H), 2.92 (m, 1H), 3.06 (m, 1H), 3.23 (m, 2H), 3.96 (m, 2H), 4.10 (m, 1H), 4.21 (m 1H), 7.19 (m, 1H), 7.31 (m, 3H) |
| I-76a | (3R)-3-((S)-1-(3-chlorophenyl)-1-hydroxy-6-oxoheptyl)-N-((S)-1-cyclohexyl-3-(methylamino)propan-2-yl)piperidine-1-carboxamide | 5.1 | 1.53 | 520, 522 | 7.34 (t, J = 1.76 Hz, 1H), 7.24-7.12 (m, 3H), 4.21 (d, J = 13.2 Hz, 1H), 4.08-4.01 (m, 1H), 3.88 (d, J = 12.6 Hz, 1H), 2.98 (dd, J = 12.7, 3.4 Hz, 1H), 2.87 (dd, J = 12.6, 10.0 Hz, 1H), 2.63 (s, 3H), 2.50-2.42 (m, 2H), 2.33 (t, J = 7.2 Hz, 2H), 1.99 (s, 3H), 1.94-0.77 (m, 24H). |

The following are examples of aspartic protease inhibitors of the invention. When the stereochemistry at a chiral center is not defined in the compound name, this indicates that the sample prepared contained a mixture of isomers at this center.

| | Table of Compounds of Formula (XL) | | | | |
|---|---|---|---|---|---|
| Cpd. No. | Cpd Name | Example | LC-MS[a] (3 min) $t_R$ (min) | Mass Observed | Selected $^1$H NMR[b] |
| XL-1 | methyl 2-((R)-((R)-1-((S)-2-amino-3-((R)-tetrahydro-2H-pyran-3-yl)propylcarbamoyl)piperidin-3-yl)(3-chlorophenyl)methoxy)ethylcarbamate | 11 | 1.29 | 511 (M$^+$) | 7.36-7.32 (m, 3H), 7.23 (d, J = 7.6 Hz, 1H), 4.20 (br d, J = 13.6 Hz, 1H), 4.04 (d, J = 8.8 Hz, 1H), 3.89-3.78 (m, 3H), 3.64 (s, 3H), 3.48-3.42 (m, 2H), 3.37 (m, 1H), 3.28-3.24 (m, 5H), 3.15 (dd, J = 10.8, 9.2 Hz, 1H), 2.92 (m, 2H), 1.97 (m, 1H), 1.78 (m, 2H), 1.68-1.54 (m, 4H), 1.45-1.07 (m, 5H) |
| XL-2 | methyl 2-((R)-((R)-1-((S)-2-amino-3-((R)-tetrahydro-2H-pyran-3-yl)propylcarbamoyl)piperidin-3-yl)(3-fluorophenyl)methoxy)ethylcarbamate | 11.1 | 1.22 | 495 (M + 1) | 7.39 (m, 1H), 7.12 (d, J = 7.6 Hz, 1H), 7.09-7.04 (m, 2H), 7.23 (d, J = 7.6 Hz, 1H), 4.21 (br d, J = 14.0 Hz, 1H), 4.07 (d, J = 8.8 Hz, 1H), 3.90-3.79 (m, 3H), 3.65 (s, 3H), 3.49-3.43 (m, 2H), 3.39-3.37 (m, 2H), 3.28-3.25 (m, 4H), 3.16 (dd, J = 10.8, 10.0 Hz, 1H), 2.94 (m, 2H), 1.98 (m, 1H), 1.79 (m, 2H), 1.68-1.53 (m, 4H), 1.46-1.07 (m, 5H) |
| XL-3 | methyl 2-((R)-((R)-1-((S)-2-amino-3-((R)-tetrahydro-2H-pyran-3-yl)propylcarbamoyl)piperidin-3-yl)(3-chloro-5-fluorophenyl)methoxy)ethylcarbamate | 11.2 | 1.32 | 529 (M$^+$) | 7.19 (s, 1H), 7.16 (m, 1H), 7.23 (d, J = 8.8 Hz, 1H), 4.19 (br d, J = 14.4 Hz, 1H), 4.07 (d, J = 8.8 Hz, 1H), 3.89-3.79 (m, 3H), 3.64 (s, 3H), 3.48-3.42 (m, 2H), 3.40-3.34 (m, 2H), 3.30-3.24 (m, 4H), 3.19 (dd, J = 11.2, 9.2 Hz, 1H), 2.91 (m, 2H), 1.97 (m, 1H), 1.75 (m, 2H), 1.70-1.52 (m, 4H), 1.45-1.17 (m, 5H) |
| XL-4 | methyl 2-((R)-((R)-1-((S)-2-amino-3-((R)-tetrahydro-2H-pyran-3-yl)propylcarbamoyl)piperidin-3-yl)(3,5-difluorophenyl)methoxy)ethylcarbamate | 11.3 | 1.25 | 513 (M + 1) | 6.96-6.91 (m, 3H), 4.19 (br d, J = 13.6 Hz, 1H), 4.09 (d, J = 8.8 Hz, 1H), 3.89-3.79 (m, 3H), 3.65 (s, 3H), 3.49-3.43 (m, 2H), 3.39-3.37 (m, 2H), 3.30-3.25 (m, 4H), 3.16 (dd, J = 10.8, 10.0 Hz, 1H), 2.92 (m, 2H), 1.97 (m, 1H), 1.77 (m, 2H), 1.68-1.53 (m, 4H), 1.45-1.09 (m, 5H) |

-continued

Table of Compounds of Formula (XL)

| Cpd. No. | Cpd Name | Example | LC-MS[a] (3 min) $t_R$ (min) | Mass Observed | Selected $^1$H NMR[b] |
|---|---|---|---|---|---|
| XL-5 | methyl 2-((R)-((R)-1-((S)-2-amino-3-((R)-tetrahydro-2H-pyran-3-yl)propylcarbamoyl)piperidin-3-yl)(5-chloro-2-methylphenyl)methoxy)ethylcarbamate | 11.4 | 1.34 | 525 (M⁺) | 7.32 (s, 1H), 7.21-7.15 (m, 2H), 4.34 (d, J = 8.8 Hz, 1H), 4.29 (br d, J = 14.4 Hz, 1H), 3.87 (m, 3H), 3.64 (s, 3H), 3.48-3.42 (m, 2H), 3.38-3.34 (m, 2H), 3.30-3.26 (m, 4H), 3.19 (dd, J = 10.8, 9.6 Hz, 1H), 2.87 (m, 2H), 2.34 (s, 3H), 1.98 (m, 1H), 1.79 (m, 2H), 1.71-1.53 (m, 4H), 1.45-1.24 (m, 5H) |
| XL-6 | methyl 2-((R)-((R)-1-((S)-2-amino-3-((R)-tetrahydro-2H-pyran-3-yl)propylcarbamoyl)piperidin-3-yl)(5-fluoro-2-methylphenyl)methoxy)ethylcarbamate | 11.5 | 1.28 | 509 (M + 1) | 7.20 (dd, J = 6.8, 2.4 Hz, 1H), 7.14 (m, 1H), 6.97 (dd, J = 10.0, 8.4 Hz, 1H), 4.41 (d, J = 8.8 Hz, 1H), 4.16 (br d, J = 12.4 Hz, 1H), 3.87 (m, 2H), 3.77 (br d, J = 12.8 Hz, 1H), 3.45 (m, 2H), 3.35 (m, 1H), 3.48-3.42 (m, 2H), 3.38-3.34 (m, 2H), 3.29-3.26 (m, 4H), 3.16 (dd, J = 11.2, 9.6 Hz, 1H), 3.00 (m, 2H), 2.34 (s, 3H), 1.97 (m, 1H), 1.86 (m, 1H), 1.71 (m, 1H), 1.66 (m, 3H), 1.56 (m, 1H), 1.45-1.21 (m, 5H) |
| XL-7 | methyl 2-((R)-(3-chlorophenyl)((R)-1-((S)-2-(methylamino)-3-((R)-tetrahydro-2H-pyran-3-yl)propylcarbamoyl)piperidin-3-yl)methoxy)ethylcarbamate | 11.6 | 1.3 | 525 (M⁺) | 7.37-7.29 (m, 3H), 7.21 (d, J = 6.8 Hz, 1H), 4.20 (br d, J = 12.4 Hz, 1H), 4.02 (d, J = 9.2 Hz, 1H), 3.87-3.78 (m, 3H), 3.62 (s, 3H), 3.57 (d, J = 15.2 Hz, 1H), 3.44 (dd, J = 11.2, 3.6 Hz, 1H), 3.28-3.22 (m, 6H), 3.15 (td, J = 10.8, 9.6 Hz, 1H), 2.89 (m, 2H), 2.75 (s, 3H), 1.97 (m, 1H), 1.77 (m, 2H), 1.65-1.17 (m, 9H) |
| XL-8 | methyl 2-((R)-(5-chloro-2-methylphenyl)((R)-1-((S)-2-(methylamino)-3-((R)-tetrahydro-2H-pyran-3-yl)propylcarbamoyl)piperidin-3-yl)methoxy)ethylcarbamate | 11.7 | 1.34 | 539 (M⁺) | 7.30 (d, J = 2.4 Hz, 1H), 7.19-7.13 (m, 2H), 4.33-4.27 (m, 2H), 3.87-3.84 (m, 3H), 3.62 (s, 3H), 3.57 (d, J = 13.2 Hz, 1H), 3.44 (td, J = 10.8, 3.2 Hz, 1H), 3.29-3.21 (m, 6H), 3.15 (dd, J = 11.2, 9.6 Hz, 1H), 2.85 (m, 2H), 2.74 (s, 3H), 2.32 (s, 3H), 1.98 (m, 1H), 1.76 (m, 2H), 1.65-1.21 (m, 9H) |

Table of Compounds of Formula (L)

| Cpd. No. | Cpd Name | Example | LC-MS[a] (3 min) $t_R$ (min) | Mass Observed | Selected $^1$H NMR[b] |
|---|---|---|---|---|---|
| L-1 | methyl 2-((R)-((R)-1-((S)-1-(methylamino)-3-(tetrahydro-2H-pyran-3-yl)propan-2-ylcarbamoyl)-piperidin-3-yl)(m-tolyl)methoxy)ethylcarbamate | 13.1 | 1.942 | 505 (M + 1) | 7.21 (m, 1H), 7.11 (m, 3H), 4.12 (m, 2H), 3.87 (m, 4H), 3.61 (s, 3H), 3.41 (m, 1H), 2.95 (m, 3H), 2.72 (s, 3H), 2.34 (s, 3H) |
| L-2b | methyl 2-((R)-(3-fluorophenyl)((R)-1-((S)-1-(methylamino)-3-((S)-tetrahydro-2H-pyran-3-yl)propan-2-ylcarbamoyl)-piperidin-3-yl)methoxy)-ethylcarbamate | 15 | | | 7.26 (q, 1), 7.01-6.83 (m, 3), 3.51 (s, 3), 2.61 (s, 3) |
| L-2a | methyl 2-((R)-(3-fluorophenyl)((R)-1-((S)-1-(methylamino)-3-((R)-tetrahydro-2H-pyran-3-yl)propan-2-ylcarbamoyl)-piperidin-3-yl)methoxy)-ethylcarbamate | 15 | | | 7.25 (q, 1), 7.01-6.89 (m, 3), 3.50 (s, 3), 2.59 (s, 3) |
| L-3a | methyl 2-((R)-(3-chloro-5-fluorophenyl)((R)-1-((S)-1-(methylamino)-3-((R)-tetrahydro-2H-pyran-3-yl)propan-2-ylcarbamoyl)-piperidin-3-yl)methoxy)-ethylcarbamate | 14 | 1.34 | 543, 545 (M + 1) | 7.12 (m, 1H), 7.08-7.06 (m, 1H), 7.00-6.98 (m, 1H), 4.03-3.95 (m, 2H), 3.97 (d, J = 9.1 Hz, 1H), 3.83-3.74 (m, 3H), 3.55 (s, 3H), 3.36-2.82 (m, 10H), 2.63 (s, 3H), 1.80-1.11 (m, 12H). |
| L-3b | methyl 2-((R)-(3-chloro-5-fluorophenyl)((R)-1-((S)-1-(methylamino)-3-((S)-tetrahydro-2H-pyran-3-yl)propan-2-ylcarbamoyl)-piperidin-3-yl)methoxy)-ethylcarbamate | | 1.34 | 543, 545 (M + 1) | 7.08 (m, 1H), 7.03-7.01 (m, 1H), 6.95-6.93 (m, 1H), 4.08-3.96 (m, 2H), 3.91 (d, J = 8.8 Hz, 1H), 3.82-3.73 (m, 3H), 3.49 (s, 3H), 3.32-2.67 (m, 10H), 2.59 (s, 3H), 1.81-1.02 (m, 12H). |
| L-4b | methyl 2-((R)-(3,5-difluorophenyl)((R)-1-((S)-1-(methylamino)-3-((S)-tetrahydro-2H-pyran-3-yl)propan-2-ylcarbamoyl)-piperidin-3-yl)methoxy)-ethylcarbamate | 14.1 | 1.26 | 527 (M + 1) | 6.87-6.76 (m, 3H), 4.10-3.99 (m, 2H), 3.95 (d, J = 8.8 Hz, 1H), 3.84-3.75 (m, 3H), 3.52 (s, 3H), 3.35-2.17 (m, 10H), 2.62 (s, 3H), 1.84-1.05 (m, 12H). |
| L-4a | methyl 2-((R)-(3,5-difluorophenyl)((R)-1-((S)-1-(methylamino)-3-((R)-tetrahydro-2H-pyran-3-yl)propan-2-ylcarbamoyl)-piperidin-3-yl)methoxy)-ethylcarbamate | 14.2 | 1.29 | 527 (M + 1) | 6.87-6.76 (m, 3H), 4.02-3.98 (m, 2H), 3.96 (d, J = 9.1 Hz, 1H), 3.80-3.73 (m, 3H), 3.53 (s, 3H), 3.34-2.78 (m, 10H), 2.61 (s, 3H), 1.78-1.09 (m, 12H). |

Table of Compounds of Formula (L)

| Cpd. No. | Cpd Name | Example | LC-MS[a] (3 min) $t_R$ (min) | Mass Observed | Selected $^1$H NMR[b] |
|---|---|---|---|---|---|
| L-5b | methyl 2-((R)-(5-fluoro-2-methylphenyl)((R)-1-((S)-1-(methylamino)-3-((S)-tetrahydro-2H-pyran-3-yl)propan-2-ylcarbamoyl)-piperidin-3-yl)methoxy)-ethylcarbamate | 14.3 | 1.25 | 523 (M + 1) | 7.10-7.08 (m, 1H), 7.00-6.97 (m, 1H), 6.84-6.79 (m, 1H), 4.25 (d, J = 9.4 Hz, 1H), 4.04-3.97 (m, 2H), 3.79-3.72 (m, 3H), 3.48 (s, 3H), 3.31-2.72 (m, 10H), 2.59 (s, 3H), 2.19 (s, 3H), 1.81-1.05 (m, 12H). |
| L-5a | methyl 2-((R)-(5-fluoro-2-methylphenyl)((R)-1-((S)-1-(methylamino)-3-((R)-tetrahydro-2H-pyran-3-yl)propan-2-ylcarbamoyl)piperidin-3-yl)methoxy)ethylcarbamate | 14.4 | 1.25 | 523 (M + 1) | 7.09-7.07 (m, 1H), 7.00-6.97 (m, 1H), 6.84-6.79 (m, 1H), 4.26 (d, J = 9.2 Hz, 1H), 3.98-3.95 (m, 2H), 3.77-3.66 (m, 3H), 3.49 (s, 3H), 3.31-2.77 (m, 10H), 2.58 (s, 3H), 2.19 (s, 3H), 1.75-1.07 (m, 12H). |
| L-6b | methyl 2-((R)-(3-chlorophenyl)((R)-1-((S)-1-(methylamino)-3-((S)-tetrahydro-2H-pyran-3-yl)propan-2-ylcarbamoyl)-piperidin-3-yl)methoxy)-ethylcarbamate | 14.5 | 1.26 | 525, 527 (M + 1) | 7.18-7.04 (m, 4H), 4.04-3.93 (m, 2H), 3.83 (d, J = 9.1 Hz, 1H), 3.77-3.68 (m, 3H), 3.44 (s, 3H), 3.27-2.64 (m, 10H), 2.54 (s, 3H), 1.77-0.97 (m, 12H). |
| L-6a | methyl 2-((R)-(3-chlorophenyl)((R)-1-((S)-1-(methylamino)-3-((R)-tetrahydro-2H-pyran-3-yl)propan-2-ylcarbamoyl)-piperidin-3-yl)methoxy)-ethylcarbamate | 13 | 1.26 | 525, 527 (M + 1) | 7.23-7.10 (m, 4H), 4.02-3.93 (m, 2H), 3.89 (d, J = 8.8 Hz, 1H), 3.78-3.70 (m, 3H), 3.50 (s, 3H), 3.31-2.76 (m, 10H), 2.59 (s, 3H), 1.76-1.02 (m, 12H). |
| L-3c | methyl 2-((R)-(3-chloro-5-fluorophenyl)((R)-1-((R)-1-(methylamino)-3-(tetrahydro-2H-pyran-3-yl)propan-2-ylcarbamoyl)-piperidin-3-yl)methoxy)ethylcarbamate Isomer 1 | | 1.33 | 543, 545 (M + 1) | 7.10-6.92 (m, 3H), 4.22 (dm, J = 11.1 Hz, 1H), 4.06-3.99 (m, 1H), 3.95 (d, J = 8.2 Hz, 1H), 3.76-3.67 (m, 3H), 3.52 (s, 3H), 3.32-2.76 (m, 10H), 2.61 (s, 3H), 1.86-1.03 (m, 12H). |
| L-3d | methyl 2-((R)-(3-chloro-5-fluorophenyl)((R)-1-((R)-1-(methylamino)-3-(tetrahydro-2H-pyran-3-yl)propan-2-ylcarbamoyl)-piperidin-3-yl)methoxy)ethylcarbamate Isomer 2 | | 1.36 | 543, 545 (M + 1) | 7.10-6.93 (m, 3H), 4.23 (dm, J = 11.7 Hz, 1H), 3.99-3.93 (m, 1H), 3.95 (d, J = 8.8 Hz, 1H), 3.80-3.69 (m, 3H), 3.51 (s, 3H), 3.33-2.75 (m, 10H), 2.60 (s, 3H), 1.75-1.07 (m, 12H). |
| L-7 | methyl 2-((R)-((R)-1-((S)-1-(methylamino)-3-((R)-tetrahydro-2H-pyran-3-yl)propan-2-ylcarbamoyl)-piperidin-3-yl)-(phenyl)methoxy)-ethylcarbamate | 16 | 1.25 | 491 (M + 1) | |

-continued

Table of Compounds of Formula (L)

| Cpd. No. | Cpd Name | Example | LC-MS[a] (3 min) $t_R$ (min) | Mass Observed | Selected $^1$H NMR[b] |
|---|---|---|---|---|---|
| L-8 | methyl 2-((R)-(3-chloro-4-fluorophenyl)((R)-1-((S)-1-12.2(methylamino)-3-((R)-tetrahydro-2H-pyran-3-yl)propan-2-ylcarbamoyl)-piperidin-3-yl)methoxy)-ethylcarbamate | 13.2 | 1.903 | 543 (M+) | 7.44 (m, 1H), 7.23 (m, 2H), 4.05 (m, 3H), 3.86 (m, 3H), 3.61 (s, 3H), 3.40 (m, 1H), 3.10 (m, 3H), 2.94 (m, 2H), 2.71 (s, 3H) |
| L-9 | ethyl 2-((R)-(3-chloro-5-fluorophenyl)((R)-1-((S)-1-(methylamino)-3-((R)-tetrahydro-2H-pyran-3-yl)propan-2-ylcarbamoyl)-piperidin-3-yl)methoxy)ethylcarbamate | 13.3 | 2.045 | 557 (M+) | 7.20 (s, 1H), 7.14 (m, 1H), 7.07 (m, 1H), 4.08 (m, 5H), 3.87 (m, 3H), 3.10 (m, 3H), 2.90 (m, 2H), 2.71 (s, 3H), 1.23 (t, 3H) |
| L-10 | methyl 2-((R)-(5-chloro-2-methylphenyl)((R)-1-((S)-1-(methylamino)-3-((R)-tetrahydro-2H-pyran-3-yl)propan-2-ylcarbamoyl)-piperidin-3-yl)methoxy)-ethylcarbamate | 13.4 | 1.993 | 539 (M+) | 7.31 (s, 1H), 7.13 (m, 2H), 4.31 (m, 1H), 4.23 (m, 1H), 3.61 (s, 3H), 3.12 (m, 1H), 2.86 (m, 2H), 2.67 (m, 2H), 2.45 (s, 3H), 2.31 (s, 3H). |

For Tables containing compounds XL1-8 and X-1-10 notations "a" and "b" have the following meanings:

a. LC-MS (3 min) method

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 | b. d$_4$-MeOH was used as $^1$H NMR solvent.

Pharmacological Methods

In Vitro Activity Studies

The disclosed aspartic protease inhibitors have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the blood, lungs, the kidneys and other organs by angiotensin converting enzyme to form the octapeptide angiotensin II. The octapeptide increases blood pressure both directly by binding to its receptor, causing arterial vasoconstriction, and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

Fluorescence Assay

The action of renin inhibitors in vitro can be demonstrated experimentally by means of a test which measures the increase in fluorescence of an internally quenched peptide substrate. The sequence of this peptide corresponds to the sequence of human angiotensinogen. The following test protocol can be used. All reactions are carried out in a flat bottom white opaque microtiter plate. A 4 µL aliquot of 400 µM renin substrate (DABCYL-γ-Abu-Ile-His-Pro-Phe-His-Leu-Val-Ile-His-Thr-EDANS) in 192 µL assay buffer (50 mM BES, 150 mM NaCl, 0.25 mg/mL bovine serum albumin, pH7.0) is added to 4 µL of test compound in DMSO at various concentrations ranging from 10 µM to 1 nM final concentrations. Next, 100 µL of trypsin-activated recombinant human renin (final enzyme concentration of 0.2-2 nM) in assay buffer is added, and the solution is mixed by pipetting. The increase in fluorescence at 495 nm (excitation at 340 nm) is measured for 60-360 minutes at rt using a Perkin-Elmer Fusion microplate reader. The slope of a linear portion of the plot of fluorescence-increase as a function of time is then determined, and the rate is used for calculating percent inhibition in relation to uninhibited control. The percent inhibition values are then plotted as a function of inhibitor concentration, and the $IC_{50}$ is determined from a fit of this data to a four parameter equation. The $IC_{50}$ is defined as the concentration of a particular inhibitor that reduces the formation of product by 50% relative to a control sample containing no inhibitor. In the in vitro systems, the disclosed aspartic protease inhibitors exhibit inhibiting activities at minimum concentrations of from approximately $5\times10^{-5}$ M to approximately $10^{-12}$ M. Specific aspartic protease inhibitors exhibit inhibiting activities at minimum concentrations of from approximately $10^{-7}$ M to approximately $10^{-12}$ M. (Wang G. T. et al. *Anal. Biochem.* 1993, 210, 351; Nakamura, N. et al. *J. Biochem. (Tokyo)* 1991, 109, 741; Murakami, K. et al. *Anal Biochem.* 1981, 110, 232).

Plasma Assay

The action of renin inhibitors in vitro in human plasma can also be demonstrated experimentally by the decrease in plasma renin activity (PRA) levels observed in the presence of the compounds. Incubations mixtures contain in the final volume of 250 μL 95.5 mM N,N-bis(2-hydroxyethyl)-2-aminoethanesulfonic acid, pH 7.0, 8 mM EDTA, 0.1 mM neomycin sulfate, 1 mg/mL sodium azide, 1 mM phenylmethanesulfonyl fluoride, 2% DMSO and 87.3% of pooled mixed-gender human plasma stabilized with EDTA. For plasma batches with low PRA (less than 1 ng/ml/hr) ~2 pM of recombinant human renin is added to achieve PRA of 3-4 ng/ml/hr. The cleavage of endogenous angiotensinogen in plasma is carried out at 37° C. for 90 min and the product angiotensin I is measured by competitive radioimmunoassay using DiaSorin PRA kit. Uninhibited incubations containing 2% DMSO and fully inhibited controls with 2 μM of isovaleryl-Phe-Nle-Sta-Ala-Sta-OH are then used for deriving percent of inhibition for each concentration of inhibitors and fitting dose-response data into a four parametric model from which $IC_{50}$ values, defined as concentrations of inhibitors at which 50% inhibition occurs, are determined.

Results

The in vitro enzyme activity studies were carried out for compounds of the invention and the data is shown below:

Compounds I-1a through I-76a have an $IC_{50}$ for renin (fluorescence assay) of between about 5,000 nM to about 0.001 nM. Many of these compounds have an $IC_{50}$ between about 50 nM to about 0.001 nM; and others between about 5 nM to about 0.001 nM.

| Cpd No. | $IC_{50}$ |
|---|---|
| I*-1a | # |
| I*-2a | *** |
| I*-3a | * |
| I*-4a | **** |
| I*-5a | *** |
| I*-6a | # |
| I*-7a | *** |
| I*-8a | *** |
| I*-9a | **** |
| I*-10a | *** |
| I*-11a | * |
| I*-12a | # |
| I*-13a | ** |
| I*-14a | # |
| I*-15a | # |
| I*-16a | # |
| I*-17a | # |
| I*-18a | **** |
| I*-19a | *** |
| I*-20a | * |
| I*-21a | *** |
| I*-22a | # |
| I*-23a | *** |
| I*-24a | **** |
| I*-25a | # |
| I*-26a | * |
| I*-27a | *** |
| I*-28a | *** |
| I*-29a | **** |
| I*-30a | ** |
| I*-31a | # |
| I*-32a | *** |
| I*-33a | # |
| I*-34a | *** |
| I*-35a | ** |
| I*-36a | * |
| I*-37a | ** |
| I*-38a | * |
| I*-39a | **** |
| I*-40a | **** |
| I*-41a | *** |
| I*-42a | # |
| I*-43a | *** |
| I*-44a | *** |
| I*-45a | * |
| I*-46a | # |
| I*-47a | *** |
| I*-48a | *** |
| I*-49a | # |
| I*-50a | *** |
| I*-51a | # |
| I*-52a | *** |
| I*-53a | ** |
| I*-54a | * |
| I*-55a | **** |
| I*-56a | *** |
| I*-57a | *** |
| I*-58a | *** |
| I*-59a | *** |
| I*-60a | **** |
| I*-61a | *** |
| I*-62a | NA |
| I*-63a | **** |
| I*-64a | **** |
| I*-65a | *** |
| I*-66a | *** |
| I*-67a | *** |
| I*-68a | **** |
| I*-69a | * |
| I*-70a | ** |
| I*-71a | ** |
| I*-72a | *** |
| I*-73a | *** |
| I*-74a | ** |
| I*-75a | # |
| I*-76a | # |
| I*-77a | # |
| I*-78a | # |
| I*-79a | *** |
| I*-80a | *** |
| I*-81a | NA |
| I*-82a | **** |
| I*-83a | **** |
| I*-84a | **** |
| I*-85a | **** |
| I*-86a | **** |
| I*-87a | * |
| I*-88a | **** |
| I*-89a | # |
| I*-90a | **** |
| I*-91a | *** |
| I*-92a | # |
| I*-93a | # |
| I*-94a | # |
| I*-95a | *** |
| I*-96a | *** |
| I*-97a | ** |
| I*-98a | *** |
| I*-99a | *** |
| I*-100a | **** |

| Cpd No. | IC$_{50}$ |
|---|---|
| I*-101a | *** |
| I*-102a | * |
| I*-103a | ** |
| I*-104a | ** |
| I*-105a | *** |
| I*-106a | **** |
| I*-107a | *** |
| I*-108a | * |
| I*-109a | **** |
| I*-110a | **** |
| I*-111a | **** |
| I*-112a | **** |
| I*-113a | *** |
| I*-114a | *** |
| I*-115a | *** |
| I*-116a | *** |
| I*-117a | **** |
| I*-118a | **** |
| I*-119a | *** |
| I*-120a | **** |
| I*-121a | ** |
| I*-122a | *** |
| I*-123a | *** |
| I*-124a | ** |
| I*-125a | *** |
| I*-126a | # |
| I*-127a | ** |
| I*-128a | # |
| I*-129a | # |
| I*-130a | ** |
| I*-131a | # |
| I*-132a | # |
| I*-133a | **** |
| I*-134a | # |
| I*-135a | *** |
| I*-136a | *** |
| I*-137a | *** |
| I*-138a | *** |
| I*-139a | *** |
| I*-140a | **** |
| I*-141a | **** |
| I*-142a | *** |
| I*-143a | **** |
| I*-144a | # |
| I*-145a | *** |
| I*-146a | **** |
| I*-147a | **** |
| I*-148a | # |
| I*-149a | *** |
| I*-150a | * |
| I*-151a | **** |
| I*-152a | *** |
| I*-153a | **** |
| I*-154a | ** |
| I*-155a | *** |
| I*-156a | ** |
| I*-157a | *** |
| I*-158a | *** |
| I*-159a | *** |
| I*-160a | **** |

* represents less than 50 nM;
** represents less than 20 nM;
*** represents less than 10 nM;
**** represents less than 1 nM.;
# represents greater than 50 nM;
NA = Not Available In vitro IC$_{50}$ and PRA data for aspartic protease inhibitors of Formula (XL)

| Cpd No. | IC$_{50}$ | PRA |
|---|---|---|
| XL-1 | *** | *** |
| XL-2 | *** | ** |
| XL-3 | *** | *** |
| XL-4 | *** | *** |
| XL-5 | **** | **** |
| XL-6 | *** | * |
| XL-7 | **** | *** |
| XL-8 | **** | *** |

* represents less than 50 nM;
** represents less than 20 nM;
*** represents less than 10 nM;
**** represents less than 1 nM.

The in vitro enzyme activity studies were carried out for compounds L-1, L-2a, L-2b, L-3a, L-3b, L-3c, L-3d, L-4a, L-4-b, L-5a, L-5b, L-6a, L-6b, L-7, L-8, L-9 and L-10 and the data is shown in the table below.

In vitro IC$_{50}$ and PRA data for aspartic protease inhibitors of Formula (L)

| Cpd No. | IC$_{50}$ | PRA |
|---|---|---|
| 1 | *** | *** |
| 2a | *** | *** |
| 2b | *** | ** |
| 3a | **** | **** |
| 3b | *** | *** |
| 3c | *** | *** |
| 3d | ** | ** |
| 4a | *** | *** |
| 4b | *** | * |
| 5a | *** | *** |
| 5b | ** | * |
| 6a | **** | **** |
| 6b | *** | *** |
| 7 | ** | * |
| 8 | *** | *** |
| 9 | *** | * |
| 10 | *** | **** |

* represents less than 50 nM;
** represents less than 20 nM;
*** represents less than 10 nM;
**** represents less than 1 nM.

In Vivo Activity Studies

The cardiac and systemic hemodynamic efficacy of selective renin inhibitors can be evaluated in vivo in sodium-depleted, normotensive cynomolgus monkeys and in sodium-depleted, normotensive beagle dogs following a single oral and intravenous administration of the test compound. Arterial blood pressure is monitored by telemetry in freely moving, conscious animals.

Cynomolgus Monkey: Six male naïve cynomolgus monkeys weighing between 2.5 and 3.5 kg can be used in the studies. At least 4 weeks before the experiment, the monkeys are anesthetized with ketamine hydrochloride (15 mg/kg, i.m.) and xylazine hydrochloride (0.7 mg/kg, i.m.), and are implanted into the abdominal cavity with a transmitter (Model #TL11M2-D70-PCT, Data Sciences, St. Paul, Minn.). The pressure catheter is inserted into the lower abdominal aorta via the femoral artery. The bipotential leads are placed in Lead II configuration. The animals are housed under constant temperature (19-25° C.), humidity (>40%) and lighting conditions (12 h light and dark cycle), are fed once daily, and are allowed free access to water. The animals are sodium depleted by placing them on a low sodium diet (0.026%, Expanded Primate Diet 829552 MP-VENaCl (P), Special Diet Services, Ltd., UK) 7 days before the experiment and furosemide (3 mg/kg, intramuscularly i.m., Aventis Pharmaceuticals) is administered at −40 h and −16 h prior to administration of test compound.

For oral dosing, the renin inhibitors are formulated in 0.5% methylcellulose at dose levels of 10 and 30 mg/kg (5 mL/kg) by infant feeding tubes. For intravenous delivery, a silastic catheter is implanted into posterior vena cava via a femoral vein. The catheter is attached to the delivery pump via a tether system and a swivel joint. Test compound (dose levels of 0.1 to 10 mg/kg, formulated at 5% dextrose) is administered by continuous infusion (1.67 mL/kg/h) or by bolus injection (3.33 mL/kg in 2 min).

Arterial blood pressures (systolic, diastolic and mean) and body temperature are recorded continuously at 500 Hz and 50 Hz, respectively, using the Dataquest™ A.R.T. (Advanced Research Technology) software. Heart rate is derived from the phasic blood pressure tracing. During the recording period, the monkeys are kept in a separate room without human presence to avoid pressure changes secondary to stress. All data are expressed as mean±SEM. Effects of the renin inhibitors on blood pressure are assessed by ANOVA, taking into account the factors dose and time compared with the vehicle group.

Beagle Dogs: Non-naive Beagle dogs (2 per sex) weighing between 9 and 11 kg can be used in the studies. Each animal is implanted subcutaneously with a telemetry transmitter (Data Sciences) and the blood pressure catheter is inserted into the left femoral artery. The electrocardiogram leads are also tunneled subcutaneously to the appropriate anatomical regions. The animals are housed under constant temperature and lighting conditions, are fed once daily, and are allowed free access to water. A sodium depleted state is produced by placing them on a low-sodium diet (<4 meq/day, a combination of canned Prescription Diet canine h/d, from Hill's Pet Products and dry pellets from Bio-Serv Inc., Frenchtown, N.J.) beginning 10 days before the experiment, and furosemide (3 mg/kg i.m.; Aventis Pharmaceuticals) is administered at −40 and −16 h prior to administration of test compound.

A renin inhibitor is orally administered by orogastric gavage to all overnight fasted animals at a dose level of 30 mg/kg (4 mL/kg formulated in 0.5% methylcellulose). Food is given 4 h postdose. In some experiments, the renin inhibitor is administered by bolus i.v. at increasing dose levels of 1, 3 and 6 mg/kg (2, 6 and 20 mg/mL formulated in sterile saline). Cardiovascular parameters are collected continuously at least 80 min predose and 3 h postdose, followed by every 10 min for 5 h and every 30 min for 16 h postdose. The Dataquest™ ART (version 2.2) software package from DSI (Data Sciences International) is used to collect telemetered cardiovascular data.

Double Transgenic Rats: The efficacy of the renin inhibitors can also evaluated in vivo in double transgenic rats engineered to express human renin and human angiotensinogen (Bohlender J, Fukamizu A, Lippoldt A, Nomura T, Dietz R, Menard J, Murakami K, Luft F C, Ganten D. High human renin hypertension in transgenic rats. *Hypertension* 1997, 29, 428-434). In vivo activity for compound 7 was conducted according to the following procedures.

Experiments were conducted in 6-week-old double transgenic rats (dTGRs). The model has been described in detail earlier. Briefly, the human renin construct used to generate transgenic animals made up the entire genomic human renin gene (10 exons and 9 introns), with 3.0 kB of the 5'-promoter region and 1.2 kB of 3' additional sequences. The human angiotensinogen construct made up the entire human angiotensinogen gene (5 exons and 4 introns), with 1.3 kB of 5'-flanking and 2.4 kB of 3'-flanking sequences. The rats were purchased from RCC Ltd (Füllinsdorf, Switzerland). Radio telemetry transmitters were surgically implanted at 4 weeks of age. The telemetry system provided 24-h recordings of systolic, mean, diastolic arterial pressure (SAP, MAP, DAP, respectively) and heart rate (HR). Beginning on day 42, animals were transferred to telemetry cages. A 24 h telemetry reading was obtained. Rats were then dosed orally on the following 4 consecutive days (days 43-46). The rats were monitored continuously and allowed free access to standard 0.3%-sodium rat chow and drinking water.

Results

The in vivo double transgenic rat activity for compound XL-7 is shown in the FIG. 1. As shown in the FIG. 1, compound XL-7 exhibited significant effect in lowering blood pressures of double transgenic rats at a dosage of 10 mg/kg.

Figure 2:
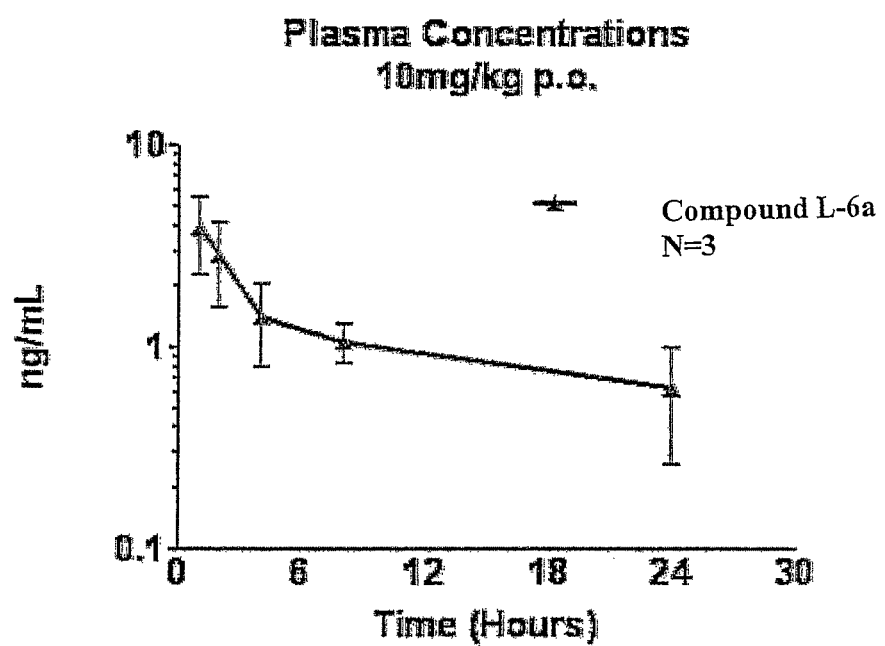
Figure 3:
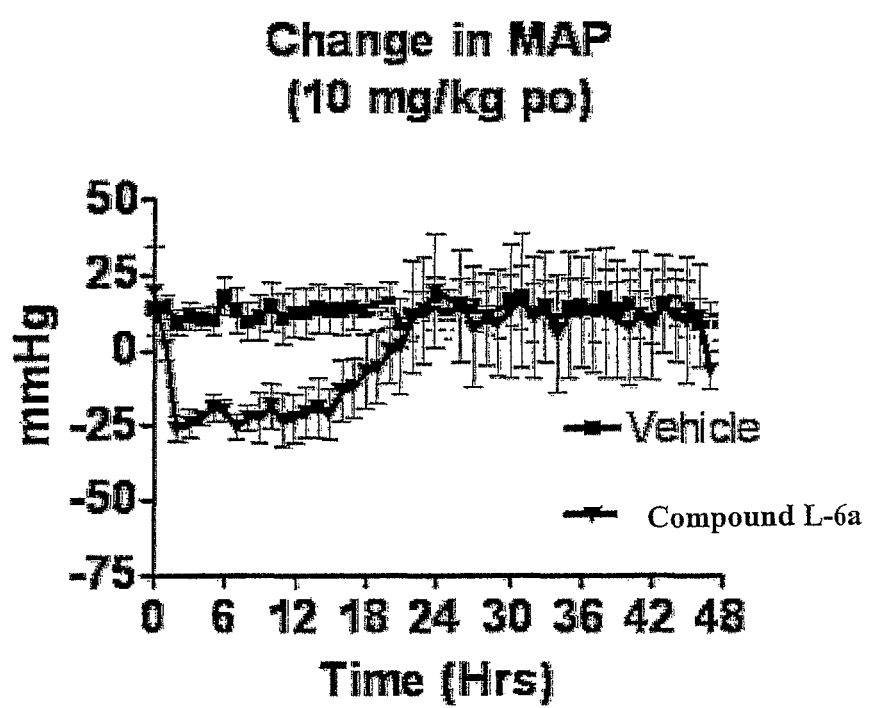
Figure 4:
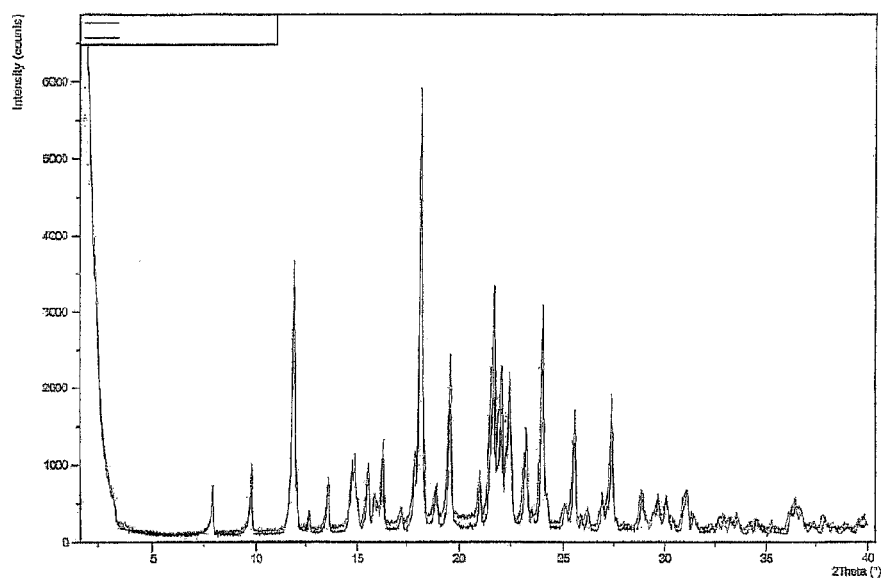

The in vivo double transgenic rat activities for compound L-6a are shown in FIGS. 2 and 3. As shown in FIG. 2, compound L-6a is readily available in rat's plasma following oral administration and the plasma concentration of compound L-6a remains relatively high over 24 h period, demonstrating its excellent oral bioavailability and metabolic stability. In addition, compound L-6a exhibited significant effect in lowering blood pressures of double transgenic rats at a dosage of 10 mg/kg, as shown in FIG. 3.

What is claimed is:

1. A compound represented by the following structural formula

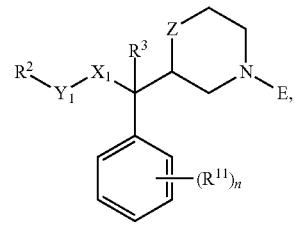

or a salt thereof, wherein

Z is —O— or —CH$_2$—;

X$_1$ is a covalent bond, —O—, —S—, —S(O)—, or —S(O)$_2$—;

Y$_1$ is a covalent bond, C$_1$-C$_{10}$ alkylene, C$_2$-C$_{10}$ alkenylene or C$_2$-C$_{10}$ alkynylene, each optionally substituted at one or more substitutable carbon atom with halogen, cyano, hydroxyl, (C$_1$-C$_3$)alkyl, (C$_1$-C$_3$)alkoxy or halo(C$_1$-C$_3$) alkoxy, provided that Y$_1$ is a covalent bond only when X$_1$ is a covalent bond;

n is 0, 1, 2 or 3;

E with the ring nitrogen that it protects is a carbamate, amide or sulfonamide;

R$^2$ is —NHC(O)OR$^9$;

R$^3$ is —H, C$_1$-C$_5$ alkyl, —NHC(O)R$^{10}$, or —OR$^{10}$, wherein R$^{10}$ is C$_1$-C$_3$ alkyl;

R$^9$ is a straight or branched C$_1$-C$_5$ alkyl, straight or branched C$_1$-C$_5$ haloalkyl, (C$_3$-C$_4$)cycloalkyl or straight or branched C$_1$-C$_5$ alkoxyalkyl; and R$^{11}$ is 1) fluorine, chlorine, bromine, cyano, nitro, (C$_1$-C$_6$) alkyl, (C$_3$-C$_6$)cycloalkyl, (C$_4$-C$_7$)cycloalkylalkyl, (C$_2$-C$_6$)alkenyl, (C$_5$-C$_7$)cycloalkylalkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, halo(C$_2$-C$_6$)alkenyl, halo(C$_3$-C$_6$)alkynyl, halo(C$_5$-C$_7$)-cycloalkylalkynyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy or (C$_1$-C$_6$)alkanesulfonyl; or 2) phenyl, heteroaryl, phenoxy, heteroaryloxy, phenylthio, heteroarylthio, benzyl, heteroarylmethyl, benzyloxy or heteroarylmethoxy, each optionally substituted with 1 to 3 groups independently selected from: fluorine, chlorine, cyano, (C$_1$-C$_3$)alkyl, halo(C$_1$-C$_3$)alkyl, (C$_1$-C$_3$)-alkoxy, halo(C$_1$-C$_3$)alkoxy, and aminocarbonyl.

2. The compound of claim 1, wherein E is tert-butoxycarbonyl- or benzyloxycarbonyl.

3. The compound represented by the following structural formula:
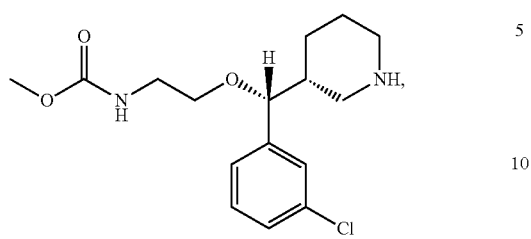
or a salt thereof.
4. The compound of claim 1, wherein the compound is represented by the following structural formula:
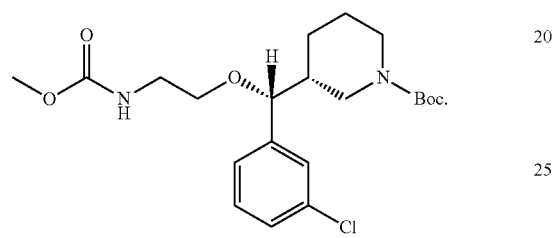
* * * * *

UNITED STATES PATENT AND TRADEMARK OFFICE
CERTIFICATE OF CORRECTION

| | | |
|---|---|---|
| PATENT NO. | : 8,487,108 B2 | Page 1 of 1 |
| APPLICATION NO. | : 12/084928 | |
| DATED | : July 16, 2013 | |
| INVENTOR(S) | : John J. Baldwin et al. | |

It is certified that error appears in the above-identified patent and that said Letters Patent is hereby corrected as shown below:

On the title page item (75) Inventors, after Alexey V. Ishchenko, delete "Somerville, PA" and insert --Somerville, MA--

Signed and Sealed this
Twenty-ninth Day of October, 2013

Teresa Stanek Rea
*Deputy Director of the United States Patent and Trademark Office*